US011965171B2

(12) United States Patent
Tresch et al.

(10) Patent No.: US 11,965,171 B2
(45) **Date of Patent: *Apr. 23, 2024**

(54) PLANTS HAVING INCREASED TOLERANCE TO HERBICIDES

(71) Applicant: BASF SE, Ludwigshafen (DE)

(72) Inventors: Stefan Tresch, Ludwigshafen (DE); Doreen Schachtschabel, Ludwigshafen (DE); Mihiret Tekeste Sisay, Ludwigshafen (DE); Jens Lerchl, Limburgerhof (DE); Julia Major, Freinsheim (DE); Florian Vogt, Ludwigshafen (DE); Frederick Calo, Dusseldorf (DE); Jill Marie Paulik, Durham, NC (US)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/842,427

(22) Filed: Jun. 16, 2022

(65) Prior Publication Data

US 2022/0333127 A1 Oct. 20, 2022

Related U.S. Application Data

(63) Continuation of application No. 16/824,787, filed on Mar. 20, 2020, now Pat. No. 11,365,426, which is a continuation of application No. 15/305,931, filed as application No. PCT/EP2015/058633 on Apr. 22, 2015, now Pat. No. 10,597,673.

(60) Provisional application No. 61/982,903, filed on Apr. 23, 2014, provisional application No. 61/982,904, filed on Apr. 23, 2014, provisional application No. 61/982,894, filed on Apr. 23, 2014, provisional application No. 61/982,900, filed on Apr. 23, 2014, provisional application No. 61/982,895, filed on Apr. 23, 2014, provisional application No. 61/982,901, filed on Apr. 23, 2014, provisional application No. 61/982,897, filed on Apr. 23, 2014, provisional application No. 61/982,899, filed on Apr. 23, 2014, provisional application No. 61/982,898, filed on Apr. 23, 2014, provisional application No. 61/982,896, filed on Apr. 23, 2014, provisional application No. 61/982,893, filed on Apr. 23, 2014.

(51) Int. Cl.

| | |
|---|---|
| ***C12N 15/82*** | (2006.01) |
| ***A01H 4/00*** | (2006.01) |
| ***A01N 43/68*** | (2006.01) |
| ***C12N 9/10*** | (2006.01) |

(52) U.S. Cl.

CPC ......... *C12N 15/8274* (2013.01); *A01H 4/008* (2013.01); *A01N 43/68* (2013.01); *C12N 9/1059* (2013.01); *C12Y 204/01012* (2013.01)

(58) Field of Classification Search

None

See application file for complete search history.

(56) References Cited

U.S. PATENT DOCUMENTS

| | | | | |
|---|---|---|---|---|
| 7,241,878 B1 * | 7/2007 | Somerville | C12N 9/2434 800/300 |
| 10,597,673 B2 | 3/2020 | Tresch et al. | |
| 11,365,426 B2 | 6/2022 | Tresch et al. | |
| 2011/0191897 A1 * | 8/2011 | Poree | C12N 9/0069 800/300 |

FOREIGN PATENT DOCUMENTS

| | | |
|---|---|---|
| CN | 101379190 A | 3/2009 |
| CN | 102471779 A | 5/2012 |
| WO | WO-2004/080171 A2 | 9/2004 |
| WO | WO-2010/025499 A1 | 3/2010 |
| WO | WO-2013/142968 A1 | 10/2013 |

OTHER PUBLICATIONS

Brabham, Chad, et al. "Grass cell walls have a role in the inherent tolerance of grasses to the cellulose biosynthesis inhibitor isoxaben." Pest management science 74.4 (2018): 878-884. Included in the IDS of Dec. 12, 2022 (Year: 2018).*

Kiedaisch, Brett M., Richard L. Blanton, and Candace H. Haigler. "Characterization of a novel cellulose synthesis inhibitor." Planta 217.6 (2003): 922-930. Included in the IDS of Dec. 12, 2022 (Year: 2003).*

Brabham et al., Grass cell walls have a role in the inherent tolerance of grasses to the cellulose biosynthesis inhibitor isoxaben, Pest Management Science, 74.4:878-884 (2018).

Desprez et al., Resistance against herbicide isoxaben and cellulose deficiency caused by distinct mutations in same cellulose synthase isoform CESA6, Plant Physiol., 128(2):482-90 (2002).

Kiedaisch et al., Characterization of a novel cellulose synthesis inhibitor, Planta, 217.6:922-30 (2003).

Scheible et al., Modifications of cellulose synthase confer resistance to isoxaben and thiazolidinone herbicides in *Arabidopsis* lxr1 mutants, Proc. Natl. Acad. Sci. USA, 98(18):10079-84 (2001).

* cited by examiner

*Primary Examiner* — Weihua Fan

(74) *Attorney, Agent, or Firm* — MARSHALL, GERSTEIN & BORUN LLP

(57) ABSTRACT

The present invention refers to a plant or plant part comprising a polynucleotide encoding a wildtype or mutated cellulose synthase (CESA) polypeptide, the expression of said polynucleotide confers to the plant or plant part tolerance to CESA-inhibiting herbicides, such as azines.

10 Claims, 13 Drawing Sheets

Specification includes a Sequence Listing.

Figure 2:
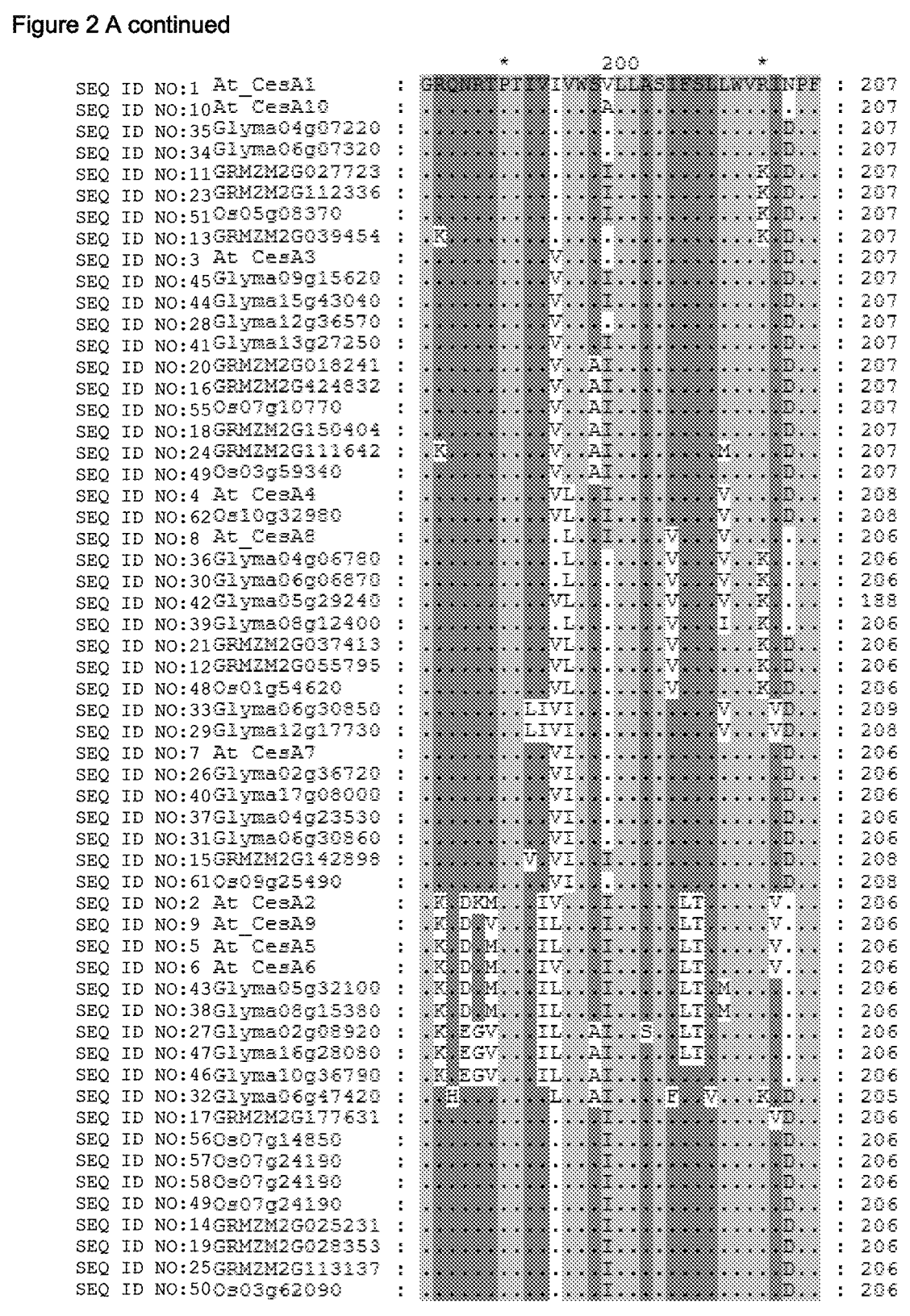

Figure 2 A continued

```
                                      *       200        *
SEQ ID NO:1 At_CesA1       : GRQNRIPTIYIVWSVLLASIFSLLWVRINPF : 207
SEQ ID NO:10At_CesA10      : ..............A................ : 207
SEQ ID NO:35Glyma04g07220  : ............................D.. : 207
SEQ ID NO:34Glyma06g07320  : ............................D.. : 207
SEQ ID NO:11GRMZM2G027723  : ..............I...........K.D.. : 207
SEQ ID NO:23GRMZM2G112336  : ..............I...........K.D.. : 207
SEQ ID NO:51Os05g08370     : ..............I...........K.D.. : 207
SEQ ID NO:13GRMZM2G039454  : .K........................K.D.. : 207
SEQ ID NO:3 At CesA3       : ..........V.................D.. : 207
SEQ ID NO:45Glyma09g15620  : ..........V...I.............D.. : 207
SEQ ID NO:44Glyma15g43040  : ..........V...I.............D.. : 207
SEQ ID NO:28Glyma12g36570  : ..........V.................D.. : 207
SEQ ID NO:41Glyma13g27250  : ..........V...I.............D.. : 207
SEQ ID NO:20GRMZM2G018241  : ..........V..AI.............D.. : 207
SEQ ID NO:16GRMZM2G424832  : ..........V..AI.............D.. : 207
SEQ ID NO:55Os07g10770     : ..........V..AI.............D.. : 207
SEQ ID NO:18GRMZM2G150404  : ..........V..AI.............D.. : 207
SEQ ID NO:24GRMZM2G111642  : .K........V..AI........M....D.. : 207
SEQ ID NO:49Os03g59340     : ..........V..AI.............D.. : 207
SEQ ID NO:4 At CesA4       : ..........VL..I........V....D.. : 208
SEQ ID NO:62Os10g32980     : ..........VL..I........V....D.. : 208
SEQ ID NO:8 At_CesA8       : ...........L..I....V...V....... : 206
SEQ ID NO:36Glyma04g06780  : ...........L.......V...V..K.... : 206
SEQ ID NO:30Glyma06g06870  : ...........L.......V...V..K.... : 206
SEQ ID NO:42Glyma05g29240  : ..........VL.......V...V..K.... : 188
SEQ ID NO:39Glyma08g12400  : ...........L.......V...I..K.... : 206
SEQ ID NO:21GRMZM2G037413  : ..........VL.......V......K.D.. : 206
SEQ ID NO:12GRMZM2G055795  : ..........VL.......V......K.D.. : 206
SEQ ID NO:48Os01g54620     : ..........VL.......V......K.D.. : 206
SEQ ID NO:33Glyma06g30850  : ........LIVI...........V...VD.. : 209
SEQ ID NO:29Glyma12g17730  : ........LIVI...........V...VD.. : 208
SEQ ID NO:7 At CesA7       : ..........VI................D.. : 206
SEQ ID NO:26Glyma02g36720  : ..........VI................D.. : 206
SEQ ID NO:40Glyma17g08000  : ..........VI................D.. : 206
SEQ ID NO:37Glyma04g23530  : ..........VI................D.. : 206
SEQ ID NO:31Glyma06g30860  : ..........VI................D.. : 206
SEQ ID NO:15GRMZM2G142898  : ........V.VI..I.............D.. : 208
SEQ ID NO:61Os09g25490     : ..........VI................D.. : 208
SEQ ID NO:2 At CesA2       : .K.DKM...IV...I.....LT.....V... : 206
SEQ ID NO:9 At_CesA9       : .K.D.V...IL...I.....LT.....V... : 206
SEQ ID NO:5 At CesA5       : .K.D.M...IL...I.....LT.....V... : 206
SEQ ID NO:6 At CesA6       : .K.D.M...IV...I.....LT.....V... : 206
SEQ ID NO:43Glyma05g32100  : .K.D.M...IL...I.....LT.M....... : 206
SEQ ID NO:38Glyma08g15380  : .K.D.M...IL...I.....LT.M....... : 206
SEQ ID NO:27Glyma02g08920  : .K.EGV...IL..AI..S..LT......... : 206
SEQ ID NO:47Glyma16g28080  : .K.EGV...IL..AI.....LT......... : 206
SEQ ID NO:46Glyma10g36790  : .K.EGV...IL..AI................ : 206
SEQ ID NO:32Glyma06g47420  : ..H.......L..AI....F..V...K.D.. : 205
SEQ ID NO:17GRMZM2G177631  : ..............I............VD.. : 206
SEQ ID NO:56Os07g14850     : ..............I.............D.. : 206
SEQ ID NO:57Os07g24190     : ..............I.............D.. : 206
SEQ ID NO:58Os07g24190     : ..............I.............D.. : 206
SEQ ID NO:49Os07g24190     : ..............I.............D.. : 206
SEQ ID NO:14GRMZM2G025231  : ..............I.............D.. : 206
SEQ ID NO:19GRMZM2G028353  : ..............I.............D.. : 206
SEQ ID NO:25GRMZM2G113137  : ..............I.............D.. : 206
SEQ ID NO:50Os03g62090     : ..............I.............D.. : 206
```

Figure 2B continued

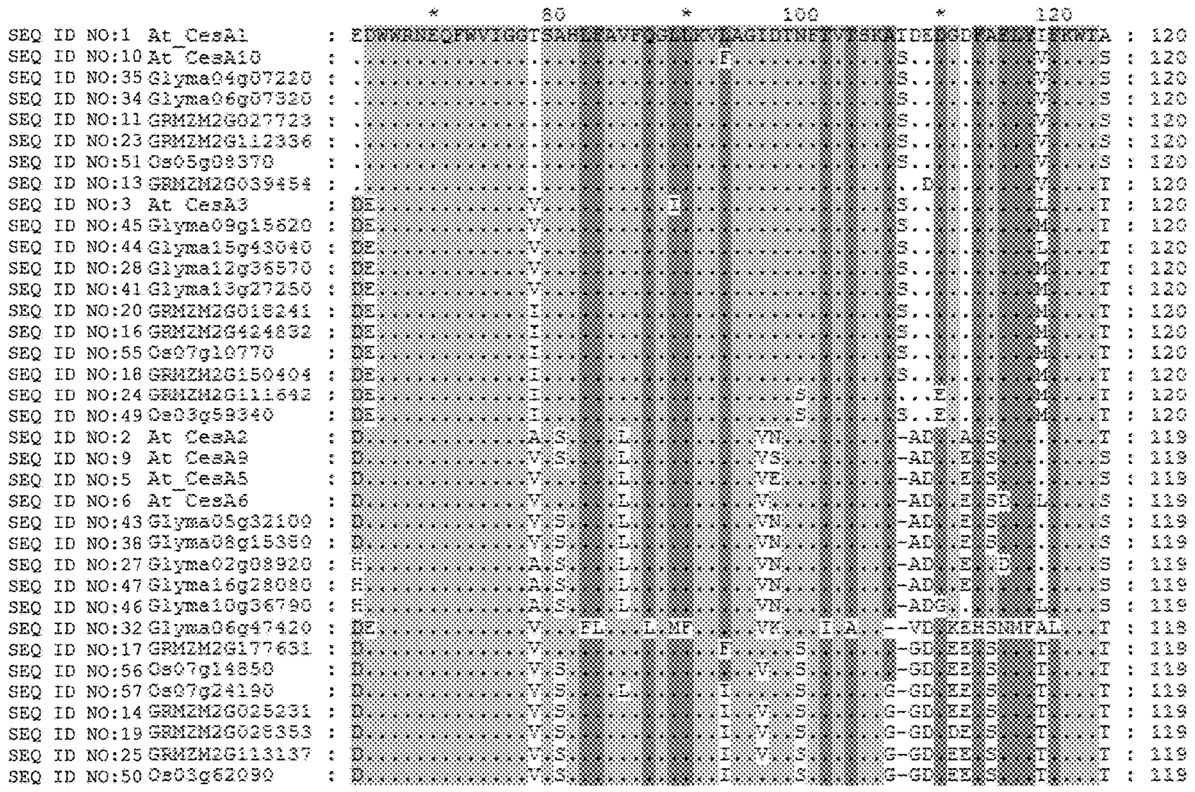

```
                                        *        80         *        100        *        120
SEQ ID NO:1  At_CesA1        : E....................F..............S....I....E....V....A : 120
SEQ ID NO:10 At_CesA10       : ..................................S....I....E....V....S : 120
SEQ ID NO:35 Glyma04g07220   : ..................................S....I....E....V....S : 120
SEQ ID NO:34 Glyma06g07320   : ..................................S....I....E....V....S : 120
SEQ ID NO:11 GRMZM2G027723   : ..................................S....I....E....V....S : 120
SEQ ID NO:23 GRMZM2G112336   : ..................................S....I....E....V....S : 120
SEQ ID NO:51 Os05g08370      : ..................................S....I....E....V....S : 120
SEQ ID NO:13 GRMZM2G039454   : ....................................D..I....E....V....T : 120
SEQ ID NO:3  At_CesA3        : DE............V.........I.........S....I....E....M....T : 120
SEQ ID NO:45 Glyma09g15620   : DE............V...................S....I....E....M....T : 120
SEQ ID NO:44 Glyma15g43040   : DE............V...................S....I....E....M....T : 120
SEQ ID NO:28 Glyma12g36570   : DE............V...................S....I....E....M....T : 120
SEQ ID NO:41 Glyma13g27250   : DE............V...................S....I....E....M....T : 120
SEQ ID NO:20 GRMZM2G018241   : DE............I...................S....I....E....M....T : 120
SEQ ID NO:16 GRMZM2G424832   : DE............I...................S....I....E....M....T : 120
SEQ ID NO:55 Os07g10770      : DE............I...................S....I....E....M....T : 120
SEQ ID NO:18 GRMZM2G150404   : DE............I.................S.S....I....E....M....T : 120
SEQ ID NO:24 GRMZM2G111642   : DE............I................E....I....E....M....T : 120
SEQ ID NO:49 Os03g59340      : DE............I.................S..S..E.I....E....M....T : 120
SEQ ID NO:2  At_CesA2        : D.............A.S....L......VN....-AD..A.S......T : 119
SEQ ID NO:9  At_CesA9        : D.............V.S....L......VS....-AD..E.S......S : 119
SEQ ID NO:5  At_CesA5        : D.............V......L......VE....-AD..E.S......S : 119
SEQ ID NO:6  At_CesA6        : D.............V......L......V.....-AD..E.SD.L....S : 119
SEQ ID NO:43 Glyma05g32100   : D.............V.S....L......VN....-AD..E.S......S : 119
SEQ ID NO:38 Glyma08g15380   : D.............V.S....L......VN....-AD..E.S......S : 119
SEQ ID NO:27 Glyma02g08920   : H.............A.S....L......VN....-AD..E.D......S : 119
SEQ ID NO:47 Glyma16g28080   : H.............A.S....L......VN....-AD..E.S......S : 119
SEQ ID NO:46 Glyma18g36790   : H.............A.S....L......VN....-ADG...L......S : 119
SEQ ID NO:32 Glyma06g47420   : DE............V...FL..L.MF..VK...I.A..--VD.KERSNMFAL.T : 118
SEQ ID NO:17 GRMZM2G177631   : D.............V...........F....S..-GD.EE.S....T....T : 118
SEQ ID NO:56 Os07g14850      : D.............V.S....L......V.S...-GD.EE.S....T....T : 118
SEQ ID NO:57 Os07g24190      : D.............V.S....L......I.S...G-GD.EE.S....T....T : 118
SEQ ID NO:14 GRMZM2G025231   : D.............V.S........I..V.S...G-GD.EE.S....T....T : 118
SEQ ID NO:19 GRMZM2G028353   : D.............V.S........I..V.S...G-GD.DE.S....T....T : 118
SEQ ID NO:25 GRMZM2G113137   : D.............V.S........I..V.S...G-GD.EE.S....T....T : 118
SEQ ID NO:50 Os03g62090      : D.............V.S........I..V.S...G-GD.EE.S....T....T : 118
```

Figure 2B continued

```
                                          *        200
SEQ ID NO:1  At_CesA1       : RTPIIVIVWSVLLASIFSLLWVRINPF : 207
SEQ ID NO:10 At_CesA10      : ..........A................ : 207
SEQ ID NO:35 Glyma04g07220  : ........................D.. : 207
SEQ ID NO:34 Glyma06g07320  : ........................D.. : 207
SEQ ID NO:11 GRMZM2G027723  : ......................K.D.. : 207
SEQ ID NO:23 GRMZM2G112336  : ......................K.D.. : 207
SEQ ID NO:51 Os05g08370     : ......................K.D.. : 207
SEQ ID NO:13 GRMZM2G039454  : ......................K.D.. : 207
SEQ ID NO:3  At_CesA3      : ......V.................D.. : 207
SEQ ID NO:45 Glyma09g15620  : ......V.................D.. : 207
SEQ ID NO:44 Glyma15g43040  : ......V.................D.. : 207
SEQ ID NO:28 Glyma12g36570  : ......V.................D.. : 207
SEQ ID NO:41 Glyma13g27250  : ......V.................D.. : 207
SEQ ID NO:20 GRMZM2G018241  : ......V..A..............D.. : 207
SEQ ID NO:16 GRMZM2G424832  : ......V..A..............D.. : 207
SEQ ID NO:55 Os07g10770     : ......V..A..............D.. : 207
SEQ ID NO:18 GRMZM2G150404  : ......V..A..............D.. : 207
SEQ ID NO:24 GRMZM2G111642  : ......V..A.........M....D.. : 207
SEQ ID NO:49 Os03g59340     : ......V..A..............D.. : 207
SEQ ID NO:2  At_CesA2       : KM...IV.........LT.....V... : 206
SEQ ID NO:9  At_CesA9       : .V...IL.........LT.....V... : 206
SEQ ID NO:5  At_CesA5       : .M...IL.........LT.....V... : 206
SEQ ID NO:6  At_CesA6       : .M...IV.........LT.....V... : 206
SEQ ID NO:43 Glyma05g32100  : .M...IL.........LT.M....... : 206
SEQ ID NO:38 Glyma08g15380  : .M...IL.........LT.M....... : 206
SEQ ID NO:27 Glyma02g08920  : GV...IL..A...S..LT......... : 206
SEQ ID NO:47 Glyma16g28080  : GV...IL..A......LT......... : 206
SEQ ID NO:46 Glyma10g36790  : GV...IL..A................. : 206
SEQ ID NO:32 Glyma06g47420  : ......L..A.....F..V...K.D.. : 205
SEQ ID NO:17 GRMZM2G177631  : .......................VD.. : 206
SEQ ID NO:56 Os07g14850     : ........................D.. : 206
SEQ ID NO:57 Os07g24190     : ........................D.. : 206
SEQ ID NO:14 GRMZM2G025231  : ........................D.. : 206
SEQ ID NO:19 GRMZM2G028353  : ........................D.. : 206
SEQ ID NO:25 GRMZM2G113137  : ........................D.. : 206
SEQ ID NO:50 Os03g62090     : ........................D.. : 206
```

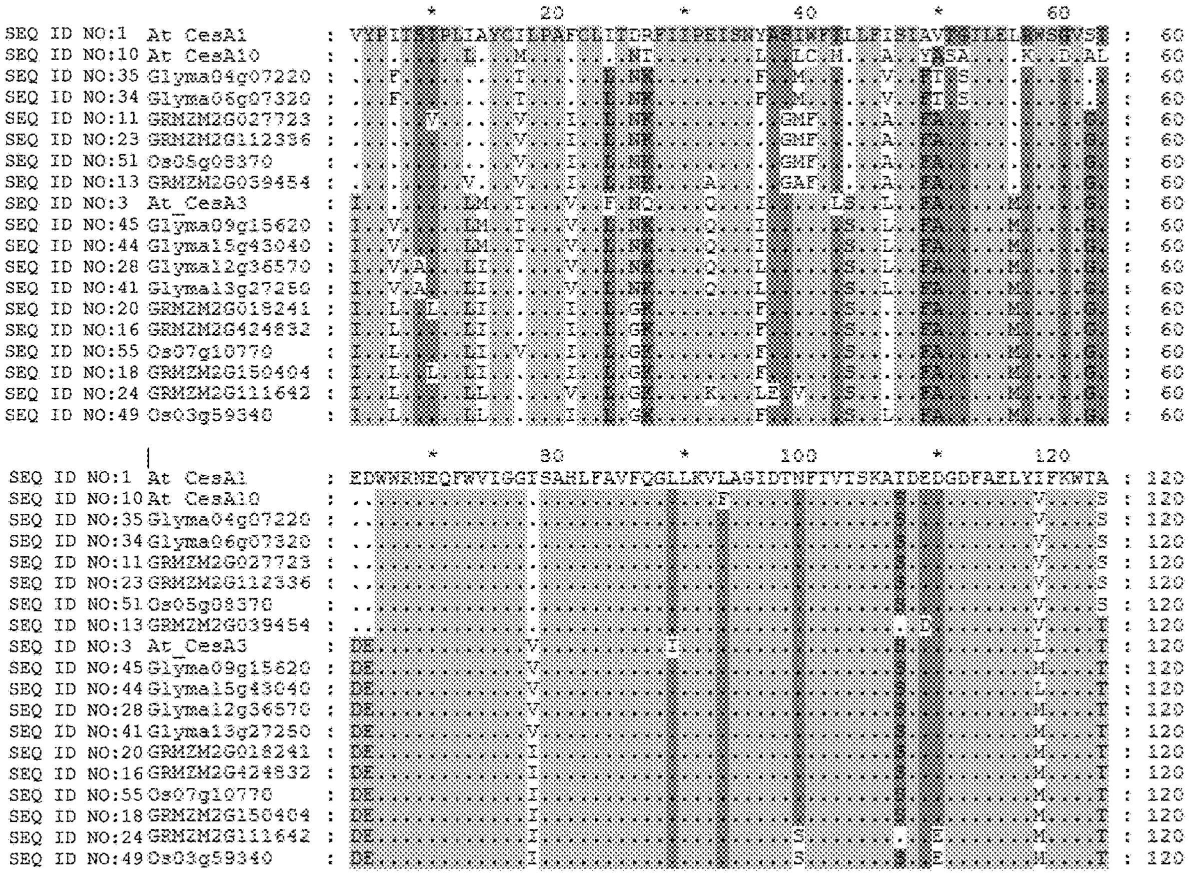

Figure 2C

```
                                       *        20         *        40         *        60
SEQ ID NO:1  At CesA1         : VYPI...........AYCI.PAFCI.......PE..NY....NF.LFI.AV....EL..G.YS. :  60
SEQ ID NO:10 At CesA10        : .........L..M........NT........L..LC.M..A..Y.A...K..D.AL     :  60
SEQ ID NO:35 Glyma04g07220    : ...F......T..............F.M...V..T.C.........              :  60
SEQ ID NO:34 Glyma06g07320    : ...F......T..............F.M...V..T.S.........              :  60
SEQ ID NO:11 GRMZM2G027723    : ...V......V..I...........GMF...A.............              :  60
SEQ ID NO:23 GRMZM2G112336    : .........V..I............GMF...A.............              :  60
SEQ ID NO:51 Os05g08370       : .........V..I............GMF...A.............              :  60
SEQ ID NO:13 GRMZM2G039454    : .....V..V...I..........A..GAF...A.............              :  60
SEQ ID NO:3  At_CesA3         : I.....LM.T..V.F.Q......Q..I....LS..L........M.              :  60
SEQ ID NO:45 Glyma09g15620    : I.V...LM.T..V..........Q..I......L..........M.              :  60
SEQ ID NO:44 Glyma15g43040    : I.V...LM.T..V..........Q..I......L..........M.              :  60
SEQ ID NO:28 Glyma12g36570    : I.VA..LI....V..........Q..L....................              :  60
SEQ ID NO:41 Glyma13g27250    : I.VA..LI....V..M.......Q..L....................              :  60
SEQ ID NO:20 GRMZM2G018241    : I.L..LLI....I..G.......F.......................              :  60
SEQ ID NO:16 GRMZM2G424832    : I.L..LLI....I..G.......F.......................              :  60
SEQ ID NO:55 Os07g10770       : I.L..LLI..V.I..G.......F......S.............M.              :  60
SEQ ID NO:18 GRMZM2G150404    : I.L..LLI....I..G.......F......S.............M.              :  60
SEQ ID NO:24 GRMZM2G111642    : I.L..LLI....V..G...K..LE.V..S...............M.              :  60
SEQ ID NO:49 Os03g59340       : I.L..LLI....I..G.......F...L.................M.             :  60

                                       *        80         *       100         *       120
SEQ ID NO:1  At CesA1         : EDWWRMEQFWVIGGISAHLFAVFQGLLKVLAGIDTNFTVTSKAIDEDGDFAELYIFKWTA : 120
SEQ ID NO:10 At CesA10        : ...........................F.................V...S         : 120
SEQ ID NO:35 Glyma04g07220    : ..........................................V...S            : 120
SEQ ID NO:34 Glyma06g07320    : ..........................................V...S            : 120
SEQ ID NO:11 GRMZM2G027723    : ..........................................V...S            : 120
SEQ ID NO:23 GRMZM2G112336    : ..........................................V...S            : 120
SEQ ID NO:51 Os05g08370       : ..........................................V...S            : 120
SEQ ID NO:13 GRMZM2G039454    : .....................................D....V...S            : 120
SEQ ID NO:3  At_CesA3         : DE........V........I......................L...T            : 120
SEQ ID NO:45 Glyma09g15620    : DE........V................................M...T           : 120
SEQ ID NO:44 Glyma15g43040    : DE........V................................M...T           : 120
SEQ ID NO:28 Glyma12g36570    : DE........V................................M...T           : 120
SEQ ID NO:41 Glyma13g27250    : DE........V................................M...T           : 120
SEQ ID NO:20 GRMZM2G018241    : DE........I................................M...T           : 120
SEQ ID NO:16 GRMZM2G424832    : DE........I................................M...T           : 120
SEQ ID NO:55 Os07g10770       : DE........I................................M...T           : 120
SEQ ID NO:18 GRMZM2G150404    : DE........I................................M...T           : 120
SEQ ID NO:24 GRMZM2G111642    : DE........I.....................S.......E..M...T           : 120
SEQ ID NO:49 Os03g59340       : DE........I.....................S.......E..M...T           : 120
```

PLANTS HAVING INCREASED TOLERANCE TO HERBICIDES

This application is a continuation of U.S. patent application Ser. No. 16/824,787, filed Mar. 20, 2020, which is a continuation of U.S. patent application Ser. No. 15/305,931, which is the U.S. National Stage application of International Application No. PCT/EP2015/058633, filed Apr. 22, 2015, which claims the benefit of U.S. Patent Application Nos. 61/982,893, 61/982,894, 61/982,895, 61/982,896, 61/982,897, 61/982,898, 61/982,899, 61/982,900, 61/982,901, 61/982,903, and 61/982,904, which were all filed on Apr. 23, 2014; the contents of aforementioned applications are incorporated herein by reference in their entirety.

INCORPORATION BY REFERENCE OF MATERIAL SUBMITTED ELECTRONICALLY

This application incorporates by reference in its entirety a computer-readable nucleotide/amino acid sequence listing identified as one 635,445-byte ASCII (text) file named "76908B_Seqlisting.txt," created Mar. 15, 2022.

FIELD OF THE INVENTION

The present invention relates in general to methods for conferring on plants agricultural level tolerance to herbicides. Particularly, the invention refers to plants having an increased tolerance to herbicides, more specifically to herbicides which inhibit the enzyme cellulose synthase (CESA), also known cellulose biosynthesis inhibitors (CBI). More specifically, the present invention relates to methods and plants obtained by mutagenesis and cross-breeding and transformation that have an increased tolerance to herbicides, particularly CESA-inhibiting herbicides.

BACKGROUND OF THE INVENTION

Plant cell walls are complex structures composed of high-molecular-weight polysaccharides, proteins, and lignins. Among the wall polysaccharides, cellulose, a hydrogen-bonded β-1,4-linked glucan microfibril, is the main load-bearing wall component and a key precursor for industrial applications. Cellulose is synthesized by large multimeric cellulose synthase (CESA) complexes (E.C.2.4.1.12), tracking along cortical microtubules at the plasma membrane. The only known components of these complexes are the cellulose synthase proteins. Recent studies have identified tentative interaction partners for the CESAs and shown that the migratory patterns of the CESA complexes depend on phosphorylation status (for review see Endler and Persson, Molecular Plant, 2011, Volume 4, Number 2, Pages 199-211, and references contained therein). For example, cotton cellulose synthase genes, termed CESA1 and CESA2, were identified in a collection of expressed sequence tag (EST) sequences on the basis of weak sequence similarity to genes for cellulose synthase from bacteria (Richmond and Somerville. Plant Physiology, 2000, Vol. 124, 495-498; and references contained therein) In addition, the genes were expressed at high levels in cotton fibers at the onset of secondary wall synthesis and a purified fragment of one of the corresponding proteins as shown to bind UDP-Glc, the proposed substrate for cellulose biosynthesis. The conclusion that the cotton CESA genes are cellulose synthases is supported by results obtained with two cellulose-deficient *Arabidopsis* mutants, rsw1 and irx3 (Richmond and Somerville. Plant Physiology, Vol. 124, 2000, 495-498; and references contained therein). The genes corresponding to the RSW1 and IRX3 loci exhibit a high degree of sequence similarity to the cotton CESA genes and are considered orthologs. Ten full-length CESA genes have been sequenced from *Arabidopsis*, and there is a genome survey sequence that may indicate one additional family member. Reiterative database searches using the *Arabidopsis* Rsw1 (AtCESA1) and the cotton CESA polypeptide sequences as the initial query sequences revealed a large superfamily of at least 41 CESA-like genes in *Arabidopsis*. Based on predicted protein sequences, these genes were grouped into seven clearly distinguishable families (Richmond and Somerville. Plant Physiology, Vol. 124, 2000, 495-498; and references contained therein): the CESA family, which includes RSW1 and IRX3 (AtCESA7), and six families of structurally related genes of unknown function designated as the "cellulose synthase-like" genes (CslA, CslB, CslC, CslD, CslE, and CslG).

WO 2013/142968 describes plant cellulose synthase (CESA) alleles identified by mutagenizing plants and screening said plants with a cellulose biosynthetic inhibitor (CBI). CBIs employed in WO 2013/142968 include dichlobenil, chlorthiamid, isoxaben, flupoxam, and quinclorac, particularly isoxaben or flupoxam (named fpx1-1 to fxp1-3 [CESA3], fxp2-1 to fxp2-3 [CESA1] and ixr1-1 to ixr1-7 [CESA3], ixr2-1 to ixr2-2 [CESA6] mutants of *Arabidopsis* CESA wildtype enzymes)

The inventors of the present invention have now surprisingly found that over-expression of the mutant cellulose synthase forms disclosed in WO 2013/142968 confers in plants tolerance/resistance to particular classes of CESA-inhibiting herbicides (cellulose biosynthesis inhibitors; CBIs) as compared to the non-transformed and/or non-mutagenized plants or plant cells, respectively. More specifically, the inventors of the present invention have found that CESA expression confers tolerance/resistance to azines. More specifically, the inventors of the present invention have found that modifications of the C-terminal part of CESA proteins confer tolerance/resistance to azines.

The problem of the present invention can be seen as to the provision of novel traits by identifying target polypeptides, the manipulation of which makes plants tolerant to herbicides.

Three main strategies are available for making plants tolerant to herbicides, i.e. (1) detoxifying the herbicide with an enzyme which transforms the herbicide, or its active metabolite, into non-toxic products, such as, for example, the enzymes for tolerance to bromoxynil or to basta (EP242236, EP337899); (2) mutating the target enzyme into a functional enzyme which is less sensitive to the herbicide, or to its active metabolite, such as, for example, the enzymes for tolerance to glyphosate (EP293356, Padgette S. R. et al., J. Biol. Chem., 266, 33, 1991); or (3) overexpressing the sensitive enzyme so as to produce quantities of the target enzyme in the plant which are sufficient in relation to the herbicide, in view of the kinetic constants of this enzyme, so as to have enough of the functional enzyme available despite the presence of its inhibitor.

The problem is solved by the subject-matter of the present invention.

SUMMARY OF THE INVENTION

Accordingly, in one aspect, the present invention provides a plant or plant part comprising a polynucleotide encoding a wildtype or mutated CESA polypeptide, the expression of said polynucleotide confers to the plant or plant part tolerance to CESA-inhibiting herbicides.

In some aspects, the present invention provides a seed capable of germination into a plant comprising in at least some of its cells a polynucleotide operably linked to a promoter operable in plant cells, the promoter capable of expressing a wildtype or mutated CESA polypeptide encoded by the polynucleotide, the expression of the wildtype or mutated CESA polypeptide conferring to the plant tolerance to CESA-inhibiting herbicides.

In one aspect, the present invention provides a plant cell of or capable of regenerating a plant comprising in at least some of its cells a polynucleotide operably linked to a promoter operable in plant cells, the promoter capable of expressing a wildtype or mutated CESA polypeptide encoded by the polynucleotide, the expression of the wildtype or mutated CESA polypeptide conferring to the plant tolerance to CESA-inhibiting herbicides, wherein the plant cell comprises the polynucleotide operably linked to a promoter.

In another aspect, the present invention provides a plant cell comprising a polynucleotide operably linked to a promoter operable in a cell, the promoter capable of expressing a wildtype or mutated CESA polypeptide encoded by the polynucleotide, the expression of the wildtype or mutated CESA polypeptide conferring to the plant tolerance to CESA-inhibiting herbicides.

In other aspects, the present invention provides a plant product prepared from a plant or plant part comprising in at least some of its cells a polynucleotide operably linked to a promoter operable in plant cells, the promoter capable of expressing a wildtype or mutated CESA polypeptide encoded by the polynucleotide, the expression of the wildtype or mutated CESA polypeptide conferring to the plant tolerance to CESA-inhibiting herbicides.

In some aspects, the present invention provides a progeny or descendant plant derived from a plant comprising in at least some of its cells a polynucleotide operably linked to a promoter operable in plant cells, the promoter capable of expressing a wildtype or mutated CESA polypeptide encoded by the polynucleotide, wherein the progeny or descendant plant comprises in at least some of its cells the recombinant polynucleotide operably linked to the promoter, the expression of the wildtype or mutated CESA polypeptide conferring to the progeny or descendant plant tolerance to the CESA-inhibiting herbicides.

In other aspects, the present invention provides a method for controlling weeds at a locus for growth of a plant, the method comprising: (a) applying an herbicide composition comprising CESA-inhibiting herbicides to the locus; and (b) planting a seed at the locus, wherein the seed is capable of producing a plant that comprises in at least some of its cells a polynucleotide operably linked to a promoter operable in plant cells, the promoter capable of expressing a wildtype or mutated CESA polypeptide encoded by the polynucleotide, the expression of the wildtype or mutated CESA polypeptide conferring to the plant tolerance to CESA-inhibiting herbicides.

In some aspects, the present invention provides a method for controlling weeds at a locus for growth of a plant, the method comprising: applying an herbicidal composition comprising CESA-inhibiting herbicides to the locus; wherein said locus is: (a) a locus that contains: a plant or a seed capable of producing said plant; or (b) a locus that is to be after said applying is made to contain the plant or the seed; wherein the plant or the seed comprises in at least some of its cells a polynucleotide operably linked to a promoter operable in plant cells, the promoter capable of expressing a wildtype or mutated CESA polypeptide encoded by the polynucleotide, the expression of the wildtype or mutated CESA polypeptide conferring to the plant tolerance to CESA-inhibiting herbicides.

In one aspect, step (a) occurs before, after, or concurrently with step (b).

In other aspects, the present invention provides a method of producing a plant having tolerance to CESA-inhibiting herbicides, the method comprising regenerating a plant from a plant cell transformed with a polynucleotide operably linked to a promoter operable in plant cells, the promoter capable of expressing a wildtype or mutated CESA polypeptide encoded by the polynucleotide, the expression of the wildtype or mutated CESA polypeptide conferring to the plant tolerance to CESA-inhibiting herbicides.

In one aspect, the present invention provides a method of producing a progeny plant having tolerance to CESA-inhibiting herbicides, the method comprising: crossing a first CESA-inhibiting herbicides-tolerant plant with a second plant to produce a CESA-inhibiting herbicides-tolerant progeny plant, wherein the first plant and the progeny plant comprise in at least some of their cells a polynucleotide operably linked to a promoter operable in plant cells, the promoter capable of expressing a wildtype or mutated CESA polypeptide encoded by the polynucleotide, the expression of the wildtype or mutated CESA polypeptide conferring to the plant tolerance to CESA-inhibiting herbicides.

In addition, the present invention refers to a method for identifying a CESA-inhibiting herbicide by using a wildtype or mutated CESA of the present invention encoded by a nucleic acid which comprises the nucleotide sequence of SEQ ID NO: 65, 66, 67, 68, 69, 70, 71, 72, 73, 74, 75, 76, or 77, or a variant, homologue, paralogue or orthologue thereof.

Said method comprises the steps of:

a) generating a transgenic cell or plant comprising a nucleic acid encoding a wildtype or mutated CESA of the present invention, wherein the wildtype or mutated CESA of the present invention is expressed;
b) applying a CESA-inhibiting herbicide to the transgenic cell or plant of a) and to a control cell or plant of the same variety;
c) determining the growth or the viability of the transgenic cell or plant and the control cell or plant after application of said test compound, and
d) selecting test compounds which confer reduced growth to the control cell or plant as compared to the growth of the transgenic cell or plant.

Another object refers to a method of identifying a nucleotide sequence encoding a wildtype or mutated CESA which is resistant or tolerant to a CESA-inhibiting herbicide, the method comprising:

a) generating a library of wildtype or mutated CESA-encoding nucleic acids,
b) screening a population of the resulting wildtype or mutated CESA-encoding nucleic acids by expressing each of said nucleic acids in a cell or plant and treating said cell or plant with a CESA-inhibiting herbicide,
c) comparing the CESA-inhibiting herbicide-tolerance levels provided by said population of wildtype or mutated CESA encoding nucleic acids with the CESA-inhibiting herbicide-tolerance level provided by a control CESA-encoding nucleic acid,
d) selecting at least one wildtype or mutated CESA-encoding nucleic acid that provides a significantly increased level of tolerance to a CESA-inhibiting herbicide as compared to that provided by the control CESA-encoding nucleic acid.

In a preferred embodiment, the wildtype or mutated CESA-encoding nucleic acid selected in step d) provides at least 2-fold as much tolerance to a CESA-inhibiting herbicide as compared to that provided by the control CESA-encoding nucleic acid.

The resistance or tolerance can be determined by generating a transgenic plant comprising a nucleic acid sequence of the library of step a) and comparing said transgenic plant with a control plant.

Another object refers to a method of identifying a plant or algae containing a nucleic acid encoding a wildtype or mutated CESA which is resistant or tolerant to a CESA-inhibiting herbicide, the method comprising:

a) identifying an effective amount of a CESA-inhibiting herbicide in a culture of plant cells or green algae.
b) treating said plant cells or green algae with a mutagenizing agent,
c) contacting said mutagenized cells population with an effective amount of CESA-inhibiting herbicide, identified in a),
d) selecting at least one cell surviving these test conditions,
e) PCR-amplification and sequencing of CESA genes from cells selected in d) and comparing such sequences to wild-type CESA gene sequences, respectively.

In a preferred embodiment, the mutagenizing agent is ethylmethanesulfonate.

Another object refers to an isolated recombinantly produced, and/or chemically synthesized nucleic acid encoding a wildtype or mutated CESA, the nucleic acid comprising the sequence of SEQ ID NO: 65, 66, 67, 68, 69, 70, 71, 72, 73, 74, 75, 76, or 77, or a variant thereof, as defined hereinafter.

In a preferred embodiment, the nucleic acid being identifiable by a method as defined above.

Another object refers to an isolated, recombinantly produced, and/or chemically synthesized wildtype or mutated CESA polypeptide, the polypeptide comprising the sequence set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64, a variant, derivative, orthologue, paralogue or homologue thereof, as defined hereinafter.

In still further aspects, the present invention provides a plant or plant part comprising in at least some of its cells a polynucleotide operably linked to a promoter operable in plant cells, the promoter capable of expressing a wildtype or mutated CESA polypeptide encoded by the polynucleotide, the expression of the wildtype or mutated CESA polypeptide conferring to the plant tolerance to CESA-inhibiting herbicides, wherein the plant or plant part further exhibits a second or third herbicide-tolerant trait.

In another embodiment, the invention refers to a plant cell transformed by and expressing a a wildtype or mutated CESA nucleic acid according to the present invention or a plant which has been mutated to obtain a plant expressing, preferably over-expressing a wildtype or mutated CESA nucleic acid according to the present invention, wherein expression of said nucleic acid in the plant cell results in increased resistance or tolerance to a CESA-inhibiting herbicide as compared to a wild type variety of the plant cell In another embodiment, the invention refers to a plant comprising a plant cell according to the present invention, wherein expression of the nucleic acid in the plant results in the plant's increased resistance to CESA-inhibiting herbicide as compared to a wild type variety of the plant.

The plants of the present invention can be transgenic or non-transgenic.

Preferably, the expression of the nucleic acid of the invention in the plant results in the plant's increased resistance to CESA-inhibiting herbicides as compared to a wild type variety of the plant. In another embodiment, the invention refers to a seed produced by a transgenic plant comprising a plant cell of the present invention, wherein the seed is true breeding for an increased resistance to a CESA-inhibiting herbicide as compared to a wild type variety of the seed.

In another embodiment, the invention refers to a method of producing a transgenic plant cell with an increased resistance to a CESA-inhibiting herbicide as compared to a wild type variety of the plant cell comprising, transforming the plant cell with an expression cassette comprising a polynucleotide operably linked to a promoter operable in plant cells, the promoter capable of expressing a wildtype or mutated CESA polypeptide encoded by the polynucleotide.

In another embodiment, the invention refers to a method of producing a transgenic plant comprising, (a) transforming a plant cell with an expression cassette comprising a polynucleotide operably linked to a promoter operable in plant cells, the promoter capable of expressing a wildtype or mutated CESA polypeptide encoded by the polynucleotide, and (b) generating a plant with an increased resistance to CESA-inhibiting herbicide from the plant cell.

Preferably, the expression cassette further comprises a transcription initiation regulatory region and a translation initiation regulatory region that are functional in the plant.

KEY TO SEQUENCE LISTING

TABLE 1

Figure 1A:
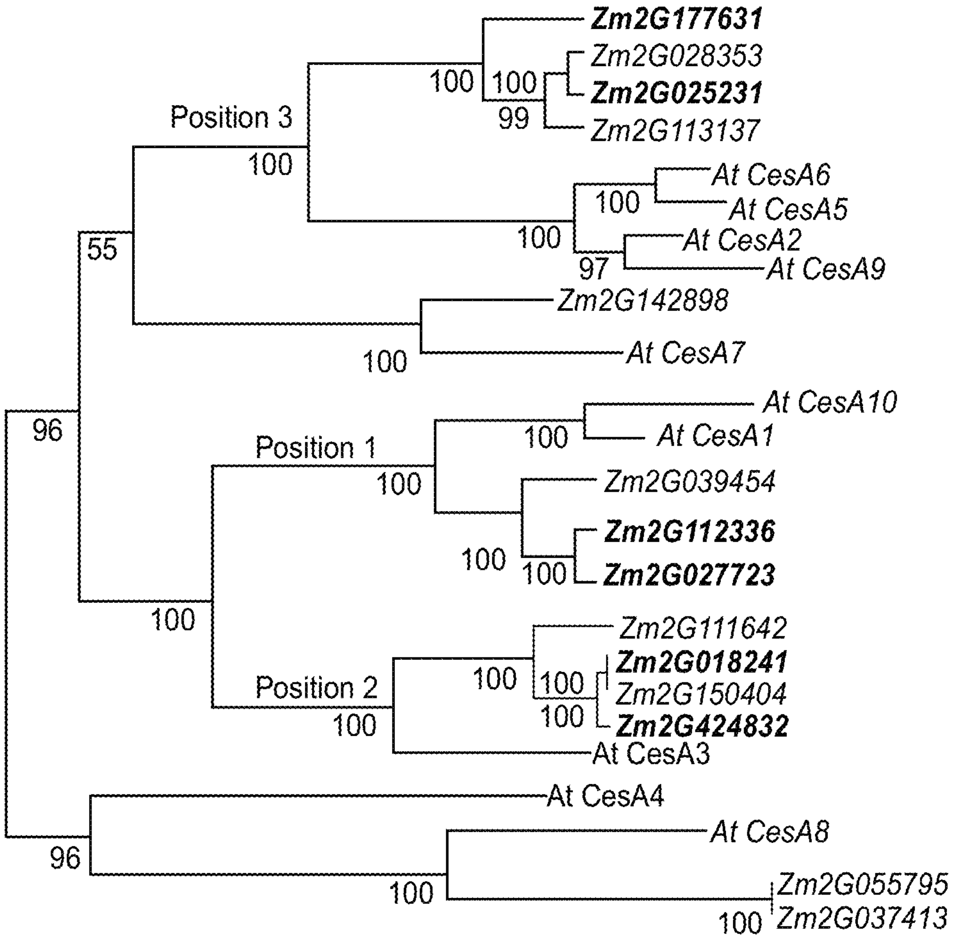
FIG. 1 shows phylogenetic trees of cellulose synthase homologues in corn (A), soy (B) and rice (C).

| SEQ ID NO Amino acid | Sequence/Origin |
|---|---|
| 1 | At_CESA1 |
| 2 | At_CESA2 |
| 3 | At_CESA3 |
| 4 | At_CESA4 |
| 5 | At_CESA5 |
| 6 | At_CESA6 |
| 7 | At_CESA7 |
| 8 | At_CESA8 |
| 9 | At_CESA9 |
| 10 | At_CESA10 |
| 11 | GRMZM2G027723\|GRMZM2G027723_T01 |
| 12 | GRMZM2G055795\|GRMZM2G055795_T01 |
| 13 | GRMZM2G039454\|GRMZM2G039454_T01 |
| 14 | GRMZM2G025231\|GRMZM2G025231_T02 |
| 15 | GRMZM2G142898\|GRMZM2G142898_T01 |
| 16 | GRMZM2G424832\|GRMZM2G424832_T01 |
| 17 | GRMZM2G177631\|GRMZM2G177631_T01 |
| 18 | GRMZM2G150404\|GRMZM2G150404_T01 |
| 19 | GRMZM2G028353\|GRMZM2G028353_T01 |
| 20 | GRMZM2G018241\|GRMZM2G018241_T01 |
| 21 | GRMZM2G037413\|GRMZM2G037413_T01 |

TABLE 1-continued

| SEQ ID NO Amino acid | Sequence/Origin |
|---|---|
| 22 | GRMZM2G082580\|GRMZM2G082580_T01 |
| 23 | GRMZM2G112336\|GRMZM2G112336_T01 |
| 24 | GRMZM2G111642\|GRMZM2G111642_T01 |
| 25 | GRMZM2G113137\|GRMZM2G113137_T01 |
| 26 | Glyma02g36720\|Glyma02g36720.1 |
| 27 | Glyma02g08920\|Glyma02g08920.1 |
| 28 | Glyma12g36570\|Glyma12g36570.1 |
| 29 | Glyma12g17730\|Glyma12g17730.1 |
| 30 | Glyma06g06870\|Glyma06g06870.1 |
| 31 | Glyma06g30860\|Glyma06g30860.1 |
| 32 | Glyma06g47420\|Glyma06g47420.1 |
| 33 | Glyma06g30850\|Glyma06g30850.1 |
| 34 | Glyma06g07320\|Glyma06g07320.1 |
| 35 | Glyma04g07220\|Glyma04g07220.1 |
| 36 | Glyma04g06780\|Glyma04g06780.1 |
| 37 | Glyma04g23530\|Glyma04g23530.2 |
| 38 | Glyma08g15380\|Glyma08g15380.1 |
| 39 | Glyma08g12400\|Glyma08g12400.1 |
| 40 | Glyma17g08000\|Glyma17g08000.1 |
| 41 | Glyma13g27250\|Glyma13g27250.3 |
| 42 | Glyma05g29240\|Glyma05g29240.2 |
| 43 | Glyma05g32100\|Glyma05g32100.1 |
| 44 | Glyma15g43040\|Glyma15g43040.1 |
| 45 | Glyma09g15620\|Glyma09g15620.2 |
| 46 | Glyma10g36790\|Glyma10g36790.1 |
| 47 | Glyma16g28080\|Glyma16g28080.2 |
| 48 | Os01g54620.1 |
| 49 | Os03g59340.1 |
| 50 | Os03g62090.1 |
| 51 | Os05g08370.1 |
| 52 | Os06g02180.1 |
| 53 | Os06g22980.1 |
| 54 | Os06g39970.1 |
| 55 | Os07g10770.1 |
| 56 | Os07g14850.1 |
| 57 | Os07g24190.1 |
| 58 | Os07g24190.2 |
| 59 | Os07g24190.3 |
| 60 | Os08g25710.1 |
| 61 | Os09g25490.1 |
| 62 | Os10g32980.1 |
| 63 | Os10g42750.1 |
| 64 | Os12g36890.1 |

DETAILED DESCRIPTION

The articles "a" and "an" are used herein to refer to one or more than one (i.e., to at least one) of the grammatical object of the article. By way of example, "an element" means one or more elements.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps.

The term "control of undesired vegetation or weeds" is to be understood as meaning the killing of weeds and/or otherwise retarding or inhibiting the normal growth of the weeds.

Weeds, in the broadest sense, are understood as meaning all those plants which grow in locations where they are undesired. The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus*, and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus*, and *Apera*. In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

The term "plant" is used in its broadest sense as it pertains to organic material and is intended to encompass eukaryotic organisms that are members of the Kingdom Plantae, examples of which include but are not limited to vascular plants, vegetables, grains, flowers, trees, herbs, bushes, grasses, vines, ferns, mosses, fungi and algae, etc, as well as clones, offsets, and parts of plants used for asexual propagation (e.g. cuttings, pipings, shoots, rhizomes, underground stems, clumps, crowns, bulbs, corms, tubers, rhizomes, plants/tissues produced in tissue culture, etc.). The term "plant" further encompasses whole plants, ancestors and progeny of the plants and plant parts, including seeds, shoots, stems, leaves, roots (including tubers), flowers, florets, fruits, pedicles, peduncles, stamen, anther, stigma, style, ovary, petal, sepal, carpel, root tip, root cap, root hair, leaf hair, seed hair, pollen grain, microspore, cotyledon, hypocotyl, epicotyl, xylem, phloem, parenchyma, endosperm, a companion cell, a guard cell, and any other known organs, tissues, and cells of a plant, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising Acer spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus*, Annona spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Eragrostis tef, Erianthus* sp., *Eriobotrya japonica, Eucalyptus* sp., *Eugenia uniflora, Fag-*

*opyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja* max), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g. *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris*, Ziziphus spp., amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others. According to a preferred embodiment of the present invention, the plant is a crop plant. Examples of crop plants include inter alia soybean, sunflower, canola, alfalfa, rapeseed, cotton, tomato, potato or tobacco. Further preferably, the plant is a monocotyledonous plant, such as sugarcane. Further preferably, the plant is a cereal, such as rice, maize, wheat, barley, millet, rye, sorghum or oats.

Generally, the term "herbicide" is used herein to mean an active ingredient that kills, controls or otherwise adversely modifies the growth of plants. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, the effective amount of a herbicide is an amount that is routinely used in agricultural production systems to kill weeds of interest. Such an amount is known to those of ordinary skill in the art. Herbicidal activity is exhibited by herbicides useful for the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the herbicide postemergence to relatively immature undesirable vegetation to achieve the maximum control of weeds.

By a "herbicide-tolerant" or "herbicide-resistant" plant, it is intended that a plant that is tolerant or resistant to at least one herbicide at a level that would normally kill, or inhibit the growth of, a normal or wild-type plant. Levels of herbicide that normally inhibit growth of a non-tolerant plant are known and readily determined by those skilled in the art. Examples include the amounts recommended by manufacturers for application. The maximum rate is an example of an amount of herbicide that would normally inhibit growth of a non-tolerant plant. For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope. Similarly, the terms "tolerant" and "resistant" are used interchangeably and are intended to have an equivalent meaning and an equivalent scope. As used herein, in regard to an herbicidal composition useful in various embodiments hereof, terms such as CESA-inhibiting herbicides, and the like, refer to those agronomically acceptable herbicide active ingredients (A.I.) recognized in the art. Similarly, terms such as fungicide, nematicide, pesticide, and the like, refer to other agronomically acceptable active ingredients recognized in the art.

When used in reference to a particular mutant enzyme or polypeptide, terms such as herbicide-tolerant and herbicide-tolerance refer to the ability of such enzyme or polypeptide to perform its physiological activity in the presence of an amount of an herbicide A.I. that would normally inactivate or inhibit the activity of the wild-type (non-mutant) version of said enzyme or polypeptide. For example, when used specifically in regard to a CESA enzyme, it refers specifically to the ability to tolerate a CESA-inhibitor. By "herbicide-tolerant wildtype or mutated CESA protein" or "herbicide-resistant wildtype or mutated CESA protein", it is intended that such a CESA protein displays higher CESA activity, relative to the CESA activity of a wild-type CESA protein, when in the presence of at least one herbicide that is known to interfere with CESA activity and at a concentration or level of the herbicide that is known to inhibit the CESA activity of the wild-type CESA protein. Furthermore, the CESA activity of such a herbicide-tolerant or herbicide-resistant wildtype or mutated CESA protein may be referred to herein as "herbicide-tolerant" or "herbicide-resistant" CESA activity.

As used herein, "recombinant," when referring to nucleic acid or polypeptide, indicates that such material has been altered as a result of human application of a recombinant technique, such as by polynucleotide restriction and ligation, by polynucleotide overlap-extension, or by genomic insertion or transformation. A gene sequence open reading frame is recombinant if that nucleotide sequence has been removed from it natural text and cloned into any type of artificial nucleic acid vector. The term recombinant also can refer to an organism having a recombinant material, e.g., a plant that comprises a recombinant nucleic acid can be considered a recombinant plant.

The term "transgenic plant" refers to a plant that comprises a heterologous polynucleotide. Preferably, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been so altered by the presence of heterologous nucleic acid including those transgenic organisms or cells initially so altered, as well as those created by crosses or asexual propagation from the initial transgenic organism or cell. In some embodiments, a "recombinant" organism is a "transgenic" organism. The term "transgenic" as used herein is not intended to encompass the alteration of the genome (chromosomal or extra-chromosomal) by conventional plant breeding methods (e.g., crosses) or by naturally occurring events such as, e.g., self-fertilization, random cross-fertilization, non-recombinant viral infection, non-recombinant bacterial transformation, non-recombinant transposition, or spontaneous mutation.

As used herein, "mutagenized" refers to an organism or DNA thereof having alteration(s) in the biomolecular sequence of its native genetic material as compared to the sequence of the genetic material of a corresponding wild-type organism or DNA, wherein the alteration(s) in genetic material were induced and/or selected by human action. Examples of human action that can be used to produce a mutagenized organism or DNA include, but are not limited to, as illustrated in regard to herbicide tolerance: tissue culture of plant cells (e.g., calli) and selection thereof with herbicides (e.g., CESA-inhibiting herbicides), treatment of plant cells with a chemical mutagen such as EMS and subsequent selection with herbicide(s); or by treatment of plant cells with x-rays and subsequent selection with herbicide(s). Any method known in the art can be used to induce mutations. Methods of inducing mutations can induce mutations in random positions in the genetic material or can induce mutations in specific locations in the genetic material (i.e., can be directed mutagenesis techniques), such as by use of a genoplasty technique.

As used herein, a "genetically modified organism" (GMO) is an organism whose genetic characteristics contain alteration(s) that were produced by human effort causing transfection that results in transformation of a target organism with genetic material from another or "source" organism, or with synthetic or modified-native genetic material, or an organism that is a descendant thereof that retains the inserted genetic material. The source organism can be of a different type of organism (e.g., a GMO plant can contain bacterial genetic material) or from the same type of organism (e.g., a GMO plant can contain genetic material from another plant). As used herein in regard to plants and other organisms, "recombinant," "transgenic," and "GMO" are considered synonyms and indicate the presence of genetic material from a different source; in contrast, "mutagenized" is used to refer to a plant or other organism, or the DNA thereof, in which no such transgenic material is present, but in which the native genetic material has become mutated so as to differ from a corresponding wild-type organism or DNA.

As used herein, "wild-type" or "corresponding wild-type plant" means the typical form of an organism or its genetic material, as it normally occurs, as distinguished from, e.g., mutagenized and/or recombinant forms. Similarly, by "control cell" or "similar, wild-type, plant, plant tissue, plant cell or host cell" is intended a plant, plant tissue, plant cell, or host cell, respectively, that lacks the herbicide-resistance characteristics and/or particular polynucleotide of the invention that are disclosed herein. The use of the term "wild-type" is not, therefore, intended to imply that a plant, plant tissue, plant cell, or other host cell lacks recombinant DNA in its genome, and/or does not possess herbicide-resistant characteristics that are different from those disclosed herein.

As used herein, "descendant" refers to any generation plant. In some embodiments, a descendant is a first, second, third, fourth, fifth, sixth, seventh, eight, ninth, or tenth generation plant.

As used herein, "progeny" refers to a first generation plant.

The term "seed" comprises seeds of all types, such as, for example, true seeds, caryopses, achenes, fruits, tubers, seedlings and similar forms. In the context of *Brassica* and *Sinapis* species, "seed" refers to true seed(s) unless otherwise specified. For example, the seed can be seed of transgenic plants or plants obtained by traditional breeding methods. Examples of traditional breeding methods can include cross-breeding, selfing, back-crossing, embryo rescue, in-crossing, out-crossing, inbreeding, selection, asexual propagation, and other traditional techniques as are known in the art.

Although exemplified with reference to specific plants or plant varieties and their hybrids, in various embodiments, the presently described methods using CESA-inhibiting herbicides can be employed with a variety of commercially valuable plants. CESA-inhibiting herbicides-tolerant plant lines described as useful herein can be employed in weed control methods either directly or indirectly, i. e. either as crops for herbicide treatment or as CESA-inhibiting herbicides-tolerance trait donor lines for development, as by traditional plant breeding, to produce other varietal and/or hybrid crops containing such trait or traits. All such resulting variety or hybrids crops, containing the ancestral CESA-inhibiting herbicides-tolerance trait or traits can be referred to herein as progeny or descendant of the ancestral, CESA-inhibiting herbicides-tolerant line(s). Such resulting plants can be said to retain the "herbicide tolerance characteristic(s)" of the ancestral plant, i.e. meaning that they possess and express the ancestral genetic molecular components responsible for the trait.

In one aspect, the present invention provides a plant or plant part comprising a polynucleotide encoding a wildtype or mutated CESA polypeptide, the expression of said polynucleotide confers to the plant or plant part tolerance to CESA-inhibiting herbicides.

In a preferred embodiment, the plant has been previously produced by a process comprising recombinantly preparing a plant by introducing and over-expressing a wildtype or mutated CESA transgene according to the present invention, as described in greater detail hereinafter.

In another preferred embodiment, the plant has been previously produced by a process comprising in situ mutagenizing plant cells or seeds, to obtain plant cells or plants which express a wildtype or mutated CESA.

In another embodiment, the polynucleotide encoding the wildtype or mutated CESA polypeptide comprises the nucleic acid sequence set forth in SEQ ID NO: 65, 66, 67, 68, 69, 70, 71, 72, 73, 74, 75, 76, or 77, or a variant or derivative thereof.

In other embodiments, the wildtype or mutated CESA polypeptide for use according to the present invention is a functional variant having, over the full-length of the variant, at least about 80%, illustratively, at least about 80%, 90%, 95%, 98%, 99% or more amino acid sequence identity to SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64.

In another embodiment, the wildtype or mutated CESA polypeptide for use according to the present invention is a functional fragment of a polypeptide having the amino acid sequence set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64.

It is recognized that the CESA polynucleotide molecules and CESA polypeptides of the invention encompass polynucleotide molecules and polypeptides comprising a nucleotide or an amino acid sequence that is sufficiently identical to nucleotide sequences set forth in SEQ ID Nos: 65, 66, 67, 68, 69, 70, 71, 72, 73, 74, 75, 76, or 77, or to the amino acid sequences set forth in SEQ ID Nos: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity.

Generally, "sequence identity" refers to the extent to which two optimally aligned DNA or amino acid sequences are invariant throughout a window of alignment of components, e.g., nucleotides or amino acids. An "identity fraction" for aligned segments of a test sequence and a reference sequence is the number of identical components that are shared by the two aligned sequences divided by the total number of components in reference sequence segment, i.e., the entire reference sequence or a smaller defined part of the reference sequence. "Percent identity" is the identity fraction times 100. Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG. Wisconsin Package. (Accelrys Inc. Burlington, Mass.)

Polynucleotides and Oligonucleotides

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated. As the skilled addressee would be aware, an isolated polynucleotide can be an exogenous polynucleotide present in, for example, a transgenic organism which does not naturally comprise the polynucleotide. Furthermore, the terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

The term "mutated CESA nucleic acid" refers to a CESA nucleic acid having a sequence that is mutated from a wild-type CESA nucleic acid and that confers increased CESA-inhibiting herbicide tolerance to a plant in which it is expressed. Furthermore, the term "mutated cellulose synthase (mutated CESA)" refers to the replacement of an amino acid of the wild-type primary sequences of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64, or a variant, a derivative, a homologue, an orthologue, or paralogue thereof, with another amino acid. The expression "mutated amino acid" will be used below to designate the amino acid which is replaced by another amino acid, thereby designating the site of the mutation in the primary sequence of the protein.

In a preferred embodiment, the CESA nucleotide sequence encoding a mutated CESA comprises the sequence of SEQ ID NO: 65, 66, 67, 68, 69, 70, 71, 72, 73, 74, 75, 76, or 77, or a variant or derivative thereof Furthermore, it will be understood by the person skilled in the art that the CESA nucleotide sequences encompasse homologues, paralogues and orthologues of SEQ ID NO: 65, 66, 67, 68, 69, 70, 71, 72, 73, 74, 75, 76, or 77, as defined hereinafter.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein comprising the sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64, as well as those that encode a polypeptide having amino acid substitutions relative to the native protein, e.g. the mutated CESA according to the present invention as disclosed herein. Generally, nucleotide sequence variants of the invention will have at least 30, 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide "sequence identity" to the nucleotide sequence of SEQ ID NO: 65, 66, 67, 68, 69, 70, 71, 72, 73, 74, 75, 76, or 77. The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

Polypeptides

By "substantially purified polypeptide" or "purified" a polypeptide is meant that has been separated from one or more lipids, nucleic acids, other polypeptides, or other contaminating molecules with which it is associated in its native state. It is preferred that the substantially purified polypeptide is at least 60% free, more preferably at least 75% free, and more preferably at least 90% free from other components with which it is naturally associated. As the skilled addressee will appreciate, the purified polypeptide can be a recombinantly produced polypeptide. The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, modifications, analogous and/or derivatives of the polypeptides of the invention as described herein.

The % identity of a polypeptide is determined by GAP (Needleman and Wunsch, 1970) analysis (GCG program) with a gap creation penalty=5, and a gap extension penalty=0.3. The query sequence is at least 25 amino acids in length, and the GAP analysis aligns the two sequences over a region of at least 25 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

With regard to a defined polypeptide, it will be appreciated that % identity figures higher than those provided above will encompass preferred embodiments. Thus, where applicable, in light of the minimum % identity figures, it is preferred that the CESA polypeptide of the invention comprises an amino acid sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64.

By "variant" polypeptide is intended a polypeptide derived from the protein of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64, by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

"Derivatives" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. Thus, functional variants and fragments of the CESA polypeptides, and nucleic acid molecules encoding them, also are within the scope of the present invention, and unless specifically described otherwise, irrespective of the origin of said polypeptide and irrespective of whether it occurs naturally. Various assays for functionality of a CESA polypeptide can be employed. For example, a functional variant or fragment of the CESA polypeptide can be assayed to determine its ability to confer CESA-inhibiting herbicides tolerance. By way of illustration, a CESA-inhibiting herbicides tolerance can be defined as insensitivity to CESA inhibiting herbicides sufficient to provide a determinable increase in tolerance to CESA-inhibiting herbicides in a plant or plant part comprising a recombinant polynucleotide encoding the variant or fragment of the CESA polypeptide, wherein the plant or plant part expresses the variant or fragment at up to about 0.5%, illustratively, about 0.05 to about 0.5%, about 0.1 to about 0.4%, and about 0.2 to about 0.3%, of the total cellular protein relative to a similarly treated control plant that does not express the variant or fragment.

In a preferred embodiment, the mutated CESA polypeptide is a functional variant or fragment of a cellulose synthase having the amino acid sequence set forth in SEQ ID NO: 1 or 3, wherein the functional variant or fragment has at least about 80% amino acid sequence identity to SEQ ID NO:1 or 3.

In other embodiments, the functional variant or fragment further has a CESA-inhibiting herbicides tolerance defined as insensitivity to CESA inhibiting herbicides sufficient to provide a determinable increase in tolerance to CESA-inhibiting herbicides in a plant or plant part comprising a recombinant polynucleotide encoding the variant or fragment, wherein the plant or plant part expresses the variant or fragment at up to about 0.5% of the total cellular protein to a similarly treated control plant that does not express the variant or fragment.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

In addition, one of ordinary skill in the art will further appreciate that changes can be introduced by mutation into the nucleotide sequences of the invention thereby leading to changes in the amino acid sequence of the encoded proteins without altering the biological activity of the proteins. Thus, for example, an isolated polynucleotide molecule encoding a mutated CESA polypeptide having an amino acid sequence that differs from that of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64, can be created by introducing one or more nucleotide substitutions, additions, or deletions into the corresponding nucleotide sequence, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention. For example, preferably, conservative amino acid substitutions may be made at one or more predicted preferably nonessential amino acid residues. A "nonessential" amino acid residue is a residue that can be altered from the wild-type sequence of a protein without altering the biological activity, whereas an "essential" amino acid residue is required for biological activity.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide and may range from 1 to 10 amino acids; insertions will usually be of the order of about 1 to 10 amino acid residues. A conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif. Conservative substitution tables are well known in the art (see for example Creighton (1984) Proteins. W.H. Freeman and Company (Eds).

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, OH), QuickChange Site Directed mutagenesis (Stratagene, San Diego, CA), PCR-mediated site-directed mutagenesis or other site-directed mutagenesis protocols.

"Derivatives" further include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

"Orthologues" and "paralogues" encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene. A non-limiting list of examples of such orthologues is shown in Table 1. It will be understood by the person skilled in the art that the sequences of SEQ ID NOs: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64, as listed in Table 1 represent orthologues and paralogues to SEQ ID NO:1.

It is well-known in the art that paralogues and orthologues may share distinct domains harboring suitable amino acid residues at given sites, such as binding pockets for particular substrates or binding motifs for interaction with other proteins.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

The term "motif" or "consensus sequence" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

In a preferred embodiment, the CESA polypeptide useful for the present invention, comprises one or more of the following motifs:

i) Motif 1a:

(SEQ ID NO: 78)
[V/I][A/V]G[V/I/F][S/T][Y/D/N/A]A[V/I/L][N/S/G]

[S/N]G[Y/F/E][Q/D/G/E/H][S/A]WG[P/A]L[F/M/L]G[K/R]

[L/V][F/L]F.

Preferably said motif is (motif 1b; SEQ ID NO: 79)
[V/I]AG[V/I]S[Y/D/N]A[V/I][N/S][S/N]G[Y/F][Q/D]

SWGPL[F/M/L]G[K/R]L[F/L]F.

More preferably said motif is (motif 1c; SEQ ID NO: 80)
VAG[V/I]SYA[V/I]NSGYQSWGPL[F/M]GKL[F/L]F ii) Motif 2a:

(SEQ ID NO: 81)
[V/L/I]W[S/A][V/A/I]LL[A/S]S[I/F/V][F/L][S/T][L/V]

[L/M/V/I]WV[R/K][I/V][N/D]PF

Preferably, said motif is (motif 2b; SEQ ID NO: 82)
VW[S/A][V/A/I]LL[A/S]S[I/F][F/L][S/T][LN]

Figure 2A:
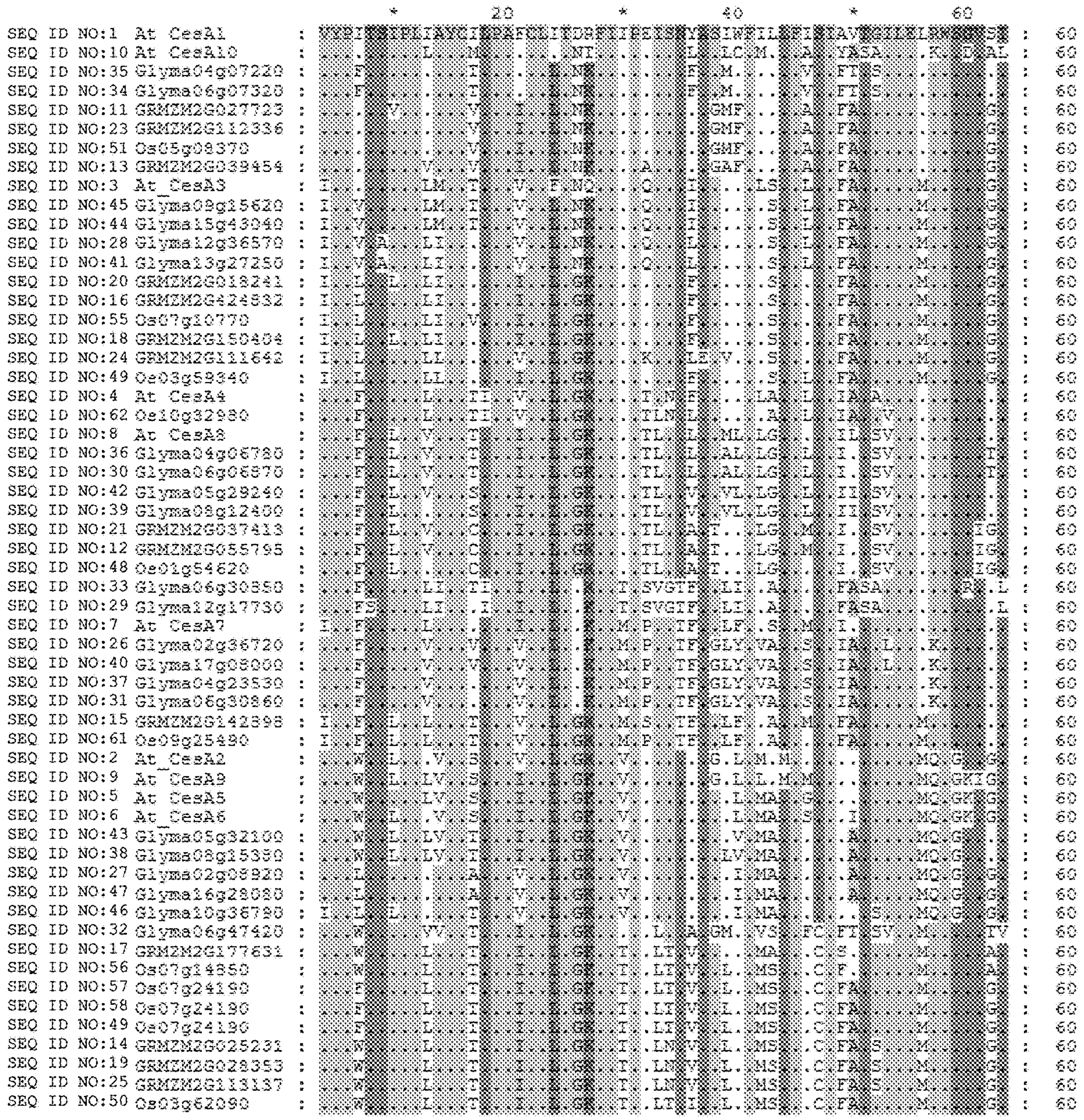
FIG. 2 shows alignment of all cellulose synthase homologues (A), *Arabidopsis* CESA1, CESA3 and CESA 6 homologues (B) and *Arabidopsis* CESA1 and CESA3 homologues (C).
Figure 2A:
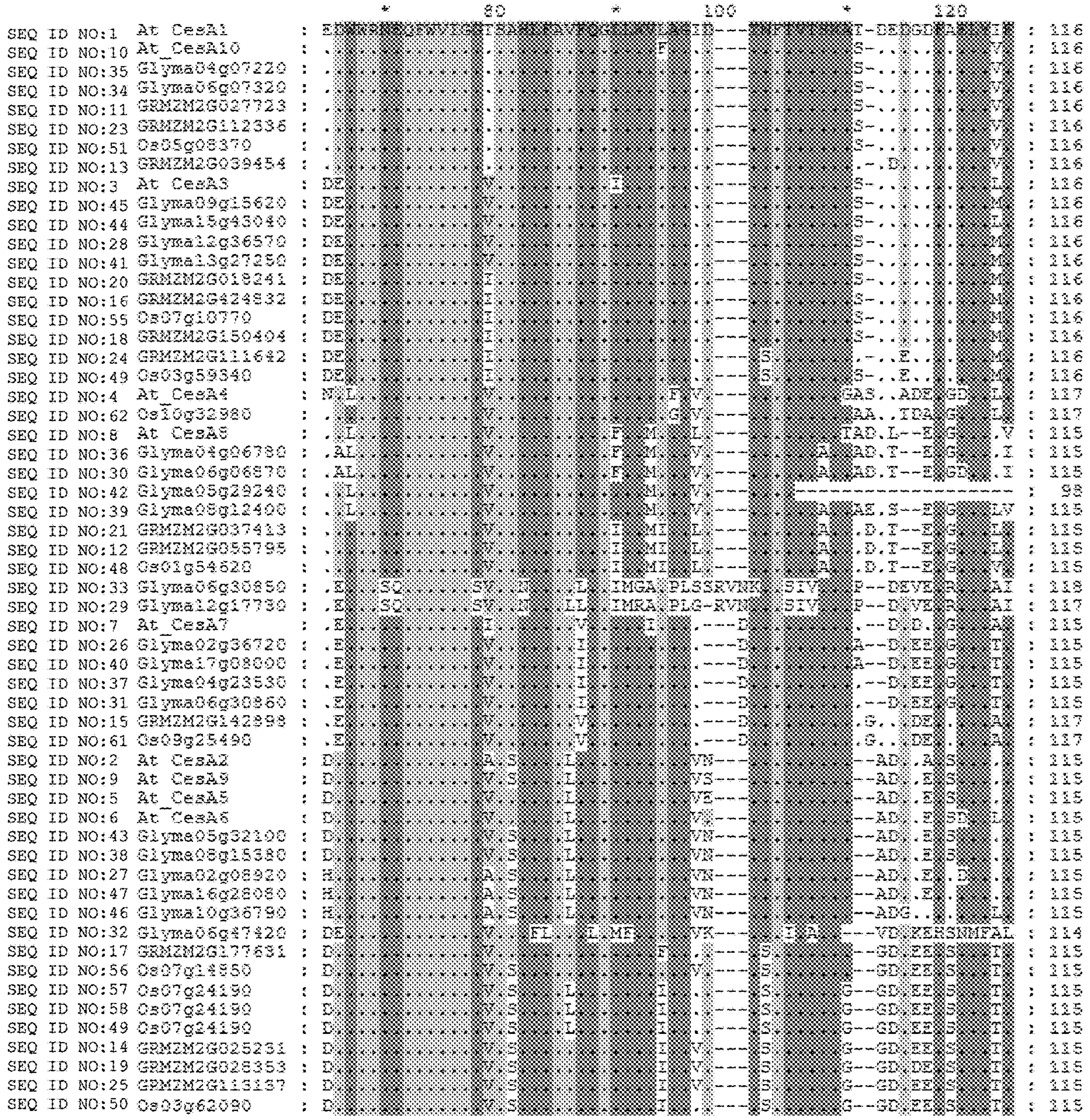
Figure 2A:
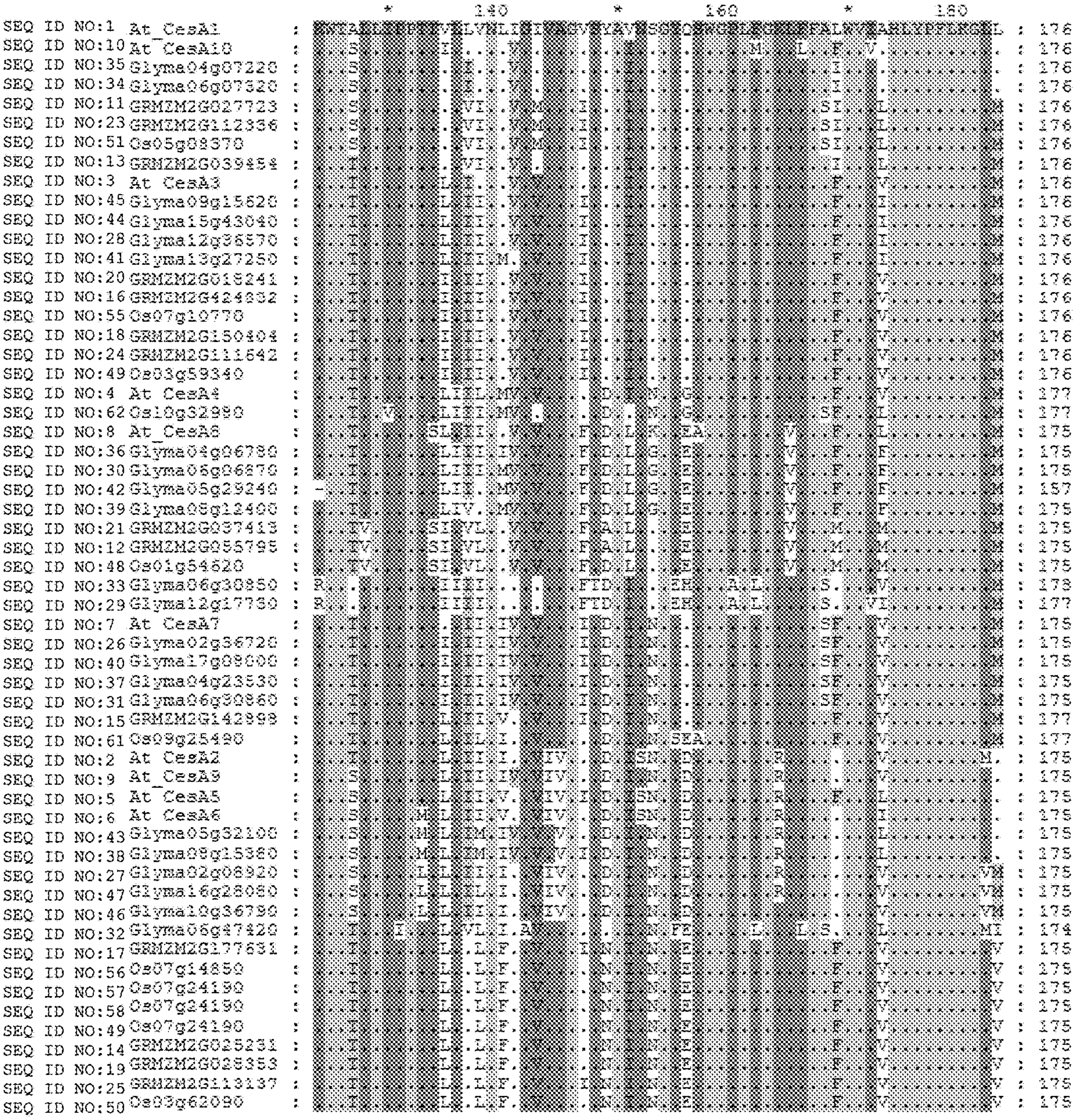
Figure 2B:
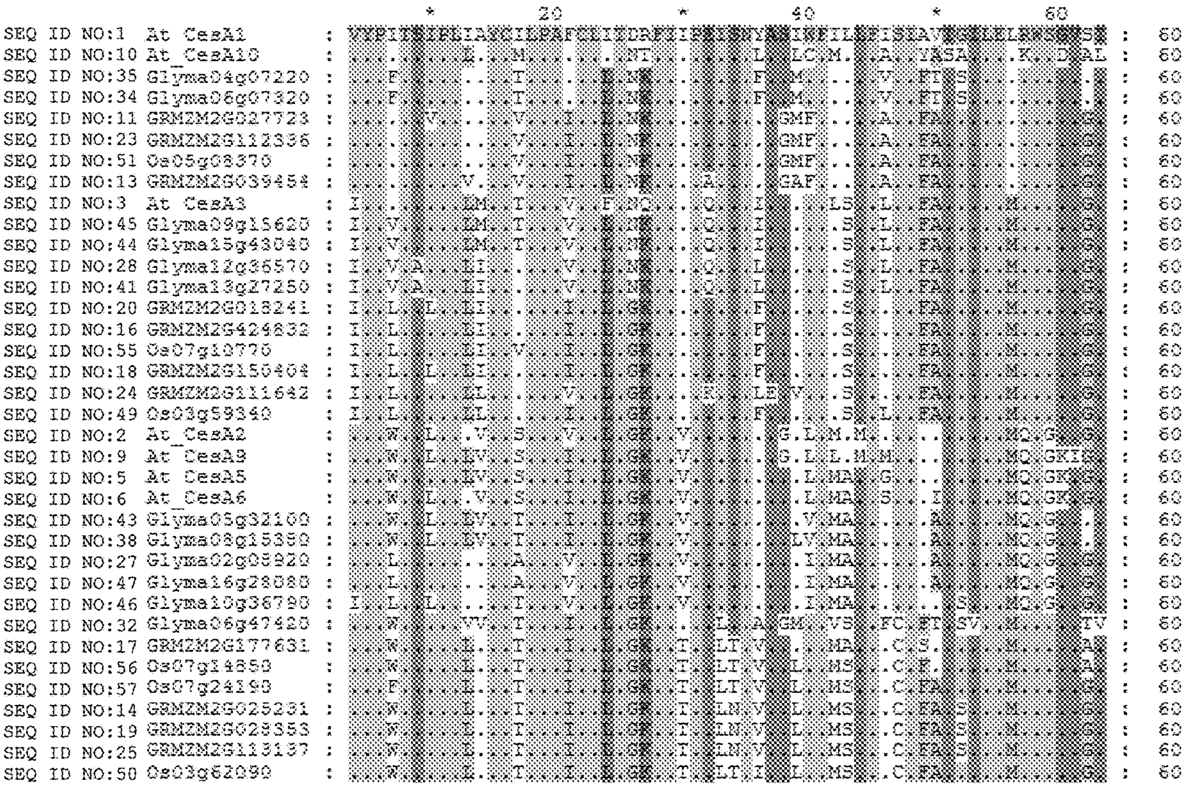
Figure 2B:
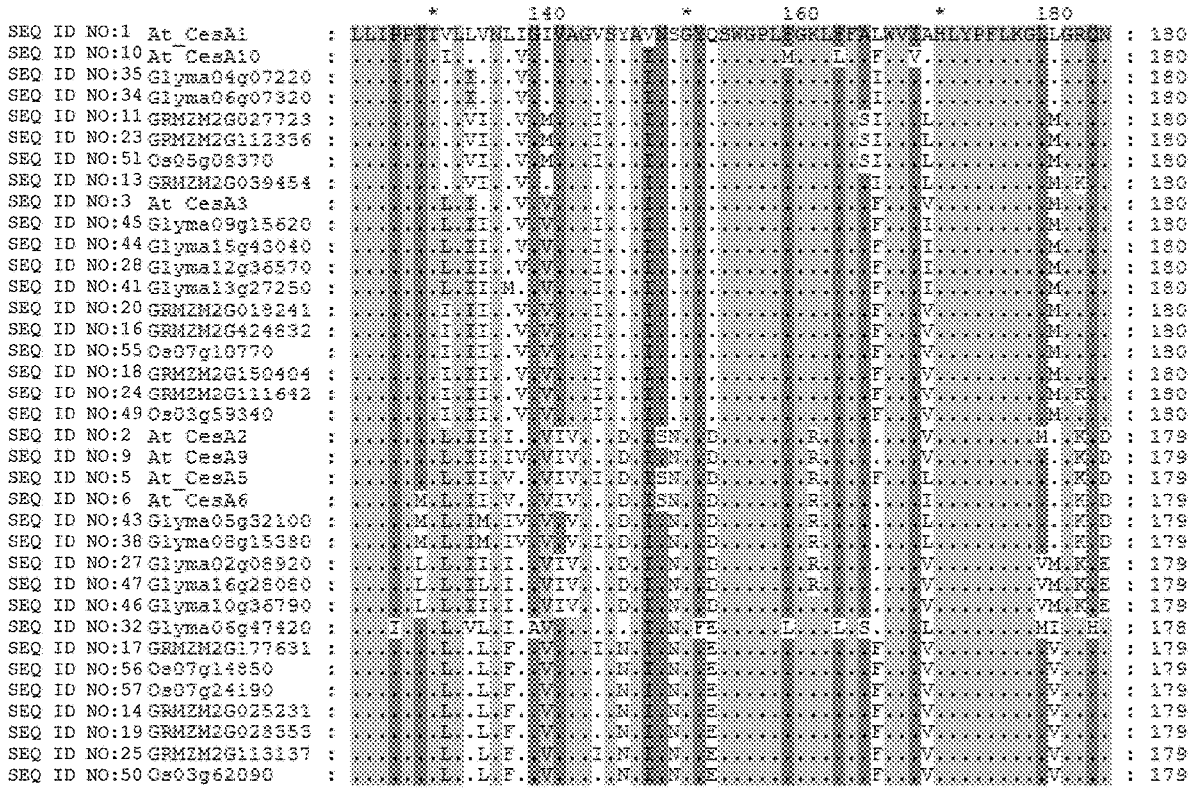
Figure 2C:
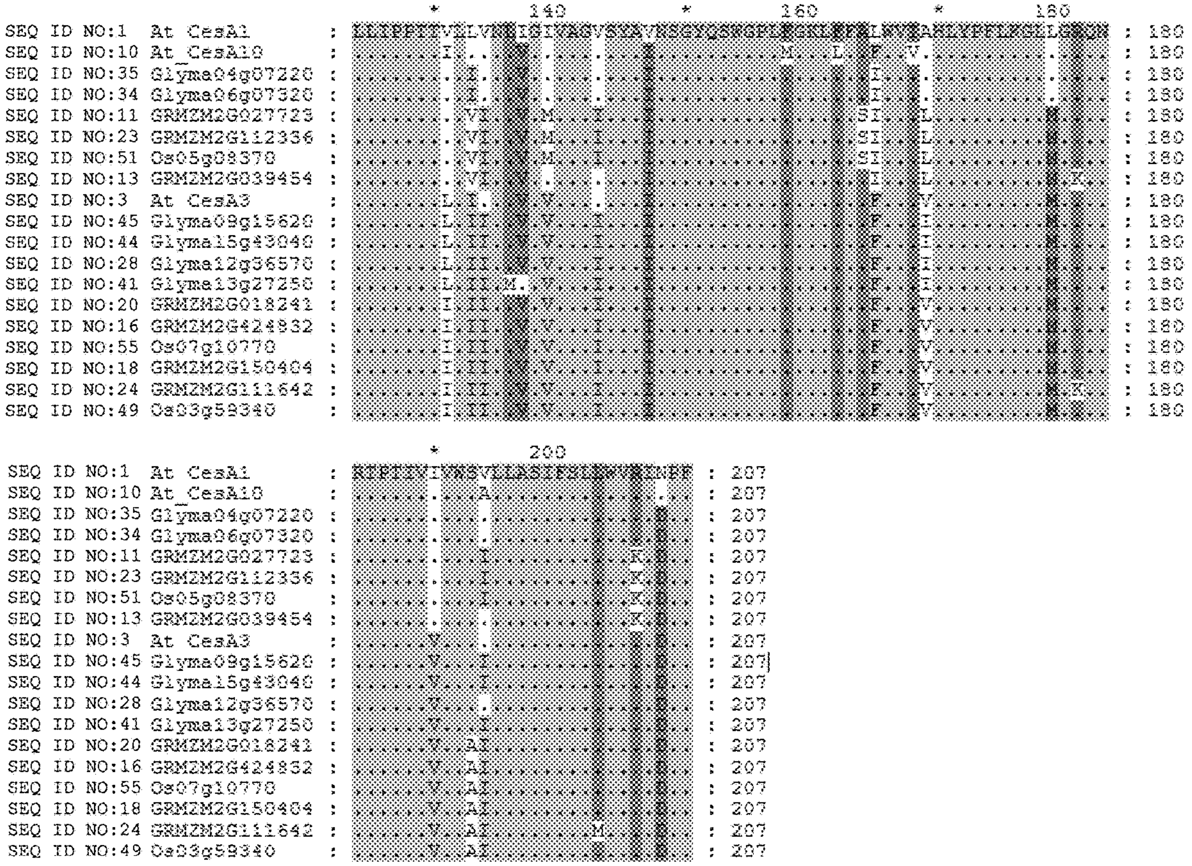

[L/M]WV[R/K][I/V][N/D]PF;

More preferably said motif is (motif 2c; SEQ ID NO: 83)
VW[S/A][V/A/I]LLASIFSL[L/M]WV[R/K]I[N/D]PF Motifs 1a-c, 2a-c, given above were derived using the ClustalW algorithm to generate the alignments of cellulose synthase sequences (FIG. 2A-C) (Larkin et al., Bioinformatics 23:21 (2007) 2947-2948 pp. 28-36). The motifs were essentially derived based on sequence alignment; highly conserved regions were identified that contain the site of mutations conferring azine-herbicide tolerance. Residues within square brackets represent alternatives.

In a preferred embodiment, a CESA polypeptide as applied herein comprises, at least 1, at least 2, selected from the group comprising motifs 1a, 2a, as given above. Alternatively or in addition, in another preferred embodiment, a CESA polypeptide as applied herein comprises at least 1, at least 2, motifs selected from the group comprising motifs 1b, 2b, as given above. Alternatively or in addition, in another preferred embodiment, a CESA polypeptide as applied herein comprises at least 1, at least 2, motifs selected from the group comprising motifs 1c, 2c, as given above.

Additionally or alternatively, the homologue of a CESA protein has in increasing order of preference at least 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% overall sequence identity to the amino acid represented by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64, provided that the homologous protein comprises any one or more of the conserved motifs 1 and/or 2 as outlined above. The overall sequence identity is determined using a global alignment algorithm, such as the Needleman Wunsch algorithm in the program GAP (GCG Wisconsin Package, Accelrys), preferably with default parameters and preferably with sequences of mature proteins (i.e. without taking into account secretion signals or transit peptides). Compared to overall sequence identity, the sequence identity will generally be higher when only conserved domains or motifs are considered. Preferably the motifs in a CESA polypeptide have, in increasing order of preference, at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to any one or more of the motifs represented by SEQ ID NO: 78, 79, 80, 81, 82, and 83 (Motifs 1a, 1b, 1c, 2a, 2b, 2c).

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Figure 1B:
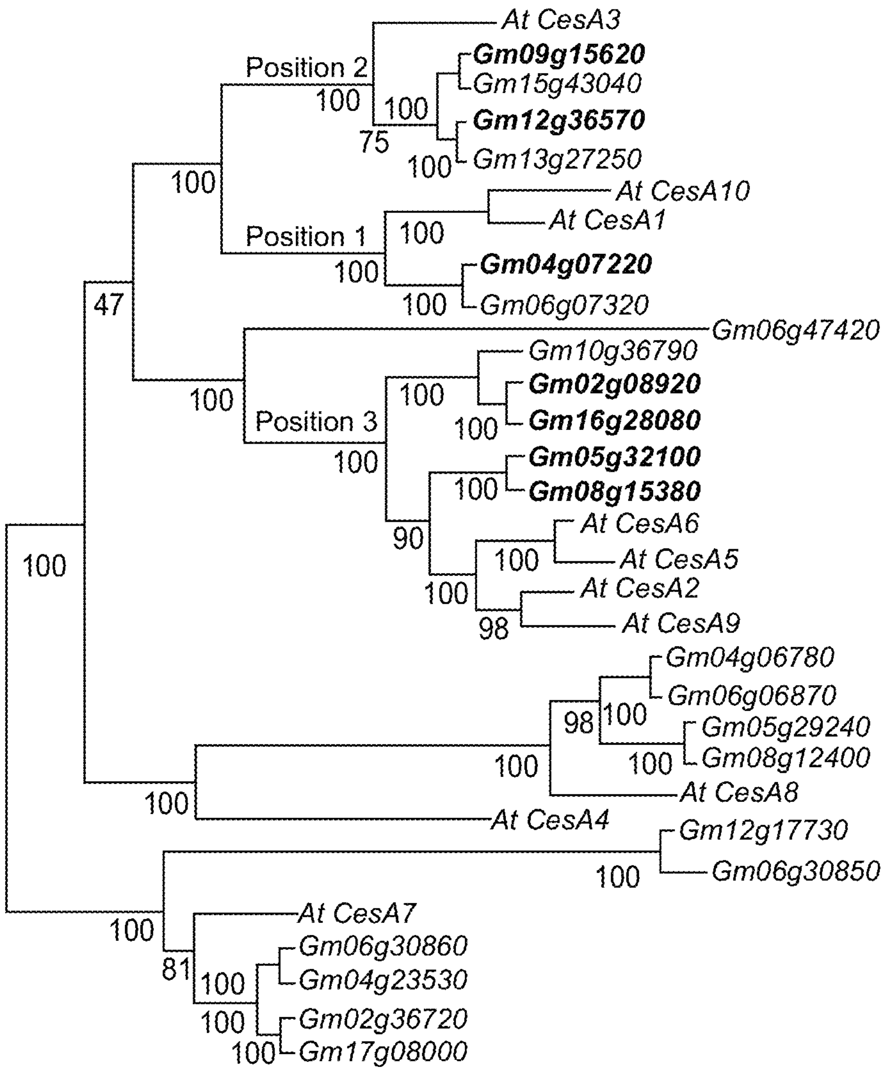
Figure 1C:
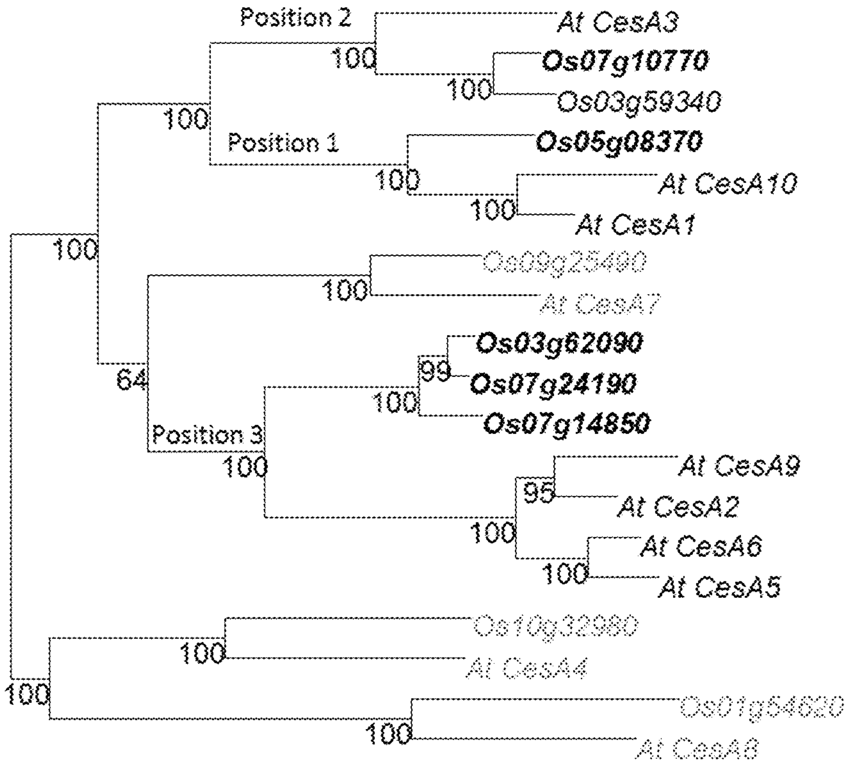

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage (See FIG. 1). Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

The proteins of the invention may be altered in various ways including amino acid substitutions, deletions, truncations, and insertions. Methods for such manipulations are generally known in the art. For example, amino acid sequence variants can be prepared by mutations in the DNA. Methods for mutagenesis and nucleotide sequence alterations are well known in the art. See, for example, Kunkel (1985) PNAS, 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D. C), herein incorporated by reference. Conservative substitutions, such as exchanging one amino acid with another having similar properties, may be preferable.

Alternatively, variant nucleotide sequences can be made by introducing mutations randomly along all or part of a coding sequence, such as by saturation mutagenesis, and the resultant mutants can be screened to identify mutants that encode proteins that retain activity. For example, following mutagenesis, the encoded protein can be expressed recombinantly, and the activity of the protein can be determined using standard assay techniques.

The inventors of the present invention have found that by substituting one or more of the key amino acid residues of the CESA enzyme of SEQ ID NO: 1 or 3, e.g. by employing one of the above described methods to mutate the CESA encoding nucleic acids, the tolerance or resistance to particular CESA-inhibiting herbicides, collectively named azines, and described in greated detail herein below, could be remarkably increased Preferred substitutions of mutated CESA are those that increase the herbicide tolerance of the plant, but leave the biological activity of the cellulose synthase activity substantially unaffected.

Accordingly, in another object of the present invention refers to a CESA polypeptide, comprising the sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64, a variant, derivative, orthologue, paralogue or homologue thereof, the key amino acid residues of which is substituted by any other amino acid.

It will be understood by the person skilled in the art that amino acids located in a close proximity to the positions of amino acids mentioned below may also be substituted. Thus, in another embodiment the variant of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64, a variant, derivative, orthologue, paralogue or homologue thereof comprises a mutated CESA, wherein an amino acid ±3, ±2 or ±1 amino acid positions from a key amino acid is substituted by any other amino acid.

Based on techniques well-known in the art, a highly characteristic sequence pattern can be developed, by means of which further of mutated CESA candidates with the desired activity may be searched.

Searching for further mutated CESA candidates by applying a suitable sequence pattern would also be encompassed by the present invention. It will be understood by a skilled reader that the present sequence pattern is not limited by the exact distances between two adjacent amino acid residues of said pattern. Each of the distances between two neighbours in the above patterns may, for example, vary independently of each other by up to ±10, ±5, ±3, ±2 or ±1 amino acid positions without substantially affecting the desired activity.

Furthermore, by applying the method of site directed mutagenesis, in particular saturation mutagenes (see e.g. Schenk et al., Biospektrum 03/2006, pages 277-279) PCR based site-directed mutagenesis (e.g. directed mutagenesis kit, Stratagene, California, USA or GeneArt Mutagenesis Service, ThermoFisher Scientific Inc., Massachusetts, USA) or systematic mutagenesis (GeneArt Systematic Mutagenesis Service, ThermoFisher Scientific Inc., Massachusetts, USA), the inventors of the present invention have identified and generated specific amino acid subsitutions and combinations thereof, which—when introduced into a plant by transforming and expressing the respective mutated CESA encoding nucleic acid—confer increased herbicide resistance or tolerance to a CESA inhibiting herbicide to said plant.

Thus, in preferred embodiment, the variant or derivative of the CESA polypeptide refers to a mutated CESA polypeptide which comprises one or more of the following motifs:

i) Motif 1a:

```
                                        (SEQ ID NO: 78)
[V/I] [A/V]G [V/I/F] [S/T] [Y/D/N/A]A

[V/I/L] [N/S/G] [S/N]G [Y/F/E] [Q/D/G/E/H]

[S/A]WG [P/A]L [F/M/L]G [K/R] [L/V] [F/L]F.
```

Preferably said motif is

```
                              (motif 1b; SEQ ID NO: 79)
[V/I]AG [V/I]S [Y/D/N]A [V/I] [N/S] [S/N]G

[Y/F] [Q/D]SWGPL [F/M/L]G [K/R]L[F/L]F.
```

More preferably said motif is (motif 1c; SEQ ID NO: 80)
VAG [V/I]SYA [V/I]NSGYQSWGPL [F/M]GKL [F/L]F;

Wherein the amino acid at position 5, 16, 17, and/or 20 within said motif is substituted by any other amino acid.

ii) Motif 2a:

(SEQ ID NO: 81)
[V/L/I]W [S/A] [V/A/I]LL [A/S]S [I/F/V] [F/L]
[S/T] [L/V] [L/M/V/I]WV [R/K] [I/V][N/D]PF

Preferably, said motif is (motif 2b; SEQ ID NO: 82)
VW [S/A] [V/A/I]LL [A/S]S [I/F] [F/L][S/T][L/V]
[L/M]WV [R/K] [I/V] [N/D]PF;

More preferably said motif is (motif 2c; SEQ ID NO: 83)
VW [S/A] [V/A/I]LLASIFSL [L/M]WV [R/K]I [N/D]PF Wherein the amino acid at position 8, and/or 11 within said motif is substituted by any other amino acid In a more preferred embodiment, the amino acid corresponding to position 5 of motif 1a, 1b, or 1c is:

Arg, His, Lys, Asp, Glu, Thr, Asn, Gln, Cys, Gly,
Pro, Ala, Val, Leu, Ile, Met, Phe, Tyr, or Trp;

And/or the amino acid corresponding to position 16 of motif 1a, 1b, or 1c is

Arg, His, Lys, Asp, Glu, Ser, Thr, Asn, Gln, Cys,
Pro, Ala, Val, Leu, Ile, Met, Phe, Tyr, or Trp,

And/or the amino acid corresponding to position 17 of motif 1a, 1b, or 1c is

Arg, His, Lys, Asp, Glu, Ser, Thr, Asn, Gln, Cys,
Gly, Ala, Val, Leu, Ile, Met, Phe, Tyr, or Trp,

And/or the amino acid corresponding to position 20 of motif 1a, 1b, or 1c is

Arg, His, Lys, Asp, Glu, Ser, Thr, Asn, Gln, Cys,
Pro, Ala, Val, Leu, Ile, Met, Phe, Tyr, or Trp,

In another more preferred embodiment, the amino acid corresponding to position 8 of motif 2a, 2b, or 2c is:

Arg, His, Lys, Asp, Glu, Thr, Asn, Gln, Cys, Gly,
Pro, Ala, Val, Leu, Ile, Met, Phe, Tyr, or Trp;

And/or the amino acid corresponding to position 11 of motif 2a, 2b, or 2c is

Arg, His, Lys, Asp, Glu, Thr, Asn, Gln, Cys, Gly,
Pro, Ala, Val, Leu, Ile, Met, Phe, Tyr, or Trp,

In a particularly preferred embodiment, the amino acid corresponding to position 5 of motif 1a, 1b, or 1c is Phe, And/or the amino acid corresponding to position 16 of motif 1a, 1b, or 1c is Asp, And/or the amino acid corresponding to position 17 of motif 1a, 1b, or 1c is Leu, And/or the amino acid corresponding to position 20 of motif 1a, 1b, or 1c is Arg.

In another more preferred embodiment, the amino acid corresponding to position 8 of motif 2a, 2b, or 2c is Phe, And/or the amino acid corresponding to position 11 of motif 2a, 2b, or 2c is Leu, In another preferred embodiment, the variant or derivative of the CESA polypeptide refers to a CESA polypeptide comprising SEQ ID NO: 1, a orthologue, paralogue, or homologue thereof, wherein the amino acid sequence differs from the wildtype amino acid sequence of a CESA polypeptide at one or more positions corresponding to the following positions of SEQ ID NO:1:

998, 1009, 1010, 1013, 1052, 1055.

Examples of differences at these amino acid positions include, but are not limited to, one or more of the following:

the amino acid at or corresponding to position 998 is other than serine;

the amino acid at or corresponding to position 1009 is other than glycine;

the amino acid at or corresponding to position 1010 is other than proline;

the amino acid at or corresponding to position 1013 is other than glycine, the amino acid at or corresponding to position 1052 is other than serine, the amino acid at or corresponding to position 1055 is other than serine, In some embodiments, the mutated CESA enzyme comprising SEQ ID NO: 1, a orthologue, paralogue, or homologue thereof, comprises one or more of the following:

the amino acid corresponding to position 998 of SEQ ID NO:1 is

Arg, His, Lys, Asp, Glu, Thr, Asn, Gln, Cys, Gly,
Pro, Ala, Val, Leu, Ile, Met, Phe, Tyr, or Trp;

the amino acid corresponding to position 1009 of SEQ ID NO:1 is

```
Arg, His, Lys, Asp, Glu, Ser, Thr, Asn, Gln, Cys,

Pro, Ala, Val, Leu, Ile, Met, Phe, Tyr, or Trp,
```

the amino acid corresponding to position 1010 of SEQ ID NO:1 is

```
Arg, His, Lys, Asp, Glu, Ser, Thr, Asn, Gln, Cys,

Gly, Ala, Val, Leu, Ile, Met, Phe, Tyr, or Trp,
```

the amino acid corresponding to position 1013 of SEQ ID NO:1 is

```
Arg, His, Lys, Asp, Glu, Ser, Thr, Asn, Gln, Cys,

Pro, Ala, Val, Leu, Ile, Met, Phe, Tyr, or Trp,
```

the amino acid corresponding to position 1052 of SEQ ID NO:1 is

```
Arg, His, Lys, Asp, Glu, Thr, Asn, Gln, Cys, Gly,

Pro, Ala, Val, Leu, Ile, Met, Phe, Tyr, or Trp,
```

the amino acid corresponding to position 1055 of SEQ ID NO:1 is

```
Arg, His, Lys, Asp, Glu, Thr, Asn, Gln, Cys, Gly,

Pro, Ala, Val, Leu, Ile, Met, Phe, Tyr, or Trp.
```

In a preferred embodiment, the amino acid corresponding to position 1009 of SEQ ID NO: 1 is Asp.

In another preferred embodiment, the amino acid corresponding to position 1010 of SEQ ID NO: 1 is Leu.

In another preferred embodiment, the amino acid corresponding to position 1013 of SEQ ID NO: 1 is Arg.

In another preferred embodiment, the amino acid corresponding to position 983 of SEQ ID NO: 3 is Phe.

In another preferred embodiment, the amino acid corresponding to position 1037 of SEQ ID NO: 3 is Phe.

In another preferred embodiment, the amino acid corresponding to position 1040 of SEQ ID NO: 3 is Leu.

It will be within the knowledge of the skilled artisan to identify conserved regions and motifs shared between the homologues, orthologues and paralogues encoded by SEQ ID NO: 65, 66, 67, 68, 69, 70, 71, 72, 73, 74, 75, 76, or 77, such as those depicted in Table 1. Having identified such conserved regions that may represent suitable binding motifs, amino acids corresponding to the amino acids listed below in Table 2, can be chosen to be substituted by any other amino acid, for example by conserved amino acids, preferably by the amino acid substitutions described SUPRA using SEQ ID NO:1 as reference.

Table 2 provides an overview of positions in the orthologues and homologues to SEQ ID NO:1, i.e. the corresponding positions in SEQ ID NOs: 1 to 64.

TABLE 2

| ID | Pos 1 | Pos 2 | Pos 3 | Pos 4 | Pos 5 | Pos 6 |
|---|---|---|---|---|---|---|
| 1 | S998 | G1009 | P1010 | G1013 | S1052 | S1055 |
| 2 | S1001 | G1012 | P1013 | G1016 | S1055 | T1058 |
| 3 | S983 | G994 | P995 | G998 | S1037 | S1040 |
| 4 | S967 | G978 | P979 | G982 | S1021 | S1024 |
| 5 | S987 | G998 | P999 | G1002 | S1041 | T1044 |
| 6 | S1002 | G1013 | P1014 | G1017 | S1056 | T1059 |
| 7 | S944 | G955 | P956 | G959 | S998 | S1001 |
| 8 | S901 | G912 | P913 | G916 | S955 | S958 |
| 9 | S1005 | G1016 | P1017 | G1020 | S1059 | T1062 |
| 10 | S985 | G996 | P997 | G1000 | S1039 | S1042 |
| 11 | S991 | G1002 | P1003 | G1006 | S1045 | S1048 |
| 12 | S900 | G911 | P912 | G915 | S954 | S957 |
| 13 | S991 | G1002 | P1003 | G1006 | S1045 | S1048 |
| 14 | S1003 | G1014 | P1015 | G1018 | S1057 | S1060 |
| 15 | S974 | G985 | P986 | G989 | S1028 | S1031 |
| 16 | S995 | G1006 | P1007 | G1010 | S1049 | S1052 |
| 17 | S1011 | G1022 | P1023 | G1026 | S1065 | S1068 |
| 18 | S514 | G525 | P526 | G529 | S568 | S571 |
| 19 | S1000 | G1011 | P1012 | G1015 | S1054 | S1057 |
| 20 | S997 | G1008 | P1009 | G1012 | S1051 | S1054 |
| 21 | S900 | G911 | P912 | G915 | S954 | S957 |
| 22 | — | — | — | — | — | — |
| 23 | S992 | G1003 | P1004 | G1007 | S1046 | S1049 |
| 24 | S994 | G1005 | P1006 | G1009 | S1048 | S1051 |
| 25 | S1006 | G1017 | P1018 | G1021 | S1060 | S1063 |
| 26 | S951 | G962 | P963 | G966 | S1005 | S1008 |
| 27 | S996 | G1007 | P1008 | G1011 | S1050 | T1053 |
| 28 | S997 | G1008 | P1009 | G1012 | S1051 | S1054 |
| 29 | T891 | G902 | A903 | G906 | S945 | S948 |
| 30 | S891 | G902 | P903 | G906 | S945 | S948 |
| 31 | S957 | G968 | P969 | G972 | S1011 | S1014 |
| 32 | S884 | G895 | P896 | G899 | S938 | S941 |
| 33 | T908 | G919 | A920 | G923 | S962 | S965 |
| 34 | S1002 | G1013 | P1014 | G1017 | S1056 | S1059 |
| 35 | S1002 | G1013 | P1014 | G1017 | S1056 | S1059 |
| 36 | S892 | G903 | P904 | G907 | S946 | S949 |
| 37 | S957 | G968 | P969 | G972 | S1011 | S1014 |
| 38 | S1013 | G1024 | P1025 | G1028 | S1067 | T1070 |
| 39 | S905 | G916 | P917 | G920 | S959 | S962 |
| 40 | S951 | G962 | P963 | G966 | S1005 | S1008 |
| 41 | S998 | G1009 | P1010 | G1013 | S1052 | S1055 |
| 42 | S874 | G885 | P886 | G889 | S928 | S931 |
| 43 | S1013 | G1024 | P1025 | G1028 | S1067 | T1070 |
| 44 | S991 | G1002 | P1003 | G1006 | S1045 | S1048 |
| 45 | S992 | G1003 | P1004 | G1007 | S1046 | S1049 |
| 46 | S1013 | G1024 | P1025 | G1028 | S1067 | S1070 |
| 47 | S996 | G1007 | P1008 | G1011 | S1050 | T1053 |
| 48 | S906 | G917 | P918 | G921 | S960 | S963 |
| 49 | S991 | G1002 | P1003 | G1006 | S1045 | S1048 |
| 50 | S1009 | G1020 | P1021 | G1024 | S1063 | S1066 |
| 51 | S993 | G1004 | P1005 | G1008 | S1047 | S1050 |
| 52 | S1091 | S1102 | K1103 | G1106 | I1145 | S1148 |
| 53 | S935 | S946 | K947 | G950 | I989 | S992 |
| 54 | A778 | G790 | A791 | A794 | S834 | S837 |
| 55 | S999 | G1010 | P1011 | G1014 | S1053 | S1056 |
| 56 | S1009 | G1020 | P1021 | G1024 | S1063 | S1066 |
| 57 | S1010 | G1021 | P1022 | G1025 | S1064 | S1067 |
| 58 | S754 | G765 | P766 | G769 | S808 | S811 |
| 59 | S883 | G894 | P895 | G898 | S937 | S940 |
| 60 | A1033 | G1044 | K1045 | G1048 | I1087 | S1090 |
| 61 | S973 | G984 | P985 | G988 | S1027 | S1030 |
| 62 | S981 | G992 | P993 | G996 | S1035 | S1038 |
| 63 | S1046 | S1057 | K1058 | G1061 | I1100 | S1103 |
| 64 | A1134 | S1145 | K1146 | G1149 | M1188 | S1191 |

Another object refers to a method of identifying a nucleotide sequence encoding a mutated CESA which is resistant or tolerant to a CESA-inhibiting herbicide, the method comprising:

a) generating a library of mutated CESA-encoding nucleic acids, b) screening a population of the resulting mutated CESA-encoding nucleic acids by expressing each of said nucleic acids in a cell or plant and treating said cell or plant with a CESA-inhibiting herbicide, c) comparing the CESA-inhibiting herbicide-tolerance levels provided by said population of mutated CESA encoding nucleic acids with the CESA-inhibiting herbicide-tolerance level provided by a control CESA-encoding nucleic acid, d) selecting at least one mutated CESA-encoding nucleic acid that provides a significantly increased level of tolerance to a CESA-inhibiting herbicide as compared to that provided by the control CESA-encoding nucleic acid.

In a preferred embodiment, the mutated CESA-encoding nucleic acid selected in step d) provides at least 2-fold as much resistance or tolerance of a cell or plant to a CESA-inhibiting herbicide as compared to that provided by the control CESA-encoding nucleic acid.

In a further preferred embodiment, the mutated CESA-encoding nucleic acid selected in step d) provides at least 2-fold, at least 5-fold, at least 10-fold, at least 20-fold, at least 50-fold, at least 100-fold, at least 500-fold, as much resistance or tolerance of a cell or plant to a CESA-inhibiting herbicide as compared to that provided by the control CESA-encoding nucleic acid.

The resistance or tolerance can be determined by generating a transgenic plant or host cell, preferably a plant cell, comprising a nucleic acid sequence of the library of step a) and comparing said transgenic plant with a control plant or host cell, preferably a plant cell.

Another object refers to a method of identifying a plant or algae containing a nucleic acid comprising a nucleotide sequence encoding a wildtype or mutated CESA which is resistant or tolerant to a CESA-inhibiting herbicide, the method comprising:

a) identifying an effective amount of a CESA-inhibiting herbicide in a culture of plant cells or green algae that leads to death of said cells.

b) treating said plant cells or green algae with a mutagenizing agent, c) contacting said mutagenized cells population with an effective amount of CESA-inhibiting herbicide, identified in a), d) selecting at least one cell surviving these test conditions, e) PCR-amplification and sequencing of CESA genes from cells selected in d) and comparing such sequences to wild-type CESA gene sequences, respectively.

In a preferred embodiment, said mutagenizing agent is ethylmethanesulfonate (EMS).

Many methods well known to the skilled artisan are available for obtaining suitable candidate nucleic acids for identifying a nucleotide sequence encoding a wildtype or mutated CESA from a variety of different potential source organisms including microbes, plants, fungi, algae, mixed cultures etc. as well as environmental sources of DNA such as soil. These methods include inter alia the preparation of cDNA or genomic DNA libraries, the use of suitably degenerate oligonucleotide primers, the use of probes based upon known sequences or complementation assays (for example, for growth upon tyrosine) as well as the use of mutagenesis and shuffling in order to provide recombined or shuffled wildtype or mutated CESA-encoding sequences.

Nucleic acids comprising candidate and control CESA encoding sequences can be expressed in yeast, in a bacterial host strain, in an alga or in a higher plant such as tobacco or *Arabidopsis* and the relative levels of inherent tolerance of the CESA encoding sequences screened according to a visible indicator phenotype of the transformed strain or plant in the presence of different concentrations of the selected CESA-inhibiting herbicide. Dose responses and relative shifts in dose responses associated with these indicator phenotypes (formation of necrosis, growth inhibition, herbicidal effect etc) are conveniently expressed in terms, for example, of GR50 (concentration for 50% reduction of growth) or MIC (minimum inhibitory concentration) values where increases in values correspond to increases in inherent tolerance of the expressed CESA. For example, in a relatively rapid assay system based upon transformation of *Arabidopsis* as described in the Example section (Example 7), each wildtype or mutated CESA encoding sequence may be expressed, for example, as a DNA sequence under expression control of a suitable promoter and T1 plants can be selected for differential tolerance to selected CESA-inhibiting herbicides, measured by growth.

In another embodiment, candidate nucleic acids are transformed into plant material to generate a transgenic plant, regenerated into morphologically normal fertile plants which are then measured for differential tolerance to selected CESA-inhibiting herbicides as described in the Example section hereinafter. Many suitable methods for transformation using suitable selection markers such as kanamycin, binary vectors such as from *Agrobacterium* and plant regeneration as, for example, from tobacco leaf discs are well known in the art. Optionally, a control population of plants is likewise transformed with a nucleic acid expressing the control CESA. Alternatively, an untransformed dicot plant such as *Arabidopsis* or Tobacco can be used as a control since this, in any case, expresses its own endogenous CESA. The average, and distribution, of herbicide tolerance levels of a range of primary plant transformation events or their progeny to CESA-inhibiting herbicides described supra are evaluated in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance of the expressed CESA. Herbicides can suitably be applied pre-emergence or post-emergence.

Another object of the present invention refers to an isolated and or recombinantly produced and/or synthetic nucleic acid encoding a mutated CESA as disclosed SUPRA, wherein the nucleic acid comprises the nucleotide sequence of SEQ ID NO: 65, 66, 67, 68, 69, 70, 71, 72, 73, 74, 75, 76, or 77, or a variant or derivative thereof.

In one embodiment, the nucleic acid is identifiable by a method as defined above.

For the purposes of the invention "recombinant" means with regard for example to a nucleic acid sequence, an expression cassette (=gene construct, nucleic acid construct) or a vector containing the nucleic acid sequence according to the invention or an organism transformed by said nucleic acid sequences, expression cassette or vector according to the invention all those constructions produced by genetic engineering methods in which either (a) the nucleic acid sequence comprising the sequence of SEQ ID NO: 65, 66, 67, 68, 69, 70, 71, 72, 73, 74, 75, 76, or 77, or a homolog thereof, or its derivatives or parts thereof; or (b) a genetic control sequence functionally linked to the nucleic acid sequence described under (a), for example a 3'- and/or 5'-genetic control sequence such as a promoter or terminator, or (c) (a) and (b);

are not found in their natural, genetic environment or have been modified by genetic engineering methods, wherein the modification may by way of example be a substitution, addition, deletion, inversion or insertion of one or more nucleotide residues.

"Natural genetic environment" means the natural genomic or chromosomal locus in the organism of origin or inside the host organism or presence in a genomic library. In the case of a genomic library the natural genetic environment of the nucleic acid sequence is preferably retained at least in part. The environment borders the nucleic acid sequence at least on one side and has a sequence length of at least 50 bp, preferably at least 500 bp, particularly preferably at least 1,000 bp, most particularly preferably at least 5,000 bp. A naturally occurring expression cassette—for example the naturally occurring combination of the natural promoter of the nucleic acid sequence according to the invention with the corresponding gene—turns into a transgenic expression cassette when the latter is modified by unnatural, synthetic ("artificial") methods such as by way of example a mutagenation. Appropriate methods are described by way of example in U.S. Pat. No. 5,565,350 or WO 00/15815

In a preferred embodiment, the encoded mutated CESA is a variant of SEQ ID NO: 1, which includes one or more of the following:

the amino acid corresponding to position 998 of SEQ ID NO:1 is

Arg, His, Lys, Asp, Glu, Thr, Asn, Gln, Cys, Gly, Pro, Ala, Val, Leu, Ile, Met, Phe, Tyr, or Trp;

the amino acid corresponding to position 1009 of SEQ ID NO:1 is

Arg, His, Lys, Asp, Glu, Ser, Thr, Asn, Gln, Cys, Pro, Ala, Val, Leu, Ile, Met, Phe, Tyr, or Trp, the amino acid corresponding to position 1010 of SEQ ID NO:1 is Arg, His, Lys, Asp, Glu, Ser, Thr, Asn, Gln, Cys, Gly, Ala, Val, Leu, Ile, Met, Phe, Tyr, or Trp, the amino acid corresponding to position 1013 of SEQ ID NO:1 is Arg, His, Lys, Asp, Glu, Ser, Thr, Asn, Gln, Cys, Pro, Ala, Val, Leu, Ile, Met, Phe, Tyr, or Trp, the amino acid corresponding to position 1052 of SEQ ID NO:1 is Arg, His, Lys, Asp, Glu, Thr, Asn, Gln, Cys, Gly, Pro, Ala, Val, Leu, Ile, Met, Phe, Tyr, or Trp, the amino acid corresponding to position 1055 of SEQ ID NO:1 is Arg, His, Lys, Asp, Glu,, Thr, Asn, Gln, Cys, Gly, Pro, Ala, Val, Leu, Ile, Met, Phe, Tyr, or Trp.

In a preferred embodiment, the amino acid corresponding to position 1009 of SEQ ID NO: 1 is Asp.

In another preferred embodiment, the amino acid corresponding to position 1010 of SEQ ID NO: 1 is Leu.

In another preferred embodiment, the amino acid corresponding to position 1013 of SEQ ID NO: 1 is Arg.

In another preferred embodiment, the amino acid corresponding to position 983 of SEQ ID NO: 3 is Phe.

In another preferred embodiment, the amino acid corresponding to position 1037 of SEQ ID NO: 3 is Phe.

In another preferred embodiment, the amino acid corresponding to position 1040 of SEQ ID NO: 3 is Leu.

In other aspects, the present invention encompasses a progeny or a descendant of a CESA-inhibiting herbicides-tolerant plant of the present invention as well as seeds derived from the CESA-inhibiting herbicides-tolerant plants of the invention and cells derived from the CESA-inhibiting herbicides-tolerant plants of the invention.

In some embodiments, the present invention provides a progeny or descendant plant derived from a plant comprising in at least some of its cells a polynucleotide operably linked to a promoter operable in plant cells, the promoter capable of expressing a wildtype or mutated CESA polypeptide encoded by the polynucleotide, wherein the progeny or descendant plant comprises in at least some of its cells the recombinant polynucleotide operably linked to the promoter, the expression of the wildtype or mutated CESA polypeptide conferring to the progeny or descendant plant tolerance to the CESA-inhibiting herbicides.

In one embodiment, seeds of the present invention preferably comprise the CESA-inhibiting herbicides-tolerance characteristics of the CESA-inhibiting herbicides-tolerant plant. In other embodiments, a seed is capable of germination into a plant comprising in at least some of its cells a polynucleotide operably linked to a promoter operable in plant cells, the promoter capable of expressing a wildtype or mutated CESA polypeptide encoded by the polynucleotide, the expression of the wildtype or mutated CESA polypeptide conferring to the progeny or descendant plant tolerance to the CESA-inhibiting herbicides.

In some embodiments, plant cells of the present invention are capable of regenerating a plant or plant part. In other embodiments, plant cells are not capable of regenerating a plant or plant part. Examples of cells not capable of regenerating a plant include, but are not limited to, endosperm, seed coat (testa & pericarp), and root cap.

In another embodiment, the present invention provides a plant cell of or capable of regenerating a plant comprising in at least some of its cells a polynucleotide operably linked to a promoter operable in plant cells, the promoter capable of expressing a wildtype or mutated CESA polypeptide encoded by the polynucleotide, the expression of the wildtype or mutated CESA polypeptide conferring to the plant tolerance to the CESA-inhibiting herbicides, wherein the plant cell comprises the recombinant polynucleotide operably linked to a promoter.

In other embodiments, the present invention provides a plant cell comprising a polynucleotide operably linked to a promoter operable in plant cells, the promoter capable of expressing a wildtype or mutated CESA polypeptide encoded by the polynucleotide, the expression of the wildtype or mutated CESA polypeptide conferring to the cell tolerance to the CESA-inhibiting herbicides.

In another embodiment, the invention refers to a plant cell transformed by a nucleic acid encoding a wildtype or mutated CESA polypeptide according to the present invention or to a plant cell which has been mutated to obtain a plant expressing a nucleic acid encoding a wildtype or mutated CESA polypeptide according to the present invention, wherein expression of the nucleic acid in the plant cell results in increased resistance or tolerance to a CESA-inhibiting herbicide as compared to a wild type variety of the plant cell. Preferably, the wildtype or mutated CESA polypeptide encoding nucleic acid comprises a polynucleotide sequence selected from the group consisting of: a) a polynucleotide as shown in SEQ ID NO: 65, 66, 67, 68, 69, 70, 71, 72, 73, 74, 75, 76, or 77, or a variant or derivative thereof; b) a polynucleotide encoding a polypeptide as shown in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64, or a variant or derivative thereof; c) a polynucleotide comprising at least 60 consecutive nucleotides of any of a) or b); and d) a polynucleotide complementary to the polynucleotide of any of a) through c).

In some aspects, the present invention provides a plant product prepared from the CESA-inhibiting herbicides-tolerant plants hereof. In some embodiments, examples of plant products include, without limitation, grain, oil, and meal. In one embodiment, a plant product is plant grain (e.g., grain suitable for use as feed or for processing), plant oil (e.g., oil suitable for use as food or biodiesel), or plant meal (e.g., meal suitable for use as feed).

In one embodiment, a plant product prepared from a plant or plant part is provided, wherein the plant or plant part comprises in at least some of its cells a polynucleotide operably linked to a promoter operable in plant cells, the promoter capable of expressing a wildtype or mutated CESA polypeptide encoded by the polynucleotide, the expression of the wildtype or mutated CESA polypeptide conferring to the a plant or plant part tolerance to the CESA-inhibiting herbicides.

In another embodiment, the invention refers to a method of producing a transgenic plant cell with an increased resistance to a CESA-inhibiting herbicide as compared to a wild type variety of the plant cell comprising, transforming the plant cell with an expression cassette comprising a polynucleotide operably linked to a promoter operable in plant cells, the promoter capable of expressing a wildtype or mutated CESA polypeptide encoded by the polynucleotide.

In another embodiment, the invention refers to a method of producing a transgenic plant comprising, (a) transforming a plant cell with an expression cassette comprising a polynucleotide operably linked to a promoter operable in plant cells, the promoter capable of expressing a wildtype or mutated CESA polypeptide encoded by the polynucleotide, and (b) generating a plant with an increased resistance to CESA-inhibiting herbicide from the plant cell.

In some aspects, the present invention provides a method for producing a CESA-inhibiting herbicides-tolerant plant. In one embodiment, the method comprises: regenerating a plant from a plant cell transformed with a polynucleotide operably linked to a promoter operable in plant cells, the promoter capable of expressing a wildtype or mutated CESA polypeptide encoded by the polynucleotide, the expression of the wildtype or mutated CESA polypeptide conferring to the plant tolerance to the CESA-inhibiting herbicides.

The term "expression/expressing" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

To obtain the desired effect, i.e. plants that are tolerant or resistant to the CESA-inhibiting herbicide derivative herbicide of the present invention, it will be understood that the at least one nucleic acid is "over-expressed" by methods and means known to the person skilled in the art.

The term "increased expression" or "overexpression" as used herein means any form of expression that is additional to the original wild-type expression level. Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene. If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene. An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

Where appropriate, nucleic acid sequences may be optimized for increased expression in a transformed plant. For example, coding sequences that comprise plant-preferred codons for improved expression in a plant can be provided. See, for example, Campbell and Gowri (1990) Plant Physiol., 92: 1-11 for a discussion of host-preferred codon usage. Methods also are known in the art for preparing plant-preferred genes. See, for example, U.S. Pat. Nos. 5,380,831, and 5,436,391, and Murray et al. (1989) Nucleic Acids Res. 17:477-498, herein incorporated by reference.

Consequently, wildtype or mutated CESA nucleic acids of the invention are provided in expression cassettes for expression in the plant of interest. The cassette will include regulatory sequences operably linked to a wildtype or mutated CESA nucleic acid sequence of the invention. The term "regulatory element" as used herein refers to a polynucleotide that is capable of regulating the transcription of an operably linked polynucleotide. It includes, but not limited to, promoters, enhancers, introns, 5' UTRs, and 3' UTRs. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the wildtype or mutated CESA nucleic acid sequence to be under the transcriptional regulation of the regulatory regions. The expression cassette may additionally contain selectable marker genes. The expression cassette of the present invention will include in the 5'-3' direction of transcription, a transcriptional and translational initiation region (i.e., a promoter), a wildtype or mutated CESA encoding nucleic acid sequence of the invention, and a transcriptional and translational termination region (i.e., termination region) functional in plants. The promoter may be native or analogous, or foreign or heterologous, to the plant host and/or to the wildtype or mutated CESA nucleic acid sequence of the invention. Additionally, the promoter may be the natural sequence or alternatively a synthetic sequence. Where the promoter is “foreign” or “heterologous” to the plant host, it is intended that the promoter is not found in the native plant into which the promoter is introduced. Where the promoter is “foreign” or “heterologous” to the wildtype or mutated CESA nucleic acid sequence of the invention, it is intended that the promoter is not the native or naturally occurring promoter for the operably linked wildtype or mutated CESA nucleic acid sequence of the invention. As used herein, a chimeric gene comprises a coding sequence operably linked to a transcription initiation region that is heterologous to the coding sequence. While it may be preferable to express the wildtype or mutated CESA nucleic acids of the invention using heterologous promoters, the native promoter sequences may be used. Such constructs would change expression levels of the wildtype or mutated CESA protein in the plant or plant cell. Thus, the phenotype of the plant or plant cell is altered.

The termination region may be native with the transcriptional initiation region, may be native with the operably linked wildtype or mutated CESA sequence of interest, may be native with the plant host, or may be derived from another source (i.e., foreign or heterologous to the promoter, the wildtype or mutated CESA nucleic acid sequence of interest, the plant host, or any combination thereof). Convenient termination regions are available from the Ti-plasmid of *A. tumefaciens*, such as the octopine synthase and nopaline synthase termination regions. See also Guerineau et al. (1991) Mol. Gen. Genet. 262: 141-144; Proudfoot (1991) Cell 64:671-674; Sanfacon et al. (1991) Genes Dev. 5: 141-149; Mogen et al. (1990) Plant Cell 2: 1261-1272; Munroe et al. (1990) Gene 91: 151-158; Ballas t al. (1989) Nucleic Acids Res. 17:7891-7903; and Joshi et al. (1987) Nucleic Acid Res. 15:9627-9639. Where appropriate, the gene(s) may be optimized for increased expression in the transformed plant. That is, the genes can be synthesized using plant-preferred codons for improved expression. See, for example, Campbell and Gowri (1990) Plant Physiol. 92: 1-11 for a discussion of host-preferred codon usage. Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference.

While the polynucleotides of the invention may find use as selectable marker genes for plant transformation, the expression cassettes of the invention can include another selectable marker gene for the selection of transformed cells. Selectable marker genes, including those of the present invention, are utilized for the selection of transformed cells or tissues. Marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) Curr. Opin. Biotech. 3:506-511; Christophers on et al (1992) Proc. Natl. Acad. ScL USA 89:6314-6318; Yao et al. (1992) Cell 71:63-72; Reznikoff (1992) Mol Microbiol 6:2419-2422; Barkley et al (1980) in The Operon, pp. 177-220; Hu et al (1987) Cell 48:555-566; Brown et al (1987) Cell 49:603-612; Figge et al (1988) Cell 52:713-722; Deuschle et al (1989) Proc. Natl Acad. AcL USA 86:5400-5404; Fuerst et al (1989) Proc. Natl Acad. ScL USA 86:2549-2553; Deuschle et al (1990) Science 248:480-483; Gossen (1993) Ph.D. Thesis, University of Heidelberg; Reines et al (1993) Proc. Natl Acad. ScL USA 90: 1917-1921; Labow et al (1990) Mol Cell Biol 10:3343-3356; Zambretti et al (1992) Proc. Natl Acad. ScL USA 89:3952-3956; Bairn et al (1991) Proc. Natl Acad. ScL USA 88:5072-5076; Wyborski et al (1991) Nucleic Acids Res. 19:4647-4653; Hillenand-Wissman (1989) Topics Mol Struc. Biol 10: 143-162; Degenkolb et al (1991) Antimicrob. Agents Chemother. 35: 1591-1595; Kleinschnidt et al (1988) Biochemistry 27: 1094-1104; Bonin (1993) Ph.D. Thesis, University of Heidelberg; Gossen et al (1992) Proc. Natl Acad. ScL USA 89:5547-5551; Oliva et al (1992) Antimicrob. Agents Chemother. 36:913-919; Hlavka et al (1985) Handbook of Experimental Pharmacology, Vol. 78 (Springer-Verlag, Berlin); Gill et al (1988) Nature 334:721-724. Such disclosures are herein incorporated by reference. The above list of selectable marker genes is not meant to be limiting. Any selectable marker gene can be used in the present invention.

Further, additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. Also, if desired, sequences can be readily modified to avoid predicted hairpin secondary mRNA structures. Nucleotide sequences for enhancing gene expression can also be used in the plant expression vectors. These include, for example, introns of the maize Adh gene Adh1-S intron 1, 2, and 6 (Callis et al. Genes and Development 1: 1183-1200, 1987), and leader sequences, (W-sequence) from the Tobacco Mosaic virus (TMV), Maize Chlorotic Mottle Virus and Alfalfa Mosaic Virus (Gallie et al. Nucleic Acid Res. 15:8693-8711, 1987 and Skuzeski et al. Plant Mol. Biol. 15:65-79, 1990). The first intron from the shrunken-1 locus of maize has been shown to increase expression of genes in chimeric gene constructs. U.S. Pat. Nos. 5,424,412 and 5,593,874 disclose the use of specific introns in gene expression constructs, and Gallie et al. (Plant Physiol. 106:929-939, 1994) also have shown that introns are useful for regulating gene expression on a tissue specific basis. To further enhance or to optimize gene expression, the plant expression vectors of the invention also may contain DNA sequences containing matrix attachment regions (MARs). Plant cells transformed with such modified expression systems, then, may exhibit overexpression or constitutive expression of a nucleotide sequence of the invention.

The invention further provides an isolated recombinant expression vector comprising the expression cassette containing a wildtype or mutated CESA nucleic acid nucleic acid as described above, wherein expression of the vector in a host cell results in increased tolerance to a CESA-inhibiting herbicide as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., wildtype or mutated CESA polypeptides, fusion polypeptides, etc.)

Expression vectors may additionally contain 5' leader sequences in the expression construct. Such leader sequences can act to enhance translation. Translation leaders are known in the art and include: picornavirus leaders, for example, EMCV leader (Encephalomyo carditis 5' noncoding region) (Elroy-Stein et al. (1989) PNAS, 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968.

Other methods known to enhance translation also can be utilized, for example, introns, and the like. In preparing an expression vector, the various nucleic acid fragments may be manipulated, so as to provide for the nucleic acid sequences in the proper orientation and, as appropriate, in the proper reading frame. Toward this end, adapters or linkers may be employed to join the nucleic acid fragments or other manipulations may be involved to provide for convenient restriction sites, removal of superfluous nucleic acid, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2: 163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced expression within a particular plant tissue. Such tissue-preferred promoters include, but are not limited to, leaf-preferred promoters, root-preferred promoters, seed-preferred promoters, and stem-preferred promoters. Some examples of tissue-preferred promoters are described by, e.g., Yamamoto et al. (1997) Plant J. 12(2):255-265; Kawamata et al. (1997) Plant Cell Physiol. 38(7):792-803; Hansen et al. (1997) Mol. Gen Genet. 254(3):337-343; Russell et al. (1997) Transgenic Res. 6(2): 157-168; Rinehart et al. (1996) Plant Physiol. 1 12(3): 1331-1341; Van Camp et al. (1996) Plant Physiol. 112(2):525-535; Canevascini et al. (1996) Plant Physiol. 1 12(2):513-524; Yamamoto et al. (1994) Plant Cell Physiol. 35(5):773-778; Lam (1994) Results Probl. Cell Differ. 20:181-196; Orozco of al. (1993) Plant Mol Biol. 23(6): 1 129-1138; Matsuoka et al. (1993) Voc Natl. Acad. ScL USA 90(20):9586-9590; and Guevara-Garcia et al. (1993) Plant J 4(3):495-505. Promoters can be modified, if necessary, for weak expression.

In some embodiments, the nucleic acids of interest can be targeted to the chloroplast for expression. In this manner, where the nucleic acid of interest is not directly inserted into the chloroplast, the expression vector will additionally contain a chloroplast-targeting sequence comprising a nucleotide sequence that encodes a chloroplast transit peptide to direct the gene product of interest to the chloroplasts. Such transit peptides are known in the art. With respect to chloroplast-targeting sequences, "operably linked" means that the nucleic acid sequence encoding a transit peptide (i.e., the chloroplast-targeting sequence) is linked to the desired coding sequence of the invention such that the two sequences are contiguous and in the same reading frame. See, for example, Von Heijne et al. (1991) Plant Mol. Biol. Rep. 9: 104-126; Clark et al. (1989) J Biol. Chem. 264: 17544-17550; Della-Cioppa et al. (1987) Plant Physiol. 84:965-968; Romer et al. (1993) Biochem. Biophys. Res. Commun. 196: 1414-1421; and Shah et al. (1986) Science 233:478-481. For example, a chloroplast transit peptide known in the art can be fused to the amino acid sequence of a CESA polypeptide of the invention by operably linking a chloroplast-targeting sequence to the 5'-end of a nucleotide sequence encoding the CESA polypeptide.

Chloroplast targeting sequences are known in the art and include the chloroplast small subunit of ribulose-1,5-bisphosphate carboxylase (Rubisco) (de Castro Silva Filho et al. (1996) Plant Mol. Biol. 30:769-780; Schnell et al. (1991) J Biol. Chem. 266(5):3335-3342); EPSPS (Archer et al. (1990) J Bioenerg. Biomemb. 22(6):789-810); tryptophan synthase (Zhao et al. (1995) J Biol. Chem. 270(11):6081-6087); plastocyanin (Lawrence et al. (1997) J Biol. Chem. 272(33):20357-20363); chorismate synthase (Schmidt et al. (1993) J Biol. Chem. 268(36):27447-27457); and the light harvesting chlorophyll a/b binding protein (LHBP) (Lamppa et al. (1988) J Biol. Chem. 263: 14996-14999). See also Von Heijne et al. (1991) Plant Mol. Biol. Rep. 9: 104-126; Clark et al. (1989) J Biol. Chem. 264: 17544-17550; Della-Cioppa et al. (1987) Plant Physiol. 84:965-968; Romer et al. (1993) Biochem Biophys. Res. Commun. 196: 1414-1421; and Shah et al. (1986) Science 233:478-481.

Methods for transformation of chloroplasts are known in the art. See, for example, Svab et al. (1990) Proc. Natl. Acad. ScL USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Numerous plant transformation vectors and methods for transforming plants are available. See, for example, An, G. et al. (1986) Plant PysioL, 81:301-305; Fry, J., et al. (1987) Plant Cell Rep. 6:321-325; Block, M. (1988) Theor. Appl. Genet 0.16: 161-1 1 A; Hinchee, et al. (1990) Stadler. Genet. Symp. 2032₩2.203-2₩2; Cousins, et al. (1991) Aust. J. Plant Physiol. 18:481-494; Chee, P. P. and Slightom, J. L. (1992) Gene. I I 8:255-260; Christou, et al. (1992) Trends. Biotechnol. 10:239-246; Halluin, et al. (1992) Bio/Technol. 10:309-314; Dhir, et al. (1992) Plant Physiol. 99:81-88; Casas et al. (1993) Proc. Nat. Acad Sd. USA 90: 1 1212-1 1216; Christou, P. (1993) In Vitro Cell. Dev. Biol.-Plant; 29P.119-124; Davies, et al. (1993) Plant Cell Rep. 12: 180-183; Dong, J. A. and Mchughen, A. (1993) Plant ScL 91: 139-148; Franklin, C. I. and Trieu, T. N. (1993) Plant. Physiol. 102: 167; Golovkin, et al. (1993) Plant ScL 90:41-52; Guo Chin ScL Bull. 38:2072-2078; Asano, et al. (1994) Plant Cell Rep. 13; Ayeres N. M. and Park, W. D. (1994) Crit. Rev. Plant. Sci. 13:219-239; Barcelo, et al. (1994) Plant. J. 5:583-592; Becker, et al. (1994) Plant. J. 5:299-307; Borkowska et al. (1994) Acta. Physiol Plant. 16:225-230; Christou, P. (1994) Agro. Food. Ind. Hi Tech. 5: 17-27; Eapen et al. (1994) Plant Cell Rep. 13:582-586; Hartman, et al. (1994) Bio-Technology 12: 919923; Ritala, et al. (1994) Plant. Mol. Biol. 24:317-325; and Wan, Y. C. and Lemaux, P. G. (1994) Plant Physiol. 104:3748.

In some embodiments, the methods of the invention involve introducing a polynucleotide construct into a plant. By "introducing" is intended presenting to the plant the polynucleotide construct in such a manner that the construct gains access to the interior of a cell of the plant. The methods of the invention do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods. The term "introduction" or "transformation" as referred to herein further means the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

By "stable transformation" is intended that the polynucleotide construct introduced into a plant integrates into the genome of the plant and is capable of being inherited by descendent thereof. By "transient transformation" is intended that a polynucleotide construct introduced into a plant does not integrate into the genome of the plant. For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed. In an embodiment of the invention, the encoding nucleotide sequence is operably linked to a plant promoter, e.g. a promoter known in the art for high-level expression in a plant cell, and this construct is then introduced into a plant cell that is susceptible to CESA-inhibiting herbicides; and a transformed plant is regenerated. In some embodiments, the transformed plant is tolerant to exposure to a level of CESA-inhibiting herbicides that would kill or significantly injure a plant regenerated from an untransformed cell. This method can be applied to any plant species or crops.

Methodologies for constructing plant expression vectors and introducing foreign nucleic acids into plants are generally known in the art. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) Gene 100: 247-250; Scheid et al., (1991) MoL Gen. Genet., 228: 104-1 12; Guerche et al., (1987) Plant Science 52: 1 1 1-1 16; Neuhause et al., (1987) Theor. Appl Genet. 75: 30-36; Klein et al., (1987) Nature 327: 70-73; Howell et al., (1980) Science 208: 1265; Horsch et al., (1985) Science 227: 1229-1231; DeBlock et al., (1989) Plant Physiology 91: 694-701; Methods for Plant Molecular Biology (Weissbach and Weissbach, eds.) Academic Press, Inc. (1988) and Methods in Plant Molecular Biology (Schuler and Zielinski, eds.) Academic Press, Inc. (1989).

Other suitable methods of introducing nucleotide sequences into plant cells include microinjection as described by e.g., Crossway et al. (1986) Biotechniques 4:320-334, electroporation as described by e.g., Riggs et al. (1986) Proc. Natl. Acad. ScL USA 83:5602-5606, *Agrobacterium*-mediated transformation as described by e.g., Townsend et al., U.S. Pat. No. 5,563,055, Zhao et al., U.S. Pat. No. 5,981,840, direct gene transfer as described by, e.g., Paszkowski et al. (1984) EMBO J. 3:2717-2722, and ballistic particle acceleration as described by, e.g., U.S. Pat. Nos. 4,945,050; 5,879,918; 5,886,244; and 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); McCabe et al. (1988) Biotechnology 6:923-926); and Led transformation (WO 00/28058). Also see, Weissinger et al., (1988) Ann. Rev. Genet. 22:421-477; Sanford et al, (1987) Particulate Science and Technology 5:27-37 (onion); Christou et al, (1988) Plant Physiol. 87:671-674 (soybean); McCabe et al., (1988) Bio/Technology 6:923-926 (soybean); Finer and McMullen (1991) In Vitro Cell Dev. Biol. 27P: 175-182 (soybean); Singh et al, (1998) Theor. Appl. Genet. 96:319-324 (soybean); Datta et al., (1990) Biotechnology 8:736-740 (rice); Klein et al., (1988) PNAS, 85:4305-4309 (maize); Klein et al., (1988) Biotechnology 6:559-563 (maize); U.S. Pat. Nos. 5,240,855; 5,322,783; and 5,324,646; Tomes et al., (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al., (1988) Plant Physiol. 91:440-444 (maize); Fromm et al., (1990) Biotechnology 8:833-839 (maize); Hooykaas-Van Slogteren et al., (1984) Nature (London) 31 1:763-764; Bowen et al, U.S. Pat. No. 5,736,369 (cereals); Bytebier et al, (1987) PNAS 84:5345-5349 (Liliaceae); De Wet et al., (1985) in The Experimental Manipulation of Ovule Tissues, ed. Chapman et al, (Longman, New York), pp. 197-209 (pollen); Kaeppler et al., (1990) Plant Cell Reports 9:415-418 and Kaeppler et al., (1992) Theor. Apph Genet. 84:560-566 (whisker-mediated transformation); D'Halluin et al., (1992) Plant Cell 4: 1495-1505 (electroporation); Li et al., (1993) Plant Cell Reports 12:250-255 and Christou and Ford (1995) Annals of Botany 75:407-413 (rice); Osjoda et al, (1996) Nature Biotechnology 14:745-750 (maize via *Agrobacterium tumefaciens*); each of which is herein incorporated by reference.

Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

One transformation method known to those of skill in the art is the dipping of a flowering plant into an Agrobacteria solution, wherein the Agrobacteria contains the CESA nucleic acid, followed by breeding of the transformed gametes. *Agrobacterium* mediated plant transformation can be performed using for example the GV3101 (pMP90) (Koncz and Schell, 1986, Mol. Gen. Genet. 204:383-396) or LBA4404 (Clontech) *Agrobacterium tumefaciens* strain. Transformation can be performed by standard transformation and regeneration techniques (Deblaere et al., 1994, Nucl. Acids. Res. 13:4777-4788; Gelvin, Stanton B. and Schilperoort, Robert A, Plant Molecular Biology Manual, 2nd Ed.—Dordrecht: Kluwer Academic Publ., 1995.—in Sect., Ringbuc Zentrale Signatur: BT11-P ISBN 0-7923-2731-4; Glick, Bernard R. and Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant Cell Report 8:238-242; De Block et al., 1989, Plant Physiol. 91:694-701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake, or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

In some embodiments, polynucleotides of the present invention may be introduced into plants by contacting plants with a virus or viral nucleic acids. Generally, such methods involve incorporating a polynucleotide construct of the invention within a viral DNA or RNA molecule. It is recognized that the polypeptides of the invention may be initially synthesized as part of a viral polyprotein, which later may be processed by proteolysis in vivo or in vitro to produce the desired recombinant polypeptide. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference. The cells that have been transformed may be grown into plants in accordance with conventional ways. See, for example, McCormick et al. (1986) Plant Cell Reports 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The present invention may be used for transformation of any plant species, including, but not limited to, monocots and dicots. Examples of plant species of interest include, but are not limited to, corn or maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet e.g., pearl millet (*Pennisetum glaucum*), proso millet (*Panicum miliaceum*), foxtail millet (*Setaria italica*), finger millet (*Eleusine coracana*)), sunflower (*Helianthus annu*), saffiower (*Carthamus tinctorius*), wheat (*Triticum aestivum, T. Turgidum* ssp. *durum*), soybean (*Glycine max*), tobacco (*Nicotiana tabacum*), potato (*Solarium tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), *papaya* (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. Preferably, plants of the present invention are crop plants (for example, sunflower, *Brassica* sp., cotton, sugar, beet, soybean, peanut, alfalfa, safflower, tobacco, corn, rice, wheat, rye, barley triticale, sorghum, millet, etc.).

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, Eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, Si and Bent AF (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229). The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the expression of the nucleic acid in the plant results in the plant's increased tolerance to CESA-inhibiting herbicide as compared to a wild type variety of the plant.

In another embodiment, the invention refers to a plant, comprising a plant cell according to the present invention, wherein expression of the nucleic acid in the plant results in the plant's increased resistance to CESA-inhibiting herbicide as compared to a wild type variety of the plant.

The plants described herein can be either transgenic crop plants or non-transgenic plants.

In addition to the general definition, give SUPRA, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or
(b) genetic control sequence(s) which is operably linked with the nucleic acid sequence according to the invention, for example a promoter, or
(c) a) and b)

are not located in their natural genetic environment or have been modified by recombinant methods, it being possible for the modification to take the form of, for example, a substitution, addition, deletion, inversion or insertion of one or more nucleotide residues in order to allow for the expression of the wildtype or mutated CESA of the present invention. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein. Furthermore, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

Plants containing mutations arising due to non-spontaneous mutagenesis and selective breeding are referred to herein as non-transgenic plants and are included in the present invention. In embodiments wherein the plant is transgenic and comprises multiple wildtype or mutated CESA nucleic acids, the nucleic acids can be derived from different genomes or from the same genome. Alternatively, in embodiments wherein the plant is non-transgenic and comprises multiple wildtype or mutated CESA nucleic acids, the nucleic acids are located on different genomes or on the same genome.

In certain embodiments, the present invention involves herbicide-resistant plants that are produced by mutation breeding. Such plants comprise a polynucleotide encoding a wildtype or mutated CESA and are tolerant to one or more CESA-inhibiting herbicides. Such methods can involve, for example, exposing the plants or seeds to a mutagen, particularly a chemical mutagen such as, for example, ethyl methanesulfonate (EMS) and selecting for plants that have enhanced tolerance to at least one or more CESA-inhibiting herbicide [see Example 1].

However, the present invention is not limited to herbicide-tolerant plants that are produced by a mutagenesis method involving the chemical mutagen EMS. Any mutagenesis method known in the art may be used to produce the herbicide-resistant plants of the present invention. Such mutagenesis methods can involve, for example, the use of any one or more of the following mutagens: radiation, such as X-rays, Gamma rays (e.g., cobalt 60 or cesium 137), neutrons, (e.g., product of nuclear fission by uranium 235 in an atomic reactor), Beta radiation (e.g., emitted from radioisotopes such as phosphorus 32 or carbon 14), and ultraviolet radiation (preferably from 250 to 290 nm), and chemical mutagens such as base analogues (e.g., 5-bromo-uracil), related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, or acridines. Herbicide-resistant plants can also be produced by using tissue culture methods to select for plant cells comprising herbicide-resistance mutations and then regenerating herbicide-resistant plants therefrom. See, for example, U.S. Pat. Nos. 5,773,702 and 5,859,348, both of which are herein incorporated in their entirety by reference. Further details of mutation breeding can be found in "Principals of Cultivar Development" Fehr, 1993 Macmillan Publishing Company the disclosure of which is incorporated herein by reference The plant of the present invention comprises at least one wildtype or mutated CESA nucleic acid or over-expressed wild-type CESA nucleic acid, and has increased tolerance to a CESA-inhibiting herbicide as compared to a wild-type variety of the plant. It is possible for the plants of the present invention to have multiple wildtype or mutated CESA nucleic acids from different genomes since these plants can contain more than one genome. For example, a plant contains two genomes, usually referred to as the A and B genomes. Because CESA is a required metabolic enzyme, it is assumed that each genome has at least one gene coding for the CESA enzyme (i.e. at least one CESA gene). As used herein, the term "CESA gene locus" refers to the position of a CESA gene on a genome, and the terms "CESA gene" and "CESA nucleic acid" refer to a nucleic acid encoding the CESA enzyme. The CESA nucleic acid on each genome differs in its nucleotide sequence from a CESA nucleic acid on another genome. One of skill in the art can determine the genome of origin of each CESA nucleic acid through genetic crossing and/or either sequencing methods or exonuclease digestion methods known to those of skill in the art.

The present invention includes plants comprising one, two, three, or more wildtype or mutated CESA alleles, wherein the plant has increased tolerance to a CESA-inhibiting herbicide as compared to a wild-type variety of the plant. The wildtype or mutated CESA alleles can comprise a nucleotide sequence selected from the group consisting of a polynucleotide as defined in SEQ ID NO: 65, 66, 67, 68, 69, 70, 71, 72, 73, 74, 75, 76, or 77, or a variant or derivative thereof, a polynucleotide encoding a polypeptide as defined in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64, or a variant or derivative, homologue, orthologue, paralogue thereof, a polynucleotide comprising at least 60 consecutive nucleotides of any of the aforementioned polynucleotides; and a polynucleotide complementary to any of the aforementioned polynucleotides.

"Alleles" or "allelic variants" are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms The term "variety" refers to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci. A cultivar or variety is considered "true breeding" for a particular trait if, when the true-breeding cultivar or variety is self-pollinated, all of the progeny contain the trait. The terms "breeding line" or "line" refer to a group of plants within a cultivar defined by the sharing of a common set of characteristics or traits accepted by those skilled in the art as sufficient to distinguish one breeding line or line from another breeding line or line. There is no implication in either term that all plants of any given breeding line or line will be genetically identical at either the whole gene or molecular level or that any given plant will be homozygous at all loci. A breeding line or line is considered "true breeding" for a particular trait if, when the true-breeding line or breeding line is self-pollinated, all of the progeny contain the trait. In the present invention, the trait arises from a mutation in a CESA gene of the plant or seed.

The herbicide-resistant plants of the invention that comprise polynucleotides encoding wildtype or mutated CESA polypeptides also find use in methods for increasing the herbicide-resistance of a plant through conventional plant breeding involving sexual reproduction. The methods comprise crossing a first plant that is a herbicide-resistant plant of the invention to a second plant that may or may not be resistant to the same herbicide or herbicides as the first plant or may be resistant to different herbicide or herbicides than the first plant. The second plant can be any plant that is capable of producing viable progeny plants (i.e., seeds) when crossed with the first plant. Typically, but not necessarily, the first and second plants are of the same species. The methods can optionally involve selecting for progeny plants that comprise the wildtype or mutated CESA polypeptides of the first plant and the herbicide resistance characteristics of the second plant. The progeny plants produced by this method of the present invention have increased resistance to a herbicide when compared to either the first or second plant or both. When the first and second plants are resistant to different herbicides, the progeny plants will have the combined herbicide tolerance characteristics of the first and second plants. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The present invention also provides plants, plant organs, plant tissues, plant cells, seeds, and non-human host cells that are transformed with the at least one polynucleotide molecule, expression cassette, or transformation vector of the invention. Such transformed plants, plant organs, plant tissues, plant cells, seeds, and non-human host cells have enhanced tolerance or resistance to at least one herbicide, at levels of the herbicide that kill or inhibit the growth of an untransformed plant, plant tissue, plant cell, or non-human host cell, respectively. Preferably, the transformed plants, plant tissues, plant cells, and seeds of the invention are *Arabidopsis thaliana* and crop plants.

It is to be understood that the plant of the present invention can comprise a wild type CESA nucleic acid in addition to a mutated CESA nucleic acid. It is contemplated that the CESA-inhibiting herbicide tolerant lines may contain a mutation in only one of multiple CESA isoenzymes. Therefore, the present invention includes a plant comprising one or more mutated CESA nucleic acids in addition to one or more wild type CESA nucleic acids.

In another embodiment, the invention refers to a seed produced by a transgenic plant comprising a plant cell of the present invention, wherein the seed is true breeding for an increased resistance to a CESA-inhibiting herbicide as compared to a wild type variety of the seed.

In other aspects, CESA-inhibiting herbicides-tolerant plants of the present invention can be employed as CESA-inhibiting herbicides-tolerance trait donor lines for development, as by traditional plant breeding, to produce other varietal and/or hybrid crops containing such trait or traits. All such resulting variety or hybrids crops, containing the ancestral CESA-inhibiting herbicides-tolerance trait or traits can be referred to herein as progeny or descendant of the ancestral, CESA-inhibiting herbicides-tolerant line(s).

In other embodiments, the present invention provides a method for producing a CESA-inhibiting herbicides-tolerant plant. The method comprises: crossing a first CESA-inhibiting herbicides-tolerant plant with a second plant to produce a CESA-inhibiting herbicides-tolerant progeny plant, wherein the first plant and the progeny plant comprise in at least some of their cells a polynucleotide operably linked to a promoter operable in plant cells, the recombinant polynucleotide being effective in the cells of the first plant to express a wildtype or mutated CESA polypeptide encoded by the polynucleotide, the expression of the wildtype or mutated CESA polypeptide conferring to the plant tolerance to CESA-inhibiting herbicides.

In some embodiments, traditional plant breeding is employed whereby the CESA-inhibiting herbicides-tolerant trait is introduced in the progeny plant resulting therefrom. In one embodiment, the present invention provides a method for producing a CESA-inhibiting herbicides-tolerant progeny plant, the method comprising: crossing a parent plant with a CESA-inhibiting herbicides-tolerant plant to introduce the CESA-inhibiting herbicides-tolerance characteristics of the CESA-inhibiting herbicides-tolerant plant into the germplasm of the progeny plant, wherein the progeny plant has increased tolerance to the CESA-inhibiting herbicides relative to the parent plant. In other embodiments, the method further comprises the step of introgressing the CESA-inhibiting herbicides-tolerance characteristics through traditional plant breeding techniques to obtain a descendent plant having the CESA-inhibiting herbicides-tolerance characteristics.

In other aspects, plants of the invention include those plants which, in addition to being CESA-inhibiting herbicides-tolerant, have been subjected to further genetic modifications by breeding, mutagenesis or genetic engineering, e.g. have been rendered tolerant to applications of specific other classes of herbicides, such as AHAS inhibitors; auxinic herbicides; bleaching herbicides such as hydroxyphenylpyruvate dioxygenase (HPPD) inhibitors or phytoene desaturase (PDS) inhibitors; EPSPS inhibitors such as glyphosate; glutamine synthetase (GS) inhibitors such as glufosinate; lipid biosynthesis inhibitors such as acetyl CoA carboxylase (ACCase) inhibitors; or oxynil {i.e. bromoxynil or ioxynil) herbicides as a result of conventional methods of breeding or genetic engineering, Thus, CESA-inhibiting herbicides-tolerant plants of the invention can be made resistant to multiple classes of herbicides through multiple genetic modifications, such as resistance to both glyphosate and glufosinate or to both glyphosate and a herbicide from another class such as HPPD inhibitors, AHAS inhibitors, or ACCase inhibitors. These herbicide resistance technologies are, for example, described in Pest Management Science (at volume, year, page): 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. For example, CESA-inhibiting herbicides-tolerant plants of the invention, in some embodiments, may be tolerant to ACCase inhibitors, such as "dims" {e.g., cycloxydim, sethoxydim, clethodim, or tepraloxydim), "fops" {e.g., clodinafop, diclofop, fluazifop, haloxyfop, or quizalofop), and "dens" (such as pinoxaden); to auxinic herbicides, such as dicamba; to EPSPS inhibitors, such as glyphosate; to other CESA inhibitors; and to GS inhibitors, such as glufosinate.

In addition to these classes of inhibitors, CESA-inhibiting herbicides-tolerant plants of the invention may also be tolerant to herbicides having other modes of action, for example, chlorophyll/carotenoid pigment inhibitors, cell membrane disrupters, photosynthesis inhibitors, cell division inhibitors, root inhibitors, shoot inhibitors, and combinations thereof.

Such tolerance traits may be expressed, e.g.: as mutant or wildtype HPPD proteins, as mutant AHASL proteins, mutant ACCase proteins, mutant EPSPS proteins, or mutant glutamine synthetase proteins; or as mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or CYP450s proteins having an herbicide-degrading activity. CESA-inhibiting herbicides-tolerant plants hereof can also be stacked with other traits including, but not limited to, pesticidal traits such as Bt Cry and other proteins having pesticidal activity toward coleopteran, lepidopteran, nematode, or other pests; nutrition or nutraceutical traits such as modified oil content or oil profile traits, high protein or high amino acid concentration traits, and other trait types known in the art.

Furthermore, in other embodiments, CESA-inhibiting herbicides-tolerant plants are also covered which are, by the use of recombinant DNA techniques and/or by breeding and/or otherwise selected for such characteristics, rendered able to synthesize one or more insecticidal proteins, especially those known from the bacterial genus *Bacillus*, particularly from *Bacillus thuringiensis*, such as [delta]-endotoxins, e.g. CryIA(b), CryIA(c), CryIF, CryIF(a2), CryIIA (b), CryIIIA, CryIIIB(bI) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or Xenorhabdus spp.; toxins produced by animals, such as scorpion toxins, arachnid toxins, wasp toxins, or other insect-specific neurotoxins; toxins produced by fungi, such streptomycete toxins; plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda).

In some embodiments, expression of one or more protein toxins (e.g., insecticidal proteins) in the CESA-inhibiting herbicides-tolerant plants is effective for controlling organisms that include, for example, members of the classes and orders: Coleoptera such as the American bean weevil *Acanthoscelides obtectus*; the leaf beetle *Agelastica alni*; click beetles (*Agriotes lineatus, Agriotes obscurus, Agriotes* bicolor); the grain beetle *Ahasverus advena*; the summer schafer *Amphimallon solstitialis*; the furniture beetle *Anobium punctatum; Anthonomus* spp. (weevils); the Pygmy mangold beetle *Atomaria linearis*; carpet beetles (*Anthrenus* spp., *Attagenus* spp.); the cowpea weevil *Callosobruchus maculates*; the fried fruit beetle *Carpophilus hemipterus*; the cabbage seedpod weevil *Ceutorhynchus assimilis*; the rape winter stem weevil *Ceutorhynchus picitarsis*; the wireworms *Conoderus vespertinus* and *Conoderus falli*; the banana weevil *Cosmopolites sordidus*; the New Zealand grass grub *Costelytra zealandica*; the June beetle *Cotinis nitida*; the sunflower stem weevil *Cylindrocopturus adspersus*; the larder beetle *Dermestes lardarius*; the corn rootworms *Diabrotica virgifera, Diabrotica virgifera virgifera*, and *Diabrotica barberi*; the Mexican bean beetle *Epilachna varivestis*; the old house borer *Hylotropes bajulus*; the lucerne weevil *Hypera postica*; the shiny spider beetle *Gibbium psylloides*; the cigarette beetle *Lasioderma serricorne*; the Colorado potato beetle *Leptinotarsa decemlineata; Lyctus* beetles {*Lyctus* spp., the pollen beetle *Meligethes aeneus*; the common cockshafer *Melolontha melolontha*; the American spider beetle *Mezium americanum*; the golden spider beetle *Niptus hololeucs*; the grain beetles *Oryzaephilus surinamensis* and *Oryzaephilus Mercator*; the black vine weevil *Otiorhynchus sulcatus*; the mustard beetle *Phaedon cochleariae*, the crucifer flea beetle *Phyllotreta cruciferae*; the striped flea beetle *Phyllotreta striolata*; the cabbage steam flea beetle *Psylliodes chrysocephala; Ptinus* spp. (spider beetles); the lesser grain borer *Rhizopertha dominica*; the pea and been weevil *Sitona lineatus*; the rice and granary beetles *Sitophilus oryzae* and *Sitophilus* granaries; the red sunflower seed weevil *Smicronyx fulvus*; the drugstore beetle *Stegobium paniceum*; the yellow mealworm beetle *Tenebrio molitor*, the flour beetles *Tribolium castaneum* and *Tribolium confusum*; warehouse and cabinet beetles {*Trogoderma* spp.); the sunflower beetle *Zygogramma* exclamation's; *Dermaptera* (earwigs) such as the European earwig *Forficula auricularia* and the striped earwig *Labidura riparia; Dictyoptera* such as the oriental cockroach *Blatta orientalis*; the greenhouse millipede *Oxidus gracilis*; the beet fly *Pegomyia betae*; the frit fly *Oscinella frit*; fruitflies (*Dacus* spp., *Drosophila* spp.); Isoptera (termites) including species from the familes Hodotermitidae, Kalotermitidae, Mastotermitidae, Rhinotermitidae, Serritermitidae, Termitidae, Termopsidae; the tarnished plant bug *Lygus lineolaris*; the black bean aphid *Aphis fabae*; the cotton or melon aphid *Aphis gossypii*; the green apple aphid *Aphis pomi*; the citrus spiny whitefly *Aleurocanthus spiniferus*; the sweet potato whitefly *Bemesia tabaci*; the cabbage aphid *Brevicoryne brassicae*; the pear *psylla Cacopsylla pyricola*; the currant aphid *Cryptomyzus* rib's; the grape *phylloxera Daktulosphaira vitifoliae*; the citrus *psylla Diaphorina citri*; the potato leafhopper *Empoasca fabae*; the bean leafhopper *Empoasca* Solana; the vine leafhopper *Empoasca vitis*; the woolly aphid *Eriosoma lanigerum*; the European fruit scale *Eulecanium corni*; the mealy plum aphid *Hyalopterus arundinis*; the small brown planthopper *Laodelphax striatellus*; the potato aphid *Macrosiphum euphorbiae*; the green peach aphid *Myzus persicae*; the green rice leafhopper *Nephotettix cinticeps*; the brown planthopper *Nilaparvata lugens*; the hop aphid *Phorodon humuli*; the bird-cherry aphid *Rhopalosiphum padi*; the grain aphid *Sitobion avenae*; Lepidoptera such as *Adoxophyes orana* (summer fruit *tortrix* moth); *Archips podana* (fruit tree *tortrix* moth); *Bucculatrix pyrivorella* (pear leafminer); *Bucculatrix thurberiella* (cotton leaf perforator); *Bupalus piniarius* (pine looper); *Carpocapsa pomonella* (codling moth); *Chilo suppressalis* (striped rice borer); *Choristoneura fumiferana* (eastern spruce budworm); *Cochylis hospes* (banded sunflower moth); *Diatraea grandiosella* (southwestern corn borer); *Eupoecilia ambiguella* (European grape berry moth); *Helicoverpa armigera* (cotton bollworm); *Helicoverpa zea* (cotton bollworm); *Heliothis vires cens* (tobacco budworm), *Homeosoma electellum* (sunflower moth); *Homona magnanima* (oriental tea tree *tortrix* moth); *Lithocolletis blancardella* (spotted tentiform leafminer); *Lymantria dispar* (gypsy moth); *Malacosoma neustria* (tent caterpillar); *Mamestra brassicae* (cabbage armyworm); *Mamestra configurata* (Bertha armyworm); *Operophtera brumata* (winter moth); *Ostrinia nubilalis* (European corn borer), *Panolis flammea* (pine beauty moth), *Phyllocnistis citrella* (citrus leafminer); *Pieris brassicae* (cabbage white butterfly); *Rachiplusia ni* (soybean looper); *Spodoptera exigua* (beet armywonn); *Spodoptera* littoral's (cotton leafworm); *Sylepta derogata* (cotton leaf roller); *Trichoplusia ni* (cabbage looper); Orthoptera such as the common cricket *Acheta domesticus*, tree locusts (*Anacridium* spp.), the migratory locust *Locusta migratoria*, the twostriped grasshopper *Melanoplus bivittatus*, the differential grasshopper *Melanoplus differ entialis*, the red-legged grasshopper *Melanoplus femurrubrum*, the migratory grasshopper *Melanoplus sanguinipes*, the northern mole cricket *Neocurtilla hexadectyla*, the red locust *Nomadacris septemfasciata*, the shortwinged mole cricket *Scapteriscus abbreviatus*, the southern mole cricket *Scapteriscus borellii*, the tawny mole cricket *Scapteriscus vicinus*, and the desert locust *Schistocerca gregaria; Symphyla* such as the garden symphylan *Scutigerella immaculata*; Thysanoptera such as the tobacco *thrips Frankliniella fusca*, the flower *thrips*

*Frankliniella intonsa*, the western flower *thrips Frankliniella occidentalism* the cotton bud *thrips Frankliniella schultzei*, the banded greenhouse *thrips Hercinothrips femoralis*, the soybean *thrips Neohydatothrips variabilis*, Kelly's citrus *thrips Pezothrips kellyanus*, the avocado *thrips Scirtothrips perseae*, the melon *thrips Thrips palmi*, and the onion *thrips Thrips tabaci*; and the like, and combinations comprising one or more of the foregoing organisms.

In some embodiments, expression of one or more protein toxins (e.g., insecticidal proteins) in the CESA-inhibiting herbicides-tolerant plants is effective for controlling flea beetles, i.e. members of the flea beetle tribe of family Chrysomelidae, preferably against *Phyllotreta* spp., such as *Phyllotreta cruciferae* and/or *Phyllotreta triolata*. In other embodiments, expression of one or more protein toxins {e.g., insecticidal proteins) in the CESA-inhibiting herbicides-tolerant plants is effective for controlling cabbage seedpod weevil, the Bertha armyworm, *Lygus* bugs, or the diamondback moth.

Furthermore, in one embodiment, CESA-inhibiting herbicides-tolerant plants are also covered which are, e.g. by the use of recombinant DNA techniques and/or by breeding and/or otherwise selected for such traits, rendered able to synthesize one or more proteins to increase the resistance or tolerance of those plants to bacterial, viral or fungal pathogens. The methods for producing such genetically modified plants are generally known to the person skilled in the art.

Furthermore, in another embodiment, CESA-inhibiting herbicides-tolerant plants are also covered which are, e.g. by the use of recombinant DNA techniques and/or by breeding and/or otherwise selected for such traits, rendered able to synthesize one or more proteins to increase the productivity (e.g. oil content), tolerance to drought, salinity or other growth-limiting environmental factors or tolerance to pests and fungal, bacterial or viral pathogens of those plants.

Furthermore, in other embodiments, CESA-inhibiting herbicides-tolerant plants are also covered which are, e.g. by the use of recombinant DNA techniques and/or by breeding and/or otherwise selected for such traits, altered to contain a modified amount of one or more substances or new substances, for example, to improve human or animal nutrition, e.g. oil crops that produce health-promoting long-chain omega-3 fatty acids or unsaturated omega-9 fatty acids (e.g. Nexera® rape, Dow Agro Sciences, Canada).

Furthermore, in some embodiments, CESA-inhibiting herbicides-tolerant plants are also covered which are, e.g. by the use of recombinant DNA techniques and/or by breeding and/or otherwise selected for such traits, altered to contain increased amounts of vitamins and/or minerals, and/or improved profiles of nutraceutical compounds.

In one embodiment, CESA-inhibiting herbicides-tolerant plants of the present invention, relative to a wild-type plant, comprise an increased amount of, or an improved profile of, a compound selected from the group consisting of: glucosinolates (e.g., glucoraphanin (4-methylsulfinylbutyl-glucosinolate), sulforaphane, 3-indolylmethyl-glucosinolate (glucobrassicin), l-methoxy-3-indolylmethyl-glucosinolate (neoglucobrassicin)); phenolics (e.g., flavonoids (e.g., quercetin, kaempferol), hydroxycinnamoyl derivatives (e.g., 1,2, 2'-trisinapoylgentiobiose, 1,2-diferuloylgentiobiose, 1,2'-disinapoyl-2-feruloylgentiobiose, 3-0-caffeoyl-quinic (neochlorogenic acid)); and vitamins and minerals (e.g., vitamin C, vitamin E, carotene, folic acid, niacin, riboflavin, thiamine, calcium, iron, magnesium, potassium, selenium, and zinc).

In another embodiment, CESA-inhibiting herbicides-tolerant plants of the present invention, relative to a wild-type plant, comprise an increased amount of, or an improved profile of, a compound selected from the group consisting of: progoitrin; isothiocyanates; indoles (products of glucosinolate hydrolysis); glutathione; carotenoids such as beta-carotene, lycopene, and the xanthophyll carotenoids such as lutein and zeaxanthin; phenolics comprising the flavonoids such as the flavonols (e.g. quercetin, rutin), the flavans/tannins (such as the procyanidins comprising coumarin, proanthocyanidins, catechins, and anthocyanins); flavones; phytoestrogens such as coumestans, lignans, resveratrol, isoflavones e.g. genistein, daidzein, and glycitein; resorcyclic acid lactones; organosulphur compounds; phytosterols; terpenoids such as carnosol, rosmarinic acid, glycyrrhizin and saponins; chlorophyll; chlorphyllin, sugars, anthocyanins, and vanilla.

In other embodiments, CESA-inhibiting herbicides-tolerant plants of the present invention, relative to a wild-type plant, comprise an increased amount of, or an improved profile of, a compound selected from the group consisting of: vincristine, vinblastine, taxanes (e.g., taxol (paclitaxel), baccatin III, 10-desacetylbaccatin III, 10-desacetyl taxol, xylosyl taxol, 7-epitaxol, 7-epibaccatin III, 10-desacetylcephalomannine, 7-epicephalomannine, taxotere, cephalomannine, xylosyl cephalomannine, taxagifine, 8-benxoyloxy taxagifine, 9-acetyloxy taxusin, 9-hydroxy taxusin, taiwanxam, taxane Ia, taxane Ib, taxane Ic, taxane Id, GMP paclitaxel, 9-dihydro 13-acetylbaccatin III, 10-desacetyl-7-epitaxol, tetrahydrocannabinol (THC), cannabidiol (CBD), genistein, diadzein, codeine, morphine, quinine, shikonin, ajmalacine, serpentine, and the like.

In other aspects, a method for treating a plant of the present invention is provided.

In some embodiments, the method comprises contacting the plant with an agronomically acceptable composition. In one embodiment, the agronomically acceptable composition comprises a CESA inhibiting herbicide A. I, such as an azine as described herein.

In another aspect, the present invention provides a method for preparing a descendent seed. The method comprises planting a seed of or capable of producing a plant of the present invention. In one embodiment, the method further comprises growing a descendent plant from the seed; and harvesting a descendant seed from the descendent plant. In other embodiments, the method further comprises applying a CESA-inhibiting herbicides herbicidal composition to the descendent plant.

In another embodiment, the invention refers to harvestable parts of the plant according to the present invention. Preferably, the harvestable parts comprise the CESA nucleic acid or CESA protein of the present invention. The harvestable parts may be seeds, roots, leaves and/or flowers comprising the CESA nucleic acid or CESA protein or parts thereof. Preferred parts of soy plants are soy beans comprising the CESA nucleic acid or CESA protein.

In another embodiment, the invention refers to products derived from a plant according to the present invention, parts thereof or harvestable parts thereof. A preferred plant product is fodder, seed meal, oil, or seed-treatment-coated seeds. Preferably, the meal and/or oil comprise the CESA nucleic acids or CESA proteins.

In another embodiment, the invention refers to a method for the production of a product, which method comprises a) growing the plants of the invention or obtainable by the methods of invention and b) producing said product from or by the plants of the invention and/or parts, e.g. seeds, of these plants.

In a further embodiment the method comprises the steps a) growing the plants of the invention, b) removing the harvestable parts as defined above from the plants and c) producing said product from or by the harvestable parts of the invention.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

Herbicides

As described above, the present invention provides nucleic acids, polypeptides, conferring tolerance of plants to compounds/herbicides interfering or inhibiting cell wall (cellulose) biosynthesis by interfering with the activity of cellulose synthase ("CESA-inhibiting herbicides"), also known to the person skilled in the art as Cellulose Biosynthesis Inhibitors (CBI).

Examples of herbicides which can be used according to the present invention, i.e. to which the plants according to the present invention are tolerant/resistant to, are compounds known to the skilled artisan as azines. Examples of Azines are described in detail in the following patent applications depicted in the following Table 1, which are incorporated by reference in its entirety.

TABLE 1

| No.: | Structural Formula | Publication or Application number/Internal reference |
|---|---|---|
| 1 | 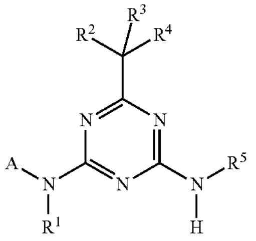 I, | WO 2014/064094 PF74283 |
| 2 | 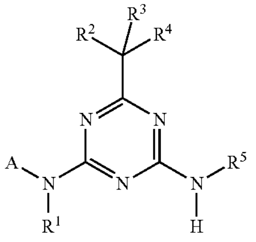 (I), | WO 2015/007711 PF75365 |
| 3 | 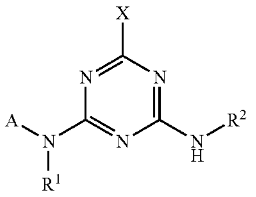 (I) | PCT/EP2015/056711 PF76068 |
| 4 | 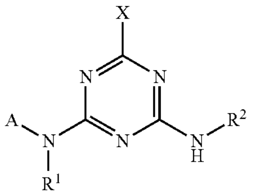 (I) | EP 14163356.0 PF76069 |
| 5 | 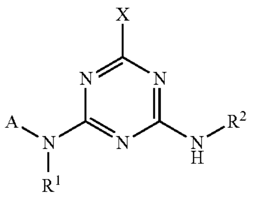 (I) | EP 14163742.1 PF76635 |
| 6 | 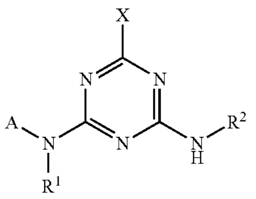 (I) | EP 14163743.9 PF76636 |

TABLE 1-continued

| No.: | Structural Formula | Publication or Application number/Internal reference |
|---|---|---|
| 7 | 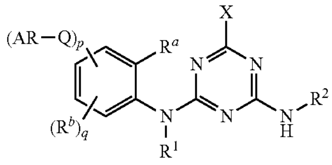 | EP 14165565.4 PF76857 |
| 8 | 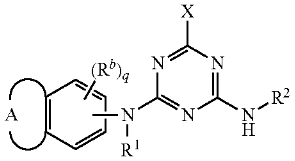 | EP 14165624.9 PF76888 |
| 9 | 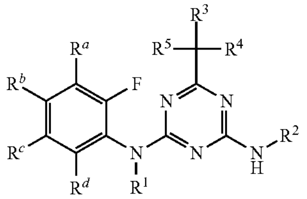 | EP 14164431.0 PF76890 |
| 10 | 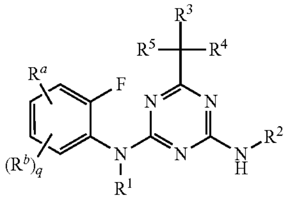 | EP 14164434.4 PF76930 |
| 11 | 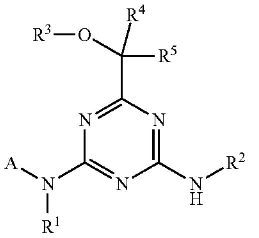 (I) | EP 14164433.6 PF77027 |
| 12 | 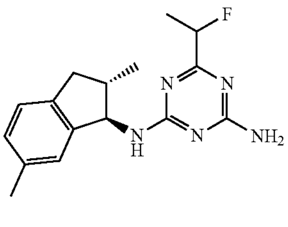 [SMILES: Cc1ccc2c(c1)[C@H](Nc1nc(N)nc(C(C)F)n1)[C@@H](C)C2] | Indaziflam |
| 13 | 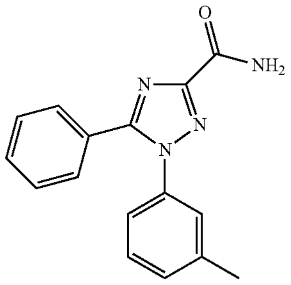 [SMILES: Cc1cccc(-n2nc(C(N)=O)nc2-c2ccccc2)c1] | Triazofenamid |

Examples of preferred CESA inhibiting herbicides from the group of so-called azines which can be used according to the present invention are compounds having the Formula (I), known to the skilled artisan as azines.

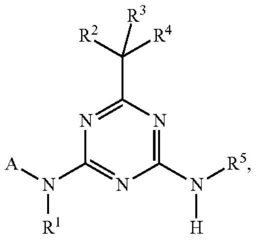

I wherein

A is phenyl, which is substituted by two to five substituents selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_1$-$C_6$-haloalkynyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

$R^1$ H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl, wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

$R^2$ H, halogen, CN, $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, OH, $C_1$-$C_6$-alkoxy or $C_1$-$C_6$-alkoxy-$C_1$-$C_6$-alkyl;

$R^3$ H, halogen, CN, $C_1$-$C_6$-alkyl, $C_1$-$C_6$-haloalkyl or $C_1$-$C_6$-alkoxy;

$R^4$ H, halogen, CN, $C_1$-$C_6$-alkyl or $C_1$-$C_6$-haloalkyl; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl, wherein the $C_3$-$C_6$-cycloalkyl, $C_3$-$C_6$-cycloalkenyl, or three- to six-membered heterocyclyl is unsubstituted or substituted by one to three substituents selected from halogen, CN, $C_1$-$C_6$-alkyl and $C_1$-$C_6$-alkoxy; and $R^5$ H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl, wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

including their agriculturally acceptable salts or N-oxides.

Preferably the present invention provides azines of formula (I), wherein

A is 2-fluoro-phenyl, which is substituted by one to four substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl and ($C_1$-$C_6$-alkoxy)-carbonyl;

$R^1$ H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl, wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

$R^2$ H, halogen, CN, $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, OH, $C_1$-$C_6$-alkoxy or $C_1$-$C_6$-alkoxy-$C_1$-$C_6$-alkyl;

$R^3$ H, halogen, CN, $C_1$-$C_6$-alkyl, $C_1$-$C_6$-haloalkyl or $C_1$-$C_6$-alkoxy;

$R^4$ H, halogen, CN, $C_1$-$C_6$-alkyl or $C_1$-$C_6$-haloalkyl; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl, wherein the $C_3$-$C_6$-cycloalkyl, $C_3$-$C_6$-cycloalkenyl or and three- to six-membered heterocyclyl is unsubstituted or substituted by one to three substituents selected from halogen, CN, $C_1$-$C_6$-alkyl and $C_1$-$C_6$-alkoxy; and $R^5$ H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl, wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

including their agriculturally acceptable salts or N-oxides.

Useful for the present invention are also agrochemical compositions comprising at least one azines of formula (I) and auxiliaries customary for formulating crop protection agents.

The present invention also provides the use of azines of formula (I) as herbicides, i.e. for controlling harmful plants.

If the azines of formula (I) as described herein are capable of forming geometrical isomers, for example E/Z isomers, it is possible to use both, the pure isomers and mixtures thereof, in the compositions according to the invention.

If the azines of formula (I) as described herein have one or more centres of chirality and, as a consequence, are present as enantiomers or diastereomers, it is possible to use both, the pure enantiomers and diastereomers and their mixtures, in the compositions according to the invention.

If the azines of formula (I) as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

The organic moieties mentioned in the definition of the variables, e.g. $R^1$ to $R^5$, are—like the term halogen—collective terms for individual enumerations of the individual group members. The term halogen denotes in each case fluorine, chlorine, bromine or iodine. All hydrocarbon chains, i.e. all alkyl, haloalkyl, alkenyl, alkynyl, alkoxy, alkylthio, alkylsulfinyl, alkylsulfonyl, (alkyl)amino, di(alkyl)amino chains can be straight-chain or branched, the prefix $C_n$-$C_m$ denoting in each case the possible number of carbon atoms in the group.

Examples of such meanings are:

$C_1$-$C_1$-alkyl: for example $CH_3$, $C_2H_5$, n-propyl, $CH(CH_3)_2$, n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of ($C_1$-$C_6$-alkyl)carbonyl, $C_1$-$C_6$-alkyoxy-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_1$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl: monocyclic saturated hydrocarbons having 3 to 6 ring members, such as cyclopropyl, cyclobutyl, cyclopentyl and cyclohexyl;

$C_2$-$C_6$-alkenyl: for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_3$-$C_6$-cycloalkenyl: 1-cyclopropenyl, 2-cyclopropenyl, 1-cyclobutenyl, 2-cyclobutenyl, 1-cyclopentenyl, 2-cyclopentenyl, 1,3-cyclopentadienyl, 1,4-cyclopentadienyl, 2,4-cyclopentadienyl, 1-cyclohexenyl, 2-cyclohexenyl, 3-cyclohexenyl, 1,3-cyclohexadienyl, 1,4-cyclohexadienyl, 2,5-cyclohexadienyl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of ($C_1$-$C_6$-alkoxy)carbonyl, $C_1$-$C_6$-alkoxy-$C_1$-$C_6$-alkyl: $C_1$-$C_4$-alkoxy as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-alkylsulfinyl ($C_1$-$C_6$-alkyl-S(═O)—): z.B. methylsulfinyl, ethylsulfinyl, propylsulfinyl, 1-methylethylsulfinyl, butylsulfinyl, 1-methylpropylsulfinyl, 2-methylpropylsulfinyl, 1,1-di-methylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentyl-sulfinyl, 1,1-dimethylbutylsulfinyl, 1,2-dimethylbutylsulfinyl, 1,3-dimethylbutyl-sulfinyl, 2,2-dimethylbutylsulfinyl, 2,3-dimethylbutylsulfinyl, 3,3-dimethylbutyl-sulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-alkylsulfonyl ($C_1$-$C_6$-alkyl-$S(O)_2$—): for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethyl-propylsulfonyl, 1,2,2-trimethylpropylsulfonyl, 1-ethyl-1-methylpropylsulfonyl and 1-ethyl-2-methylpropylsulfonyl;

($C_1$-$C_4$-alkyl)amino: for example methylamino, ethylamino, propylamino, 1-methylethyl-amino, butylamino, 1-methylpropylamino, 2-methylpropylamino or 1,1-dimethylethylamino;

($C_1$-$C_6$-alkyl)amino: ($C_1$-$C_4$-alkylamino) as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutyl-amino 3,3-dimethylbutyl-amino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

di($C_1$-$C_4$-alkyl)amino: for example N,N-dimethylamino, N,N-diethylamino, N,N-di(1-methylethyl)amino, N,N-dipropylamino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$-$C_6$-alkyl)amino: di($C_1$-$C_4$-alkyl)amino as mentioned above, and also, for example, N-methyl-N-pentylamino, N-methyl-N-(1-methylbutyl)amino, N-methyl-N-(2-methyl-butyl)amino, N-methyl-N-(3-methylbutyl)amino, N-methyl-N-(2,2-dimethylpropyl)amino, N-methyl-N-(1-ethylpropyl)amino, N-methyl-N-hexylamino, N-methyl-N-(1,1-dimethyl-propyl)amino, N-methyl-N-(1,2-dimethylpropyl)amino, N-methyl-N-(1-methylpentyl)amino, N-methyl-N-(2-methylpentyl)amino, N-methyl-N-(3-methylpentyl)amino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethyl-butyl)amino, N-methyl-N-(2,3-dimethylbutyl)amino, N-methyl-N-(3,3-dimethylbutyl)amino, N-methyl-N-(1-ethylbutyl)amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methylpentyl)amino, N-ethyl-N-(3-methylpentyl)amino, N-ethyl-N-(4-methylpentyl)amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethylbutyl)amino, N-ethyl-N-(3,3-dimethylbutyl)amino, N-ethyl-N-(1-ethylbutyl)amino, N-ethyl-N-(2-ethylbutyl)amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

three- to six-membered heterocyclyl: monocyclic saturated or partially unsaturated hydrocarbon having three to six ring members as mentioned above which, in addition to carbon atoms, contains one or two heteroatoms selected from O, S and N;

for example 2-oxiranyl, 2-oxetanyl, 3-oxetanyl, 2-aziridinyl, 3-thietanyl, 1-azetidinyl, 2-azetidinyl, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl;

for example 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 4,5-dihydropyrrol-2-yl, 4,5-dihydropyrrol-3-yl, 2,5-dihydropyrrol-2-yl, 2,5-dihydropyrrol-3-yl, 4,5-dihydroisoxazol-3-yl, 2,5-dihydroisoxazol-3-yl, 2,3-dihydroisoxazol-3-yl, 4,5-dihydroisoxazol-4-yl, 2,5-dihydroisoxazol-4-yl, 2,3-dihydroisoxazol-4-yl, 4,5-dihydroisoxazol-5-yl, 2,5-dihydroisoxazol-5-yl, 2,3-dihydroisoxazol-5-yl, 4,5-dihydroisothiazol-3-yl, 2,5-dihydroisothiazol-3-yl, 2,3-dihydroisothiazol-3-yl, 4,5-dihydroisothiazol-4-yl, 2,5-dihydroisothiazol-4-yl, 2,3-dihydroisothiazol-4-yl, 4,5-dihydroisothiazol-5-yl, 2,5-dihydroisothiazol-5-yl, 2,3-dihydroisothiazol-5-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-3-yl, 3,4-dihydropyrazol-4-yl, 3,4-dihydropyrazol-5-yl, 4,5-dihydropyrazol-3-yl, 4,5-dihydropyrazol-4-yl, 4,5-dihydropyrazol-5-yl, 2,3-dihydroimidazol-2-yl, 2,3- dihydroimidazol-3-yl, 2,3-dihydroimidazol-4-yl, 2,3-dihydroimidazol-5-yl, 4,5-dihydroimidazol-2-yl, 4,5-di-hydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2,3-dihydrooxazol-3-yl, 2,3-dihydrooxazol-4-yl, 2,3-dihydrooxazol-5-yl, 3,4-dihydrooxazol-3-yl, 3,4-dihydrooxazol-4-yl, 3,4-dihydrooxazol-5-yl, 2,3-dihydrothiazol-3-yl, 2,3-dihydrothiazol-4-yl, 2,3-dihydrothiazol-5-yl, 3,4-dihydrothiazol-3-yl, 3,4-dihydrothiazol-4-yl, 3,4-dihydrothiazol-5-yl, 3,4-dihydrothiazol-2-yl, 3,4-dihydrothiazol-3-yl, 3,4-dihydrothiazol-4-yl;

for example 2-piperidinyl, 3-piperidinyl, 4-piperidinyl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,4-dithian-2-yl, 1,3-dithian-5-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, tetrahydro-1,3-oxazin-2-yl, tetrahydro-1,3-oxazin-6-yl, 2-morpholinyl, 3-morpholinyl;

for example 2H-pyran-2-yl, 2H-pyran-3-yl, 2H-pyran-4-yl, 2H-pyran-5-yl, 2H-pyran-6-yl, 3,6-dihydro-2H-pyran-2-yl, 3,6-dihydro-2H-pyran-3-yl, 3,6-dihydro-2H-pyran-4-yl, 3,6-dihydro-2H-pyran-5-yl, 3,6-dihydro-2H-pyran-6-yl, 3,4-dihydro-2H-pyran-3-yl, 3,4-dihydro-2H-pyran-4-yl, 3,4-dihydro-2H-pyran-6-yl, 2H-thiopyran-2-yl, 2H-thiopyran-3-yl, 2H-thiopyran-4-yl, 2H-thiopyran-5-yl, 2H-thiopyran-6-yl, 5,6-dihydro-4H-1,3-oxazin-2-yl;

The preferred embodiments of the invention mentioned herein below have to be understood as being preferred either independently from each other or in combination with one another.

According to a preferred embodiment of the invention preference is also given to those azines of formula (I), wherein the variables, either independently of one another or in combination with one another, have the following meanings:

Preferred are the azines of formula (I), wherein

A is phenyl, which is substituted by two to five substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy) carbonyl;
- particularly preferred phenyl, which is substituted by two to five substituents selected from the group consisting of halogen, CN, $C_1$-$C_6$-alkyl and $C_1$-$C_6$-alkoxy;
  - particularly preferred selected from halogen and CN;
  - also particularly preferred selected from the group consisting of F, Cl, CN and $CH_3$;
  - especially preferred selected from the group consisting of F, Cl and CN;
- especially preferred phenyl, which is substituted by two to four substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;
  - particularly preferred selected from the group consisting of halogen, CN, $C_1$-$C_6$-alkyl and $C_1$-$C_6$-alkoxy;
  - especially preferred selected from halogen and CN;
  - also especially preferred selected from the group consisting of F, Cl, CN and $CH_3$;
  - more preferred selected from the group consisting of F, Cl and CN;
- more preferred phenyl, which is substituted by two substituents
  - selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl) amino, di($C_1$-$C_6$-alkyl)amino, ($C_1$-$C_6$-alkyl)-carbonyl, ($C_1$-$C_6$-alkoxy)carbonyl;
  - particularly preferred selected from the group consisting of halogen, CN, $C_1$-$C_6$-alkyl and $C_1$-$C_6$-alkoxy;
  - especially preferred selected from halogen and CN;
  - also especially preferred selected from the group consisting of F, Cl, CN and $CH_3$; more preferred selected from the group consisting of F, Cl and CN;
- also more preferred phenyl, which is substituted by three substituents
  - selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl) amino, di($C_1$-$C_6$-alkyl)amino, ($C_1$-$C_6$-alkyl)-carbonyl, ($C_1$-$C_6$-alkoxy)carbonyl;
  - particularly preferred selected from the group consisting of halogen, CN, $C_1$-$C_6$-alkyl and $C_1$-$C_6$-alkoxy;
  - especially preferred selected from halogen and CN;
  - also especially preferred selected from the group consisting of F, Cl, CN and $CH_3$; more preferred selected from the group consisting of F, Cl and CN;
- also more preferred phenyl, which is substituted by four substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl) sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;
  - particularly preferred selected from the group consisting of halogen, CN, $C_1$-$C_6$-alkyl and $C_1$-$C_6$-alkoxy;
  - especially preferred selected from halogen and CN;
  - also especially preferred selected from the group consisting of F, Cl, CN and $CH_3$;
  - more preferred selected from the group consisting of F, Cl and CN.

Also preferred are the azines of formula (I), wherein A is (A.1)

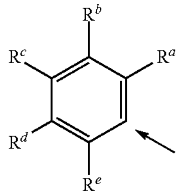

wherein $R^a$ and $R^e$ independently of one another are halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl; and $R^b$, $R^c$ and $R^d$ independently of one another are hydrogen, halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;

particularly preferred $R^a$ and $R^e$ independently of one another are halogen, CN, $C_1$-$C_6$-alkyl or $C_1$-$C_6$-alkoxy; and $R^b$, $R^c$ and $R^d$ independently of one another are hydrogen, halogen, CN, $NO_2$, $C_1$-$C_6$-alkyl, $C_1$-$C_6$-haloalkyl or $C_1$-$C_6$-alkoxy;

especially preferred $R^a$ and $R^e$ independently of one another are halogen or CN; and $R^b$, $R^c$ and $R^d$ independently of one another are hydrogen, halogen, CN, $C_1$-$C_6$-alkyl or $C_1$-$C_6$-alkoxy;

more preferred $R^a$ and $R^e$ are halogen; and $R^b$, $R^c$ and $R^d$ independently of one another are hydrogen, halogen or CN;

most preferred $R^a$ and $R^e$ are halogen; and $R^b$, $R^c$ and $R^d$ are hydrogen;

also most preferred $R^a$, $R^b$, $R^d$ and $R^e$ are halogen; and $R^c$ hydrogen;

also most preferred $R^a$, $R^b$, $R^c$, $R^d$ and $R^e$ are halogen.

Also preferred are the azines of formula (I), wherein A is (A.1)

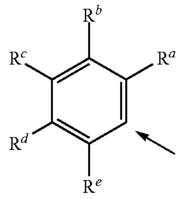

wherein $R^a$ is halogen or CN;

$R^b$ and $R^d$ are H, halogen or CN;

$R^c$ is H or halogen;

$R^e$ is halogen, CN or $C_1$-$C_6$-alkyl;

particularly preferred $R^a$ is halogen;

$R^b$, $R^c$ and $R^d$ are H or halogen; and $R^e$ is halogen or CN;

especially preferred $R^a$, $R^b$, $R^d$ and $R^e$ are halogen; and $R^c$ is H or halogen;

more preferred $R^a$, $R^b$, $R^d$ and $R^e$ are F; and $R^c$ is H or F.

Especially preferred are the azines of formula (I), wherein A is selected from the group consisting of (A.1.1), (A.1.2) and (A.1.3);

more preferred selected from the group consisting of (A.1.2) and (A.1.3);

(A.1.1)

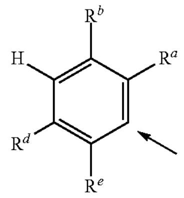

(A.1.2)

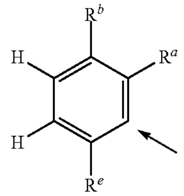

(A.1.3)

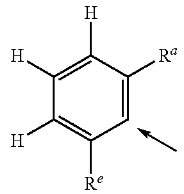

wherein $R^a$ and $R^e$ independently of one another are halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl; and $R^b$ and $R^d$ independently of one another are halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;

particularly preferred $R^a$ and $R^e$ independently of one another are halogen, CN, $C_1$-$C_6$-alkyl or $C_1$-$C_6$-alkoxy; and $R^b$ and $R^d$ independently of one another are halogen, CN, $NO_2$, $C_1$-$C_6$-alkyl, $C_1$-$C_6$-haloalkyl or $C_1$-$C_6$-alkoxy;

especially preferred $R^a$ and $R^e$ independently of one another halogen or CN; and $R^b$ and $R^d$ independently of one another are halogen, CN, $C_1$-$C_6$-alkyl or $C_1$-$C_6$-alkoxy;

more preferred $R^a$ and $R^e$ are halogen; and $R^b$ and $R^d$ independently of one another are halogen or CN;

most preferred $R^a$, $R^b$, $R^d$ and $R^e$ are halogen.

Also especially preferred are the azines of formula (I), wherein

A is (A.1.1)

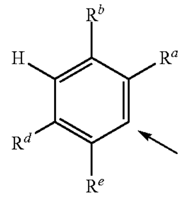

wherein $R^a$, $R^b$, $R^d$ and $R^e$ have the meanings, in particular the preferred meanings, as defined above.

Also especially preferred are the azines of formula (I), wherein

A is (A.1.2)

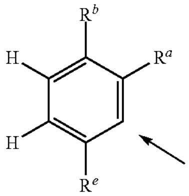

wherein $R^a$, $R^b$ and $R^e$ have the meanings, in particular the preferred meanings, as defined above.

Also especially preferred are the azines of formula (I), wherein

A is (A.1.3)

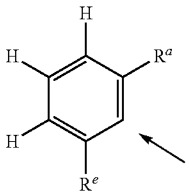

wherein $R^a$ and $R^e$ have the meanings, in particular the preferred meanings, as defined above.

Also preferred are the azines of formula (I), wherein

A is 2-fluoro-phenyl, which is substituted by one to four substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl and ($C_1$-$C_6$-alkoxy)carbonyl;

particularly preferred 2-fluoro-phenyl, which is substituted by one to four substituents selected from the group consisting of halogen, CN, $C_1$-$C_6$-alkyl and $C_1$-$C_6$-alkoxy;

particularly preferred selected from halogen and CN;

also particularly preferred selected from the group consisting of F, Cl, CN and $CH_3$;

especially preferred selected from the group consisting of F, Cl and CN;

especially preferred 2-fluoro-phenyl, which is substituted by one to three substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl and ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

more preferred 2-fluoro-phenyl, which is substituted by one substituent selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl) sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl and ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

also more preferred 2-fluoro-phenyl, which is substituted by two substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl and ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

also more preferred 2-fluoro-phenyl, which is substituted by three substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl and ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN.

Also preferred are the azines of formula (I), wherein A is (A.1a)

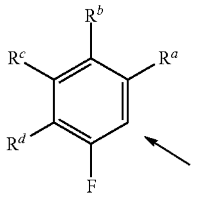

wherein $R^a$ is halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl; and $R^b$, $R^c$ and $R^d$ independently of one another are hydrogen, halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;

particularly preferred $R^a$ is halogen, CN, $C_1$-$C_6$-alkyl or $C_1$-$C_6$-alkoxy; and $R^b$, $R^c$ and $R^d$ independently of one another are hydrogen, halogen, CN, $NO_2$, $C_1$-$C_6$-alkyl, $C_1$-$C_6$-haloalkyl or $C_1$-$C_6$-alkoxy;

especially preferred $R^a$ is halogen or CN; and $R^b$, $R^c$ and $R^d$ independently of one another are hydrogen, halogen, CN, $C_1$-$C_6$-alkyl or $C_1$-$C_6$-alkoxy;

more preferred $R^a$ is halogen; and $R^b$, $R^c$ and $R^d$ independently of one another are hydrogen, halogen or CN;

most preferred $R^a$ is halogen; and $R^b$, $R^c$ and $R^d$ are hydrogen;

also most preferred $R^a$, $R^b$ and $R^d$ are halogen; and $R^c$ is hydrogen;

also most preferred $R^a$, $R^b$, $R^c$ and $R^d$ are halogen.

Also preferred are the azines of formula (I), wherein A is (A.1a)

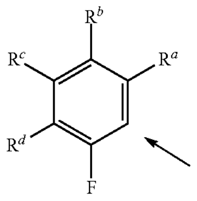

wherein $R^a$ is halogen, CN or $C_1$-$C_6$-alkyl;

$R^b$ and $R^d$ are H, halogen or CN; and $R^c$ is H or halogen;

particularly preferred $R^a$ is halogen or CN; and $R^b$, $R^c$ and $R^d$ are H or halogen;

especially preferred $R^a$, $R^b$ and $R^d$ are halogen; and $R^c$ is H or halogen;

Also especially preferred $R^a$, $R^b$ and $R^d$ are halogen; and $R^c$ is H, F, Br or I;

more preferred $R^a$, $R^b$ and $R^d$ are F; and $R^c$ is F, Br or I;

also more preferred $R^a$, $R^b$ and $R^d$ are F; and $R^c$ is H or F.

Especially preferred are the azines of formula (I), wherein A is selected from the group consisting of (A.1a.1), (A.1a.2) and (A.1a.3);

more preferred selected from the group consisting of (A.1.2) and (A.1.3);

(A.1a.1)

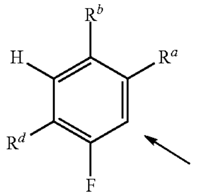

(A.1a.2)

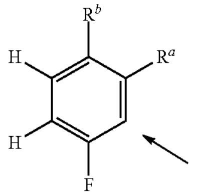

(A.1a.3)

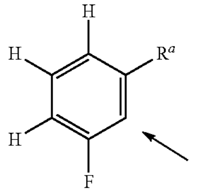

wherein $R^a$ is halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl; and $R^b$ and $R^d$ independently of one another are halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;

particularly preferred $R^a$ is halogen, CN, $C_1$-$C_6$-alkyl or $C_1$-$C_6$-alkoxy; and $R^b$ and $R^d$ independently of one another are halogen, CN, $NO_2$, $C_1$-$C_6$-alkyl, $C_1$-$C_6$-haloalkyl or $C_1$-$C_6$-alkoxy;

especially preferred $R^a$ is halogen or CN; and $R^b$ and $R^d$ independently of one another are halogen, CN, $C_1$-$C_6$-alkyl or $C_1$-$C_6$-alkoxy;

more preferred $R^a$ is halogen; and $R^b$ and $R^d$ independently of one another are halogen or CN;

most preferred $R^a$, $R^b$ and $R^d$ are halogen.

Also especially preferred are the azines of formula (I), wherein

A is (A.1a.1)

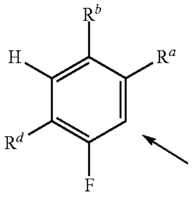

wherein $R^a$, $R^b$ and $R^d$ have the meanings, in particular the preferred meanings, as defined above.

Also especially preferred are the azines of formula (I), wherein

A is (A.1a.2)

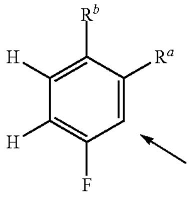

wherein $R^a$ and $R^b$ have the meanings, in particular the preferred meanings, as defined above.

Also especially preferred are the azines of formula (I), wherein

A is (A.1a.3)

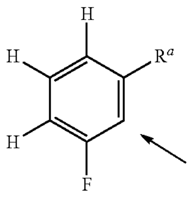

wherein $R^a$ has the meanings, in particular the preferred meanings, as defined above.

Also preferred are the azines of formula (I), wherein $R^1$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;

particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl) carbonyl or ($C_1$-$C_6$-alkyl)sulfonyl;

especially preferred H, CN, $CH_3$, $CH_2OCH_3$, $OCH_3$, $COCH_3$ or $SO_2CH_3$;

more preferred hydrogen.

Also preferred are the azines of formula (I), wherein $R^2$ is H, halogen, $C_1$-$C_6$-alkyl or $C_1$-$C_6$-haloalkyl;

particularly preferred halogen, $C_1$-$C_6$-alkyl or $C_1$-$C_6$-haloalkyl;

also particularly preferred H, F, Cl, $CH_3$ or $CF_3$.

Also preferred are the azines of formula (I), wherein $R^3$ and $R^4$ are independently of one another H, halogen, $C_1$-$C_6$-alkyl or $C_1$-$C_6$-haloalkyl; or together with the carbon atom to which they are attached form a moiety selected from the group consisting of $C_3$-$C_6$-cycloalkyl, $C_3$-$C_6$-cycloalkenyl and three- to six-membered heterocyclyl, wherein the $C_3$-$C_6$-cycloalkyl, $C_3$-$C_6$-cycloalkenyl or the three- to six-membered heterocyclyl is unsubstituted or substituted by one to three substituents selected from halogen, CN, $C_1$-$C_6$-alkyl and $C_1$-$C_6$-alkoxy;

independently of one another particularly preferred H, halogen, $C_1$-$C_6$-alkyl or $C_1$-$C_6$-haloalkyl; or together with the carbon atom to which they are attached form a moiety selected from the group consisting of $C_3$-$C_6$-cycloalkyl and $C_3$-$C_6$-cycloalkenyl, wherein the $C_3$-$C_6$-cycloalkyl or $C_3$-$C_6$-cycloalkenyl is unsubstituted or substituted by one to three substituents selected from halogen, CN, $C_1$-$C_6$-alkyl and $C_1$-$C_6$-alkoxy;

independently of one another especially preferred H, halogen, $C_1$-$C_6$-alkyl or $C_1$-$C_6$-haloalkyl;

independently of one another more preferred H, halogen or $C_1$-$C_6$-alkyl.

Also preferred are the azines of formula (I), wherein $R^2$ is H, halogen, $C_1$-$C_6$-alkyl; and $R^3$ and $R^4$ are independently of one another H, halogen, $C_1$-$C_6$-alkyl, or together with the carbon atom to which they are attached form a $C_3$-$C_6$-cycloalkyl;

particularly preferred $R^2$ is H, halogen or $C_1$-$C_6$-alkyl;

$R^3$ is $C_1$-$C_6$-alkyl;

$R^4$ is H, halogen or $C_1$-$C_6$-alkyl;

$R^3$ and $R^4$ together with the carbon atom to which they are attached form a $C_3$-$C_6$-cycloalkyl;

especially preferred $R^2$ is halogen or $C_1$-$C_6$-alkyl;

$R^3$ is $C_1$-$C_6$-alkyl;

$R^4$ is H or $C_1$-$C_6$-alkyl;

more preferred $R^2$ is halogen; and $R^3$ and $R^4$ are $C_1$-$C_6$-alkyl.

Also preferred are the azines of formula (I), wherein $R^5$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;

particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl) carbonyl or ($C_1$-$C_6$-alkyl)sulfonyl;

especially preferred H, CN, $CH_3$, $CH_2OCH_3$, $OCH_3$, $COCH_3$ or $SO_2CH_3$;

more preferred hydrogen.

Also preferred are the azines of formula (I), wherein

A is phenyl, which is substituted by two to five substituents selected from the group consisting of halogen, CN, $C_1$-$C_6$-alkyl and $C_1$-$C_6$-alkoxy; particularly preferred selected from halogen and CN;

also particularly preferred selected from the group consisting of F, Cl, CN and $CH_3$;

especially preferred selected from the group consisting of F, Cl and CN;

particularly preferred phenyl, which is substituted by two to four substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$; more preferred selected from the group consisting of F, Cl and CN;

especially preferred phenyl, which is substituted by two substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

also especially preferred phenyl, which is substituted by three substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$; more preferred selected from the group consisting of F, Cl and CN;

also specially preferred phenyl, which is substituted by four substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)carbonyl;

particularly preferred selected from the group consisting of halogen, CN, $C_1$-$C_6$-alkyl and $C_1$-$C_6$-alkoxy;

especially preferred selected from halogen and CN;

also especially preferred selected from the group consisting of F, Cl, CN and $CH_3$;

more preferred selected from the group consisting of F, Cl and CN;

$R^1$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;

particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;

especially preferred H, CN, $CH_3$, $CH_2OCH_3$, $OCH_3$, $COCH_3$ or $SO_2CH_3$;

more preferred hydrogen.

$R^2$ is H, halogen, $C_1$-$C_6$-alkyl or $C_1$-$C_6$-haloalkyl;

particularly preferred halogen, $C_1$-$C_6$-alkyl or $C_1$-$C_6$-haloalkyl;

also particularly preferred H, F, $CH_3$ or $CF_3$;

$R^3$ and $R^4$ are independently of one another H, halogen, $C_1$-$C_6$-alkyl or $C_1$-$C_6$-haloalkyl; or together with the carbon atom to which they are attached form a moiety selected from the group consisting of $C_3$-$C_6$-cycloalkyl, $C_3$-$C_6$-cycloalkenyl and three- to six-membered heterocyclyl, wherein the $C_3$-$C_6$-cycloalkyl, $C_3$-$C_6$-cycloalkenyl or the three- to six-membered heterocyclyl is unsubstituted or substituted by one to three substituents selected from halogen, CN, $C_1$-$C_6$-alkyl and $C_1$-$C_6$-alkoxy;

independently of one another particularly preferred H, halogen, $C_1$-$C_6$-alkyl or $C_1$-$C_6$-haloalkyl; or together with the carbon atom to which they are attached form a moiety selected from the group consisting of $C_3$-$C_6$-cycloalkyl and $C_3$-$C_6$-cycloalkenyl, wherein the $C_3$-$C_6$-cycloalkyl or $C_3$-$C_6$-cycloalkenyl is unsubstituted or substituted by one to three substituents selected from halogen, CN, $C_1$-$C_6$-alkyl and $C_1$-$C_6$-alkoxy;

independently of one another especially preferred H, halogen, $C_1$-$C_6$-alkyl or $C_1$-$C_6$-haloalkyl;

independently of one another more preferred H, halogen or $C_1$-$C_6$-alkyl;

and $R^5$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;

particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;

especially preferred H, CN, $CH_3$, $CH_2OCH_3$, $OCH_3$, $COCH_3$ or $SO_2CH_3$;

more preferred hydrogen.

Particular preference is given to azines of formula (I.a), which correspond to azines of formula (I) wherein A is (A.1) and $R^1$ and $R^5$ are H:

1.a

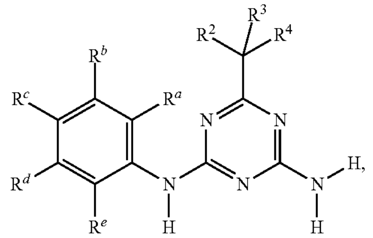

wherein the variables $R^a$, $R^b$, $R^c$, $R^d$, $R^e$, $R^2$, $R^3$ and $R^4$ have the meanings, in particular the preferred meanings, as defined above;

special preference is given to the azines of the formulae (I.a.1) to (I.a.1406) of Table A, where the definitions of the variables $R^a$, $R^b$, $R^c$, $R^d$, $R^e$, $R^2$, $R^3$ and $R^4$ are of particular importance for the compounds according to the invention not only in combination with one another but in each case also on their own:

TABLE A

| No. | $R^a$ | $R^b$ | $R^c$ | $R^d$ | $R^e$ | $R^2$ | $R^3$ | $R^4$ |
|---|---|---|---|---|---|---|---|---|
| I.a.1 | F | H | H | H | F | $CH_3$ | H | H |
| I.a.2 | Cl | H | H | H | F | $CH_3$ | H | H |
| I.a.3 | Br | H | H | H | F | $CH_3$ | H | H |
| I.a.4 | CN | H | H | H | F | $CH_3$ | H | H |
| I.a.5 | $CH_3$ | H | H | H | F | $CH_3$ | H | H |
| I.a.6 | F | H | H | F | F | $CH_3$ | H | H |
| I.a.7 | Cl | H | H | F | F | $CH_3$ | H | H |
| I.a.8 | F | H | H | Cl | F | $CH_3$ | H | H |
| I.a.9 | Cl | H | H | F | F | $CH_3$ | H | H |
| I.a.10 | CN | H | H | F | F | $CH_3$ | H | H |
| I.a.11 | F | H | H | CN | F | $CH_3$ | H | H |
| I.a.12 | CN | H | H | F | F | $CH_3$ | H | H |
| I.a.13 | F | H | F | H | F | $CH_3$ | H | H |
| I.a.14 | Cl | H | F | H | F | $CH_3$ | H | H |
| I.a.15 | CN | H | F | H | F | $CH_3$ | H | H |
| I.a.16 | F | F | F | H | F | $CH_3$ | H | H |
| I.a.17 | Cl | F | F | H | F | $CH_3$ | H | H |
| I.a.18 | F | Cl | F | H | F | $CH_3$ | H | H |
| I.a.19 | Cl | F | F | H | F | $CH_3$ | H | H |
| I.a.20 | CN | F | F | H | F | $CH_3$ | H | H |
| I.a.21 | F | CN | F | H | F | $CH_3$ | H | H |
| I.a.22 | CN | F | F | H | F | $CH_3$ | H | H |
| I.a.23 | F | F | H | F | F | $CH_3$ | H | H |
| I.a.24 | Cl | F | H | F | F | $CH_3$ | H | H |
| I.a.25 | F | Cl | H | F | F | $CH_3$ | H | H |
| I.a.26 | CN | F | H | F | F | $CH_3$ | H | H |
| I.a.27 | F | CN | H | F | F | $CH_3$ | H | H |
| I.a.28 | F | F | F | F | F | $CH_3$ | H | H |
| I.a.29 | Cl | F | F | F | F | $CH_3$ | H | H |
| I.a.30 | F | Cl | F | F | F | $CH_3$ | H | H |
| I.a.31 | CN | F | F | F | F | $CH_3$ | H | H |
| I.a.32 | F | CN | F | F | F | $CH_3$ | H | H |
| I.a.33 | H | F | F | F | F | $CH_3$ | H | H |
| I.a.34 | F | F | Br | F | F | $CH_3$ | H | H |
| I.a.35 | F | F | C≡CH | F | F | $CH_3$ | H | H |
| I.a.36 | $CF_3$ | Cl | H | H | F | $CH_3$ | H | H |
| I.a.37 | F | F | I | F | F | $CH_3$ | H | H |
| I.a.38 | F | H | H | H | F | $CH_3$ | $CH_3$ | H |
| I.a.39 | Cl | H | H | H | F | $CH_3$ | $CH_3$ | H |
| I.a.40 | Br | H | H | H | F | $CH_3$ | $CH_3$ | H |
| I.a.41 | CN | H | H | H | F | $CH_3$ | $CH_3$ | H |
| I.a.42 | $CH_3$ | H | H | H | F | $CH_3$ | $CH_3$ | H |
| I.a.43 | F | H | H | F | F | $CH_3$ | $CH_3$ | H |
| I.a.44 | Cl | H | H | F | F | $CH_3$ | $CH_3$ | H |
| I.a.45 | F | H | H | Cl | F | $CH_3$ | $CH_3$ | H |
| I.a.46 | Cl | H | H | F | F | $CH_3$ | $CH_3$ | H |
| I.a.47 | CN | H | H | F | F | $CH_3$ | $CH_3$ | H |
| I.a.48 | F | H | H | CN | F | $CH_3$ | $CH_3$ | H |
| I.a.49 | CN | H | H | F | F | $CH_3$ | $CH_3$ | H |
| I.a.50 | F | H | F | H | F | $CH_3$ | $CH_3$ | H |
| I.a.51 | Cl | H | F | H | F | $CH_3$ | $CH_3$ | H |
| I.a.52 | CN | H | F | H | F | $CH_3$ | $CH_3$ | H |
| I.a.53 | F | F | F | H | F | $CH_3$ | $CH_3$ | H |
| I.a.54 | Cl | F | F | H | F | $CH_3$ | $CH_3$ | H |
| I.a.55 | F | Cl | F | H | F | $CH_3$ | $CH_3$ | H |
| I.a.56 | Cl | F | F | H | F | $CH_3$ | $CH_3$ | H |
| I.a.57 | CN | F | F | H | F | $CH_3$ | $CH_3$ | H |
| I.a.58 | F | CN | F | H | F | $CH_3$ | $CH_3$ | H |
| I.a.59 | CN | F | F | H | F | $CH_3$ | $CH_3$ | H |
| I.a.60 | F | F | H | F | F | $CH_3$ | $CH_3$ | H |
| I.a.61 | Cl | F | H | F | F | $CH_3$ | $CH_3$ | H |
| I.a.62 | F | Cl | H | F | F | $CH_3$ | $CH_3$ | H |
| I.a.63 | CN | F | H | F | F | $CH_3$ | $CH_3$ | H |
| I.a.64 | F | CN | H | F | F | $CH_3$ | $CH_3$ | H |
| I.a.65 | F | F | F | F | F | $CH_3$ | $CH_3$ | H |
| I.a.66 | Cl | F | F | F | F | $CH_3$ | $CH_3$ | H |
| I.a.67 | F | Cl | F | F | F | $CH_3$ | $CH_3$ | H |
| I.a.68 | CN | F | F | F | F | $CH_3$ | $CH_3$ | H |
| I.a.69 | F | CN | F | F | F | $CH_3$ | $CH_3$ | H |
| I.a.70 | H | F | F | F | F | $CH_3$ | $CH_3$ | H |
| I.a.71 | F | F | Br | F | F | $CH_3$ | $CH_3$ | H |
| I.a.72 | F | F | C≡CH | F | F | $CH_3$ | $CH_3$ | H |
| I.a.73 | $CF_3$ | Cl | H | H | F | $CH_3$ | $CH_3$ | H |
| I.a.74 | F | F | I | F | F | $CH_3$ | $CH_3$ | H |
| I.a.75 | F | H | H | H | F | $CH_3$ | $CH_3$ | $CH_3$ |
| I.a.76 | Cl | H | H | H | F | $CH_3$ | $CH_3$ | $CH_3$ |
| I.a.77 | Br | H | H | H | F | $CH_3$ | $CH_3$ | $CH_3$ |
| I.a.78 | CN | H | H | H | F | $CH_3$ | $CH_3$ | $CH_3$ |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.79 | $CH_3$ | H | H | H | F | $CH_3$ | $CH_3$ | $CH_3$ |
| I.a.80 | F | H | H | F | F | $CH_3$ | $CH_3$ | $CH_3$ |
| I.a.81 | Cl | H | H | F | F | $CH_3$ | $CH_3$ | $CH_3$ |
| I.a.82 | F | H | H | Cl | F | $CH_3$ | $CH_3$ | $CH_3$ |
| I.a.83 | Cl | H | H | F | F | $CH_3$ | $CH_3$ | $CH_3$ |
| I.a.84 | CN | H | H | F | F | $CH_3$ | $CH_3$ | $CH_3$ |
| I.a.85 | F | H | H | CN | F | $CH_3$ | $CH_3$ | $CH_3$ |
| I.a.86 | CN | H | H | F | F | $CH_3$ | $CH_3$ | $CH_3$ |
| I.a.87 | F | H | F | H | F | $CH_3$ | $CH_3$ | $CH_3$ |
| I.a.88 | Cl | H | F | H | F | $CH_3$ | $CH_3$ | $CH_3$ |
| I.a.89 | CN | H | F | H | F | $CH_3$ | $CH_3$ | $CH_3$ |
| I.a.90 | F | F | F | H | F | $CH_3$ | $CH_3$ | $CH_3$ |
| I.a.91 | Cl | F | F | H | F | $CH_3$ | $CH_3$ | $CH_3$ |
| I.a.92 | F | Cl | F | H | F | $CH_3$ | $CH_3$ | $CH_3$ |
| I.a.93 | Cl | F | F | H | F | $CH_3$ | $CH_3$ | $CH_3$ |
| I.a.94 | CN | F | F | H | F | $CH_3$ | $CH_3$ | $CH_3$ |
| I.a.95 | F | CN | F | H | F | $CH_3$ | $CH_3$ | $CH_3$ |
| I.a.96 | CN | F | F | H | F | $CH_3$ | $CH_3$ | $CH_3$ |
| I.a.97 | F | F | H | F | F | $CH_3$ | $CH_3$ | $CH_3$ |
| I.a.98 | Cl | F | H | F | F | $CH_3$ | $CH_3$ | $CH_3$ |
| I.a.99 | F | Cl | H | F | F | $CH_3$ | $CH_3$ | $CH_3$ |
| I.a.100 | CN | F | H | F | F | $CH_3$ | $CH_3$ | $CH_3$ |
| I.a.101 | F | CN | H | F | F | $CH_3$ | $CH_3$ | $CH_3$ |
| I.a.102 | F | F | F | F | F | $CH_3$ | $CH_3$ | $CH_3$ |
| I.a.103 | Cl | F | F | F | F | $CH_3$ | $CH_3$ | $CH_3$ |
| I.a.104 | F | Cl | F | F | F | $CH_3$ | $CH_3$ | $CH_3$ |
| I.a.105 | CN | F | F | F | F | $CH_3$ | $CH_3$ | $CH_3$ |
| I.a.106 | F | CN | F | F | F | $CH_3$ | $CH_3$ | $CH_3$ |
| I.a.107 | H | F | F | F | F | $CH_3$ | $CH_3$ | $CH_3$ |
| I.a.108 | F | F | Br | F | F | $CH_3$ | $CH_3$ | $CH_3$ |
| I.a.109 | F | F | C≡CH | F | F | $CH_3$ | $CH_3$ | $CH_3$ |
| I.a.110 | $CF_3$ | Cl | H | H | F | $CH_3$ | $CH_3$ | $CH_3$ |
| I.a.111 | F | F | I | F | F | $CH_3$ | $CH_3$ | $CH_3$ |
| I.a.112 | F | H | H | H | F | F | F | F |
| I.a.113 | Cl | H | H | H | F | F | F | F |
| I.a.114 | Br | H | H | H | F | F | F | F |
| I.a.115 | CN | H | H | H | F | F | F | F |
| I.a.116 | $CH_3$ | H | H | H | F | F | F | F |
| I.a.117 | F | H | H | F | F | F | F | F |
| I.a.118 | Cl | H | H | F | F | F | F | F |
| I.a.119 | F | H | H | Cl | F | F | F | F |
| I.a.120 | Cl | H | H | F | F | F | F | F |
| I.a.121 | CN | H | H | F | F | F | F | F |
| I.a.122 | F | H | H | CN | F | F | F | F |
| I.a.123 | CN | H | H | F | F | F | F | F |
| I.a.124 | F | H | F | H | F | F | F | F |
| I.a.125 | Cl | H | F | H | F | F | F | F |
| I.a.126 | CN | H | F | H | F | F | F | F |
| I.a.127 | F | F | F | H | F | F | F | F |
| I.a.128 | Cl | F | F | H | F | F | F | F |
| I.a.129 | F | Cl | F | H | F | F | F | F |
| I.a.130 | Cl | F | F | H | F | F | F | F |
| I.a.131 | CN | F | F | H | F | F | F | F |
| I.a.132 | F | CN | F | H | F | F | F | F |
| I.a.133 | CN | F | F | H | F | F | F | F |
| I.a.134 | F | F | H | F | F | F | F | F |
| I.a.135 | Cl | F | H | F | F | F | F | F |
| I.a.136 | F | Cl | H | F | F | F | F | F |
| I.a.137 | CN | F | H | F | F | F | F | F |
| I.a.138 | F | CN | H | F | F | F | F | F |
| I.a.139 | F | F | F | F | F | F | F | F |
| I.a.140 | Cl | F | F | F | F | F | F | F |
| I.a.141 | F | Cl | F | F | F | F | F | F |
| I.a.142 | CN | F | F | F | F | F | F | F |
| I.a.143 | F | CN | F | F | F | F | F | F |
| I.a.144 | H | F | F | F | F | F | F | F |
| I.a.145 | F | F | Br | F | F | F | F | F |
| I.a.146 | F | F | C≡CH | F | F | F | F | F |
| I.a.147 | $CF_3$ | Cl | H | H | F | F | F | F |
| I.a.148 | F | F | I | F | F | F | F | F |
| I.a.149 | F | H | H | H | F | F | $CF_3$ | F |
| I.a.150 | Cl | H | H | H | F | F | $CF_3$ | F |
| I.a.151 | Br | H | H | H | F | F | $CF_3$ | F |
| I.a.152 | CN | H | H | H | F | F | $CF_3$ | F |
| I.a.153 | $CH_3$ | H | H | H | F | F | $CF_3$ | F |
| I.a.154 | F | H | H | F | F | F | $CF_3$ | F |
| I.a.155 | Cl | H | H | F | F | F | $CF_3$ | F |
| I.a.156 | F | H | H | Cl | F | F | $CF_3$ | F |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.157 | Cl | H | H | F | F | F | $CF_3$ | F |
| I.a.158 | CN | H | H | F | F | F | $CF_3$ | F |
| I.a.159 | F | H | H | CN | F | F | $CF_3$ | F |
| I.a.160 | CN | H | H | F | F | F | $CF_3$ | F |
| I.a.161 | F | H | F | H | F | F | $CF_3$ | F |
| I.a.162 | Cl | H | F | H | F | F | $CF_3$ | F |
| I.a.163 | CN | H | F | H | F | F | $CF_3$ | F |
| I.a.164 | F | F | F | H | F | F | $CF_3$ | F |
| I.a.165 | Cl | F | F | H | F | F | $CF_3$ | F |
| I.a.166 | F | Cl | F | H | F | F | $CF_3$ | F |
| I.a.167 | Cl | F | F | H | F | F | $CF_3$ | F |
| I.a.168 | CN | F | F | H | F | F | $CF_3$ | F |
| I.a.169 | F | CN | F | H | F | F | $CF_3$ | F |
| I.a.170 | CN | F | F | H | F | F | $CF_3$ | F |
| I.a.171 | F | F | H | F | F | F | $CF_3$ | F |
| I.a.172 | Cl | F | H | F | F | F | $CF_3$ | F |
| I.a.173 | F | Cl | H | F | F | F | $CF_3$ | F |
| I.a.174 | CN | F | H | F | F | F | $CF_3$ | F |
| I.a.175 | F | CN | H | F | F | F | $CF_3$ | F |
| I.a.176 | F | F | F | F | F | F | $CF_3$ | F |
| I.a.177 | Cl | F | F | F | F | F | $CF_3$ | F |
| I.a.178 | F | Cl | F | F | F | F | $CF_3$ | F |
| I.a.179 | CN | F | F | F | F | F | $CF_3$ | F |
| I.a.180 | F | CN | F | F | F | F | $CF_3$ | F |
| I.a.181 | H | F | F | F | F | F | $CF_3$ | F |
| I.a.182 | F | F | Br | F | F | F | $CF_3$ | F |
| I.a.183 | F | F | C≡CH | F | F | F | $CF_3$ | F |
| I.a.184 | $CF_3$ | Cl | H | H | F | F | $CF_3$ | F |
| I.a.185 | F | F | I | F | F | F | $CF_3$ | F |
| I.a.186 | F | H | H | H | F | F | $CH_3$ | F |
| I.a.187 | Cl | H | H | H | F | F | $CH_3$ | F |
| I.a.188 | Br | H | H | H | F | F | $CH_3$ | F |
| I.a.189 | CN | H | H | H | F | F | $CH_3$ | F |
| I.a.190 | $CH_3$ | H | H | H | F | F | $CH_3$ | F |
| I.a.191 | F | H | H | F | F | F | $CH_3$ | F |
| I.a.192 | Cl | H | H | F | F | F | $CH_3$ | F |
| I.a.193 | F | H | H | Cl | F | F | $CH_3$ | F |
| I.a.194 | Cl | H | H | F | F | F | $CH_3$ | F |
| I.a.195 | CN | H | H | F | F | F | $CH_3$ | F |
| I.a.196 | F | H | H | CN | F | F | $CH_3$ | F |
| I.a.197 | CN | H | H | F | F | F | $CH_3$ | F |
| I.a.198 | F | H | F | H | F | F | $CH_3$ | F |
| I.a.199 | Cl | H | F | H | F | F | $CH_3$ | F |
| I.a.200 | CN | H | F | H | F | F | $CH_3$ | F |
| I.a.201 | F | F | F | H | F | F | $CH_3$ | F |
| I.a.202 | Cl | F | F | H | F | F | $CH_3$ | F |
| I.a.203 | F | Cl | F | H | F | F | $CH_3$ | F |
| I.a.204 | Cl | F | F | H | F | F | $CH_3$ | F |
| I.a.205 | CN | F | F | H | F | F | $CH_3$ | F |
| I.a.206 | F | CN | F | H | F | F | $CH_3$ | F |
| I.a.207 | CN | F | F | H | F | F | $CH_3$ | F |
| I.a.208 | F | F | H | F | F | F | $CH_3$ | F |
| I.a.209 | Cl | F | H | F | F | F | $CH_3$ | F |
| I.a.210 | F | Cl | H | F | F | F | $CH_3$ | F |
| I.a.211 | CN | F | H | F | F | F | $CH_3$ | F |
| I.a.212 | F | CN | H | F | F | F | $CH_3$ | F |
| I.a.213 | F | F | F | F | F | F | $CH_3$ | F |
| I.a.214 | Cl | F | F | F | F | F | $CH_3$ | F |
| I.a.215 | F | Cl | F | F | F | F | $CH_3$ | F |
| I.a.216 | CN | F | F | F | F | F | $CH_3$ | F |
| I.a.217 | F | CN | F | F | F | F | $CH_3$ | F |
| I.a.218 | H | F | F | F | F | F | $CH_3$ | F |
| I.a.219 | F | F | Br | F | F | F | $CH_3$ | F |
| I.a.220 | F | F | C≡CH | F | F | F | $CH_3$ | F |
| I.a.221 | $CF_3$ | Cl | H | H | F | F | $CH_3$ | F |
| I.a.222 | F | F | I | F | F | F | $CH_3$ | F |
| I.a.223 | F | H | H | H | F | F | $CH_3$ | H |
| I.a.224 | Cl | H | H | H | F | F | $CH_3$ | H |
| I.a.225 | Br | H | H | H | F | F | $CH_3$ | H |
| I.a.226 | CN | H | H | H | F | F | $CH_3$ | H |
| I.a.227 | $CH_3$ | H | H | H | F | F | $CH_3$ | H |
| I.a.228 | F | H | H | F | F | F | $CH_3$ | H |
| I.a.229 | Cl | H | H | F | F | F | $CH_3$ | H |
| I.a.230 | F | H | H | Cl | F | F | $CH_3$ | H |
| I.a.231 | Cl | H | H | F | F | F | $CH_3$ | H |
| I.a.232 | CN | H | H | F | F | F | $CH_3$ | H |
| I.a.233 | F | H | H | CN | F | F | $CH_3$ | H |
| I.a.234 | CN | H | H | F | F | F | $CH_3$ | H |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.235 | F | H | F | H | F | F | $CH_3$ | H |
| I.a.236 | Cl | H | F | H | F | F | $CH_3$ | H |
| I.a.237 | CN | H | F | H | F | F | $CH_3$ | H |
| I.a.238 | F | F | F | H | F | F | $CH_3$ | H |
| I.a.239 | Cl | F | F | H | F | F | $CH_3$ | H |
| I.a.240 | F | Cl | F | H | F | F | $CH_3$ | H |
| I.a.241 | Cl | F | F | H | F | F | $CH_3$ | H |
| I.a.242 | CN | F | F | H | F | F | $CH_3$ | H |
| I.a.243 | F | CN | F | H | F | F | $CH_3$ | H |
| I.a.244 | CN | F | F | H | F | F | $CH_3$ | H |
| I.a.245 | F | F | H | F | F | F | $CH_3$ | H |
| I.a.246 | Cl | F | H | F | F | F | $CH_3$ | H |
| I.a.247 | F | Cl | H | F | F | F | $CH_3$ | H |
| I.a.248 | CN | F | H | F | F | F | $CH_3$ | H |
| I.a.249 | F | CN | H | F | F | F | $CH_3$ | H |
| I.a.250 | F | F | F | F | F | F | $CH_3$ | H |
| I.a.251 | Cl | F | F | F | F | F | $CH_3$ | H |
| I.a.252 | F | Cl | F | F | F | F | $CH_3$ | H |
| I.a.253 | CN | F | F | F | F | F | $CH_3$ | H |
| I.a.254 | F | CN | F | F | F | F | $CH_3$ | H |
| I.a.255 | H | F | F | F | F | F | $CH_3$ | H |
| I.a.256 | F | F | Br | F | F | F | $CH_3$ | H |
| I.a.257 | F | F | C≡CH | F | F | F | $CH_3$ | H |
| I.a.258 | $CF_3$ | Cl | H | H | F | F | $CH_3$ | H |
| I.a.259 | F | F | I | F | F | F | $CH_3$ | H |
| I.a.260 | F | H | H | H | F | F | $CH_3$ | $CH_3$ |
| I.a.261 | Cl | H | H | H | F | F | $CH_3$ | $CH_3$ |
| I.a.262 | Br | H | H | H | F | F | $CH_3$ | $CH_3$ |
| I.a.263 | CN | H | H | H | F | F | $CH_3$ | $CH_3$ |
| I.a.264 | $CH_3$ | H | H | H | F | F | $CH_3$ | $CH_3$ |
| I.a.265 | F | H | H | F | F | F | $CH_3$ | $CH_3$ |
| I.a.266 | Cl | H | H | F | F | F | $CH_3$ | $CH_3$ |
| I.a.267 | F | H | H | Cl | F | F | $CH_3$ | $CH_3$ |
| I.a.268 | Cl | H | H | F | F | F | $CH_3$ | $CH_3$ |
| I.a.269 | CN | H | H | F | F | F | $CH_3$ | $CH_3$ |
| I.a.270 | F | H | H | CN | F | F | $CH_3$ | $CH_3$ |
| I.a.271 | CN | H | H | F | F | F | $CH_3$ | $CH_3$ |
| I.a.272 | F | H | F | H | F | F | $CH_3$ | $CH_3$ |
| I.a.273 | Cl | H | F | H | F | F | $CH_3$ | $CH_3$ |
| I.a.274 | CN | H | F | H | F | F | $CH_3$ | $CH_3$ |
| I.a.275 | F | F | F | H | F | F | $CH_3$ | $CH_3$ |
| I.a.276 | Cl | F | F | H | F | F | $CH_3$ | $CH_3$ |
| I.a.277 | F | Cl | F | H | F | F | $CH_3$ | $CH_3$ |
| I.a.278 | Cl | F | F | H | F | F | $CH_3$ | $CH_3$ |
| I.a.279 | CN | F | F | H | F | F | $CH_3$ | $CH_3$ |
| I.a.280 | F | CN | F | H | F | F | $CH_3$ | $CH_3$ |
| I.a.281 | CN | F | F | H | F | F | $CH_3$ | $CH_3$ |
| I.a.282 | F | F | H | F | F | F | $CH_3$ | $CH_3$ |
| I.a.283 | Cl | F | H | F | F | F | $CH_3$ | $CH_3$ |
| I.a.284 | F | Cl | H | F | F | F | $CH_3$ | $CH_3$ |
| I.a.285 | CN | F | H | F | F | F | $CH_3$ | $CH_3$ |
| I.a.286 | F | CN | H | F | F | F | $CH_3$ | $CH_3$ |
| I.a.287 | F | F | F | F | F | F | $CH_3$ | $CH_3$ |
| I.a.288 | Cl | F | F | F | F | F | $CH_3$ | $CH_3$ |
| I.a.289 | F | Cl | F | F | F | F | $CH_3$ | $CH_3$ |
| I.a.290 | CN | F | F | F | F | F | $CH_3$ | $CH_3$ |
| I.a.291 | F | CN | F | F | F | F | $CH_3$ | $CH_3$ |
| I.a.292 | H | F | F | F | F | F | $CH_3$ | $CH_3$ |
| I.a.293 | F | F | Br | F | F | F | $CH_3$ | $CH_3$ |
| I.a.294 | F | F | C≡CH | F | F | F | $CH_3$ | $CH_3$ |
| I.a.295 | $CF_3$ | Cl | H | H | F | F | $CH_3$ | $CH_3$ |
| I.a.296 | F | F | I | F | F | F | $CH_3$ | $CH_3$ |
| I.a.297 | F | H | H | H | F | Cl | $CH_3$ | $CH_3$ |
| I.a.298 | Cl | H | H | H | F | Cl | $CH_3$ | $CH_3$ |
| I.a.299 | Br | H | H | H | F | Cl | $CH_3$ | $CH_3$ |
| I.a.300 | CN | H | H | H | F | Cl | $CH_3$ | $CH_3$ |
| I.a.301 | $CH_3$ | H | H | H | F | Cl | $CH_3$ | $CH_3$ |
| I.a.302 | F | H | H | F | F | Cl | $CH_3$ | $CH_3$ |
| I.a.303 | Cl | H | H | F | F | Cl | $CH_3$ | $CH_3$ |
| I.a.304 | F | H | H | Cl | F | Cl | $CH_3$ | $CH_3$ |
| I.a.305 | Cl | H | H | F | F | Cl | $CH_3$ | $CH_3$ |
| I.a.306 | CN | H | H | F | F | Cl | $CH_3$ | $CH_3$ |
| I.a.307 | F | H | H | CN | F | Cl | $CH_3$ | $CH_3$ |
| I.a.308 | CN | H | H | F | F | Cl | $CH_3$ | $CH_3$ |
| I.a.309 | F | H | F | H | F | Cl | $CH_3$ | $CH_3$ |
| I.a.310 | Cl | H | F | H | F | Cl | $CH_3$ | $CH_3$ |
| I.a.311 | CN | H | F | H | F | Cl | $CH_3$ | $CH_3$ |
| I.a.312 | F | F | F | H | F | Cl | $CH_3$ | $CH_3$ |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.313 | Cl | F | F | H | F | Cl | $CH_3$ | $CH_3$ |
| I.a.314 | F | Cl | F | H | F | Cl | $CH_3$ | $CH_3$ |
| I.a.315 | Cl | F | F | H | F | Cl | $CH_3$ | $CH_3$ |
| I.a.316 | CN | F | F | H | F | Cl | $CH_3$ | $CH_3$ |
| I.a.317 | F | CN | F | H | F | Cl | $CH_3$ | $CH_3$ |
| I.a.318 | CN | F | F | H | F | Cl | $CH_3$ | $CH_3$ |
| I.a.319 | F | F | H | F | F | Cl | $CH_3$ | $CH_3$ |
| I.a.320 | Cl | F | H | F | F | Cl | $CH_3$ | $CH_3$ |
| I.a.321 | F | Cl | H | F | F | Cl | $CH_3$ | $CH_3$ |
| I.a.322 | CN | F | H | F | F | Cl | $CH_3$ | $CH_3$ |
| I.a.323 | F | CN | H | F | F | Cl | $CH_3$ | $CH_3$ |
| I.a.324 | F | F | F | F | F | Cl | $CH_3$ | $CH_3$ |
| I.a.325 | Cl | F | F | F | F | Cl | $CH_3$ | $CH_3$ |
| I.a.326 | F | Cl | F | F | F | Cl | $CH_3$ | $CH_3$ |
| I.a.327 | CN | F | F | F | F | Cl | $CH_3$ | $CH_3$ |
| I.a.328 | F | CN | F | F | F | Cl | $CH_3$ | $CH_3$ |
| I.a.329 | H | F | F | F | F | Cl | $CH_3$ | $CH_3$ |
| I.a.330 | F | F | Br | F | F | Cl | $CH_3$ | $CH_3$ |
| I.a.331 | F | F | C≡CH | F | F | Cl | $CH_3$ | $CH_3$ |
| I.a.332 | $CF_3$ | Cl | H | H | F | Cl | $CH_3$ | $CH_3$ |
| I.a.333 | F | F | I | F | F | Cl | $CH_3$ | $CH_3$ |
| I.a.334 | F | H | H | H | F | F | $C_2H_5$ | $CH_3$ |
| I.a.335 | Cl | H | H | H | F | F | $C_2H_5$ | $CH_3$ |
| I.a.336 | Br | H | H | H | F | F | $C_2H_5$ | $CH_3$ |
| I.a.337 | CN | H | H | H | F | F | $C_2H_5$ | $CH_3$ |
| I.a.338 | $CH_3$ | H | H | H | F | F | $C_2H_5$ | $CH_3$ |
| I.a.339 | F | H | H | F | F | F | $C_2H_5$ | $CH_3$ |
| I.a.340 | Cl | H | H | F | F | F | $C_2H_5$ | $CH_3$ |
| I.a.341 | F | H | H | Cl | F | F | $C_2H_5$ | $CH_3$ |
| I.a.342 | Cl | H | H | F | F | F | $C_2H_5$ | $CH_3$ |
| I.a.343 | CN | H | H | F | F | F | $C_2H_5$ | $CH_3$ |
| I.a.344 | F | H | H | CN | F | F | $C_2H_5$ | $CH_3$ |
| I.a.345 | CN | H | H | F | F | F | $C_2H_5$ | $CH_3$ |
| I.a.346 | F | H | F | H | F | F | $C_2H_5$ | $CH_3$ |
| I.a.347 | Cl | H | F | H | F | F | $C_2H_5$ | $CH_3$ |
| I.a.348 | CN | H | F | H | F | F | $C_2H_5$ | $CH_3$ |
| I.a.349 | F | F | F | H | F | F | $C_2H_5$ | $CH_3$ |
| I.a.350 | Cl | F | F | H | F | F | $C_2H_5$ | $CH_3$ |
| I.a.351 | F | Cl | F | H | F | F | $C_2H_5$ | $CH_3$ |
| I.a.352 | Cl | F | F | H | F | F | $C_2H_5$ | $CH_3$ |
| I.a.353 | CN | F | F | H | F | F | $C_2H_5$ | $CH_3$ |
| I.a.354 | F | CN | F | H | F | F | $C_2H_5$ | $CH_3$ |
| I.a.355 | CN | F | F | H | F | F | $C_2H_5$ | $CH_3$ |
| I.a.356 | F | F | H | F | F | F | $C_2H_5$ | $CH_3$ |
| I.a.357 | Cl | F | H | F | F | F | $C_2H_5$ | $CH_3$ |
| I.a.358 | F | Cl | H | F | F | F | $C_2H_5$ | $CH_3$ |
| I.a.359 | CN | F | H | F | F | F | $C_2H_5$ | $CH_3$ |
| I.a.360 | F | CN | H | F | F | F | $C_2H_5$ | $CH_3$ |
| I.a.361 | F | F | F | F | F | F | $C_2H_5$ | $CH_3$ |
| I.a.362 | Cl | F | F | F | F | F | $C_2H_5$ | $CH_3$ |
| I.a.363 | F | Cl | F | F | F | F | $C_2H_5$ | $CH_3$ |
| I.a.364 | CN | F | F | F | F | F | $C_2H_5$ | $CH_3$ |
| I.a.365 | F | CN | F | F | F | F | $C_2H_5$ | $CH_3$ |
| I.a.366 | H | F | F | F | F | F | $C_2H_5$ | $CH_3$ |
| I.a.367 | F | F | Br | F | F | F | $C_2H_5$ | $CH_3$ |
| I.a.368 | F | F | C≡CH | F | F | F | $C_2H_5$ | $CH_3$ |
| I.a.369 | $CF_3$ | Cl | H | H | F | F | $C_2H_5$ | $CH_3$ |
| I.a.370 | F | F | I | F | F | F | $C_2H_5$ | $CH_3$ |
| I.a.371 | F | H | H | H | F | F | $C_2H_5$ | $C_2H_5$ |
| I.a.372 | Cl | H | H | H | F | F | $C_2H_5$ | $C_2H_5$ |
| I.a.373 | Br | H | H | H | F | F | $C_2H_5$ | $C_2H_5$ |
| I.a.374 | CN | H | H | H | F | F | $C_2H_5$ | $C_2H_5$ |
| I.a.375 | $CH_3$ | H | H | H | F | F | $C_2H_5$ | $C_2H_5$ |
| I.a.376 | F | H | H | F | F | F | $C_2H_5$ | $C_2H_5$ |
| I.a.377 | Cl | H | H | F | F | F | $C_2H_5$ | $C_2H_5$ |
| I.a.378 | F | H | H | Cl | F | F | $C_2H_5$ | $C_2H_5$ |
| I.a.379 | Cl | H | H | F | F | F | $C_2H_5$ | $C_2H_5$ |
| I.a.380 | CN | H | H | F | F | F | $C_2H_5$ | $C_2H_5$ |
| I.a.381 | F | H | H | CN | F | F | $C_2H_5$ | $C_2H_5$ |
| I.a.382 | CN | H | H | F | F | F | $C_2H_5$ | $C_2H_5$ |
| I.a.383 | F | H | F | H | F | F | $C_2H_5$ | $C_2H_5$ |
| I.a.384 | Cl | H | F | H | F | F | $C_2H_5$ | $C_2H_5$ |
| I.a.385 | CN | H | F | H | F | F | $C_2H_5$ | $C_2H_5$ |
| I.a.386 | F | F | F | H | F | F | $C_2H_5$ | $C_2H_5$ |
| I.a.387 | Cl | F | F | H | F | F | $C_2H_5$ | $C_2H_5$ |
| I.a.388 | F | Cl | F | H | F | F | $C_2H_5$ | $C_2H_5$ |
| I.a.389 | Cl | F | F | H | F | F | $C_2H_5$ | $C_2H_5$ |
| I.a.390 | CN | F | F | H | F | F | $C_2H_5$ | $C_2H_5$ |
| I.a.391 | F | CN | F | H | F | F | $C_2H_5$ | $C_2H_5$ |
| I.a.392 | CN | F | F | H | F | F | $C_2H_5$ | $C_2H_5$ |
| I.a.393 | F | F | H | F | F | F | $C_2H_5$ | $C_2H_5$ |
| I.a.394 | Cl | F | H | F | F | F | $C_2H_5$ | $C_2H_5$ |
| I.a.395 | F | Cl | H | F | F | F | $C_2H_5$ | $C_2H_5$ |
| I.a.396 | CN | F | H | F | F | F | $C_2H_5$ | $C_2H_5$ |
| I.a.397 | F | CN | H | F | F | F | $C_2H_5$ | $C_2H_5$ |
| I.a.398 | F | F | F | F | F | F | $C_2H_5$ | $C_2H_5$ |
| I.a.399 | Cl | F | F | F | F | F | $C_2H_5$ | $C_2H_5$ |
| I.a.400 | F | Cl | F | F | F | F | $C_2H_5$ | $C_2H_5$ |
| I.a.401 | CN | F | F | F | F | F | $C_2H_5$ | $C_2H_5$ |
| I.a.402 | F | CN | F | F | F | F | $C_2H_5$ | $C_2H_5$ |
| I.a.403 | H | F | F | F | F | F | $C_2H_5$ | $C_2H_5$ |
| I.a.404 | F | F | Br | F | F | F | $C_2H_5$ | $C_2H_5$ |
| I.a.405 | F | F | C≡CH | F | F | F | $C_2H_5$ | $C_2H_5$ |
| I.a.406 | $CF_3$ | Cl | H | H | F | F | $C_2H_5$ | $C_2H_5$ |
| I.a.407 | F | F | I | F | F | F | $C_2H_5$ | $C_2H_5$ |
| I.a.408 | F | H | H | H | F | H | $—(CH_2)_2—$ | |
| I.a.409 | Cl | H | H | H | F | H | $—(CH_2)_2—$ | |
| I.a.410 | Br | H | H | H | F | H | $—(CH_2)_2—$ | |
| I.a.411 | CN | H | H | H | F | H | $—(CH_2)_2—$ | |
| I.a.412 | $CH_3$ | H | H | H | F | H | $—(CH_2)_2—$ | |
| I.a.413 | F | H | H | F | F | H | $—(CH_2)_2—$ | |
| I.a.414 | Cl | H | H | F | F | H | $—(CH_2)_2—$ | |
| I.a.415 | F | H | H | Cl | F | H | $—(CH_2)_2—$ | |
| I.a.416 | Cl | H | H | F | F | H | $—(CH_2)_2—$ | |
| I.a.417 | CN | H | H | F | F | H | $—(CH_2)_2—$ | |
| I.a.418 | F | H | H | CN | F | H | $—(CH_2)_2—$ | |
| I.a.419 | CN | H | H | F | F | H | $—(CH_2)_2—$ | |
| I.a.420 | F | H | F | H | F | H | $—(CH_2)_2—$ | |
| I.a.421 | Cl | H | F | H | F | H | $—(CH_2)_2—$ | |
| I.a.422 | CN | H | F | H | F | H | $—(CH_2)_2—$ | |
| I.a.423 | F | F | F | H | F | H | $—(CH_2)_2—$ | |
| I.a.424 | Cl | F | F | H | F | H | $—(CH_2)_2—$ | |
| I.a.425 | F | Cl | F | H | F | H | $—(CH_2)_2—$ | |
| I.a.426 | Cl | F | F | H | F | H | $—(CH_2)_2—$ | |
| I.a.427 | CN | F | F | H | F | H | $—(CH_2)_2—$ | |
| I.a.428 | F | CN | F | H | F | H | $—(CH_2)_2—$ | |
| I.a.429 | CN | F | F | H | F | H | $—(CH_2)_2—$ | |
| I.a.430 | F | F | H | F | F | H | $—(CH_2)_2—$ | |
| I.a.431 | Cl | F | H | F | F | H | $—(CH_2)_2—$ | |
| I.a.432 | F | Cl | H | F | F | H | $—(CH_2)_2—$ | |
| I.a.433 | CN | F | H | F | F | H | $—(CH_2)_2—$ | |
| I.a.434 | F | CN | H | F | F | H | $—(CH_2)_2—$ | |
| I.a.435 | F | F | F | F | F | H | $—(CH_2)_2—$ | |
| I.a.436 | Cl | F | F | F | F | H | $—(CH_2)_2—$ | |
| I.a.437 | F | Cl | F | F | F | H | $—(CH_2)_2—$ | |
| I.a.438 | CN | F | F | F | F | H | $—(CH_2)_2—$ | |
| I.a.439 | F | CN | F | F | F | H | $—(CH_2)_2—$ | |
| I.a.440 | H | F | F | F | F | H | $—(CH_2)_2—$ | |
| I.a.441 | F | F | Br | F | F | H | $—(CH_2)_2—$ | |
| I.a.442 | F | F | C≡CH | F | F | H | $—(CH_2)_2—$ | |
| I.a.443 | $CF_3$ | Cl | H | H | F | H | $—(CH_2)_2—$ | |
| I.a.444 | F | F | I | F | F | H | $—(CH_2)_2—$ | |
| I.a.445 | F | H | H | H | F | H | $—(CH_2)_3—$ | |
| I.a.446 | Cl | H | H | H | F | H | $—(CH_2)_3—$ | |
| I.a.447 | Br | H | H | H | F | H | $—(CH_2)_3—$ | |
| I.a.448 | CN | H | H | H | F | H | $—(CH_2)_3—$ | |
| I.a.449 | $CH_3$ | H | H | H | F | H | $—(CH_2)_3—$ | |
| I.a.450 | F | H | H | F | F | H | $—(CH_2)_3—$ | |
| I.a.451 | Cl | H | H | F | F | H | $—(CH_2)_3—$ | |
| I.a.452 | F | H | H | Cl | F | H | $—(CH_2)_3—$ | |
| I.a.453 | Cl | H | H | F | F | H | $—(CH_2)_3—$ | |
| I.a.454 | CN | H | H | F | F | H | $—(CH_2)_3—$ | |
| I.a.455 | F | H | H | CN | F | H | $—(CH_2)_3—$ | |
| I.a.456 | CN | H | H | F | F | H | $—(CH_2)_3—$ | |
| I.a.457 | F | H | F | H | F | H | $—(CH_2)_3—$ | |
| I.a.458 | Cl | H | F | H | F | H | $—(CH_2)_3—$ | |
| I.a.459 | CN | H | F | H | F | H | $—(CH_2)_3—$ | |
| I.a.460 | F | F | F | H | F | H | $—(CH_2)_3—$ | |
| I.a.461 | Cl | F | F | H | F | H | $—(CH_2)_3—$ | |
| I.a.462 | F | Cl | F | H | F | H | $—(CH_2)_3—$ | |
| I.a.463 | Cl | F | F | H | F | H | $—(CH_2)_3—$ | |
| I.a.464 | CN | F | F | H | F | H | $—(CH_2)_3—$ | |
| I.a.465 | F | CN | F | H | F | H | $—(CH_2)_3—$ | |
| I.a.466 | CN | F | F | H | F | H | $—(CH_2)_3—$ | |
| I.a.467 | F | F | H | F | F | H | $—(CH_2)_3—$ | |
| I.a.468 | Cl | F | H | F | F | H | $—(CH_2)_3—$ | |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.469 | F | Cl | H | F | F | H | $—(CH_2)_3—$ | |
| I.a.470 | CN | F | H | F | F | H | $—(CH_2)_3—$ | |
| I.a.471 | F | CN | H | F | F | H | $—(CH_2)_3—$ | |
| I.a.472 | F | F | F | F | F | H | $—(CH_2)_3—$ | |
| I.a.473 | Cl | F | F | F | F | H | $—(CH_2)_3—$ | |
| I.a.474 | F | Cl | F | F | F | H | $—(CH_2)_3—$ | |
| I.a.475 | CN | F | F | F | F | H | $—(CH_2)_3—$ | |
| I.a.476 | F | CN | F | F | F | H | $—(CH_2)_3—$ | |
| I.a.477 | H | F | F | F | F | H | $—(CH_2)_3—$ | |
| I.a.478 | F | F | Br | F | F | H | $—(CH_2)_3—$ | |
| I.a.479 | F | F | $C\equiv CH$ | F | F | H | $—(CH_2)_3—$ | |
| I.a.480 | $CF_3$ | Cl | H | H | F | H | $—(CH_2)_3—$ | |
| I.a.481 | F | F | I | F | F | H | $—(CH_2)_3—$ | |
| I.a.482 | F | H | H | H | F | H | $—(CH_2)_4—$ | |
| I.a.483 | Cl | H | H | H | F | H | $—(CH_2)_4—$ | |
| I.a.484 | Br | H | H | H | F | H | $—(CH_2)_4—$ | |
| I.a.485 | CN | H | H | H | F | H | $—(CH_2)_4—$ | |
| I.a.486 | $CH_3$ | H | H | H | F | H | $—(CH_2)_4—$ | |
| I.a.487 | F | H | H | F | F | H | $—(CH_2)_4—$ | |
| I.a.488 | Cl | H | H | F | F | H | $—(CH_2)_4—$ | |
| I.a.489 | F | H | H | Cl | F | H | $—(CH_2)_4—$ | |
| I.a.490 | Cl | H | H | F | F | H | $—(CH_2)_4—$ | |
| I.a.491 | CN | H | H | F | F | H | $—(CH_2)_4—$ | |
| I.a.492 | F | H | H | CN | F | H | $—(CH_2)_4—$ | |
| I.a.493 | CN | H | H | F | F | H | $—(CH_2)_4—$ | |
| I.a.494 | F | H | F | H | F | H | $—(CH_2)_4—$ | |
| I.a.495 | Cl | H | F | H | F | H | $—(CH_2)_4—$ | |
| I.a.496 | CN | H | F | H | F | H | $—(CH_2)_4—$ | |
| I.a.497 | F | F | F | H | F | H | $—(CH_2)_4—$ | |
| I.a.498 | Cl | F | F | H | F | H | $—(CH_2)_4—$ | |
| I.a.499 | F | Cl | F | H | F | H | $—(CH_2)_4—$ | |
| I.a.500 | Cl | F | F | H | F | H | $—(CH_2)_4—$ | |
| I.a.501 | CN | F | F | H | F | H | $—(CH_2)_4—$ | |
| I.a.502 | F | CN | F | H | F | H | $—(CH_2)_4—$ | |
| I.a.503 | CN | F | F | H | F | H | $—(CH_2)_4—$ | |
| I.a.504 | F | F | H | F | F | H | $—(CH_2)_4—$ | |
| I.a.505 | Cl | F | H | F | F | H | $—(CH_2)_4—$ | |
| I.a.506 | F | Cl | H | F | F | H | $—(CH_2)_4—$ | |
| I.a.507 | CN | F | H | F | F | H | $—(CH_2)_4—$ | |
| I.a.508 | F | CN | H | F | F | H | $—(CH_2)_4—$ | |
| I.a.509 | F | F | F | F | F | H | $—(CH_2)_4—$ | |
| I.a.510 | Cl | F | F | F | F | H | $—(CH_2)_4—$ | |
| I.a.511 | F | Cl | F | F | F | H | $—(CH_2)_4—$ | |
| I.a.512 | CN | F | F | F | F | H | $—(CH_2)_4—$ | |
| I.a.513 | F | CN | F | F | F | H | $—(CH_2)_4—$ | |
| I.a.514 | H | F | F | F | F | H | $—(CH_2)_4—$ | |
| I.a.515 | F | F | Br | F | F | H | $—(CH_2)_4—$ | |
| I.a.516 | F | F | $C\equiv CH$ | F | F | H | $—(CH_2)_4—$ | |
| I.a.517 | $CF_3$ | Cl | H | H | F | H | $—(CH_2)_4—$ | |
| I.a.518 | F | F | I | F | F | H | $—(CH_2)_4—$ | |
| I.a.519 | F | H | H | H | F | H | $—(CH_2)_5—$ | |
| I.a.520 | Cl | H | H | H | F | H | $—(CH_2)_5—$ | |
| I.a.521 | Br | H | H | H | F | H | $—(CH_2)_5—$ | |
| I.a.522 | CN | H | H | H | F | H | $—(CH_2)_5—$ | |
| I.a.523 | $CH_3$ | H | H | H | F | H | $—(CH_2)_5—$ | |
| I.a.524 | F | H | H | F | F | H | $—(CH_2)_5—$ | |
| I.a.525 | Cl | H | H | F | F | H | $—(CH_2)_5—$ | |
| I.a.526 | F | H | H | Cl | F | H | $—(CH_2)_5—$ | |
| I.a.527 | Cl | H | H | F | F | H | $—(CH_2)_5—$ | |
| I.a.528 | CN | H | H | F | F | H | $—(CH_2)_5—$ | |
| I.a.529 | F | H | H | CN | F | H | $—(CH_2)_5—$ | |
| I.a.530 | CN | H | H | F | F | H | $—(CH_2)_5—$ | |
| I.a.531 | F | H | F | H | F | H | $—(CH_2)_5—$ | |
| I.a.532 | Cl | H | F | H | F | H | $—(CH_2)_5—$ | |
| I.a.533 | CN | H | F | H | F | H | $—(CH_2)_5—$ | |
| I.a.534 | F | F | F | H | F | H | $—(CH_2)_5—$ | |
| I.a.535 | Cl | F | F | H | F | H | $—(CH_2)_5—$ | |
| I.a.536 | F | Cl | F | H | F | H | $—(CH_2)_5—$ | |
| I.a.537 | Cl | F | F | H | F | H | $—(CH_2)_5—$ | |
| I.a.538 | CN | F | F | H | F | H | $—(CH_2)_5—$ | |
| I.a.539 | F | CN | F | H | F | H | $—(CH_2)_5—$ | |
| I.a.540 | CN | F | F | H | F | H | $—(CH_2)_5—$ | |
| I.a.541 | F | F | H | F | F | H | $—(CH_2)_5—$ | |
| I.a.542 | Cl | F | H | F | F | H | $—(CH_2)_5—$ | |
| I.a.543 | F | Cl | H | F | F | H | $—(CH_2)_5—$ | |
| I.a.544 | CN | F | H | F | F | H | $—(CH_2)_5—$ | |
| I.a.545 | F | CN | H | F | F | H | $—(CH_2)_5—$ | |
| I.a.546 | F | F | F | F | F | H | $—(CH_2)_5—$ | |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.547 | Cl | F | F | F | F | H | $—(CH_2)_5—$ | |
| I.a.548 | F | Cl | F | F | F | H | $—(CH_2)_5—$ | |
| I.a.549 | CN | F | F | F | F | H | $—(CH_2)_5—$ | |
| I.a.550 | F | CN | F | F | F | H | $—(CH_2)_5—$ | |
| I.a.551 | H | F | F | F | F | H | $—(CH_2)_5—$ | |
| I.a.552 | F | F | Br | F | F | H | $—(CH_2)_5—$ | |
| I.a.553 | F | F | $C\equiv CH$ | F | F | H | $—(CH_2)_5—$ | |
| I.a.554 | $CF_3$ | Cl | H | H | F | H | $—(CH_2)_5—$ | |
| I.a.555 | F | F | I | F | F | H | $—(CH_2)_5—$ | |
| I.a.556 | F | H | H | H | F | $CH_3$ | $—(CH_2)_2—$ | |
| I.a.557 | Cl | H | H | H | F | $CH_3$ | $—(CH_2)_2—$ | |
| I.a.558 | Br | H | H | H | F | $CH_3$ | $—(CH_2)_2—$ | |
| I.a.559 | CN | H | H | H | F | $CH_3$ | $—(CH_2)_2—$ | |
| I.a.560 | $CH_3$ | H | H | H | F | $CH_3$ | $—(CH_2)_2—$ | |
| I.a.561 | F | H | H | F | F | $CH_3$ | $—(CH_2)_2—$ | |
| I.a.562 | Cl | H | H | F | F | $CH_3$ | $—(CH_2)_2—$ | |
| I.a.563 | F | H | H | Cl | F | $CH_3$ | $—(CH_2)_2—$ | |
| I.a.564 | Cl | H | H | F | F | $CH_3$ | $—(CH_2)_2—$ | |
| I.a.565 | CN | H | H | F | F | $CH_3$ | $—(CH_2)_2—$ | |
| I.a.566 | F | H | H | CN | F | $CH_3$ | $—(CH_2)_2—$ | |
| I.a.567 | CN | H | H | F | F | $CH_3$ | $—(CH_2)_2—$ | |
| I.a.568 | F | H | F | H | F | $CH_3$ | $—(CH_2)_2—$ | |
| I.a.569 | Cl | H | F | H | F | $CH_3$ | $—(CH_2)_2—$ | |
| I.a.570 | CN | H | F | H | F | $CH_3$ | $—(CH_2)_2—$ | |
| I.a.571 | F | F | F | H | F | $CH_3$ | $—(CH_2)_2—$ | |
| I.a.572 | Cl | F | F | H | F | $CH_3$ | $—(CH_2)_2—$ | |
| I.a.573 | F | Cl | F | H | F | $CH_3$ | $—(CH_2)_2—$ | |
| I.a.574 | Cl | F | F | H | F | $CH_3$ | $—(CH_2)_2—$ | |
| I.a.575 | CN | F | F | H | F | $CH_3$ | $—(CH_2)_2—$ | |
| I.a.576 | F | CN | F | H | F | $CH_3$ | $—(CH_2)_2—$ | |
| I.a.577 | CN | F | F | H | F | $CH_3$ | $—(CH_2)_2—$ | |
| I.a.578 | F | F | H | F | F | $CH_3$ | $—(CH_2)_2—$ | |
| I.a.579 | Cl | F | H | F | F | $CH_3$ | $—(CH_2)_2—$ | |
| I.a.580 | F | Cl | H | F | F | $CH_3$ | $—(CH_2)_2—$ | |
| I.a.581 | CN | F | H | F | F | $CH_3$ | $—(CH_2)_2—$ | |
| I.a.582 | F | CN | H | F | F | $CH_3$ | $—(CH_2)_2—$ | |
| I.a.583 | F | F | F | F | F | $CH_3$ | $—(CH_2)_2—$ | |
| I.a.584 | Cl | F | F | F | F | $CH_3$ | $—(CH_2)_2—$ | |
| I.a.585 | F | Cl | F | F | F | $CH_3$ | $—(CH_2)_2—$ | |
| I.a.586 | CN | F | F | F | F | $CH_3$ | $—(CH_2)_2—$ | |
| I.a.587 | F | CN | F | F | F | $CH_3$ | $—(CH_2)_2—$ | |
| I.a.588 | H | F | F | F | F | $CH_3$ | $—(CH_2)_2—$ | |
| I.a.589 | F | F | Br | F | F | $CH_3$ | $—(CH_2)_2—$ | |
| I.a.590 | F | F | $C\equiv CH$ | F | F | $CH_3$ | $—(CH_2)_2—$ | |
| I.a.591 | $CF_3$ | Cl | H | H | F | $CH_3$ | $—(CH_2)_2—$ | |
| I.a.592 | F | F | I | F | F | $CH_3$ | $—(CH_2)_2—$ | |
| I.a.593 | F | H | H | H | F | $CH_3$ | $—(CH_2)_3—$ | |
| I.a.594 | Cl | H | H | H | F | $CH_3$ | $—(CH_2)_3—$ | |
| I.a.595 | Br | H | H | H | F | $CH_3$ | $—(CH_2)_3—$ | |
| I.a.596 | CN | H | H | H | F | $CH_3$ | $—(CH_2)_3—$ | |
| I.a.597 | $CH_3$ | H | H | H | F | $CH_3$ | $—(CH_2)_3—$ | |
| I.a.598 | F | H | H | F | F | $CH_3$ | $—(CH_2)_3—$ | |
| I.a.599 | Cl | H | H | F | F | $CH_3$ | $—(CH_2)_3—$ | |
| I.a.600 | F | H | H | Cl | F | $CH_3$ | $—(CH_2)_3—$ | |
| I.a.601 | Cl | H | H | F | F | $CH_3$ | $—(CH_2)_3—$ | |
| I.a.602 | CN | H | H | F | F | $CH_3$ | $—(CH_2)_3—$ | |
| I.a.603 | F | H | H | CN | F | $CH_3$ | $—(CH_2)_3—$ | |
| I.a.604 | CN | H | H | F | F | $CH_3$ | $—(CH_2)_3—$ | |
| I.a.605 | F | H | F | H | F | $CH_3$ | $—(CH_2)_3—$ | |
| I.a.606 | Cl | H | F | H | F | $CH_3$ | $—(CH_2)_3—$ | |
| I.a.607 | CN | H | F | H | F | $CH_3$ | $—(CH_2)_3—$ | |
| I.a.608 | F | F | F | H | F | $CH_3$ | $—(CH_2)_3—$ | |
| I.a.609 | Cl | F | F | H | F | $CH_3$ | $—(CH_2)_3—$ | |
| I.a.610 | F | Cl | F | H | F | $CH_3$ | $—(CH_2)_3—$ | |
| I.a.611 | Cl | F | F | H | F | $CH_3$ | $—(CH_2)_3—$ | |
| I.a.612 | CN | F | F | H | F | $CH_3$ | $—(CH_2)_3—$ | |
| I.a.613 | F | CN | F | H | F | $CH_3$ | $—(CH_2)_3—$ | |
| I.a.614 | CN | F | F | H | F | $CH_3$ | $—(CH_2)_3—$ | |
| I.a.615 | F | F | H | F | F | $CH_3$ | $—(CH_2)_3—$ | |
| I.a.616 | Cl | F | H | F | F | $CH_3$ | $—(CH_2)_3—$ | |
| I.a.617 | F | Cl | H | F | F | $CH_3$ | $—(CH_2)_3—$ | |
| I.a.618 | CN | F | H | F | F | $CH_3$ | $—(CH_2)_3—$ | |
| I.a.619 | F | CN | H | F | F | $CH_3$ | $—(CH_2)_3—$ | |
| I.a.620 | F | F | F | F | F | $CH_3$ | $—(CH_2)_3—$ | |
| I.a.621 | Cl | F | F | F | F | $CH_3$ | $—(CH_2)_3—$ | |
| I.a.622 | F | Cl | F | F | F | $CH_3$ | $—(CH_2)_3—$ | |
| I.a.623 | CN | F | F | F | F | $CH_3$ | $—(CH_2)_3—$ | |
| I.a.624 | F | CN | F | F | F | $CH_3$ | $—(CH_2)_3—$ | |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.625 | H | F | F | F | F | $CH_3$ | | —$(CH_2)_3$— |
| I.a.626 | F | F | Br | F | F | $CH_3$ | | —$(CH_2)_3$— |
| I.a.627 | F | F | C≡CH | F | F | $CH_3$ | | —$(CH_2)_3$— |
| I.a.628 | $CF_3$ | Cl | H | H | F | $CH_3$ | | —$(CH_2)_3$— |
| I.a.629 | F | F | I | F | F | $CH_3$ | | —$(CH_2)_3$— |
| I.a.630 | F | H | H | H | F | $CH_3$ | | —$(CH_2)_4$— |
| I.a.631 | Cl | H | H | H | F | $CH_3$ | | —$(CH_2)_4$— |
| I.a.632 | Br | H | H | H | F | $CH_3$ | | —$(CH_2)_4$— |
| I.a.633 | CN | H | H | H | F | $CH_3$ | | —$(CH_2)_4$— |
| I.a.634 | $CH_3$ | H | H | H | F | $CH_3$ | | —$(CH_2)_4$— |
| I.a.635 | F | H | H | F | F | $CH_3$ | | —$(CH_2)_4$— |
| I.a.636 | Cl | H | H | F | F | $CH_3$ | | —$(CH_2)_4$— |
| I.a.637 | F | H | H | Cl | F | $CH_3$ | | —$(CH_2)_4$— |
| I.a.638 | Cl | H | H | F | F | $CH_3$ | | —$(CH_2)_4$— |
| I.a.639 | CN | H | H | F | F | $CH_3$ | | —$(CH_2)_4$— |
| I.a.640 | F | H | H | CN | F | $CH_3$ | | —$(CH_2)_4$— |
| I.a.641 | CN | H | H | F | F | $CH_3$ | | —$(CH_2)_4$— |
| I.a.642 | F | H | F | H | F | $CH_3$ | | —$(CH_2)_4$— |
| I.a.643 | Cl | H | F | H | F | $CH_3$ | | —$(CH_2)_4$— |
| I.a.644 | CN | H | F | H | F | $CH_3$ | | —$(CH_2)_4$— |
| I.a.645 | F | F | F | H | F | $CH_3$ | | —$(CH_2)_4$— |
| I.a.646 | Cl | F | F | H | F | $CH_3$ | | —$(CH_2)_4$— |
| I.a.647 | F | Cl | F | H | F | $CH_3$ | | —$(CH_2)_4$— |
| I.a.648 | Cl | F | F | H | F | $CH_3$ | | —$(CH_2)_4$— |
| I.a.649 | CN | F | F | H | F | $CH_3$ | | —$(CH_2)_4$— |
| I.a.650 | F | CN | F | H | F | $CH_3$ | | —$(CH_2)_4$— |
| I.a.651 | CN | F | F | H | F | $CH_3$ | | —$(CH_2)_4$— |
| I.a.652 | F | F | H | F | F | $CH_3$ | | —$(CH_2)_4$— |
| I.a.653 | Cl | F | H | F | F | $CH_3$ | | —$(CH_2)_4$— |
| I.a.654 | F | Cl | H | F | F | $CH_3$ | | —$(CH_2)_4$— |
| I.a.655 | CN | F | H | F | F | $CH_3$ | | —$(CH_2)_4$— |
| I.a.656 | F | CN | H | F | F | $CH_3$ | | —$(CH_2)_4$— |
| I.a.657 | F | F | F | F | F | $CH_3$ | | —$(CH_2)_4$— |
| I.a.658 | Cl | F | F | F | F | $CH_3$ | | —$(CH_2)_4$— |
| I.a.659 | F | Cl | F | F | F | $CH_3$ | | —$(CH_2)_4$— |
| I.a.660 | CN | F | F | F | F | $CH_3$ | | —$(CH_2)_4$— |
| I.a.661 | F | CN | F | F | F | $CH_3$ | | —$(CH_2)_4$— |
| I.a.662 | H | F | F | F | F | $CH_3$ | | —$(CH_2)_4$— |
| I.a.663 | F | F | Br | F | F | $CH_3$ | | —$(CH_2)_4$— |
| I.a.664 | F | F | C≡CH | F | F | $CH_3$ | | —$(CH_2)_4$— |
| I.a.665 | $CF_3$ | Cl | H | H | F | $CH_3$ | | —$(CH_2)_4$— |
| I.a.666 | F | F | I | F | F | $CH_3$ | | —$(CH_2)_4$— |
| I.a.667 | F | H | H | H | F | $CH_3$ | | —$(CH_2)_5$— |
| I.a.668 | Cl | H | H | H | F | $CH_3$ | | —$(CH_2)_5$— |
| I.a.669 | Br | H | H | H | F | $CH_3$ | | —$(CH_2)_5$— |
| I.a.670 | CN | H | H | H | F | $CH_3$ | | —$(CH_2)_5$— |
| I.a.671 | $CH_3$ | H | H | H | F | $CH_3$ | | —$(CH_2)_5$— |
| I.a.672 | F | H | H | F | F | $CH_3$ | | —$(CH_2)_5$— |
| I.a.673 | Cl | H | H | F | F | $CH_3$ | | —$(CH_2)_5$— |
| I.a.674 | F | H | H | Cl | F | $CH_3$ | | —$(CH_2)_5$— |
| I.a.675 | Cl | H | H | F | F | $CH_3$ | | —$(CH_2)_5$— |
| I.a.676 | CN | H | H | F | F | $CH_3$ | | —$(CH_2)_5$— |
| I.a.677 | F | H | H | CN | F | $CH_3$ | | —$(CH_2)_5$— |
| I.a.678 | CN | H | H | F | F | $CH_3$ | | —$(CH_2)_5$— |
| I.a.679 | F | H | F | H | F | $CH_3$ | | —$(CH_2)_5$— |
| I.a.680 | Cl | H | F | H | F | $CH_3$ | | —$(CH_2)_5$— |
| I.a.681 | CN | H | F | H | F | $CH_3$ | | —$(CH_2)_5$— |
| I.a.682 | F | F | F | H | F | $CH_3$ | | —$(CH_2)_5$— |
| I.a.683 | Cl | F | F | H | F | $CH_3$ | | —$(CH_2)_5$— |
| I.a.684 | F | Cl | F | H | F | $CH_3$ | | —$(CH_2)_5$— |
| I.a.685 | Cl | F | F | H | F | $CH_3$ | | —$(CH_2)_5$— |
| I.a.686 | CN | F | F | H | F | $CH_3$ | | —$(CH_2)_5$— |
| I.a.687 | F | CN | F | H | F | $CH_3$ | | —$(CH_2)_5$— |
| I.a.688 | CN | F | F | H | F | $CH_3$ | | —$(CH_2)_5$— |
| I.a.689 | F | F | H | F | F | $CH_3$ | | —$(CH_2)_5$— |
| I.a.690 | Cl | F | H | F | F | $CH_3$ | | —$(CH_2)_5$— |
| I.a.691 | F | Cl | H | F | F | $CH_3$ | | —$(CH_2)_5$— |
| I.a.692 | CN | F | H | F | F | $CH_3$ | | —$(CH_2)_5$— |
| I.a.693 | F | CN | H | F | F | $CH_3$ | | —$(CH_2)_5$— |
| I.a.694 | F | F | F | F | F | $CH_3$ | | —$(CH_2)_5$— |
| I.a.695 | Cl | F | F | F | F | $CH_3$ | | —$(CH_2)_5$— |
| I.a.696 | F | Cl | F | F | F | $CH_3$ | | —$(CH_2)_5$— |
| I.a.697 | CN | F | F | F | F | $CH_3$ | | —$(CH_2)_5$— |
| I.a.698 | F | CN | F | F | F | $CH_3$ | | —$(CH_2)_5$— |
| I.a.699 | H | F | F | F | F | $CH_3$ | | —$(CH_2)_5$— |
| I.a.700 | F | F | Br | F | F | $CH_3$ | | —$(CH_2)_5$— |
| I.a.701 | F | F | C≡CH | F | F | $CH_3$ | | —$(CH_2)_5$— |
| I.a.702 | $CF_3$ | Cl | H | H | F | $CH_3$ | | —$(CH_2)_5$— |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.703 | F | F | I | F | F | $CH_3$ | | —$(CH_2)_5$— |
| I.a.704 | F | H | H | H | F | F | | —$(CH_2)_2$— |
| I.a.705 | Cl | H | H | H | F | F | | —$(CH_2)_2$— |
| I.a.706 | Br | H | H | H | F | F | | —$(CH_2)_2$— |
| I.a.707 | CN | H | H | H | F | F | | —$(CH_2)_2$— |
| I.a.708 | $CH_3$ | H | H | H | F | F | | —$(CH_2)_2$— |
| I.a.709 | F | H | H | F | F | F | | —$(CH_2)_2$— |
| I.a.710 | Cl | H | H | F | F | F | | —$(CH_2)_2$— |
| I.a.711 | F | H | H | Cl | F | F | | —$(CH_2)_2$— |
| I.a.712 | Cl | H | H | F | F | F | | —$(CH_2)_2$— |
| I.a.713 | CN | H | H | F | F | F | | —$(CH_2)_2$— |
| I.a.714 | F | H | H | CN | F | F | | —$(CH_2)_2$— |
| I.a.715 | CN | H | H | F | F | F | | —$(CH_2)_2$— |
| I.a.716 | F | H | F | H | F | F | | —$(CH_2)_2$— |
| I.a.717 | Cl | H | F | H | F | F | | —$(CH_2)_2$— |
| I.a.718 | CN | H | F | H | F | F | | —$(CH_2)_2$— |
| I.a.719 | F | F | F | H | F | F | | —$(CH_2)_2$— |
| I.a.720 | Cl | F | F | H | F | F | | —$(CH_2)_2$— |
| I.a.721 | F | Cl | F | H | F | F | | —$(CH_2)_2$— |
| I.a.722 | Cl | F | F | H | F | F | | —$(CH_2)_2$— |
| I.a.723 | CN | F | F | H | F | F | | —$(CH_2)_2$— |
| I.a.724 | F | CN | F | H | F | F | | —$(CH_2)_2$— |
| I.a.725 | CN | F | F | H | F | F | | —$(CH_2)_2$— |
| I.a.726 | F | F | H | F | F | F | | —$(CH_2)_2$— |
| I.a.727 | Cl | F | H | F | F | F | | —$(CH_2)_2$— |
| I.a.728 | F | Cl | H | F | F | F | | —$(CH_2)_2$— |
| I.a.729 | CN | F | H | F | F | F | | —$(CH_2)_2$— |
| I.a.730 | F | CN | H | F | F | F | | —$(CH_2)_2$— |
| I.a.731 | F | F | F | F | F | F | | —$(CH_2)_2$— |
| I.a.732 | Cl | F | F | F | F | F | | —$(CH_2)_2$— |
| I.a.733 | F | Cl | F | F | F | F | | —$(CH_2)_2$— |
| I.a.734 | CN | F | F | F | F | F | | —$(CH_2)_2$— |
| I.a.735 | F | CN | F | F | F | F | | —$(CH_2)_2$— |
| I.a.736 | H | F | F | F | F | F | | —$(CH_2)_2$— |
| I.a.737 | F | F | Br | F | F | F | | —$(CH_2)_2$— |
| I.a.738 | F | F | C≡CH | F | F | F | | —$(CH_2)_2$— |
| I.a.739 | $CF_3$ | Cl | H | H | F | F | | —$(CH_2)_2$— |
| I.a.740 | F | F | I | F | F | F | | —$(CH_2)_2$— |
| I.a.741 | F | H | H | H | F | F | | —$(CH_2)_3$— |
| I.a.742 | Cl | H | H | H | F | F | | —$(CH_2)_3$— |
| I.a.743 | Br | H | H | H | F | F | | —$(CH_2)_3$— |
| I.a.744 | CN | H | H | H | F | F | | —$(CH_2)_3$— |
| I.a.745 | $CH_3$ | H | H | H | F | F | | —$(CH_2)_3$— |
| I.a.746 | F | H | H | F | F | F | | —$(CH_2)_3$— |
| I.a.747 | Cl | H | H | F | F | F | | —$(CH_2)_3$— |
| I.a.748 | F | H | H | Cl | F | F | | —$(CH_2)_3$— |
| I.a.749 | Cl | H | H | F | F | F | | —$(CH_2)_3$— |
| I.a.750 | CN | H | H | F | F | F | | —$(CH_2)_3$— |
| I.a.751 | F | H | H | CN | F | F | | —$(CH_2)_3$— |
| I.a.752 | CN | H | H | F | F | F | | —$(CH_2)_3$— |
| I.a.753 | F | H | F | H | F | F | | —$(CH_2)_3$— |
| I.a.754 | Cl | H | F | H | F | F | | —$(CH_2)_3$— |
| I.a.755 | CN | H | F | H | F | F | | —$(CH_2)_3$— |
| I.a.756 | F | F | F | H | F | F | | —$(CH_2)_3$— |
| I.a.757 | Cl | F | F | H | F | F | | —$(CH_2)_3$— |
| I.a.758 | F | Cl | F | H | F | F | | —$(CH_2)_3$— |
| I.a.759 | Cl | F | F | H | F | F | | —$(CH_2)_3$— |
| I.a.760 | CN | F | F | H | F | F | | —$(CH_2)_3$— |
| I.a.761 | F | CN | F | H | F | F | | —$(CH_2)_3$— |
| I.a.762 | CN | F | F | H | F | F | | —$(CH_2)_3$— |
| I.a.763 | F | F | H | F | F | F | | —$(CH_2)_3$— |
| I.a.764 | Cl | F | H | F | F | F | | —$(CH_2)_3$— |
| I.a.765 | F | Cl | H | F | F | F | | —$(CH_2)_3$— |
| I.a.766 | CN | F | H | F | F | F | | —$(CH_2)_3$— |
| I.a.767 | F | CN | H | F | F | F | | —$(CH_2)_3$— |
| I.a.768 | F | F | F | F | F | F | | —$(CH_2)_3$— |
| I.a.769 | Cl | F | F | F | F | F | | —$(CH_2)_3$— |
| I.a.770 | F | Cl | F | F | F | F | | —$(CH_2)_3$— |
| I.a.771 | CN | F | F | F | F | F | | —$(CH_2)_3$— |
| I.a.772 | F | CN | F | F | F | F | | —$(CH_2)_3$— |
| I.a.773 | H | F | F | F | F | F | | —$(CH_2)_3$— |
| I.a.774 | F | F | Br | F | F | F | | —$(CH_2)_3$— |
| I.a.775 | F | F | C≡CH | F | F | F | | —$(CH_2)_3$— |
| I.a.776 | $CF_3$ | Cl | H | H | F | F | | —$(CH_2)_3$— |
| I.a.777 | F | F | I | F | F | F | | —$(CH_2)_3$— |
| I.a.778 | F | H | H | H | F | F | | —$(CH_2)_4$— |
| I.a.779 | Cl | H | H | H | F | F | | —$(CH_2)_4$— |
| I.a.780 | Br | H | H | H | F | F | | —$(CH_2)_4$— |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.781 | CN | H | H | H | F | F | $-(CH_2)_4-$ | |
| I.a.782 | $CH_3$ | H | H | H | F | F | $-(CH_2)_4-$ | |
| I.a.783 | F | H | H | F | F | F | $-(CH_2)_4-$ | |
| I.a.784 | Cl | H | H | F | F | F | $-(CH_2)_4-$ | |
| I.a.785 | F | H | H | Cl | F | F | $-(CH_2)_4-$ | |
| I.a.786 | Cl | H | H | F | F | F | $-(CH_2)_4-$ | |
| I.a.787 | CN | H | H | F | F | F | $-(CH_2)_4-$ | |
| I.a.788 | F | H | H | CN | F | F | $-(CH_2)_4-$ | |
| I.a.789 | CN | H | H | F | F | F | $-(CH_2)_4-$ | |
| I.a.790 | F | H | F | H | F | F | $-(CH_2)_4-$ | |
| I.a.791 | Cl | H | F | H | F | F | $-(CH_2)_4-$ | |
| I.a.792 | CN | H | F | H | F | F | $-(CH_2)_4-$ | |
| I.a.793 | F | F | F | H | F | F | $-(CH_2)_4-$ | |
| I.a.794 | Cl | F | F | H | F | F | $-(CH_2)_4-$ | |
| I.a.795 | F | Cl | F | H | F | F | $-(CH_2)_4-$ | |
| I.a.796 | Cl | F | F | H | F | F | $-(CH_2)_4-$ | |
| I.a.797 | CN | F | F | H | F | F | $-(CH_2)_4-$ | |
| I.a.798 | F | CN | F | H | F | F | $-(CH_2)_4-$ | |
| I.a.799 | CN | F | F | H | F | F | $-(CH_2)_4-$ | |
| I.a.800 | F | F | H | F | F | F | $-(CH_2)_4-$ | |
| I.a.801 | Cl | F | H | F | F | F | $-(CH_2)_4-$ | |
| I.a.802 | F | Cl | H | F | F | F | $-(CH_2)_4-$ | |
| I.a.803 | CN | F | H | F | F | F | $-(CH_2)_4-$ | |
| I.a.804 | F | CN | H | F | F | F | $-(CH_2)_4-$ | |
| I.a.805 | F | F | F | F | F | F | $-(CH_2)_4-$ | |
| I.a.806 | Cl | F | F | F | F | F | $-(CH_2)_4-$ | |
| I.a.807 | F | Cl | F | F | F | F | $-(CH_2)_4-$ | |
| I.a.808 | CN | F | F | F | F | F | $-(CH_2)_4-$ | |
| I.a.809 | F | CN | F | F | F | F | $-(CH_2)_4-$ | |
| I.a.810 | H | F | F | F | F | F | $-(CH_2)_4-$ | |
| I.a.811 | F | F | Br | F | F | F | $-(CH_2)_4-$ | |
| I.a.812 | F | F | C≡CH | F | F | F | $-(CH_2)_4-$ | |
| I.a.813 | $CF_3$ | Cl | H | H | F | F | $-(CH_2)_4-$ | |
| I.a.814 | F | F | I | F | F | F | $-(CH_2)_4-$ | |
| I.a.815 | F | H | H | H | F | F | $-(CH_2)_5-$ | |
| I.a.816 | Cl | H | H | H | F | F | $-(CH_2)_5-$ | |
| I.a.817 | Br | H | H | H | F | F | $-(CH_2)_5-$ | |
| I.a.818 | CN | H | H | H | F | F | $-(CH_2)_5-$ | |
| I.a.819 | $CH_3$ | H | H | H | F | F | $-(CH_2)_5-$ | |
| I.a.820 | F | H | H | F | F | F | $-(CH_2)_5-$ | |
| I.a.821 | Cl | H | H | F | F | F | $-(CH_2)_5-$ | |
| I.a.822 | F | H | H | Cl | F | F | $-(CH_2)_5-$ | |
| I.a.823 | Cl | H | H | F | F | F | $-(CH_2)_5-$ | |
| I.a.824 | CN | H | H | F | F | F | $-(CH_2)_5-$ | |
| I.a.825 | F | H | H | CN | F | F | $-(CH_2)_5-$ | |
| I.a.826 | CN | H | H | F | F | F | $-(CH_2)_5-$ | |
| I.a.827 | F | H | F | H | F | F | $-(CH_2)_5-$ | |
| I.a.828 | Cl | H | F | H | F | F | $-(CH_2)_5-$ | |
| I.a.829 | CN | H | F | H | F | F | $-(CH_2)_5-$ | |
| I.a.830 | F | F | F | H | F | F | $-(CH_2)_5-$ | |
| I.a.831 | Cl | F | F | H | F | F | $-(CH_2)_5-$ | |
| I.a.832 | F | Cl | F | H | F | F | $-(CH_2)_5-$ | |
| I.a.833 | Cl | F | F | H | F | F | $-(CH_2)_5-$ | |
| I.a.834 | CN | F | F | H | F | F | $-(CH_2)_5-$ | |
| I.a.835 | F | CN | F | H | F | F | $-(CH_2)_5-$ | |
| I.a.836 | CN | F | F | H | F | F | $-(CH_2)_5-$ | |
| I.a.837 | F | F | H | F | F | F | $-(CH_2)_5-$ | |
| I.a.838 | Cl | F | H | F | F | F | $-(CH_2)_5-$ | |
| I.a.839 | F | Cl | H | F | F | F | $-(CH_2)_5-$ | |
| I.a.840 | CN | F | H | F | F | F | $-(CH_2)_5-$ | |
| I.a.841 | F | CN | H | F | F | F | $-(CH_2)_5-$ | |
| I.a.842 | F | F | F | F | F | F | $-(CH_2)_5-$ | |
| I.a.843 | Cl | F | F | F | F | F | $-(CH_2)_5-$ | |
| I.a.844 | F | Cl | F | F | F | F | $-(CH_2)_5-$ | |
| I.a.845 | CN | F | F | F | F | F | $-(CH_2)_5-$ | |
| I.a.846 | F | CN | F | F | F | F | $-(CH_2)_5-$ | |
| I.a.847 | H | F | F | F | F | F | $-(CH_2)_5-$ | |
| I.a.848 | F | F | Br | F | F | F | $-(CH_2)_5-$ | |
| I.a.849 | F | F | C≡CH | F | F | F | $-(CH_2)_5-$ | |
| I.a.850 | $CF_3$ | Cl | H | H | F | F | $-(CH_2)_5-$ | |
| I.a.851 | F | F | I | F | F | F | $-(CH_2)_5-$ | |
| I.a.852 | F | H | H | H | F | Cl | $-(CH_2)_2-$ | |
| I.a.853 | Cl | H | H | H | F | Cl | $-(CH_2)_2-$ | |
| I.a.854 | Br | H | H | H | F | Cl | $-(CH_2)_2-$ | |
| I.a.855 | CN | H | H | H | F | Cl | $-(CH_2)_2-$ | |
| I.a.856 | $CH_3$ | H | H | H | F | Cl | $-(CH_2)_2-$ | |
| I.a.857 | F | H | H | F | F | Cl | $-(CH_2)_2-$ | |
| I.a.858 | Cl | H | H | F | F | Cl | $-(CH_2)_2-$ | |
| I.a.859 | F | H | H | Cl | F | Cl | $-(CH_2)_2-$ | |
| I.a.860 | Cl | H | H | F | F | Cl | $-(CH_2)_2-$ | |
| I.a.861 | CN | H | H | F | F | Cl | $-(CH_2)_2-$ | |
| I.a.862 | F | H | H | CN | F | Cl | $-(CH_2)_2-$ | |
| I.a.863 | CN | H | H | F | F | Cl | $-(CH_2)_2-$ | |
| I.a.864 | F | H | F | H | F | Cl | $-(CH_2)_2-$ | |
| I.a.865 | Cl | H | F | H | F | Cl | $-(CH_2)_2-$ | |
| I.a.866 | CN | H | F | H | F | Cl | $-(CH_2)_2-$ | |
| I.a.867 | F | F | F | H | F | Cl | $-(CH_2)_2-$ | |
| I.a.868 | Cl | F | F | H | F | Cl | $-(CH_2)_2-$ | |
| I.a.869 | F | Cl | F | H | F | Cl | $-(CH_2)_2-$ | |
| I.a.870 | Cl | F | F | H | F | Cl | $-(CH_2)_2-$ | |
| I.a.871 | CN | F | F | H | F | Cl | $-(CH_2)_2-$ | |
| I.a.872 | F | CN | F | H | F | Cl | $-(CH_2)_2-$ | |
| I.a.873 | CN | F | F | H | F | Cl | $-(CH_2)_2-$ | |
| I.a.874 | F | F | H | F | F | Cl | $-(CH_2)_2-$ | |
| I.a.875 | Cl | F | H | F | F | Cl | $-(CH_2)_2-$ | |
| I.a.876 | F | Cl | H | F | F | Cl | $-(CH_2)_2-$ | |
| I.a.877 | CN | F | H | F | F | Cl | $-(CH_2)_2-$ | |
| I.a.878 | F | CN | H | F | F | Cl | $-(CH_2)_2-$ | |
| I.a.879 | F | F | F | F | F | Cl | $-(CH_2)_2-$ | |
| I.a.880 | Cl | F | F | F | F | Cl | $-(CH_2)_2-$ | |
| I.a.881 | F | Cl | F | F | F | Cl | $-(CH_2)_2-$ | |
| I.a.882 | CN | F | F | F | F | Cl | $-(CH_2)_2-$ | |
| I.a.883 | F | CN | F | F | F | Cl | $-(CH_2)_2-$ | |
| I.a.884 | H | F | F | F | F | Cl | $-(CH_2)_2-$ | |
| I.a.885 | F | F | Br | F | F | Cl | $-(CH_2)_2-$ | |
| I.a.886 | F | F | C≡CH | F | F | Cl | $-(CH_2)_2-$ | |
| I.a.887 | $CF_3$ | Cl | H | H | F | Cl | $-(CH_2)_2-$ | |
| I.a.888 | F | F | I | F | F | Cl | $-(CH_2)_2-$ | |
| I.a.889 | F | H | H | H | F | Cl | $-(CH_2)_3-$ | |
| I.a.890 | Cl | H | H | H | F | Cl | $-(CH_2)_3-$ | |
| I.a.891 | Br | H | H | H | F | Cl | $-(CH_2)_3-$ | |
| I.a.892 | CN | H | H | H | F | Cl | $-(CH_2)_3-$ | |
| I.a.893 | $CH_3$ | H | H | H | F | Cl | $-(CH_2)_3-$ | |
| I.a.894 | F | H | H | F | F | Cl | $-(CH_2)_3-$ | |
| I.a.895 | Cl | H | H | F | F | Cl | $-(CH_2)_3-$ | |
| I.a.896 | F | H | H | Cl | F | Cl | $-(CH_2)_3-$ | |
| I.a.897 | Cl | H | H | F | F | Cl | $-(CH_2)_3-$ | |
| I.a.898 | CN | H | H | F | F | Cl | $-(CH_2)_3-$ | |
| I.a.899 | F | H | H | CN | F | Cl | $-(CH_2)_3-$ | |
| I.a.900 | CN | H | H | F | F | Cl | $-(CH_2)_3-$ | |
| I.a.901 | F | H | F | H | F | Cl | $-(CH_2)_3-$ | |
| I.a.902 | Cl | H | F | H | F | Cl | $-(CH_2)_3-$ | |
| I.a.903 | CN | H | F | H | F | Cl | $-(CH_2)_3-$ | |
| I.a.904 | F | F | F | H | F | Cl | $-(CH_2)_3-$ | |
| I.a.905 | Cl | F | F | H | F | Cl | $-(CH_2)_3-$ | |
| I.a.906 | F | Cl | F | H | F | Cl | $-(CH_2)_3-$ | |
| I.a.907 | Cl | F | F | H | F | Cl | $-(CH_2)_3-$ | |
| I.a.908 | CN | F | F | H | F | Cl | $-(CH_2)_3-$ | |
| I.a.909 | F | CN | F | H | F | Cl | $-(CH_2)_3-$ | |
| I.a.910 | CN | F | F | H | F | Cl | $-(CH_2)_3-$ | |
| I.a.911 | F | F | H | F | F | Cl | $-(CH_2)_3-$ | |
| I.a.912 | Cl | F | H | F | F | Cl | $-(CH_2)_3-$ | |
| I.a.913 | F | Cl | H | F | F | Cl | $-(CH_2)_3-$ | |
| I.a.914 | CN | F | H | F | F | Cl | $-(CH_2)_3-$ | |
| I.a.915 | F | CN | H | F | F | Cl | $-(CH_2)_3-$ | |
| I.a.916 | F | F | F | F | F | Cl | $-(CH_2)_3-$ | |
| I.a.917 | Cl | F | F | F | F | Cl | $-(CH_2)_3-$ | |
| I.a.918 | F | Cl | F | F | F | Cl | $-(CH_2)_3-$ | |
| I.a.919 | CN | F | F | F | F | Cl | $-(CH_2)_3-$ | |
| I.a.920 | F | CN | F | F | F | Cl | $-(CH_2)_3-$ | |
| I.a.921 | H | F | F | F | F | Cl | $-(CH_2)_3-$ | |
| I.a.922 | F | F | Br | F | F | Cl | $-(CH_2)_3-$ | |
| I.a.923 | F | F | C≡CH | F | F | Cl | $-(CH_2)_3-$ | |
| I.a.924 | $CF_3$ | Cl | H | H | F | Cl | $-(CH_2)_3-$ | |
| I.a.925 | F | F | I | F | F | Cl | $-(CH_2)_3-$ | |
| I.a.926 | F | H | H | H | F | Cl | $-(CH_2)_4-$ | |
| I.a.927 | Cl | H | H | H | F | Cl | $-(CH_2)_4-$ | |
| I.a.928 | Br | H | H | H | F | Cl | $-(CH_2)_4-$ | |
| I.a.929 | CN | H | H | H | F | Cl | $-(CH_2)_4-$ | |
| I.a.930 | $CH_3$ | H | H | H | F | Cl | $-(CH_2)_4-$ | |
| I.a.931 | F | H | H | F | F | Cl | $-(CH_2)_4-$ | |
| I.a.932 | Cl | H | H | F | F | Cl | $-(CH_2)_4-$ | |
| I.a.933 | F | H | H | Cl | F | Cl | $-(CH_2)_4-$ | |
| I.a.934 | Cl | H | H | F | F | Cl | $-(CH_2)_4-$ | |
| I.a.935 | CN | H | H | F | F | Cl | $-(CH_2)_4-$ | |
| I.a.936 | F | H | H | CN | F | Cl | $-(CH_2)_4-$ | |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.937 | CN | H | H | F | F | Cl | —$(CH_2)_4$— | |
| I.a.938 | F | H | F | H | F | Cl | —$(CH_2)_4$— | |
| I.a.939 | Cl | H | F | H | F | Cl | —$(CH_2)_4$— | |
| I.a.940 | CN | H | F | H | F | Cl | —$(CH_2)_4$— | |
| I.a.941 | F | F | F | H | F | Cl | —$(CH_2)_4$— | |
| I.a.942 | Cl | F | F | H | F | Cl | —$(CH_2)_4$— | |
| I.a.943 | F | Cl | F | H | F | Cl | —$(CH_2)_4$— | |
| I.a.944 | Cl | F | F | H | F | Cl | —$(CH_2)_4$— | |
| I.a.945 | CN | F | F | H | F | Cl | —$(CH_2)_4$— | |
| I.a.946 | F | CN | F | H | F | Cl | —$(CH_2)_4$— | |
| I.a.947 | CN | F | F | H | F | Cl | —$(CH_2)_4$— | |
| I.a.948 | F | F | H | F | F | Cl | —$(CH_2)_4$— | |
| I.a.949 | Cl | F | H | F | F | Cl | —$(CH_2)_4$— | |
| I.a.950 | F | Cl | H | F | F | Cl | —$(CH_2)_4$— | |
| I.a.951 | CN | F | H | F | F | Cl | —$(CH_2)_4$— | |
| I.a.952 | F | CN | H | F | F | Cl | —$(CH_2)_4$— | |
| I.a.953 | F | F | F | F | F | Cl | —$(CH_2)_4$— | |
| I.a.954 | Cl | F | F | F | F | Cl | —$(CH_2)_4$— | |
| I.a.955 | F | Cl | F | F | F | Cl | —$(CH_2)_4$— | |
| I.a.956 | CN | F | F | F | F | Cl | —$(CH_2)_4$— | |
| I.a.957 | F | CN | F | F | F | Cl | —$(CH_2)_4$— | |
| I.a.958 | H | F | F | F | F | Cl | —$(CH_2)_4$— | |
| I.a.959 | F | F | Br | F | F | Cl | —$(CH_2)_4$— | |
| I.a.960 | F | F | C≡CH | F | F | Cl | —$(CH_2)_4$— | |
| I.a.961 | $CF_3$ | Cl | H | H | F | Cl | —$(CH_2)_4$— | |
| I.a.962 | F | F | I | F | F | Cl | —$(CH_2)_4$— | |
| I.a.963 | F | H | H | H | F | Cl | —$(CH_2)_5$— | |
| I.a.964 | Cl | H | H | H | F | Cl | —$(CH_2)_5$— | |
| I.a.965 | Br | H | H | H | F | Cl | —$(CH_2)_5$— | |
| I.a.966 | CN | H | H | H | F | Cl | —$(CH_2)_5$— | |
| I.a.967 | $CH_3$ | H | H | H | F | Cl | —$(CH_2)_5$— | |
| I.a.968 | F | H | H | F | F | Cl | —$(CH_2)_5$— | |
| I.a.969 | Cl | H | H | F | F | Cl | —$(CH_2)_5$— | |
| I.a.970 | F | H | H | Cl | F | Cl | —$(CH_2)_5$— | |
| I.a.971 | Cl | H | H | F | F | Cl | —$(CH_2)_5$— | |
| I.a.972 | CN | H | H | F | F | Cl | —$(CH_2)_5$— | |
| I.a.973 | F | H | H | CN | F | Cl | —$(CH_2)_5$— | |
| I.a.974 | CN | H | H | F | F | Cl | —$(CH_2)_5$— | |
| I.a.975 | F | H | F | H | F | Cl | —$(CH_2)_5$— | |
| I.a.976 | Cl | H | F | H | F | Cl | —$(CH_2)_5$— | |
| I.a.977 | CN | H | F | H | F | Cl | —$(CH_2)_5$— | |
| I.a.978 | F | F | F | H | F | Cl | —$(CH_2)_5$— | |
| I.a.979 | Cl | F | F | H | F | Cl | —$(CH_2)_5$— | |
| I.a.980 | F | Cl | F | H | F | Cl | —$(CH_2)_5$— | |
| I.a.981 | Cl | F | F | H | F | Cl | —$(CH_2)_5$— | |
| I.a.982 | CN | F | F | H | F | Cl | —$(CH_2)_5$— | |
| I.a.983 | F | CN | F | H | F | Cl | —$(CH_2)_5$— | |
| I.a.984 | CN | F | F | H | F | Cl | —$(CH_2)_5$— | |
| I.a.985 | F | F | H | F | F | Cl | —$(CH_2)_5$— | |
| I.a.986 | Cl | F | H | F | F | Cl | —$(CH_2)_5$— | |
| I.a.987 | F | Cl | H | F | F | Cl | —$(CH_2)_5$— | |
| I.a.988 | CN | F | H | F | F | Cl | —$(CH_2)_5$— | |
| I.a.989 | F | CN | H | F | F | Cl | —$(CH_2)_5$— | |
| I.a.990 | F | F | F | F | F | Cl | —$(CH_2)_5$— | |
| I.a.991 | Cl | F | F | F | F | Cl | —$(CH_2)_5$— | |
| I.a.992 | F | Cl | F | F | F | Cl | —$(CH_2)_5$— | |
| I.a.993 | CN | F | F | F | F | Cl | —$(CH_2)_5$— | |
| I.a.994 | F | CN | F | F | F | Cl | —$(CH_2)_5$— | |
| I.a.995 | H | F | F | F | F | Cl | —$(CH_2)_5$— | |
| I.a.996 | F | F | Br | F | F | Cl | —$(CH_2)_5$— | |
| I.a.997 | F | F | C≡CH | F | F | Cl | —$(CH_2)_5$— | |
| I.a.998 | $CF_3$ | Cl | H | H | F | Cl | —$(CH_2)_5$— | |
| I.a.999 | F | F | I | F | F | Cl | —$(CH_2)_5$— | |
| I.a.1000 | F | H | H | H | F | $C_2H_5$ | $CH_3$ | H |
| I.a.1001 | Cl | H | H | H | F | $C_2H_5$ | $CH_3$ | H |
| I.a.1002 | Br | H | H | H | F | $C_2H_5$ | $CH_3$ | H |
| I.a.1003 | CN | H | H | H | F | $C_2H_5$ | $CH_3$ | H |
| I.a.1004 | $CH_3$ | H | H | H | F | $C_2H_5$ | $CH_3$ | H |
| I.a.1005 | F | H | H | F | F | $C_2H_5$ | $CH_3$ | H |
| I.a.1006 | Cl | H | H | F | F | $C_2H_5$ | $CH_3$ | H |
| I.a.1007 | F | H | H | Cl | F | $C_2H_5$ | $CH_3$ | H |
| I.a.1008 | Cl | H | H | F | F | $C_2H_5$ | $CH_3$ | H |
| I.a.1009 | CN | H | H | F | F | $C_2H_5$ | $CH_3$ | H |
| I.a.1010 | F | H | H | CN | F | $C_2H_5$ | $CH_3$ | H |
| I.a.1011 | CN | H | H | F | F | $C_2H_5$ | $CH_3$ | H |
| I.a.1012 | F | H | F | H | F | $C_2H_5$ | $CH_3$ | H |
| I.a.1013 | Cl | H | F | H | F | $C_2H_5$ | $CH_3$ | H |
| I.a.1014 | CN | H | F | H | F | $C_2H_5$ | $CH_3$ | H |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.1015 | F | F | F | H | F | $C_2H_5$ | $CH_3$ | H |
| I.a.1016 | Cl | F | F | H | F | $C_2H_5$ | $CH_3$ | H |
| I.a.1017 | F | Cl | F | H | F | $C_2H_5$ | $CH_3$ | H |
| I.a.1018 | Cl | F | F | H | F | $C_2H_5$ | $CH_3$ | H |
| I.a.1019 | CN | F | F | H | F | $C_2H_5$ | $CH_3$ | H |
| I.a.1020 | F | CN | F | H | F | $C_2H_5$ | $CH_3$ | H |
| I.a.1021 | CN | F | F | H | F | $C_2H_5$ | $CH_3$ | H |
| I.a.1022 | F | F | H | F | F | $C_2H_5$ | $CH_3$ | H |
| I.a.1023 | Cl | F | H | F | F | $C_2H_5$ | $CH_3$ | H |
| I.a.1024 | F | Cl | H | F | F | $C_2H_5$ | $CH_3$ | H |
| I.a.1025 | CN | F | H | F | F | $C_2H_5$ | $CH_3$ | H |
| I.a.1026 | F | CN | H | F | F | $C_2H_5$ | $CH_3$ | H |
| I.a.1027 | F | F | F | F | F | $C_2H_5$ | $CH_3$ | H |
| I.a.1028 | Cl | F | F | F | F | $C_2H_5$ | $CH_3$ | H |
| I.a.1029 | F | Cl | F | F | F | $C_2H_5$ | $CH_3$ | H |
| I.a.1030 | CN | F | F | F | F | $C_2H_5$ | $CH_3$ | H |
| I.a.1031 | F | CN | F | F | F | $C_2H_5$ | $CH_3$ | H |
| I.a.1032 | H | F | F | F | F | $C_2H_5$ | $CH_3$ | H |
| I.a.1033 | F | F | Br | F | F | $C_2H_5$ | $CH_3$ | H |
| I.a.1034 | F | F | C≡CH | F | F | $C_2H_5$ | $CH_3$ | H |
| I.a.1035 | $CF_3$ | Cl | H | H | F | $C_2H_5$ | $CH_3$ | H |
| I.a.1036 | F | F | I | F | F | $C_2H_5$ | $CH_3$ | H |
| I.a.1037 | F | H | H | H | F | $C_2H_5$ | $C_2H_5$ | H |
| I.a.1038 | Cl | H | H | H | F | $C_2H_5$ | $C_2H_5$ | H |
| I.a.1039 | Br | H | H | H | F | $C_2H_5$ | $C_2H_5$ | H |
| I.a.1040 | CN | H | H | H | F | $C_2H_5$ | $C_2H_5$ | H |
| I.a.1041 | $CH_3$ | H | H | H | F | $C_2H_5$ | $C_2H_5$ | H |
| I.a.1042 | F | H | H | F | F | $C_2H_5$ | $C_2H_5$ | H |
| I.a.1043 | Cl | H | H | F | F | $C_2H_5$ | $C_2H_5$ | H |
| I.a.1044 | F | H | H | Cl | F | $C_2H_5$ | $C_2H_5$ | H |
| I.a.1045 | Cl | H | H | F | F | $C_2H_5$ | $C_2H_5$ | H |
| I.a.1046 | CN | H | H | F | F | $C_2H_5$ | $C_2H_5$ | H |
| I.a.1047 | F | H | H | CN | F | $C_2H_5$ | $C_2H_5$ | H |
| I.a.1048 | CN | H | H | F | F | $C_2H_5$ | $C_2H_5$ | H |
| I.a.1049 | F | H | F | H | F | $C_2H_5$ | $C_2H_5$ | H |
| I.a.1050 | Cl | H | F | H | F | $C_2H_5$ | $C_2H_5$ | H |
| I.a.1051 | CN | H | F | H | F | $C_2H_5$ | $C_2H_5$ | H |
| I.a.1052 | F | F | F | H | F | $C_2H_5$ | $C_2H_5$ | H |
| I.a.1053 | Cl | F | F | H | F | $C_2H_5$ | $C_2H_5$ | H |
| I.a.1054 | F | Cl | F | H | F | $C_2H_5$ | $C_2H_5$ | H |
| I.a.1055 | Cl | F | F | H | F | $C_2H_5$ | $C_2H_5$ | H |
| I.a.1056 | CN | F | F | H | F | $C_2H_5$ | $C_2H_5$ | H |
| I.a.1057 | F | CN | F | H | F | $C_2H_5$ | $C_2H_5$ | H |
| I.a.1058 | CN | F | F | H | F | $C_2H_5$ | $C_2H_5$ | H |
| I.a.1059 | F | F | H | F | F | $C_2H_5$ | $C_2H_5$ | H |
| I.a.1060 | Cl | F | H | F | F | $C_2H_5$ | $C_2H_5$ | H |
| I.a.1061 | F | Cl | H | F | F | $C_2H_5$ | $C_2H_5$ | H |
| I.a.1062 | CN | F | H | F | F | $C_2H_5$ | $C_2H_5$ | H |
| I.a.1063 | F | CN | H | F | F | $C_2H_5$ | $C_2H_5$ | H |
| I.a.1064 | F | F | F | F | F | $C_2H_5$ | $C_2H_5$ | H |
| I.a.1065 | Cl | F | F | F | F | $C_2H_5$ | $C_2H_5$ | H |
| I.a.1066 | F | Cl | F | F | F | $C_2H_5$ | $C_2H_5$ | H |
| I.a.1067 | CN | F | F | F | F | $C_2H_5$ | $C_2H_5$ | H |
| I.a.1068 | F | CN | F | F | F | $C_2H_5$ | $C_2H_5$ | H |
| I.a.1069 | H | F | F | F | F | $C_2H_5$ | $C_2H_5$ | H |
| I.a.1070 | F | F | Br | F | F | $C_2H_5$ | $C_2H_5$ | H |
| I.a.1071 | F | F | C≡CH | F | F | $C_2H_5$ | $C_2H_5$ | H |
| I.a.1072 | $CF_3$ | Cl | H | H | F | $C_2H_5$ | $C_2H_5$ | H |
| I.a.1073 | F | F | I | F | F | $C_2H_5$ | $C_2H_5$ | H |
| I.a.1074 | F | H | H | H | F | $C_2H_5$ | $C_2H_5$ | $CH_3$ |
| I.a.1075 | Cl | H | H | H | F | $C_2H_5$ | $C_2H_5$ | $CH_3$ |
| I.a.1076 | Br | H | H | H | F | $C_2H_5$ | $C_2H_5$ | $CH_3$ |
| I.a.1077 | CN | H | H | H | F | $C_2H_5$ | $C_2H_5$ | $CH_3$ |
| I.a.1078 | $CH_3$ | H | H | H | F | $C_2H_5$ | $C_2H_5$ | $CH_3$ |
| I.a.1079 | F | H | H | F | F | $C_2H_5$ | $C_2H_5$ | $CH_3$ |
| I.a.1080 | Cl | H | H | F | F | $C_2H_5$ | $C_2H_5$ | $CH_3$ |
| I.a.1081 | F | H | H | Cl | F | $C_2H_5$ | $C_2H_5$ | $CH_3$ |
| I.a.1082 | Cl | H | H | F | F | $C_2H_5$ | $C_2H_5$ | $CH_3$ |
| I.a.1083 | CN | H | H | F | F | $C_2H_5$ | $C_2H_5$ | $CH_3$ |
| I.a.1084 | F | H | H | CN | F | $C_2H_5$ | $C_2H_5$ | $CH_3$ |
| I.a.1085 | CN | H | H | F | F | $C_2H_5$ | $C_2H_5$ | $CH_3$ |
| I.a.1086 | F | H | F | H | F | $C_2H_5$ | $C_2H_5$ | $CH_3$ |
| I.a.1087 | Cl | H | F | H | F | $C_2H_5$ | $C_2H_5$ | $CH_3$ |
| I.a.1088 | CN | H | F | H | F | $C_2H_5$ | $C_2H_5$ | $CH_3$ |
| I.a.1089 | F | F | F | H | F | $C_2H_5$ | $C_2H_5$ | $CH_3$ |
| I.a.1090 | Cl | F | F | H | F | $C_2H_5$ | $C_2H_5$ | $CH_3$ |
| I.a.1091 | F | Cl | F | H | F | $C_2H_5$ | $C_2H_5$ | $CH_3$ |
| I.a.1092 | Cl | F | F | H | F | $C_2H_5$ | $C_2H_5$ | $CH_3$ |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.1093 | CN | F | F | H | F | $C_2H_5$ | $C_2H_5$ | $CH_3$ |
| I.a.1094 | F | CN | F | H | F | $C_2H_5$ | $C_2H_5$ | $CH_3$ |
| I.a.1095 | CN | F | F | H | F | $C_2H_5$ | $C_2H_5$ | $CH_3$ |
| I.a.1096 | F | F | H | F | F | $C_2H_5$ | $C_2H_5$ | $CH_3$ |
| I.a.1097 | Cl | F | H | F | F | $C_2H_5$ | $C_2H_5$ | $CH_3$ |
| I.a.1098 | F | Cl | H | F | F | $C_2H_5$ | $C_2H_5$ | $CH_3$ |
| I.a.1099 | CN | F | H | F | F | $C_2H_5$ | $C_2H_5$ | $CH_3$ |
| I.a.1100 | F | CN | H | F | F | $C_2H_5$ | $C_2H_5$ | $CH_3$ |
| I.a.1101 | F | F | F | F | F | $C_2H_5$ | $C_2H_5$ | $CH_3$ |
| I.a.1102 | Cl | F | F | F | F | $C_2H_5$ | $C_2H_5$ | $CH_3$ |
| I.a.1103 | F | Cl | F | F | F | $C_2H_5$ | $C_2H_5$ | $CH_3$ |
| I.a.1104 | CN | F | F | F | F | $C_2H_5$ | $C_2H_5$ | $CH_3$ |
| I.a.1105 | F | CN | F | F | F | $C_2H_5$ | $C_2H_5$ | $CH_3$ |
| I.a.1106 | H | F | F | F | F | $C_2H_5$ | $C_2H_5$ | $CH_3$ |
| I.a.1107 | F | F | Br | F | F | $C_2H_5$ | $C_2H_5$ | $CH_3$ |
| I.a.1108 | F | F | C≡CH | F | F | $C_2H_5$ | $C_2H_5$ | $CH_3$ |
| I.a.1109 | $CF_3$ | Cl | H | H | F | $C_2H_5$ | $C_2H_5$ | $CH_3$ |
| I.a.1110 | F | F | I | F | F | $C_2H_5$ | $C_2H_5$ | $CH_3$ |
| I.a.1111 | F | H | H | H | F | $C_2H_5$ | $CH_3$ | $CH_3$ |
| I.a.1112 | Cl | H | H | H | F | $C_2H_5$ | $CH_3$ | $CH_3$ |
| I.a.1113 | Br | H | H | H | F | $C_2H_5$ | $CH_3$ | $CH_3$ |
| I.a.1114 | CN | H | H | H | F | $C_2H_5$ | $CH_3$ | $CH_3$ |
| I.a.1115 | $CH_3$ | H | H | H | F | $C_2H_5$ | $CH_3$ | $CH_3$ |
| I.a.1116 | F | H | H | F | F | $C_2H_5$ | $CH_3$ | $CH_3$ |
| I.a.1117 | Cl | H | H | F | F | $C_2H_5$ | $CH_3$ | $CH_3$ |
| I.a.1118 | F | H | H | Cl | F | $C_2H_5$ | $CH_3$ | $CH_3$ |
| I.a.1119 | Cl | H | H | F | F | $C_2H_5$ | $CH_3$ | $CH_3$ |
| I.a.1120 | CN | H | H | F | F | $C_2H_5$ | $CH_3$ | $CH_3$ |
| I.a.1121 | F | H | H | CN | F | $C_2H_5$ | $CH_3$ | $CH_3$ |
| I.a.1122 | CN | H | H | F | F | $C_2H_5$ | $CH_3$ | $CH_3$ |
| I.a.1123 | F | H | F | H | F | $C_2H_5$ | $CH_3$ | $CH_3$ |
| I.a.1124 | Cl | H | F | H | F | $C_2H_5$ | $CH_3$ | $CH_3$ |
| I.a.1125 | CN | H | F | H | F | $C_2H_5$ | $CH_3$ | $CH_3$ |
| I.a.1126 | F | F | F | H | F | $C_2H_5$ | $CH_3$ | $CH_3$ |
| I.a.1127 | Cl | F | F | H | F | $C_2H_5$ | $CH_3$ | $CH_3$ |
| I.a.1128 | F | Cl | F | H | F | $C_2H_5$ | $CH_3$ | $CH_3$ |
| I.a.1129 | Cl | F | F | H | F | $C_2H_5$ | $CH_3$ | $CH_3$ |
| I.a.1130 | CN | F | F | H | F | $C_2H_5$ | $CH_3$ | $CH_3$ |
| I.a.1131 | F | CN | F | H | F | $C_2H_5$ | $CH_3$ | $CH_3$ |
| I.a.1132 | CN | F | F | H | F | $C_2H_5$ | $CH_3$ | $CH_3$ |
| I.a.1133 | F | F | H | F | F | $C_2H_5$ | $CH_3$ | $CH_3$ |
| I.a.1134 | Cl | F | H | F | F | $C_2H_5$ | $CH_3$ | $CH_3$ |
| I.a.1135 | F | Cl | H | F | F | $C_2H_5$ | $CH_3$ | $CH_3$ |
| I.a.1136 | CN | F | H | F | F | $C_2H_5$ | $CH_3$ | $CH_3$ |
| I.a.1137 | F | CN | H | F | F | $C_2H_5$ | $CH_3$ | $CH_3$ |
| I.a.1138 | F | F | F | F | F | $C_2H_5$ | $CH_3$ | $CH_3$ |
| I.a.1139 | Cl | F | F | F | F | $C_2H_5$ | $CH_3$ | $CH_3$ |
| I.a.1140 | F | Cl | F | F | F | $C_2H_5$ | $CH_3$ | $CH_3$ |
| I.a.1141 | CN | F | F | F | F | $C_2H_5$ | $CH_3$ | $CH_3$ |
| I.a.1142 | F | CN | F | F | F | $C_2H_5$ | $CH_3$ | $CH_3$ |
| I.a.1143 | H | F | F | F | F | $C_2H_5$ | $CH_3$ | $CH_3$ |
| I.a.1144 | F | F | Br | F | F | $C_2H_5$ | $CH_3$ | $CH_3$ |
| I.a.1145 | F | F | C≡CH | F | F | $C_2H_5$ | $CH_3$ | $CH_3$ |
| I.a.1146 | $CF_3$ | Cl | H | H | F | $C_2H_5$ | $CH_3$ | $CH_3$ |
| I.a.1147 | F | F | I | F | F | $C_2H_5$ | $CH_3$ | $CH_3$ |
| I.a.1148 | F | H | H | H | F | Cl | $CH_3$ | H |
| I.a.1149 | Cl | H | H | H | F | Cl | $CH_3$ | H |
| I.a.1150 | Br | H | H | H | F | Cl | $CH_3$ | H |
| I.a.1151 | CN | H | H | H | F | Cl | $CH_3$ | H |
| I.a.1152 | $CH_3$ | H | H | H | F | Cl | $CH_3$ | H |
| I.a.1153 | F | H | H | F | F | Cl | $CH_3$ | H |
| I.a.1154 | Cl | H | H | F | F | Cl | $CH_3$ | H |
| I.a.1155 | F | H | H | Cl | F | Cl | $CH_3$ | H |
| I.a.1156 | Cl | H | H | F | F | Cl | $CH_3$ | H |
| I.a.1157 | CN | H | H | F | F | Cl | $CH_3$ | H |
| I.a.1158 | F | H | H | CN | F | Cl | $CH_3$ | H |
| I.a.1159 | CN | H | H | F | F | Cl | $CH_3$ | H |
| I.a.1160 | F | H | F | H | F | Cl | $CH_3$ | H |
| I.a.1161 | Cl | H | F | H | F | Cl | $CH_3$ | H |
| I.a.1162 | CN | H | F | H | F | Cl | $CH_3$ | H |
| I.a.1163 | F | F | F | H | F | Cl | $CH_3$ | H |
| I.a.1164 | Cl | F | F | H | F | Cl | $CH_3$ | H |
| I.a.1165 | F | Cl | F | H | F | Cl | $CH_3$ | H |
| I.a.1166 | Cl | F | F | H | F | Cl | $CH_3$ | H |
| I.a.1167 | CN | F | F | H | F | Cl | $CH_3$ | H |
| I.a.1168 | F | CN | F | H | F | Cl | $CH_3$ | H |
| I.a.1169 | CN | F | F | H | F | Cl | $CH_3$ | H |
| I.a.1170 | F | F | H | F | F | Cl | $CH_3$ | H |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.1171 | Cl | F | H | F | F | Cl | $CH_3$ | H |
| I.a.1172 | F | Cl | H | F | F | Cl | $CH_3$ | H |
| I.a.1173 | CN | F | H | F | F | Cl | $CH_3$ | H |
| I.a.1174 | F | CN | H | F | F | Cl | $CH_3$ | H |
| I.a.1175 | F | F | F | F | F | Cl | $CH_3$ | H |
| I.a.1176 | Cl | F | F | F | F | Cl | $CH_3$ | H |
| I.a.1177 | F | Cl | F | F | F | Cl | $CH_3$ | H |
| I.a.1178 | CN | F | F | F | F | Cl | $CH_3$ | H |
| I.a.1179 | F | CN | F | F | F | Cl | $CH_3$ | H |
| I.a.1180 | H | F | F | F | F | Cl | $CH_3$ | H |
| I.a.1181 | F | F | Br | F | F | Cl | $CH_3$ | H |
| I.a.1182 | F | F | C≡CH | F | F | Cl | $CH_3$ | H |
| I.a.1183 | $CF_3$ | Cl | H | H | F | Cl | $CH_3$ | H |
| I.a.1184 | F | F | I | F | F | Cl | $CH_3$ | H |
| I.a.1185 | F | H | H | H | F | $CH_2Cl$ | Cl | $CH_3$ |
| I.a.1186 | Cl | H | H | H | F | $CH_2Cl$ | Cl | $CH_3$ |
| I.a.1187 | Br | H | H | H | F | $CH_2Cl$ | Cl | $CH_3$ |
| I.a.1188 | CN | H | H | H | F | $CH_2Cl$ | Cl | $CH_3$ |
| I.a.1189 | $CH_3$ | H | H | H | F | $CH_2Cl$ | Cl | $CH_3$ |
| I.a.1190 | F | H | H | F | F | $CH_2Cl$ | Cl | $CH_3$ |
| I.a.1191 | Cl | H | H | F | F | $CH_2Cl$ | Cl | $CH_3$ |
| I.a.1192 | F | H | H | Cl | F | $CH_2Cl$ | Cl | $CH_3$ |
| I.a.1193 | Cl | H | H | F | F | $CH_2Cl$ | Cl | $CH_3$ |
| I.a.1194 | CN | H | H | F | F | $CH_2Cl$ | Cl | $CH_3$ |
| I.a.1195 | F | H | H | CN | F | $CH_2Cl$ | Cl | $CH_3$ |
| I.a.1196 | CN | H | H | F | F | $CH_2Cl$ | Cl | $CH_3$ |
| I.a.1197 | F | H | F | H | F | $CH_2Cl$ | Cl | $CH_3$ |
| I.a.1198 | Cl | H | F | H | F | $CH_2Cl$ | Cl | $CH_3$ |
| I.a.1199 | CN | H | F | H | F | $CH_2Cl$ | Cl | $CH_3$ |
| I.a.1200 | F | F | F | H | F | $CH_2Cl$ | Cl | $CH_3$ |
| I.a.1201 | Cl | F | F | H | F | $CH_2Cl$ | Cl | $CH_3$ |
| I.a.1202 | F | Cl | F | H | F | $CH_2Cl$ | Cl | $CH_3$ |
| I.a.1203 | Cl | F | F | H | F | $CH_2Cl$ | Cl | $CH_3$ |
| I.a.1204 | CN | F | F | H | F | $CH_2Cl$ | Cl | $CH_3$ |
| I.a.1205 | F | CN | F | H | F | $CH_2Cl$ | Cl | $CH_3$ |
| I.a.1206 | CN | F | F | H | F | $CH_2Cl$ | Cl | $CH_3$ |
| I.a.1207 | F | F | H | F | F | $CH_2Cl$ | Cl | $CH_3$ |
| I.a.1208 | Cl | F | H | F | F | $CH_2Cl$ | Cl | $CH_3$ |
| I.a.1209 | F | Cl | H | F | F | $CH_2Cl$ | Cl | $CH_3$ |
| I.a.1210 | CN | F | H | F | F | $CH_2Cl$ | Cl | $CH_3$ |
| I.a.1211 | F | CN | H | F | F | $CH_2Cl$ | Cl | $CH_3$ |
| I.a.1212 | F | F | F | F | F | $CH_2Cl$ | Cl | $CH_3$ |
| I.a.1213 | Cl | F | F | F | F | $CH_2Cl$ | Cl | $CH_3$ |
| I.a.1214 | F | Cl | F | F | F | $CH_2Cl$ | Cl | $CH_3$ |
| I.a.1215 | CN | F | F | F | F | $CH_2Cl$ | Cl | $CH_3$ |
| I.a.1216 | F | CN | F | F | F | $CH_2Cl$ | Cl | $CH_3$ |
| I.a.1217 | H | F | F | F | F | $CH_2Cl$ | Cl | $CH_3$ |
| I.a.1218 | F | F | Br | F | F | $CH_2Cl$ | Cl | $CH_3$ |
| I.a.1219 | F | F | C≡CH | F | F | $CH_2Cl$ | Cl | $CH_3$ |
| I.a.1220 | $CF_3$ | Cl | H | H | F | $CH_2Cl$ | Cl | $CH_3$ |
| I.a.1221 | F | F | I | F | F | $CH_2Cl$ | Cl | $CH_3$ |
| I.a.1222 | F | H | H | H | F | CN | $CH_3$ | $CH_3$ |
| I.a.1223 | Cl | H | H | H | F | CN | $CH_3$ | $CH_3$ |
| I.a.1224 | Br | H | H | H | F | CN | $CH_3$ | $CH_3$ |
| I.a.1225 | CN | H | H | H | F | CN | $CH_3$ | $CH_3$ |
| I.a.1226 | $CH_3$ | H | H | H | F | CN | $CH_3$ | $CH_3$ |
| I.a.1227 | F | H | H | F | F | CN | $CH_3$ | $CH_3$ |
| I.a.1228 | Cl | H | H | F | F | CN | $CH_3$ | $CH_3$ |
| I.a.1229 | F | H | H | Cl | F | CN | $CH_3$ | $CH_3$ |
| I.a.1230 | Cl | H | H | F | F | CN | $CH_3$ | $CH_3$ |
| I.a.1231 | CN | H | H | F | F | CN | $CH_3$ | $CH_3$ |
| I.a.1232 | F | H | H | CN | F | CN | $CH_3$ | $CH_3$ |
| I.a.1233 | CN | H | H | F | F | CN | $CH_3$ | $CH_3$ |
| I.a.1234 | F | H | F | H | F | CN | $CH_3$ | $CH_3$ |
| I.a.1235 | Cl | H | F | H | F | CN | $CH_3$ | $CH_3$ |
| I.a.1236 | CN | H | F | H | F | CN | $CH_3$ | $CH_3$ |
| I.a.1237 | F | F | F | H | F | CN | $CH_3$ | $CH_3$ |
| I.a.1238 | Cl | F | F | H | F | CN | $CH_3$ | $CH_3$ |
| I.a.1239 | F | Cl | F | H | F | CN | $CH_3$ | $CH_3$ |
| I.a.1240 | Cl | F | F | H | F | CN | $CH_3$ | $CH_3$ |
| I.a.1241 | CN | F | F | H | F | CN | $CH_3$ | $CH_3$ |
| I.a.1242 | F | CN | F | H | F | CN | $CH_3$ | $CH_3$ |
| I.a.1243 | CN | F | F | H | F | CN | $CH_3$ | $CH_3$ |
| I.a.1244 | F | F | H | F | F | CN | $CH_3$ | $CH_3$ |
| I.a.1245 | Cl | F | H | F | F | CN | $CH_3$ | $CH_3$ |
| I.a.1246 | F | Cl | H | F | F | CN | $CH_3$ | $CH_3$ |
| I.a.1247 | CN | F | H | F | F | CN | $CH_3$ | $CH_3$ |
| I.a.1248 | F | CN | H | F | F | CN | $CH_3$ | $CH_3$ |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.1249 | F | F | F | F | F | CN | $CH_3$ | $CH_3$ |
| I.a.1250 | Cl | F | F | F | F | CN | $CH_3$ | $CH_3$ |
| I.a.1251 | F | Cl | F | F | F | CN | $CH_3$ | $CH_3$ |
| I.a.1252 | CN | F | F | F | F | CN | $CH_3$ | $CH_3$ |
| I.a.1253 | F | CN | F | F | F | CN | $CH_3$ | $CH_3$ |
| I.a.1254 | H | F | F | F | F | CN | $CH_3$ | $CH_3$ |
| I.a.1255 | F | F | Br | F | F | CN | $CH_3$ | $CH_3$ |
| I.a.1256 | F | F | C≡CH | F | F | CN | $CH_3$ | $CH_3$ |
| I.a.1257 | $CF_3$ | Cl | H | H | F | CN | $CH_3$ | $CH_3$ |
| I.a.1258 | F | F | I | F | F | CN | $CH_3$ | $CH_3$ |
| I.a.1259 | F | H | H | H | F | $OCH_3$ | H | H |
| I.a.1260 | Cl | H | H | H | F | $OCH_3$ | H | H |
| I.a.1261 | Br | H | H | H | F | $OCH_3$ | H | H |
| I.a.1262 | CN | H | H | H | F | $OCH_3$ | H | H |
| I.a.1263 | $CH_3$ | H | H | H | F | $OCH_3$ | H | H |
| I.a.1264 | F | H | H | F | F | $OCH_3$ | H | H |
| I.a.1265 | Cl | H | H | F | F | $OCH_3$ | H | H |
| I.a.1266 | F | H | H | Cl | F | $OCH_3$ | H | H |
| I.a.1267 | Cl | H | H | F | F | $OCH_3$ | H | H |
| I.a.1268 | CN | H | H | F | F | $OCH_3$ | H | H |
| I.a.1269 | F | H | H | CN | F | $OCH_3$ | H | H |
| I.a.1270 | CN | H | H | F | F | $OCH_3$ | H | H |
| I.a.1271 | F | H | F | H | F | $OCH_3$ | H | H |
| I.a.1272 | Cl | H | F | H | F | $OCH_3$ | H | H |
| I.a.1273 | CN | H | F | H | F | $OCH_3$ | H | H |
| I.a.1274 | F | F | F | H | F | $OCH_3$ | H | H |
| I.a.1275 | Cl | F | F | H | F | $OCH_3$ | H | H |
| I.a.1276 | F | Cl | F | H | F | $OCH_3$ | H | H |
| I.a.1277 | Cl | F | F | H | F | $OCH_3$ | H | H |
| I.a.1278 | CN | F | F | H | F | $OCH_3$ | H | H |
| I.a.1279 | F | CN | F | H | F | $OCH_3$ | H | H |
| I.a.1280 | CN | F | F | H | F | $OCH_3$ | H | H |
| I.a.1281 | F | F | H | F | F | $OCH_3$ | H | H |
| I.a.1282 | Cl | F | H | F | F | $OCH_3$ | H | H |
| I.a.1283 | F | Cl | H | F | F | $OCH_3$ | H | H |
| I.a.1284 | CN | F | H | F | F | $OCH_3$ | H | H |
| I.a.1285 | F | CN | H | F | F | $OCH_3$ | H | H |
| I.a.1286 | F | F | F | F | F | $OCH_3$ | H | H |
| I.a.1287 | Cl | F | F | F | F | $OCH_3$ | H | H |
| I.a.1288 | F | Cl | F | F | F | $OCH_3$ | H | H |
| I.a.1289 | CN | F | F | F | F | $OCH_3$ | H | H |
| I.a.1290 | F | CN | F | F | F | $OCH_3$ | H | H |
| I.a.1291 | H | F | F | F | F | $OCH_3$ | H | H |
| I.a.1292 | F | F | Br | F | F | $OCH_3$ | H | H |
| I.a.1293 | F | F | C≡CH | F | F | $OCH_3$ | H | H |
| I.a.1294 | $CF_3$ | Cl | H | H | F | $OCH_3$ | H | H |
| I.a.1295 | F | F | I | F | F | $OCH_3$ | H | H |
| I.a.1296 | F | H | H | H | F | $OCH_3$ | $CH_3$ | H |
| I.a.1297 | Cl | H | H | H | F | $OCH_3$ | $CH_3$ | H |
| I.a.1298 | Br | H | H | H | F | $OCH_3$ | $CH_3$ | H |
| I.a.1299 | CN | H | H | H | F | $OCH_3$ | $CH_3$ | H |
| I.a.1300 | $CH_3$ | H | H | H | F | $OCH_3$ | $CH_3$ | H |
| I.a.1301 | F | H | H | F | F | $OCH_3$ | $CH_3$ | H |
| I.a.1302 | Cl | H | H | F | F | $OCH_3$ | $CH_3$ | H |
| I.a.1303 | F | H | H | Cl | F | $OCH_3$ | $CH_3$ | H |
| I.a.1304 | Cl | H | H | F | F | $OCH_3$ | $CH_3$ | H |
| I.a.1305 | CN | H | H | F | F | $OCH_3$ | $CH_3$ | H |
| I.a.1306 | F | H | H | CN | F | $OCH_3$ | $CH_3$ | H |
| I.a.1307 | CN | H | H | F | F | $OCH_3$ | $CH_3$ | H |
| I.a.1308 | F | H | F | H | F | $OCH_3$ | $CH_3$ | H |
| I.a.1309 | Cl | H | F | H | F | $OCH_3$ | $CH_3$ | H |
| I.a.1310 | CN | H | F | H | F | $OCH_3$ | $CH_3$ | H |
| I.a.1311 | F | F | F | H | F | $OCH_3$ | $CH_3$ | H |
| I.a.1312 | Cl | F | F | H | F | $OCH_3$ | $CH_3$ | H |
| I.a.1313 | F | Cl | F | H | F | $OCH_3$ | $CH_3$ | H |
| I.a.1314 | Cl | F | F | H | F | $OCH_3$ | $CH_3$ | H |
| I.a.1315 | CN | F | F | H | F | $OCH_3$ | $CH_3$ | H |
| I.a.1316 | F | CN | F | H | F | $OCH_3$ | $CH_3$ | H |
| I.a.1317 | CN | F | F | H | F | $OCH_3$ | $CH_3$ | H |
| I.a.1318 | F | F | H | F | F | $OCH_3$ | $CH_3$ | H |
| I.a.1319 | Cl | F | H | F | F | $OCH_3$ | $CH_3$ | H |
| I.a.1320 | F | Cl | H | F | F | $OCH_3$ | $CH_3$ | H |
| I.a.1321 | CN | F | H | F | F | $OCH_3$ | $CH_3$ | H |
| I.a.1322 | F | CN | H | F | F | $OCH_3$ | $CH_3$ | H |
| I.a.1323 | F | F | F | F | F | $OCH_3$ | $CH_3$ | H |
| I.a.1324 | Cl | F | F | F | F | $OCH_3$ | $CH_3$ | H |
| I.a.1325 | F | Cl | F | F | F | $OCH_3$ | $CH_3$ | H |
| I.a.1326 | CN | F | F | F | F | $OCH_3$ | $CH_3$ | H |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.1327 | F | CN | F | F | F | $OCH_3$ | $CH_3$ | H |
| I.a.1328 | H | F | F | F | F | $OCH_3$ | $CH_3$ | H |
| I.a.1329 | F | F | Br | F | F | $OCH_3$ | $CH_3$ | H |
| I.a.1330 | F | F | C≡CH | F | F | $OCH_3$ | $CH_3$ | H |
| I.a.1331 | $CF_3$ | Cl | H | H | F | $OCH_3$ | $CH_3$ | H |
| I.a.1332 | F | F | I | F | F | $OCH_3$ | $CH_3$ | H |
| I.a.1333 | F | H | H | H | F | $OCH_3$ | $CH_3$ | $CH_3$ |
| I.a.1334 | Cl | H | H | H | F | $OCH_3$ | $CH_3$ | $CH_3$ |
| I.a.1335 | Br | H | H | H | F | $OCH_3$ | $CH_3$ | $CH_3$ |
| I.a.1336 | CN | H | H | H | F | $OCH_3$ | $CH_3$ | $CH_3$ |
| I.a.1337 | $CH_3$ | H | H | H | F | $OCH_3$ | $CH_3$ | $CH_3$ |
| I.a.1338 | F | H | H | F | F | $OCH_3$ | $CH_3$ | $CH_3$ |
| I.a.1339 | Cl | H | H | F | F | $OCH_3$ | $CH_3$ | $CH_3$ |
| I.a.1340 | F | H | H | Cl | F | $OCH_3$ | $CH_3$ | $CH_3$ |
| I.a.1341 | Cl | H | H | F | F | $OCH_3$ | $CH_3$ | $CH_3$ |
| I.a.1342 | CN | H | H | F | F | $OCH_3$ | $CH_3$ | $CH_3$ |
| I.a.1343 | F | H | H | CN | F | $OCH_3$ | $CH_3$ | $CH_3$ |
| I.a.1344 | CN | H | H | F | F | $OCH_3$ | $CH_3$ | $CH_3$ |
| I.a.1345 | F | H | F | H | F | $OCH_3$ | $CH_3$ | $CH_3$ |
| I.a.1346 | Cl | H | F | H | F | $OCH_3$ | $CH_3$ | $CH_3$ |
| I.a.1347 | CN | H | F | H | F | $OCH_3$ | $CH_3$ | $CH_3$ |
| I.a.1348 | F | F | F | H | F | $OCH_3$ | $CH_3$ | $CH_3$ |
| I.a.1349 | Cl | F | F | H | F | $OCH_3$ | $CH_3$ | $CH_3$ |
| I.a.1350 | F | Cl | F | H | F | $OCH_3$ | $CH_3$ | $CH_3$ |
| I.a.1351 | Cl | F | F | H | F | $OCH_3$ | $CH_3$ | $CH_3$ |
| I.a.1352 | CN | F | F | H | F | $OCH_3$ | $CH_3$ | $CH_3$ |
| I.a.1353 | F | CN | F | H | F | $OCH_3$ | $CH_3$ | $CH_3$ |
| I.a.1354 | CN | F | F | H | F | $OCH_3$ | $CH_3$ | $CH_3$ |
| I.a.1355 | F | F | H | F | F | $OCH_3$ | $CH_3$ | $CH_3$ |
| I.a.1356 | Cl | F | H | F | F | $OCH_3$ | $CH_3$ | $CH_3$ |
| I.a.1357 | F | Cl | H | F | F | $OCH_3$ | $CH_3$ | $CH_3$ |
| I.a.1358 | CN | F | H | F | F | $OCH_3$ | $CH_3$ | $CH_3$ |
| I.a.1359 | F | CN | H | F | F | $OCH_3$ | $CH_3$ | $CH_3$ |
| I.a.1360 | F | F | F | F | F | $OCH_3$ | $CH_3$ | $CH_3$ |
| I.a.1361 | Cl | F | F | F | F | $OCH_3$ | $CH_3$ | $CH_3$ |
| I.a.1362 | F | Cl | F | F | F | $OCH_3$ | $CH_3$ | $CH_3$ |
| I.a.1363 | CN | F | F | F | F | $OCH_3$ | $CH_3$ | $CH_3$ |
| I.a.1364 | F | CN | F | F | F | $OCH_3$ | $CH_3$ | $CH_3$ |
| I.a.1365 | H | F | F | F | F | $OCH_3$ | $CH_3$ | $CH_3$ |
| I.a.1366 | F | F | Br | F | F | $OCH_3$ | $CH_3$ | $CH_3$ |
| I.a.1367 | F | F | C≡CH | F | F | $OCH_3$ | $CH_3$ | $CH_3$ |
| I.a.1368 | $CF_3$ | Cl | H | H | F | $OCH_3$ | $CH_3$ | $CH_3$ |
| I.a.1369 | F | F | I | F | F | $OCH_3$ | $CH_3$ | $CH_3$ |
| I.a.1370 | F | H | H | H | F | H | $-O(CH_2)_3-$ | |
| I.a.1371 | Cl | H | H | H | F | H | $-O(CH_2)_3-$ | |
| I.a.1372 | Br | H | H | H | F | H | $-O(CH_2)_3-$ | |
| I.a.1373 | CN | H | H | H | F | H | $-O(CH_2)_3-$ | |
| I.a.1374 | $CH_3$ | H | H | H | F | H | $-O(CH_2)_3-$ | |
| I.a.1375 | F | H | H | F | F | H | $-O(CH_2)_3-$ | |
| I.a.1376 | Cl | H | H | F | F | H | $-O(CH_2)_3-$ | |
| I.a.1377 | F | H | H | Cl | F | H | $-O(CH_2)_3-$ | |
| I.a.1378 | Cl | H | H | F | F | H | $-O(CH_2)_3-$ | |
| I.a.1379 | CN | H | H | F | F | H | $-O(CH_2)_3-$ | |
| I.a.1380 | F | H | H | CN | F | H | $-O(CH_2)_3-$ | |
| I.a.1381 | CN | H | H | F | F | H | $-O(CH_2)_3-$ | |
| I.a.1382 | F | H | F | H | F | H | $-O(CH_2)_3-$ | |
| I.a.1383 | Cl | H | F | H | F | H | $-O(CH_2)_3-$ | |
| I.a.1384 | CN | H | F | H | F | H | $-O(CH_2)_3-$ | |
| I.a.1385 | F | F | F | H | F | H | $-O(CH_2)_3-$ | |
| I.a.1386 | Cl | F | F | H | F | H | $-O(CH_2)_3-$ | |
| I.a.1387 | F | Cl | F | H | F | H | $-O(CH_2)_3-$ | |
| I.a.1388 | Cl | F | F | H | F | H | $-O(CH_2)_3-$ | |
| I.a.1389 | CN | F | F | H | F | H | $-O(CH_2)_3-$ | |
| I.a.1390 | F | CN | F | H | F | H | $-O(CH_2)_3-$ | |
| I.a.1391 | CN | F | F | H | F | H | $-O(CH_2)_3-$ | |
| I.a.1392 | F | F | H | F | F | H | $-O(CH_2)_3-$ | |
| I.a.1393 | Cl | F | H | F | F | H | $-O(CH_2)_3-$ | |
| I.a.1394 | F | Cl | H | F | F | H | $-O(CH_2)_3-$ | |
| I.a.1395 | CN | F | H | F | F | H | $-O(CH_2)_3-$ | |
| I.a.1396 | F | CN | H | F | F | H | $-O(CH_2)_3-$ | |
| I.a.1397 | F | F | F | F | F | H | $-O(CH_2)_3-$ | |
| I.a.1398 | Cl | F | F | F | F | H | $-O(CH_2)_3-$ | |
| I.a.1399 | F | Cl | F | F | F | H | $-O(CH_2)_3-$ | |
| I.a.1400 | CN | F | F | F | F | H | $-O(CH_2)_3-$ | |
| I.a.1401 | F | CN | F | F | F | H | $-O(CH_2)_3-$ | |
| I.a.1402 | H | F | F | F | F | H | $-O(CH_2)_3-$ | |
| I.a.1403 | F | F | Br | F | F | H | $-O(CH_2)_3-$ | |
| I.a.1404 | F | F | C≡CH | F | F | H | $-O(CH_2)_3-$ | |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.1405 | $CF_3$ | Cl | H | H | F | H | $—O(CH_2)_3—$ | |
| I.a.1406 | F | F | I | F | F | H | $—O(CH_2)_3—$ | |

In another preferred embodiment, the azines useful for the present invention are azines of formula (I)

(I)

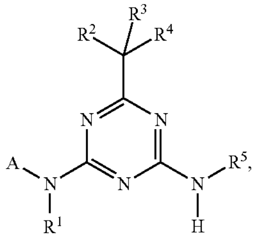

wherein

A is heteroaryl, which is substituted by 1, 2, 3, 4, 5 or 6 substituents $R^A$ selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, carbonyl, ($C_1$-$C_6$-alkoxy)-carbonyl, ($C_1$-$C_6$-alkyl)-carbonyloxy, $C_3$ $C_6$ cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups;

$R^1$ is selected from the group consisting of H, OH, $S(O)_2NH_2$, CN, $C_1$-$C_6$ alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, phenyl, phenyl-$C_1$-$C_6$-alkyl, phenylsulfonyl, phenylaminosulfonyl, phenylcarbonyl and phenoxycarbonyl, wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkoxy and $C_1$-$C_6$-haloalkoxy;

$R^2$ is H, halogen, OH, CN, $C_1$-$C_6$ alkyl, $C_2$-$C_6$-alkenyl, $C_3$-$C_6$-alkynyl, $C_3$-$C_6$-cycloalkyl, $C_3$-$C_6$-cycloalkenyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy or ($C_3$-$C_6$-cycloalkyl)-$C_1$-$C_4$-alkoxy, where the aliphatic and cycloaliphatic parts of the 9 aforementioned radicals are unsubstituted, partly or completely halogenated, phenyl, phenyl-$C_1$-$C_6$-alkyl, wherein phenyl in the last 2 mentioned radicals are unsubstituted or substituted by 1, 2, 3, 4 or 5 identical or different substituents selected from the group consisting of halogen, CN, $NO_2$, $C_1$-$C_6$-alkoxy and $C_1$-$C_6$-haloalkoxy;

$R^3$ is selected from the group consisting of H, halogen, CN, $C_1$-$C_6$-alkoxy and $C_1$-$C_6$-haloalkoxy;

$R^4$ is selected from the group consisting of H, halogen, CN, $C_1$-$C_6$ alkyl, $C_2$-$C_6$-alkenyl, $C_3$-$C_6$-alkynyl, $C_3$-$C_6$-cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, where the aliphatic and cycloaliphatic parts of the 7 aforementioned radicals are unsubstituted, partly or completely halogenated; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl, wherein the $C_3$-$C_6$-cycloalkyl, $C_3$-$C_6$-cycloalkenyl, or three- to six-membered heterocyclyl is unsubstituted or substituted by one to three substituents selected from halogen, CN, $C_1$-$C_6$-alkyl and $C_1$-$C_6$-alkoxy; and $R^5$ is selected from the group consisting of H, OH, $S(O)_2NH_2$, CN, $C_1$-$C_6$ alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, phenyl, phenyl-$C_1$-$C_6$-alkyl, phenylsulfonyl, phenylaminosulfonyl, phenylcarbonyl and phenoxycarbonyl, wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkoxy and $C_1$-$C_6$-haloalkoxy;

and wherein the variables A, $R^1$, $R^2$, $R^3$, $R^4$ and $R^5$ are in particular:

A is heteroaryl, which is substituted by 1, 2, 3, 4, 5 or 6 substituents $R^A$ selected from the group consisting of halogen, OH, CN, amino, $NO_2$, $C_1$-$C_6$ alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$ alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$ $C_6$ cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups;

$R^1$ is selected from the group consisting of H, OH, $S(O)_2NH_2$, CN, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-

$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, phenyl, phenyl-$C_1$-$C_6$-alkyl, phenylsulfonyl, phenylaminosulfonyl, phenylcarbonyl and phenoxycarbonyl, wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkoxy and $C_1$-$C_6$-haloalkoxy;

$R^2$ is H, halogen, OH, CN, $C_2$-$C_6$-alkenyl, $C_3$-$C_6$-alkynyl, ($C_1$-$C_6$-alkoxy)-$C_1$-$C_6$-alkyl, $C_3$-$C_6$-cycloalkyl, $C_3$-$C_6$-cycloalkenyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy or ($C_3$-$C_6$-cycloalkyl)-$C_1$-$C_4$-alkoxy, where the aliphatic and cycloaliphatic parts of the 9 aforementioned radicals are unsubstituted, partly or completely halogenated or phenyl, wherein phenyl is unsubstituted or substituted by 1, 2, 3, 4 or 5 identical or different substituents selected from the group consisting of halogen, CN, $NO_2$, $C_1$-$C_6$-haloalkyl, $C_1$-$C_6$-alkoxy and $C_1$-$C_6$-haloalkoxy;

$R^3$ is selected from the group consisting of H, halogen, CN, $C_1$-$C_6$ alkyl, $C_1$-$C_6$ haloalkyl, $C_1$-$C_6$-alkoxy and $C_1$-$C_6$-haloalkoxy;

$R^4$ is selected from the group consisting of H, halogen, CN, $C_2$-$C_6$-alkenyl, $C_3$-$C_6$-alkynyl, $C_3$ $C_6$ cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, where the aliphatic and cycloaliphatic parts of the 7 aforementioned radicals are unsubstituted, partly or completely halogenated; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl, wherein the $C_3$-$C_6$-cycloalkyl, $C_3$-$C_6$-cycloalkenyl, or three- to six-membered heterocyclyl is unsubstituted or substituted by one to three substituents selected from halogen, CN, $C_1$-$C_6$-alkyl and $C_1$-$C_6$-alkoxy; and $R^5$ is selected from the group consisting of H, OH, $S(O)_2NH_2$, CN, $C_1$-$C_6$ alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$ alkyl, ($C_1$-$C_6$-alkyl)-carbonyl, ($C_1$-$C_6$-alkoxy)carbonyl, ($C_1$-$C_6$-alkyl) sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy) sulfonyl, where the aliphatic and cycloaliphatic parts of the 14 aforementioned radicals are unsubstituted, partly or completely halogenated, phenyl, phenyl-$C_1$-$C_6$-alkyl, phenylsulfonyl, phenylaminosulfonyl, phenylcarbonyl and phenoxycarbonyl, wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-haloalkyl, $C_1$-$C_6$-alkoxy and $C_1$-$C_6$-haloalkoxy;

and wherein the variables A, $R^1$, $R^2$, $R^3$, $R^4$ and $R^5$ are in more particular:

A is heteroaryl, which is substituted by 1, 2, 3, 4, 5 or 6 substituents $R^A$ selected from the group consisting of halogen, OH, CN, amino, $NO_2$, $C_1$-$C_6$ alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$ alkylthiol, ($C_1$-$C_6$ alkyl)sulfinyl, ($C_1$-$C_6$ alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups;

$R^1$ is selected from the group consisting of H, OH, $S(O)_2NH_2$, CN, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_6$ alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy) sulfonyl, where the aliphatic and cycloaliphatic parts of the 14 aforementioned radicals are unsubstituted, partly or completely halogenated, phenyl, phenyl-$C_1$-$C_6$-alkyl, phenylsulfonyl, phenylaminosulfonyl, phenylcarbonyl and phenoxycarbonyl, wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkoxy and $C_1$-$C_6$-haloalkoxy;

$R^2$ is H, halogen, OH, CN, $C_1$-$C_6$ alkyl, $C_2$-$C_6$-alkenyl, $C_3$-$C_6$-alkynyl, ($C_1$-$C_6$-alkoxy)-$C_1$-$C_6$-alkyl, $C_3$-$C_6$-cycloalkyl, $C_3$-$C_6$-cycloalkenyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy or ($C_3$-$C_6$-cycloalkyl)-$C_1$-$C_4$-alkoxy, where the aliphatic and cycloaliphatic parts of the 9 aforementioned radicals are unsubstituted, partly or completely halogenated, $R^3$ is selected from the group consisting of H, halogen, CN, $C_1$-$C_6$-haloalkyl, $C_1$-$C_6$-alkoxy and $C_1$-$C_6$-haloalkoxy;

$R^4$ is selected from the group consisting of H, halogen, CN, $C_2$-$C_6$-alkenyl, $C_3$-$C_6$-alkynyl, $C_3$-$C_6$-cycloalkenyl and $C_1$-$C_6$-alkoxy-$C_1$-$C_6$-alkyl, where the aliphatic and cycloaliphatic parts of the 7 aforementioned radicals are unsubstituted, partly or completely halogenated; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl, wherein the $C_3$-$C_6$-cycloalkyl, $C_3$-$C_6$-cycloalkenyl, or three- to six-membered heterocyclyl is unsubstituted or substituted by one to three substituents selected from halogen, CN, $C_1$-$C_6$-alkyl and $C_1$-$C_6$-alkoxy; and $R^5$ is selected from the group consisting of H, OH, $S(O)_2NH_2$, CN, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, phenyl, phenyl-$C_1$-$C_6$-alkyl, phenylsulfonyl, phenylaminosulfonyl, phenylcarbonyl and phenoxycarbonyl, wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkoxy and $C_1$-$C_6$-haloalkoxy;

and wherein the variables A, $R^1$, $R^2$, $R^3$, $R^4$ and $R^5$ are preferred:

A is heteroaryl, which is substituted by one to six substituents selected from the group consisting of halogen, CN, $NO_2$, $C_1$-$C_6$ alkyl, $C_1$-$C_6$-haloalkyl, OH, $C_1$-$C_6$-alkoxy, $C_1$-$C_6$-alkylthio, ($C_1$-$C_6$-alkyl)sulfonyl, amino, ($C_1$-$C_6$-alkyl)amino, alkyl)amino, ($C_1$-$C_6$-alkyl)carbonyl, ($C_1$-$C_6$-alkoxy)carbonyl;

$R^1$ is H, CN, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl, wherein the phenyl is unsubstituted or substituted by one to five substituents selected from the group consisting of halogen, CN, $NO_2$, $C_1$-$C_6$-haloalkyl and $C_1$-$C_6$-alkoxy;

$R^2$ is H, halogen, OH, CN, $C_2$-$C_6$-alkenyl, $C_3$-$C_6$-alkynyl, ($C_1$-$C_6$-alkoxy)-$C_1$-$C_6$-alkyl, $C_3$-$C_6$-cycloalkyl, $C_3$-$C_6$-cycloalkenyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy or ($C_3$-$C_6$-cycloalkyl)-$C_1$-$C_4$-alkoxy, where the aliphatic and cycloaliphatic parts of the 9 aforementioned radicals are unsubstituted, partly or completely halogenated $R^3$ is H, halogen, CN, $C_1$-$C_6$-haloalkyl or $C_1$-$C_6$-alkoxy;

$R^4$ is H, halogen, CN, $C_1$-$C_6$-alkyl or $C_1$-$C_6$-haloalkyl; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl, wherein the $C_3$-$C_6$-cycloalkyl, $C_3$-$C_6$-cycloalkenyl, or three- to six-membered heterocyclyl is unsubstituted or substituted by one to three substituents selected from halogen, CN, $C_1$-$C_6$-alkyl and $C_1$-$C_6$-alkoxy; and $R^5$ is H, CN, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl, wherein the phenyl is unsubstituted or substituted by one to five substituents selected from the group consisting of halogen, CN, $NO_2$, $C_1$-$C_6$-haloalkyl and $C_1$-$C_6$-alkoxy;

including their agriculturally acceptable salts or N-oxides.

In another preferred embodiment, the azines useful for the present invention comprise a diaminotriazine compound of formula (I)

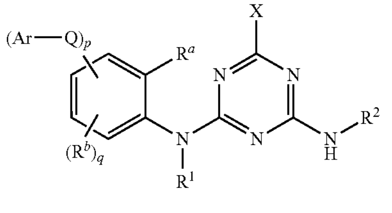

wherein p is 1 or 2;

q is 0, 1, 2 or 3 provided that p+q is 1, 2, 3 or 4;

Q is a chemical bond, O, $S(O)_m$, $CR^{q1}R^{q2}$, $NR^{q3}$, C(O), C(O)O, $CR^{q1}R^{q2}$—O, $S(O)_mNR^{q3}$ or $C(O)NR^{q3}$, wherein m is 0, 1 or 2;

$R^{q1}$, $R^{q2}$ are hydrogen, halogen or $C_1$-$C_4$-alkyl;

$R^{q3}$ is H, CN, $C_1$-$C_6$ alkyl, ($C_1$-$C_6$ alkoxy)-$C_1$-$C_6$ alkyl, ($C_1$-$C_6$ alkyl) carbonyl, ($C_1$-$C_6$-alkoxy)carbonyl, ($C_1$-$C_6$-alkyl)sulfonyl, where the aliphatic parts of the 6 aforementioned radicals are unsubstituted, partly or completely halogenated;

Ar is phenyl, which is unsubstituted or carries 1, 2, 3, 4 or 5 radicals $R^A$ which are selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl) sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups, phenyl, phenyl-$C_1$-$C_6$-alkyl, phenylsulfonyl, phenylaminosulfonyl, phenylaminocarbonyl, phenyl ($C_1$-$C_6$-alkyl)aminocarbonyl, phenylcarbonyl and phenoxycarbonyl, wherein phenyl in the last 8 mentioned radicals are unsubstituted or substituted by 1, 2, 3, 4 or 5 identical or different substituents selected from the group consisting of halogen, CN, $NO_2$, $C_1$-$C_6$-alkoxy and $C_1$-$C_6$-haloalkoxy, it being possible that $R^A$ are identical or different;

$R^a$ is selected from the group consisting of hydrogen, halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, where the aliphatic and cycloaliphatic parts of the 14 aforementioned radicals are unsubstituted, partly or completely halogenated;

$R^b$ is selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$ alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups, for q=2 or 3 it being possible that $R^b$ are identical or different;

$R^1$ is selected from the group consisting of H, OH, $S(O)_2NH_2$, CN, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_3$-$C_6$-cycloalkyl)-carbonyl, ($C_1$-$C_6$-alkyl)-carbonyl, alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 15 aforementioned radicals are unsubstituted, partly or completely halogenated, phenyl, phenyl-$C_1$-$C_6$-alkyl, phenylsulfonyl, phenylaminosulfonyl, phenylaminocarbonyl, phenyl($C_1$-$C_6$-alkyl)aminocarbonyl, phenylcarbonyl and phenoxycarbonyl, wherein phenyl in the last 8 mentioned radicals are unsubstituted or substituted by 1, 2, 3, 4 or 5 identical or different substituents selected from the group consisting of halogen, CN, $NO_2$, $C_1$-$C_6$-alkoxy and $C_1$-$C_6$-haloalkoxy;

$R^2$ is selected from the group consisting of H, OH, $S(O)_2NH_2$, CN, $C_1$-$C_6$ alkyl, $C_2$-$C_6$-alkenyl, $C_2$-$C_6$-alkynyl, ($C_3$-$C_6$-cycloalkyl)-$C_1$-$C_4$-alkyl, $C_3$-$C_6$-cycloalkyl)-carbonyl $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 15 aforementioned radicals are unsubstituted, partly or completely halogenated, phenyl, phenylsulfonyl, phenylaminosulfonyl, phenylaminocarbonyl, phenyl($C_1$-$C_6$-alkyl)aminocarbonyl, phenyl-$C_1$-$C_6$ alkyl, phenoxy, phenylcarbonyl and phenoxycarbonyl, wherein phenyl in the last 9 mentioned radicals is unsubstituted or substituted by 1, 2, 3, 4 or 5 identical or different substituents selected from the group consisting of halogen, CN, $NO_2$, $C_1$-$C_6$-alkoxy and $C_1$-$C_6$-haloalkoxy;

X is a radical selected from the group consisting of $CR^3R^4R^5$, phenyl, which is unsubstituted or carries 1, 2, 3, 4 or 5 radicals $R^{Ar}$ which are identical or different;

$NR^{3a}R^{3b}$, $OR^{3c}$ and $S(O)_kR^{3d}$ with k being 0, 1 or 2 wherein $R^3$ is selected from the group consisting of H, halogen, OH, CN, ($C_1$-$C_6$-alkoxy)-$C_1$-$C_6$-alkyl, $C_3$-$C_6$-cycloalkyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy, ($C_3$-$C_6$-cycloalkyl)-$C_1$-$C_4$-alkoxy, where the aliphatic and cycloaliphatic parts of the 9 aforementioned radicals are unsubstituted, partly or completely halogenated;

$R^4$ is selected from the group consisting of H, halogen, CN, $C_1$-$C_6$-haloalkyl, $C_1$-$C_6$-alkoxy and $C_1$-$C_6$-haloalkoxy;

$R^5$ is selected from the group consisting of halogen, CN, $C_1$-$C_6$ alkyl, $C_2$-$C_6$-alkenyl, $C_3$-$C_6$-alkynyl, $C_3$-$C_6$-cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, where the aliphatic and cycloaliphatic parts of the 7 aforementioned radicals are unsubstituted, partly or completely halogenated;

$R^4$ and $R^5$ together with the carbon atom to which they are attached form a moiety selected from the group consisting of carbonyl, $C_3$-$C_6$-cycloalkyl, $C_3$-$C_6$-cycloalkenyl, three- to six-membered saturated or partially unsaturated heterocyclyl, and the moiety >C═$CR^xR^y$, where $R^x$ and $R^y$ are hydrogen, $C_1$-$C_4$-alkyl or $C_1$-$C_4$-haloalkyl;

$R^{Ar}$ selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$ alkylthiol, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups, $R^{3a}$, $R^{3b}$, $R^{3c}$ or $R^{3d}$ are independently of one another are selected from the group consisting of H, CN, $S(O)_2NH_2$, $C_2$-$C_6$-alkenyl, $C_2$-$C_6$-alkynyl, $C_3$-$C_6$-cycloalkyl, ($C_3$-$C_6$-cycloalkyl)-$C_1$-$C_6$-alkyl, carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_3$-$C_6$-cycloalkyl)-carbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 15 aforementioned radicals are unsubstituted, partly or completely halogenated, phenyl, phenylsulfonyl, phenyl-$C_1$-$C_6$ alkyl, phenylaminosulfonyl, phenylcarbonyl and phenoxycarbonyl, wherein phenyl in the last 6 mentioned radicals is unsubstituted or substituted by 1, 2, 3, 4 or 5 identical or different substituents selected from the group consisting of halogen, CN, $NO_2$, $C_1$-$C_6$ alkyl, $C_1$-$C_6$-haloalkyl, $C_1$-$C_6$-alkoxy and $C_1$-$C_6$-haloalkoxy, or $R^{3a}$, $R^{3b}$ together with the nitrogen atom, to which they are bound, form an N-bound, mono- or bicyclic heterocyclic radical, which may have 1, 2, 3 or 4 further heteroatoms which are selected from N, O and S, which is unsubstituted or substituted by one or more identical or different substituents selected from the group consisting of halogen, CN, $NO_2$, $C_1$-$C_6$-alkoxy and $C_1$-$C_6$-haloalkoxy, one of $R^{3a}$, $R^{3b}$ may also be OH, $C_1$-$C_6$-alkoxy, $C_3$-$C_6$-cycloalkoxy, ($C_3$-$C_6$-cycloalkyl)-$C_1$-$C_4$-alkoxy $C_2$-$C_6$-alkenyloxy, $C_2$-$C_6$-alkynyloxy, ($C_1$-$C_6$-alkoxy)-$C_1$-$C_6$-alkoxy, where the aliphatic and cycloaliphatic parts of the 7 aforementioned radicals are unsubstituted, partly or completely halogenated, or phenoxy, which is unsubstituted or substituted by 1, 2, 3, 4 or 5 identical or different substituents selected from the group consisting of halogen, CN, $NO_2$, $C_1$-$C_6$-alkoxy and $C_1$-$C_6$-haloalkoxy;

including their agriculturally acceptable salts

In another preferred embodiment, the azines useful for the present invention comprises a diaminotriazine compound of the formula:

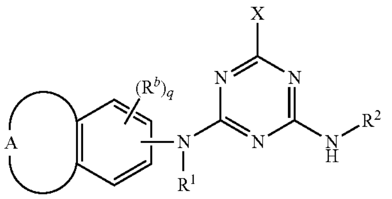

wherein

A is a fused saturated or unsaturated, 5- or 6-membered carbocycle or a fused saturated or unsaturated, 5- or 6-membered heterocycle having 1, 2 or 3 heteroatoms or heteroatom moieties, selected from O, S, $S(O)_p$, N or NRC as ring members, where the carbocycle and the heterocycle are unsubstituted or carry 1, 2, 3 or 4 radicals $R^A$;

p is 0, 1 or 2 q is 0, 1, 2 or 3;

$R^A$ is selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl) sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups, it being possible that $R^A$ are identical or different, it being possible that two radicals $R^A$ which are bound at the same carbon atom may together be =O or =$NR^d$;

$R^b$ is selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$-alkylthio, ($C_1$-$C_6$-alkyl)sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups, for q=2 or 3 it being possible that $R^b$ are identical or different;

$R^c$ is selected from the group consisting of H, OH, $S(O)_2NH_2$, CN, $C_2$-$C_6$-alkenyl, $C_2$-$C_6$-alkynyl, $C_3$-$C_6$-cycloalkyl, $C_3$-$C_6$-cycloalkoxy, ($C_3$ $C_6$ cycloalkyl) $C_1$-$C_4$ alkyl, $C_1$-$C_6$-alkoxy, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 16 aforementioned radicals are unsubstituted, partly or completely halogenated, $R^d$ is selected from the group consisting of H, CN, $C_1$-$C_6$ alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, where the aliphatic and cycloaliphatic parts of the 8 aforementioned radicals are unsubstituted, partly or completely halogenated;

$R^1$ is selected from the group consisting of H, OH, $S(O)_2NH_2$, CN, $C_3$-$C_6$-cycloalkyl, $C_3$-$C_6$-cycloalkoxy, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_3$-$C_6$-cycloalkyl)-carbonyl, ($C_1$-$C_6$-alkoxy)carbonyl, ($C_1$-$C_6$-alkylamino)carbonyl, di($C_1$-$C_6$-alkyl)aminocarbonyl, ($C_1$-$C_6$-alkylamino) sulfonyl, di($C_1$-$C_6$-alkyl)aminosulfonyl and ($C_1$-$C_6$-alkoxy)sulfonyl, where the aliphatic and cycloaliphatic parts of the 17 aforementioned radicals are unsubstituted, partly or completely halogenated, phenyl, phenyl-$C_1$-$C_6$-alkyl, phenylsulfonyl, phenylaminosulfonyl, phenylaminocarbonyl, phenyl ($C_1$-$C_6$-alkyl)aminocarbonyl, phenylcarbonyl and phenoxycarbonyl, wherein phenyl in the last 8 mentioned radicals are unsubstituted or substituted by 1, 2, 3, 4 or 5 identical or different substituents selected from the group consisting of halogen, CN, $NO_2$, $C_1$-$C_6$-alkoxy and $C_1$-$C_6$-haloalkoxy;

$R^2$ is selected from the group consisting of H, OH, $S(O)_2NH_2$, CN, $C_3$-$C_6$-cycloalkyl, $C_3$-$C_6$-cycloalkoxy, $C_1$-$C_6$ alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)carbonyl, ($C_3$-$C_6$-cycloalkyl)-carbonyl, ($C_1$-$C_6$-alkoxy)carbonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 17 aforementioned radicals are unsubstituted, partly or completely halogenated, phenyl, phenylsulfonyl, phenylaminosulfonyl, phenyl-$C_1$-$C_6$ alkyl, phenoxy, phenylaminocarbonyl, phenyl ($C_1$-$C_6$-alkyl)aminocarbonyl, phenylcarbonyl and phenoxycarbonyl, wherein phenyl in the last 8 mentioned radicals is unsubstituted or substituted by 1, 2, 3, 4 or 5 identical or different substituents selected from the group consisting of halogen, CN, $NO_2$, $C_1$-$C_6$-alkoxy and $C_1$-$C_6$-haloalkoxy;

X is a radical selected from the group consisting of $CR^3R^4R^5$ phenyl, which is unsubstituted or carries 1, 2, 3, 4 or 5 radicals $R^{Ar}$ which are identical or different;

$NR^{3a}R^{3b}$, $OR^3c$ and $S(O)_kR^{3d}$ with k being 0, 1 or 2, wherein $R^3$ is selected from the group consisting of H, halogen, OH, CN, ($C_1$-$C_6$-alkoxy)-$C_1$-$C_6$-alkyl, $C_3$-$C_6$-cycloalkyl, ($C_3$-$C_6$-cycloalkyl)-$C_1$-$C_4$-alkyl, $C_1$-$C_6$-alkoxy, $C_2$-$C_6$-alkenyloxy, $C_2$-$C_6$-alkynyloxy, $C_3$-$C_6$-cycloalkoxy, ($C_3$-$C_6$-cycloalkyl)-$C_1$-$C_4$-alkoxy, where the aliphatic and cycloaliphatic parts of the 9 aforementioned radicals are unsubstituted, partly or completely halogenated;

$R^4$ is selected from the group consisting of H, halogen, CN, $C_1$-$C_6$-haloalkyl, $C_1$-$C_6$-alkoxy and $C_1$-$C_6$-haloalkoxy;

$R^5$ is selected from the group consisting of halogen, CN, $C_2$-$C_6$-alkenyl, $C_3$-$C_6$-alkynyl, $C_3$-$C_6$-cycloalkyl, ($C_3$-$C_6$-cycloalkyl)-$C_1$-$C_4$-alkyl, $C_3$-$C_6$-cycloalkenyl and $C_1$-$C_6$-alkoxy-$C_1$-$C_6$-alkyl, where the aliphatic and cycloaliphatic parts of the 7 aforementioned radicals are unsubstituted, partly or completely halogenated;

$R^4$ and $R^5$ together with the carbon atom to which they are attached form a moiety selected from the group consisting of carbonyl, thiocarbonyl, $C_3$-$C_6$-cycloalkyl, $C_3$-$C_6$-cycloalkenyl, three- to six-membered saturated or partially unsaturated heterocyclyl, and the moiety >C=$CR^xR^y$, where $R^x$ and $R^y$ are hydrogen, $C_1$-$C_4$-alkyl or $C_1$-$C_4$-haloalkyl;

$R^{Ar}$ selected from the group consisting of halogen, OH, CN, amino, $NO_2$, $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl, $C_1$-$C_6$ alkylthio, ($C_1$-$C_6$-alkyl) sulfinyl, ($C_1$-$C_6$-alkyl)sulfonyl, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl, ($C_1$-$C_6$-alkyl)-carbonyloxy, $C_3$-$C_6$-cycloalkyl, $C_3$-$C_6$-cycloalkoxy, ($C_3$-$C_6$-cycloalkyl)-$C_1$-$C_4$-alkyl, ($C_3$-$C_6$-cycloalkyl)-$C_1$-$C_4$-alkoxy, where the aliphatic and cycloaliphatic parts of the 22 aforementioned radicals are unsubstituted, partly or completely halogenated and where the cycloaliphatic parts of the last 4 mentioned radicals may carry 1, 2, 3, 4, 5 or 6 methyl groups, $R^{3a}$, $R^{3b}$, $R^{3c}$ or $R^{3d}$ are independently of one another are selected from the group consisting of H, CN, $S(O)_2NH_2$, $C_1$-$C_6$-alkoxy, $C_2$-$C_6$-alkenyl, $C_2$-$C_6$-alkynyl, $C_3$-$C_6$-cycloalkyl, ($C_3$-$C_6$-cycloalkyl)-$C_1$-$C_6$-alkyl, ($C_1$-$C_6$-alkoxy)-$C_1$-$C_6$-alkyl, ($C_1$-$C_6$-alkyl)-carbonyl, ($C_3$-$C_6$-cycloalkyl)-carbonyl, ($C_1$-$C_6$-alkoxy) carbonyl, ($C_1$-$C_6$-alkyl)sulfonyl, ($C_1$-$C_6$-alkylamino) carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 16 aforementioned radicals are unsubstituted, partly or completely halogenated, phenyl, phenylsulfonyl, phenyl-$C_1$-$C_6$ alkyl, phenylaminosulfonyl, phenylcarbonyl and phenoxycarbonyl, wherein phenyl in the last 6 mentioned radicals is unsubstituted or substituted by 1, 2, 3, 4 or 5 identical or different substituents selected from the group consisting of halogen, CN, $NO_2$, $C_1$-$C_6$-haloalkyl, $C_1$-$C_6$-alkoxy and $C_1$-$C_6$-haloalkoxy, or $R^{3a}$, $R^{3b}$ together with the nitrogen atom, to which they are bound, form an N-bound, mono- or bicyclic heterocyclic radical, which may have 1, 2, 3 or 4 further heteroatoms which are selected from N, O and S, which is unsubstituted or substituted by one or more identical or different substituents selected from the group consisting of halogen, CN, $NO_2$, $C_1$-$C_6$-alkoxy and $C_1$-$C_6$-haloalkoxy, one of $R^{3a}$, $R^{3b}$ may also be OH, $C_1$-$C_6$-alkoxy, $C_3$-$C_6$-cycloalkoxy, ($C_3$-$C_6$-cycloalkyl)-$C_1$-$C_4$-alkoxy, $C_2$-$C_6$-alkenyloxy, $C_2$-$C_6$-alkynyloxy, ($C_1$-$C_6$-alkoxy)-$C_1$-$C_6$-alkoxy, where the aliphatic and cycloaliphatic parts of the 6 aforementioned radicals are unsubstituted, partly or completely halogenated, or phenoxy, which is unsubstituted or substituted by 1, 2, 3, 4 or 5 identical or different substituents selected from the group consisting of halogen, CN, $NO_2$, $C_1$-$C_6$-alkoxy and $C_1$-$C_6$-haloalkoxy;

including their agriculturally acceptable salts.

In another preferred embodiment, the azines useful for the present invention comprise a diaminotriazine compound of formula (I)

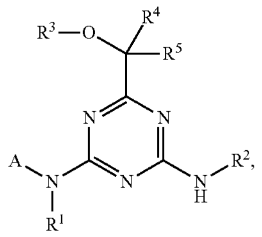

(I)

wherein

A is phenyl, which is substituted by fluorine in the ortho-position and which may additionally carry 1, 2, 3 or 4 identical or different substituents $R^A$ selected from the group consisting of halogen, OH, CN, amino, $NO_2$, $C_2$-$C_6$-alkenyl, $C_2$-$C_6$-alkynyl, ($C_1$-$C_6$-alkoxy)-$C_2$-$C_6$-alkyl, ($C_1$-$C_6$-alkoxy)-$C_2$-$C_6$-alkenyl, ($C_1$-$C_6$-alkoxy)-$C_2$-$C_6$-alkynyl, ($C_1$-$C_6$-alkyl)amino, di($C_1$-$C_6$-alkyl) amino, ($C_1$-$C_6$-alkyl)-carbonyl, ($C_1$-$C_6$-alkoxy)-carbonyl, $C_3$-$C_6$-cycloalkyl, ($C_3$-$C_6$-cycloalkyl)-$C_1$-$C_4$-alkyl, where the aliphatic and cycloaliphatic parts of the 11 aforementioned radicals are unsubstituted, partly or completely halogenated and where the cycloaliphatic parts of the last 4 mentioned radicals may carry 1, 2, 3, 4, 5 or 6 methyl groups;

$R^1$ is selected from the group consisting of H, OH, $S(O)_2NH_2$, CN, $C_1$-$C_6$ alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$ alkyl, ($C_1$-$C_6$-alkoxy) carbonyl, ($C_1$-$C_6$-alkyl)sulfonyl, ($C_1$-$C_6$-alkylamino) carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, phenyl, phenyl-$C_1$-$C_6$-alkyl, phenylsulfonyl, phenylaminosulfonyl, phenylcarbonyl and phenoxycarbonyl, wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkoxy and $C_1$-$C_6$-haloalkoxy;

$R^2$ is selected from the group consisting of H, OH, $S(O)_2NH_2$, CN, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$- alkoxy)-$C_1$-$C_6$-alkyl, ($C_1$-$C_6$-alkyl)carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, phenyl, phenylsulfonyl, phenylaminosulfonyl, phenyl-$C_1$-$C_6$ alkyl, phenoxy, phenylcarbonyl and phenoxycarbonyl, wherein phenyl in the last 6 mentioned radicals is unsubstituted or substituted by 1, 2, 3, 4 or 5 identical or different substituents selected from the group consisting of halogen, CN, $NO_2$, $C_1$-$C_6$-haloalkyl, $C_1$-$C_6$-alkoxy and $C_1$-$C_6$-haloalkoxy;

$R^3$ is selected from the group consisting of $C_1$-$C_6$-alkyl, $C_2$-$C_6$-alkenyl, $C_2$-$C_6$-alkynyl, ($C_3$-$C_6$-cycloalkyl)-Q-$C_4$-alkyl, ($C_1$-$C_6$-alkoxy)-$C_1$-$C_6$-alkyl, ($C_1$-$C_6$-alkyl) carbonyl, ($C_1$-$C_6$-alkoxy)carbonyl, ($C_1$-$C_6$-alkylamino)carbonyl and di($C_1$-$C_6$-alkyl)aminocarbonyl, where the aliphatic and cycloaliphatic parts of the 9 aforementioned radicals are unsubstituted, partly or completely halogenated, $R^4$ and $R^5$, together with the carbon atom, to which they are bound form a saturated 3-, 4-, 5- or 6-membered carbocyclic radical or a saturated 3-, 4-, 5- or 6-membered heterocyclic radical, where the carbocyclic radical and the heterocyclic radical are unsubstituted, partly or completely halogenated or carry from 1 to 6 $C_1$-$C_6$-alkyl groups;

including their agriculturally acceptable salts.

The herbicidal compounds (component A) useful for the present invention as disclosed SUPRA may further be used in conjunction with additional herbicides to which the crop plant is naturally tolerant or to which has been made tolerant by mutagenesis as described SUPRA, or to which it is resistant via expression of one or more additional transgenes as mentioned supra. The CESA-inhibiting herbicides useful for the present invention are often best applied in conjunction with one or more other herbicides to obtain control of a wider variety of undesirable vegetation. When used in conjunction with other herbicides (hereinafter referred to a compound B), the presently claimed compounds can be formulated with the other herbicide or herbicides, tank mixed with the other herbicide or herbicides, or applied sequentially with the other herbicide or herbicides.

The further herbicidal compound B (component B) is in particular selected from the herbicides of class b1) to b15):

b1) lipid biosynthesis inhibitors;

b2) acetolactate synthase inhibitors (ALS inhibitors);

b3) photosynthesis inhibitors;

b4) protoporphyrinogen-IX oxidase inhibitors, b5) bleacher herbicides;

b6) enolpyruvyl shikimate 3-phosphate synthase inhibitors (EPSP inhibitors);

b7) glutamine synthetase inhibitors;

b8) 7,8-dihydropteroate synthase inhibitors (DHP inhibitors);

b9) mitosis inhibitors;

b10) inhibitors of the synthesis of very long chain fatty acids (VLCFA inhibitors);

b11) cellulose biosynthesis inhibitors;

b12) decoupler herbicides;

b13) auxinic herbicides;

b14) auxin transport inhibitors; and b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;

including their agriculturally acceptable salts or derivatives such as ethers, esters or amides.

Preference is given to those compositions according to the present invention comprising at least one herbicide B selected from herbicides of class b1, b6, b9, b10 and b11.

Examples of herbicides B which can be used in combination with the compounds of formula (I) according to the present invention are:

b1) from the group of the lipid biosynthesis inhibitors:

ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2",4'-dichloro-4-cyclopropyl-[1,1-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2",4'-Dichloro-4-cyclopropyl-[1,1-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:

sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;

among these, a preferred embodiment of the invention relates to those compositions comprising at least one imidazolinone herbicide;

b3) from the group of the photosynthesis inhibitors:

amicarbazone, inhibitors of the photosystem II, e.g. triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione, methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3], and 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:

PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, clomazone, fenquintrione, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole and flumeturon;

b6) from the group of the EPSP synthase inhibitors:

glyphosate, glyphosate-isopropylammonium, glyposate-potassium and glyphosate-trimesium (sulfosate);

b7) from the group of the glutamine synthase inhibitors:

bilanaphos (bialaphos), bilanaphos-sodium, glufosinate, glufosinate-P and glufosinate-ammonium;

b8) from the group of the DHP synthase inhibitors:

asulam;

b9) from the group of the mitosis inhibitors:

compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

b10) from the group of the VLCFA inhibitors:

chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

II.1

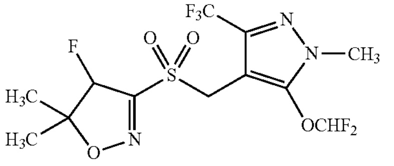

II.2

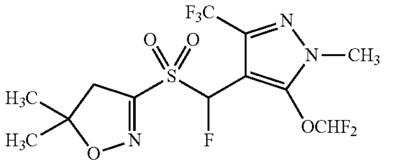

II.3

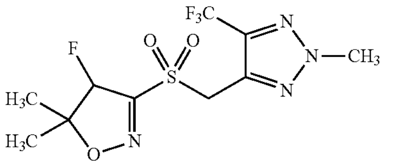

II.4

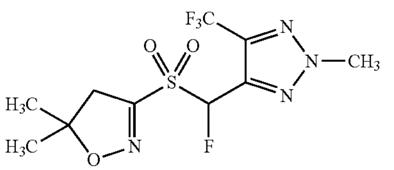

II.5

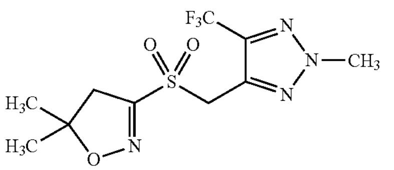

-continued

II.6

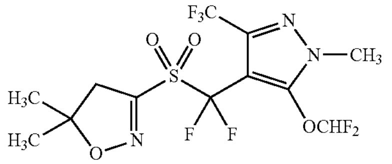

II.7

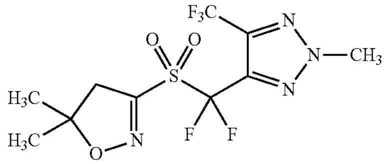

II.8

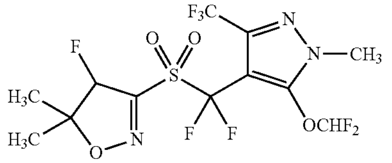

II.9

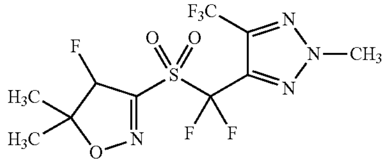

the isoxazoline compounds of the formula (I)I are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors:

chlorthiamid, dichlobenil, flupoxam, isoxaben and 1-Cyclohexyl-5-pentafluorphenyloxy-$1^4$-[1,2,4,6]thiatriazin-3-ylamine;

b12) from the group of the decoupler herbicides:

dinoseb, dinoterb and DNOC and its salts;

b13) from the group of the auxinic herbicides:

2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters and triclopyr and its salts and esters;

b14) from the group of the auxin transport inhibitors: diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam and tridiphane.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanol-ammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl) ammonium, 2,4-D-tris(isopropyl)ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isoctyl.

Suitable salts of dichlorprop are for example dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl) ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium, aminopyralid-dimethylammonium, and aminopyralid-tris(2-hydroxypropyl)ammonium.

Suitable salts of glyphosate are for example glyphosate-ammonium, glyphosate-diammonium, glyphoste-dimethyl-ammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinclorac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

Particularly preferred herbicidal compounds B are the herbicides B as defined above; in particular the herbicides B.1-B.189 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-ethyl |
| B.6 | fenoxaprop-P-ethyl |
| B.7 | metamifop |
| B.8 | pinoxaden |
| B.9 | profoxydim |
| B.10 | sethoxydim |
| B.11 | tepraloxydim |
| B.12 | tralkoxydim |
| B.13 | esprocarb |
| B.14 | ethofumesate |
| B.15 | molinate |
| B.16 | prosulfocarb |
| B.17 | thiobencarb |
| B.18 | triallate |
| B.19 | bensulfuron-methyl |
| B.20 | bispyribac-sodium |
| B.21 | cloransulam-methyl |
| B.22 | chlorsulfuron |
| B.23 | clorimuron |
| B.24 | cyclosulfamuron |
| B.25 | diclosulam |
| B.26 | florasulam |
| B.27 | flumetsulam |
| B.28 | flupyrsulfuron-methyl-sodium |
| B.29 | foramsulfuron |
| B.30 | imazamox |
| B.31 | imazamox-ammonium |
| B.32 | imazapic |
| B.33 | imazapic-ammonium |
| B.34 | imazapic-isopropylammonium |
| B.35 | imazapyr |
| B.36 | imazapyr-ammonium |
| B.37 | imazapyr-isopropylammonium |
| B.38 | imazaquin |
| B.39 | imazaquin-ammonium |
| B.40 | imazethapyr |
| B.41 | imazethapyr-ammonium |
| B.42 | imazethapyr-isopropylammonium |
| B.43 | imazosulfuron |
| B.44 | iodosulfuron-methyl-sodium |
| B.45 | iofensulfuron |
| B.46 | iofensulfuron-sodium |
| B.47 | mesosulfuron-methyl |
| B.48 | metazosulfuron |
| B.49 | metsulfuron-methyl |
| B.50 | metosulam |
| B.51 | nicosulfuron |
| B.52 | penoxsulam |
| B.53 | propoxycarbazon-sodium |
| B.54 | pyrazosulfuron-ethyl |
| B.55 | pyribenzoxim |
| B.56 | pyriftalid |
| B.57 | pyroxsulam |
| B.58 | propyrisulfuron |
| B.59 | rimsulfuron |
| B.60 | sulfosulfuron |
| B.61 | thiencarbazone-methyl |
| B.62 | thifensulfuron-methyl |
| B.63 | tribenuron-methyl |
| B.64 | tritosulfuron |
| B.65 | triafamone |
| B.66 | ametryne |
| B.67 | atrazine |
| B.68 | bentazon |
| B.69 | bromoxynil |
| B.70 | bromoxynil-octanoate |
| B.71 | bromoxynil-heptanoate |
| B.72 | bromoxynil-potassium |

TABLE B-continued

| | Herbicide B |
|---|---|
| B.73 | diuron |
| B.74 | fluometuron |
| B.75 | hexazinone |
| B.76 | isoproturon |
| B.77 | linuron |
| B.78 | metamitron |
| B.79 | metribuzin |
| B.80 | propanil |
| B.81 | simazin |
| B.82 | terbuthylazine |
| B.83 | terbutryn |
| B.84 | paraquat-dichloride |
| B.85 | acifluorfen |
| B.86 | butafenacil |
| B.87 | carfentrazone-ethyl |
| B.88 | flumioxazin |
| B.89 | fomesafen |
| B.90 | oxadiargyl |
| B.91 | oxyfluorfen |
| B.92 | saflufenacil |
| B.93 | sulfentrazone |
| B.94 | ethyl [3-[2-chloro-4-fluoro-5-(1-methyl-6-trifluoromethyl-2,4-dioxo-1,2,3,4-tetrahydro-pyrimidin-3-yl)phenoxy]-2-pyridyloxy]acetate (CAS 353292-31-6) |
| B.95 | 1,5-dimethyl-6-thioxo-3-(2,2,7-trifluoro-3-oxo-4-(prop-2-ynyl)-3,4-dihydro-2H-benzo[b][1,4]-oxazin-6-yl)-1,3,5-triazinane-2,4-dione (CAS 1258836-72-4) |
| B.96 | benzobicyclon |
| B.97 | clomazone |
| B.98 | diflufenican |
| B.99 | flurochloridone |
| B.100 | isoxaflutole |
| B.101 | mesotrione |
| B.102 | norflurazone |
| B.103 | picolinafen |
| B.104 | sulcotrione |
| B.105 | tefuryltrione |
| B.106 | tembotrione |
| B.107 | topramezone |
| B.108 | topramezone-sodium |
| B.109 | bicyclopyrone |
| B.110 | amitrole |
| B.111 | fluometuron |
| B.112 | fenquintrione |
| B.113 | glyphosate |
| B.114 | glyphosate-ammonium |
| B.115 | glyphosate-dimethylammonium |
| B.116 | glyphosate-isopropylammonium |
| B.117 | glyphosate-trimesium (sulfosate) |
| B.118 | glyphosate-potassium |
| B.119 | glufosinate |
| B.120 | glufosinate-ammonium |
| B.121 | glufosinate-P |
| B.122 | glufosinate-P-ammonium |
| B.123 | pendimethalin |
| B.124 | trifluralin |
| B.125 | acetochlor |
| B.126 | butachlor |
| B.127 | cafenstrole |
| B.128 | dimethenamid-P |
| B.129 | fentrazamide |
| B.130 | flufenacet |
| B.131 | mefenacet |
| B.132 | metazachlor |
| B.133 | metolachlor |
| B.134 | S-metolachlor |
| B.135 | pretilachlor |
| B.136 | fenoxasulfone |
| B.137 | isoxaben |

TABLE B-continued

| | Herbicide B |
|---|---|
| B.138 | ipfencarbazone |
| B.139 | pyroxasulfone |
| B.140 | 2,4-D |
| B.141 | 2,4-D-isobutyl |
| B.142 | 2,4-D-dimethylammonium |
| B.143 | 2,4-D-N,N,N-trimethylethanolammonium |
| B.144 | aminopyralid |
| B.145 | aminopyralid-methyl |
| B.146 | aminopyralid-dimethyl-ammonium |
| B.147 | aminopyralid-tris(2-hydroxypropyl)ammonium |
| B.148 | clopyralid |
| B.149 | clopyralid-methyl |
| B.150 | clopyralid-olamine |
| B.151 | dicamba |
| B.152 | dicamba-butotyl |
| B.153 | dicamba-diglycolamine |
| B.154 | dicamba-dimethylammonium |
| B.155 | dicamba-diolamine |
| B.156 | dicamba-isopropylammonium |
| B.157 | dicamba-potassium |
| B.158 | dicamba-sodium |
| B.159 | dicamba-trolamine |
| B.160 | dicamba-N,N-bis-(3-aminopropyl)methylamine |
| B.161 | dicamba-diethylenetriamine |
| B.162 | fluroxypyr |
| B.163 | fluroxypyr-meptyl |
| B.164 | MCPA |
| B.165 | MCPA-2-ethylhexyl |
| B.166 | MCPA-dimethylammonium |
| B.167 | quinclorac |
| B.168 | quinclorac-dimethylammonium |
| B.169 | quinmerac |
| B.170 | quinmerac-dimethylammonium |
| B.171 | aminocyclopyrachlor |
| B.172 | aminocyclopyrachlor-potassium |
| B.173 | aminocyclopyrachlor-methyl |
| B.174 | diflufenzopyr |
| B.175 | diflufenzopyr-sodium |
| B.176 | dymron |
| B.177 | indanofan |
| B.178 | indaziflam |
| B.179 | oxaziclomefone |
| B.180 | triaziflam |
| B.181 | II.1 |
| B.182 | II.2 |
| B.183 | II.3 |
| B.184 | II.4 |
| B.185 | II.5 |
| B.186 | II.6 |
| B.187 | II.7 |
| B.188 | II.8 |
| B.189 | II.9 |

Moreover, it may be useful to apply the compounds of formula (I) in combination with safeners and optionally with one or more further herbicides. Safeners are chemical compounds which prevent or reduce damage on useful plants without having a major impact on the herbicidal action of the compounds of the formula (I) towards unwanted plants. They can be applied either before sowings (e.g. on seed treatments, shoots or seedlings) or in the pre-emergence application or post-emergence application of the useful plant. The safeners and the compounds of formula (I) and optionally the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diary)-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro [4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Particularly preferred safeners C are the following compounds C.1 to C.17

| | | | |
|---|---|---|---|
| C.1 | benoxacor | C.2 | cloquintocet |
| C.3 | cloquintocet-mexyl | C.4 | cyprosulfamide |
| C.5 | dichlormid | C.6 | fenchlorazole |
| C.7 | fenchlorazole-ethyl | C.8 | fenclorim |
| C.9 | furilazole | C.10 | isoxadifen |
| C.11 | isoxadifen-ethyl | C.12 | mefenpyr |
| C.13 | mefenpyr-diethyl | C.14 | naphtalic acid anhydride |
| C.15 | 4-(dichloroacetyl)-1-oxa-4-azaspiro[4.5]decane | C.16 | 2,2,5-trimethyl-3-(dichloro-acetyl)-1,3-oxazolidine |
| C.17 | N-(2-Methoxybenzoyl)-4-[(methylamino-carbonyl)amino]ben-zenesulfonamide | | |

The active compounds B of groups b1) to b15) and the safener compounds C are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro [4.5]decane [CAS No. 71526-07-3] is also referred to as AD-67 and MON 4660. The assignment of the active compounds to the respective mechanisms of action is based on current knowledge. If several mechanisms of action apply to one active compound, this substance was only assigned to one mechanism of action.

It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

In another embodiment, the present invention refers to a method for identifying a CESA-inhibiting herbicide by using a wildtype or mutated CESA encoded by a nucleic acid which comprises the nucleotide sequence of SEQ ID NO: 65, 66, 67, 68, 69, 70, 71, 72, 73, 74, 75, 76, or 77, or a variant or derivative thereof.

Said method comprises the steps of:

a) generating a transgenic cell or plant comprising a nucleic acid encoding a wildtype or mutated CESA, wherein the wildtype or mutated CESA is expressed;
b) applying a CESA-inhibiting herbicide to the transgenic cell or plant of a) and to a control cell or plant of the same variety;
c) determining the growth or the viability of the transgenic cell or plant and the control cell or plant after application of said CESA-inhibiting herbicide, and
d) selecting "CESA-inhibiting herbicides" which confer reduced growth to the control cell or plant as compared to the growth of the transgenic cell or plant.

As described above, the present invention teaches compositions and methods for increasing the CESA-inhibiting tolerance of a crop plant or seed as compared to a wild-type variety of the plant or seed. In a preferred embodiment, the CESA-inhibiting tolerance of a crop plant or seed is increased such that the plant or seed can withstand a CESA-inhibiting herbicide application of preferably approximately 1-1000 g ai $ha^{-1}$, more preferably 1-200 g ai $ha^{-1}$, even more preferably 5-150 g ai $ha^{-1}$, and most preferably 10-100 g ai $ha^{-1}$. As used herein, to "withstand" a CESA-inhibiting herbicide application means that the plant is either not killed or only moderately injured by such application. It will be understood by the person skilled in the art that the application rates may vary, depending on the environmental conditions such as temperature or humidity, and depending on the chosen kind of herbicide (active ingredient ai).

Pre- and/or Post-emergent weed control methods useful in various embodiments hereof utilize about >0.3× application rates of CESA-inhibiting herbicides; in some embodiments, this can be about, for example, >0.3×, >0.4×, >0.5×, >0.6×, >0.7×, >0.8×, >0.9×, or >1× of CESA-inhibiting herbicides. In one embodiment, CESA-inhibiting herbicides-tolerant plants of the present invention have tolerance to a pre- and/or post-emergant application of a CESA-inhibiting herbicides at an amount of about 25 to about 500 g ai/ha. In some embodiments, wherein the CESA-inhibiting herbicides-tolerant plant is a dicot (e.g., soy, cotton), the pre- and/or post-emergant application of the CESA-inhibiting herbicides is at an amount of about 25-250 g ai/ha. In another embodiment, wherein the CESA-inhibiting herbicides-tolerant plant is a monocot (e.g., maize, rice, sorghum), the pre- and/or post-emergant application of the CESA-inhibiting herbicides is at an amount of about 50-500 g ai/ha. In other embodiments, wherein the CESA-inhibiting herbicides-tolerant plant is a *Brassica* (e.g., canola), the pre- and/or post-emergant application of the CESA-inhibiting herbicides is at an amount of about 25-200 g ai/ha. In pre- and/or post-emergent weed control methods hereof, in some embodiments, the method can utilize CESA-inhibiting herbicides application rates at pre-emergent and/or about 7 to 10 days post-emergent. In another embodiment, the application rate can exceed 8×CESA-inhibiting herbicides; in some embodiments, the rate can be up to 4×CESA-inhibiting herbicides, though more typically it will be about 2.5× or less, or about 2× or less, or about 1× or less.

Furthermore, the present invention provides methods that involve the use of at least one CESA-inhibiting herbicide, optionally in combination with one or more herbicidal compounds B, and, optionally, a safener C, as described in detail supra.

In these methods, the CESA-inhibiting herbicide can be applied by any method known in the art including, but not limited to, seed treatment, soil treatment, and foliar treatment. Prior to application, the CESA-inhibiting herbicide can be converted into the customary formulations, for example solutions, emulsions, suspensions, dusts, powders, pastes and granules. The use form depends on the particular intended purpose; in each case, it should ensure a fine and even distribution of the compound according to the invention.

By providing plants having increased tolerance to CESA-inhibiting herbicide, a wide variety of formulations can be employed for protecting plants from weeds, so as to enhance plant growth and reduce competition for nutrients. A CESA-inhibiting herbicide can be used by itself for pre-emergence, post-emergence, pre-planting, and at-planting control of weeds in areas surrounding the crop plants described herein, or a CESA-inhibiting herbicide formulation can be used that contains other additives. The CESA-inhibiting herbicide can also be used as a seed treatment. Additives found in a CESA-inhibiting herbicide formulation include other herbicides, detergents, adjuvants, spreading agents, sticking agents, stabilizing agents, or the like. The CESA-inhibiting herbicide formulation can be a wet or dry preparation and can include, but is not limited to, flowable powders, emulsifiable concentrates, and liquid concentrates. The CESA-inhibiting herbicide and herbicide formulations can be applied in accordance with conventional methods, for example, by spraying, irrigation, dusting, or the like.

Suitable formulations are described in detail in PCT/EP2009/063387 and PCT/EP2009/063386, which are incorporated herein by reference.

As disclosed herein, the CESA nucleic acids of the invention find use in enhancing the CBI herbicide tolerance of plants that comprise in their genomes a gene encoding a herbicide-tolerant wildtype or mutated CESA protein. Such a gene may be an endogenous gene or a transgene, as described above. Additionally, in certain embodiments, the nucleic acids of the present invention can be stacked with any combination of polynucleotide sequences of interest in order to create plants with a desired phenotype. For example, the nucleic acids of the present invention may be stacked with any other polynucleotides encoding polypeptides having pesticidal and/or insecticidal activity, such as, for example, the *Bacillus thuringiensis* toxin proteins (described in U.S. Pat. Nos. 5,366,892; 5,747,450; 5,737,514; 5,723,756; 5,593,881; and Geiser et al (1986) Gene 48: 109), 5-enolpyruvylshikimate-3-phosphate synthase (EPSPS), Glyphosate acetyl transferase (GAT), cytochrome P450 monooxygenase, phosphinothricin acetyltransferase (PAT), Acetohydroxyacid synthase (AHAS; EC 4.1.3.18, also known as acetolactate synthase or ALS), hydroxyphenyl pyruvate dioxygenase (HPPD), Phytoene desaturase (PD), Protoporphyrinogen oxidase (PPO) and dicamba degrading enzymes as disclosed in WO 02/068607, or phenoxyaceticacid- and phenoxypropionicacid-derivative degrading enzymes as disclosed in WO 2008141154 or WO 2005107437. The combinations generated can also include multiple copies of any one of the polynucleotides of interest.

Consequently, Herbicide-tolerant plants of the invention can be used in conjunction with an herbicide to which they are tolerant. Herbicides can be applied to the plants of the invention using any techniques known to those skilled in the art. Herbicides can be applied at any point in the plant cultivation process. For example, herbicides can be applied pre-planting, at planting, pre-emergence, post-emergence or combinations thereof. Herbicides may be applied to seeds and dried to form a layer on the seeds.

In some embodiments, seeds are treated with a safener, followed by a post-emergent application of a CESA-inhibiting herbicides. In one embodiment, the post-emergent application of the CESA-inhibiting herbicides is about 7 to 10 days following planting of safener-treated seeds. In some embodiments, the safener is cloquintocet, dichlormid, fluxofenim, or combinations thereof.

Methods of controlling weeds or undesired vegetation

In other aspects, the present invention provides a method for controlling weeds at a locus for growth of a plant or plant part thereof, the method comprising: applying a composition comprising a CESA-inhibiting herbicides to the locus.

In some aspects, the present invention provides a method for controlling weeds at a locus for growth of a plant, the method comprising: applying an herbicide composition comprising CESA-inhibiting herbicides to the locus; wherein said locus is: (a) a locus that contains: a plant or a seed capable of producing said plant; or (b) a locus that is to be after said applying is made to contain the plant or the seed; wherein the plant or the seed comprises in at least some of its cells a polynucleotide operably linked to a promoter operable in plant cells, the promoter capable of expressing a wildtype or mutated CESA polypeptide encoded by the polynucleotide, the expression of the wildtype or mutated CESA polypeptide conferring to the plant tolerance to CESA-inhibiting herbicides.

Herbicide compositions hereof can be applied, e.g., as foliar treatments, soil treatments, seed treatments, or soil drenches. Application can be made, e.g., by spraying, dusting, broadcasting, or any other mode known useful in the art.

In one embodiment, herbicides can be used to control the growth of weeds that may be found growing in the vicinity of the herbicide-tolerant plants invention. In embodiments of this type, an herbicide can be applied to a plot in which herbicide-tolerant plants of the invention are growing in vicinity to weeds. An herbicide to which the herbicide-tolerant plant of the invention is tolerant can then be applied to the plot at a concentration sufficient to kill or inhibit the growth of the weed. Concentrations of herbicide sufficient to kill or inhibit the growth of weeds are known in the art and are disclosed above.

In other embodiments, the present invention provides a method for controlling weeds in the vicinity of a CESA-inhibiting herbicides-tolerant plant of the invention. The method comprises applying an effective amount of a CESA-inhibiting herbicides to the weeds and to the herbicide-tolerant plant, wherein the plant has increased tolerance to CESA-inhibiting herbicide when compared to a wild-type plant. In some embodiments, the CESA-inhibiting herbicides-tolerant plants of the invention are preferably crop plants, including, but not limited to, sunflower, alfalfa, *Brassica* sp., soybean, cotton, safflower, peanut, tobacco, tomato, potato, wheat, rice, maize, sorghum, barley, rye, millet, and sorghum.

In other aspects, herbicide(s) (e.g., CESA-inhibiting herbicides) can also be used as a seed treatment. In some embodiments, an effective concentration or an effective amount of herbicide(s), or a composition comprising an effective concentration or an effective amount of herbicide(s) can be applied directly to the seeds prior to or during the sowing of the seeds. Seed Treatment formulations may additionally comprise binders and optionally colorants.

Binders can be added to improve the adhesion of the active materials on the seeds after treatment. In one embodiments, suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers. Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15: 1, pigment blue 80, pigment yellow 1, pigment yellow 13, pigment red 1 12, pigment red 48:2, pigment red 48: 1, pigment red 57: 1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

The term seed treatment comprises all suitable seed treatment techniques known in the art, such as seed dressing, seed coating, seed dusting, seed soaking, and seed pelleting. In one embodiment, the present invention provides a method of treating soil by the application, in particular into the seed drill: either of a granular formulation containing the CESA-inhibiting herbicides as a composition/formulation (e.g., a granular formulation), with optionally one or more solid or liquid, agriculturally acceptable carriers and/or optionally with one or more agriculturally acceptable surfactants. This method is advantageously employed, for example, in seedbeds of cereals, maize, cotton, and sunflower.

The present invention also comprises seeds coated with or containing with a seed treatment formulation comprising CESA-inhibiting herbicides and at least one other herbicide such as, e.g., an AHAS-inhibitor selected from the group consisting of amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

In some embodiments, the seed treatment application with CESA-inhibiting herbicides or with a formulation comprising the CESA-inhibiting herbicides is carried out by spraying or dusting the seeds before sowing of the plants and before emergence of the plants.

In other embodiments, in the treatment of seeds, the corresponding formulations are applied by treating the seeds with an effective amount of CESA-inhibiting herbicides or a formulation comprising the CESA-inhibiting herbicides.

In other aspects, the present invention provides a method for combating undesired vegetation or controlling weeds comprising contacting the seeds of the CESA-inhibiting herbicides-tolerant plants of the present invention before sowing and/or after pregermination with CESA-inhibiting herbicides. The method can further comprise sowing the seeds, for example, in soil in a field or in a potting medium in greenhouse. The method finds particular use in combating undesired vegetation or controlling weeds in the immediate vicinity of the seed. The control of undesired vegetation is understood as the killing of weeds and/or otherwise retarding or inhibiting the normal growth of the weeds. Weeds, in the broadest sense, are understood as meaning all those plants which grow in locations where they are undesired.

The weeds of the present invention include, for example, dicotyledonous and monocotyledonous weeds. Dicotyledonous weeds include, but are not limited to, weeds of the genera: *Sinapis, Lepiclium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solarium, Rorippa, Rotala, Lindernia, Lamium, Veronica, Abutilon, Emex, Datura, Viola, Galeopsis, Papaver, Centaurea, Trifolium, Ranunculus*, and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus*, and *Apera*.

In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

In other embodiments, in the treatment of seeds, the corresponding formulations are applied by treating the seeds with an effective amount of CESA-inhibiting herbicides or a formulation comprising the CESA-inhibiting herbicides.

In still further aspects, treatment of loci, plants, plant parts, or seeds of the present invention comprises application of an agronomically acceptable composition that does not contain an A.I. In one embodiment, the treatment comprises application of an agronomically acceptable composition that does not contain a CESA-inhibiting herbicides A.I. In some embodiments, the treatment comprises application of an agronomically acceptable composition that does not contain a CESA-inhibiting herbicides A.L, wherein the composition comprises one or more of agronomically-acceptable carriers, diluents, excipients, plant growth regulators, and the like. In other embodiments, the treatment comprises application of an agronomically acceptable composition that does not contain a CESA-inhibiting herbicides A.I., wherein the composition comprises an adjuvant. In one embodiment, the adjuvant is a surfactant, a spreader, a sticker, a penetrant, a drift-control agent, a crop oil, an emulsifier, a compatibility agent, or combinations thereof.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1: Identification of Cellulose Biosynthesis Inhibitor (CBI; CESA Inhibitor) Resistant Plants For selection of cellulose biosynthesis inhibitor resistant plants EMS mutagenized seed populations of *Arabidopsis thaliana* are used. EMS mutagenized seed populations are either bought from Lehle Seeds (1102 South Industrial Blvd. Suite D, Round Rock, Texas USA) or are generated as described elsewhere (Heim D R, et. al. (1989) Plant Physiol. 90: 146-150). Causative mutations in CESA wildtype sequences (e.g. SEQ ID NO: 1 or 3) are identified as described by Scheible W R et al. (2001, Proc. Natl. Acad. of Sci. 98: 10079-10084), McCourt et. al. (WO2013/142968) or with the use of next generation sequencing methods as described by Austin R S, et. al (2011) Plant Journal 67: 715-725.

Selected *Arabidopsis thaliana* lines were assayed for improved resistance to azines like 6-cyclopentyl-N4-(2,3,4,5,6-pentafluorophenyl)-1,3,5-triazine-2,4-diamine; 6-(1-fluoro-1-methyl-ethyl)-N4-(2,3,4,5,6-pentafluorophenyl)-1,3,5-triazine-2,4-diamine; 6-cyclohexyl-N2-(2,3,4,5,6-pentafluorophenyl)-1,3,5-triazine-2,4-diamine; 6-(2,6-difluorophenyl)-N2-(2,3,5,6-tetrafluorophenyl)-1,3,5-triazine-2,4-diamine; N2-(4-chloro-3,5,6-trifluoro-2-pyridyl)-6-(1-fluoro-1-methyl-ethyl)-1,3,5-triazine-2,4-diamine in 48-well plates. Therefore, M2 or M3 seeds are surface sterilized by stirring for 5 min in ethanol+water (70+30 by volume), rinsing one time with ethanol+water (70+30 by volume) and two times with sterile, deionized water. The seeds are resuspended in 0.1% agar dissolved in water (w/v) Four to five seeds per well are plated on solid nutrient medium consisting of half-strength murashige skoog nutrient solution, pH 5.8 (Murashige and Skoog (1962) Physiologia *Plantarum* 15: 473-497). Compounds are dissolved in dimethylsulfoxid (DMSO) and added to the medium prior solidification (final DMSO concentration 0.1%). Multi well plates are incubated in a growth chamber at 22° C., 75% relative humidity and 110 μmol Phot*$m^{-2}$*$s^{-1}$ with 14: 10 h light: dark photoperiod. Growth inhibition is evaluated seven to ten days after seeding in comparison to wild type plants. Tolerance factors are calculated based on IC50 values of growth inhibition of transformed versus non-transformed *Arabidopsis* plants (Table 3).

TABLE 3

Tolerance of cellulose synthase mutant lines compared to wildtype plants. Relative tolerance rates of mutant *Arabidopsis* lines compared to a wildtype *Arabidopsis* plants (wildtype = 1.0), treated with various cellulose biosynthesis inhibitors. Growth inhibition is evaluated seven to ten days after seeding in comparison to wild type plants.

| Mutant | 6-cyclopentyl-N4-(2,3,4,5,6-pentafluoro-phenyl)-1,3,5-triazine-2,4-diamine | 6-(1-fluoro-1-methyl-ethyl)-N4-(2,3,4,5,6-pentafluoro-phenyl)-1,3,5-triazine-2,4-diamine | 6-cyclohexyl-N2-(2,3,4,5,6-pentafluoro-phenyl)-1,3,5-triazine-2,4-diamine | 6-(2,6-difluorophe-nyl)-N2-(2,3,5,6-tetrafluorophe-nyl)-1,3,5-triazine-2,4-diamine | N2-(4-chloro-3,5,6-trifluoro-2-pyridyl)-6-(1-fluoro-1-methyl-ethyl)-1,3,5-triazine-2,4-diamine |
|---|---|---|---|---|---|
| wildtype | 1 | 1 | 1 | 1 | 1 |
| Cesa3_S1040L | 56 | 2 | 10 | 13 | 4 |
| Cesa3_S1037F | 75 | 4 | 1 | 1 | 10 |
| Cesa3_S983F | 75 | 1 | 1 | 1 | 4 |
| Cesa1_G1013R | 25 | 4 | 4 | 13 | 10 |
| Cesa1_P1010L | 3 | 1 | 1 | 2 | 1 |
| Cesa1_G1009D | 3 | 2 | 1 | 1 | 1 |

Additionally, M2 or M3 *Arabidopsis* plants are tested for improved tolerance to cellulose biosynthesis-inhibiting herbicides in greenhouse studies (e. g. with the following cellulose biosynthesis-inhibiting herbicides: 6-cyclopentyl-N4-(2,3,4,5,6-pentafluorophenyl)-1,3,5-triazine-2,4-diamine; 6-(1-fluoro-1-methyl-ethyl)-N4-(2,3,4,5,6-pentafluorophenyl)-1,3,5-triazine-2,4-diamine; N4-(4-chloro-3,5,6-trifluoro-2-pyridyl)-6-(1-fluoro-1-methyl-ethyl)-1,3,5-triazine-2,4-diamine; 6-(2,6-difluorophenyl)-N4-(2,3,5,6-tetrafluorophenyl)-1,3,5-triazine-2,4-diamine; N4-(4-bromo-2,3,5,6-tetrafluoro-phenyl)-6-(1-fluoro-1-methyl-ethyl)-1,3,5-triazine-2,4-diamine.

TABLE 4

Phytotox values of cellulose synthase mutant lines to various cellulose biosynthesis inhibitors when treated pre-emergent. Shown are phytotox values on a scale from 0-100, were 100 is 100% damage.

| compound | g ai/ha | *A. thaliana* WT L. erecta | Cesa3_ S1040L, fpx1-1 | Cesa3_ S1037F, fpx1-2 | Cesa3_ S983F, fpx1-3 | Cesa1_ G1013R, fpx2-1 | Cesa1_ P1010L, fpx2-2 | Cesa1_ G1009D, fpx2-3 |
|---|---|---|---|---|---|---|---|---|
| 6-cyclopentyl-N4-(2,3,4,5,6-pentafluorophenyl)-1,3,5-triazine-2,4-diamine | 15.63 | 100 | 40 | 5 | 40 | 15 | 98 | 88 |
| | 3.91 | 99 | 25 | 15 | 20 | 25 | 63 | 58 |
| | 0.98 | 80 | 20 | 23 | 5 | 15 | 33 | 25 |
| | 0.25 | 38 | 5 | 0 | 0 | 5 | 0 | 5 |
| 1-(m-tolyl)-5-phenyl-1,2,4-triazole-3-carboxamide | 250 | 100 | 25 | 68 | 30 | 15 | 35 | 45 |
| | 62.5 | 100 | 0 | 23 | 5 | 20 | 13 | 30 |
| | 15.63 | 63 | 30 | 30 | 8 | 15 | 20 | 18 |
| | 3.91 | 0 | 38 | 0 | 0 | 5 | 0 | 0 |
| 6-(1-fluoro-1-methyl-ethyl)-N4-(2,3,4,5,6-pentafluorophenyl)-1,3,5-triazine-2,4-diamine | 3.91 | 100 | 98 | 80 | 98 | 97 | 100 | 100 |
| | 0.98 | 100 | 75 | 30 | 75 | 63 | 99 | 97 |
| | 0.25 | 78 | 65 | 20 | 45 | 65 | 50 | 78 |
| | 0.0625 | 38 | 20 | 10 | 78 | 13 | 43 | 65 |
| N4-(4-chloro-3,5,6-trifluoro-2-pyridyl)-6-(1-fluoro-1-methyl-ethyl)-1,3,5-triazine-2,4-diamine | 3.91 | 99 | 53 | 25 | 13 | 80 | 98 | 99 |
| | 0.98 | 83 | 78 | 25 | 48 | 70 | 78 | 93 |
| | 0.25 | 60 | 15 | 15 | 55 | 50 | 25 | 43 |
| | 0.0625 | 45 | 13 | 5 | 23 | 40 | 50 | 30 |
| 6-(2,6-difluorophenyl)-N4-(2,3,5,6-tetrafluorophenyl)-1,3,5-triazine-2,4-diamine | 62.5 | 100 | 28 | 99 | 33 | 40 | 98 | 95 |
| | 15.63 | 90 | 25 | 73 | 43 | 28 | 65 | 18 |
| | 3.91 | 70 | 8 | 65 | 35 | 35 | 35 | 38 |
| | 0.98 | 30 | 13 | 28 | 18 | 15 | 48 | 65 |
| N4-(4-bromo-2,3,5,6-tetrafluoro-phenyl)-6-(1-fluoro-1-methyl-ethyl)-1,3,5-triazine-2,4-diamine | 15.63 | 100 | 93 | 30 | 45 | 73 | 99 | 99 |
| | 3.91 | 97 | 63 | 33 | 25 | 35 | 88 | 68 |
| | 0.98 | 35 | 5 | 18 | 23 | 10 | 25 | 35 |
| | 0.25 | 8 | 13 | 28 | 35 | 10 | 25 | 50 |

TABLE 5

Phytotox values of cellulose synthase mutant lines to various cellulose biosynthesis inhibitors when treated post-emergent, 6 weeks after sowing. Shown are phytotox values on a scale from 0-100, were 100 is 100% damage.

| compound | g ai/ha | *A. thaliana* WT L. erecta | Cesa3__ S1040L, fpx1-1 | Cesa3__ S1037F, fpx1-2 | Cesa3__ S983F, fpx1-3 | Cesa1__ G1013R, fpx2-1 | Cesa1__ P1010L, fpx2-2 | Cesa1__ G1009D, fpx2-3 |
|---|---|---|---|---|---|---|---|---|
| 6-cyclopentyl-N4-(2,3,4,5,6-pentafluorophenyl)-1,3,5-triazine-2,4-diamine | 63 | 98 | 68 | 78 | 73 | 80 | 93 | 75 |
| | 31.5 | 78 | 35 | 70 | 55 | 65 | 78 | 73 |
| | 15.75 | 80 | 5 | 58 | 65 | 55 | 70 | 63 |
| | 7.88 | 68 | 0 | 55 | 25 | 38 | 63 | 45 |
| 1-(m-tolyl)-5-phenyl-1,2,4-triazole-3-carboxamide | 250 | 95 | 55 | 68 | 53 | 40 | 48 | 45 |
| | 125 | 83 | 23 | 50 | 23 | 33 | 15 | 33 |
| | 62.5 | 78 | 0 | 30 | 28 | 23 | 15 | 23 |

Example 2: Identification of Homologue Cellulose Synthase Isoforms in Crop Plants To identify homologue cellulose synthase genes from soy, corn and rice, BLAST searches using the protein sequences of *Arabidopsis thaliana* cellulose synthase isoforms were performed (Altschul et al. (1990) J Mol Biol 215: 403-10). Cellulose synthase protein encoding genes from corn, soy and rice were analyzed regarding their phylogenetic relationship by the R software library phangorn (Schliep K P. (2011) Bioinformatics 27: 592-593). Bootstrap analyses to statistically confirm monophyletic groups were calculated. In addition genes were classified by their expression level and expression pattern (Hruz T, et. al. (2008) Adv. in Bioinformatics 2008: 1-5) (FIGS. 1-3) and selected for plant transformation.

Example 3: Tissue Culture Conditions

An in vitro tissue culture mutagenesis assay is developed to isolate and characterize plant tissue (e.g., maize, rice) that is tolerant to cellulose synthase inhibiting herbicides, (e. g. 6-cyclopentyl-N4-(2,3,4,5,6-pentafluorophenyl)-1,3,5-triazine-2,4-diamine, and photosynthesis inhibitor diuron as negative control). The assay utilizes the somaclonal variation that is found in in vitro tissue culture. Spontaneous mutations derived from somaclonal variation can be enhanced by chemical mutagenesis (e. g. ethylmethane sulfonate; ethylethane sulfonate, N-nitroso-N-ethyl urea, ethylnitrosourea, nitrose acid, bromouracil, 2.-aminopurine, 5-fluorodeoxyuridine, hydroxylamine, N-methyl-N'-nitro-N-nitrosoguanidine) and subsequent selection in a stepwise manner, on increasing concentrations of herbicide.

The present invention provides tissue culture conditions for encouraging growth of friable, embryogenic maize or rice callus that is regenerable. Calli are initiated from 4 different maize or rice cultivars encompassing *Zea mays* and *Japonica* (Taipei 309, Nipponbare, Koshihikari) and Indica (Indica 1) varieties, respectively. Seeds are surface sterilized in 70% ethanol for approximately 1 min followed by 20% commercial Clorox bleach for 20 minutes. Seeds are rinsed with sterile water and plated on callus induction media. Various callus induction media are tested. The ingredient lists for the media tested are presented in Table 6.

TABLE 6

| Ingredient | Supplier | R001M | R025M | R026M | R327M | R008M | MS711R |
|---|---|---|---|---|---|---|---|
| B5 Vitamins | Sigma | | | | | 1.0 X | |
| MS salts | Sigma | | | 1.0 X | 1.0 X | 1.0 X | 1.0 X |
| MS Vitamins | Sigma | | | 1.0 X | 1.0 X | | |
| N6 salts | Phytotech | 4.0 g/L | 4.0 g/L | | | | |
| N6 vitamins | Phytotech | 1.0 X | 1.0 X | | | | |
| L-Proline | Sigma | 2.9 g/L | 0.5 g/L | | | | 1.2 g/L |
| Casamino Acids | BD | 0.3 g/L | 0.3 g/L | 2 g/L | | | |
| Casein Hydrolysate | Sigma | | | | | | 1.0 g/L |
| L-Asp Monohydrate | Phytotech | | | | | | 150 mg/L |
| Nicotinic Acid | Sigma | | | | | | 0.5 mg/L |
| Pyridoxine HCl | Sigma | | | | | | 0.5 mg/L |
| Thiamine HCl | Sigma | | | | | | 1.0 mg/L |
| Myo-inositol | Sigma | | | | | | 100 mg/L |
| MES | Sigma | 500 mg/L | 500 mg/L | 500 mg/L | 500 mg/L | 500 mg/L | 500 mg/L |
| Maltose | VWR | 30 g/L | 30 g/L | 30 g/L | 30 g/L | | |
| Sorbitol | Duchefa | | | 30 g/L | | | |
| Sucrose | VWR | | | | | 10 g/L | 30 g/L |
| NAA | Duchefa | | | | | 50 μg/L | |
| 2,4-D | Sigma | 2.0 mg/L | | | | | 1.0 mg/L |
| $MgCl_2 \cdot 6H_2O$ | VWR | | | | | 750 mg/L | |
| →pH | | 5.8 | 5.8 | 5.8 | 5.8 | 5.8 | 5.7 |
| Gelrite | Duchefa | 4.0 g/L | | | | 2.5 g/L | |
| Agarose Type1 | Sigma | | 7.0 g/L | 10 g/L | 10 g/L | | |
| →Autoclave | | 15 min | 15 min | 15 min | 15 min | 15 min | 20 min |
| Kinetin | Sigma | | 2.0 mg/L | 2.0 mg/L | | | |
| NAA | Duchefa | | 1.0 mg/L | 1.0 mg/L | | | |

TABLE 6-continued

| Ingredient | Supplier | R001M | R025M | R026M | R327M | R008M | MS711R |
|---|---|---|---|---|---|---|---|
| ABA | Sigma | | 5.0 mg/L | | | | |
| Cefotaxime | Duchefa | | 0.1 g/L | 0.1 g/L | 0.1 g/L | | |
| Vancomycin | Duchefa | | 0.1 g/L | 0.1 g/L | 0.1 g/L | | |
| G418 Disulfate | Sigma | | 20 mg/L | 20 mg/L | 20 mg/L | | |

R001M callus induction media was selected after testing numerous variations. Cultures were kept in the dark at 30° C. Embryogenic callus was subcultured to fresh media after 10-14 days.

Example 4: Selection of Herbicide-Tolerant Calli

Once tissue culture conditions were determined, further establishment of selection conditions are established through the analysis of tissue survival in kill curves with azine herbicides e. g. like 6-cyclopentyl-N4-(2,3,4,5,6-pentafluorophenyl)-1,3,5-triazine-2,4-diamine, and photosynthesis inhibitor diuron as negative control. Careful consideration of accumulation of the herbicide in the tissue, as well as its persistence and stability in the cells and the culture media are performed. Through these experiments, a sub-lethal dose is established for the initial selection of mutated material. After the establishment of the starting dose of azine herbicides like e. g. 6-cyclopentyl-N4-(2,3,4,5,6-pentafluorophenyl)-1,3,5-triazine-2,4-diamine, and photosynthesis inhibitor diuron as negative control in selection media, the tissues were selected in a step-wise fashion by increasing the concentration of the cellulose synthase inhibitor with each transfer until cells are recovered that grew vigorously in the presence of toxic doses. The resulting calli are further subcultured every 3-4 weeks to R001M with selective agent. Over 26,000 calli are subjected to selection for 4-5 subcultures until the selective pressure is above toxic levels as determined by kill curves and observations of continued culture. Alternatively, liquid cultures initiated from calli in MS711R with slow shaking and weekly subcultures. Once liquid cultures are established, selection agent is added directly to the flask at each subculture. Following 2-4 rounds of liquid selection, cultures are transferred to filters on solid R001M media for further growth.

Example 5: Regeneration of Plants

Tolerant tissue is regenerated and characterized molecularly for cellulose synthase gene sequences mutations. In addition, genes involved directly and/or indirectly in cell wall biosynthesis and/or metabolism pathways are also sequenced to characterize mutations. Finally, enzymes that change the fate (e.g. metabolism, translocation, transportation) are also sequenced to characterize mutations. Following herbicide selection, calli are regenerated using a media regime of R025M for 10-14 days, R026M for ca. 2 weeks, R327M until well formed shoots were developed, and R008S until shoots are well rooted for transfer to the greenhouse. Regeneration was carried out in the light. No selection agent is included during regeneration. Once strong roots are established, M0 regenerants are transplant to the greenhouse in square or round pots. Transplants are maintained under a clear plastic cup until they were adapted to greenhouse conditions. The greenhouse was set to a day/night cycle of 27° C./21° C. (80° F./70° F.) with 600 W high pressure sodium lights supplementing light to maintain a 14 hour day length. Plants are watered according to need, depending in the weather and fertilized daily.

Example 6: Sequence Analysis

Leaf tissue is collected from clonal plants separated for transplanting and analyzed as individuals. Genomic DNA is extracted using a Wizard® 96 Magnetic DNA Plant System kit (Promega, U.S. Pat. Nos. 6,027,945 & 6,368,800) as directed by the manufacturer. Isolated DNA is PCR amplified using the appropriate forward and reverse primer.

PCR amplification is performed using Hotstar Taq DNA Polymerase (Qiagen) using touchdown thermocycling program as follows: 96° C. for 15 min, followed by 35 cycles (96° C., 30 sec; 58° C. — 0.2° C. per cycle, 30 sec; 72° C., 3 min and 30 sec), 10 min at 72° C. PCR products were verified for concentration and fragment size via agarose gel electrophoresis. Dephosphorylated PCR products are analyzed by direct sequence using the PCR primers (DNA Landmarks). Chromatogram trace files (.scf) are analyzed for mutation relative to the wild-type gene using Vector NTI Advance 10™ (Invitrogen). Based on sequence information, mutations are identified in several individuals. Sequence analysis is performed on the representative chromatograms and corresponding AlignX alignment with default settings and edited to call secondary peaks.

Example 7: Engineering Azine-Tolerant *Arabidopsis* Plants Having Wildtype or Mutated Cellulose Synthase Sequences For transformation of *Arabidopsis thaliana*, wildtype or mutated cellulose synthase sequences based on one of the following sequences SEQ ID NO: 72, 73, 74, 75, 76, or 77, are cloned with standard cloning techniques as described in Sambrook et al. (Molecular cloning (2001) Cold Spring Harbor Laboratory Press) in a binary vector containing resistance marker gene cassette (AHAS) and mutated cellulose synthase sequence (marked as GOI) in between ubiquitin promoter (PcUbi) and nopaline synthase terminator (NOS) sequence. Binary plasmids are introduced to *Agrobacterium tumefaciens* for plant transformation. *Arabidopsis thaliana* are transformed with wildtype or mutated cellulose synthase sequences by floral dip method as described by McElver and Singh (WO 2008/124495). Transgenic *Arabidopsis* plants are subjected to TaqMan analysis for analysis of the number of integration loci.

Transgenic *Arabidopsis thaliana* plants are assayed for improved tolerance to azine herbicides like e. g. 6-cyclopentyl-N4-(2,3,4,5,6-pentafluorophenyl)-1,3,5-triazine-2,4-diamine in 48-well plates. Therefore, T2 seeds are surface sterilized by stirring for 5 min in ethanol+water (70+30 by volume), rinsing one time with ethanol+water (70+30 by volume) and two times with sterile, deionized water. The seeds are resuspended in 0.1% agar dissolved in water (w/v) Four to five seeds per well are plated on solid nutrient medium consisting of half-strength murashige skoog nutrient solution, pH 5.8 (Murashige and Skoog (1962) Physiologia *Plantarum* 15: 473-497). Compounds are dissolved in dimethylsulfoxid (DMSO) and added to the medium prior solidification (final DMSO concentration 0.1%). Multi well plates are incubated in a growth chamber at 22° C., 75% relative humidity and 110 μmol Phot*$m^{-2}$*$s^{-1}$ with 14:10 h light:dark photoperiod. Growth inhibition is evaluated seven to ten days after seeding in comparison to wild type plants. Tolerance factors are calculated based on IC50 values of growth inhibition of transformed versus non-transformed *Arabidopsis* plants.

all constructs. Healthy looking plants are sent to the greenhouse for hardening and subsequent spray testing. The plants are individually transplanted into MetroMix 360 soil in 4" pots. Once in the greenhouse (day/night cycle of 27° C./21° C. with 14 hour day length supported by 600 W high pressure sodium lights), they are allowed to grow for 14 days. Transformation of *Oryza sativa* (rice) are done by protoplast transformation as described by Peng et al. (U.S. Pat. No. 6,653,529). Transgenic corn and rice plants are cultivated to T1 seeds for herbicide tolerance testing.

TABLE 7

Relative tolerance rates of transgenic *Arabidopsis* plants as compared to a non-transgenic *Arabidopsis* plant (non-transgenic = 1.0), treated with various cellulose biosynthesis inhibitors. Growth inhibition is evaluated seven to ten days after seeding in comparison to wild type plants.

| construct | AtCESA1 wt | AtCESA1_G1013R | AtCESA3_wt | AtCESA3_S1040L | AtCESA3_S1037F |
|---|---|---|---|---|---|
| SEQ ID NO | 1 | 1 | 3 | 3 | 3 |
| substitution | — | G1013R | — | S1040L | S1037F |
| 1-(m-tolyl)-5-phenyl-1,2,4-triazole-3-carboxamide | 3 | 33 | 4 | 2 | 1333 |
| 6-cyclopentyl-N4-(2,3,4,5,6-pentafluorophenyl)-1,3,5-triazine-2,4-diamine | 1 | 3 | 1 | 1 | 17 |

Additionally, transgenic T2 *Arabidopsis* plants are tested for improved tolerance to CESA-inhibiting herbicides in greenhouse studies with azine compounds like e. g. 6-cyclopentyl-N4-(2,3,4,5,6-pentafluorophenyl)-1,3,5-triazine-2,4-diamine.

Example 8: Soybean Transformation and Cellulose Biosynthesis Inhibitor Tolerance Testing Binary vectors are generated as described in EXAMPLE 7. Soybean cv Jake are transformed as previously described by Siminszky et al., Phytochem Rev. 5:445-458 (2006). After regeneration, transformants are transplanted to soil in small pots, placed in growth chambers (16 hr day/8 hr night; 25° C. day/23° C. night; 65% relative humidity; 130-150 microE m-2 s-1) and subsequently tested for the presence of the T-DNA via Taqman analysis. After a few weeks, healthy, transgenic positive, single copy events are transplanted to larger pots and allowed to grow in the growth chamber. An optimal shoot for cutting is about 3-4 inches tall, with at least two nodes present. Each cutting is taken from the original transformant (mother plant) and dipped into rooting hormone powder (indole-3-butyric acid, IBA). The cutting is then placed in oasis wedges inside a bio-dome. The mother plant is taken to maturity in the greenhouse and harvested for seed. Wild type cuttings are also taken simultaneously to serve as negative controls. The cuttings are kept in the bio-dome for 5-7 days. 3-4 days after transfer to oasis wedges, the shoots are treated via nutrient solution with the herbicide. Typical phytotox symptoms, like club shaped root, are evaluated 3-4 days after treatment. Less or no injury of transgenic plants compared to wildtype plants are interpreted as herbicide tolerance.

Example 9: Engineering Cellulose Biosynthesis Inhibitor Tolerant Corn or Rice Plants Having Mutated Cellulose Synthase Sequences Immature embryos can be transformed according to the procedure outlined in Peng et al. (WO2006/136596). Plants are tested for the presence of the T-DNA by Taqman analysis with the target being the nos terminator which is present in

Example 10: Demonstration of Herbicide Tolerance

T0 or T1 transgenic plant of soybean, corn and rice containing cellulose synthase sequences or mutated gene variants thereof are tested for improved tolerance to herbicides in greenhouse studies and mini-plot studies with azine herbicides. For the pre-emergence treatment, the herbicides are applied directly after sowing by means of finely distributing nozzles. The containers are irrigated gently to promote germination and growth and subsequently covered with transparent plastic hoods until the plants have rooted. This cover causes uniform germination of the test plants, unless this has been impaired by the herbicides. For post emergence treatment, the test plants are first grown to a height of 3 to 15 cm, depending on the plant habit, and only then treated with the herbicides. For this purpose, the test plants are either sown directly, and grown in the same containers or they are first grown separately and transplanted into the test containers a few days prior to treatment.

Herbicide injury evaluations are taken at 2 and 3 weeks after treatment. Plant injury is rated on a scale of 0% to 100%, 0% being no injury and 100% being complete death.

The following gives a definition of the injury scores measured above:

Score Description of Injury

0 No Injury

1 Minimal injury, only a few patches of leaf injury or chlorosis.

2 Minimal injury with slightly stronger chlorosis. Overall growth points remain undamaged.

3 Slightly stronger injury on secondary leaf tissue, but primary leaf and growth points are still undamaged.

4 Overall plant morphology is slightly different, some chlorosis and necrosis in secondary growth points and leaf tissue. Stems are intact. Regrowth is highly probable within 1 week.

5 Overall plant morphology is clearly different, some chlorosis and necrosis on a few leaves and growth points, but primary growth point is intact. Stem tissue is still green. Regrowth is highly probably within 1 week.

6 Strong injury can be seen on the new leaflet growth. Plant has a high probability to survive only through regrowth at different growth points. Most of the leaves are chlorotic/necrotic but stem tissue is still green. May have regrowth but with noticeable injured appearance.

7 Most of the active growth points are necrotic. There may be a single growth point that could survive and may be partially chlorotic or green and partially necrotic. Two leaves may still be chlorotic with some green; the rest of the plant including stem is necrotic.

8 Plant will likely die, and all growth points are necrotic. One leaf may still be chlorotic with some green. The remainder of the plant is necrotic.

9 Plant is dead.

* Not tested

The invention claimed is:

1. A plant or plant part comprising a polynucleotide encoding a mutated cellulose synthase (CESA) polypeptide, the expression of said polynucleotide confers to the plant or plant part tolerance to CESA-inhibiting herbicides, wherein the mutated CESA polypeptide comprises one or more of the following motifs:

i) Motif 1a:

(SEQ ID NO: 78)
[V/I][A/V]G[V/I/F][S/T][Y/D/N/A]A[V/I/L][N/S/G]

[S/N]G[Y/F/E][Q/D/G/E/H][S/A]WG[P/A]L[[F/M/L]G

[K/R][L/V][F/L]F, wherein the amino acid at position 5 within said motif is substituted by any other amino acid than S or T;

wherein the amino acid at position 16 within said motif is substituted by any other amino acid; and/or wherein the amino acid at position 17 within said motif is substituted by any other amino acid than P or A;

ii) Motif 2a:

(SEQ ID NO: 81)
[V/L/I]W[S/A][V/A/I]LL[A/S]S[I/F/V][F/L][S/T][L/V]

[L/M/V/I]WV[R/K][I/V][N/D]PF, wherein the amino acid at position 8 within said motif is substituted by any other amino acid, and/or position 11 by any other amino acid than S or T;

wherein the mutated CESA polypeptide comprises an amino acid sequence having, over the full-length, at least 80% sequence identity to SEQ ID NO: 28, and wherein the amino acid sequence of the mutated CESA polypeptide differs from the wildtype amino acid sequence at one or more positions corresponding to positions 1009, 1010, 1013, 1052, and 1055 of SEQ ID NO: 1.

2. A seed comprising a polynucleotide encoding a mutated cellulose synthase (CESA) polypeptide, wherein the mutated CESA polypeptide comprises one or more of the following motifs:

i) Motif 1a:

(SEQ ID NO: 78
[V/I][A/V]G[V/I/F][S/T][Y/D/N/A]A[V/I/L][N/S/G]
[S/N]G[Y/F/E][Q/D/G/E/H][S/A]WG[P/A]L[[F/M/L]G
[K/R][L/V][F/L]F, wherein the amino acid at position 5 within said motif is substituted by any other amino acid than S or T;
wherein the amino acid at position 16 within said motif is substituted by any other amino acid; and/or
wherein the amino acid at position 17 within said motif is substituted by any other amino acid than P or A;

ii) Motif 2a:

(SEQ ID NO: 81)
[V/L/I]W[S/A][V/A/I]LL[A/S]S[I/F/V][F/L][S/T][L/V]
[L/M/V/I]WV[R/K][I/V][N/D]PF, wherein the amino acid at position 8 within said motif is substituted by any other amino acid, and/or position 11 by any other amino acid than S or T;

wherein the mutated CESA polypeptide comprises an amino acid sequence having, over the full-length, at least 80% sequence identity to SEQ ID NO: 28, and wherein the amino acid sequence of the mutated CESA polypeptide differs from the wildtype amino acid sequence at one or more positions corresponding to positions 1009, 1010, 1013, 1052, and 1055 of SEQ ID NO: 1.

3. A plant cell comprising a polynucleotide encoding a mutated cellulose synthase (CESA) polypeptide, wherein the mutated CESA polypeptide comprises one or more of the following motifs:

i) Motif 1a:

(SEQ ID NO: 78)
[V/I][A/V]G[V/I/F][S/T][Y/D/N/A]A[V/I/L][N/S/G][S/
N]G[Y/F/E][Q/D/G/E/H][S/A]WG[P/A]L[F/M/L]G[K/R][L/
V][F/L]F, wherein the amino acid at position 5 within said motif is substituted by any other amino acid than S or T;
wherein the amino acid at position 16 within said motif is substituted by any other amino acid; and/or
wherein the amino acid at position 17 within said motif is substituted by any other amino acid than P or A;

ii) Motif 2a:

(SEQ ID NO: 81)
[V/L/I]W[S/A][V/A/I]LL[A/S]S[I/F/V][F/L][S/T][L/V]
[L/M/V/1]WV[R/K][I/V][N/D]PF, wherein the amino acid at position 8 within said motif is substituted by any other amino acid, and/or position 11 by any other amino acid than S or T;

wherein the mutated CESA polypeptide comprises an amino acid sequence having, over the full-length, at least 80% sequence identity to SEQ ID NO: 28, and wherein the amino acid sequence of the mutated CESA polypeptide differs from the wildtype amino acid sequence at one or more positions corresponding to positions 1009, 1010, 1013, 1052, and 1055 of SEQ ID NO: 1.

4. A method for controlling weeds at a locus for growth of a plant, the method comprising:

(a) applying an herbicide composition comprising CESA-inhibiting herbicides to the locus; and (b) planting a seed at the locus, wherein the seed is capable of producing a plant that comprises in at least some of its cells a polynucleotide operably linked to a promoter operable in plant cells, the promoter capable of expressing a mutated CESA polypeptide encoded by the polynucleotide, the expression of the mutated CESA polypeptide conferring to the plant tolerance to CESA-inhibiting herbicides, wherein the mutated CESA polypeptide comprises one or more of the following motifs:

i) Motif 1a:

(SEQ ID NO: 78)
[V/I][A/V]G[V/I/F][S/T][Y/D/N/A]A[V/I/L][N/S/G][S/
N]G[Y/F/E][Q/D/G/E/H][S/A]WG[P/A]L[F/M/L]G[K/R][L/
V][F/L]F, wherein the amino acid at position 5 within said motif is substituted by any other amino acid than S or T;
wherein the amino acid at position 16 within said motif is substituted by any other amino acid; and/or
wherein the amino acid at position 17 within said motif is substituted by any other amino acid than P or A;

ii) Motif 2a:

(SEQ ID NO: 81)
[V/L/I]W[S/A][V/A/I]LL[A/S]S[I/F/V][F/L][S/T][L/V]
[L/M/V/1]WV[R/K][I/V][N/D]PF, wherein the amino acid at position 8 within said motif is substituted by any other amino acid, and/or position 11 by any other amino acid than S or T;

wherein the mutated CESA polypeptide comprises an amino acid sequence having, over the full-length, at least 80% sequence identity to SEQ ID NO: 28, and wherein the amino acid sequence of the mutated CESA polypeptide differs from the wildtype amino acid sequence at one or more positions corresponding to positions 1009, 1010, 1013, 1052, and 1055 of SEQ ID NO: 1.

5. The method of claim 4, wherein herbicide composition is applied to the weeds and to the plant produced by the seed.

6. A method of producing a plant having tolerance to CESA-inhibiting herbicide, the method comprising regenerating a plant from the plant cell of claim 3.

7. A method of producing a progeny plant having tolerance to CESA-inhibiting herbicide, the method comprising: crossing the plant of claim 1 with a second plant to produce a CESA-inhibiting herbicide-tolerant progeny plant, wherein the progeny plant comprises in at least some of its cells the polynucleotide encoding the mutated CESA polypeptide.

8. The plant or plant part of claim 1, wherein the plant or plant part further exhibits a second or third herbicide-tolerant trait.

9. A method for producing a plant product from the plant of claim 1, the method comprising processing the plant or a plant part thereof to obtain the plant product.

10. The method of claim 9, wherein the plant product is fodder, seed meal, oil, or seed-treatment-coated seeds.

* * * * *

SEQUENCE LISTING

```
<160> NUMBER OF SEQ ID NOS: 83

<210> SEQ ID NO 1
<211> LENGTH: 1081
<212> TYPE: PRT
<213> ORGANISM: Arabidopsis thaliana

<400> SEQUENCE: 1

Met Glu Ala Ser Ala Gly Leu Val Ala Gly Ser Tyr Arg Arg Asn Glu
1               5                   10                  15

Leu Val Arg Ile Arg His Glu Ser Asp Gly Gly Thr Lys Pro Leu Lys
            20                  25                  30

Asn Met Asn Gly Gln Ile Cys Gln Ile Cys Gly Asp Asp Val Gly Leu
        35                  40                  45

Ala Glu Thr Gly Asp Val Phe Val Ala Cys Asn Glu Cys Ala Phe Pro
    50                  55                  60

Val Cys Arg Pro Cys Tyr Glu Tyr Glu Arg Lys Asp Gly Thr Gln Cys
65                  70                  75                  80

Cys Pro Gln Cys Lys Thr Arg Phe Arg Arg His Arg Gly Ser Pro Arg
                85                  90                  95

Val Glu Gly Asp Glu Asp Glu Asp Asp Val Asp Asp Ile Glu Asn Glu
            100                 105                 110

Phe Asn Tyr Ala Gln Gly Ala Asn Lys Ala Arg His Gln Arg His Gly
        115                 120                 125

Glu Glu Phe Ser Ser Ser Ser Arg His Glu Ser Gln Pro Ile Pro Leu
    130                 135                 140

Leu Thr His Gly His Thr Val Ser Gly Glu Ile Arg Thr Pro Asp Thr
145                 150                 155                 160

Gln Ser Val Arg Thr Thr Ser Gly Pro Leu Gly Pro Ser Asp Arg Asn
                165                 170                 175

Ala Ile Ser Ser Pro Tyr Ile Asp Pro Arg Gln Pro Val Pro Val Arg
            180                 185                 190

Ile Val Asp Pro Ser Lys Asp Leu Asn Ser Tyr Gly Leu Gly Asn Val
        195                 200                 205

Asp Trp Lys Glu Arg Val Glu Gly Trp Lys Leu Lys Gln Glu Lys Asn
    210                 215                 220

Met Leu Gln Met Thr Gly Lys Tyr His Glu Gly Lys Gly Gly Glu Ile
225                 230                 235                 240

Glu Gly Thr Gly Ser Asn Gly Glu Glu Leu Gln Met Ala Asp Asp Thr
                245                 250                 255

Arg Leu Pro Met Ser Arg Val Val Pro Ile Pro Ser Ser Arg Leu Thr
            260                 265                 270

Pro Tyr Arg Val Val Ile Ile Leu Arg Leu Ile Ile Leu Cys Phe Phe
        275                 280                 285

Leu Gln Tyr Arg Thr Thr His Pro Val Lys Asn Ala Tyr Pro Leu Trp
    290                 295                 300

Leu Thr Ser Val Ile Cys Glu Ile Trp Phe Ala Phe Ser Trp Leu Leu
```

-continued

```
305                 310                 315                 320

Asp Gln Phe Pro Lys Trp Tyr Pro Ile Asn Arg Glu Thr Tyr Leu Asp
                325                 330                 335

Arg Leu Ala Ile Arg Tyr Asp Arg Asp Gly Glu Pro Ser Gln Leu Val
            340                 345                 350

Pro Val Asp Val Phe Val Ser Thr Val Asp Pro Leu Lys Glu Pro Pro
        355                 360                 365

Leu Val Thr Ala Asn Thr Val Leu Ser Ile Leu Ser Val Asp Tyr Pro
    370                 375                 380

Val Asp Lys Val Ala Cys Tyr Val Ser Asp Asp Gly Ser Ala Met Leu
385                 390                 395                 400

Thr Phe Glu Ser Leu Ser Glu Thr Ala Glu Phe Ala Lys Lys Trp Val
                405                 410                 415

Pro Phe Cys Lys Lys Phe Asn Ile Glu Pro Arg Ala Pro Glu Phe Tyr
            420                 425                 430

Phe Ala Gln Lys Ile Asp Tyr Leu Lys Asp Lys Ile Gln Pro Ser Phe
        435                 440                 445

Val Lys Glu Arg Arg Ala Met Lys Arg Glu Tyr Glu Glu Phe Lys Val
    450                 455                 460

Arg Ile Asn Ala Leu Val Ala Lys Ala Gln Lys Ile Pro Glu Glu Gly
465                 470                 475                 480

Trp Thr Met Gln Asp Gly Thr Pro Trp Pro Gly Asn Asn Thr Arg Asp
                485                 490                 495

His Pro Gly Met Ile Gln Val Phe Leu Gly His Ser Gly Gly Leu Asp
            500                 505                 510

Thr Asp Gly Asn Glu Leu Pro Arg Leu Ile Tyr Val Ser Arg Glu Lys
        515                 520                 525

Arg Pro Gly Phe Gln His His Lys Lys Ala Gly Ala Met Asn Ala Leu
    530                 535                 540

Ile Arg Val Ser Ala Val Leu Thr Asn Gly Ala Tyr Leu Leu Asn Val
545                 550                 555                 560

Asp Cys Asp His Tyr Phe Asn Asn Ser Lys Ala Ile Lys Glu Ala Met
                565                 570                 575

Cys Phe Met Met Asp Pro Ala Ile Gly Lys Lys Cys Cys Tyr Val Gln
            580                 585                 590

Phe Pro Gln Arg Phe Asp Gly Ile Asp Leu His Asp Arg Tyr Ala Asn
        595                 600                 605

Arg Asn Ile Val Phe Phe Asp Ile Asn Met Lys Gly Leu Asp Gly Ile
    610                 615                 620

Gln Gly Pro Val Tyr Val Gly Thr Gly Cys Cys Phe Asn Arg Gln Ala
625                 630                 635                 640

Leu Tyr Gly Tyr Asp Pro Val Leu Thr Glu Glu Asp Leu Glu Pro Asn
                645                 650                 655

Ile Ile Val Lys Ser Cys Cys Gly Ser Arg Lys Lys Gly Lys Ser Ser
            660                 665                 670

Lys Lys Tyr Asn Tyr Glu Lys Arg Arg Gly Ile Asn Arg Ser Asp Ser
        675                 680                 685

Asn Ala Pro Leu Phe Asn Met Glu Asp Ile Asp Glu Gly Phe Glu Gly
    690                 695                 700

Tyr Asp Asp Glu Arg Ser Ile Leu Met Ser Gln Arg Ser Val Glu Lys
705                 710                 715                 720

Arg Phe Gly Gln Ser Pro Val Phe Ile Ala Ala Thr Phe Met Glu Gln
                725                 730                 735
```

```
Gly Gly Ile Pro Pro Thr Thr Asn Pro Ala Thr Leu Leu Lys Glu Ala
            740                 745                 750

Ile His Val Ile Ser Cys Gly Tyr Glu Asp Lys Thr Glu Trp Gly Lys
        755                 760                 765

Glu Ile Gly Trp Ile Tyr Gly Ser Val Thr Glu Asp Ile Leu Thr Gly
    770                 775                 780

Phe Lys Met His Ala Arg Gly Trp Ile Ser Ile Tyr Cys Asn Pro Pro
785                 790                 795                 800

Arg Pro Ala Phe Lys Gly Ser Ala Pro Ile Asn Leu Ser Asp Arg Leu
                805                 810                 815

Asn Gln Val Leu Arg Trp Ala Leu Gly Ser Ile Glu Ile Leu Leu Ser
            820                 825                 830

Arg His Cys Pro Ile Trp Tyr Gly Tyr His Gly Arg Leu Arg Leu Leu
        835                 840                 845

Glu Arg Ile Ala Tyr Ile Asn Thr Ile Val Tyr Pro Ile Thr Ser Ile
    850                 855                 860

Pro Leu Ile Ala Tyr Cys Ile Leu Pro Ala Phe Cys Leu Ile Thr Asp
865                 870                 875                 880

Arg Phe Ile Ile Pro Glu Ile Ser Asn Tyr Ala Ser Ile Trp Phe Ile
                885                 890                 895

Leu Leu Phe Ile Ser Ile Ala Val Thr Gly Ile Leu Glu Leu Arg Trp
            900                 905                 910

Ser Gly Val Ser Ile Glu Asp Trp Trp Arg Asn Glu Gln Phe Trp Val
        915                 920                 925

Ile Gly Gly Thr Ser Ala His Leu Phe Ala Val Phe Gln Gly Leu Leu
    930                 935                 940

Lys Val Leu Ala Gly Ile Asp Thr Asn Phe Thr Val Thr Ser Lys Ala
945                 950                 955                 960

Thr Asp Glu Asp Gly Asp Phe Ala Glu Leu Tyr Ile Phe Lys Trp Thr
                965                 970                 975

Ala Leu Leu Ile Pro Pro Thr Thr Val Leu Leu Val Asn Leu Ile Gly
            980                 985                 990

Ile Val Ala Gly Val Ser Tyr Ala  Val Asn Ser Gly Tyr  Gln Ser Trp
        995                 1000                1005

Gly Pro  Leu Phe Gly Lys Leu  Phe Phe Ala Leu Trp  Val Ile Ala
    1010                1015                1020

His Leu  Tyr Pro Phe Leu Lys  Gly Leu Leu Gly Arg  Gln Asn Arg
    1025                1030                1035

Thr Pro  Thr Ile Val Ile Val  Trp Ser Val Leu Leu  Ala Ser Ile
    1040                1045                1050

Phe Ser  Leu Leu Trp Val Arg  Ile Asn Pro Phe Val  Asp Ala Asn
    1055                1060                1065

Pro Asn  Ala Asn Asn Phe Asn  Gly Lys Gly Gly Val  Phe
    1070                1075                1080


<210> SEQ ID NO 2
<211> LENGTH: 1084
<212> TYPE: PRT
<213> ORGANISM: Arabidopsis thaliana

<400> SEQUENCE: 2

Met Asn Thr Gly Gly Arg Leu Ile Ala Gly Ser His Asn Arg Asn Glu
1               5                   10                  15

Phe Val Leu Ile Asn Ala Asp Glu Ser Ala Arg Ile Arg Ser Val Gln
```

```
            20                  25                  30

Glu Leu Ser Gly Gln Thr Cys Gln Ile Cys Gly Asp Glu Ile Glu Leu
        35                  40                  45

Thr Val Ser Ser Glu Leu Phe Val Ala Cys Asn Glu Cys Ala Phe Pro
    50                  55                  60

Val Cys Arg Pro Cys Tyr Glu Tyr Glu Arg Arg Glu Gly Asn Gln Ala
65                  70                  75                  80

Cys Pro Gln Cys Lys Thr Arg Tyr Lys Arg Ile Lys Gly Ser Pro Arg
                85                  90                  95

Val Asp Gly Asp Asp Glu Glu Glu Glu Asp Ile Asp Asp Leu Glu Tyr
            100                 105                 110

Glu Phe Asp His Gly Met Asp Pro Glu His Ala Ala Glu Ala Ala Leu
        115                 120                 125

Ser Ser Arg Leu Asn Thr Gly Arg Gly Gly Leu Asp Ser Ala Pro Pro
    130                 135                 140

Gly Ser Gln Ile Pro Leu Leu Thr Tyr Cys Asp Glu Asp Ala Asp Met
145                 150                 155                 160

Tyr Ser Asp Arg His Ala Leu Ile Val Pro Pro Ser Thr Gly Tyr Gly
                165                 170                 175

Asn Arg Val Tyr Pro Ala Pro Phe Thr Asp Ser Ser Ala Pro Pro Gln
            180                 185                 190

Ala Arg Ser Met Val Pro Gln Lys Asp Ile Ala Glu Tyr Gly Tyr Gly
        195                 200                 205

Ser Val Ala Trp Lys Asp Arg Met Glu Val Trp Lys Arg Arg Gln Gly
    210                 215                 220

Glu Lys Leu Gln Val Ile Lys His Glu Gly Gly Asn Asn Gly Arg Gly
225                 230                 235                 240

Ser Asn Asp Asp Asp Glu Leu Asp Asp Pro Asp Met Pro Met Met Asp
                245                 250                 255

Glu Gly Arg Gln Pro Leu Ser Arg Lys Leu Pro Ile Arg Ser Ser Arg
            260                 265                 270

Ile Asn Pro Tyr Arg Met Leu Ile Leu Cys Arg Leu Ala Ile Leu Gly
        275                 280                 285

Leu Phe Phe His Tyr Arg Ile Leu His Pro Val Asn Asp Ala Tyr Gly
    290                 295                 300

Leu Trp Leu Thr Ser Val Ile Cys Glu Ile Trp Phe Ala Val Ser Trp
305                 310                 315                 320

Ile Leu Asp Gln Phe Pro Lys Trp Tyr Pro Ile Glu Arg Glu Thr Tyr
                325                 330                 335

Leu Asp Arg Leu Ser Leu Arg Tyr Glu Lys Glu Gly Lys Pro Ser Gly
            340                 345                 350

Leu Ala Pro Val Asp Val Phe Val Ser Thr Val Asp Pro Leu Lys Glu
        355                 360                 365

Pro Pro Leu Ile Thr Ala Asn Thr Val Leu Ser Ile Leu Ala Val Asp
    370                 375                 380

Tyr Pro Val Asp Lys Val Ala Cys Tyr Val Ser Asp Asp Gly Ala Ala
385                 390                 395                 400

Met Leu Thr Phe Glu Ala Leu Ser Asp Thr Ala Glu Phe Ala Arg Lys
                405                 410                 415

Trp Val Pro Phe Cys Lys Lys Phe Asn Ile Glu Pro Arg Ala Pro Glu
            420                 425                 430

Trp Tyr Phe Ser Gln Lys Met Asp Tyr Leu Lys Asn Lys Val His Pro
        435                 440                 445
```

-continued

```
Ala Phe Val Arg Glu Arg Arg Ala Met Lys Arg Asp Tyr Glu Glu Phe
    450                 455                 460

Lys Val Lys Ile Asn Ala Leu Val Ala Thr Ala Gln Lys Val Pro Glu
465                 470                 475                 480

Glu Gly Trp Thr Met Gln Asp Gly Thr Pro Trp Pro Gly Asn Asn Val
                485                 490                 495

Arg Asp His Pro Gly Met Ile Gln Val Phe Leu Gly His Ser Gly Val
            500                 505                 510

Arg Asp Thr Asp Gly Asn Glu Leu Pro Arg Leu Val Tyr Val Ser Arg
        515                 520                 525

Glu Lys Arg Pro Gly Phe Asp His His Lys Lys Ala Gly Ala Met Asn
    530                 535                 540

Ser Leu Ile Arg Val Ser Ala Val Leu Ser Asn Ala Pro Tyr Leu Leu
545                 550                 555                 560

Asn Val Asp Cys Asp His Tyr Ile Asn Asn Ser Lys Ala Ile Arg Glu
                565                 570                 575

Ser Met Cys Phe Met Met Asp Pro Gln Ser Gly Lys Lys Val Cys Tyr
            580                 585                 590

Val Gln Phe Pro Gln Arg Phe Asp Gly Ile Asp Arg His Asp Arg Tyr
        595                 600                 605

Ser Asn Arg Asn Val Val Phe Phe Asp Ile Asn Met Lys Gly Leu Asp
    610                 615                 620

Gly Ile Gln Gly Pro Ile Tyr Val Gly Thr Gly Cys Val Phe Arg Arg
625                 630                 635                 640

Gln Ala Leu Tyr Gly Phe Asp Ala Pro Lys Lys Lys Lys Pro Pro Gly
                645                 650                 655

Lys Thr Cys Asn Cys Trp Pro Lys Trp Cys Cys Leu Cys Cys Gly Leu
            660                 665                 670

Arg Lys Lys Ser Lys Thr Lys Ala Lys Asp Lys Lys Thr Asn Thr Lys
        675                 680                 685

Glu Thr Ser Lys Gln Ile His Ala Leu Glu Asn Val Asp Glu Gly Val
    690                 695                 700

Ile Val Pro Val Ser Asn Val Glu Lys Arg Ser Glu Ala Thr Gln Leu
705                 710                 715                 720

Lys Leu Glu Lys Lys Phe Gly Gln Ser Pro Val Phe Val Ala Ser Ala
                725                 730                 735

Val Leu Gln Asn Gly Gly Val Pro Arg Asn Ala Ser Pro Ala Cys Leu
            740                 745                 750

Leu Arg Glu Ala Ile Gln Val Ile Ser Cys Gly Tyr Glu Asp Lys Thr
        755                 760                 765

Glu Trp Gly Lys Glu Ile Gly Trp Ile Tyr Gly Ser Val Thr Glu Asp
    770                 775                 780

Ile Leu Thr Gly Phe Lys Met His Cys His Gly Trp Arg Ser Val Tyr
785                 790                 795                 800

Cys Met Pro Lys Arg Ala Ala Phe Lys Gly Ser Ala Pro Ile Asn Leu
                805                 810                 815

Ser Asp Arg Leu His Gln Val Leu Arg Trp Ala Leu Gly Ser Val Glu
            820                 825                 830

Ile Phe Leu Ser Arg His Cys Pro Ile Trp Tyr Gly Tyr Gly Gly Gly
        835                 840                 845

Leu Lys Trp Leu Glu Arg Phe Ser Tyr Ile Asn Ser Val Val Tyr Pro
    850                 855                 860
```

```
Trp Thr Ser Leu Pro Leu Ile Val Tyr Cys Ser Leu Pro Ala Val Cys
865                 870                 875                 880

Leu Leu Thr Gly Lys Phe Ile Val Pro Glu Ile Ser Asn Tyr Ala Gly
                885                 890                 895

Ile Leu Phe Met Leu Met Phe Ile Ser Ile Ala Val Thr Gly Ile Leu
            900                 905                 910

Glu Met Gln Trp Gly Gly Val Gly Ile Asp Asp Trp Trp Arg Asn Glu
        915                 920                 925

Gln Phe Trp Val Ile Gly Gly Ala Ser Ser His Leu Phe Ala Leu Phe
    930                 935                 940

Gln Gly Leu Leu Lys Val Leu Ala Gly Val Asn Thr Asn Phe Thr Val
945                 950                 955                 960

Thr Ser Lys Ala Ala Asp Asp Gly Ala Phe Ser Glu Leu Tyr Ile Phe
                965                 970                 975

Lys Trp Thr Thr Leu Leu Ile Pro Pro Thr Thr Leu Leu Ile Ile Asn
            980                 985                 990

Ile Ile Gly Val Ile Val Gly Val  Ser Asp Ala Ile Ser  Asn Gly Tyr
        995                 1000                1005

Asp Ser  Trp Gly Pro Leu Phe  Gly Arg Leu Phe Phe  Ala Leu Trp
    1010                1015                1020

Val Ile  Val His Leu Tyr Pro  Phe Leu Lys Gly Met  Leu Gly Lys
    1025                1030                1035

Gln Asp  Lys Met Pro Thr Ile  Ile Val Val Trp Ser  Ile Leu Leu
    1040                1045                1050

Ala Ser  Ile Leu Thr Leu Leu  Trp Val Arg Val Asn  Pro Phe Val
    1055                1060                1065

Ala Lys  Gly Gly Pro Val Leu  Glu Ile Cys Gly Leu  Asn Cys Gly
    1070                1075                1080

Asn


<210> SEQ ID NO 3
<211> LENGTH: 1065
<212> TYPE: PRT
<213> ORGANISM: Arabidopsis thaliana

<400> SEQUENCE: 3

Met Glu Ser Glu Gly Glu Thr Ala Gly Lys Pro Met Lys Asn Ile Val
1               5                   10                  15

Pro Gln Thr Cys Gln Ile Cys Ser Asp Asn Val Gly Lys Thr Val Asp
            20                  25                  30

Gly Asp Arg Phe Val Ala Cys Asp Ile Cys Ser Phe Pro Val Cys Arg
        35                  40                  45

Pro Cys Tyr Glu Tyr Glu Arg Lys Asp Gly Asn Gln Ser Cys Pro Gln
    50                  55                  60

Cys Lys Thr Arg Tyr Lys Arg Leu Lys Gly Ser Pro Ala Ile Pro Gly
65                  70                  75                  80

Asp Lys Asp Glu Asp Gly Leu Ala Asp Glu Gly Thr Val Glu Phe Asn
                85                  90                  95

Tyr Pro Gln Lys Glu Lys Ile Ser Glu Arg Met Leu Gly Trp His Leu
            100                 105                 110

Thr Arg Gly Lys Gly Glu Glu Met Gly Glu Pro Gln Tyr Asp Lys Glu
        115                 120                 125

Val Ser His Asn His Leu Pro Arg Leu Thr Ser Arg Gln Asp Thr Ser
    130                 135                 140
```

```
Gly Glu Phe Ser Ala Ala Ser Pro Glu Arg Leu Ser Val Ser Ser Thr
145                 150                 155                 160

Ile Ala Gly Gly Lys Arg Leu Pro Tyr Ser Ser Asp Val Asn Gln Ser
                165                 170                 175

Pro Asn Arg Arg Ile Val Asp Pro Val Gly Leu Gly Asn Val Ala Trp
            180                 185                 190

Lys Glu Arg Val Asp Gly Trp Lys Met Lys Gln Glu Lys Asn Thr Gly
        195                 200                 205

Pro Val Ser Thr Gln Ala Ala Ser Glu Arg Gly Gly Val Asp Ile Asp
    210                 215                 220

Ala Ser Thr Asp Ile Leu Ala Asp Glu Ala Leu Leu Asn Asp Glu Ala
225                 230                 235                 240

Arg Gln Pro Leu Ser Arg Lys Val Ser Ile Pro Ser Ser Arg Ile Asn
                245                 250                 255

Pro Tyr Arg Met Val Ile Met Leu Arg Leu Val Ile Leu Cys Leu Phe
            260                 265                 270

Leu His Tyr Arg Ile Thr Asn Pro Val Pro Asn Ala Phe Ala Leu Trp
        275                 280                 285

Leu Val Ser Val Ile Cys Glu Ile Trp Phe Ala Leu Ser Trp Ile Leu
    290                 295                 300

Asp Gln Phe Pro Lys Trp Phe Pro Val Asn Arg Glu Thr Tyr Leu Asp
305                 310                 315                 320

Arg Leu Ala Leu Arg Tyr Asp Arg Glu Gly Glu Pro Ser Gln Leu Ala
                325                 330                 335

Ala Val Asp Ile Phe Val Ser Thr Val Asp Pro Leu Lys Glu Pro Pro
            340                 345                 350

Leu Val Thr Ala Asn Thr Val Leu Ser Ile Leu Ala Val Asp Tyr Pro
        355                 360                 365

Val Asp Lys Val Ser Cys Tyr Val Ser Asp Asp Gly Ala Ala Met Leu
    370                 375                 380

Ser Phe Glu Ser Leu Ala Glu Thr Ser Glu Phe Ala Arg Lys Trp Val
385                 390                 395                 400

Pro Phe Cys Lys Lys Tyr Ser Ile Glu Pro Arg Ala Pro Glu Trp Tyr
                405                 410                 415

Phe Ala Ala Lys Ile Asp Tyr Leu Lys Asp Lys Val Gln Thr Ser Phe
            420                 425                 430

Val Lys Asp Arg Arg Ala Met Lys Arg Glu Tyr Glu Glu Phe Lys Ile
        435                 440                 445

Arg Ile Asn Ala Leu Val Ser Lys Ala Leu Lys Cys Pro Glu Glu Gly
    450                 455                 460

Trp Val Met Gln Asp Gly Thr Pro Trp Pro Gly Asn Asn Thr Arg Asp
465                 470                 475                 480

His Pro Gly Met Ile Gln Val Phe Leu Gly Gln Asn Gly Gly Leu Asp
                485                 490                 495

Ala Glu Gly Asn Glu Leu Pro Arg Leu Val Tyr Val Ser Arg Glu Lys
            500                 505                 510

Arg Pro Gly Phe Gln His His Lys Lys Ala Gly Ala Met Asn Ala Leu
        515                 520                 525

Val Arg Val Ser Ala Val Leu Thr Asn Gly Pro Phe Ile Leu Asn Leu
    530                 535                 540

Asp Cys Asp His Tyr Ile Asn Asn Ser Lys Ala Leu Arg Glu Ala Met
545                 550                 555                 560

Cys Phe Leu Met Asp Pro Asn Leu Gly Lys Gln Val Cys Tyr Val Gln
```

```
                565                 570                 575

Phe Pro Gln Arg Phe Asp Gly Ile Asp Lys Asn Asp Arg Tyr Ala Asn
            580                 585                 590

Arg Asn Thr Val Phe Phe Asp Ile Asn Leu Arg Gly Leu Asp Gly Ile
        595                 600                 605

Gln Gly Pro Val Tyr Val Gly Thr Gly Cys Val Phe Asn Arg Thr Ala
    610                 615                 620

Leu Tyr Gly Tyr Glu Pro Pro Ile Lys Val Lys His Lys Lys Pro Ser
625                 630                 635                 640

Leu Leu Ser Lys Leu Cys Gly Gly Ser Arg Lys Lys Asn Ser Lys Ala
                645                 650                 655

Lys Lys Glu Ser Asp Lys Lys Lys Ser Gly Arg His Thr Asp Ser Thr
            660                 665                 670

Val Pro Val Phe Asn Leu Asp Asp Ile Glu Glu Gly Val Glu Gly Ala
        675                 680                 685

Gly Phe Asp Asp Glu Lys Ala Leu Leu Met Ser Gln Met Ser Leu Glu
    690                 695                 700

Lys Arg Phe Gly Gln Ser Ala Val Phe Val Ala Ser Thr Leu Met Glu
705                 710                 715                 720

Asn Gly Gly Val Pro Pro Ser Ala Thr Pro Glu Asn Leu Leu Lys Glu
                725                 730                 735

Ala Ile His Val Ile Ser Cys Gly Tyr Glu Asp Lys Ser Asp Trp Gly
            740                 745                 750

Met Glu Ile Gly Trp Ile Tyr Gly Ser Val Thr Glu Asp Ile Leu Thr
        755                 760                 765

Gly Phe Lys Met His Ala Arg Gly Trp Arg Ser Ile Tyr Cys Met Pro
    770                 775                 780

Lys Leu Pro Ala Phe Lys Gly Ser Ala Pro Ile Asn Leu Ser Asp Arg
785                 790                 795                 800

Leu Asn Gln Val Leu Arg Trp Ala Leu Gly Ser Val Glu Ile Leu Phe
                805                 810                 815

Ser Arg His Cys Pro Ile Trp Tyr Gly Tyr Asn Gly Arg Leu Lys Phe
            820                 825                 830

Leu Glu Arg Phe Ala Tyr Val Asn Thr Thr Ile Tyr Pro Ile Thr Ser
        835                 840                 845

Ile Pro Leu Leu Met Tyr Cys Thr Leu Pro Ala Val Cys Leu Phe Thr
    850                 855                 860

Asn Gln Phe Ile Ile Pro Gln Ile Ser Asn Ile Ala Ser Ile Trp Phe
865                 870                 875                 880

Leu Ser Leu Phe Leu Ser Ile Phe Ala Thr Gly Ile Leu Glu Met Arg
                885                 890                 895

Trp Ser Gly Val Gly Ile Asp Glu Trp Trp Arg Asn Glu Gln Phe Trp
            900                 905                 910

Val Ile Gly Gly Val Ser Ala His Leu Phe Ala Val Phe Gln Gly Ile
        915                 920                 925

Leu Lys Val Leu Ala Gly Ile Asp Thr Asn Phe Thr Val Thr Ser Lys
    930                 935                 940

Ala Ser Asp Glu Asp Gly Asp Phe Ala Glu Leu Tyr Leu Phe Lys Trp
945                 950                 955                 960

Thr Thr Leu Leu Ile Pro Pro Thr Thr Leu Leu Ile Val Asn Leu Val
                965                 970                 975

Gly Val Val Ala Gly Val Ser Tyr Ala Ile Asn Ser Gly Tyr Gln Ser
            980                 985                 990
```

```
Trp Gly Pro Leu Phe Gly Lys Leu  Phe Phe Ala Phe Trp  Val Ile Val
        995                 1000                 1005

His Leu  Tyr Pro Phe Leu Lys  Gly Leu Met Gly Arg  Gln Asn Arg
    1010                 1015                 1020

Thr Pro  Thr Ile Val Val Val  Trp Ser Val Leu Leu  Ala Ser Ile
    1025                 1030                 1035

Phe Ser  Leu Leu Trp Val Arg  Ile Asp Pro Phe Thr  Ser Arg Val
    1040                 1045                 1050

Thr Gly  Pro Asp Ile Leu Glu  Cys Gly Ile Asn Cys
    1055                 1060                 1065


<210> SEQ ID NO 4
<211> LENGTH: 1049
<212> TYPE: PRT
<213> ORGANISM: Arabidopsis thaliana

<400> SEQUENCE: 4

Met Glu Pro Asn Thr Met Ala Ser Phe Asp Asp Glu His Arg His Ser
1               5                   10                  15

Ser Phe Ser Ala Lys Ile Cys Lys Val Cys Gly Asp Glu Val Lys Asp
            20                  25                  30

Asp Asp Asn Gly Gln Thr Phe Val Ala Cys His Val Cys Val Tyr Pro
        35                  40                  45

Val Cys Lys Pro Cys Tyr Glu Tyr Glu Arg Ser Asn Gly Asn Lys Cys
    50                  55                  60

Cys Pro Gln Cys Asn Thr Leu Tyr Lys Arg His Lys Gly Ser Pro Lys
65                  70                  75                  80

Ile Ala Gly Asp Glu Glu Asn Asn Gly Pro Asp Asp Ser Asp Asp Glu
                85                  90                  95

Leu Asn Ile Lys Tyr Arg Gln Asp Gly Ser Ser Ile His Gln Asn Phe
            100                 105                 110

Ala Tyr Gly Ser Glu Asn Gly Asp Tyr Asn Ser Lys Gln Gln Trp Arg
        115                 120                 125

Pro Asn Gly Arg Ala Phe Ser Ser Thr Gly Ser Val Leu Gly Lys Asp
    130                 135                 140

Phe Glu Ala Glu Arg Asp Gly Tyr Thr Asp Ala Glu Trp Lys Glu Arg
145                 150                 155                 160

Val Asp Lys Trp Lys Ala Arg Gln Glu Lys Arg Gly Leu Val Thr Lys
                165                 170                 175

Gly Glu Gln Thr Asn Glu Asp Lys Glu Asp Asp Glu Glu Glu Tyr Leu
            180                 185                 190

Asp Ala Glu Ala Arg Gln Pro Leu Trp Arg Lys Val Pro Ile Ser Ser
        195                 200                 205

Ser Lys Ile Ser Pro Tyr Arg Ile Val Ile Val Leu Arg Leu Val Ile
    210                 215                 220

Leu Val Phe Phe Phe Arg Phe Arg Ile Leu Thr Pro Ala Lys Asp Ala
225                 230                 235                 240

Tyr Pro Leu Trp Leu Ile Ser Val Ile Cys Glu Ile Trp Phe Ala Leu
                245                 250                 255

Ser Trp Ile Leu Asp Gln Phe Pro Lys Trp Phe Pro Ile Asn Arg Glu
            260                 265                 270

Thr Tyr Leu Asp Arg Leu Ser Met Arg Phe Glu Arg Asp Gly Glu Lys
        275                 280                 285

Asn Lys Leu Ala Pro Val Asp Val Phe Val Ser Thr Val Asp Pro Leu
```

```
    290                 295                 300

Lys Glu Pro Pro Ile Ile Thr Ala Asn Thr Ile Leu Ser Ile Leu Ala
305                 310                 315                 320

Val Asp Tyr Pro Val Asn Lys Val Ser Cys Tyr Val Ser Asp Asp Gly
                325                 330                 335

Ala Ser Met Leu Leu Phe Asp Thr Leu Ser Glu Thr Ser Glu Phe Ala
            340                 345                 350

Arg Arg Trp Val Pro Phe Cys Lys Lys Tyr Asn Val Glu Pro Arg Ala
        355                 360                 365

Pro Glu Phe Tyr Phe Ser Glu Lys Ile Asp Tyr Leu Lys Asp Lys Val
    370                 375                 380

Gln Thr Thr Phe Val Lys Asp Arg Arg Ala Met Lys Arg Glu Tyr Glu
385                 390                 395                 400

Glu Phe Lys Val Arg Ile Asn Ala Leu Val Ala Lys Ala Gln Lys Lys
                405                 410                 415

Pro Glu Glu Gly Trp Val Met Gln Asp Gly Thr Pro Trp Pro Gly Asn
            420                 425                 430

Asn Thr Arg Asp His Pro Gly Met Ile Gln Val Tyr Leu Gly Lys Glu
        435                 440                 445

Gly Ala Phe Asp Ile Asp Gly Asn Glu Leu Pro Arg Leu Val Tyr Val
    450                 455                 460

Ser Arg Glu Lys Arg Pro Gly Tyr Ala His His Lys Lys Ala Gly Ala
465                 470                 475                 480

Met Asn Ala Met Val Arg Val Ser Ala Val Leu Thr Asn Ala Pro Phe
                485                 490                 495

Met Leu Asn Leu Asp Cys Asp His Tyr Ile Asn Asn Ser Lys Ala Ile
            500                 505                 510

Arg Glu Ser Met Cys Phe Leu Met Asp Pro Gln Leu Gly Lys Lys Leu
        515                 520                 525

Cys Tyr Val Gln Phe Pro Gln Arg Phe Asp Gly Ile Asp Leu Asn Asp
    530                 535                 540

Arg Tyr Ala Asn Arg Asn Ile Val Phe Phe Asp Ile Asn Met Arg Gly
545                 550                 555                 560

Leu Asp Gly Ile Gln Gly Pro Val Tyr Val Gly Thr Gly Cys Val Phe
                565                 570                 575

Asn Arg Pro Ala Leu Tyr Gly Tyr Glu Pro Pro Val Ser Glu Lys Arg
            580                 585                 590

Lys Lys Met Thr Cys Asp Cys Trp Pro Ser Trp Ile Cys Cys Cys Cys
        595                 600                 605

Gly Gly Gly Asn Arg Asn His Lys Ser Asp Ser Ser Lys Lys Lys Ser
    610                 615                 620

Gly Ile Lys Ser Leu Phe Ser Lys Leu Lys Lys Lys Thr Lys Lys Lys
625                 630                 635                 640

Ser Asp Asp Lys Thr Met Ser Ser Tyr Ser Arg Lys Arg Ser Ser Thr
                645                 650                 655

Glu Ala Ile Phe Asp Leu Glu Asp Ile Glu Glu Gly Leu Glu Gly Tyr
            660                 665                 670

Asp Glu Leu Glu Lys Ser Ser Leu Met Ser Gln Lys Asn Phe Glu Lys
        675                 680                 685

Arg Phe Gly Met Ser Pro Val Phe Ile Ala Ser Thr Leu Met Glu Asn
    690                 695                 700

Gly Gly Leu Pro Glu Ala Thr Asn Thr Ser Ser Leu Ile Lys Glu Ala
705                 710                 715                 720
```

```
Ile His Val Ile Ser Cys Gly Tyr Glu Glu Lys Thr Glu Trp Gly Lys
                725                 730                 735

Glu Ile Gly Trp Ile Tyr Gly Ser Val Thr Glu Asp Ile Leu Thr Gly
            740                 745                 750

Phe Arg Met His Cys Arg Gly Trp Lys Ser Val Tyr Cys Met Pro Lys
        755                 760                 765

Arg Pro Ala Phe Lys Gly Ser Ala Pro Ile Asn Leu Ser Asp Arg Leu
    770                 775                 780

His Gln Val Leu Arg Trp Ala Leu Gly Ser Val Glu Ile Phe Phe Ser
785                 790                 795                 800

Arg His Cys Pro Leu Trp Tyr Ala Trp Gly Gly Lys Leu Lys Ile Leu
                805                 810                 815

Glu Arg Leu Ala Tyr Ile Asn Thr Ile Val Tyr Pro Phe Thr Ser Ile
            820                 825                 830

Pro Leu Leu Ala Tyr Cys Thr Ile Pro Ala Val Cys Leu Leu Thr Gly
        835                 840                 845

Lys Phe Ile Ile Pro Thr Ile Asn Asn Phe Ala Ser Ile Trp Phe Leu
    850                 855                 860

Ala Leu Phe Leu Ser Ile Ile Ala Thr Ala Ile Leu Glu Leu Arg Trp
865                 870                 875                 880

Ser Gly Val Ser Ile Asn Asp Leu Trp Arg Asn Glu Gln Phe Trp Val
                885                 890                 895

Ile Gly Gly Val Ser Ala His Leu Phe Ala Val Phe Gln Gly Leu Leu
            900                 905                 910

Lys Val Leu Phe Gly Val Asp Thr Asn Phe Thr Val Thr Ser Lys Gly
        915                 920                 925

Ala Ser Asp Glu Ala Asp Glu Phe Gly Asp Leu Tyr Leu Phe Lys Trp
    930                 935                 940

Thr Thr Leu Leu Ile Pro Pro Thr Thr Leu Ile Ile Leu Asn Met Val
945                 950                 955                 960

Gly Val Val Ala Gly Val Ser Asp Ala Ile Asn Asn Gly Tyr Gly Ser
                965                 970                 975

Trp Gly Pro Leu Phe Gly Lys Leu Phe Phe Ala Phe Trp Val Ile Val
            980                 985                 990

His Leu Tyr Pro Phe Leu Lys Gly  Leu Met Gly Arg Gln  Asn Arg Thr
        995                 1000                1005

Pro Thr  Ile Val Val Leu Trp  Ser Ile Leu Leu Ala  Ser Ile Phe
    1010                1015                1020

Ser Leu  Val Trp Val Arg Ile  Asp Pro Phe Leu Pro  Lys Gln Thr
    1025                1030                1035

Gly Pro  Leu Leu Lys Gln Cys  Gly Val Asp Cys
    1040                1045
```

<210> SEQ ID NO 5
<211> LENGTH: 1069
<212> TYPE: PRT
<213> ORGANISM: Arabidopsis thaliana

<400> SEQUENCE: 5

```
Met Asn Thr Gly Gly Arg Leu Ile Ala Gly Ser His Asn Arg Asn Glu
1               5                   10                  15

Phe Val Leu Ile Asn Ala Asp Glu Ser Ala Arg Ile Arg Ser Val Glu
            20                  25                  30

Glu Leu Ser Gly Gln Thr Cys Gln Ile Cys Gly Asp Glu Ile Glu Leu
```

```
        35                  40                  45

Ser Val Asp Gly Glu Ser Phe Val Ala Cys Asn Glu Cys Ala Phe Pro
    50                  55                  60

Val Cys Arg Pro Cys Tyr Glu Tyr Glu Arg Arg Glu Gly Asn Gln Ser
65                  70                  75                  80

Cys Pro Gln Cys Lys Thr Arg Tyr Lys Arg Ile Lys Gly Ser Pro Arg
                85                  90                  95

Val Glu Gly Asp Glu Glu Asp Asp Gly Ile Asp Asp Leu Asp Phe Glu
            100                 105                 110

Phe Asp Tyr Ser Arg Ser Gly Leu Glu Ser Glu Thr Phe Ser Arg Arg
        115                 120                 125

Asn Ser Glu Phe Asp Leu Ala Ser Ala Pro Pro Gly Ser Gln Ile Pro
    130                 135                 140

Leu Leu Thr Tyr Gly Glu Glu Asp Val Glu Ile Ser Ser Asp Ser His
145                 150                 155                 160

Ala Leu Ile Val Ser Pro Ser Pro Gly His Ile His Arg Val His Gln
                165                 170                 175

Pro His Phe Pro Asp Pro Ala Ala His Pro Arg Pro Met Val Pro Gln
            180                 185                 190

Lys Asp Leu Ala Val Tyr Gly Tyr Gly Ser Val Ala Trp Lys Asp Arg
        195                 200                 205

Met Glu Glu Trp Lys Arg Lys Gln Asn Glu Lys Tyr Gln Val Val Lys
    210                 215                 220

His Asp Gly Asp Ser Ser Leu Gly Asp Gly Asp Asp Ala Asp Ile Pro
225                 230                 235                 240

Met Met Asp Glu Gly Arg Gln Pro Leu Ser Arg Lys Val Pro Ile Lys
                245                 250                 255

Ser Ser Lys Ile Asn Pro Tyr Arg Met Leu Ile Val Leu Arg Leu Val
            260                 265                 270

Ile Leu Gly Leu Phe Phe His Tyr Arg Ile Leu His Pro Val Asn Asp
        275                 280                 285

Ala Tyr Ala Leu Trp Leu Ile Ser Val Ile Cys Glu Ile Trp Phe Ala
    290                 295                 300

Val Ser Trp Val Leu Asp Gln Phe Pro Lys Trp Tyr Pro Ile Glu Arg
305                 310                 315                 320

Glu Thr Tyr Leu Asp Arg Leu Ser Leu Arg Tyr Glu Lys Glu Gly Lys
                325                 330                 335

Pro Ser Glu Leu Ala Gly Val Asp Val Phe Val Ser Thr Val Asp Pro
            340                 345                 350

Met Lys Glu Pro Pro Leu Ile Thr Ala Asn Thr Val Leu Ser Ile Leu
        355                 360                 365

Ala Val Asp Tyr Pro Val Asp Arg Val Ala Cys Tyr Val Ser Asp Asp
    370                 375                 380

Gly Ala Ala Met Leu Thr Phe Glu Ala Leu Ser Glu Thr Ala Glu Phe
385                 390                 395                 400

Ala Arg Lys Trp Val Pro Phe Cys Lys Lys Tyr Thr Ile Glu Pro Arg
                405                 410                 415

Ala Pro Glu Trp Tyr Phe Cys His Lys Met Asp Tyr Leu Lys Asn Lys
            420                 425                 430

Val His Pro Ala Phe Val Arg Glu Arg Arg Ala Met Lys Arg Asp Tyr
        435                 440                 445

Glu Glu Phe Lys Val Lys Ile Asn Ala Leu Val Ala Thr Ala Gln Lys
    450                 455                 460
```

```
Val Pro Glu Glu Gly Trp Thr Met Gln Asp Gly Thr Pro Trp Pro Gly
465                 470                 475                 480

Asn Asn Val Arg Asp His Pro Gly Met Ile Gln Val Phe Leu Gly Asn
                485                 490                 495

Asn Gly Val Arg Asp Val Glu Asn Asn Glu Leu Pro Arg Leu Val Tyr
            500                 505                 510

Val Ser Arg Glu Lys Arg Pro Gly Phe Asp His His Lys Lys Ala Gly
        515                 520                 525

Ala Met Asn Ser Leu Ile Arg Val Ser Gly Val Leu Ser Asn Ala Pro
    530                 535                 540

Tyr Leu Leu Asn Val Asp Cys Asp His Tyr Ile Asn Asn Ser Lys Ala
545                 550                 555                 560

Leu Arg Glu Ala Met Cys Phe Met Met Asp Pro Gln Ser Gly Lys Lys
                565                 570                 575

Ile Cys Tyr Val Gln Phe Pro Gln Arg Phe Asp Gly Ile Asp Lys Ser
            580                 585                 590

Asp Arg Tyr Ser Asn Arg Asn Val Val Phe Phe Asp Ile Asn Met Lys
        595                 600                 605

Gly Leu Asp Gly Leu Gln Gly Pro Ile Tyr Val Gly Thr Gly Cys Val
    610                 615                 620

Phe Arg Arg Gln Ala Leu Tyr Gly Phe Asp Ala Pro Lys Lys Lys Lys
625                 630                 635                 640

Thr Lys Arg Met Thr Cys Asn Cys Trp Pro Lys Trp Cys Leu Phe Cys
                645                 650                 655

Cys Gly Leu Arg Lys Asn Arg Lys Ser Lys Thr Thr Asp Lys Lys Lys
            660                 665                 670

Lys Asn Arg Glu Ala Ser Lys Gln Ile His Ala Leu Glu Asn Ile Glu
        675                 680                 685

Glu Gly Thr Lys Gly Thr Asn Asp Ala Ala Lys Ser Pro Glu Ala Ala
    690                 695                 700

Gln Leu Lys Leu Glu Lys Lys Phe Gly Gln Ser Pro Val Phe Val Ala
705                 710                 715                 720

Ser Ala Gly Met Glu Asn Gly Gly Leu Ala Arg Asn Ala Ser Pro Ala
                725                 730                 735

Ser Leu Leu Arg Glu Ala Ile Gln Val Ile Ser Cys Gly Tyr Glu Asp
            740                 745                 750

Lys Thr Glu Trp Gly Lys Glu Ile Gly Trp Ile Tyr Gly Ser Val Thr
        755                 760                 765

Glu Asp Ile Leu Thr Gly Phe Lys Met His Ser His Gly Trp Arg Ser
    770                 775                 780

Val Tyr Cys Thr Pro Lys Ile Pro Ala Phe Lys Gly Ser Ala Pro Ile
785                 790                 795                 800

Asn Leu Ser Asp Arg Leu His Gln Val Leu Arg Trp Ala Leu Gly Ser
                805                 810                 815

Val Glu Ile Phe Leu Ser Arg His Cys Pro Ile Trp Tyr Gly Tyr Gly
            820                 825                 830

Gly Gly Leu Lys Trp Leu Glu Arg Leu Ser Tyr Ile Asn Ser Val Val
        835                 840                 845

Tyr Pro Trp Thr Ser Ile Pro Leu Leu Val Tyr Cys Ser Leu Pro Ala
    850                 855                 860

Ile Cys Leu Leu Thr Gly Lys Phe Ile Val Pro Glu Ile Ser Asn Tyr
865                 870                 875                 880
```

```
Ala Ser Ile Leu Phe Met Ala Leu Phe Gly Ser Ile Ala Val Thr Gly
                885                 890                 895

Ile Leu Glu Met Gln Trp Gly Lys Val Gly Ile Asp Asp Trp Trp Arg
            900                 905                 910

Asn Glu Gln Phe Trp Val Ile Gly Gly Val Ser Ala His Leu Phe Ala
        915                 920                 925

Leu Phe Gln Gly Leu Leu Lys Val Leu Ala Gly Val Glu Thr Asn Phe
    930                 935                 940

Thr Val Thr Ser Lys Ala Ala Asp Asp Gly Glu Phe Ser Glu Leu Tyr
945                 950                 955                 960

Ile Phe Lys Trp Thr Ser Leu Leu Ile Pro Pro Thr Thr Leu Leu Ile
                965                 970                 975

Ile Asn Val Ile Gly Val Ile Val Gly Ile Ser Asp Ala Ile Ser Asn
            980                 985                 990

Gly Tyr Asp Ser Trp Gly Pro Leu  Phe Gly Arg Leu Phe  Phe Ala Phe
        995                 1000                1005

Trp Val  Ile Leu His Leu Tyr  Pro Phe Leu Lys Gly  Leu Leu Gly
    1010                 1015                1020

Lys Gln  Asp Arg Met Pro Thr  Ile Ile Leu Val Trp  Ser Ile Leu
    1025                 1030                1035

Leu Ala  Ser Ile Leu Thr Leu  Leu Trp Val Arg Val  Asn Pro Phe
    1040                 1045                1050

Val Ala  Lys Gly Gly Pro Ile  Leu Glu Ile Cys Gly  Leu Asp Cys
    1055                 1060                1065

Leu


<210> SEQ ID NO 6
<211> LENGTH: 1084
<212> TYPE: PRT
<213> ORGANISM: Arabidopsis thaliana

<400> SEQUENCE: 6

Met Asn Thr Gly Gly Arg Leu Ile Ala Gly Ser His Asn Arg Asn Glu
1               5                   10                  15

Phe Val Leu Ile Asn Ala Asp Glu Asn Ala Arg Ile Arg Ser Val Gln
            20                  25                  30

Glu Leu Ser Gly Gln Thr Cys Gln Ile Cys Arg Asp Glu Ile Glu Leu
        35                  40                  45

Thr Val Asp Gly Glu Pro Phe Val Ala Cys Asn Glu Cys Ala Phe Pro
    50                  55                  60

Val Cys Arg Pro Cys Tyr Glu Tyr Glu Arg Arg Glu Gly Asn Gln Ala
65                  70                  75                  80

Cys Pro Gln Cys Lys Thr Arg Phe Lys Arg Leu Lys Gly Ser Pro Arg
                85                  90                  95

Val Glu Gly Asp Glu Glu Glu Asp Asp Ile Asp Asp Leu Asp Asn Glu
            100                 105                 110

Phe Glu Tyr Gly Asn Asn Gly Ile Gly Phe Asp Gln Val Ser Glu Gly
        115                 120                 125

Met Ser Ile Ser Arg Arg Asn Ser Gly Phe Pro Gln Ser Asp Leu Asp
    130                 135                 140

Ser Ala Pro Pro Gly Ser Gln Ile Pro Leu Leu Thr Tyr Gly Asp Glu
145                 150                 155                 160

Asp Val Glu Ile Ser Ser Asp Arg His Ala Leu Ile Val Pro Pro Ser
                165                 170                 175
```

-continued

```
Leu Gly Gly His Gly Asn Arg Val His Pro Val Ser Leu Ser Asp Pro
            180                 185                 190

Thr Val Ala Ala His Pro Arg Pro Met Val Pro Gln Lys Asp Leu Ala
        195                 200                 205

Val Tyr Gly Tyr Gly Ser Val Ala Trp Lys Asp Arg Met Glu Glu Trp
    210                 215                 220

Lys Arg Lys Gln Asn Glu Lys Leu Gln Val Val Arg His Glu Gly Asp
225                 230                 235                 240

Pro Asp Phe Glu Asp Gly Asp Asp Ala Asp Phe Pro Met Met Asp Glu
                245                 250                 255

Gly Arg Gln Pro Leu Ser Arg Lys Ile Pro Ile Lys Ser Ser Lys Ile
            260                 265                 270

Asn Pro Tyr Arg Met Leu Ile Val Leu Arg Leu Val Ile Leu Gly Leu
        275                 280                 285

Phe Phe His Tyr Arg Ile Leu His Pro Val Lys Asp Ala Tyr Ala Leu
    290                 295                 300

Trp Leu Ile Ser Val Ile Cys Glu Ile Trp Phe Ala Val Ser Trp Val
305                 310                 315                 320

Leu Asp Gln Phe Pro Lys Trp Tyr Pro Ile Glu Arg Glu Thr Tyr Leu
                325                 330                 335

Asp Arg Leu Ser Leu Arg Tyr Glu Lys Glu Gly Lys Pro Ser Gly Leu
            340                 345                 350

Ser Pro Val Asp Val Phe Val Ser Thr Val Asp Pro Leu Lys Glu Pro
        355                 360                 365

Pro Leu Ile Thr Ala Asn Thr Val Leu Ser Ile Leu Ala Val Asp Tyr
    370                 375                 380

Pro Val Asp Lys Val Ala Cys Tyr Val Ser Asp Asp Gly Ala Ala Met
385                 390                 395                 400

Leu Thr Phe Glu Ala Leu Ser Glu Thr Ala Glu Phe Ala Arg Lys Trp
                405                 410                 415

Val Pro Phe Cys Lys Lys Tyr Cys Ile Glu Pro Arg Ala Pro Glu Trp
            420                 425                 430

Tyr Phe Cys His Lys Met Asp Tyr Leu Lys Asn Lys Val His Pro Ala
        435                 440                 445

Phe Val Arg Glu Arg Arg Ala Met Lys Arg Asp Tyr Glu Glu Phe Lys
    450                 455                 460

Val Lys Ile Asn Ala Leu Val Ala Thr Ala Gln Lys Val Pro Glu Asp
465                 470                 475                 480

Gly Trp Thr Met Gln Asp Gly Thr Pro Trp Pro Gly Asn Ser Val Arg
                485                 490                 495

Asp His Pro Gly Met Ile Gln Val Phe Leu Gly Ser Asp Gly Val Arg
            500                 505                 510

Asp Val Glu Asn Asn Glu Leu Pro Arg Leu Val Tyr Val Ser Arg Glu
        515                 520                 525

Lys Arg Pro Gly Phe Asp His His Lys Lys Ala Gly Ala Met Asn Ser
    530                 535                 540

Leu Ile Arg Val Ser Gly Val Leu Ser Asn Ala Pro Tyr Leu Leu Asn
545                 550                 555                 560

Val Asp Cys Asp His Tyr Ile Asn Asn Ser Lys Ala Leu Arg Glu Ala
                565                 570                 575

Met Cys Phe Met Met Asp Pro Gln Ser Gly Lys Lys Ile Cys Tyr Val
            580                 585                 590

Gln Phe Pro Gln Arg Phe Asp Gly Ile Asp Arg His Asp Arg Tyr Ser
```

-continued

```
        595                 600                 605

Asn Arg Asn Val Val Phe Phe Asp Ile Asn Met Lys Gly Leu Asp Gly
    610                 615                 620

Leu Gln Gly Pro Ile Tyr Val Gly Thr Gly Cys Val Phe Arg Arg Gln
625                 630                 635                 640

Ala Leu Tyr Gly Phe Asp Ala Pro Lys Lys Lys Lys Gly Pro Arg Lys
                645                 650                 655

Thr Cys Asn Cys Trp Pro Lys Trp Cys Leu Leu Cys Phe Gly Ser Arg
            660                 665                 670

Lys Asn Arg Lys Ala Lys Thr Val Ala Ala Asp Lys Lys Lys Lys Asn
        675                 680                 685

Arg Glu Ala Ser Lys Gln Ile His Ala Leu Glu Asn Ile Glu Glu Gly
    690                 695                 700

Arg Val Thr Lys Gly Ser Asn Val Glu Gln Ser Thr Glu Ala Met Gln
705                 710                 715                 720

Met Lys Leu Glu Lys Lys Phe Gly Gln Ser Pro Val Phe Val Ala Ser
                725                 730                 735

Ala Arg Met Glu Asn Gly Gly Met Ala Arg Asn Ala Ser Pro Ala Cys
            740                 745                 750

Leu Leu Lys Glu Ala Ile Gln Val Ile Ser Cys Gly Tyr Glu Asp Lys
        755                 760                 765

Thr Glu Trp Gly Lys Glu Ile Gly Trp Ile Tyr Gly Ser Val Thr Glu
    770                 775                 780

Asp Ile Leu Thr Gly Phe Lys Met His Ser His Gly Trp Arg Ser Val
785                 790                 795                 800

Tyr Cys Thr Pro Lys Leu Ala Ala Phe Lys Gly Ser Ala Pro Ile Asn
                805                 810                 815

Leu Ser Asp Arg Leu His Gln Val Leu Arg Trp Ala Leu Gly Ser Val
            820                 825                 830

Glu Ile Phe Leu Ser Arg His Cys Pro Ile Trp Tyr Gly Tyr Gly Gly
        835                 840                 845

Gly Leu Lys Trp Leu Glu Arg Leu Ser Tyr Ile Asn Ser Val Val Tyr
    850                 855                 860

Pro Trp Thr Ser Leu Pro Leu Ile Val Tyr Cys Ser Leu Pro Ala Ile
865                 870                 875                 880

Cys Leu Leu Thr Gly Lys Phe Ile Val Pro Glu Ile Ser Asn Tyr Ala
                885                 890                 895

Ser Ile Leu Phe Met Ala Leu Phe Ser Ser Ile Ala Ile Thr Gly Ile
            900                 905                 910

Leu Glu Met Gln Trp Gly Lys Val Gly Ile Asp Asp Trp Trp Arg Asn
        915                 920                 925

Glu Gln Phe Trp Val Ile Gly Gly Val Ser Ala His Leu Phe Ala Leu
    930                 935                 940

Phe Gln Gly Leu Leu Lys Val Leu Ala Gly Val Asp Thr Asn Phe Thr
945                 950                 955                 960

Val Thr Ser Lys Ala Ala Asp Asp Gly Glu Phe Ser Asp Leu Tyr Leu
                965                 970                 975

Phe Lys Trp Thr Ser Leu Leu Ile Pro Pro Met Thr Leu Leu Ile Ile
            980                 985                 990

Asn Val Ile Gly Val Ile Val Gly  Val Ser Asp Ala Ile  Ser Asn Gly
        995                 1000                1005

Tyr Asp  Ser Trp Gly Pro Leu  Phe Gly Arg Leu Phe  Phe Ala Leu
    1010                1015                1020
```

```
Trp Val  Ile Ile His Leu Tyr  Pro Phe Leu Lys Gly  Leu Leu Gly
    1025                 1030                 1035

Lys Gln  Asp Arg Met Pro Thr  Ile Ile Val Val Trp  Ser Ile Leu
    1040                 1045                 1050

Leu Ala  Ser Ile Leu Thr Leu  Leu Trp Val Arg Val  Asn Pro Phe
    1055                 1060                 1065

Val Ala  Lys Gly Gly Pro Ile  Leu Glu Ile Cys Gly  Leu Asp Cys
    1070                 1075                 1080

Leu


<210> SEQ ID NO 7
<211> LENGTH: 1026
<212> TYPE: PRT
<213> ORGANISM: Arabidopsis thaliana

<400> SEQUENCE: 7

Met Glu Ala Ser Ala Gly Leu Val Ala Gly Ser His Asn Arg Asn Glu
1               5                   10                  15

Leu Val Val Ile His Asn His Glu Glu Pro Lys Pro Leu Lys Asn Leu
            20                  25                  30

Asp Gly Gln Phe Cys Glu Ile Cys Gly Asp Gln Ile Gly Leu Thr Val
        35                  40                  45

Glu Gly Asp Leu Phe Val Ala Cys Asn Glu Cys Gly Phe Pro Ala Cys
    50                  55                  60

Arg Pro Cys Tyr Glu Tyr Glu Arg Arg Glu Gly Thr Gln Asn Cys Pro
65                  70                  75                  80

Gln Cys Lys Thr Arg Tyr Lys Arg Leu Arg Gly Ser Pro Arg Val Glu
                85                  90                  95

Gly Asp Glu Asp Glu Glu Asp Ile Asp Asp Ile Glu Tyr Glu Phe Asn
            100                 105                 110

Ile Glu His Glu Gln Asp Lys His Lys His Ser Ala Glu Ala Met Leu
        115                 120                 125

Tyr Gly Lys Met Ser Tyr Gly Arg Gly Pro Glu Asp Asp Glu Asn Gly
    130                 135                 140

Arg Phe Pro Pro Val Ile Ala Gly Gly His Ser Gly Glu Phe Pro Val
145                 150                 155                 160

Gly Gly Gly Tyr Gly Asn Gly Glu His Gly Leu His Lys Arg Val His
                165                 170                 175

Pro Tyr Pro Ser Ser Glu Ala Gly Ser Glu Gly Gly Trp Arg Glu Arg
            180                 185                 190

Met Asp Asp Trp Lys Leu Gln His Gly Asn Leu Gly Pro Glu Pro Asp
        195                 200                 205

Asp Asp Pro Glu Met Gly Leu Ile Asp Glu Ala Arg Gln Pro Leu Ser
    210                 215                 220

Arg Lys Val Pro Ile Ala Ser Ser Lys Ile Asn Pro Tyr Arg Met Val
225                 230                 235                 240

Ile Val Ala Arg Leu Val Ile Leu Ala Val Phe Leu Arg Tyr Arg Leu
                245                 250                 255

Leu Asn Pro Val His Asp Ala Leu Gly Leu Trp Leu Thr Ser Val Ile
            260                 265                 270

Cys Glu Ile Trp Phe Ala Val Ser Trp Ile Leu Asp Gln Phe Pro Lys
        275                 280                 285

Trp Phe Pro Ile Glu Arg Glu Thr Tyr Leu Asp Arg Leu Ser Leu Arg
    290                 295                 300
```

-continued

Tyr Glu Arg Glu Gly Glu Pro Asn Met Leu Ala Pro Val Asp Val Phe
305 310 315 320

Val Ser Thr Val Asp Pro Leu Lys Glu Pro Pro Leu Val Thr Ser Asn
325 330 335

Thr Val Leu Ser Ile Leu Ala Met Asp Tyr Pro Val Glu Lys Ile Ser
340 345 350

Cys Tyr Val Ser Asp Asp Gly Ala Ser Met Leu Thr Phe Glu Ser Leu
355 360 365

Ser Glu Thr Ala Glu Phe Ala Arg Lys Trp Val Pro Phe Cys Lys Lys
370 375 380

Phe Ser Ile Glu Pro Arg Ala Pro Glu Met Tyr Phe Thr Leu Lys Val
385 390 395 400

Asp Tyr Leu Gln Asp Lys Val His Pro Thr Phe Val Lys Glu Arg Arg
405 410 415

Ala Met Lys Arg Glu Tyr Glu Glu Phe Lys Val Arg Ile Asn Ala Gln
420 425 430

Val Ala Lys Ala Ser Lys Val Pro Leu Glu Gly Trp Ile Met Gln Asp
435 440 445

Gly Thr Pro Trp Pro Gly Asn Asn Thr Lys Asp His Pro Gly Met Ile
450 455 460

Gln Val Phe Leu Gly His Ser Gly Gly Phe Asp Val Glu Gly His Glu
465 470 475 480

Leu Pro Arg Leu Val Tyr Val Ser Arg Glu Lys Arg Pro Gly Phe Gln
485 490 495

His His Lys Lys Ala Gly Ala Met Asn Ala Leu Val Arg Val Ala Gly
500 505 510

Val Leu Thr Asn Ala Pro Phe Met Leu Asn Leu Asp Cys Asp His Tyr
515 520 525

Val Asn Asn Ser Lys Ala Val Arg Glu Ala Met Cys Phe Leu Met Asp
530 535 540

Pro Gln Ile Gly Lys Lys Val Cys Tyr Val Gln Phe Pro Gln Arg Phe
545 550 555 560

Asp Gly Ile Asp Thr Asn Asp Arg Tyr Ala Asn Arg Asn Thr Val Phe
565 570 575

Phe Asp Ile Asn Met Lys Gly Leu Asp Gly Ile Gln Gly Pro Val Tyr
580 585 590

Val Gly Thr Gly Cys Val Phe Lys Arg Gln Ala Leu Tyr Gly Tyr Glu
595 600 605

Pro Pro Lys Gly Pro Lys Arg Pro Lys Met Ile Ser Cys Gly Cys Cys
610 615 620

Pro Cys Phe Gly Arg Arg Arg Lys Asn Lys Lys Phe Ser Lys Asn Asp
625 630 635 640

Met Asn Gly Asp Val Ala Ala Leu Gly Gly Ala Glu Gly Asp Lys Glu
645 650 655

His Leu Met Ser Glu Met Asn Phe Glu Lys Thr Phe Gly Gln Ser Ser
660 665 670

Ile Phe Val Thr Ser Thr Leu Met Glu Glu Gly Gly Val Pro Pro Ser
675 680 685

Ser Ser Pro Ala Val Leu Leu Lys Glu Ala Ile His Val Ile Ser Cys
690 695 700

Gly Tyr Glu Asp Lys Thr Glu Trp Gly Thr Glu Leu Gly Trp Ile Tyr
705 710 715 720

-continued

```
Gly Ser Ile Thr Glu Asp Ile Leu Thr Gly Phe Lys Met His Cys Arg
                725                 730                 735

Gly Trp Arg Ser Ile Tyr Cys Met Pro Lys Arg Pro Ala Phe Lys Gly
            740                 745                 750

Ser Ala Pro Ile Asn Leu Ser Asp Arg Leu Asn Gln Val Leu Arg Trp
        755                 760                 765

Ala Leu Gly Ser Val Glu Ile Phe Phe Ser Arg His Ser Pro Leu Trp
    770                 775                 780

Tyr Gly Tyr Lys Gly Gly Lys Leu Lys Trp Leu Glu Arg Phe Ala Tyr
785                 790                 795                 800

Ala Asn Thr Thr Ile Tyr Pro Phe Thr Ser Ile Pro Leu Leu Ala Tyr
                805                 810                 815

Cys Ile Leu Pro Ala Ile Cys Leu Leu Thr Asp Lys Phe Ile Met Pro
            820                 825                 830

Pro Ile Ser Thr Phe Ala Ser Leu Phe Phe Ile Ser Leu Phe Met Ser
        835                 840                 845

Ile Ile Val Thr Gly Ile Leu Glu Leu Arg Trp Ser Gly Val Ser Ile
    850                 855                 860

Glu Glu Trp Trp Arg Asn Glu Gln Phe Trp Val Ile Gly Gly Ile Ser
865                 870                 875                 880

Ala His Leu Phe Ala Val Val Gln Gly Leu Leu Lys Ile Leu Ala Gly
                885                 890                 895

Ile Asp Thr Asn Phe Thr Val Thr Ser Lys Ala Thr Asp Asp Asp Asp
            900                 905                 910

Phe Gly Glu Leu Tyr Ala Phe Lys Trp Thr Thr Leu Leu Ile Pro Pro
        915                 920                 925

Thr Thr Val Leu Ile Ile Asn Ile Val Gly Val Val Ala Gly Ile Ser
    930                 935                 940

Asp Ala Ile Asn Asn Gly Tyr Gln Ser Trp Gly Pro Leu Phe Gly Lys
945                 950                 955                 960

Leu Phe Phe Ser Phe Trp Val Ile Val His Leu Tyr Pro Phe Leu Lys
                965                 970                 975

Gly Leu Met Gly Arg Gln Asn Arg Thr Pro Thr Ile Val Val Ile Trp
            980                 985                 990

Ser Val Leu Leu Ala Ser Ile Phe  Ser Leu Leu Trp Val  Arg Ile Asp
        995                 1000                 1005

Pro Phe  Val Leu Lys Thr Lys  Gly Pro Asp Thr Ser  Lys Cys Gly
    1010                 1015                 1020

Ile Asn  Cys
    1025


<210> SEQ ID NO 8
<211> LENGTH: 985
<212> TYPE: PRT
<213> ORGANISM: Arabidopsis thaliana

<400> SEQUENCE: 8

Met Met Glu Ser Arg Ser Pro Ile Cys Asn Thr Cys Gly Glu Glu Ile
1               5                   10                  15

Gly Val Lys Ser Asn Gly Glu Phe Phe Val Ala Cys His Glu Cys Ser
            20                  25                  30

Phe Pro Ile Cys Lys Ala Cys Leu Glu Tyr Glu Phe Lys Glu Gly Arg
        35                  40                  45

Arg Ile Cys Leu Arg Cys Gly Asn Pro Tyr Asp Glu Asn Val Phe Asp
    50                  55                  60
```

-continued

```
Asp Val Glu Thr Lys Thr Ser Lys Thr Gln Ser Ile Val Pro Thr Gln
65                  70                  75                  80

Thr Asn Asn Thr Ser Gln Asp Ser Gly Ile His Ala Arg His Ile Ser
                85                  90                  95

Thr Val Ser Thr Ile Asp Ser Glu Leu Asn Asp Glu Tyr Gly Asn Pro
            100                 105                 110

Ile Trp Lys Asn Arg Val Glu Ser Trp Lys Asp Lys Lys Asp Lys Lys
        115                 120                 125

Ser Lys Lys Lys Lys Lys Asp Pro Lys Ala Thr Lys Ala Glu Gln His
    130                 135                 140

Glu Ala Gln Ile Pro Thr Gln Gln His Met Glu Asp Thr Pro Pro Asn
145                 150                 155                 160

Thr Glu Ser Gly Ala Thr Asp Val Leu Ser Val Val Ile Pro Ile Pro
                165                 170                 175

Arg Thr Lys Ile Thr Ser Tyr Arg Ile Val Ile Ile Met Arg Leu Ile
            180                 185                 190

Ile Leu Ala Leu Phe Phe Asn Tyr Arg Ile Thr His Pro Val Asp Ser
        195                 200                 205

Ala Tyr Gly Leu Trp Leu Thr Ser Val Ile Cys Glu Ile Trp Phe Ala
    210                 215                 220

Val Ser Trp Val Leu Asp Gln Phe Pro Lys Trp Ser Pro Ile Asn Arg
225                 230                 235                 240

Glu Thr Tyr Ile Asp Arg Leu Ser Ala Arg Phe Glu Arg Glu Gly Glu
                245                 250                 255

Gln Ser Gln Leu Ala Ala Val Asp Phe Phe Val Ser Thr Val Asp Pro
            260                 265                 270

Leu Lys Glu Pro Pro Leu Ile Thr Ala Asn Thr Val Leu Ser Ile Leu
        275                 280                 285

Ala Leu Asp Tyr Pro Val Asp Lys Val Ser Cys Tyr Val Ser Asp Asp
    290                 295                 300

Gly Ala Ala Met Leu Ser Phe Glu Ser Leu Val Glu Thr Ala Asp Phe
305                 310                 315                 320

Ala Arg Lys Trp Val Pro Phe Cys Lys Lys Tyr Ser Ile Glu Pro Arg
                325                 330                 335

Ala Pro Glu Phe Tyr Phe Ser Leu Lys Ile Asp Tyr Leu Arg Asp Lys
            340                 345                 350

Val Gln Pro Ser Phe Val Lys Glu Arg Arg Ala Met Lys Arg Asp Tyr
        355                 360                 365

Glu Glu Phe Lys Ile Arg Met Asn Ala Leu Val Ala Lys Ala Gln Lys
    370                 375                 380

Thr Pro Glu Glu Gly Trp Thr Met Gln Asp Gly Thr Ser Trp Pro Gly
385                 390                 395                 400

Asn Asn Thr Arg Asp His Pro Gly Met Ile Gln Val Phe Leu Gly Tyr
                405                 410                 415

Ser Gly Ala Arg Asp Ile Glu Gly Asn Glu Leu Pro Arg Leu Val Tyr
            420                 425                 430

Val Ser Arg Glu Lys Arg Pro Gly Tyr Gln His His Lys Lys Ala Gly
        435                 440                 445

Ala Glu Asn Ala Leu Val Arg Val Ser Ala Val Leu Thr Asn Ala Pro
    450                 455                 460

Phe Ile Leu Asn Leu Asp Cys Asp His Tyr Val Asn Asn Ser Lys Ala
465                 470                 475                 480
```

-continued

```
Val Arg Glu Ala Met Cys Phe Leu Met Asp Pro Val Val Gly Gln Asp
                485                 490                 495

Val Cys Phe Val Gln Phe Pro Gln Arg Phe Asp Gly Ile Asp Lys Ser
            500                 505                 510

Asp Arg Tyr Ala Asn Arg Asn Ile Val Phe Phe Asp Val Asn Met Arg
        515                 520                 525

Gly Leu Asp Gly Ile Gln Gly Pro Val Tyr Val Gly Thr Gly Thr Val
    530                 535                 540

Phe Arg Arg Gln Ala Leu Tyr Gly Tyr Ser Pro Pro Ser Lys Pro Arg
545                 550                 555                 560

Ile Leu Pro Gln Ser Ser Ser Ser Ser Cys Cys Cys Leu Thr Lys Lys
                565                 570                 575

Lys Gln Pro Gln Asp Pro Ser Glu Ile Tyr Lys Asp Ala Lys Arg Glu
            580                 585                 590

Glu Leu Asp Ala Ala Ile Phe Asn Leu Gly Asp Leu Asp Asn Tyr Asp
        595                 600                 605

Glu Tyr Asp Arg Ser Met Leu Ile Ser Gln Thr Ser Phe Glu Lys Thr
    610                 615                 620

Phe Gly Leu Ser Thr Val Phe Ile Glu Ser Thr Leu Met Glu Asn Gly
625                 630                 635                 640

Gly Val Pro Asp Ser Val Asn Pro Ser Thr Leu Ile Lys Glu Ala Ile
                645                 650                 655

His Val Ile Ser Cys Gly Tyr Glu Glu Lys Thr Glu Trp Gly Lys Glu
            660                 665                 670

Ile Gly Trp Ile Tyr Gly Ser Ile Thr Glu Asp Ile Leu Thr Gly Phe
        675                 680                 685

Lys Met His Cys Arg Gly Trp Arg Ser Ile Tyr Cys Met Pro Leu Arg
    690                 695                 700

Pro Ala Phe Lys Gly Ser Ala Pro Ile Asn Leu Ser Asp Arg Leu His
705                 710                 715                 720

Gln Val Leu Arg Trp Ala Leu Gly Ser Val Glu Ile Phe Leu Ser Arg
                725                 730                 735

His Cys Pro Leu Trp Tyr Gly Cys Ser Gly Gly Arg Leu Lys Leu Leu
            740                 745                 750

Gln Arg Leu Ala Tyr Ile Asn Thr Ile Val Tyr Pro Phe Thr Ser Leu
        755                 760                 765

Pro Leu Val Ala Tyr Cys Thr Leu Pro Ala Ile Cys Leu Leu Thr Gly
    770                 775                 780

Lys Phe Ile Ile Pro Thr Leu Ser Asn Leu Ala Ser Met Leu Phe Leu
785                 790                 795                 800

Gly Leu Phe Ile Ser Ile Ile Leu Thr Ser Val Leu Glu Leu Arg Trp
                805                 810                 815

Ser Gly Val Ser Ile Glu Asp Leu Trp Arg Asn Glu Gln Phe Trp Val
            820                 825                 830

Ile Gly Gly Val Ser Ala His Leu Phe Ala Val Phe Gln Gly Phe Leu
        835                 840                 845

Lys Met Leu Ala Gly Leu Asp Thr Asn Phe Thr Val Thr Ser Lys Thr
    850                 855                 860

Ala Asp Asp Leu Glu Phe Gly Glu Leu Tyr Ile Val Lys Trp Thr Thr
865                 870                 875                 880

Leu Leu Ile Pro Pro Thr Ser Leu Leu Ile Ile Asn Leu Val Gly Val
                885                 890                 895

Val Ala Gly Phe Ser Asp Ala Leu Asn Lys Gly Tyr Glu Ala Trp Gly
```

```
            900                 905                 910

Pro Leu Phe Gly Lys Val Phe Phe Ala Phe Trp Val Ile Leu His Leu
        915                 920                 925

Tyr Pro Phe Leu Lys Gly Leu Met Gly Arg Gln Asn Arg Thr Pro Thr
    930                 935                 940

Ile Val Ile Leu Trp Ser Ile Leu Leu Ala Ser Val Phe Ser Leu Val
945                 950                 955                 960

Trp Val Arg Ile Asn Pro Phe Val Ser Lys Thr Asp Thr Thr Ser Leu
                965                 970                 975

Ser Leu Asn Cys Leu Leu Ile Asp Cys
            980                 985


<210> SEQ ID NO 9
<211> LENGTH: 1088
<212> TYPE: PRT
<213> ORGANISM: Arabidopsis thaliana

<400> SEQUENCE: 9

Met Asn Thr Gly Gly Arg Leu Ile Ala Gly Ser His Asn Arg Asn Glu
1               5                   10                  15

Phe Val Leu Ile Asn Ala Asp Asp Thr Ala Arg Ile Arg Ser Ala Glu
            20                  25                  30

Glu Leu Ser Gly Gln Thr Cys Lys Ile Cys Arg Asp Glu Ile Glu Leu
        35                  40                  45

Thr Asp Asn Gly Glu Pro Phe Ile Ala Cys Asn Glu Cys Ala Phe Pro
    50                  55                  60

Thr Cys Arg Pro Cys Tyr Glu Tyr Glu Arg Arg Glu Gly Asn Gln Ala
65                  70                  75                  80

Cys Pro Gln Cys Gly Thr Arg Tyr Lys Arg Ile Lys Gly Ser Pro Arg
                85                  90                  95

Val Glu Gly Asp Glu Glu Asp Asp Asp Ile Asp Asp Leu Glu His Glu
            100                 105                 110

Phe Tyr Gly Met Asp Pro Glu His Val Thr Glu Ala Ala Leu Tyr Tyr
        115                 120                 125

Met Arg Leu Asn Thr Gly Arg Gly Thr Asp Glu Val Ser His Leu Tyr
    130                 135                 140

Ser Ala Ser Pro Gly Ser Glu Val Pro Leu Leu Thr Tyr Cys Asp Glu
145                 150                 155                 160

Asp Ser Asp Met Tyr Ser Asp Arg His Ala Leu Ile Val Pro Pro Ser
                165                 170                 175

Thr Gly Leu Gly Asn Arg Val His His Val Pro Phe Thr Asp Ser Phe
            180                 185                 190

Ala Ser Ile His Thr Arg Pro Met Val Pro Gln Lys Asp Leu Thr Val
        195                 200                 205

Tyr Gly Tyr Gly Ser Val Ala Trp Lys Asp Arg Met Glu Val Trp Lys
    210                 215                 220

Lys Gln Gln Ile Glu Lys Leu Gln Val Val Lys Asn Glu Arg Val Asn
225                 230                 235                 240

Asp Gly Asp Gly Asp Gly Phe Ile Val Asp Glu Leu Asp Asp Pro Gly
                245                 250                 255

Leu Pro Met Met Asp Glu Gly Arg Gln Pro Leu Ser Arg Lys Leu Pro
            260                 265                 270

Ile Arg Ser Ser Arg Ile Asn Pro Tyr Arg Met Leu Ile Phe Cys Arg
        275                 280                 285
```

```
Leu Ala Ile Leu Gly Leu Phe Phe His Tyr Arg Ile Leu His Pro Val
    290                 295                 300

Asn Asp Ala Phe Gly Leu Trp Leu Thr Ser Val Ile Cys Glu Ile Trp
305                 310                 315                 320

Phe Ala Val Ser Trp Ile Leu Asp Gln Phe Pro Lys Trp Tyr Pro Ile
                325                 330                 335

Glu Arg Glu Thr Tyr Leu Asp Arg Leu Ser Leu Arg Tyr Glu Lys Glu
            340                 345                 350

Gly Lys Pro Ser Glu Leu Ala Pro Val Asp Val Phe Val Ser Thr Val
        355                 360                 365

Asp Pro Leu Lys Glu Pro Pro Leu Ile Thr Ala Asn Thr Val Leu Ser
    370                 375                 380

Ile Leu Ala Val Asp Tyr Pro Val Glu Lys Val Ala Cys Tyr Val Ser
385                 390                 395                 400

Asp Asp Gly Ala Ala Met Leu Thr Phe Glu Ala Leu Ser Tyr Thr Ala
                405                 410                 415

Glu Phe Ala Arg Lys Trp Val Pro Phe Cys Lys Lys Phe Ser Ile Glu
            420                 425                 430

Pro Arg Ala Pro Glu Trp Tyr Phe Ser Gln Lys Met Asp Tyr Leu Lys
        435                 440                 445

His Lys Val Asp Pro Ala Phe Val Met Glu Arg Arg Ala Met Lys Arg
    450                 455                 460

Asp Tyr Glu Glu Phe Lys Val Lys Ile Asn Ala Leu Val Ser Val Ser
465                 470                 475                 480

Gln Lys Val Pro Glu Asp Gly Trp Thr Met Gln Asp Gly Thr Pro Trp
                485                 490                 495

Pro Gly Asn Asn Val Arg Asp His Pro Gly Met Ile Gln Val Phe Leu
            500                 505                 510

Gly His Ser Gly Val Cys Asp Met Asp Gly Asn Glu Leu Pro Arg Leu
        515                 520                 525

Val Tyr Val Ser Arg Glu Lys Arg Pro Gly Phe Asp His His Lys Lys
    530                 535                 540

Ala Gly Ala Met Asn Ser Leu Ile Arg Val Ser Ala Val Leu Ser Asn
545                 550                 555                 560

Ala Pro Tyr Leu Leu Asn Val Asp Cys Asp His Tyr Ile Asn Asn Ser
                565                 570                 575

Lys Ala Ile Arg Glu Ala Met Cys Phe Met Met Asp Pro Gln Ser Gly
            580                 585                 590

Lys Lys Ile Cys Tyr Val Gln Phe Pro Gln Arg Phe Asp Gly Ile Asp
        595                 600                 605

Arg His Asp Arg Tyr Ser Asn Arg Asn Val Val Phe Phe Asp Ile Asn
    610                 615                 620

Met Lys Gly Leu Asp Gly Ile Gln Gly Pro Ile Tyr Val Gly Thr Gly
625                 630                 635                 640

Cys Val Phe Arg Arg Gln Ala Leu Tyr Gly Phe Asp Ala Pro Lys Lys
                645                 650                 655

Lys Gln Pro Pro Gly Arg Thr Cys Asn Cys Trp Pro Lys Trp Cys Cys
            660                 665                 670

Leu Cys Cys Gly Met Arg Lys Lys Lys Thr Gly Lys Val Lys Asp Asn
        675                 680                 685

Gln Arg Lys Lys Pro Lys Glu Thr Ser Lys Gln Ile His Ala Leu Glu
    690                 695                 700

His Ile Glu Glu Gly Leu Gln Val Thr Asn Ala Glu Asn Asn Ser Glu
```

-continued

```
705                 710                 715                 720

Thr Ala Gln Leu Lys Leu Glu Lys Lys Phe Gly Gln Ser Pro Val Leu
                725                 730                 735

Val Ala Ser Thr Leu Leu Leu Asn Gly Gly Val Pro Ser Asn Val Asn
            740                 745                 750

Pro Ala Ser Leu Leu Arg Glu Ser Ile Gln Val Ile Ser Cys Gly Tyr
        755                 760                 765

Glu Glu Lys Thr Glu Trp Gly Lys Glu Ile Gly Trp Ile Tyr Gly Ser
    770                 775                 780

Val Thr Glu Asp Ile Leu Thr Gly Phe Lys Met His Cys His Gly Trp
785                 790                 795                 800

Arg Ser Val Tyr Cys Met Pro Lys Arg Ala Ala Phe Lys Gly Ser Ala
                805                 810                 815

Pro Ile Asn Leu Ser Asp Arg Leu His Gln Val Leu Arg Trp Ala Leu
            820                 825                 830

Gly Ser Val Glu Ile Phe Leu Ser Arg His Cys Pro Ile Trp Tyr Gly
        835                 840                 845

Tyr Gly Gly Gly Leu Lys Trp Leu Glu Arg Phe Ser Tyr Ile Asn Ser
    850                 855                 860

Val Val Tyr Pro Trp Thr Ser Leu Pro Leu Leu Val Tyr Cys Ser Leu
865                 870                 875                 880

Pro Ala Ile Cys Leu Leu Thr Gly Lys Phe Ile Val Pro Glu Ile Ser
                885                 890                 895

Asn Tyr Ala Gly Ile Leu Phe Leu Leu Met Phe Met Ser Ile Ala Val
            900                 905                 910

Thr Gly Ile Leu Glu Met Gln Trp Gly Lys Ile Gly Ile Asp Asp Trp
        915                 920                 925

Trp Arg Asn Glu Gln Phe Trp Val Ile Gly Gly Val Ser Ser His Leu
    930                 935                 940

Phe Ala Leu Phe Gln Gly Leu Leu Lys Val Leu Ala Gly Val Ser Thr
945                 950                 955                 960

Asn Phe Thr Val Thr Ser Lys Ala Ala Asp Asp Gly Glu Phe Ser Glu
                965                 970                 975

Leu Tyr Ile Phe Lys Trp Thr Ser Leu Leu Ile Pro Pro Thr Thr Leu
            980                 985                 990

Leu Ile Ile Asn Ile Val Gly Val  Ile Val Gly Val Ser  Asp Ala Ile
        995                 1000                1005

Asn Asn  Gly Tyr Asp Ser Trp  Gly Pro Leu Phe Gly  Arg Leu Phe
    1010                1015                1020

Phe Ala  Leu Trp Val Ile Val  His Leu Tyr Pro Phe  Leu Lys Gly
    1025                1030                1035

Leu Leu  Gly Lys Gln Asp Arg  Val Pro Thr Ile Ile  Leu Val Trp
    1040                1045                1050

Ser Ile  Leu Leu Ala Ser Ile  Leu Thr Leu Leu Trp  Val Arg Val
    1055                1060                1065

Asn Pro  Phe Val Ser Lys Asp  Gly Pro Val Leu Glu  Ile Cys Gly
    1070                1075                1080

Leu Asp  Cys Leu Lys
    1085
```

<210> SEQ ID NO 10
<211> LENGTH: 1065
<212> TYPE: PRT
<213> ORGANISM: Arabidopsis thaliana

<400> SEQUENCE: 10

Met Val Ala Gly Ser Tyr Arg Arg Tyr Glu Phe Val Arg Asn Arg Asp
1               5                   10                  15

Asp Ser Asp Asp Gly Leu Lys Pro Leu Lys Asp Leu Asn Gly Gln Ile
            20                  25                  30

Cys Gln Ile Cys Gly Asp Asp Val Gly Leu Thr Lys Thr Gly Asn Val
        35                  40                  45

Phe Val Ala Cys Asn Glu Cys Gly Phe Pro Leu Cys Gln Ser Cys Tyr
    50                  55                  60

Glu Tyr Glu Arg Lys Asp Gly Ser Gln Cys Cys Pro Gln Cys Lys Ala
65                  70                  75                  80

Arg Phe Arg Arg His Asn Gly Ser Pro Arg Val Glu Val Asp Glu Lys
                85                  90                  95

Glu Asp Asp Val Asn Asp Ile Glu Asn Glu Phe Asp Tyr Thr Gln Gly
            100                 105                 110

Asn Asn Lys Ala Arg Leu Pro His Arg Ala Glu Glu Phe Ser Ser Ser
        115                 120                 125

Ser Arg His Glu Glu Ser Leu Pro Val Ser Leu Leu Thr His Gly His
    130                 135                 140

Pro Val Ser Gly Glu Ile Pro Thr Pro Asp Arg Asn Ala Thr Leu Ser
145                 150                 155                 160

Pro Cys Ile Asp Pro Gln Leu Pro Gly Ile Tyr Gln Leu Leu Leu Leu
                165                 170                 175

Pro Val Arg Ile Leu Asp Pro Ser Lys Asp Leu Asn Ser Tyr Gly Leu
            180                 185                 190

Val Asn Val Asp Trp Lys Lys Arg Ile Gln Gly Trp Lys Leu Lys Gln
        195                 200                 205

Asp Lys Asn Met Ile His Met Thr Gly Lys Tyr His Glu Gly Lys Gly
    210                 215                 220

Gly Glu Phe Glu Gly Thr Gly Ser Asn Gly Asp Glu Leu Gln Met Val
225                 230                 235                 240

Asp Asp Ala Arg Leu Pro Met Ser Arg Val Val His Phe Pro Ser Ala
                245                 250                 255

Arg Met Thr Pro Tyr Arg Ile Val Ile Val Leu Arg Leu Ile Ile Leu
            260                 265                 270

Gly Val Phe Leu His Tyr Arg Thr Thr His Pro Val Lys Asp Ala Tyr
        275                 280                 285

Ala Leu Trp Leu Thr Ser Val Ile Cys Glu Ile Trp Phe Ala Phe Ser
    290                 295                 300

Trp Leu Leu Asp Gln Phe Pro Lys Trp Tyr Pro Ile Asn Arg Glu Thr
305                 310                 315                 320

Phe Leu Asp Arg Leu Ala Leu Arg Tyr Asp Arg Asp Gly Glu Pro Ser
                325                 330                 335

Gln Leu Ala Pro Val Asp Val Phe Val Ser Thr Val Asp Pro Met Lys
            340                 345                 350

Glu Pro Pro Leu Val Thr Ala Asn Thr Val Leu Ser Ile Leu Ala Val
        355                 360                 365

Asp Tyr Pro Val Asp Lys Val Ala Cys Tyr Val Ser Asp Asp Gly Ser
    370                 375                 380

Ala Met Leu Thr Phe Glu Ala Leu Ser Glu Thr Ala Glu Phe Ser Lys
385                 390                 395                 400

Lys Trp Val Pro Phe Cys Lys Lys Phe Asn Ile Glu Pro Arg Ala Pro

-continued

```
                405                 410                 415

Glu Phe Tyr Phe Ser Gln Lys Ile Asp Tyr Leu Lys Asp Lys Ile Gln
            420                 425                 430

Pro Ser Phe Val Lys Glu Arg Arg Ala Met Lys Arg Glu Tyr Glu Glu
        435                 440                 445

Phe Lys Val Arg Ile Asn Ile Leu Val Ala Lys Ala Gln Lys Ile Pro
    450                 455                 460

Glu Asp Gly Trp Thr Met Glu Asp Gly Thr Ser Trp Pro Gly Asn Asn
465                 470                 475                 480

Pro Arg Asp His Pro Gly Met Ile Gln Val Phe Leu Gly His Ser Gly
                485                 490                 495

Gly Leu Asp Thr Asp Gly Asn Glu Leu Pro Arg Leu Ile Tyr Val Ser
            500                 505                 510

Arg Glu Lys Arg Pro Gly Phe Gln His His Lys Lys Ala Gly Ala Met
        515                 520                 525

Asn Ala Leu Ile Arg Val Ser Ala Val Leu Thr Asn Gly Ala Tyr Leu
    530                 535                 540

Leu Asn Val Asp Cys Asp His Tyr Phe Asn Asn Ser Lys Ala Ile Lys
545                 550                 555                 560

Glu Ala Met Cys Phe Met Met Asp Pro Ala Ile Gly Lys Lys Cys Cys
                565                 570                 575

Tyr Val Gln Phe Pro Gln Arg Phe Asp Gly Ile Asp Leu His Asp Arg
            580                 585                 590

Tyr Ala Asn Arg Asn Thr Val Phe Phe Asp Ile Asn Leu Lys Gly Leu
        595                 600                 605

Asp Gly Ile Gln Gly Pro Val Tyr Val Gly Thr Gly Cys Cys Phe Asn
    610                 615                 620

Arg Gln Ala Leu Tyr Gly Tyr Asp Pro Val Leu Thr Glu Glu Asp Leu
625                 630                 635                 640

Glu Pro Asn Ile Ile Val Lys Ser Cys Phe Gly Ser Arg Lys Lys Gly
                645                 650                 655

Lys Ser Arg Lys Ile Pro Asn Tyr Glu Asp Asn Arg Ser Ile Lys Arg
            660                 665                 670

Ser Asp Ser Asn Val Pro Leu Phe Asn Met Glu Asp Ile Asp Glu Asp
        675                 680                 685

Val Glu Gly Tyr Glu Asp Glu Met Ser Leu Leu Val Ser Gln Lys Arg
    690                 695                 700

Leu Glu Lys Arg Phe Gly Gln Ser Pro Val Phe Ile Ala Ala Thr Phe
705                 710                 715                 720

Met Glu Gln Gly Gly Leu Pro Ser Thr Thr Asn Pro Leu Thr Leu Leu
                725                 730                 735

Lys Glu Ala Ile His Val Ile Ser Cys Gly Tyr Glu Ala Lys Thr Asp
            740                 745                 750

Trp Gly Lys Glu Ile Gly Trp Ile Tyr Gly Ser Val Thr Glu Asp Ile
        755                 760                 765

Leu Thr Gly Phe Lys Met His Ala Arg Gly Trp Ile Ser Ile Tyr Cys
    770                 775                 780

Val Pro Ser Arg Pro Ala Phe Lys Gly Ser Ala Pro Ile Asn Leu Ser
785                 790                 795                 800

Asp Arg Leu Asn Gln Val Leu Arg Trp Ala Leu Gly Ser Ile Glu Ile
                805                 810                 815

Leu Leu Ser Arg His Cys Pro Ile Trp Tyr Gly Tyr Asn Gly Arg Leu
            820                 825                 830
```

```
Lys Leu Leu Glu Arg Ile Ala Tyr Ile Asn Thr Ile Val Tyr Pro Ile
        835                 840                 845

Thr Ser Ile Pro Leu Leu Ala Tyr Cys Met Leu Pro Ala Phe Cys Leu
    850                 855                 860

Ile Thr Asn Thr Phe Ile Ile Pro Glu Ile Ser Asn Leu Ala Ser Leu
865                 870                 875                 880

Cys Phe Met Leu Leu Phe Ala Ser Ile Tyr Ala Ser Ala Ile Leu Glu
                885                 890                 895

Leu Lys Trp Ser Asp Val Ala Leu Glu Asp Trp Trp Arg Asn Glu Gln
            900                 905                 910

Phe Trp Val Ile Gly Gly Thr Ser Ala His Leu Phe Ala Val Phe Gln
        915                 920                 925

Gly Leu Leu Lys Val Phe Ala Gly Ile Asp Thr Asn Phe Thr Val Thr
    930                 935                 940

Ser Lys Ala Ser Asp Glu Asp Gly Asp Phe Ala Glu Leu Tyr Val Phe
945                 950                 955                 960

Lys Trp Thr Ser Leu Leu Ile Pro Pro Thr Thr Ile Leu Leu Val Asn
                965                 970                 975

Leu Val Gly Ile Val Ala Gly Val Ser Tyr Ala Ile Asn Ser Gly Tyr
            980                 985                 990

Gln Ser Trp Gly Pro Leu Met Gly  Lys Leu Leu Phe Ala  Phe Trp Val
        995                 1000                 1005

Val Ala  His Leu Tyr Pro Phe  Leu Lys Gly Leu Leu  Gly Arg Gln
    1010                 1015                 1020

Asn Arg  Thr Pro Thr Ile Val  Ile Val Trp Ser Ala  Leu Leu Ala
    1025                 1030                 1035

Ser Ile  Phe Ser Leu Leu Trp  Val Arg Ile Asn Pro  Phe Val Ser
    1040                 1045                 1050

Thr Thr  Gly Val Met Ser Asn  Ser Phe Met Gly Glu
    1055                 1060                 1065
```

<210> SEQ ID NO 11
<211> LENGTH: 1074
<212> TYPE: PRT
<213> ORGANISM: Zea mays

<400> SEQUENCE: 11

```
Met Ala Ala Asn Lys Gly Met Val Ala Gly Ser His Asn Arg Asn Glu
1               5                   10                  15

Phe Val Met Ile Arg His Asp Gly Asp Ala Pro Val Pro Ala Lys Pro
            20                  25                  30

Thr Lys Ser Ala Asn Gly Gln Val Cys Gln Ile Cys Gly Asp Thr Val
        35                  40                  45

Gly Val Ser Ala Thr Gly Asp Val Phe Val Ala Cys Asn Glu Cys Ala
    50                  55                  60

Phe Pro Val Cys Arg Pro Cys Tyr Glu Tyr Glu Arg Lys Glu Gly Asn
65                  70                  75                  80

Gln Cys Cys Pro Gln Cys Lys Thr Arg Tyr Lys Arg Gln Lys Gly Ser
                85                  90                  95

Pro Arg Val His Gly Asp Asp Glu Glu Glu Asp Val Asp Asp Leu Asp
            100                 105                 110

Asn Glu Phe Asn Tyr Lys Gln Gly Asn Gly Lys Gly Pro Glu Trp Gln
        115                 120                 125

Leu Gln Gly Asp Asp Ala Asp Leu Ser Ser Ser Ala Arg His Asp Pro
```

```
    130                 135                 140

His His Arg Ile Pro Arg Leu Thr Ser Gly Gln Gln Ile Ser Gly Glu
145                 150                 155                 160

Ile Pro Asp Ala Ser Pro Asp Arg His Ser Ile Arg Ser Pro Thr Ser
                165                 170                 175

Ser Tyr Val Asp Pro Ser Val Pro Val Pro Val Arg Ile Val Asp Pro
            180                 185                 190

Ser Lys Asp Leu Asn Ser Tyr Gly Leu Asn Ser Val Asp Trp Lys Glu
        195                 200                 205

Arg Val Glu Ser Trp Arg Val Lys Gln Asp Lys Asn Met Leu Gln Val
    210                 215                 220

Thr Asn Lys Tyr Pro Glu Ala Arg Gly Asp Met Glu Gly Thr Gly Ser
225                 230                 235                 240

Asn Gly Glu Asp Met Gln Met Val Asp Asp Ala Arg Leu Pro Leu Ser
                245                 250                 255

Arg Ile Val Pro Ile Ser Ser Asn Gln Leu Asn Leu Tyr Arg Ile Val
            260                 265                 270

Ile Ile Leu Arg Leu Ile Ile Leu Cys Phe Phe Phe Gln Tyr Arg Ile
        275                 280                 285

Ser His Pro Val Arg Asn Ala Tyr Gly Leu Trp Leu Val Ser Val Ile
    290                 295                 300

Cys Glu Val Trp Phe Ala Leu Ser Trp Leu Leu Asp Gln Phe Pro Lys
305                 310                 315                 320

Trp Tyr Pro Ile Asn Arg Glu Thr Tyr Leu Asp Arg Leu Ala Leu Arg
                325                 330                 335

Tyr Asp Arg Glu Gly Glu Pro Ser Gln Leu Ala Pro Ile Asp Val Phe
            340                 345                 350

Val Ser Thr Val Asp Pro Leu Lys Glu Pro Pro Leu Ile Thr Ala Asn
        355                 360                 365

Thr Val Leu Ser Ile Leu Ala Val Asp Tyr Pro Val Asp Lys Val Ser
    370                 375                 380

Cys Tyr Val Ser Asp Asp Gly Ser Ala Met Leu Thr Phe Glu Ser Leu
385                 390                 395                 400

Ser Glu Thr Ala Glu Phe Ala Arg Lys Trp Val Pro Phe Cys Lys Lys
                405                 410                 415

His Asn Ile Glu Pro Arg Ala Pro Glu Phe Tyr Phe Ala Gln Lys Ile
            420                 425                 430

Asp Tyr Leu Lys Asp Lys Ile Gln Pro Ser Phe Val Lys Glu Arg Arg
        435                 440                 445

Ala Met Lys Arg Glu Tyr Glu Glu Phe Lys Ile Arg Ile Asn Ala Leu
    450                 455                 460

Val Ala Lys Ala Gln Lys Val Pro Glu Glu Gly Trp Thr Met Ala Asp
465                 470                 475                 480

Gly Thr Ala Trp Pro Gly Asn Asn Pro Arg Asp His Pro Gly Met Ile
                485                 490                 495

Gln Val Phe Leu Gly His Ser Gly Gly Leu Asp Thr Asp Gly Asn Glu
            500                 505                 510

Leu Pro Arg Leu Val Tyr Val Ser Arg Glu Lys Arg Pro Gly Phe Gln
        515                 520                 525

His His Lys Lys Ala Gly Ala Met Asn Ala Leu Ile Arg Val Ser Ala
    530                 535                 540

Val Leu Thr Asn Gly Ala Tyr Leu Leu Asn Val Asp Cys Asp His Tyr
545                 550                 555                 560
```

-continued

```
Phe Asn Ser Ser Lys Ala Leu Arg Glu Ala Met Cys Phe Met Met Asp
                565                 570                 575

Pro Ala Leu Gly Arg Lys Thr Cys Tyr Val Gln Phe Pro Gln Arg Phe
            580                 585                 590

Asp Gly Ile Asp Leu His Asp Arg Tyr Ala Asn Arg Asn Ile Val Phe
        595                 600                 605

Phe Asp Ile Asn Met Lys Gly Leu Asp Gly Ile Gln Gly Pro Val Tyr
    610                 615                 620

Val Gly Thr Gly Cys Cys Phe Asn Arg Gln Ala Leu Tyr Gly Tyr Asp
625                 630                 635                 640

Pro Val Leu Thr Glu Ala Asp Leu Glu Pro Asn Ile Val Val Lys Ser
                645                 650                 655

Cys Cys Gly Arg Arg Lys Arg Lys Asn Lys Ser Tyr Met Asp Ser Gln
            660                 665                 670

Ser Arg Ile Met Lys Arg Thr Glu Ser Ser Ala Pro Ile Phe Asn Met
        675                 680                 685

Glu Asp Ile Glu Glu Gly Ile Glu Gly Tyr Glu Asp Glu Arg Ser Val
    690                 695                 700

Leu Met Ser Gln Arg Lys Leu Glu Lys Arg Phe Gly Gln Ser Pro Ile
705                 710                 715                 720

Phe Ile Ala Ser Thr Phe Met Thr Gln Gly Gly Ile Pro Pro Ser Thr
                725                 730                 735

Asn Pro Ala Ser Leu Leu Lys Glu Ala Ile His Val Ile Ser Cys Gly
            740                 745                 750

Tyr Glu Asp Lys Thr Glu Trp Gly Lys Glu Ile Gly Trp Ile Tyr Gly
        755                 760                 765

Ser Val Thr Glu Asp Ile Leu Thr Gly Phe Lys Met His Ala Arg Gly
    770                 775                 780

Trp Gln Ser Ile Tyr Cys Met Pro Pro Arg Pro Cys Phe Lys Gly Ser
785                 790                 795                 800

Ala Pro Ile Asn Leu Ser Asp Arg Leu Asn Gln Val Leu Arg Trp Ala
                805                 810                 815

Leu Gly Ser Val Glu Ile Leu Leu Ser Arg His Cys Pro Ile Trp Tyr
            820                 825                 830

Gly Tyr Asn Gly Arg Leu Lys Leu Leu Glu Arg Leu Ala Tyr Ile Asn
        835                 840                 845

Thr Ile Val Tyr Pro Ile Thr Ser Val Pro Leu Ile Ala Tyr Cys Val
    850                 855                 860

Leu Pro Ala Ile Cys Leu Leu Thr Asn Lys Phe Ile Ile Pro Glu Ile
865                 870                 875                 880

Ser Asn Tyr Ala Gly Met Phe Phe Ile Leu Leu Phe Ala Ser Ile Phe
                885                 890                 895

Ala Thr Gly Ile Leu Glu Leu Arg Trp Ser Gly Val Gly Ile Glu Asp
            900                 905                 910

Trp Trp Arg Asn Glu Gln Phe Trp Val Ile Gly Gly Thr Ser Ala His
        915                 920                 925

Leu Phe Ala Val Phe Gln Gly Leu Leu Lys Val Leu Ala Gly Ile Asp
    930                 935                 940

Thr Asn Phe Thr Val Thr Ser Lys Ala Ser Asp Glu Asp Gly Asp Phe
945                 950                 955                 960

Ala Glu Leu Tyr Val Phe Lys Trp Thr Ser Leu Leu Ile Pro Pro Thr
                965                 970                 975
```

```
Thr Val Leu Val Ile Asn Leu Val Gly Met Val Ala Gly Ile Ser Tyr
            980                 985                 990

Ala Ile Asn Ser Gly Tyr Gln Ser  Trp Gly Pro Leu Phe  Gly Lys Leu
        995                 1000                1005

Phe Phe  Ser Ile Trp Val Ile  Leu His Leu Tyr Pro  Phe Leu Lys
    1010                 1015                 1020

Gly Leu  Met Gly Arg Gln Asn  Arg Thr Pro Thr Ile  Val Ile Val
    1025                 1030                 1035

Trp Ser  Ile Leu Leu Ala Ser  Ile Phe Ser Leu Leu  Trp Val Lys
    1040                 1045                 1050

Ile Asp  Pro Phe Ile Ser Pro  Thr Gln Lys Ala Ala  Ala Leu Gly
    1055                 1060                 1065

Gln Cys  Gly Val Asn Cys
    1070


<210> SEQ ID NO 12
<211> LENGTH: 983
<212> TYPE: PRT
<213> ORGANISM: Zea mays

<400> SEQUENCE: 12

Met Met Glu Ser Ala Ala Ala Gln Ser Cys Ala Ala Cys Gly Asp Asp
1               5                   10                  15

Ala Arg Ala Ala Cys Arg Ala Cys Ser Tyr Ala Leu Cys Arg Ala Cys
            20                  25                  30

Leu Asp Glu Asp Ala Ala Glu Gly Arg Thr Thr Cys Ala Arg Cys Gly
        35                  40                  45

Gly Asp Tyr Ala Ala Ile Asn Pro Ala Arg Ala Ser Glu Gly Thr Glu
    50                  55                  60

Ala Glu Glu Glu Val Val Glu Asn His His Thr Ala Gly Gly Leu Arg
65                  70                  75                  80

Glu Arg Val Thr Met Gly Ser His Leu Asn Asp Arg Gln Asp Glu Val
                85                  90                  95

Ser His Ala Arg Thr Met Ser Ser Leu Ser Gly Ile Gly Ser Glu Leu
            100                 105                 110

Asn Asp Glu Ser Gly Lys Pro Ile Trp Lys Asn Arg Val Glu Ser Trp
        115                 120                 125

Lys Glu Lys Lys Asn Glu Lys Lys Ala Ser Ala Lys Lys Thr Ala Ala
    130                 135                 140

Lys Ala Gln Pro Pro Pro Val Glu Glu Gln Ile Met Asp Glu Lys Asp
145                 150                 155                 160

Leu Thr Asp Ala Tyr Glu Pro Leu Ser Arg Val Ile Pro Ile Ser Lys
                165                 170                 175

Asn Lys Leu Thr Pro Tyr Arg Ala Val Ile Ile Met Arg Leu Ile Val
            180                 185                 190

Leu Gly Leu Phe Phe His Tyr Arg Ile Thr Asn Pro Val Asn Ser Ala
        195                 200                 205

Phe Gly Leu Trp Met Thr Ser Val Ile Cys Glu Ile Trp Phe Gly Phe
    210                 215                 220

Ser Trp Ile Leu Asp Gln Phe Pro Lys Trp Tyr Pro Ile Asn Arg Glu
225                 230                 235                 240

Thr Tyr Val Asp Arg Leu Ile Ala Arg Tyr Gly Asp Gly Glu Glu Ser
                245                 250                 255

Gly Leu Ala Pro Val Asp Phe Phe Val Ser Thr Val Asp Pro Leu Lys
            260                 265                 270
```

```
Glu Pro Pro Leu Ile Thr Ala Asn Thr Val Leu Ser Ile Leu Ala Val
        275                 280                 285

Asp Tyr Pro Val Glu Lys Ile Ser Cys Tyr Val Ser Asp Asp Gly Ser
    290                 295                 300

Ala Met Leu Thr Phe Glu Ser Leu Ala Glu Thr Ala Glu Tyr Ala Arg
305                 310                 315                 320

Lys Trp Val Pro Phe Cys Lys Lys Tyr Ala Ile Glu Pro Arg Ala Pro
                325                 330                 335

Glu Phe Tyr Phe Ser Gln Lys Ile Asp Tyr Leu Lys Asp Lys Ile His
            340                 345                 350

Pro Ser Phe Val Lys Glu Arg Arg Ala Met Lys Arg Asp Tyr Glu Glu
        355                 360                 365

Tyr Lys Val Arg Ile Asn Ala Leu Val Ala Lys Ala Gln Lys Thr Pro
    370                 375                 380

Asp Glu Gly Trp Ile Met Gln Asp Gly Thr Pro Trp Pro Gly Asn Asn
385                 390                 395                 400

Pro Arg Asp His Pro Gly Met Ile Gln Val Phe Leu Gly Glu Thr Gly
                405                 410                 415

Ala Arg Asp Phe Asp Gly Asn Glu Leu Pro Arg Leu Val Tyr Val Ser
            420                 425                 430

Arg Glu Lys Arg Pro Gly Tyr Gln His His Lys Lys Ala Gly Ala Met
        435                 440                 445

Asn Ala Leu Val Arg Val Ser Ala Val Leu Thr Asn Ala Pro Tyr Ile
    450                 455                 460

Leu Asn Leu Asp Cys Asp His Tyr Val Asn Asn Ser Lys Ala Val Arg
465                 470                 475                 480

Glu Ala Met Cys Phe Met Met Asp Pro Thr Val Gly Arg Asp Val Cys
                485                 490                 495

Tyr Val Gln Phe Pro Gln Arg Phe Asp Gly Ile Asp Arg Ser Asp Arg
            500                 505                 510

Tyr Ala Asn Arg Asn Val Val Phe Phe Asp Val Asn Met Lys Gly Leu
        515                 520                 525

Asp Gly Leu Gln Gly Pro Val Tyr Val Gly Thr Gly Cys Cys Phe Asn
    530                 535                 540

Arg Gln Ala Leu Tyr Gly Tyr Gly Pro Pro Ser Leu Pro Ala Leu Pro
545                 550                 555                 560

Lys Ser Ser Ile Cys Ser Trp Cys Cys Cys Cys Cys Pro Lys Lys Lys
                565                 570                 575

Val Glu Arg Ser Glu Arg Glu Ile Asn Arg Asp Ser Arg Arg Glu Asp
            580                 585                 590

Leu Glu Ser Ala Ile Phe Asn Leu Arg Glu Ile Asp Asn Tyr Asp Glu
        595                 600                 605

Tyr Glu Arg Ser Met Leu Ile Ser Gln Met Ser Phe Glu Lys Ser Phe
    610                 615                 620

Gly Leu Ser Ser Val Phe Ile Glu Ser Thr Leu Met Glu Asn Gly Gly
625                 630                 635                 640

Val Pro Glu Ser Ala Asn Pro Ser Thr Leu Ile Lys Glu Ala Ile His
                645                 650                 655

Val Ile Ser Cys Gly Tyr Glu Glu Lys Thr Glu Trp Gly Lys Glu Ile
            660                 665                 670

Gly Trp Ile Tyr Gly Ser Val Thr Glu Asp Ile Leu Thr Gly Phe Lys
        675                 680                 685
```

```
Met His Cys Arg Gly Trp Arg Ser Ile Tyr Cys Met Pro Val Arg Pro
    690                 695                 700

Ala Phe Lys Gly Ser Ala Pro Ile Asn Leu Ser Asp Arg Leu His Gln
705                 710                 715                 720

Val Leu Arg Trp Ala Leu Gly Ser Val Glu Ile Phe Phe Ser Arg His
                725                 730                 735

Cys Pro Leu Trp Tyr Gly Tyr Gly Gly Gly Arg Leu Lys Trp Leu Gln
            740                 745                 750

Arg Leu Ser Tyr Ile Asn Thr Ile Val Tyr Pro Phe Thr Ser Leu Pro
        755                 760                 765

Leu Val Ala Tyr Cys Cys Leu Pro Ala Ile Cys Leu Leu Thr Gly Lys
    770                 775                 780

Phe Ile Ile Pro Thr Leu Ser Asn Ala Ala Thr Ile Trp Phe Leu Gly
785                 790                 795                 800

Leu Phe Met Ser Ile Ile Val Thr Ser Val Leu Glu Leu Arg Trp Ser
                805                 810                 815

Gly Ile Gly Ile Glu Asp Trp Trp Arg Asn Glu Gln Phe Trp Val Ile
            820                 825                 830

Gly Gly Val Ser Ala His Leu Phe Ala Val Phe Gln Gly Ile Leu Lys
        835                 840                 845

Met Ile Ala Gly Leu Asp Thr Asn Phe Thr Val Thr Ala Lys Ala Thr
    850                 855                 860

Asp Asp Thr Glu Phe Gly Glu Leu Tyr Leu Phe Lys Trp Thr Thr Val
865                 870                 875                 880

Leu Ile Pro Pro Thr Ser Ile Leu Val Leu Asn Leu Val Gly Val Val
                885                 890                 895

Ala Gly Phe Ser Ala Ala Leu Asn Ser Gly Tyr Glu Ser Trp Gly Pro
            900                 905                 910

Leu Phe Gly Lys Val Phe Phe Ala Met Trp Val Ile Met His Leu Tyr
        915                 920                 925

Pro Phe Leu Lys Gly Leu Met Gly Arg Gln Asn Arg Thr Pro Thr Ile
    930                 935                 940

Val Val Leu Trp Ser Val Leu Leu Ala Ser Val Phe Ser Leu Leu Trp
945                 950                 955                 960

Val Lys Ile Asp Pro Phe Val Gly Gly Thr Glu Thr Val Asn Thr Asn
                965                 970                 975

Asn Cys Asn Thr Ile Ile Cys
            980
```

<210> SEQ ID NO 13
<211> LENGTH: 1074
<212> TYPE: PRT
<213> ORGANISM: Zea mays

<400> SEQUENCE: 13

```
Met Glu Ala Asn Arg Gly Met Val Ala Gly Ser Arg Gly Gly Val Val
1               5                   10                  15

Thr Ile Arg His Asp Gly Asp Gly Ala Ala Ala Lys Gln Leu Lys Asn
            20                  25                  30

Val Asn Glu Gln Ile Cys Gln Ile Cys Gly Asp Thr Leu Gly Leu Ser
        35                  40                  45

Ala Thr Gly Asp Ile Phe Val Ala Cys Asn Glu Cys Ala Phe Pro Val
    50                  55                  60

Cys Arg Pro Cys Tyr Glu Tyr Glu Arg Lys Glu Gly Asn Gln Cys Cys
65                  70                  75                  80
```

```
Pro Gln Cys Lys Thr Arg Tyr Lys Arg His Lys Gly Ser Pro Arg Val
                85                  90                  95

Arg Gly Asp Glu Glu Glu Asp Gly Val Asp Asp Leu Asp Asn Glu Phe
            100                 105                 110

Asn Tyr Thr Gln Gly Asn Val Gln Gly Pro Gln Trp Gln Leu Arg Gly
        115                 120                 125

Gln Gly Glu Asp Val Asp Ile Ser Ser Ser Ser Arg His Glu Pro His
    130                 135                 140

His Arg Ile Pro Arg Leu Thr Thr Gly Gln Gln Met Ser Gly Asp Ile
145                 150                 155                 160

Pro Asp Ala Ser Pro Asp Arg His Ser Ile Arg Ser Pro Thr Pro Ser
                165                 170                 175

Tyr Val Asp Pro Ser Ile Pro Val Pro Val Arg Ile Val Asp Pro Ser
            180                 185                 190

Lys Asp Leu Asn Ser Tyr Gly Val Gly Ser Val Asp Trp Lys Glu Arg
        195                 200                 205

Val Glu Ser Trp Lys Val Arg Gln Asp Lys Asn Met Ile Gln Val Thr
    210                 215                 220

His Lys Tyr Pro Ala Glu Gly Lys Gly Asp Ile Glu Gly Thr Gly Ser
225                 230                 235                 240

Asn Gly Glu Asp Leu Gln Met Ala Asp Asp Ala Arg Leu Pro Leu Ser
                245                 250                 255

Arg Ile Val Pro Ile Ser Pro Asn Glu Leu Asn Leu Tyr Arg Ile Val
            260                 265                 270

Ile Val Leu Arg Leu Ile Ile Leu Cys Phe Phe Phe Gln Tyr Arg Ile
        275                 280                 285

Thr His Pro Val Glu Asp Ala Tyr Gly Leu Trp Leu Val Ser Val Ile
    290                 295                 300

Cys Glu Val Trp Phe Ala Leu Ser Trp Leu Leu Asp Gln Phe Pro Lys
305                 310                 315                 320

Trp Tyr Pro Ile Asn Arg Glu Thr Tyr Leu Asp Arg Leu Ala Leu Arg
                325                 330                 335

Tyr Asp Arg Glu Gly Glu Pro Ser Gln Leu Ala Pro Ile Asp Val Phe
            340                 345                 350

Val Ser Thr Val Asp Pro Leu Lys Glu Pro Pro Leu Ile Thr Gly Asn
        355                 360                 365

Thr Val Leu Ser Ile Leu Ala Val Asp Tyr Pro Val Asp Lys Val Ser
    370                 375                 380

Cys Tyr Val Ser Asp Asp Gly Ser Ala Met Leu Thr Phe Glu Ala Leu
385                 390                 395                 400

Ser Glu Thr Ala Glu Phe Ala Arg Lys Trp Val Pro Phe Cys Lys Lys
                405                 410                 415

His Asn Ile Glu Pro Arg Ala Pro Glu Phe Tyr Phe Ala Gln Lys Ile
            420                 425                 430

Asp Tyr Leu Lys Asp Lys Ile Gln Pro Ser Phe Val Lys Glu Arg Arg
        435                 440                 445

Ala Met Lys Arg Glu Tyr Glu Glu Phe Lys Val Arg Ile Asn Ala Leu
    450                 455                 460

Val Ala Lys Ala Gln Lys Ile Pro Glu Glu Gly Trp Thr Met Ala Asp
465                 470                 475                 480

Gly Thr Pro Trp Pro Gly Asn Asn Pro Arg Asp His Pro Gly Met Ile
                485                 490                 495
```

-continued

```
Gln Val Phe Leu Gly His Ser Gly Gly Leu Asp Thr Asp Gly Asn Glu
            500                 505                 510

Leu Pro Arg Leu Val Tyr Val Ser Arg Glu Lys Arg Pro Gly Phe Gln
        515                 520                 525

His His Lys Lys Ala Gly Ala Met Asn Ala Leu Ile Arg Val Ser Ala
    530                 535                 540

Val Leu Thr Asn Gly Ala Tyr Leu Leu Asn Val Asp Cys Asp His Tyr
545                 550                 555                 560

Phe Asn Ser Ser Lys Ala Leu Arg Glu Ala Met Cys Phe Met Met Asp
                565                 570                 575

Pro Ala Leu Gly Arg Lys Thr Cys Tyr Val Gln Phe Pro Gln Arg Phe
            580                 585                 590

Asp Gly Ile Asp Leu His Asp Arg Tyr Ala Asn Arg Asn Ile Val Phe
        595                 600                 605

Phe Asp Ile Asn Met Lys Gly Leu Asp Gly Ile Gln Gly Pro Val Tyr
    610                 615                 620

Val Gly Thr Gly Cys Cys Phe Asn Arg Gln Ala Leu Tyr Gly Tyr Asp
625                 630                 635                 640

Pro Val Leu Thr Glu Ala Asp Leu Glu Pro Asn Ile Ile Ile Lys Ser
                645                 650                 655

Cys Cys Gly Gly Arg Lys Lys Lys Asp Lys Ser Tyr Ile Asp Ser Lys
            660                 665                 670

Asn Arg Asp Met Lys Arg Thr Glu Ser Ser Ala Pro Ile Phe Asn Met
        675                 680                 685

Glu Asp Ile Glu Glu Gly Phe Glu Gly Tyr Glu Asp Glu Arg Ser Leu
    690                 695                 700

Leu Met Ser Gln Lys Ser Leu Glu Lys Arg Phe Gly Gln Ser Pro Ile
705                 710                 715                 720

Phe Ile Ala Ser Thr Phe Met Thr Gln Gly Gly Ile Pro Pro Ser Thr
                725                 730                 735

Asn Pro Gly Ser Leu Leu Lys Glu Ala Ile His Val Ile Ser Cys Gly
            740                 745                 750

Tyr Glu Asp Lys Thr Glu Trp Gly Lys Glu Ile Gly Trp Ile Tyr Gly
        755                 760                 765

Ser Val Thr Glu Asp Ile Leu Thr Gly Phe Lys Met His Ala Arg Gly
    770                 775                 780

Trp Ile Ser Ile Tyr Cys Met Pro Leu Arg Pro Cys Phe Lys Gly Ser
785                 790                 795                 800

Ala Pro Ile Asn Leu Ser Asp Arg Leu Asn Gln Val Leu Arg Trp Ala
                805                 810                 815

Leu Gly Ser Val Glu Ile Leu Leu Ser Arg His Cys Pro Ile Trp Tyr
            820                 825                 830

Gly Tyr Asn Gly Arg Leu Lys Leu Leu Glu Arg Leu Ala Tyr Ile Asn
        835                 840                 845

Thr Ile Val Tyr Pro Ile Thr Ser Ile Pro Leu Val Ala Tyr Cys Val
    850                 855                 860

Leu Pro Ala Ile Cys Leu Leu Thr Asn Lys Phe Ile Ile Pro Ala Ile
865                 870                 875                 880

Ser Asn Tyr Ala Gly Ala Phe Phe Ile Leu Leu Phe Ala Ser Ile Phe
                885                 890                 895

Ala Thr Gly Ile Leu Glu Leu Arg Trp Ser Gly Val Gly Ile Glu Asp
            900                 905                 910

Trp Trp Arg Asn Glu Gln Phe Trp Val Ile Gly Gly Thr Ser Ala His
```

915 920 925

Leu Phe Ala Val Phe Gln Gly Leu Leu Lys Val Leu Ala Gly Ile Asp
930 935 940

Thr Asn Phe Thr Val Thr Ser Lys Ala Thr Asp Asp Asp Gly Asp Phe
945 950 955 960

Ala Glu Leu Tyr Val Phe Lys Trp Thr Thr Leu Leu Ile Pro Pro Thr
965 970 975

Thr Val Leu Val Ile Asn Leu Val Gly Ile Val Ala Gly Val Ser Tyr
980 985 990

Ala Ile Asn Ser Gly Tyr Gln Ser Trp Gly Pro Leu Phe Gly Lys Leu
995 1000 1005

Phe Phe Ala Ile Trp Val Ile Leu His Leu Tyr Pro Phe Leu Lys
1010 1015 1020

Gly Leu Met Gly Lys Gln Asn Arg Thr Pro Thr Ile Val Ile Val
1025 1030 1035

Trp Ser Val Leu Leu Ala Ser Ile Phe Ser Leu Leu Trp Val Lys
1040 1045 1050

Ile Asp Pro Phe Ile Ser Pro Thr Gln Lys Ala Leu Ser Arg Gly
1055 1060 1065

Gln Cys Gly Val Asn Cys
1070

<210> SEQ ID NO 14
<211> LENGTH: 1086
<212> TYPE: PRT
<213> ORGANISM: Zea mays

<400> SEQUENCE: 14

Met Glu Ala Ser Ala Gly Leu Val Ala Gly Ser His Asn Arg Asn Glu
1 5 10 15

Leu Val Val Ile Arg Arg Asp Gly Asp Pro Gly Pro Lys Pro Pro Arg
20 25 30

Glu Gln Asn Gly Gln Val Cys Gln Ile Cys Gly Asp Asp Val Gly Leu
35 40 45

Ala Pro Gly Gly Asp Pro Phe Val Ala Cys Asn Glu Cys Ala Phe Pro
50 55 60

Val Cys Arg Asp Cys Tyr Glu Tyr Glu Arg Arg Glu Gly Thr Gln Asn
65 70 75 80

Cys Pro Gln Cys Lys Thr Arg Tyr Lys Arg Leu Lys Gly Cys Gln Arg
85 90 95

Val Thr Gly Asp Glu Glu Glu Asp Gly Val Asp Asp Leu Asp Asn Glu
100 105 110

Phe Asn Trp Asp Gly His Asp Ser Gln Ser Val Ala Glu Ser Met Leu
115 120 125

Tyr Gly His Met Ser Tyr Gly Arg Gly Gly Asp Pro Asn Gly Ala Pro
130 135 140

Gln Ala Phe Gln Leu Asn Pro Asn Val Pro Leu Leu Thr Asn Gly Gln
145 150 155 160

Met Val Asp Asp Ile Pro Pro Glu Gln His Ala Leu Val Pro Ser Phe
165 170 175

Met Gly Gly Gly Gly Lys Arg Ile His Pro Leu Pro Tyr Ala Asp Pro
180 185 190

Ser Leu Pro Val Gln Pro Arg Ser Met Asp Pro Ser Lys Asp Leu Ala
195 200 205

-continued

```
Ala Tyr Gly Tyr Gly Ser Val Ala Trp Lys Glu Arg Met Glu Asn Trp
    210                 215                 220

Lys Gln Arg Gln Glu Arg Met His Gln Thr Gly Asn Asp Gly Gly Gly
225                 230                 235                 240

Asp Asp Gly Asp Asp Ala Asp Leu Pro Leu Met Asp Glu Ala Arg Gln
                245                 250                 255

Gln Leu Ser Arg Lys Ile Pro Leu Pro Ser Ser Gln Ile Asn Pro Tyr
            260                 265                 270

Arg Met Ile Ile Ile Ile Arg Leu Val Val Leu Gly Phe Phe Phe His
        275                 280                 285

Tyr Arg Val Met His Pro Val Asn Asp Ala Phe Ala Leu Trp Leu Ile
    290                 295                 300

Ser Val Ile Cys Glu Ile Trp Phe Ala Met Ser Trp Ile Leu Asp Gln
305                 310                 315                 320

Phe Pro Lys Trp Phe Pro Ile Glu Arg Glu Thr Tyr Leu Asp Arg Leu
                325                 330                 335

Ser Leu Arg Phe Asp Lys Glu Gly Gln Pro Ser Gln Leu Ala Pro Ile
            340                 345                 350

Asp Phe Phe Val Ser Thr Val Asp Pro Leu Lys Glu Pro Pro Leu Val
        355                 360                 365

Thr Thr Asn Thr Val Leu Ser Ile Leu Ser Val Asp Tyr Pro Val Asp
    370                 375                 380

Lys Val Ser Cys Tyr Val Ser Asp Asp Gly Ala Ala Met Leu Thr Phe
385                 390                 395                 400

Glu Ala Leu Ser Glu Thr Ser Glu Phe Ala Lys Lys Trp Val Pro Phe
                405                 410                 415

Cys Lys Arg Tyr Asn Ile Glu Pro Arg Ala Pro Glu Trp Tyr Phe Gln
            420                 425                 430

Gln Lys Ile Asp Tyr Leu Lys Asp Lys Val Ala Ala Asn Phe Val Arg
        435                 440                 445

Glu Arg Arg Ala Met Lys Arg Glu Tyr Glu Glu Phe Lys Val Arg Ile
    450                 455                 460

Asn Ala Leu Val Ala Lys Ala Gln Lys Val Pro Glu Glu Gly Trp Thr
465                 470                 475                 480

Met Gln Asp Gly Thr Pro Trp Pro Gly Asn Asn Val Arg Asp His Pro
                485                 490                 495

Gly Met Ile Gln Val Phe Leu Gly Gln Ser Gly Gly Leu Asp Cys Glu
            500                 505                 510

Gly Asn Glu Leu Pro Arg Leu Val Tyr Val Ser Arg Glu Lys Arg Pro
        515                 520                 525

Gly Tyr Asn His His Lys Lys Ala Gly Ala Met Asn Ala Leu Val Arg
    530                 535                 540

Val Ser Ala Val Leu Thr Asn Ala Pro Tyr Leu Leu Asn Leu Asp Cys
545                 550                 555                 560

Asp His Tyr Ile Asn Asn Ser Lys Ala Ile Lys Glu Ala Met Cys Phe
                565                 570                 575

Met Met Asp Pro Leu Leu Gly Lys Lys Val Cys Tyr Val Gln Phe Pro
            580                 585                 590

Gln Arg Phe Asp Gly Ile Asp Arg His Asp Arg Tyr Ala Asn Arg Asn
        595                 600                 605

Val Val Phe Phe Asp Ile Asn Met Lys Gly Leu Asp Gly Ile Gln Gly
    610                 615                 620

Pro Ile Tyr Val Gly Thr Gly Cys Val Phe Arg Arg Gln Ala Leu Tyr
```

-continued 625 630 635 640

Gly Tyr Asp Ala Pro Lys Thr Lys Lys Pro Pro Ser Arg Thr Cys Asn
645 650 655

Cys Trp Pro Lys Trp Cys Phe Cys Cys Cys Cys Phe Gly Asn Arg Lys
660 665 670

Gln Lys Lys Thr Thr Lys Pro Lys Thr Glu Lys Lys Lys Leu Leu Phe
675 680 685

Phe Lys Lys Glu Glu Asn Gln Ser Pro Ala Tyr Ala Leu Gly Glu Ile
690 695 700

Asp Glu Ala Ala Pro Gly Ala Glu Asn Glu Lys Ala Gly Ile Val Asn
705 710 715 720

Gln Gln Lys Leu Glu Lys Lys Phe Gly Gln Ser Ser Val Phe Val Thr
725 730 735

Ser Thr Leu Leu Glu Asn Gly Gly Thr Leu Lys Ser Ala Ser Pro Ala
740 745 750

Ser Leu Leu Lys Glu Ala Ile His Val Ile Ser Cys Gly Tyr Glu Asp
755 760 765

Lys Thr Asp Trp Gly Lys Glu Ile Gly Trp Ile Tyr Gly Ser Val Thr
770 775 780

Glu Asp Ile Leu Thr Gly Phe Lys Met His Cys His Gly Trp Arg Ser
785 790 795 800

Ile Tyr Cys Ile Pro Lys Arg Val Ala Phe Lys Gly Ser Ala Pro Leu
805 810 815

Asn Leu Ser Asp Arg Leu His Gln Val Leu Arg Trp Ala Leu Gly Ser
820 825 830

Ile Glu Ile Phe Phe Ser Asn His Cys Pro Leu Trp Tyr Gly Tyr Gly
835 840 845

Gly Gly Leu Lys Phe Leu Glu Arg Phe Ser Tyr Ile Asn Ser Ile Val
850 855 860

Tyr Pro Trp Thr Ser Ile Pro Leu Leu Ala Tyr Cys Thr Leu Pro Ala
865 870 875 880

Ile Cys Leu Leu Thr Gly Lys Phe Ile Thr Pro Glu Leu Asn Asn Val
885 890 895

Ala Ser Leu Trp Phe Met Ser Leu Phe Ile Cys Ile Phe Ala Thr Ser
900 905 910

Ile Leu Glu Met Arg Trp Ser Gly Val Gly Ile Asp Asp Trp Trp Arg
915 920 925

Asn Glu Gln Phe Trp Val Ile Gly Gly Val Ser Ser His Leu Phe Ala
930 935 940

Val Phe Gln Gly Leu Leu Lys Val Ile Ala Gly Val Asp Thr Ser Phe
945 950 955 960

Thr Val Thr Ser Lys Gly Gly Asp Asp Glu Glu Phe Ser Glu Leu Tyr
965 970 975

Thr Phe Lys Trp Thr Thr Leu Leu Ile Pro Pro Thr Thr Leu Leu Leu
980 985 990

Leu Asn Phe Ile Gly Val Val Ala Gly Val Ser Asn Ala Ile Asn Asn
995 1000 1005

Gly Tyr Glu Ser Trp Gly Pro Leu Phe Gly Lys Leu Phe Phe Ala
1010 1015 1020

Phe Trp Val Ile Val His Leu Tyr Pro Phe Leu Lys Gly Leu Val
1025 1030 1035

Gly Arg Gln Asn Arg Thr Pro Thr Ile Val Ile Val Trp Ser Ile
1040 1045 1050

```
Leu Leu  Ala Ser Ile Phe Ser  Leu Leu Trp Val Arg  Ile Asp Pro
    1055                 1060                 1065

Phe Leu  Ala Lys Asp Asp Gly  Pro Leu Leu Glu Glu  Cys Gly Leu
    1070                 1075                 1080

Asp Cys  Asn
    1085


<210> SEQ ID NO 15
<211> LENGTH: 1056
<212> TYPE: PRT
<213> ORGANISM: Zea mays

<400> SEQUENCE: 15

Met Glu Ala Ser Ala Gly Leu Val Ala Gly Ser His Asn Arg Asn Glu
1               5                   10                  15

Leu Val Leu Ile Arg Gly His Glu Asp Pro Lys Pro Leu Arg Ala Leu
            20                  25                  30

Ser Gly Gln Val Cys Glu Ile Cys Gly Asp Glu Val Gly Leu Thr Val
        35                  40                  45

Asp Gly Asp Leu Phe Val Ala Cys Asn Glu Cys Gly Phe Pro Val Cys
    50                  55                  60

Arg Pro Cys Tyr Glu Tyr Glu Arg Arg Glu Gly Thr Gln Asn Cys Pro
65                  70                  75                  80

Gln Cys Lys Thr Arg Tyr Lys Arg Leu Lys Gly Thr Pro Arg Val Ala
                85                  90                  95

Gly Asp Asp Asp Glu Glu Asp Ile Asp Asp Leu Glu His Glu Phe Asn
            100                 105                 110

Ile Asp Asp Glu Asn Gln Gln Arg Gln Leu Glu Gly Asn Met Gln Asn
        115                 120                 125

Ser Gln Ile Thr Glu Ala Met Leu His Gly Arg Met Ser Tyr Gly Arg
    130                 135                 140

Gly Pro Asp Asp Gly Asp Gly Asn Asn Thr Pro Gln Ile Pro Pro Ile
145                 150                 155                 160

Ile Thr Gly Ser Arg Ser Val Pro Val Ser Gly Glu Phe Pro Ile Thr
                165                 170                 175

Asn Gly Tyr Gly His Gly Glu Val Ser Ser Ser Leu His Lys Arg Ile
            180                 185                 190

His Pro Tyr Pro Val Ser Glu Pro Gly Ser Ala Lys Trp Asp Glu Lys
        195                 200                 205

Lys Glu Val Ser Trp Lys Glu Arg Met Asp Asp Trp Lys Ser Lys Gln
    210                 215                 220

Gly Ile Leu Gly Gly Gly Ala Asp Pro Glu Asp Met Asp Ala Asp Val
225                 230                 235                 240

Ala Leu Asn Asp Glu Ala Arg Gln Pro Leu Ser Arg Lys Val Ser Ile
                245                 250                 255

Ala Ser Ser Lys Val Asn Pro Tyr Arg Met Val Ile Val Val Arg Leu
            260                 265                 270

Val Val Leu Ala Phe Phe Leu Arg Tyr Arg Ile Leu His Pro Val Pro
        275                 280                 285

Asp Ala Ile Gly Leu Trp Leu Val Ser Ile Ile Cys Glu Ile Trp Phe
    290                 295                 300

Ala Ile Ser Trp Ile Leu Asp Gln Phe Pro Lys Trp Phe Pro Ile Asp
305                 310                 315                 320

Arg Glu Thr Ser Leu Ser Gly Leu Asp Asp Ala Ala Arg Cys Arg Tyr
```

-continued

```
                325                 330                 335

Glu Arg Glu Gly Glu Pro Ser Leu Leu Ser Ala Val Asp Leu Phe Val
            340                 345                 350

Ser Thr Val Asp Pro Leu Lys Glu Pro Pro Leu Val Thr Ala Asn Thr
        355                 360                 365

Val Leu Ser Ile Leu Ala Val Asp Tyr Pro Val Asp Lys Val Ser Cys
    370                 375                 380

Tyr Val Ser Asp Asp Gly Ala Ser Met Leu Thr Phe Glu Ser Leu Ser
385                 390                 395                 400

Glu Thr Ala Glu Phe Ala Arg Lys Trp Val Pro Phe Cys Lys Lys Phe
                405                 410                 415

Gly Ile Glu Pro Arg Ala Pro Glu Phe Tyr Phe Ser Leu Lys Val Asp
            420                 425                 430

Tyr Leu Lys Asp Lys Val Gln Pro Thr Phe Val Gln Glu Arg Arg Ala
        435                 440                 445

Met Lys Arg Glu Tyr Glu Glu Phe Lys Val Arg Ile Asn Ala Leu Val
    450                 455                 460

Ala Lys Ala Met Lys Val Pro Ala Glu Gly Trp Ile Met Lys Asp Gly
465                 470                 475                 480

Thr Pro Trp Pro Gly Asn Asn Thr Arg Asp His Pro Gly Met Ile Gln
                485                 490                 495

Val Phe Leu Gly His Ser Gly Gly His Asp Thr Glu Gly Asn Glu Leu
            500                 505                 510

Pro Arg Leu Val Tyr Val Ser Arg Glu Lys Arg Pro Gly Phe Gln His
        515                 520                 525

His Lys Lys Ala Gly Ala Met Asn Ala Leu Ile Arg Val Ser Ala Val
    530                 535                 540

Leu Thr Asn Ala Pro Phe Met Leu Asn Leu Asp Cys Asp His Tyr Ile
545                 550                 555                 560

Asn Asn Ser Lys Ala Ile Arg Glu Ala Met Cys Phe Leu Met Asp Pro
                565                 570                 575

Gln Val Gly Arg Lys Val Cys Tyr Val Gln Phe Pro Gln Arg Phe Asp
            580                 585                 590

Gly Ile Asp Val His Asp Arg Tyr Ala Asn Arg Asn Thr Val Phe Phe
        595                 600                 605

Asp Ile Asn Met Lys Gly Leu Asp Gly Ile Gln Gly Pro Val Tyr Val
    610                 615                 620

Gly Thr Gly Cys Val Phe Arg Arg Gln Ala Leu Tyr Gly Tyr Asn Pro
625                 630                 635                 640

Pro Lys Gly Pro Lys Arg Pro Lys Met Val Thr Cys Asp Cys Cys Pro
                645                 650                 655

Cys Phe Gly Arg Lys Lys Arg Lys His Ala Lys Asp Gly Leu Pro Glu
            660                 665                 670

Gly Thr Ala Asp Met Gly Val Asp Ser Asp Lys Glu Met Leu Met Ser
        675                 680                 685

His Met Asn Phe Glu Lys Arg Phe Gly Gln Ser Ala Ala Phe Val Thr
    690                 695                 700

Ser Thr Leu Met Glu Glu Gly Gly Val Pro Pro Ser Ser Ser Pro Ala
705                 710                 715                 720

Ala Leu Leu Lys Glu Ala Ile His Val Ile Ser Cys Gly Tyr Glu Asp
                725                 730                 735

Lys Thr Asp Trp Gly Leu Glu Leu Gly Trp Ile Tyr Gly Ser Ile Thr
            740                 745                 750
```

Glu Asp Ile Leu Thr Gly Phe Lys Met His Cys Arg Gly Trp Arg Ser
755 760 765

Val Tyr Cys Met Pro Lys Arg Ala Ala Phe Lys Gly Ser Ala Pro Ile
770 775 780

Asn Leu Ser Asp Arg Leu Asn Gln Val Leu Arg Trp Ala Leu Gly Ser
785 790 795 800

Val Glu Ile Phe Phe Ser Arg His Ser Pro Leu Leu Tyr Gly Tyr Lys
805 810 815

Asn Gly Asn Leu Lys Trp Leu Glu Arg Phe Ala Tyr Ile Asn Thr Thr
820 825 830

Ile Tyr Pro Phe Thr Ser Leu Pro Leu Leu Ala Tyr Cys Thr Leu Pro
835 840 845

Ala Val Cys Leu Leu Thr Gly Lys Phe Ile Met Pro Ser Ile Ser Thr
850 855 860

Phe Ala Ser Leu Phe Phe Ile Ala Leu Phe Met Ser Ile Phe Ala Thr
865 870 875 880

Gly Ile Leu Glu Met Arg Trp Ser Gly Val Ser Ile Glu Glu Trp Trp
885 890 895

Arg Asn Glu Gln Phe Trp Val Ile Gly Gly Val Ser Ala His Leu Phe
900 905 910

Ala Val Val Gln Gly Leu Leu Lys Val Leu Ala Gly Ile Asp Thr Asn
915 920 925

Phe Thr Val Thr Ser Lys Ala Thr Gly Asp Glu Asp Asp Glu Phe Ala
930 935 940

Glu Leu Tyr Ala Phe Lys Trp Thr Thr Leu Leu Ile Pro Pro Thr Thr
945 950 955 960

Leu Leu Ile Ile Asn Val Ile Gly Val Val Ala Gly Ile Ser Asp Ala
965 970 975

Ile Asn Asn Gly Tyr Gln Ser Trp Gly Pro Leu Phe Gly Lys Leu Phe
980 985 990

Phe Ala Phe Trp Val Ile Val His Leu Tyr Pro Phe Leu Lys Gly Leu
995 1000 1005

Met Gly Arg Gln Asn Arg Thr Pro Thr Val Val Val Ile Trp Ser
1010 1015 1020

Ile Leu Leu Ala Ser Ile Phe Ser Leu Leu Trp Val Arg Ile Asp
1025 1030 1035

Pro Phe Ile Val Arg Thr Lys Gly Pro Asp Val Arg Gln Cys Gly
1040 1045 1050

Ile Asn Cys
1055

<210> SEQ ID NO 16
<211> LENGTH: 1077
<212> TYPE: PRT
<213> ORGANISM: Zea mays

<400> SEQUENCE: 16

Met Glu Gly Asp Ala Asp Gly Val Lys Ser Gly Arg Arg Gly Gly Gly
1 5 10 15

Gln Val Cys Gln Ile Cys Gly Asp Gly Val Gly Thr Thr Ala Glu Gly
20 25 30

Asp Val Phe Ala Ala Cys Asp Val Cys Gly Phe Pro Val Cys Arg Pro
35 40 45

Cys Tyr Glu Tyr Glu Arg Lys Asp Gly Thr Gln Ala Cys Pro Gln Cys

-continued

```
    50                  55                  60

Lys Thr Lys Tyr Lys Arg His Lys Gly Ser Pro Ala Ile Arg Gly Glu
65                  70                  75                  80

Glu Gly Asp Asp Thr Asp Ala Asp Ser Asp Phe Asn Tyr Pro Ala Ser
                85                  90                  95

Gly Asn Glu Asp Gln Lys Gln Lys Ile Ala Asp Arg Met Arg Ser Trp
            100                 105                 110

Arg Met Asn Ala Gly Gly Ser Gly Asp Val Gly Arg Pro Lys Tyr Asp
        115                 120                 125

Ser Gly Glu Ile Gly Leu Thr Lys Tyr Asp Ser Gly Glu Ile Pro Arg
    130                 135                 140

Gly Tyr Ile Pro Ser Val Thr Asn Ser Gln Ile Ser Gly Glu Ile Pro
145                 150                 155                 160

Gly Ala Ser Pro Asp His His Met Met Ser Pro Thr Gly Asn Ile Gly
                165                 170                 175

Lys Arg Ala Pro Phe Pro Tyr Val Asn His Ser Pro Asn Pro Ser Arg
            180                 185                 190

Glu Phe Ser Gly Ser Ile Gly Asn Val Ala Trp Lys Glu Arg Val Asp
        195                 200                 205

Gly Trp Lys Met Lys Gln Asp Lys Gly Thr Ile Pro Met Thr Asn Gly
    210                 215                 220

Thr Ser Ile Ala Pro Ser Glu Gly Arg Gly Val Gly Asp Ile Asp Ala
225                 230                 235                 240

Ser Thr Asp Tyr Asn Met Glu Asp Ala Leu Leu Asn Asp Glu Thr Arg
                245                 250                 255

Gln Pro Leu Ser Arg Lys Val Pro Leu Pro Ser Ser Arg Ile Asn Pro
            260                 265                 270

Tyr Arg Met Val Ile Val Leu Arg Leu Ile Val Leu Ser Ile Phe Leu
        275                 280                 285

His Tyr Arg Ile Thr Asn Pro Val Arg Asn Ala Tyr Pro Leu Trp Leu
    290                 295                 300

Leu Ser Val Ile Cys Glu Ile Trp Phe Ala Leu Ser Trp Ile Leu Asp
305                 310                 315                 320

Gln Phe Pro Lys Trp Phe Pro Ile Asn Arg Glu Thr Tyr Leu Asp Arg
                325                 330                 335

Leu Ala Leu Arg Tyr Asp Arg Glu Gly Glu Pro Ser Gln Leu Ala Ala
            340                 345                 350

Val Asp Ile Phe Val Ser Thr Val Asp Pro Met Lys Glu Pro Pro Leu
        355                 360                 365

Val Thr Ala Asn Thr Val Leu Ser Ile Leu Ala Val Asp Tyr Pro Val
    370                 375                 380

Asp Lys Val Ser Cys Tyr Val Ser Asp Asp Gly Ala Ala Met Leu Thr
385                 390                 395                 400

Phe Asp Ala Leu Ala Glu Thr Ser Glu Phe Ala Arg Lys Trp Val Pro
                405                 410                 415

Phe Val Lys Lys Tyr Asn Ile Glu Pro Arg Ala Pro Glu Trp Tyr Phe
            420                 425                 430

Ser Gln Lys Ile Asp Tyr Leu Lys Asp Lys Val His Pro Ser Phe Val
        435                 440                 445

Lys Asp Arg Arg Ala Met Lys Arg Glu Tyr Glu Glu Phe Lys Val Arg
    450                 455                 460

Val Asn Gly Leu Val Ala Lys Ala Gln Lys Val Pro Glu Glu Gly Trp
465                 470                 475                 480
```

-continued

```
Ile Met Gln Asp Gly Thr Pro Trp Pro Gly Asn Asn Thr Arg Asp His
                485                 490                 495

Pro Gly Met Ile Gln Val Phe Leu Gly His Ser Gly Gly Leu Asp Thr
            500                 505                 510

Glu Gly Asn Glu Leu Pro Arg Leu Val Tyr Val Ser Arg Glu Lys Arg
        515                 520                 525

Pro Gly Phe Gln His His Lys Lys Ala Gly Ala Met Asn Ala Leu Val
    530                 535                 540

Arg Val Ser Ala Val Leu Thr Asn Gly Gln Tyr Met Leu Asn Leu Asp
545                 550                 555                 560

Cys Asp His Tyr Ile Asn Asn Ser Lys Ala Leu Arg Glu Ala Met Cys
                565                 570                 575

Phe Leu Met Asp Pro Asn Leu Gly Arg Ser Val Cys Tyr Val Gln Phe
            580                 585                 590

Pro Gln Arg Phe Asp Gly Ile Asp Arg Asn Asp Arg Tyr Ala Asn Arg
        595                 600                 605

Asn Thr Val Phe Phe Asp Ile Asn Leu Arg Gly Leu Asp Gly Ile Gln
    610                 615                 620

Gly Pro Val Tyr Val Gly Thr Gly Cys Val Phe Asn Arg Thr Ala Leu
625                 630                 635                 640

Tyr Gly Tyr Glu Pro Pro Ile Lys Gln Lys Lys Gly Gly Phe Leu Ser
                645                 650                 655

Ser Leu Cys Gly Gly Arg Lys Lys Ala Ser Lys Ser Lys Lys Gly Ser
            660                 665                 670

Asp Lys Lys Lys Ser Gln Lys His Val Asp Ser Ser Val Pro Val Phe
        675                 680                 685

Asn Leu Glu Asp Ile Glu Glu Gly Val Glu Gly Ala Gly Phe Asp Asp
    690                 695                 700

Glu Lys Ser Leu Leu Met Ser Gln Met Ser Leu Glu Lys Arg Phe Gly
705                 710                 715                 720

Gln Ser Ala Ala Phe Val Ala Ser Thr Leu Met Glu Tyr Gly Gly Val
                725                 730                 735

Pro Gln Ser Ala Thr Pro Glu Ser Leu Leu Lys Glu Ala Ile His Val
            740                 745                 750

Ile Ser Cys Gly Tyr Glu Asp Lys Thr Glu Trp Gly Thr Glu Ile Gly
        755                 760                 765

Trp Ile Tyr Gly Ser Val Thr Glu Asp Ile Leu Thr Gly Phe Lys Met
    770                 775                 780

His Ala Arg Gly Trp Arg Ser Ile Tyr Cys Met Pro Lys Arg Pro Ala
785                 790                 795                 800

Phe Lys Gly Ser Ala Pro Ile Asn Leu Ser Asp Arg Leu Asn Gln Val
                805                 810                 815

Leu Arg Trp Ala Leu Gly Ser Val Glu Ile Leu Phe Ser Arg His Cys
            820                 825                 830

Pro Leu Trp Tyr Gly Tyr Gly Gly Arg Leu Lys Phe Leu Glu Arg Phe
        835                 840                 845

Ala Tyr Ile Asn Thr Thr Ile Tyr Pro Leu Thr Ser Ile Pro Leu Leu
    850                 855                 860

Ile Tyr Cys Ile Leu Pro Ala Ile Cys Leu Leu Thr Gly Lys Phe Ile
865                 870                 875                 880

Ile Pro Glu Ile Ser Asn Phe Ala Ser Ile Trp Phe Ile Ser Leu Phe
                885                 890                 895
```

-continued

```
Ile Ser Ile Phe Ala Thr Gly Ile Leu Glu Met Arg Trp Ser Gly Val
            900                 905                 910

Gly Ile Asp Glu Trp Trp Arg Asn Glu Gln Phe Trp Val Ile Gly Gly
        915                 920                 925

Ile Ser Ala His Leu Phe Ala Val Phe Gln Gly Leu Leu Lys Val Leu
    930                 935                 940

Ala Gly Ile Asp Thr Asn Phe Thr Val Thr Ser Lys Ala Ser Asp Glu
945                 950                 955                 960

Asp Gly Asp Phe Ala Glu Leu Tyr Met Phe Lys Trp Thr Thr Leu Leu
                965                 970                 975

Ile Pro Pro Thr Thr Ile Leu Ile Ile Asn Leu Val Gly Val Val Ala
            980                 985                 990

Gly Ile Ser Tyr Ala Ile Asn Ser  Gly Tyr Gln Ser Trp  Gly Pro Leu
        995                 1000                 1005

Phe Gly  Lys Leu Phe Phe Ala  Phe Trp Val Ile Val  His Leu Tyr
    1010                 1015                 1020

Pro Phe  Leu Lys Gly Leu Met  Gly Arg Gln Asn Arg  Thr Pro Thr
    1025                 1030                 1035

Ile Val  Val Val Trp Ala Ile  Leu Leu Ala Ser Ile  Phe Ser Leu
    1040                 1045                 1050

Leu Trp  Val Arg Ile Asp Pro  Phe Thr Thr Arg Val  Thr Gly Pro
    1055                 1060                 1065

Asp Thr  Gln Thr Cys Gly Ile  Asn Cys
    1070                 1075


<210> SEQ ID NO 17
<211> LENGTH: 1094
<212> TYPE: PRT
<213> ORGANISM: Zea mays

<400> SEQUENCE: 17

Met Glu Ala Ser Ala Gly Leu Val Ala Gly Ser His Asn Arg Asn Glu
1               5                   10                  15

Leu Val Val Ile Arg Arg Asp Arg Glu Ser Gly Ala Ala Gly Gly Gly
            20                  25                  30

Ala Ala Arg Arg Ala Glu Ala Pro Cys Gln Ile Cys Gly Asp Glu Val
        35                  40                  45

Gly Val Gly Phe Asp Gly Glu Pro Phe Val Ala Cys Asn Glu Cys Ala
    50                  55                  60

Phe Pro Val Cys Arg Ala Cys Tyr Glu Tyr Glu Arg Arg Glu Gly Ser
65                  70                  75                  80

Gln Ala Cys Pro Gln Cys Arg Thr Arg Tyr Lys Arg Leu Lys Gly Cys
                85                  90                  95

Pro Arg Val Ala Gly Asp Glu Glu Glu Asp Gly Val Asp Asp Leu Glu
            100                 105                 110

Gly Glu Phe Gly Leu Gln Asp Gly Ala Ala His Glu Asp Asp Pro Gln
        115                 120                 125

Tyr Val Ala Glu Ser Met Leu Arg Ala Gln Met Ser Tyr Gly Arg Gly
    130                 135                 140

Gly Asp Ala His Pro Gly Phe Ser Pro Val Pro Asn Val Pro Leu Leu
145                 150                 155                 160

Thr Asn Gly Gln Met Val Asp Asp Ile Pro Pro Glu Gln His Ala Leu
                165                 170                 175

Val Pro Ser Tyr Met Ser Gly Gly Gly Gly Gly Gly Lys Arg Ile His
            180                 185                 190
```

```
Pro Leu Pro Phe Ala Asp Pro Asn Leu Pro Val Gln Pro Arg Ser Met
        195                 200                 205

Asp Pro Ser Lys Asp Leu Ala Ala Tyr Gly Tyr Gly Ser Val Ala Trp
    210                 215                 220

Lys Glu Arg Met Glu Gly Trp Lys Gln Lys Gln Glu Arg Leu Gln His
225                 230                 235                 240

Val Arg Ser Glu Gly Gly Gly Asp Trp Asp Gly Asp Asp Ala Asp Leu
                245                 250                 255

Pro Leu Met Asp Glu Ala Arg Gln Pro Leu Ser Arg Lys Val Pro Ile
            260                 265                 270

Ser Ser Ser Arg Ile Asn Pro Tyr Arg Met Ile Ile Val Ile Arg Leu
        275                 280                 285

Val Val Leu Gly Phe Phe Phe His Tyr Arg Val Met His Pro Ala Lys
    290                 295                 300

Asp Ala Phe Ala Leu Trp Leu Ile Ser Val Ile Cys Glu Ile Trp Phe
305                 310                 315                 320

Ala Met Ser Trp Ile Leu Asp Gln Phe Pro Lys Trp Leu Pro Ile Glu
                325                 330                 335

Arg Glu Thr Tyr Leu Asp Arg Leu Ser Leu Arg Phe Asp Lys Glu Gly
            340                 345                 350

Gln Pro Ser Gln Leu Ala Pro Ile Asp Phe Phe Val Ser Thr Val Asp
        355                 360                 365

Pro Thr Lys Glu Pro Pro Leu Val Thr Ala Asn Thr Val Leu Ser Ile
    370                 375                 380

Leu Ser Val Asp Tyr Pro Val Glu Lys Val Ser Cys Tyr Val Ser Asp
385                 390                 395                 400

Asp Gly Ala Ala Met Leu Thr Phe Glu Ala Leu Ser Glu Thr Ser Glu
                405                 410                 415

Phe Ala Lys Lys Trp Val Pro Phe Ser Lys Lys Phe Asn Ile Glu Pro
            420                 425                 430

Arg Ala Pro Glu Trp Tyr Phe Gln Gln Lys Ile Asp Tyr Leu Lys Asp
        435                 440                 445

Lys Val Ala Ala Ser Phe Val Arg Glu Arg Arg Ala Met Lys Arg Glu
    450                 455                 460

Tyr Glu Glu Phe Lys Val Arg Ile Asn Ala Leu Val Ala Lys Ala Gln
465                 470                 475                 480

Lys Val Pro Glu Glu Gly Trp Thr Met Gln Asp Gly Ser Pro Trp Pro
                485                 490                 495

Gly Asn Asn Val Arg Asp His Pro Gly Met Ile Gln Val Phe Leu Gly
            500                 505                 510

Gln Ser Gly Gly Arg Asp Val Glu Gly Asn Glu Leu Pro Arg Leu Val
        515                 520                 525

Tyr Val Ser Arg Glu Lys Arg Pro Gly Tyr Asn His His Lys Lys Ala
    530                 535                 540

Gly Ala Met Asn Ala Leu Val Arg Val Ser Ala Val Leu Ser Asn Ala
545                 550                 555                 560

Ala Tyr Leu Leu Asn Leu Asp Cys Asp His Tyr Ile Asn Asn Ser Lys
                565                 570                 575

Ala Ile Lys Glu Ala Met Cys Phe Met Met Asp Pro Leu Val Gly Lys
            580                 585                 590

Lys Val Cys Tyr Val Gln Phe Pro Gln Arg Phe Asp Gly Ile Asp Lys
        595                 600                 605
```

```
Asn Asp Arg Tyr Ala Asn Arg Asn Val Val Phe Phe Asp Ile Asn Met
    610                 615                 620

Lys Gly Leu Asp Gly Ile Gln Gly Pro Ile Tyr Val Gly Thr Gly Cys
625                 630                 635                 640

Val Phe Arg Arg Gln Ala Leu Tyr Gly Tyr Asp Ala Pro Lys Thr Lys
                645                 650                 655

Lys Pro Pro Ser Arg Thr Cys Asn Cys Trp Pro Lys Trp Cys Leu Ser
            660                 665                 670

Cys Cys Cys Ser Arg Asn Lys Asn Lys Lys Lys Thr Thr Lys Pro Lys
        675                 680                 685

Thr Glu Lys Lys Lys Arg Leu Phe Phe Lys Lys Ala Glu Asn Pro Ser
    690                 695                 700

Pro Ala Tyr Ala Leu Gly Glu Ile Asp Glu Gly Ala Pro Gly Ala Asp
705                 710                 715                 720

Ile Glu Lys Ala Gly Ile Val Asn Gln Gln Lys Leu Glu Lys Lys Phe
                725                 730                 735

Gly Gln Ser Ser Val Phe Val Ala Ser Thr Leu Leu Glu Asn Gly Gly
            740                 745                 750

Thr Leu Lys Ser Ala Ser Pro Ala Ser Leu Leu Lys Glu Ala Ile His
        755                 760                 765

Val Ile Ser Cys Gly Tyr Glu Asp Lys Thr Asp Trp Gly Lys Glu Ile
    770                 775                 780

Gly Trp Ile Tyr Gly Ser Ile Thr Glu Asp Ile Leu Thr Gly Phe Lys
785                 790                 795                 800

Met His Cys His Gly Trp Arg Ser Ile Tyr Cys Ile Pro Lys Arg Pro
                805                 810                 815

Ala Phe Lys Gly Ser Ala Pro Leu Asn Leu Ser Asp Arg Leu His Gln
            820                 825                 830

Val Leu Arg Trp Ala Leu Gly Ser Val Glu Ile Phe Phe Ser Lys His
        835                 840                 845

Cys Pro Leu Trp Tyr Gly Tyr Gly Gly Gly Leu Lys Phe Leu Glu Arg
    850                 855                 860

Phe Ser Tyr Ile Asn Ser Ile Val Tyr Pro Trp Thr Ser Ile Pro Leu
865                 870                 875                 880

Leu Ala Tyr Cys Thr Leu Pro Ala Ile Cys Leu Leu Thr Gly Lys Phe
                885                 890                 895

Ile Thr Pro Glu Leu Thr Asn Val Ala Ser Ile Trp Phe Met Ala Leu
            900                 905                 910

Phe Ile Cys Ile Ser Val Thr Gly Ile Leu Glu Met Arg Trp Ser Gly
        915                 920                 925

Val Ala Ile Asp Asp Trp Trp Arg Asn Glu Gln Phe Trp Val Ile Gly
    930                 935                 940

Gly Val Ser Ala His Leu Phe Ala Val Phe Gln Gly Leu Leu Lys Val
945                 950                 955                 960

Phe Ala Gly Ile Asp Thr Ser Phe Thr Val Thr Ser Lys Ala Gly Asp
                965                 970                 975

Asp Glu Glu Phe Ser Glu Leu Tyr Thr Phe Lys Trp Thr Thr Leu Leu
            980                 985                 990

Ile Pro Pro Thr Thr Leu Leu Leu  Leu Asn Phe Ile Gly  Val Val Ala
        995                 1000                1005

Gly Ile  Ser Asn Ala Ile Asn  Asn Gly Tyr Glu Ser  Trp Gly Pro
    1010                1015                1020

Leu Phe  Gly Lys Leu Phe Phe  Ala Phe Trp Val Ile  Val His Leu
```

```
    1025                1030                1035

Tyr Pro  Phe Leu Lys Gly Leu  Val Gly Arg Gln Asn  Arg Thr Pro
    1040                1045                1050

Thr Ile  Val Ile Val Trp Ser  Ile Leu Leu Ala Ser  Ile Phe Ser
    1055                1060                1065

Leu Leu  Trp Val Arg Val Asp  Pro Phe Leu Ala Lys  Ser Asn Gly
    1070                1075                1080

Pro Leu  Leu Glu Glu Cys Gly  Leu Asp Cys Asn
    1085                1090


<210> SEQ ID NO 18
<211> LENGTH: 596
<212> TYPE: PRT
<213> ORGANISM: Zea mays

<400> SEQUENCE: 18

Met Gln Asp Gly Thr Pro Trp Pro Gly Asn Asn Thr Arg Asp His Pro
1               5                   10                  15

Gly Met Ile Gln Val Phe Leu Gly His Ser Gly Gly Leu Asp Thr Glu
            20                  25                  30

Gly Asn Glu Leu Pro Arg Leu Val Tyr Val Ser Arg Glu Lys Arg Pro
        35                  40                  45

Gly Phe Gln His His Lys Lys Ala Gly Ala Met Asn Ala Leu Val Arg
    50                  55                  60

Val Ser Ala Val Leu Thr Asn Gly Gln Tyr Met Leu Asn Leu Asp Cys
65                  70                  75                  80

Asp His Tyr Ile Asn Asn Ser Lys Ala Leu Arg Glu Ala Met Cys Phe
                85                  90                  95

Leu Met Asp Pro Asn Leu Gly Arg Ser Val Cys Tyr Val Gln Phe Pro
            100                 105                 110

Gln Arg Phe Asp Gly Ile Asp Arg Asn Asp Arg Tyr Ala Asn Arg Asn
        115                 120                 125

Thr Val Phe Phe Asp Ile Asn Leu Arg Gly Leu Asp Gly Ile Gln Gly
    130                 135                 140

Pro Val Tyr Val Gly Thr Gly Cys Val Phe Asn Arg Thr Ala Leu Tyr
145                 150                 155                 160

Gly Tyr Glu Pro Pro Ile Lys Gln Lys Lys Gly Gly Phe Leu Ser Ser
                165                 170                 175

Leu Cys Gly Gly Arg Lys Lys Gly Ser Lys Ser Lys Lys Gly Ser Asp
            180                 185                 190

Lys Lys Lys Ser Gln Lys His Val Asp Ser Ser Val Pro Val Phe Asn
        195                 200                 205

Leu Glu Asp Ile Glu Glu Gly Val Glu Gly Ala Gly Phe Asp Asp Glu
    210                 215                 220

Lys Ser Leu Leu Met Ser Gln Met Ser Leu Glu Lys Arg Phe Gly Gln
225                 230                 235                 240

Ser Ala Ala Phe Val Ala Ser Thr Leu Met Glu Tyr Gly Gly Val Pro
                245                 250                 255

Gln Ser Ala Thr Pro Glu Ser Leu Leu Lys Glu Ala Ile His Val Ile
            260                 265                 270

Ser Cys Gly Tyr Glu Asp Lys Thr Glu Trp Gly Thr Glu Ile Gly Trp
        275                 280                 285

Ile Tyr Gly Ser Val Thr Glu Asp Ile Leu Thr Gly Phe Lys Met His
    290                 295                 300
```

```
Ala Arg Gly Trp Arg Ser Ile Tyr Cys Met Pro Lys Arg Pro Ala Phe
305                 310                 315                 320

Lys Gly Ser Ala Pro Ile Asn Leu Ser Asp Arg Leu Asn Gln Val Leu
                325                 330                 335

Arg Trp Ala Leu Gly Ser Val Glu Ile Leu Phe Ser Arg His Cys Pro
            340                 345                 350

Leu Trp Tyr Gly Tyr Gly Gly Arg Leu Lys Phe Leu Glu Arg Phe Ala
        355                 360                 365

Tyr Ile Asn Thr Thr Ile Tyr Pro Leu Thr Ser Leu Pro Leu Leu Ile
    370                 375                 380

Tyr Cys Ile Leu Pro Ala Ile Cys Leu Leu Thr Gly Lys Phe Ile Ile
385                 390                 395                 400

Pro Glu Ile Ser Asn Phe Ala Ser Ile Trp Phe Ile Ser Leu Phe Ile
                405                 410                 415

Ser Ile Phe Ala Thr Gly Ile Leu Glu Met Arg Trp Ser Gly Val Gly
            420                 425                 430

Ile Asp Glu Trp Trp Arg Asn Glu Gln Phe Trp Val Ile Gly Gly Ile
        435                 440                 445

Ser Ala His Leu Phe Ala Val Phe Gln Gly Leu Leu Lys Val Leu Ala
    450                 455                 460

Gly Ile Asp Thr Asn Phe Thr Val Thr Ser Lys Ala Ser Asp Glu Asp
465                 470                 475                 480

Gly Asp Phe Ala Glu Leu Tyr Met Phe Lys Trp Thr Thr Leu Leu Ile
                485                 490                 495

Pro Pro Thr Thr Ile Leu Ile Ile Asn Leu Val Gly Val Val Ala Gly
            500                 505                 510

Ile Ser Tyr Ala Ile Asn Ser Gly Tyr Gln Ser Trp Gly Pro Leu Phe
        515                 520                 525

Gly Lys Leu Phe Phe Ala Phe Trp Val Ile Val His Leu Tyr Pro Phe
    530                 535                 540

Leu Lys Gly Leu Met Gly Arg Gln Asn Arg Thr Pro Thr Ile Val Val
545                 550                 555                 560

Val Trp Ala Ile Leu Leu Ala Ser Ile Phe Ser Leu Leu Trp Val Arg
                565                 570                 575

Ile Asp Pro Phe Thr Thr Arg Val Thr Gly Pro Asp Thr Arg Thr Cys
            580                 585                 590

Gly Ile Asn Cys
        595
```

<210> SEQ ID NO 19
<211> LENGTH: 1083
<212> TYPE: PRT
<213> ORGANISM: Zea mays

<400> SEQUENCE: 19

```
Met Glu Ala Ser Ala Gly Leu Val Ala Gly Ser His Asn Arg Asn Glu
1               5                   10                  15

Leu Val Val Ile Arg Arg Asp Gly Asp Pro Gly Pro Lys Pro Pro Pro
            20                  25                  30

Arg Glu Gln Asn Gly Gln Val Cys Gln Ile Cys Gly Asp Asp Val Gly
        35                  40                  45

Leu Ala Pro Gly Gly Glu Pro Phe Val Ala Cys Asn Glu Cys Ala Phe
    50                  55                  60

Pro Val Cys Arg Asp Cys Tyr Glu Tyr Glu Arg Arg Glu Gly Thr Gln
65                  70                  75                  80
```

```
Asn Cys Pro Gln Cys Arg Thr Arg Tyr Lys Arg Leu Lys Gly Cys Gln
                85                  90                  95

Arg Val Thr Gly Asp Glu Glu Glu Asp Gly Val Asp Asp Leu Asp Asn
            100                 105                 110

Glu Phe Asn Trp Asn Gly His Asp Ser Arg Ser Val Ala Asp Ser Met
        115                 120                 125

Leu Tyr Gly Arg Gly Gly Asp Pro Asn Gly Ala Pro Gln Pro Phe Gln
    130                 135                 140

Leu Asn Pro Asn Val Pro Leu Leu Thr Asn Gly Gln Met Val Asp Asp
145                 150                 155                 160

Ile Pro Pro Glu Gln His Ala Leu Val Pro Ser Phe Met Gly Gly Gly
                165                 170                 175

Gly Lys Arg Ile His Pro Leu Pro Tyr Ala Asp Pro Ser Leu Pro Val
            180                 185                 190

Gln Pro Arg Ser Met Asp Pro Ser Lys Asp Leu Ala Ala Tyr Gly Tyr
        195                 200                 205

Gly Ser Val Ala Trp Lys Glu Arg Val Glu Asn Trp Lys Gln Arg Gln
    210                 215                 220

Glu Arg Met His Gln Thr Arg Asn Asp Gly Gly Gly Asp Asp Gly Asp
225                 230                 235                 240

Asp Ala Asp Leu Pro Leu Met Asp Glu Ser Arg Gln Pro Leu Ser Arg
                245                 250                 255

Lys Ile Pro Leu Pro Ser Ser Gln Ile Asn Pro Tyr Arg Met Ile Ile
            260                 265                 270

Ile Ile Arg Leu Val Val Leu Gly Phe Phe Phe His Tyr Arg Val Met
        275                 280                 285

His Pro Val Asn Asp Ala Phe Ala Leu Trp Leu Ile Ser Val Ile Cys
    290                 295                 300

Glu Ile Trp Phe Ala Met Ser Trp Ile Leu Asp Gln Phe Pro Lys Trp
305                 310                 315                 320

Phe Pro Ile Glu Arg Glu Thr Tyr Leu Asp Arg Leu Ser Leu Arg Phe
                325                 330                 335

Asp Lys Glu Gly Gln Pro Ser Gln Leu Ala Pro Ile Asp Phe Phe Val
            340                 345                 350

Ser Thr Val Asp Pro Leu Lys Glu Pro Pro Leu Val Thr Ala Asn Thr
        355                 360                 365

Val Leu Ser Ile Leu Ser Val Asp Tyr Pro Val Asp Lys Val Ser Cys
    370                 375                 380

Tyr Val Ser Asp Asp Gly Ala Ala Met Leu Thr Phe Glu Ala Leu Ser
385                 390                 395                 400

Glu Thr Ser Glu Phe Ala Lys Lys Trp Ala Pro Phe Cys Lys Arg Tyr
                405                 410                 415

Asn Ile Glu Pro Arg Ala Pro Glu Trp Tyr Phe Gln Gln Lys Ile Asp
            420                 425                 430

Tyr Leu Lys Asp Lys Val Ala Ala Asn Phe Val Arg Glu Arg Arg Ala
        435                 440                 445

Met Lys Arg Glu Tyr Glu Glu Phe Lys Val Arg Ile Asn Ala Leu Val
    450                 455                 460

Ala Lys Ala Gln Lys Val Pro Glu Glu Gly Trp Thr Met Gln Asp Gly
465                 470                 475                 480

Thr Pro Trp Pro Gly Asn Asn Val Arg Asp His Pro Gly Met Ile Gln
                485                 490                 495
```

```
Val Phe Leu Gly Gln Ser Gly Gly Leu Asp Cys Glu Gly Asn Glu Leu
            500                 505                 510

Pro Arg Leu Val Tyr Val Ser Arg Glu Lys Arg Pro Gly Tyr Asn His
        515                 520                 525

His Lys Lys Ala Gly Ala Met Asn Ala Leu Val Arg Val Ser Ala Val
    530                 535                 540

Leu Ser Asn Ala Pro Tyr Leu Leu Asn Leu Asp Cys Asp His Tyr Ile
545                 550                 555                 560

Asn Asn Ser Lys Ala Ile Lys Glu Ala Met Cys Phe Met Met Asp Pro
                565                 570                 575

Leu Leu Gly Lys Lys Val Cys Tyr Val Gln Phe Pro Gln Arg Phe Asp
            580                 585                 590

Gly Ile Asp Arg His Asp Arg Tyr Ala Asn Arg Asn Val Val Phe Phe
        595                 600                 605

Asp Ile Asn Met Lys Gly Leu Asp Gly Ile Gln Gly Pro Ile Tyr Val
    610                 615                 620

Gly Thr Gly Cys Val Phe Arg Arg Gln Ala Leu Tyr Gly Tyr Asp Ala
625                 630                 635                 640

Pro Lys Thr Lys Lys Pro Pro Ser Arg Thr Cys Asn Cys Trp Pro Lys
                645                 650                 655

Trp Cys Phe Cys Cys Cys Cys Cys Gly Asn Arg Lys His Lys Lys Lys
            660                 665                 670

Thr Thr Lys Pro Lys Thr Glu Lys Lys Lys Leu Leu Phe Phe Lys Lys
        675                 680                 685

Glu Glu Asn Gln Ser Pro Ala Tyr Ala Leu Gly Glu Ile Asp Glu Ala
    690                 695                 700

Ala Pro Gly Ala Glu Asn Glu Lys Ala Gly Ile Val Asn Gln Gln Lys
705                 710                 715                 720

Leu Glu Lys Lys Phe Gly Gln Ser Ser Val Phe Ala Thr Ser Thr Leu
                725                 730                 735

Leu Glu Asn Gly Gly Thr Leu Lys Ser Ala Ser Pro Ala Ser Leu Leu
            740                 745                 750

Lys Glu Ala Ile His Val Ile Ser Cys Gly Tyr Glu Asp Lys Thr Asp
        755                 760                 765

Trp Gly Lys Glu Ile Gly Trp Ile Tyr Gly Ser Val Thr Glu Asp Ile
    770                 775                 780

Leu Thr Gly Phe Lys Met His Cys His Gly Trp Arg Ser Ile Tyr Cys
785                 790                 795                 800

Ile Pro Lys Arg Pro Ala Phe Lys Gly Ser Ala Pro Leu Asn Leu Ser
                805                 810                 815

Asp Arg Leu His Gln Val Leu Arg Trp Ala Leu Gly Ser Ile Glu Ile
            820                 825                 830

Phe Phe Ser Asn His Cys Pro Leu Trp Tyr Gly Tyr Gly Gly Gly Leu
        835                 840                 845

Lys Phe Leu Glu Arg Phe Ser Tyr Ile Asn Ser Ile Val Tyr Pro Trp
    850                 855                 860

Thr Ser Ile Pro Leu Leu Ala Tyr Cys Thr Leu Pro Ala Ile Cys Leu
865                 870                 875                 880

Leu Thr Gly Lys Phe Ile Thr Pro Glu Leu Asn Asn Val Ala Ser Leu
                885                 890                 895

Trp Phe Met Ser Leu Phe Ile Cys Ile Phe Ala Thr Ser Ile Leu Glu
            900                 905                 910

Met Arg Trp Ser Gly Val Gly Ile Asp Asp Trp Trp Arg Asn Glu Gln
```

-continued

```
        915                 920                 925

Phe Trp Val Ile Gly Gly Val Ser Ser His Leu Phe Ala Val Phe Gln
    930                 935                 940

Gly Leu Leu Lys Val Ile Ala Gly Val Asp Thr Ser Phe Thr Val Thr
945                 950                 955                 960

Ser Lys Gly Gly Asp Asp Asp Glu Phe Ser Glu Leu Tyr Thr Phe Lys
                965                 970                 975

Trp Thr Thr Leu Leu Ile Pro Pro Thr Thr Leu Leu Leu Leu Asn Phe
            980                 985                 990

Ile Gly Val Val Ala Gly Val Ser  Asn Ala Ile Asn Asn  Gly Tyr Glu
        995                 1000                1005

Ser Trp  Gly Pro Leu Phe Gly  Lys Leu Phe Phe Ala  Phe Trp Val
    1010                1015                1020

Ile Val  His Leu Tyr Pro Phe  Leu Lys Gly Leu Val  Gly Arg Gln
    1025                1030                1035

Asn Arg  Thr Pro Thr Ile Val  Ile Val Trp Ser Ile  Leu Leu Ala
    1040                1045                1050

Ser Ile  Phe Ser Leu Leu Trp  Val Arg Ile Asp Pro  Phe Leu Ala
    1055                1060                1065

Lys Asp  Asp Gly Pro Leu Leu  Glu Glu Cys Gly Leu  Asp Cys Asn
    1070                1075                1080


<210> SEQ ID NO 20
<211> LENGTH: 1079
<212> TYPE: PRT
<213> ORGANISM: Zea mays

<400> SEQUENCE: 20

Met Glu Gly Asp Ala Asp Gly Val Lys Ser Gly Arg Arg Gly Gly Gly
1               5                   10                  15

Gln Val Cys Gln Ile Cys Gly Asp Gly Val Gly Thr Thr Ala Glu Gly
            20                  25                  30

Asp Val Phe Thr Ala Cys Asp Val Cys Gly Phe Pro Val Cys Arg Pro
        35                  40                  45

Cys Tyr Glu Tyr Glu Arg Lys Asp Gly Thr Gln Ala Cys Pro Gln Cys
    50                  55                  60

Lys Asn Lys Tyr Lys Arg His Lys Gly Ser Pro Ala Ile Arg Gly Glu
65                  70                  75                  80

Glu Gly Asp Asp Thr Asp Ala Asp Asp Ala Ser Asp Phe Asn Tyr Pro
                85                  90                  95

Ala Ser Gly Asn Asp Asp Gln Lys Gln Lys Ile Ala Asp Arg Met Arg
            100                 105                 110

Ser Trp Arg Met Asn Ala Gly Gly Ser Gly Asp Val Gly Arg Pro Lys
        115                 120                 125

Tyr Asp Ser Gly Glu Ile Gly Leu Thr Lys Tyr Asp Ser Gly Glu Ile
    130                 135                 140

Pro Arg Gly Tyr Ile Pro Ser Val Thr Asn Ser Gln Ile Ser Gly Glu
145                 150                 155                 160

Ile Pro Gly Ala Ser Pro Asp His His Met Met Ser Pro Thr Gly Asn
                165                 170                 175

Ile Gly Arg Arg Ala Pro Phe Pro Tyr Met Asn His Ser Ser Asn Pro
            180                 185                 190

Ser Arg Glu Phe Ser Gly Ser Val Gly Asn Val Ala Trp Lys Glu Arg
        195                 200                 205
```

-continued

```
Val Asp Gly Trp Lys Met Lys Gln Asp Lys Gly Thr Ile Pro Met Thr
    210                 215                 220

Asn Gly Thr Ser Ile Ala Pro Ser Glu Gly Arg Gly Val Gly Asp Ile
225                 230                 235                 240

Asp Ala Ser Thr Asp Tyr Asn Met Glu Asp Ala Leu Leu Asn Asp Glu
                245                 250                 255

Thr Arg Gln Pro Leu Ser Arg Lys Val Pro Leu Pro Ser Ser Arg Ile
            260                 265                 270

Asn Pro Tyr Arg Met Val Ile Val Leu Arg Leu Ile Val Leu Ser Ile
        275                 280                 285

Phe Leu His Tyr Arg Ile Thr Asn Pro Val Arg Asn Ala Tyr Pro Leu
    290                 295                 300

Trp Leu Leu Ser Val Ile Cys Glu Ile Trp Phe Ala Leu Ser Trp Ile
305                 310                 315                 320

Leu Asp Gln Phe Pro Lys Trp Phe Pro Ile Asn Arg Glu Thr Tyr Leu
                325                 330                 335

Asp Arg Leu Ala Leu Arg Tyr Asp Arg Glu Gly Glu Pro Ser Gln Leu
            340                 345                 350

Ala Ala Val Asp Ile Phe Val Ser Thr Val Asp Pro Met Lys Glu Pro
        355                 360                 365

Pro Leu Val Thr Ala Asn Thr Val Leu Ser Ile Leu Ala Val Asp Tyr
    370                 375                 380

Pro Val Asp Lys Val Ser Cys Tyr Val Ser Asp Asp Gly Ala Ala Met
385                 390                 395                 400

Leu Thr Phe Asp Ala Leu Ala Glu Thr Ser Glu Phe Ala Arg Lys Trp
                405                 410                 415

Val Pro Phe Val Lys Lys Tyr Asn Ile Glu Pro Arg Ala Pro Glu Trp
            420                 425                 430

Tyr Phe Ser Gln Lys Ile Asp Tyr Leu Lys Asp Lys Val His Pro Ser
        435                 440                 445

Phe Val Lys Asp Arg Arg Ala Met Lys Arg Glu Tyr Glu Glu Phe Lys
    450                 455                 460

Ile Arg Val Asn Gly Leu Val Ala Lys Ala Gln Lys Val Pro Glu Glu
465                 470                 475                 480

Gly Trp Ile Met Gln Asp Gly Thr Pro Trp Pro Gly Asn Asn Thr Arg
                485                 490                 495

Asp His Pro Gly Met Ile Gln Val Phe Leu Gly His Ser Gly Gly Leu
            500                 505                 510

Asp Thr Glu Gly Asn Glu Leu Pro Arg Leu Val Tyr Val Ser Arg Glu
        515                 520                 525

Lys Arg Pro Gly Phe Gln His His Lys Lys Ala Gly Ala Met Asn Ala
    530                 535                 540

Leu Val Arg Val Ser Ala Val Leu Thr Asn Gly Gln Tyr Met Leu Asn
545                 550                 555                 560

Leu Asp Cys Asp His Tyr Ile Asn Asn Ser Lys Ala Leu Arg Glu Ala
                565                 570                 575

Met Cys Phe Leu Met Asp Pro Asn Leu Gly Arg Ser Val Cys Tyr Val
            580                 585                 590

Gln Phe Pro Gln Arg Phe Asp Gly Ile Asp Arg Asn Asp Arg Tyr Ala
        595                 600                 605

Asn Arg Asn Thr Val Phe Phe Asp Ile Asn Leu Arg Gly Leu Asp Gly
    610                 615                 620

Ile Gln Gly Pro Val Tyr Val Gly Thr Gly Cys Val Phe Asn Arg Thr
```

```
625                 630                 635                 640

Ala Leu Tyr Gly Tyr Glu Pro Pro Ile Lys Gln Lys Lys Gly Gly Phe
                645                 650                 655

Leu Ser Ser Leu Cys Gly Gly Arg Lys Lys Gly Ser Lys Ser Lys Lys
            660                 665                 670

Gly Ser Asp Lys Lys Lys Ser Gln Lys His Val Asp Ser Ser Val Pro
        675                 680                 685

Val Phe Asn Leu Glu Asp Ile Glu Glu Gly Val Glu Gly Ala Gly Phe
    690                 695                 700

Asp Asp Glu Lys Ser Leu Leu Met Ser Gln Met Ser Leu Glu Lys Arg
705                 710                 715                 720

Phe Gly Gln Ser Ala Ala Phe Val Ala Ser Thr Leu Met Glu Tyr Gly
                725                 730                 735

Gly Val Pro Gln Ser Ala Thr Pro Glu Ser Leu Leu Lys Glu Ala Ile
            740                 745                 750

His Val Ile Ser Cys Gly Tyr Glu Asp Lys Thr Glu Trp Gly Thr Glu
        755                 760                 765

Ile Gly Trp Ile Tyr Gly Ser Val Thr Glu Asp Ile Leu Thr Gly Phe
    770                 775                 780

Lys Met His Ala Arg Gly Trp Arg Ser Ile Tyr Cys Met Pro Lys Arg
785                 790                 795                 800

Pro Ala Phe Lys Gly Ser Ala Pro Ile Asn Leu Ser Asp Arg Leu Asn
                805                 810                 815

Gln Val Leu Arg Trp Ala Leu Gly Ser Val Glu Ile Leu Phe Ser Arg
            820                 825                 830

His Cys Pro Leu Trp Tyr Gly Tyr Gly Gly Arg Leu Lys Phe Leu Glu
        835                 840                 845

Arg Phe Ala Tyr Ile Asn Thr Thr Ile Tyr Pro Leu Thr Ser Leu Pro
    850                 855                 860

Leu Leu Ile Tyr Cys Ile Leu Pro Ala Ile Cys Leu Leu Thr Gly Lys
865                 870                 875                 880

Phe Ile Ile Pro Glu Ile Ser Asn Phe Ala Ser Ile Trp Phe Ile Ser
                885                 890                 895

Leu Phe Ile Ser Ile Phe Ala Thr Gly Ile Leu Glu Met Arg Trp Ser
            900                 905                 910

Gly Val Gly Ile Asp Glu Trp Trp Arg Asn Glu Gln Phe Trp Val Ile
        915                 920                 925

Gly Gly Ile Ser Ala His Leu Phe Ala Val Phe Gln Gly Leu Leu Lys
    930                 935                 940

Val Leu Ala Gly Ile Asp Thr Asn Phe Thr Val Thr Ser Lys Ala Ser
945                 950                 955                 960

Asp Glu Asp Gly Asp Phe Ala Glu Leu Tyr Met Phe Lys Trp Thr Thr
                965                 970                 975

Leu Leu Ile Pro Pro Thr Thr Ile Leu Ile Ile Asn Leu Val Gly Val
            980                 985                 990

Val Ala Gly Ile Ser Tyr Ala Ile  Asn Ser Gly Tyr Gln  Ser Trp Gly
        995                 1000                 1005

Pro Leu  Phe Gly Lys Leu Phe  Phe Ala Phe Trp Val  Ile Val His
    1010                 1015                 1020

Leu Tyr  Pro Phe Leu Lys Gly  Leu Met Gly Arg Gln  Asn Arg Thr
    1025                 1030                 1035

Pro Thr  Ile Val Val Val Trp  Ala Ile Leu Leu Ala  Ser Ile Phe
    1040                 1045                 1050
```

```
Ser Leu  Leu Trp Val Arg Ile  Asp Pro Phe Thr Thr  Arg Val Thr
    1055                 1060                 1065

Gly Pro  Asp Thr Arg Thr Cys  Gly Ile Asn Cys
    1070                 1075


<210> SEQ ID NO 21
<211> LENGTH: 983
<212> TYPE: PRT
<213> ORGANISM: Zea mays

<400> SEQUENCE: 21

Met Met Glu Ser Ala Ala Ala Gln Ser Cys Ala Ala Cys Gly Asp Asp
1               5                   10                  15

Ala Arg Ala Ala Cys Arg Ala Cys Ser Tyr Ala Leu Cys Arg Ala Cys
            20                  25                  30

Leu Asp Glu Asp Ala Ala Glu Gly Arg Thr Thr Cys Ala Arg Cys Gly
        35                  40                  45

Gly Asp Tyr Ala Ala Ile Asn Pro Ala Arg Ala Ser Glu Gly Thr Glu
    50                  55                  60

Ala Glu Glu Glu Val Val Glu Asn His His Thr Ala Gly Gly Leu Arg
65                  70                  75                  80

Glu Arg Val Thr Met Gly Ser His Leu Asn Asp Arg Gln Asp Glu Val
                85                  90                  95

Ser His Ala Arg Thr Met Ser Ser Leu Ser Gly Ile Gly Ser Glu Leu
            100                 105                 110

Asn Asp Glu Ser Gly Lys Pro Ile Trp Lys Asn Arg Val Glu Ser Trp
        115                 120                 125

Lys Glu Lys Lys Asn Glu Lys Lys Ala Ser Ala Lys Lys Thr Ala Ala
    130                 135                 140

Lys Ala Gln Pro Pro Pro Val Glu Glu Gln Ile Met Asp Glu Lys Asp
145                 150                 155                 160

Leu Thr Asp Ala Tyr Glu Pro Leu Ser Arg Val Ile Pro Ile Ser Lys
                165                 170                 175

Asn Lys Leu Thr Pro Tyr Arg Ala Val Ile Ile Met Arg Leu Ile Val
            180                 185                 190

Leu Gly Leu Phe Phe His Tyr Arg Ile Thr Asn Pro Val Asn Ser Ala
        195                 200                 205

Phe Gly Leu Trp Met Thr Ser Val Ile Cys Glu Ile Trp Phe Gly Phe
    210                 215                 220

Ser Trp Ile Leu Asp Gln Phe Pro Lys Trp Tyr Pro Ile Asn Arg Glu
225                 230                 235                 240

Thr Tyr Val Asp Arg Leu Ile Ala Arg Tyr Gly Asp Gly Glu Glu Ser
                245                 250                 255

Gly Leu Ala Pro Val Asp Phe Phe Val Ser Thr Val Asp Pro Leu Lys
            260                 265                 270

Glu Pro Pro Leu Ile Thr Ala Asn Thr Val Leu Ser Ile Leu Ala Val
        275                 280                 285

Asp Tyr Pro Val Glu Lys Ile Ser Cys Tyr Val Ser Asp Asp Gly Ser
    290                 295                 300

Ala Met Leu Thr Phe Glu Ser Leu Ala Glu Thr Ala Glu Tyr Ala Arg
305                 310                 315                 320

Lys Trp Val Pro Phe Cys Lys Lys Tyr Ala Ile Glu Pro Arg Ala Pro
                325                 330                 335

Glu Phe Tyr Phe Ser Gln Lys Ile Asp Tyr Leu Lys Asp Lys Ile His
```

340 345 350

Pro Ser Phe Val Lys Glu Arg Arg Ala Met Lys Arg Asp Tyr Glu Glu
355 360 365

Tyr Lys Val Arg Ile Asn Ala Leu Val Ala Lys Ala Gln Lys Thr Pro
370 375 380

Asp Glu Gly Trp Ile Met Gln Asp Gly Thr Pro Trp Pro Gly Asn Asn
385 390 395 400

Pro Arg Asp His Pro Gly Met Ile Gln Val Phe Leu Gly Glu Thr Gly
405 410 415

Ala Arg Asp Phe Asp Gly Asn Glu Leu Pro Arg Leu Val Tyr Val Ser
420 425 430

Arg Glu Lys Arg Pro Gly Tyr Gln His His Lys Lys Ala Gly Ala Met
435 440 445

Asn Ala Leu Val Arg Val Ser Ala Val Leu Thr Asn Ala Pro Tyr Ile
450 455 460

Leu Asn Leu Asp Cys Asp His Tyr Val Asn Asn Ser Lys Ala Val Arg
465 470 475 480

Glu Ala Met Cys Phe Met Met Asp Pro Thr Val Gly Arg Asp Val Cys
485 490 495

Tyr Val Gln Phe Pro Gln Arg Phe Asp Gly Ile Asp Arg Ser Asp Arg
500 505 510

Tyr Ala Asn Arg Asn Val Val Phe Phe Asp Val Asn Met Lys Gly Leu
515 520 525

Asp Gly Leu Gln Gly Pro Val Tyr Val Gly Thr Gly Cys Cys Phe Asn
530 535 540

Arg Gln Ala Leu Tyr Gly Tyr Gly Pro Pro Ser Leu Pro Ala Leu Pro
545 550 555 560

Lys Ser Ser Ile Cys Ser Trp Cys Cys Cys Cys Cys Pro Lys Lys Lys
565 570 575

Val Glu Arg Ser Glu Arg Glu Ile Asn Arg Asp Ser Arg Arg Glu Asp
580 585 590

Leu Glu Ser Ala Ile Phe Asn Leu Arg Glu Ile Asp Asn Tyr Asp Glu
595 600 605

Tyr Glu Arg Ser Met Leu Ile Ser Gln Met Ser Phe Glu Lys Ser Phe
610 615 620

Gly Leu Ser Ser Val Phe Ile Glu Ser Thr Leu Met Glu Asn Gly Gly
625 630 635 640

Val Pro Glu Ser Ala Asn Pro Ser Thr Leu Ile Lys Glu Ala Ile His
645 650 655

Val Ile Ser Cys Gly Tyr Glu Glu Lys Thr Glu Trp Gly Lys Glu Ile
660 665 670

Gly Trp Ile Tyr Gly Ser Val Thr Glu Asp Ile Leu Thr Gly Phe Lys
675 680 685

Met His Cys Arg Gly Trp Arg Ser Ile Tyr Cys Met Pro Val Arg Pro
690 695 700

Ala Phe Lys Gly Ser Ala Pro Ile Asn Leu Ser Asp Arg Leu His Gln
705 710 715 720

Val Leu Arg Trp Ala Leu Gly Ser Val Glu Ile Phe Phe Ser Arg His
725 730 735

Cys Pro Leu Trp Tyr Gly Tyr Gly Gly Gly Arg Leu Lys Trp Leu Gln
740 745 750

Arg Leu Ser Tyr Ile Asn Thr Ile Val Tyr Pro Phe Thr Ser Leu Pro
755 760 765

```
Leu Val Ala Tyr Cys Cys Leu Pro Ala Ile Cys Leu Leu Thr Gly Lys
    770                 775                 780

Phe Ile Ile Pro Thr Leu Ser Asn Ala Ala Thr Ile Trp Phe Leu Gly
785                 790                 795                 800

Leu Phe Met Ser Ile Ile Val Thr Ser Val Leu Glu Leu Arg Trp Ser
                805                 810                 815

Gly Ile Gly Ile Glu Asp Trp Trp Arg Asn Glu Gln Phe Trp Val Ile
            820                 825                 830

Gly Gly Val Ser Ala His Leu Phe Ala Val Phe Gln Gly Ile Leu Lys
        835                 840                 845

Met Ile Ala Gly Leu Asp Thr Asn Phe Thr Val Thr Ala Lys Ala Thr
    850                 855                 860

Asp Asp Thr Glu Phe Gly Glu Leu Tyr Leu Phe Lys Trp Thr Thr Val
865                 870                 875                 880

Leu Ile Pro Pro Thr Ser Ile Leu Val Leu Asn Leu Val Gly Val Val
                885                 890                 895

Ala Gly Phe Ser Ala Ala Leu Asn Ser Gly Tyr Glu Ser Trp Gly Pro
            900                 905                 910

Leu Phe Gly Lys Val Phe Phe Ala Met Trp Val Ile Met His Leu Tyr
        915                 920                 925

Pro Phe Leu Lys Gly Leu Met Gly Arg Gln Asn Arg Thr Pro Thr Ile
    930                 935                 940

Val Val Leu Trp Ser Val Leu Leu Ala Ser Val Phe Ser Leu Leu Trp
945                 950                 955                 960

Val Lys Ile Asp Pro Phe Val Gly Gly Thr Glu Thr Val Asn Thr Asn
                965                 970                 975

Asn Cys Asn Thr Ile Ile Cys
            980
```

<210> SEQ ID NO 22
<211> LENGTH: 790
<212> TYPE: PRT
<213> ORGANISM: Zea mays

<400> SEQUENCE: 22

```
Met Glu Ala Ser Ala Gly Leu Val Ala Gly Ser His Asn Arg Asn Glu
1               5                   10                  15

Leu Val Val Ile Arg Arg Glu Ser Gly Ala Gly Gly Gly Gly Gly Gly
            20                  25                  30

Gly Ala Ala Arg Arg Ala Glu Ala Pro Cys Gln Ile Cys Gly Asp Glu
        35                  40                  45

Val Gly Val Gly Phe Asp Gly Glu Pro Phe Val Ala Cys Asn Glu Cys
    50                  55                  60

Ala Phe Pro Val Cys Arg Ala Cys Tyr Glu Tyr Glu Arg Arg Glu Gly
65                  70                  75                  80

Ser Gln Ala Cys Pro Gln Cys Arg Thr Arg Tyr Lys Arg Leu Lys Gly
                85                  90                  95

Cys Pro Arg Val Ala Gly Asp Glu Glu Glu Asp Gly Val Asp Asp Leu
            100                 105                 110

Glu Gly Glu Phe Gly Leu Gln Asp Gly Ala Gly His Glu Asp Asp Pro
        115                 120                 125

Gln Tyr Val Ala Glu Ser Met Leu Arg Ala Gln Met Ser Tyr Gly Arg
    130                 135                 140

Gly Gly Asp Ala His Pro Asp Phe Asn Pro Val Pro Asn Val Pro Leu
```

-continued

```
145                 150                 155                 160

Leu Thr Asn Gly Gln Met Val Asp Asp Ile Pro Pro Glu Gln His Ala
                165                 170                 175

Leu Val Pro Ser Tyr Met Gly Ser Gly Gly Gly Gly Lys Arg Ile His
            180                 185                 190

Pro Leu Pro Phe Ala Asp Ser Asn Leu Pro Val Gln Pro Arg Ser Met
        195                 200                 205

Asp Pro Ser Lys Asp Leu Ala Ala Tyr Gly Tyr Gly Ser Val Ala Trp
    210                 215                 220

Lys Glu Arg Met Glu Gly Trp Lys Gln Lys Gln Glu Arg Leu Gln His
225                 230                 235                 240

Val Arg Ser Glu Gly Gly Gly Asp Trp Asp Gly Asp Asn Ala Asp Leu
                245                 250                 255

Pro Leu Met Asp Glu Ala Arg Gln Pro Leu Ser Arg Lys Val Pro Ile
            260                 265                 270

Ser Ser Ser Arg Ile Asn Pro Tyr Arg Met Ile Ile Val Ile Arg Leu
        275                 280                 285

Val Val Leu Gly Phe Phe Phe His Tyr Arg Val Met His Pro Ala Lys
    290                 295                 300

Asp Ala Phe Ala Leu Trp Leu Ile Ser Val Ile Cys Glu Ile Trp Phe
305                 310                 315                 320

Ala Met Ser Trp Ile Leu Asp Gln Phe Pro Lys Trp Leu Pro Ile Glu
                325                 330                 335

Arg Glu Thr Tyr Leu Asp Arg Leu Ser Leu Arg Phe Asp Lys Glu Gly
            340                 345                 350

Gln Pro Ser Gln Leu Ala Pro Ile Asp Phe Phe Val Ser Thr Val Asp
        355                 360                 365

Pro Thr Lys Glu Pro Pro Leu Val Thr Ala Asn Thr Val Leu Ser Ile
    370                 375                 380

Leu Ser Val Asp Tyr Pro Val Glu Lys Val Ser Cys Tyr Val Ser Asp
385                 390                 395                 400

Asp Gly Ala Ala Met Leu Thr Phe Glu Ala Leu Ser Glu Thr Ser Glu
                405                 410                 415

Phe Ala Lys Lys Trp Val Pro Phe Ser Lys Lys Phe Asn Ile Glu Pro
            420                 425                 430

Arg Ala Pro Glu Trp Tyr Phe Gln Gln Lys Ile Asp Tyr Leu Lys Asp
        435                 440                 445

Lys Val Ala Ala Ser Phe Val Arg Glu Arg Arg Ala Met Lys Arg Glu
    450                 455                 460

Tyr Glu Glu Phe Lys Val Arg Ile Asn Ala Leu Val Ala Lys Ala Gln
465                 470                 475                 480

Lys Val Pro Glu Glu Gly Trp Thr Met Gln Asp Gly Ser Leu Trp Pro
                485                 490                 495

Gly Asn Asn Val Arg Asp His Pro Gly Met Ile Gln Val Phe Leu Gly
            500                 505                 510

Gln Ser Gly Gly Arg Asp Val Glu Gly Asn Glu Leu Pro Arg Leu Val
        515                 520                 525

Tyr Val Ser Arg Glu Lys Arg Pro Gly Tyr Asn His His Lys Lys Ala
    530                 535                 540

Gly Ala Met Asn Ala Leu Val Arg Val Ser Ala Val Leu Ser Asn Ala
545                 550                 555                 560

Pro Tyr Leu Leu Asn Leu Asp Cys Asp His Tyr Ile Asn Asn Ser Lys
                565                 570                 575
```

Ala Ile Lys Glu Ala Met Cys Phe Met Met Asp Pro Leu Val Gly Lys
580 585 590

Lys Val Cys Tyr Val Gln Phe Pro Gln Arg Phe Asp Gly Ile Asp Arg
595 600 605

His Asp Arg Tyr Ala Asn Arg Asn Val Val Phe Phe Asp Ile Asn Met
610 615 620

Lys Gly Leu Asp Gly Ile Gln Gly Pro Ile Tyr Val Gly Thr Gly Cys
625 630 635 640

Val Phe Arg Arg Gln Ala Leu Tyr Gly Tyr Asp Ala Pro Lys Thr Lys
645 650 655

Lys Pro Pro Ser Arg Thr Cys Asn Cys Trp Pro Lys Trp Cys Leu Ser
660 665 670

Cys Cys Cys Ser Arg Asn Lys Asn Lys Lys Lys Thr Thr Lys Pro Lys
675 680 685

Thr Glu Lys Lys Lys Arg Leu Phe Phe Lys Lys Ala Glu Asn Pro Ser
690 695 700

Pro Ala Tyr Ala Leu Gly Glu Ile Glu Glu Gly Ala Pro Gly Ala Asp
705 710 715 720

Ile Glu Lys Ala Gly Ile Val Asn Gln Gln Lys Leu Glu Lys Lys Phe
725 730 735

Gly Gln Ser Ser Val Phe Val Ala Ser Thr Leu Leu Glu Asn Gly Gly
740 745 750

Thr Leu Lys Ser Ala Ser Pro Ala Ser Leu Leu Lys Glu Ala Ile His
755 760 765

Val Ile Ser Cys Gly Tyr Glu Asp Lys Thr Asp Trp Gly Lys Glu Val
770 775 780

Tyr Ile Pro Tyr Ile Thr
785 790

<210> SEQ ID NO 23
<211> LENGTH: 1075
<212> TYPE: PRT
<213> ORGANISM: Zea mays

<400> SEQUENCE: 23

Met Ala Ala Asn Lys Gly Met Val Ala Gly Ser His Asn Arg Asn Glu
1 5 10 15

Phe Val Met Ile Arg His Asp Gly Asp Ala Pro Gly Ser Ala Lys Pro
20 25 30

Thr Lys Ser Ala Asn Gly Gln Val Cys Gln Ile Cys Gly Asp Ser Val
35 40 45

Gly Val Ser Ala Thr Gly Asp Val Phe Val Ala Cys Asn Glu Cys Ala
50 55 60

Phe Pro Val Cys Arg Pro Cys Tyr Glu Tyr Glu Arg Lys Glu Gly Asn
65 70 75 80

Gln Cys Cys Pro Gln Cys Lys Thr Arg Tyr Lys Arg Gln Lys Gly Ser
85 90 95

Pro Arg Val His Gly Asp Glu Asp Glu Glu Asp Val Asp Asp Leu Asp
100 105 110

Asn Glu Phe Asn Tyr Lys Gln Gly Asn Gly Lys Gly Pro Glu Trp Gln
115 120 125

Leu Gln Gly Asp Asp Ala Asp Leu Ser Ser Ser Ala Arg His Glu Pro
130 135 140

His His Arg Ile Pro Arg Leu Thr Ser Gly Gln Gln Ile Ser Gly Glu

-continued

```
145                 150                 155                 160

Ile Pro Asp Ala Ser Pro Asp Arg His Ser Ile Arg Ser Pro Thr Ser
                165                 170                 175

Ser Tyr Val Asp Pro Ser Val Pro Val Pro Val Arg Ile Val Asp Pro
            180                 185                 190

Ser Lys Asp Leu Asn Ser Tyr Gly Leu Asn Ser Val Asp Trp Lys Glu
        195                 200                 205

Arg Val Glu Ser Trp Arg Val Lys Gln Asp Lys Asn Met Met Gln Val
    210                 215                 220

Thr Asn Lys Tyr Pro Glu Ala Arg Gly Gly Asp Met Glu Gly Thr Gly
225                 230                 235                 240

Ser Asn Gly Glu Asp Met Gln Met Val Asp Asp Ala Arg Leu Pro Leu
                245                 250                 255

Ser Arg Ile Val Pro Ile Ser Ser Asn Gln Leu Asn Leu Tyr Arg Val
            260                 265                 270

Val Ile Ile Leu Arg Leu Ile Ile Leu Cys Phe Phe Phe Gln Tyr Arg
        275                 280                 285

Val Ser His Pro Val Arg Asn Ala Tyr Gly Leu Trp Leu Val Ser Val
    290                 295                 300

Ile Cys Glu Val Trp Phe Ala Leu Ser Trp Leu Leu Asp Gln Phe Pro
305                 310                 315                 320

Lys Trp Tyr Pro Ile Asn Arg Glu Thr Tyr Leu Asp Arg Leu Ala Leu
                325                 330                 335

Arg Tyr Asp Arg Glu Gly Glu Pro Ser Gln Leu Ala Pro Ile Asp Val
            340                 345                 350

Phe Val Ser Thr Val Asp Pro Leu Lys Glu Pro Pro Leu Ile Thr Ala
        355                 360                 365

Asn Thr Val Leu Ser Ile Leu Ser Val Asp Tyr Pro Val Asp Lys Val
    370                 375                 380

Ser Cys Tyr Val Ser Asp Asp Gly Ser Ala Met Leu Thr Phe Glu Ser
385                 390                 395                 400

Leu Ser Glu Thr Ala Glu Phe Ala Arg Lys Trp Val Pro Phe Cys Lys
                405                 410                 415

Lys His Asn Ile Glu Pro Arg Ala Pro Glu Phe Tyr Phe Ala Gln Lys
            420                 425                 430

Ile Asp Tyr Leu Lys Asp Lys Ile Gln Pro Ser Phe Val Lys Glu Arg
        435                 440                 445

Arg Ala Met Lys Arg Glu Tyr Glu Glu Phe Lys Val Arg Ile Asn Ala
    450                 455                 460

Leu Val Ala Lys Ala Gln Lys Val Pro Glu Glu Gly Trp Thr Met Ala
465                 470                 475                 480

Asp Gly Thr Ala Trp Pro Gly Asn Asn Pro Arg Asp His Pro Gly Met
                485                 490                 495

Ile Gln Val Phe Leu Gly His Ser Gly Gly Leu Asp Thr Asp Gly Asn
            500                 505                 510

Glu Leu Pro Arg Leu Val Tyr Val Ser Arg Glu Lys Arg Pro Gly Phe
        515                 520                 525

Gln His His Lys Lys Ala Gly Ala Met Asn Ala Leu Ile Arg Val Ser
    530                 535                 540

Ala Val Leu Thr Asn Gly Ala Tyr Leu Leu Asn Val Asp Cys Asp His
545                 550                 555                 560

Tyr Phe Asn Ser Ser Lys Ala Leu Arg Glu Ala Met Cys Phe Met Met
                565                 570                 575
```

-continued

```
Asp Pro Ala Leu Gly Arg Lys Thr Cys Tyr Val Gln Phe Pro Gln Arg
            580                 585                 590

Phe Asp Gly Ile Asp Leu His Asp Arg Tyr Ala Asn Arg Asn Ile Val
        595                 600                 605

Phe Phe Asp Ile Asn Met Lys Gly Leu Asp Gly Ile Gln Gly Pro Val
    610                 615                 620

Tyr Val Gly Thr Gly Cys Cys Phe Asn Arg Gln Ala Leu Tyr Gly Tyr
625                 630                 635                 640

Asp Pro Val Leu Thr Glu Ala Asp Leu Glu Pro Asn Ile Val Ile Lys
                645                 650                 655

Ser Cys Cys Gly Arg Arg Lys Lys Lys Asn Lys Ser Tyr Met Asp Ser
            660                 665                 670

Gln Ser Arg Ile Met Lys Arg Thr Glu Ser Ser Ala Pro Ile Phe Asn
        675                 680                 685

Met Glu Asp Ile Glu Glu Gly Ile Glu Gly Tyr Glu Asp Glu Arg Ser
    690                 695                 700

Val Leu Met Ser Gln Arg Lys Leu Glu Lys Arg Phe Gly Gln Ser Pro
705                 710                 715                 720

Ile Phe Ile Ala Ser Thr Phe Met Thr Gln Gly Gly Ile Pro Pro Ser
                725                 730                 735

Thr Asn Pro Ala Ser Leu Leu Lys Glu Ala Ile His Val Ile Ser Cys
            740                 745                 750

Gly Tyr Glu Asp Lys Thr Glu Trp Gly Lys Glu Ile Gly Trp Ile Tyr
        755                 760                 765

Gly Ser Val Thr Glu Asp Ile Leu Thr Gly Phe Lys Met His Ala Arg
    770                 775                 780

Gly Trp Gln Ser Ile Tyr Cys Met Pro Pro Arg Pro Cys Phe Lys Gly
785                 790                 795                 800

Ser Ala Pro Ile Asn Leu Ser Asp Arg Leu Asn Gln Val Leu Arg Trp
                805                 810                 815

Ala Leu Gly Ser Val Glu Ile Leu Leu Ser Arg His Cys Pro Ile Trp
            820                 825                 830

Tyr Gly Tyr Asn Gly Arg Leu Lys Leu Leu Glu Arg Leu Ala Tyr Ile
        835                 840                 845

Asn Thr Ile Val Tyr Pro Ile Thr Ser Ile Pro Leu Ile Ala Tyr Cys
    850                 855                 860

Val Leu Pro Ala Ile Cys Leu Leu Thr Asn Lys Phe Ile Ile Pro Glu
865                 870                 875                 880

Ile Ser Asn Tyr Ala Gly Met Phe Phe Ile Leu Leu Phe Ala Ser Ile
                885                 890                 895

Phe Ala Thr Gly Ile Leu Glu Leu Arg Trp Ser Gly Val Gly Ile Glu
            900                 905                 910

Asp Trp Trp Arg Asn Glu Gln Phe Trp Val Ile Gly Gly Thr Ser Ala
        915                 920                 925

His Leu Phe Ala Val Phe Gln Gly Leu Leu Lys Val Leu Ala Gly Ile
    930                 935                 940

Asp Thr Asn Phe Thr Val Thr Ser Lys Ala Ser Asp Glu Asp Gly Asp
945                 950                 955                 960

Phe Ala Glu Leu Tyr Val Phe Lys Trp Thr Ser Leu Leu Ile Pro Pro
                965                 970                 975

Thr Thr Val Leu Val Ile Asn Leu Val Gly Met Val Ala Gly Ile Ser
            980                 985                 990
```

Tyr Ala Ile Asn Ser Gly Tyr Gln Ser Trp Gly Pro Leu Phe Gly Lys
995 1000 1005

Leu Phe Phe Ser Ile Trp Val Ile Leu His Leu Tyr Pro Phe Leu
1010 1015 1020

Lys Gly Leu Met Gly Arg Gln Asn Arg Thr Pro Thr Ile Val Ile
1025 1030 1035

Val Trp Ser Ile Leu Leu Ala Ser Ile Phe Ser Leu Leu Trp Val
1040 1045 1050

Lys Ile Asp Pro Phe Ile Ser Pro Thr Gln Lys Ala Ala Ala Leu
1055 1060 1065

Gly Gln Cys Gly Val Asn Cys
1070 1075

<210> SEQ ID NO 24
<211> LENGTH: 1076
<212> TYPE: PRT
<213> ORGANISM: Zea mays

<400> SEQUENCE: 24

Met Asp Gly Gly Asp Ala Thr Asn Ser Gly Lys His Val Ala Gly Gln
1 5 10 15

Val Cys Gln Ile Cys Gly Asp Gly Val Gly Thr Ala Ala Asp Gly Asp
20 25 30

Leu Phe Thr Ala Cys Asp Val Cys Gly Phe Pro Val Cys Arg Pro Cys
35 40 45

Tyr Glu Tyr Glu Arg Lys Asp Gly Thr Gln Ala Cys Pro Gln Cys Lys
50 55 60

Thr Lys Tyr Lys Arg His Lys Gly Ser Pro Pro Val His Gly Glu Glu
65 70 75 80

Asn Glu Asp Val Asp Ala Asp Asp Val Ser Asp Tyr Asn Tyr Gln Ala
85 90 95

Ser Gly Asn Gln Asp Gln Lys Gln Lys Ile Ala Glu Arg Met Leu Thr
100 105 110

Trp Arg Thr Asn Ser Arg Gly Ser Asp Ile Gly Leu Ala Lys Tyr Asp
115 120 125

Ser Gly Glu Ile Gly His Gly Lys Tyr Asp Ser Gly Glu Ile Pro Arg
130 135 140

Gly Tyr Ile Pro Ser Leu Thr His Ser Gln Ile Ser Gly Glu Ile Pro
145 150 155 160

Gly Ala Ser Pro Asp His Met Met Ser Pro Val Gly Asn Ile Gly Arg
165 170 175

Arg Gly His Gln Phe Pro Tyr Val Asn His Ser Pro Asn Pro Ser Arg
180 185 190

Glu Phe Ser Gly Ser Leu Gly Asn Val Ala Trp Lys Glu Arg Val Asp
195 200 205

Gly Trp Lys Met Lys Asp Lys Gly Ala Ile Pro Met Thr Asn Gly Thr
210 215 220

Ser Ile Ala Pro Ser Glu Gly Arg Gly Val Ala Asp Ile Asp Ala Ser
225 230 235 240

Thr Asp Tyr Asn Met Glu Asp Ala Leu Leu Asn Asp Glu Thr Arg Gln
245 250 255

Pro Leu Ser Arg Lys Val Pro Ile Pro Ser Ser Arg Ile Asn Pro Tyr
260 265 270

Arg Met Val Ile Val Leu Arg Leu Ala Val Leu Cys Ile Phe Leu Arg
275 280 285

-continued

```
Tyr Arg Ile Thr His Pro Val Asn Asn Ala Tyr Pro Leu Trp Leu Leu
    290                 295                 300

Ser Val Ile Cys Glu Ile Trp Phe Ala Leu Ser Trp Ile Leu Asp Gln
305                 310                 315                 320

Phe Pro Lys Trp Ser Pro Ile Asn Arg Glu Thr Tyr Leu Asp Arg Leu
                325                 330                 335

Ala Leu Arg Tyr Asp Arg Glu Gly Glu Pro Ser Gln Leu Ala Pro Val
            340                 345                 350

Asp Ile Phe Val Ser Thr Val Asp Pro Met Lys Glu Pro Pro Leu Val
        355                 360                 365

Thr Ala Asn Thr Val Leu Ser Ile Leu Ala Val Asp Tyr Pro Val Asp
    370                 375                 380

Lys Val Ser Cys Tyr Val Ser Asp Asp Gly Ala Ala Met Leu Thr Phe
385                 390                 395                 400

Asp Ala Leu Ser Glu Thr Ser Glu Phe Ala Arg Lys Trp Val Pro Phe
                405                 410                 415

Cys Lys Lys Tyr Asn Ile Glu Pro Arg Ala Pro Glu Trp Tyr Phe Ala
            420                 425                 430

Gln Lys Ile Asp Tyr Leu Lys Asp Lys Val Gln Thr Ser Phe Val Lys
        435                 440                 445

Glu Arg Arg Ala Met Lys Arg Glu Tyr Glu Glu Phe Lys Val Arg Ile
    450                 455                 460

Asn Gly Leu Val Ala Asn Ala Gln Lys Val Pro Glu Glu Gly Trp Ile
465                 470                 475                 480

Met Gln Asp Gly Thr Pro Trp Pro Gly Asn Asn Thr Arg Asp His Pro
                485                 490                 495

Gly Met Ile Gln Val Phe Leu Gly His Ser Gly Gly Leu Asp Val Glu
            500                 505                 510

Gly Asn Glu Leu Pro Arg Leu Val Tyr Val Ser Arg Glu Lys Arg Pro
        515                 520                 525

Gly Phe Gln His His Lys Lys Ala Gly Ala Met Asn Ala Leu Val Arg
    530                 535                 540

Val Ser Ala Val Leu Thr Asn Gly Gln Tyr Met Leu Asn Leu Asp Cys
545                 550                 555                 560

Asp His Tyr Ile Asn Asn Ser Lys Ala Leu Arg Glu Ala Met Cys Phe
                565                 570                 575

Leu Met Asp Pro Asn Leu Gly Arg Asn Val Cys Tyr Val Gln Phe Pro
            580                 585                 590

Gln Arg Phe Asp Gly Ile Asp Arg Asn Asp Arg Tyr Ala Asn Arg Asn
        595                 600                 605

Thr Val Phe Phe Asp Ile Asn Leu Arg Gly Leu Asp Gly Ile Gln Gly
    610                 615                 620

Pro Val Tyr Val Gly Thr Gly Cys Val Phe Asn Arg Thr Ala Leu Tyr
625                 630                 635                 640

Gly Tyr Glu Pro Pro Val Lys Lys Lys Lys Pro Gly Phe Phe Ser Ser
                645                 650                 655

Leu Cys Gly Gly Arg Lys Lys Thr Ser Lys Ser Lys Lys Ser Ser Glu
            660                 665                 670

Lys Lys Lys Ser His Arg His Ala Asp Ser Ser Val Pro Val Phe Asn
        675                 680                 685

Leu Glu Asp Ile Glu Glu Gly Ile Glu Gly Ser Gln Phe Asp Asp Glu
    690                 695                 700
```

```
Lys Ser Leu Ile Met Ser Gln Met Ser Leu Glu Lys Arg Phe Gly Gln
705                 710                 715                 720

Ser Ser Val Phe Val Ala Ser Thr Leu Met Glu Tyr Gly Gly Val Pro
                725                 730                 735

Gln Ser Ala Thr Pro Glu Ser Leu Leu Lys Glu Ala Ile His Val Ile
            740                 745                 750

Ser Cys Gly Tyr Glu Asp Lys Thr Asp Trp Gly Thr Glu Ile Gly Trp
        755                 760                 765

Ile Tyr Gly Ser Val Thr Glu Asp Ile Leu Thr Gly Phe Lys Met His
    770                 775                 780

Ala Arg Gly Trp Arg Ser Ile Tyr Cys Met Pro Lys Arg Pro Ala Phe
785                 790                 795                 800

Lys Gly Ser Ala Pro Ile Asn Leu Ser Asp Arg Leu Asn Gln Val Leu
                805                 810                 815

Arg Trp Ala Leu Gly Ser Ile Glu Ile Leu Phe Ser Arg His Cys Pro
            820                 825                 830

Ile Trp Tyr Gly Tyr Gly Gly Arg Leu Lys Phe Leu Glu Arg Phe Ala
        835                 840                 845

Tyr Ile Asn Thr Thr Ile Tyr Pro Leu Thr Ser Ile Pro Leu Leu Leu
    850                 855                 860

Tyr Cys Ile Leu Pro Ala Val Cys Leu Leu Thr Gly Lys Phe Ile Ile
865                 870                 875                 880

Pro Lys Ile Ser Asn Leu Glu Ser Val Trp Phe Ile Ser Leu Phe Ile
                885                 890                 895

Ser Ile Phe Ala Thr Gly Ile Leu Glu Met Arg Trp Ser Gly Val Gly
            900                 905                 910

Ile Asp Glu Trp Trp Arg Asn Glu Gln Phe Trp Val Ile Gly Gly Ile
        915                 920                 925

Ser Ala His Leu Phe Ala Val Phe Gln Gly Leu Leu Lys Val Leu Ala
    930                 935                 940

Gly Ile Asp Thr Ser Phe Thr Val Thr Ser Lys Ala Thr Asp Glu Glu
945                 950                 955                 960

Gly Asp Phe Ala Glu Leu Tyr Met Phe Lys Trp Thr Thr Leu Leu Ile
                965                 970                 975

Pro Pro Thr Thr Ile Leu Ile Ile Asn Leu Val Gly Val Val Ala Gly
            980                 985                 990

Ile Ser Tyr Ala Ile Asn Ser Gly  Tyr Gln Ser Trp Gly  Pro Leu Phe
        995                 1000                1005

Gly Lys  Leu Phe Phe Ala Phe  Trp Val Ile Val His  Leu Tyr Pro
    1010                 1015                1020

Phe Leu  Lys Gly Leu Met Gly  Lys Gln Asn Arg Thr  Pro Thr Ile
    1025                 1030                1035

Val Val  Val Trp Ala Ile Leu  Leu Ala Ser Ile Phe  Ser Leu Met
    1040                 1045                1050

Trp Val  Arg Ile Asp Pro Phe  Thr Thr Arg Val Thr  Gly Pro Asp
    1055                 1060                1065

Ile Ala  Lys Cys Gly Ile Asn  Cys
    1070                 1075
```

<210> SEQ ID NO 25
<211> LENGTH: 1089
<212> TYPE: PRT
<213> ORGANISM: Zea mays

<400> SEQUENCE: 25

-continued

```
Met Glu Ala Ser Ala Gly Leu Val Ala Gly Ser His Asn Arg Asn Glu
1               5                   10                  15

Leu Val Val Ile Arg Arg Asp Gly Glu Pro Gly Pro Lys Pro Met Asp
            20                  25                  30

Gln Arg Asn Gly Gln Val Cys Gln Ile Cys Gly Asp Asp Val Gly Arg
        35                  40                  45

Asn Pro Asp Gly Glu Pro Phe Val Ala Cys Asn Glu Cys Ala Phe Pro
    50                  55                  60

Ile Cys Arg Asp Cys Tyr Glu Tyr Glu Arg Arg Glu Gly Thr Gln Asn
65                  70                  75                  80

Cys Pro Gln Cys Lys Thr Arg Phe Lys Arg Leu Lys Gly Cys Ala Arg
                85                  90                  95

Val Pro Gly Asp Glu Glu Glu Asp Gly Val Asp Asp Leu Glu Asn Glu
            100                 105                 110

Phe Asn Trp Ser Asp Lys His Asp Ser Gln Tyr Leu Ala Glu Ser Met
        115                 120                 125

Leu His Ala His Met Ser Tyr Gly Arg Gly Ala Asp Leu Asp Gly Val
    130                 135                 140

Pro Gln Pro Phe His Pro Ile Pro Asn Val Pro Leu Leu Thr Asn Gly
145                 150                 155                 160

Gln Met Val Asp Asp Ile Pro Pro Asp Gln His Ala Leu Val Pro Ser
                165                 170                 175

Phe Val Gly Gly Gly Gly Lys Arg Ile His Pro Leu Pro Tyr Ala Asp
            180                 185                 190

Pro Asn Leu Pro Val Gln Pro Arg Ser Met Asp Pro Ser Lys Asp Leu
        195                 200                 205

Ala Ala Tyr Gly Tyr Gly Ser Val Ala Trp Lys Glu Arg Met Glu Ser
    210                 215                 220

Trp Lys Gln Lys Gln Glu Arg Met His Gln Thr Arg Asn Asp Gly Gly
225                 230                 235                 240

Gly Asp Asp Gly Asp Asp Ala Asp Leu Pro Leu Met Asp Glu Ala Arg
                245                 250                 255

Gln Pro Leu Ser Arg Lys Ile Pro Leu Pro Ser Ser Gln Ile Asn Pro
            260                 265                 270

Tyr Arg Met Ile Ile Ile Ile Arg Leu Val Val Leu Cys Phe Phe Phe
        275                 280                 285

His Tyr Arg Val Met His Pro Val Pro Asp Ala Phe Ala Leu Trp Leu
    290                 295                 300

Ile Ser Val Ile Cys Glu Ile Trp Phe Ala Met Ser Trp Ile Leu Asp
305                 310                 315                 320

Gln Phe Pro Lys Trp Phe Pro Ile Glu Arg Glu Thr Tyr Leu Asp Arg
                325                 330                 335

Leu Ser Leu Arg Phe Asp Lys Glu Gly His Pro Ser Gln Leu Ala Pro
            340                 345                 350

Val Asp Phe Phe Val Ser Thr Val Asp Pro Leu Lys Glu Pro Pro Leu
        355                 360                 365

Val Thr Ala Asn Thr Val Leu Ser Ile Leu Ser Val Asp Tyr Pro Val
    370                 375                 380

Asp Lys Val Ser Cys Tyr Val Ser Asp Asp Gly Ala Ala Met Leu Thr
385                 390                 395                 400

Phe Glu Ala Leu Ser Glu Thr Ser Glu Phe Ala Lys Lys Trp Val Pro
                405                 410                 415
```

-continued

```
Phe Cys Lys Arg Tyr Ser Leu Glu Pro Arg Ala Pro Glu Trp Tyr Phe
            420                 425                 430

Gln Gln Lys Ile Asp Tyr Leu Lys Asp Lys Val Ala Pro Asn Phe Val
        435                 440                 445

Arg Glu Arg Arg Ala Met Lys Arg Glu Tyr Glu Glu Phe Lys Val Arg
    450                 455                 460

Ile Asn Ala Leu Val Ala Lys Ala Gln Lys Val Pro Glu Glu Gly Trp
465                 470                 475                 480

Thr Met Gln Asp Gly Thr Pro Trp Pro Gly Asn Asn Val Arg Asp His
                485                 490                 495

Pro Gly Met Ile Gln Val Phe Leu Gly Gln Ser Gly Gly His Asp Val
            500                 505                 510

Glu Gly Asn Glu Leu Pro Arg Leu Val Tyr Val Ser Arg Glu Lys Arg
        515                 520                 525

Pro Gly Tyr Asn His His Lys Lys Ala Gly Ala Met Asn Ala Leu Val
    530                 535                 540

Arg Val Ser Ala Val Leu Thr Asn Ala Pro Tyr Leu Leu Asn Leu Asp
545                 550                 555                 560

Cys Asp His Tyr Ile Asn Asn Ser Lys Ala Ile Lys Glu Ala Met Cys
                565                 570                 575

Phe Met Met Asp Pro Leu Leu Gly Asn Lys Val Cys Tyr Val Gln Phe
            580                 585                 590

Pro Gln Arg Phe Asp Gly Ile Asp Arg His Asp Arg Tyr Ala Asn Arg
        595                 600                 605

Asn Val Val Phe Phe Asp Ile Asn Met Lys Gly Leu Asp Gly Ile Gln
    610                 615                 620

Gly Pro Ile Tyr Val Gly Thr Gly Cys Val Phe Arg Arg Gln Ala Leu
625                 630                 635                 640

Tyr Gly Tyr Asp Ala Pro Lys Thr Lys Lys Pro Pro Ser Arg Thr Cys
                645                 650                 655

Asn Cys Trp Pro Lys Trp Cys Ile Cys Cys Cys Cys Phe Gly Asn Arg
            660                 665                 670

Lys Thr Lys Lys Lys Thr Lys Thr Ser Lys Pro Lys Phe Glu Lys Ile
        675                 680                 685

Lys Lys Leu Phe Lys Lys Lys Glu Asn Gln Ala Pro Ala Tyr Ala Leu
    690                 695                 700

Gly Glu Ile Asp Glu Ala Ala Pro Gly Ala Glu Asn Glu Lys Ala Ser
705                 710                 715                 720

Ile Val Asn Gln Gln Lys Leu Glu Lys Lys Phe Gly Gln Ser Ser Val
                725                 730                 735

Phe Val Ala Ser Thr Leu Leu Glu Asn Gly Gly Thr Leu Lys Ser Ala
            740                 745                 750

Ser Pro Ala Ser Leu Leu Lys Glu Ala Ile His Val Ile Ser Cys Gly
        755                 760                 765

Tyr Glu Asp Lys Thr Gly Trp Gly Lys Asp Ile Gly Trp Ile Tyr Gly
    770                 775                 780

Ser Val Thr Glu Asp Ile Leu Thr Gly Phe Lys Met His Cys His Gly
785                 790                 795                 800

Trp Arg Ser Ile Tyr Cys Ile Pro Lys Arg Ala Ala Phe Lys Gly Ser
                805                 810                 815

Ala Pro Leu Asn Leu Ser Asp Arg Leu His Gln Val Leu Arg Trp Ala
            820                 825                 830

Leu Gly Ser Ile Glu Ile Phe Phe Ser Asn His Cys Pro Leu Trp Tyr
```

835 840 845

Gly Tyr Gly Gly Gly Leu Lys Phe Leu Glu Arg Phe Ser Tyr Ile Asn
850 855 860

Ser Ile Val Tyr Pro Trp Thr Ser Ile Pro Leu Leu Ala Tyr Cys Thr
865 870 875 880

Leu Pro Ala Ile Cys Leu Leu Thr Gly Lys Phe Ile Thr Pro Glu Leu
885 890 895

Asn Asn Val Ala Ser Leu Trp Phe Met Ser Leu Phe Ile Cys Ile Phe
900 905 910

Ala Thr Ser Ile Leu Glu Met Arg Trp Ser Gly Val Gly Ile Asp Asp
915 920 925

Trp Trp Arg Asn Glu Gln Phe Trp Val Ile Gly Gly Val Ser Ser His
930 935 940

Leu Phe Ala Val Phe Gln Gly Leu Leu Lys Val Ile Ala Gly Val Asp
945 950 955 960

Thr Ser Phe Thr Val Thr Ser Lys Gly Gly Asp Asp Glu Glu Phe Ser
965 970 975

Glu Leu Tyr Thr Phe Lys Trp Thr Thr Leu Leu Ile Pro Pro Thr Thr
980 985 990

Leu Leu Leu Leu Asn Phe Ile Gly Val Val Ala Gly Ile Ser Asn Ala
995 1000 1005

Ile Asn Asn Gly Tyr Glu Ser Trp Gly Pro Leu Phe Gly Lys Leu
1010 1015 1020

Phe Phe Ala Phe Trp Val Ile Val His Leu Tyr Pro Phe Leu Lys
1025 1030 1035

Gly Leu Val Gly Arg Gln Asn Arg Thr Pro Thr Ile Val Ile Val
1040 1045 1050

Trp Ser Ile Leu Leu Ala Ser Ile Phe Ser Leu Leu Trp Val Arg
1055 1060 1065

Ile Asp Pro Phe Leu Ala Lys Asp Asp Gly Pro Leu Leu Glu Glu
1070 1075 1080

Cys Gly Leu Asp Cys Asn
1085

<210> SEQ ID NO 26
<211> LENGTH: 1033
<212> TYPE: PRT
<213> ORGANISM: Glycine max

<400> SEQUENCE: 26

Met Glu Ala Ser Ala Gly Leu Val Ala Gly Ser His Asn Arg Asn Glu
1 5 10 15

Leu Val Val Ile His Gly His Glu Glu His Lys Pro Leu Lys Asn Leu
20 25 30

Asp Gly Gln Val Cys Glu Ile Cys Gly Asp Asp Val Gly Leu Thr Val
35 40 45

Asp Gly Asp Leu Phe Val Ala Cys Asn Glu Cys Gly Phe Pro Ala Cys
50 55 60

Arg Pro Cys Tyr Glu Tyr Glu Arg Arg Glu Gly Arg Gln Val Cys Pro
65 70 75 80

Gln Cys Lys Thr Arg Tyr Lys Arg Leu Lys Gly Ser Pro Arg Val Glu
85 90 95

Gly Asp Asp Asp Glu Glu Asp Val Asp Asp Ile Glu His Glu Phe Asn
100 105 110

-continued

```
Ile Glu Glu Gln Asn Lys His Asn His Ser Ala Glu Ala Met Leu His
        115                 120                 125

Gly Lys Met Ser Tyr Gly Arg Gly Pro Glu Asp Asp Glu Asn Ala Gln
    130                 135                 140

Phe Pro Ala Val Ile Ala Gly Gly Arg Ser Arg Pro Val Ser Gly Glu
145                 150                 155                 160

Leu Pro Ile Ala Ser His Tyr Gly Asp Gln Met Leu Ala Ser Ser Leu
                165                 170                 175

Gln Asn Arg Ser His Pro Tyr Leu Ala Ser Asp Pro Arg Asn Gly Lys
            180                 185                 190

Leu Asp Glu Ala Lys Glu Asp Arg Met Asp Asp Trp Lys Leu Gln Gln
        195                 200                 205

Gly Asn Leu Gly His Glu Pro Asp Glu Asp Pro Asp Ala Ala Met Leu
    210                 215                 220

Asp Glu Ala Arg Gln Pro Leu Ser Arg Lys Val Pro Ile Ala Ser Ser
225                 230                 235                 240

Lys Val Asn Pro Tyr Arg Met Val Ile Val Ala Arg Leu Val Ile Leu
                245                 250                 255

Ala Phe Phe Leu Arg Tyr Arg Leu Met Asn Pro Val His Asp Ala Leu
            260                 265                 270

Gly Leu Trp Leu Thr Ser Ile Ile Cys Glu Ile Trp Phe Ala Phe Ser
        275                 280                 285

Trp Ile Leu Asp Gln Phe Pro Lys Trp Phe Pro Ile Asp Arg Glu Thr
    290                 295                 300

Tyr Leu Asp Arg Leu Ser Ile Arg Tyr Glu Arg Glu Gly Glu Pro Asn
305                 310                 315                 320

Met Leu Ala Pro Val Asp Val Phe Val Ser Thr Val Asp Pro Met Lys
                325                 330                 335

Glu Pro Pro Leu Val Thr Ala Asn Thr Val Leu Ser Ile Leu Ala Met
            340                 345                 350

Asp Tyr Pro Val Asp Lys Ile Ser Cys Tyr Ile Ser Asp Asp Gly Ala
        355                 360                 365

Ser Met Cys Thr Phe Glu Ala Leu Ser Glu Thr Ala Glu Phe Ala Arg
    370                 375                 380

Lys Trp Val Pro Phe Cys Lys Lys Phe Ser Ile Glu Pro Arg Ala Pro
385                 390                 395                 400

Glu Met Tyr Phe Ser Glu Lys Val Asp Tyr Leu Lys Asp Lys Val Gln
                405                 410                 415

Pro Thr Phe Val Lys Asp Arg Arg Ala Met Lys Arg Glu Tyr Glu Glu
            420                 425                 430

Phe Lys Val Arg Ile Asn Ala Leu Val Ala Lys Ala Gln Lys Val Pro
        435                 440                 445

Gln Gly Gly Trp Ile Met Gln Asp Gly Thr Pro Trp Pro Gly Asn Asn
    450                 455                 460

Thr Lys Asp His Pro Gly Met Ile Gln Val Phe Leu Gly His Ser Gly
465                 470                 475                 480

Gly His Asp Thr Glu Gly Asn Glu Leu Pro Arg Leu Val Tyr Val Ser
                485                 490                 495

Arg Glu Lys Arg Pro Gly Phe Gln His His Lys Lys Ala Gly Ala Met
            500                 505                 510

Asn Ala Leu Ile Arg Val Ser Ala Val Leu Thr Asn Ala Pro Phe Met
        515                 520                 525

Leu Asn Leu Asp Cys Asp His Tyr Val Asn Asn Ser Lys Ala Ala Arg
```

```
    530                 535                 540

Glu Ala Met Cys Phe Leu Met Asp Pro Gln Thr Gly Lys Lys Val Cys
545                 550                 555                 560

Tyr Val Gln Phe Pro Gln Arg Phe Asp Gly Ile Asp Arg His Asp Arg
                565                 570                 575

Tyr Ala Asn Arg Asn Thr Val Phe Phe Asp Ile Asn Met Lys Gly Leu
            580                 585                 590

Asp Gly Ile Gln Gly Pro Ala Tyr Val Gly Thr Gly Cys Val Phe Arg
        595                 600                 605

Arg Gln Ala Leu Tyr Gly Tyr Asn Pro Pro Lys Gly Pro Lys Arg Pro
    610                 615                 620

Lys Met Val Ser Cys Asp Cys Cys Pro Cys Phe Gly Lys Arg Lys Lys
625                 630                 635                 640

Val Lys Tyr Glu Gly Asn Asp Ala Asn Gly Glu Ala Ala Ser Leu Arg
                645                 650                 655

Gly Met Asp Asp Asp Lys Glu Val Leu Met Ser Gln Met Asn Phe Glu
            660                 665                 670

Lys Lys Phe Gly Gln Ser Ser Ile Phe Val Thr Ser Thr Leu Met Glu
        675                 680                 685

Glu Gly Gly Val Pro Pro Ser Ala Ser Pro Ala Ser Gln Leu Lys Glu
    690                 695                 700

Ala Ile His Val Ile Ser Cys Gly Tyr Glu Asp Lys Thr Glu Trp Gly
705                 710                 715                 720

Ile Glu Leu Gly Trp Ile Tyr Gly Ser Ile Thr Glu Asp Ile Leu Thr
                725                 730                 735

Gly Phe Lys Met His Cys Arg Gly Trp Arg Ser Ile Tyr Cys Met Pro
            740                 745                 750

Lys Arg Ala Ala Phe Lys Gly Thr Ala Pro Ile Asn Leu Ser Asp Arg
        755                 760                 765

Leu Asn Gln Val Leu Arg Trp Ala Leu Gly Ser Ile Glu Ile Phe Phe
    770                 775                 780

Ser Arg His Cys Pro Leu Trp Tyr Gly Tyr Lys Glu Gly Lys Leu Lys
785                 790                 795                 800

Trp Leu Glu Arg Phe Ala Tyr Ala Asn Thr Thr Val Tyr Pro Phe Thr
                805                 810                 815

Ser Ile Pro Leu Val Ala Tyr Cys Val Leu Pro Ala Val Cys Leu Leu
            820                 825                 830

Thr Asp Lys Phe Ile Met Pro Pro Ile Ser Thr Phe Ala Gly Leu Tyr
        835                 840                 845

Phe Val Ala Leu Phe Ser Ser Ile Ile Ala Thr Gly Leu Leu Glu Leu
    850                 855                 860

Lys Trp Ser Gly Val Ser Ile Glu Glu Trp Trp Arg Asn Glu Gln Phe
865                 870                 875                 880

Trp Val Ile Gly Gly Val Ser Ala His Leu Phe Ala Val Ile Gln Gly
                885                 890                 895

Leu Leu Lys Val Leu Ala Gly Ile Asp Thr Asn Phe Thr Val Thr Ser
            900                 905                 910

Lys Ala Ala Asp Asp Glu Glu Phe Gly Glu Leu Tyr Thr Phe Lys Trp
        915                 920                 925

Thr Thr Leu Leu Ile Pro Pro Thr Thr Ile Leu Ile Ile Asn Ile Val
    930                 935                 940

Gly Val Val Ala Gly Ile Ser Asp Ala Ile Asn Asn Gly Tyr Gln Ser
945                 950                 955                 960
```

-continued

```
Trp Gly Pro Leu Phe Gly Lys Leu Phe Phe Ser Phe Trp Val Ile Val
                965                 970                 975

His Leu Tyr Pro Phe Leu Lys Gly Leu Met Gly Arg Gln Asn Arg Thr
            980                 985                 990

Pro Thr Ile Val Val Ile Trp Ser  Val Leu Leu Ala Ser  Ile Phe Ser
        995                 1000                1005

Leu Leu  Trp Val Arg Ile Asp  Pro Phe Val Leu Lys  Thr Lys Gly
    1010                1015                1020

Pro Asp  Thr Lys Leu Cys Gly  Ile Asn Cys
    1025                1030


<210> SEQ ID NO 27
<211> LENGTH: 1078
<212> TYPE: PRT
<213> ORGANISM: Glycine max

<400> SEQUENCE: 27

Met Asp Thr Lys Gly Arg Leu Val Ala Gly Ser His Asn Arg Asn Glu
1               5                   10                  15

Phe Val Leu Ile Asn Ala Asp Glu Thr Ala Arg Val Ala Val Thr Glu
            20                  25                  30

Leu Ser Gly Gln Ile Cys Gln Ile Cys Gly Asp Glu Leu Glu Val Thr
        35                  40                  45

Val Asn Gly Glu Pro Phe Val Ala Cys Asn Glu Cys Ala Phe Pro Val
    50                  55                  60

Cys Arg Pro Cys Tyr Glu Tyr Glu Arg Arg Glu Gly Asn Gln Val Cys
65                  70                  75                  80

Pro Gln Cys Lys Thr Arg Tyr Lys Arg Ile Lys Gly Ser Pro Arg Val
                85                  90                  95

Glu Gly Asp Glu Glu Glu Asp Asp Ser Asp Asp Leu Glu Ser Glu Phe
            100                 105                 110

Asp Ile Gly Ser Val Phe Ser Ala Arg Leu Asn Tyr Gly Ser Gln Val
        115                 120                 125

Asn Gly Ser Val Ile His Ala Pro Ser Glu Phe Asp Ala Ala Ser Val
    130                 135                 140

Ala Ser Glu Ile Pro Leu Leu Thr Tyr Gly Gln Glu Asp Val Gly Ile
145                 150                 155                 160

Ser Ala Asp Lys His Ala Leu Ile Leu Pro Pro Phe Thr Ala Arg Gly
                165                 170                 175

Lys Arg Val His Pro Met Pro Phe Pro Asp Ser Ser Val Pro Val Gln
            180                 185                 190

Pro Arg Pro Met Asp Pro Lys Lys Asp Ile Ala Val Tyr Gly Tyr Gly
        195                 200                 205

Ser Val Ala Trp Lys Glu Arg Met Glu Asp Trp Lys Lys Lys Gln Ser
    210                 215                 220

Glu Lys Leu Gln Val Val Arg His Glu Gly Gly Lys Asp Ser Asp Glu
225                 230                 235                 240

Leu Asp Asp Pro Asp Leu Pro Lys Met Asp Glu Gly Arg Gln Pro Leu
                245                 250                 255

Trp Arg Lys Leu Pro Ile Ser Ser Ser Arg Ile Asn Pro Tyr Arg Ile
            260                 265                 270

Ile Ile Val Leu Arg Ile Ala Ile Leu Cys Leu Phe Phe His Tyr Arg
        275                 280                 285

Ile Leu His Pro Val Asn Asp Ala Tyr Ala Leu Trp Leu Thr Ser Val
```

-continued

```
    290                 295                 300

Ile Cys Glu Ile Trp Phe Ala Val Ser Trp Ile Phe Asp Gln Phe Pro
305                 310                 315                 320

Lys Trp Ser Pro Ile Leu Arg Glu Thr Tyr Leu Asp Arg Leu Ser Leu
                325                 330                 335

Arg Tyr Glu Lys Glu Gly Lys Pro Ser Leu Leu Ala Asp Ile Asp Val
            340                 345                 350

Phe Val Ser Thr Val Asp Pro Met Lys Glu Pro Pro Leu Ile Thr Ala
        355                 360                 365

Asn Thr Val Leu Ser Ile Leu Ala Val Asp Tyr Pro Val Asp Lys Val
    370                 375                 380

Ala Cys Tyr Val Ser Asp Asp Gly Ala Ala Met Leu Thr Phe Glu Ala
385                 390                 395                 400

Leu Ser Glu Thr Ser Glu Phe Ala Arg Lys Trp Val Pro Phe Cys Lys
                405                 410                 415

Lys Phe Cys Ile Glu Pro Arg Ala Pro Glu Trp Tyr Phe Ala Gln Lys
            420                 425                 430

Val Asp Tyr Leu Lys Asp Lys Val Asp Ala Thr Phe Ile Arg Glu Arg
        435                 440                 445

Arg Ala Ile Lys Arg Glu Tyr Glu Glu Phe Lys Val Arg Ile Asn Ala
    450                 455                 460

Leu Val Ala Leu Ala Gln Lys Val Pro Glu Asp Gly Trp Thr Met Gln
465                 470                 475                 480

Asp Gly Thr Pro Trp Pro Gly Asn Asn Val Arg Asp His Pro Gly Met
                485                 490                 495

Ile Gln Val Phe Leu Gly Gln Asn Gly Val Arg Asp Ile Glu Gly Asn
            500                 505                 510

Glu Leu Pro Arg Leu Val Tyr Val Ser Arg Glu Lys Arg Pro Gly Tyr
        515                 520                 525

Asp His His Lys Lys Ala Gly Ala Met Asn Ala Leu Val Arg Val Ser
    530                 535                 540

Ala Ile Ile Thr Asn Ala Pro Tyr Val Leu Asn Val Asp Cys Asp His
545                 550                 555                 560

Tyr Ile Asn Asn Ser Lys Ala Leu Arg Glu Ala Met Cys Phe Met Met
                565                 570                 575

Asp Pro Thr Ser Gly Lys Lys Ile Cys Tyr Val Gln Phe Pro Gln Arg
            580                 585                 590

Phe Asp Gly Ile Asp Arg His Asp Arg Tyr Ser Asn Arg Asn Val Val
        595                 600                 605

Phe Phe Asp Ile Asn Met Lys Gly Leu Asp Gly Ile Gln Gly Pro Ile
    610                 615                 620

Tyr Val Gly Thr Gly Cys Val Phe Arg Arg Gln Ala Phe Tyr Gly Tyr
625                 630                 635                 640

Asp Ala Pro Thr Ser Lys Lys Ala Pro Arg Lys Thr Cys Asn Cys Trp
                645                 650                 655

Pro Lys Trp Cys Cys Cys Leu Cys Cys Gly Ser Lys Lys Lys Lys Ile
            660                 665                 670

Lys Ala Lys Ser Ser Val Lys Lys Lys Ile Lys Asn Lys Asp Asp Ile
        675                 680                 685

Lys Gln Met His Ala Leu Glu Asn Ile Glu Glu Gly Ile Glu Gly Ile
    690                 695                 700

Asp Asn Glu Lys Ser Ser Leu Met Ser Gln Ser Lys Phe Glu Lys Lys
705                 710                 715                 720
```

```
Phe Gly Gln Ser Ser Val Phe Ile Ala Ser Thr Leu Leu Glu Asp Gly
                725                 730                 735

Gly Val Pro Lys Ala Ala Ser Ser Ala Thr Leu Leu Lys Glu Ala Ile
            740                 745                 750

His Val Ile Ser Cys Gly Tyr Glu Asp Lys Thr Glu Trp Gly Lys Glu
        755                 760                 765

Val Gly Trp Ile Tyr Gly Ser Val Thr Glu Asp Ile Leu Thr Gly Phe
    770                 775                 780

Lys Met His Cys His Gly Trp Arg Ser Val Tyr Cys Met Pro Lys Arg
785                 790                 795                 800

Pro Ala Phe Lys Gly Ser Ala Pro Ile Asn Leu Ser Asp Arg Leu His
                805                 810                 815

Gln Val Leu Arg Trp Ala Leu Gly Ser Val Glu Ile Phe Phe Ser Arg
            820                 825                 830

His Cys Pro Ile Trp Tyr Gly Tyr Gly Gly Gly Leu Lys Ser Leu Glu
        835                 840                 845

Arg Phe Ser Tyr Ile Asn Ser Val Val Tyr Pro Leu Thr Ser Ile Pro
    850                 855                 860

Leu Ile Ala Tyr Cys Ala Leu Pro Ala Val Cys Leu Leu Thr Gly Lys
865                 870                 875                 880

Phe Ile Val Pro Glu Ile Ser Asn Tyr Ala Ser Ile Ile Phe Met Ala
                885                 890                 895

Leu Phe Ile Ser Ile Ala Ala Thr Gly Ile Leu Glu Met Gln Trp Gly
            900                 905                 910

Gly Val Gly Ile His Asp Trp Trp Arg Asn Glu Gln Phe Trp Val Ile
        915                 920                 925

Gly Gly Ala Ser Ser His Leu Phe Ala Leu Phe Gln Gly Leu Leu Lys
    930                 935                 940

Val Leu Ala Gly Val Asn Thr Asn Phe Thr Val Thr Ser Lys Ala Ala
945                 950                 955                 960

Asp Asp Gly Glu Phe Ala Asp Leu Tyr Ile Phe Lys Trp Thr Ser Leu
                965                 970                 975

Leu Ile Pro Pro Leu Thr Leu Leu Ile Ile Asn Ile Ile Gly Val Ile
            980                 985                 990

Val Gly Val Ser Asp Ala Ile Asn  Asn Gly Tyr Asp Ser  Trp Gly Pro
        995                 1000                1005

Leu Phe  Gly Arg Leu Phe Phe  Ala Leu Trp Val Ile  Val His Leu
    1010                1015                1020

Tyr Pro  Phe Leu Lys Gly Val  Met Gly Lys Gln Glu  Gly Val Pro
    1025                1030                1035

Thr Ile  Ile Leu Val Trp Ala  Ile Leu Leu Ser Ser  Ile Leu Thr
    1040                1045                1050

Leu Leu  Trp Val Arg Ile Asn  Pro Phe Leu Ala Lys  Ser Asp Val
    1055                1060                1065

Val Leu  Glu Ile Cys Gly Leu  Asn Cys Asp
    1070                1075
```

<210> SEQ ID NO 28
<211> LENGTH: 1079
<212> TYPE: PRT
<213> ORGANISM: Glycine max

<400> SEQUENCE: 28

```
Met Glu Ser Glu Gly Glu Ala Gly Ala Lys Pro Val Thr Ala Leu Gly
```

-continued

```
1               5                   10                  15

Ala Gln Val Cys Gln Ile Cys Gly Asp Gly Val Gly Lys Thr Val Asp
            20                  25                  30

Gly Glu Pro Phe Val Ala Cys Asp Val Cys Ala Phe Pro Val Cys Arg
        35                  40                  45

Pro Cys Tyr Glu Tyr Glu Arg Lys Asp Gly Asn Gln Ser Cys Pro Gln
    50                  55                  60

Cys Lys Thr Arg Tyr Lys Arg His Lys Gly Ser Pro Ala Ile Leu Gly
65                  70                  75                  80

Asp Met Glu Glu Asp Gly Ala Ala Ala Ala Asp Ala Ser Asp Phe Asn
                85                  90                  95

Tyr Asp Ser Glu Asn Gln Asn Gln Asn Gln Asn Gln Lys Gln Lys Ile
            100                 105                 110

Ser Glu Arg Met Leu Ser Trp Gln Leu Thr Tyr Pro Arg Gly Glu Glu
        115                 120                 125

Val Gly Ala Pro Asn Tyr Asp Lys Asp Val Ser His Asn His Ile Pro
    130                 135                 140

Leu Leu Thr Ser Gly Gln Glu Val Ser Gly Glu Leu Ser Ala Ala Ser
145                 150                 155                 160

Pro Glu Arg Leu Ser Met Ala Ser Pro Ala Val Gly Gly Gly Lys Arg
                165                 170                 175

Val His Asn Ile Pro Tyr Ser Ser Asp Ile Asn Gln Ser Pro Asn Ile
            180                 185                 190

Arg Ala Gly Asp Pro Gly Leu Gly Asn Val Ala Trp Lys Glu Arg Val
        195                 200                 205

Asp Gly Trp Lys Met Lys Gln Glu Lys Asn Val Val Pro Met Ser Thr
    210                 215                 220

Gly Gln Ala Ala Ser Glu Arg Gly Ala Gly Asp Ile Asp Ala Ser Thr
225                 230                 235                 240

Asp Val Leu Val Asp Asp Ser Leu Leu Asn Asp Glu Ala Arg Gln Pro
                245                 250                 255

Leu Ser Arg Lys Val Ser Ile Pro Ser Ser Arg Ile Asn Pro Tyr Arg
            260                 265                 270

Met Val Ile Met Leu Arg Leu Val Ile Leu Cys Ile Phe Leu His Tyr
        275                 280                 285

Arg Ile Thr Asn Pro Val Pro Asn Ala Tyr Pro Leu Trp Leu Val Ser
    290                 295                 300

Val Ile Cys Glu Ile Trp Phe Ala Ile Ser Trp Ile Leu Asp Gln Phe
305                 310                 315                 320

Pro Lys Trp Leu Pro Val Asn Arg Glu Thr Tyr Leu Asp Arg Leu Ala
                325                 330                 335

Leu Arg Tyr Asp Arg Glu Gly Glu Pro Ser Gln Leu Ala Ala Val Asp
            340                 345                 350

Ile Phe Val Ser Thr Val Asp Pro Leu Lys Glu Pro Pro Leu Val Thr
        355                 360                 365

Ala Asn Thr Val Leu Ser Ile Leu Ala Val Asp Tyr Pro Val Asp Lys
    370                 375                 380

Val Ser Cys Tyr Val Ser Asp Asp Gly Ala Ala Met Leu Thr Phe Glu
385                 390                 395                 400

Ala Leu Ala Glu Thr Ser Glu Phe Ala Arg Lys Trp Val Pro Phe Ser
                405                 410                 415

Lys Lys Tyr Ser Ile Glu Pro Arg Ala Pro Glu Trp Tyr Phe Ser Gln
            420                 425                 430
```

```
Lys Ile Asp Tyr Leu Lys Asp Lys Val His Pro Ser Phe Val Lys Asp
        435                 440                 445

Arg Arg Ala Met Lys Arg Glu Tyr Glu Glu Phe Lys Val Arg Ile Asn
    450                 455                 460

Gly Leu Val Ser Lys Ala Gln Lys Val Pro Glu Glu Gly Trp Val Met
465                 470                 475                 480

Gln Asp Gly Thr Pro Trp Pro Gly Asn Asn Thr Arg Asp His Pro Gly
                485                 490                 495

Met Ile Gln Val Phe Leu Gly Gln Ser Gly Gly Leu Asp Thr Glu Gly
            500                 505                 510

Asn Glu Leu Pro Arg Leu Val Tyr Val Ser Arg Glu Lys Arg Pro Gly
        515                 520                 525

Phe Gln His His Lys Lys Ala Gly Ala Met Asn Ala Leu Val Arg Val
    530                 535                 540

Ser Ala Val Leu Thr Asn Gly Pro Phe Leu Leu Asn Leu Asp Cys Asp
545                 550                 555                 560

His Tyr Ile Asn Asn Ser Lys Ala Leu Arg Glu Ala Met Cys Phe Met
                565                 570                 575

Met Asp Pro Asn Leu Gly Lys His Val Cys Tyr Val Gln Phe Pro Gln
            580                 585                 590

Arg Phe Asp Gly Ile Asp Arg Asn Asp Arg Tyr Ala Asn Arg Asn Thr
        595                 600                 605

Val Phe Phe Asp Ile Asn Leu Arg Gly Leu Asp Gly Ile Gln Gly Pro
    610                 615                 620

Val Tyr Val Gly Thr Gly Cys Val Phe Asn Arg Thr Ala Leu Tyr Gly
625                 630                 635                 640

Tyr Glu Pro Pro Leu Lys Pro Lys His Lys Lys Pro Gly Leu Leu Ser
                645                 650                 655

Ser Leu Cys Gly Gly Thr Arg Lys Lys Ser Ser Lys Ser Ser Lys Lys
            660                 665                 670

Gly Ser Asp Lys Lys Lys Ser Ser Lys His Val Asp Pro Thr Val Pro
        675                 680                 685

Ile Phe Asn Leu Glu Asp Ile Glu Glu Gly Val Glu Gly Thr Gly Phe
    690                 695                 700

Asp Asp Glu Lys Ser Leu Leu Met Ser Gln Met Ser Leu Glu Lys Arg
705                 710                 715                 720

Phe Gly Gln Ser Ala Val Phe Val Ala Ser Thr Leu Met Glu Asn Gly
                725                 730                 735

Gly Val Pro Gln Ser Ala Thr Pro Glu Thr Leu Leu Lys Glu Ala Ile
            740                 745                 750

His Val Ile Ser Cys Gly Tyr Glu Asp Lys Thr Asp Trp Gly Ser Glu
        755                 760                 765

Ile Gly Trp Ile Tyr Gly Ser Val Thr Glu Asp Ile Leu Thr Gly Phe
    770                 775                 780

Lys Met His Ala Arg Gly Trp Arg Ser Ile Tyr Cys Met Pro Lys Arg
785                 790                 795                 800

Pro Ala Phe Lys Gly Ser Ala Pro Ile Asn Leu Ser Asp Arg Leu Asn
                805                 810                 815

Gln Val Leu Arg Trp Ala Leu Gly Ser Val Glu Ile Leu Phe Ser Arg
            820                 825                 830

His Cys Pro Ile Trp Tyr Gly Tyr Gly Gly Arg Leu Lys Trp Leu Glu
        835                 840                 845
```

```
Arg Phe Ala Tyr Val Asn Thr Thr Ile Tyr Pro Val Thr Ala Ile Pro
    850                 855                 860

Leu Leu Ile Tyr Cys Ile Leu Pro Ala Val Cys Leu Leu Thr Asn Lys
865                 870                 875                 880

Phe Ile Ile Pro Gln Ile Ser Asn Leu Ala Ser Ile Trp Phe Ile Ser
                885                 890                 895

Leu Phe Leu Ser Ile Phe Ala Thr Gly Ile Leu Glu Met Arg Trp Ser
            900                 905                 910

Gly Val Gly Ile Asp Glu Trp Trp Arg Asn Glu Gln Phe Trp Val Ile
        915                 920                 925

Gly Gly Val Ser Ala His Leu Phe Ala Val Phe Gln Gly Leu Leu Lys
    930                 935                 940

Val Leu Ala Gly Ile Asp Thr Asn Phe Thr Val Thr Ser Lys Ala Ser
945                 950                 955                 960

Asp Glu Asp Gly Asp Phe Ala Glu Leu Tyr Met Phe Lys Trp Thr Thr
                965                 970                 975

Leu Leu Ile Pro Pro Thr Thr Leu Leu Ile Ile Asn Leu Val Gly Val
            980                 985                 990

Val Ala Gly Ile Ser Tyr Ala Ile  Asn Ser Gly Tyr Gln  Ser Trp Gly
        995                 1000                1005

Pro Leu  Phe Gly Lys Leu Phe  Phe Ala Phe Trp Val  Ile Ile His
    1010                1015                1020

Leu Tyr  Pro Phe Leu Lys Gly  Leu Met Gly Arg Gln  Asn Arg Thr
    1025                1030                1035

Pro Thr  Ile Val Val Val Trp  Ser Val Leu Leu Ala  Ser Ile Phe
    1040                1045                1050

Ser Leu  Leu Trp Val Arg Ile  Asp Pro Phe Thr Thr  Arg Val Thr
    1055                1060                1065

Gly Pro  Asp Val Glu Glu Cys  Gly Ile Asn Cys
    1070                1075


<210> SEQ ID NO 29
<211> LENGTH: 973
<212> TYPE: PRT
<213> ORGANISM: Glycine max

<400> SEQUENCE: 29

Met Glu Ala Cys Thr Gly Leu Phe Ala Gly Thr Pro Asn Ser Asn Glu
1               5                   10                  15

Leu Val Val Ile Gln Gly His Asp Glu Pro Lys Pro Val Lys Asn Leu
            20                  25                  30

Asp Gly Gln Leu Cys Glu Ile Cys Gly Asp Ser Val Gly Leu Thr Val
        35                  40                  45

Asp Gly Asp Leu Phe Val Ala Cys Glu Glu Cys Gly Phe Pro Val Cys
    50                  55                  60

Arg Pro Cys Tyr Glu Tyr Glu Arg Arg Glu Gly Thr Gln Val Cys Pro
65                  70                  75                  80

Gln Cys His Thr Arg Tyr Lys Arg Ile Lys Gly Ser Pro Arg Val Leu
                85                  90                  95

Gly Asp Glu Asp Glu Asp Asp Val Asp Asp Ile Glu His Glu Phe Lys
            100                 105                 110

His Glu Glu Met Leu Gln Gly Asn Met Thr His Gly Asp Ser Glu Gly
        115                 120                 125

Asn Ser Lys Ser Lys Pro Val Gly Leu Ala Lys Val Asn Gly Glu Leu
    130                 135                 140
```

```
Pro Val Ser Ser His Ser Val Gly Glu Pro Gly Ala Lys Leu Asp Asp
145                 150                 155                 160

Lys Glu Lys Val Asp Glu Trp Met Leu His Gln Gly Asn Leu Trp Pro
                165                 170                 175

Glu Thr Asp Ala Ser Val Asp Pro Glu Lys Ala Met Lys Glu Pro Leu
            180                 185                 190

Ser Arg Lys Val Pro Ile Pro Ser Gly Arg Leu Ser Pro Tyr Arg Met
        195                 200                 205

Met Val Val Ala Arg Leu Leu Leu Leu Leu Leu Phe Phe Gln Tyr Arg
    210                 215                 220

Ile Phe His Pro Val Pro Asp Ala Ile Gly Leu Trp Phe Ile Ser Val
225                 230                 235                 240

Thr Cys Glu Ile Trp Leu Ala Leu Ser Trp Met Ile Asp Gln Leu Pro
                245                 250                 255

Lys Trp Phe Pro Ile Asp Arg Glu Thr Tyr Leu Asp Arg Leu Ser Ile
            260                 265                 270

Arg Phe Glu Pro Glu Asn Lys Pro Asn Met Leu Ser Pro Ile Asp Ile
        275                 280                 285

Ile Val Thr Thr Val Asp Pro Ile Lys Glu Pro Pro Leu Val Thr Ala
    290                 295                 300

Asn Thr Val Leu Ser Ile Leu Ala Leu Asp Tyr Pro Ala Asp Lys Ile
305                 310                 315                 320

Ser Cys Tyr Val Ser Asp Asp Gly Ala Ser Met Leu Thr Phe Glu Ala
                325                 330                 335

Leu Gln Glu Thr Ala Glu Phe Ser Arg Lys Trp Val Pro Phe Cys Lys
            340                 345                 350

Thr Phe Ser Val Glu Pro Arg Ala Pro Glu Lys Tyr Phe Ser Glu Lys
        355                 360                 365

Ile Asp Phe Leu Lys Asp Lys Leu Gln Ser Thr Tyr Val Lys Glu Arg
    370                 375                 380

Arg Thr Met Lys Arg Glu Tyr Glu Glu Phe Lys Val Arg Ile Asn Ala
385                 390                 395                 400

Leu Val Ala Lys Ser Met Arg Val Pro Pro Glu Gly Trp Thr Met Lys
                405                 410                 415

Asp Glu Thr Pro Trp Pro Gly Asn Asn Ser Lys Asp His Pro Ser Met
            420                 425                 430

Ile Gln Val Leu Leu Pro His Asn Val Gly Asn Glu Leu Pro Cys Leu
        435                 440                 445

Val Tyr Thr Ser Arg Glu Lys Arg Pro Ala Phe Gln His His Asn Lys
    450                 455                 460

Ala Gly Ala Ile Asn Ala Met Leu Arg Val Ser Ala Val Leu Ser Asn
465                 470                 475                 480

Ala Pro Phe Val Leu Asn Leu Asp Cys Asn His Tyr Val Asn Asn Ser
                485                 490                 495

Lys Val Val Arg Glu Ala Met Cys Phe Phe Met Asp Ile Gln Leu Gly
            500                 505                 510

Asn Gly Ile Ala Phe Val Gln Phe Pro Leu Arg Phe Asp Ser Leu Asp
        515                 520                 525

Arg Asn Asp Arg Tyr Ala Asn Lys Asn Thr Val Leu Phe Asp Ile Asn
    530                 535                 540

Leu Arg Cys Leu Asp Gly Ile Gln Gly Pro Ala Tyr Ile Gly Ser Ala
545                 550                 555                 560
```

```
Cys Ile Phe Arg Arg Lys Ala Leu Thr Gly Phe Asp Ser Pro Lys Thr
                565                 570                 575

Ser Lys Arg Pro Ser Met Val Gln Val His Ser Lys Gln Asp Glu Asn
            580                 585                 590

Gly Glu Glu Ala Ser Ile Thr Gly Glu Asp Lys Glu Leu Leu Lys Ser
        595                 600                 605

Glu Met Asn Asp Glu Asn Lys Phe Gly Lys Ser Ile Leu Phe Met Asn
    610                 615                 620

Ser Ala Leu Ala Glu Glu Gly Gly Val Asp Pro Ser Ser Ser Gln Glu
625                 630                 635                 640

Ala Leu Leu Lys Glu Ala Ile His Val Met Ser Ser Arg Tyr Glu Asp
                645                 650                 655

Arg Thr Leu Trp Gly Tyr Glu Val Gly Leu Ser Tyr Gly Ser Ile Ala
            660                 665                 670

Ala Asp Thr Leu Thr Ser Leu Lys Met His Cys Gly Gly Trp Arg Ser
        675                 680                 685

Val Tyr Cys Met Pro Lys Arg Asp Pro Phe Arg Gly Thr Ala Pro Ile
    690                 695                 700

Asn Leu Thr Asp Arg Leu Asn Gln Val Leu Arg Trp Ala Val Gly Ser
705                 710                 715                 720

Leu Gln Ile Leu Phe Ser Ser His Cys Pro Leu Leu Tyr Gly Gly Arg
                725                 730                 735

Leu Lys Gly Leu Gln Arg Ile Ala Tyr Ile Asn Ser Thr Val Tyr Pro
            740                 745                 750

Phe Ser Ser Ile Pro Leu Leu Ile Tyr Cys Ile Ile Pro Ala Ile Cys
        755                 760                 765

Leu Leu Thr Asp Lys Phe Ile Thr Pro Ser Val Gly Thr Phe Ala Ser
    770                 775                 780

Leu Ile Phe Ile Ala Leu Phe Ile Ser Ile Phe Ala Ser Ala Ile Leu
785                 790                 795                 800

Glu Leu Arg Trp Ser Gly Val Ser Leu Glu Glu Trp Trp Arg Ser Gln
                805                 810                 815

Gln Phe Trp Val Ile Gly Ser Val Ser Ala Asn Leu Phe Ala Leu Leu
            820                 825                 830

Gln Gly Ile Met Arg Ala Leu Pro Leu Gly Arg Val Asn Thr Asn Phe
        835                 840                 845

Ser Ile Val Ser Lys Ala Pro Asp Asp Val Glu Phe Arg Glu Leu Tyr
    850                 855                 860

Ala Ile Arg Trp Thr Ala Leu Leu Ile Pro Pro Thr Thr Ile Ile Ile
865                 870                 875                 880

Ile Asn Leu Ile Gly Ile Val Ala Gly Phe Thr Asp Ala Ile Asn Ser
                885                 890                 895

Gly Glu His Ser Trp Gly Ala Leu Leu Gly Lys Leu Phe Phe Ser Leu
            900                 905                 910

Trp Val Val Ile His Leu Tyr Pro Phe Leu Lys Gly Leu Met Gly Arg
        915                 920                 925

Gln Asn Arg Thr Pro Thr Leu Ile Val Ile Trp Ser Val Leu Leu Ala
    930                 935                 940

Ser Ile Phe Ser Leu Val Trp Val Arg Val Asp Pro Phe Val Leu Lys
945                 950                 955                 960

Thr Lys Gly Pro Asp Val Lys Gln Cys Gly Ile Ser Cys
                965                 970
```

```
<210> SEQ ID NO 30
<211> LENGTH: 975
<212> TYPE: PRT
<213> ORGANISM: Glycine max

<400> SEQUENCE: 30

Met Met Glu Ser Gly Ala His Phe Cys Asn Ser Cys Gly Glu Gln Ile
1               5                   10                  15

Gly Leu Asp Ala Asn Gly Glu Val Phe Val Ala Cys His Glu Cys Tyr
            20                  25                  30

Phe Pro Ile Cys Lys Ala Cys Phe Glu Tyr Glu Ile Asn Glu Gly Arg
        35                  40                  45

Lys Val Cys Leu Arg Cys Ala Thr Pro Tyr Ala Asp Arg Ala Lys Asp
    50                  55                  60

Asn Asn Asp Thr Lys Val Tyr Glu Asn Gln Ser Thr Thr Ala Ala Gln
65                  70                  75                  80

Ile Asn Val Ser Gln Asp Val Gly Leu His Ala Arg His Val Ser Thr
                85                  90                  95

Val Ser Thr Val Asp Ser Glu Leu Asn Asp Glu Ser Gly Asn Pro Ile
            100                 105                 110

Trp Lys Asn Arg Val Glu Ser Trp Lys Glu Lys Asp Lys Lys Lys Lys
        115                 120                 125

Lys Lys Lys Ser Ala Pro Lys Ala Glu Asn Glu Ala Pro Ile Pro Pro
    130                 135                 140

Glu Gln Gln Met Glu Glu Met Gln Ser Ser Glu Ala Ala Ala Ala Glu
145                 150                 155                 160

Pro Leu Ser Met Val Ile Pro Ile Ser Lys Thr Arg Leu Ala Pro Tyr
                165                 170                 175

Arg Thr Val Ile Ile Val Arg Leu Ile Ile Leu Gly Leu Phe Phe His
            180                 185                 190

Tyr Arg Val Thr Asn Pro Val Asp Ser Ala Phe Gly Leu Trp Leu Thr
        195                 200                 205

Ser Ile Ile Cys Glu Ile Trp Phe Ala Phe Ser Trp Val Leu Asp Gln
    210                 215                 220

Phe Pro Lys Trp Ser Pro Val Asn Arg Glu Ala Phe Ile Asp Arg Leu
225                 230                 235                 240

Ser Leu Arg Tyr Glu Arg Pro Gly Glu Pro Ser Gln Leu Ala Ala Val
                245                 250                 255

Asp Phe Phe Val Ser Thr Val Asp Pro Leu Lys Glu Pro Pro Leu Ile
            260                 265                 270

Thr Ala Asn Thr Val Leu Ser Ile Leu Ala Val Asp Tyr Pro Val Asp
        275                 280                 285

Lys Val Ser Cys Tyr Val Ser Asp Asp Gly Ala Ala Met Leu Ser Phe
    290                 295                 300

Glu Ser Leu Val Glu Thr Ala Asp Phe Ala Arg Lys Trp Val Pro Phe
305                 310                 315                 320

Cys Lys Lys Phe Ser Ile Glu Pro Arg Ala Pro Glu Phe Tyr Phe Ser
                325                 330                 335

Gln Lys Ile Asp Tyr Leu Lys Asp Lys Val Gln Pro Ser Phe Val Lys
            340                 345                 350

Glu Arg Arg Ala Met Lys Arg Glu Tyr Glu Glu Phe Lys Val Arg Val
        355                 360                 365

Asn Ala Leu Val Ala Lys Ala Gln Lys Thr Pro Asp Glu Gly Trp Thr
    370                 375                 380
```

Met Gln Asp Gly Thr Ser Trp Pro Gly Asn Asn Ser Arg Asp His Pro
385 390 395 400

Gly Met Ile Gln Val Phe Leu Gly His Ser Gly Ala His Asp Ile Glu
405 410 415

Gly Asn Glu Leu Pro Arg Leu Val Tyr Val Ser Arg Glu Lys Arg Pro
420 425 430

Gly Tyr Gln His His Lys Lys Ala Gly Ala Glu Asn Ala Leu Val Arg
435 440 445

Val Ser Ala Val Leu Thr Asn Ala Pro Phe Ile Leu Asn Leu Asp Cys
450 455 460

Asp His Tyr Val Asn Asn Ser Lys Ala Val Arg Glu Ala Met Cys Phe
465 470 475 480

Leu Met Asp Pro Val Val Gly Arg Asp Leu Cys Tyr Val Gln Phe Pro
485 490 495

Gln Arg Phe Asp Gly Ile Asp Arg Ser Asp Arg Tyr Ala Asn Arg Asn
500 505 510

Thr Val Phe Phe Asp Val Asn Met Lys Gly Leu Asp Gly Ile Gln Gly
515 520 525

Pro Met Tyr Val Gly Thr Gly Cys Val Phe Asn Arg Gln Ala Leu Tyr
530 535 540

Gly Tyr Ser Pro Pro Ser Met Pro Lys Leu Pro Lys Ser Ser Ser Cys
545 550 555 560

Cys Cys Cys Pro Ser Lys Lys Gln Thr Lys Asp Val Ser Glu Leu Tyr
565 570 575

Arg Asp Ala Lys Arg Glu Glu Leu Asp Ala Ala Ile Phe Asn Leu Arg
580 585 590

Glu Ile Asp Asn Tyr Asp Glu Tyr Glu Arg Ser Met Leu Ile Ser Gln
595 600 605

Met Ser Phe Glu Lys Thr Phe Gly Leu Ser Thr Val Phe Ile Glu Ser
610 615 620

Thr Leu Met Glu Asn Gly Gly Leu Pro Glu Ser Ala Asp Pro Ser Met
625 630 635 640

Leu Ile Lys Glu Ala Ile His Val Ile Ser Cys Gly Tyr Glu Glu Lys
645 650 655

Thr Ala Trp Gly Lys Glu Ile Gly Trp Ile Tyr Gly Ser Val Thr Glu
660 665 670

Asp Ile Leu Thr Gly Phe Lys Met Gln Cys Arg Gly Trp Arg Ser Val
675 680 685

Tyr Cys Met Pro Leu Arg Pro Ala Phe Lys Gly Ser Ala Pro Ile Asn
690 695 700

Leu Ser Asp Arg Leu His Gln Val Leu Arg Trp Ala Leu Gly Ser Val
705 710 715 720

Glu Ile Phe Phe Ser Arg His Cys Pro Leu Trp Tyr Gly Phe Ala Gly
725 730 735

Gly Arg Leu Lys Trp Leu Gln Arg Leu Ala Tyr Ile Asn Thr Ile Val
740 745 750

Tyr Pro Phe Thr Ser Leu Pro Leu Val Ala Tyr Cys Thr Leu Pro Ala
755 760 765

Ile Cys Leu Leu Thr Gly Lys Phe Ile Ile Pro Thr Leu Ser Asn Leu
770 775 780

Ala Ser Ala Leu Phe Leu Gly Leu Phe Leu Ser Ile Ile Val Thr Ser
785 790 795 800

Val Leu Glu Leu Arg Trp Ser Gly Val Thr Ile Glu Ala Leu Trp Arg

```
                805                 810                 815

Asn Glu Gln Phe Trp Val Ile Gly Gly Val Ser Ala His Leu Phe Ala
            820                 825                 830

Val Phe Gln Gly Phe Leu Lys Met Leu Ala Gly Val Asp Thr Asn Phe
        835                 840                 845

Thr Val Thr Ala Lys Ala Ala Asp Asp Thr Glu Phe Gly Asp Leu Tyr
    850                 855                 860

Ile Ile Lys Trp Thr Thr Leu Leu Ile Pro Pro Thr Thr Leu Ile Ile
865                 870                 875                 880

Ile Asn Met Val Gly Val Val Ala Gly Phe Ser Asp Ala Leu Asn Gly
                885                 890                 895

Gly Tyr Glu Ser Trp Gly Pro Leu Phe Gly Lys Val Phe Phe Ala Phe
            900                 905                 910

Trp Val Ile Phe His Leu Tyr Pro Phe Leu Lys Gly Leu Met Gly Arg
        915                 920                 925

Gln Asn Arg Thr Pro Thr Ile Val Ile Leu Trp Ser Val Leu Leu Ala
    930                 935                 940

Ser Val Phe Ser Leu Val Trp Val Lys Ile Asn Pro Phe Ile Ser Arg
945                 950                 955                 960

Pro Asp Ser Ala Ser Ile Ser Gln Thr Cys Ile Ser Ile Asp Cys
                965                 970                 975


<210> SEQ ID NO 31
<211> LENGTH: 1039
<212> TYPE: PRT
<213> ORGANISM: Glycine max

<400> SEQUENCE: 31

Met Glu Ala Ser Ala Gly Leu Val Ala Gly Ser His Asn Arg Asn Glu
1               5                   10                  15

Leu Val Val Ile His Gly His Glu Glu Pro Lys Ala Leu Lys Asn Leu
            20                  25                  30

Asp Gly Gln Val Cys Glu Ile Cys Gly Asp Gly Val Gly Leu Thr Val
        35                  40                  45

Asp Gly Asp Leu Phe Val Ala Cys Asn Glu Cys Gly Phe Pro Val Cys
    50                  55                  60

Arg Pro Cys Tyr Glu Tyr Glu Arg Arg Glu Gly Ser His Leu Cys Pro
65                  70                  75                  80

Gln Cys Lys Thr Arg Tyr Lys Arg Leu Lys Gly Ser Pro Arg Val Glu
                85                  90                  95

Gly Asp Asp Asp Glu Glu Asp Val Asp Asp Ile Glu His Glu Phe Asn
            100                 105                 110

Ile Asp Glu Gln Lys Asn Lys His Gly Gln Val Ala Glu Ala Met Leu
        115                 120                 125

His Gly Arg Met Ser Tyr Gly Arg Gly Pro Glu Asp Asp Asp Asn Ser
    130                 135                 140

Gln Phe Pro Thr Pro Val Ile Ala Gly Gly Arg Ser Arg Pro Val Ser
145                 150                 155                 160

Gly Glu Phe Pro Ile Ser Ser Asn Ala Tyr Gly Asp Gln Met Leu Ser
                165                 170                 175

Ser Ser Leu His Lys Arg Val His Pro Tyr Pro Val Ser Glu Pro Gly
            180                 185                 190

Ser Ala Arg Trp Asp Glu Lys Lys Glu Asp Gly Trp Lys Asp Arg Met
        195                 200                 205
```

-continued

Asp Asp Trp Lys Leu Gln Gln Gly Asn Leu Gly Pro Glu Pro Asp Glu
    210                 215                 220

Asp Pro Asp Ala Ala Met Leu Asp Glu Ala Arg Gln Pro Leu Ser Arg
225                 230                 235                 240

Lys Val Pro Ile Ala Ser Ser Lys Ile Asn Pro Tyr Arg Met Val Ile
                245                 250                 255

Val Ala Arg Leu Val Ile Leu Ala Phe Phe Leu Arg Tyr Arg Leu Met
            260                 265                 270

Asn Pro Val His Asp Ala Leu Gly Leu Trp Leu Thr Ser Ile Ile Cys
        275                 280                 285

Glu Ile Trp Phe Ala Phe Ser Trp Ile Leu Asp Gln Phe Pro Lys Trp
    290                 295                 300

Phe Pro Ile Asp Arg Glu Thr Tyr Leu Asp Arg Leu Ser Ile Arg Tyr
305                 310                 315                 320

Glu Arg Glu Gly Glu Pro Asn Met Leu Ala Pro Val Asp Val Phe Val
                325                 330                 335

Ser Thr Val Asp Pro Met Lys Glu Pro Pro Leu Val Thr Ala Asn Thr
            340                 345                 350

Val Leu Ser Ile Leu Ala Met Asp Tyr Pro Val Asp Lys Ile Ser Cys
        355                 360                 365

Tyr Ile Ser Asp Asp Gly Ala Ser Met Cys Thr Phe Glu Ser Leu Ser
    370                 375                 380

Glu Thr Ala Glu Phe Ala Arg Lys Trp Val Pro Phe Cys Lys Lys Phe
385                 390                 395                 400

Ser Ile Glu Pro Arg Ala Pro Glu Met Tyr Phe Ser Glu Lys Ile Asp
                405                 410                 415

Tyr Leu Lys Asp Lys Val Gln Pro Thr Phe Val Lys Glu Arg Arg Ala
            420                 425                 430

Met Lys Arg Glu Tyr Glu Glu Phe Lys Val Arg Ile Asn Ala Leu Val
        435                 440                 445

Ala Lys Ala Gln Lys Val Pro Gln Gly Gly Trp Ile Met Gln Asp Gly
    450                 455                 460

Thr Pro Trp Pro Gly Asn Asn Thr Lys Asp His Pro Gly Met Ile Gln
465                 470                 475                 480

Val Phe Leu Gly Ser Ser Gly Gly Leu Asp Thr Glu Gly Asn Gln Leu
                485                 490                 495

Pro Arg Leu Val Tyr Val Ser Arg Glu Lys Arg Pro Gly Phe Gln His
            500                 505                 510

His Lys Lys Ala Gly Ala Met Asn Ala Leu Val Arg Val Ser Ala Val
        515                 520                 525

Leu Thr Asn Ala Pro Phe Met Leu Asn Leu Asp Cys Asp His Tyr Val
    530                 535                 540

Asn Asn Ser Lys Ala Ala Arg Glu Ala Met Cys Phe Leu Met Asp Pro
545                 550                 555                 560

Gln Thr Gly Lys Lys Val Cys Tyr Val Gln Phe Pro Gln Arg Phe Asp
                565                 570                 575

Gly Ile Asp Thr His Asp Arg Tyr Ala Asn Arg Asn Thr Val Phe Phe
            580                 585                 590

Asp Ile Asn Met Lys Gly Leu Asp Gly Ile Gln Gly Pro Val Tyr Val
        595                 600                 605

Gly Thr Gly Cys Val Phe Arg Arg Gln Ala Leu Tyr Gly Tyr Asn Pro
    610                 615                 620

Pro Lys Gly Pro Lys Arg Pro Lys Met Val Ser Cys Asp Cys Cys Pro

```
625                 630                 635                 640

Cys Phe Gly Ser Arg Lys Lys Tyr Lys Glu Lys Asn Asp Ala Asn Gly
                645                 650                 655

Glu Ala Ala Ser Leu Lys Gly Met Asp Asp Asp Lys Glu Val Leu Met
            660                 665                 670

Ser Gln Met Asn Phe Glu Lys Lys Phe Gly Gln Ser Ser Ile Phe Val
        675                 680                 685

Thr Ser Thr Leu Met Glu Glu Gly Gly Val Pro Pro Ser Ser Ser Pro
    690                 695                 700

Ala Ala Leu Leu Lys Glu Ala Ile His Val Ile Ser Cys Gly Tyr Glu
705                 710                 715                 720

Asp Lys Thr Glu Trp Gly Leu Glu Leu Gly Trp Ile Tyr Gly Ser Ile
                725                 730                 735

Thr Glu Asp Ile Leu Thr Gly Phe Lys Met His Cys Arg Gly Trp Arg
            740                 745                 750

Ser Ile Tyr Cys Met Pro Lys Arg Ala Ala Phe Lys Gly Thr Ala Pro
        755                 760                 765

Ile Asn Leu Ser Asp Arg Leu Asn Gln Val Leu Arg Trp Ala Leu Gly
    770                 775                 780

Ser Ile Glu Ile Phe Phe Ser His His Cys Pro Leu Trp Tyr Gly Phe
785                 790                 795                 800

Lys Glu Lys Lys Leu Lys Trp Leu Glu Arg Phe Ala Tyr Ala Asn Thr
                805                 810                 815

Thr Val Tyr Pro Phe Thr Ser Ile Pro Leu Val Ala Tyr Cys Ile Leu
            820                 825                 830

Pro Ala Val Cys Leu Leu Thr Asp Lys Phe Ile Met Pro Pro Ile Ser
        835                 840                 845

Thr Phe Ala Gly Leu Tyr Phe Val Ala Leu Phe Ser Ser Ile Ile Ala
    850                 855                 860

Thr Gly Ile Leu Glu Leu Lys Trp Ser Gly Val Ser Ile Glu Glu Trp
865                 870                 875                 880

Trp Arg Asn Glu Gln Phe Trp Val Ile Gly Gly Val Ser Ala His Leu
                885                 890                 895

Phe Ala Val Ile Gln Gly Leu Leu Lys Val Leu Ala Gly Ile Asp Thr
            900                 905                 910

Asn Phe Thr Val Thr Ser Lys Ala Thr Asp Asp Glu Glu Phe Gly Glu
        915                 920                 925

Leu Tyr Thr Phe Lys Trp Thr Thr Leu Leu Ile Pro Pro Thr Thr Ile
    930                 935                 940

Leu Ile Ile Asn Ile Val Gly Val Val Ala Gly Ile Ser Asp Ala Ile
945                 950                 955                 960

Asn Asn Gly Tyr Gln Ser Trp Gly Pro Leu Phe Gly Lys Leu Phe Phe
                965                 970                 975

Ser Phe Trp Val Ile Val His Leu Tyr Pro Phe Leu Lys Gly Leu Met
            980                 985                 990

Gly Arg Gln Asn Arg Thr Pro Thr  Ile Val Val Ile Trp  Ser Val Leu
        995                 1000                1005

Leu Ala  Ser Ile Phe Ser Leu  Leu Trp Val Arg Ile  Asp Pro Phe
    1010                1015                1020

Val Leu  Lys Thr Lys Gly Pro  Asp Thr Lys Leu Cys  Gly Ile Asn
    1025                1030                1035

Cys
```

<210> SEQ ID NO 32
<211> LENGTH: 967
<212> TYPE: PRT
<213> ORGANISM: Glycine max

<400> SEQUENCE: 32

```
Met Glu Thr Asn Leu Gly Leu Val Ala Gly Ser His Asn Ser Asn Glu
1               5                   10                  15

Phe Ile Ile Ile Arg Gln Asp Gly Asp Phe Ala Gln Arg Glu Leu Gln
            20                  25                  30

Pro Leu Leu His Gly Lys Ile Cys Gln Leu Cys Gly Asp Asp Ile Gly
        35                  40                  45

Val Asn Glu Asp Gly Asp Leu Phe Val Ala Cys Asn Glu Cys Ala Phe
    50                  55                  60

Pro Val Cys Lys Ser Cys Tyr Glu Tyr Glu Arg Arg Glu Gly Asn Gln
65                  70                  75                  80

Val Cys Pro Gln Cys Lys Thr Arg Phe Lys Arg Leu Lys Gly Cys Ala
                85                  90                  95

Arg Val Glu Gly Asp Glu Glu Glu Asp Ile Asp Asp Asp Leu Glu Asn
            100                 105                 110

Glu Phe Asp Phe Asp Asp Gly Gln Ser Lys Leu His Asp Met Lys Thr
        115                 120                 125

Ser Met Ser His Glu Glu Gln Gly Glu Glu Thr Ser Gln Glu His Asn
    130                 135                 140

Ala Leu Val Thr Ser Ser Ser Thr Ile Leu Gly Lys Glu Ile Val Ala
145                 150                 155                 160

Leu Gln Ala Arg Pro Met Asp Pro Ser Lys Asp Leu Ala Ala Tyr Gly
                165                 170                 175

Tyr Gly Ser Ile Ala Trp Lys Glu Lys Met Lys Ile Trp Lys Gln Arg
            180                 185                 190

Gln Met Lys Ile Ser Asp Met Lys Lys Glu Asn Asp Asn Glu Asp Pro
        195                 200                 205

Asp Asn Thr Val Glu Asp Asp Asp Thr Glu Phe Leu Ile Thr Tyr Leu
    210                 215                 220

Asp Arg Leu Ser Leu Arg Tyr Glu Lys Glu Gly Lys Pro Ser Gln Leu
225                 230                 235                 240

Ser Pro Ile Asp Ile Phe Val Ile Ser Met Asp Pro Leu Lys Glu Pro
                245                 250                 255

Pro Leu Val Thr Ala Asn Thr Val Leu Ser Ile Leu Ala Ile Asp Tyr
            260                 265                 270

Pro Ala Glu Lys Val Ser Cys Tyr Val Ser Asp Asp Gly Ala Ala Met
        275                 280                 285

Leu Thr Phe Glu Ala Leu Ser Glu Thr Ser Glu Phe Ala Lys Lys Trp
    290                 295                 300

Val Pro Phe Cys Lys Lys Phe Asn Ile Glu Pro Arg Ala Pro Glu Arg
305                 310                 315                 320

Tyr Phe Ala Glu Lys Ile Asn Phe Leu Asp Asp Lys Val Gln Pro Ser
                325                 330                 335

Phe Val Lys Glu Arg Arg Ala Met Lys Arg Glu Tyr Glu Glu Phe Arg
            340                 345                 350

Val Arg Ile Asn Thr Leu Val Ala Lys Ser Arg Lys Val Pro Glu Glu
        355                 360                 365

Gly Trp Thr Met Gln Asp Gly Thr Pro Trp Pro Gly Asn Asn Val Arg
    370                 375                 380
```

```
Asp His Pro Gly Met Ile Gln Val Phe Leu Gly Glu Thr Gly Gly Cys
385                 390                 395                 400

Asp Met Asp Gly Lys Glu Leu Pro Arg Leu Val Tyr Val Ser Arg Glu
                405                 410                 415

Lys Arg Pro Lys Phe Asn His Gln Lys Lys Ala Gly Ala Leu Asn Ala
            420                 425                 430

Leu Val Arg Val Ser Ala Val Leu Ser Asn Ala Pro Phe Val Leu Asn
        435                 440                 445

Leu Asp Tyr Asn His Cys Ile Asn Asn Ser Lys Val Val Arg Glu Ala
    450                 455                 460

Met Cys Phe Met Met Asp Pro Leu Leu Gly Lys Gly Ala Ser Tyr Val
465                 470                 475                 480

Gln Phe Ser Gln Arg Phe Asp Gly Ile Ala Ser Asp Glu Gln Tyr Ala
                485                 490                 495

Asn Gln Thr Asn Gly Phe Ile Asp Ile Asn Met Lys Gly Leu Asp Gly
            500                 505                 510

Ile Gln Gly Pro Thr Tyr Ile Gly Thr Gly Cys Val Phe Arg Arg Gln
        515                 520                 525

Ala Leu Tyr Gly Phe Asp Ser Pro Arg Lys Lys Lys Pro Pro Thr Lys
    530                 535                 540

Thr Cys Asn Cys Trp Pro Lys Trp Cys Cys Phe Gly Cys Cys Phe Met
545                 550                 555                 560

Gly Lys Arg Lys Lys Lys Lys Leu Lys Lys Pro Lys Phe Glu Ile Thr
                565                 570                 575

Glu Thr Ser His Arg Lys Val His Ser Glu Ser Ser Ile Val Glu Gly
            580                 585                 590

Lys Glu Asp Glu Thr Ser Ala His Leu Ser Asn Pro Lys Phe Val Lys
        595                 600                 605

Lys Tyr Gly Gln Ser Pro Ile Phe Ile Ala Ser Ile Gln Leu Val Asp
    610                 615                 620

Gly Glu Thr Leu Lys His Gly Asn Leu Ala Ser Gln Leu Thr Glu Ala
625                 630                 635                 640

Ile His Val Ile Ser Cys Gly Tyr Glu Glu Lys Thr Glu Trp Gly Lys
                645                 650                 655

Glu Val Gly Trp Ile Tyr Gly Ser Val Thr Glu Asp Ile Leu Thr Gly
            660                 665                 670

Phe Lys Met His Cys His Gly Trp Arg Ser Ile Tyr Cys Thr Pro Arg
        675                 680                 685

Arg Pro Gly Phe Lys Val Ser Thr Pro Arg Asn Leu Ser Asn Gly Leu
    690                 695                 700

Gln Gln Val Phe Gln Trp Ala Leu Gly Ser Ile Glu Ile Phe Met Ser
705                 710                 715                 720

Lys His Cys Pro Leu Trp Tyr Gly Tyr Gly Gly Gly Leu Lys Trp Leu
                725                 730                 735

Gln Arg Ile Ser Tyr Ile Asn Ala Ile Val Tyr Pro Trp Thr Ser Ile
            740                 745                 750

Pro Leu Val Val Tyr Cys Thr Leu Pro Ala Ile Cys Leu Leu Thr Gly
        755                 760                 765

Lys Phe Ile Ile Pro Glu Leu Ser Asn Ala Ala Gly Met Trp Phe Val
    770                 775                 780

Ser Leu Phe Phe Cys Ile Phe Thr Thr Ser Val Leu Glu Met Arg Trp
785                 790                 795                 800
```

```
Ser Gly Val Thr Val Asp Glu Trp Trp Arg Asn Glu Gln Phe Trp Val
                805                 810                 815

Ile Gly Gly Val Ser Ala His Phe Leu Ala Val Phe Leu Gly Met Phe
            820                 825                 830

Lys Val Leu Ala Gly Val Lys Thr Asn Phe Ile Val Ala Ser Lys Val
        835                 840                 845

Asp Asp Lys Glu His Ser Asn Met Phe Ala Leu Lys Trp Thr Thr Leu
    850                 855                 860

Leu Ile Ile Pro Thr Thr Leu Leu Val Leu Asn Ile Ile Ala Val Val
865                 870                 875                 880

Ala Gly Val Ser Tyr Ala Ile Asn Asn Gly Phe Glu Ser Trp Gly Pro
                885                 890                 895

Leu Leu Gly Lys Leu Leu Phe Ser Leu Trp Val Ile Leu His Leu Tyr
            900                 905                 910

Pro Phe Leu Lys Gly Met Ile Gly Arg His Asn Arg Thr Pro Thr Ile
        915                 920                 925

Val Leu Val Trp Ala Ile Leu Leu Ala Ser Phe Phe Ser Val Leu Trp
    930                 935                 940

Val Lys Ile Asp Pro Phe Leu Pro Lys Ser Asp Gly Pro Ile Leu Glu
945                 950                 955                 960

Glu Cys Gly Leu Asp Cys Asn
                965


<210> SEQ ID NO 33
<211> LENGTH: 990
<212> TYPE: PRT
<213> ORGANISM: Glycine max

<400> SEQUENCE: 33

Met Arg Thr Pro Thr Ser Leu Thr His Ala Tyr Leu His Trp Phe His
1               5                   10                  15

Ser Pro Leu Thr Met Glu Ala Ser Thr Gly Leu Phe Ala Gly Thr Pro
            20                  25                  30

Asn Ser Asn Glu Leu Val Val Ile Gln Gly His Asp Glu Pro Lys Pro
        35                  40                  45

Val Lys Asn Leu Asp Gly Gln Leu Cys Glu Ile Cys Gly Asp Ser Val
    50                  55                  60

Gly Leu Thr Val Asp Gly Asp Leu Phe Val Ala Cys Glu Glu Cys Gly
65                  70                  75                  80

Phe Pro Val Cys Arg Pro Cys Tyr Glu Tyr Glu Arg Arg Glu Gly Thr
                85                  90                  95

Gln Val Cys Pro Gln Cys His Thr Arg Tyr Lys Arg Thr Lys Gly Ser
            100                 105                 110

Pro Arg Val Leu Gly Asp Glu Asp Glu Asp Asp Val Asp Asp Ile Glu
        115                 120                 125

His Glu Phe Lys His Glu Glu Met Leu Gln Gly Asn Lys Thr His Arg
    130                 135                 140

Asp Ser Asp Val Gly Leu Ala Lys Val Asn Gly Glu Leu Pro Ile Ser
145                 150                 155                 160

Ser Asn Ser Val Glu Glu Pro Gly Ala Lys Leu Asp Asp Lys Glu Lys
                165                 170                 175

Val Asp Glu Trp Met Leu His Gln Gly Asn Leu Trp Pro Glu Thr Asp
            180                 185                 190

Ala Ser Asp Asp Pro Val Lys Ala Met Lys Glu Pro Leu Ser Arg Lys
        195                 200                 205
```

-continued

```
Val Pro Ile Pro Ser Gly Arg Leu Ser Pro Tyr Arg Met Met Val Val
    210                 215                 220

Ala Arg Leu Leu Leu Leu Leu Leu Phe Phe Gln Tyr Arg Ile Phe His
225                 230                 235                 240

Pro Val Pro Asp Ala Ile Gly Leu Trp Phe Ile Ser Val Thr Cys Glu
                245                 250                 255

Ile Trp Leu Ala Leu Ser Trp Met Ile Asp Gln Leu Pro Lys Trp Phe
            260                 265                 270

Pro Ile Asp Arg Glu Thr Tyr Leu Asp Arg Leu Ser Ile Arg Phe Glu
        275                 280                 285

Pro Glu Asn Lys Pro Asn Met Leu Ser Pro Ile Asp Ile Ile Val Thr
    290                 295                 300

Thr Val Asp Pro Ile Lys Glu Pro Pro Leu Val Thr Ala Asn Thr Val
305                 310                 315                 320

Leu Ser Ile Leu Ala Leu Asp Tyr Pro Ala Asp Lys Ile Ser Cys Tyr
                325                 330                 335

Val Ser Asp Asp Gly Ala Ser Met Leu Thr Phe Glu Val Leu Gln Glu
            340                 345                 350

Thr Ala Glu Phe Ser Arg Lys Trp Val Pro Phe Cys Lys Lys Phe Ser
        355                 360                 365

Val Glu Pro Arg Ala Pro Glu Lys Tyr Leu Thr Glu Lys Ile Asp Phe
    370                 375                 380

Leu Lys Asp Lys Leu Gln Ser Thr Tyr Val Lys Glu Arg Arg Thr Met
385                 390                 395                 400

Lys Arg Glu Tyr Glu Glu Phe Lys Val Arg Ile Asn Ala Leu Val Ala
                405                 410                 415

Lys Ser Met Arg Val Pro Pro Glu Gly Trp Thr Met Lys Asp Glu Thr
            420                 425                 430

Pro Trp Pro Gly Asn Asn Ser Lys Asp His Pro Ser Met Ile Gln Val
        435                 440                 445

Leu Leu Pro His Asn Val Gly Asn Glu Leu Pro Cys Leu Val Tyr Thr
    450                 455                 460

Ser Arg Glu Lys Arg Pro Ala Phe Gln His His Asn Lys Ala Gly Ala
465                 470                 475                 480

Ile Asn Ala Met Leu Arg Val Ser Ala Val Leu Asn Asn Ala Pro Phe
                485                 490                 495

Val Leu Asn Leu Asp Cys Asn His Tyr Val Asn Asn Ser Lys Val Val
            500                 505                 510

Arg Glu Ala Met Cys Phe Phe Met Asp Ile Gln Leu Gly Asn Gly Ile
        515                 520                 525

Gly Phe Val Gln Phe Pro Leu Arg Phe Asp Ser Leu Asp Arg Asn Asp
    530                 535                 540

Arg Tyr Ala Asn Lys Asn Thr Val Leu Phe Asp Ile Asn Leu Arg Cys
545                 550                 555                 560

Leu Asp Gly Ile Gln Gly Pro Ala Tyr Val Gly Ser Ala Cys Ile Phe
                565                 570                 575

Arg Arg Lys Ala Leu Thr Gly Phe Asp Ser Pro Lys Ala Ser Lys Arg
            580                 585                 590

Pro Ser Met Val Gln Val His Ser Lys Gln Asp Glu Asn Gly Glu Glu
        595                 600                 605

Ala Ser Lys Thr Ala Ala Ala Thr Asp Glu Asp Lys Glu Leu Leu Lys
    610                 615                 620
```

Ser Glu Asn Lys Phe Gly Met Ser Thr Ile Phe Met Asn Ser Ser Trp
625 630 635 640

Thr Glu Glu Gly Gly Val Asp Pro Ser Ser Ser Gln Glu Ala Leu Leu
645 650 655

Lys Glu Ala Ile His Val Met Asn Ser Arg Tyr Glu Asp Arg Thr Leu
660 665 670

Trp Gly Tyr Glu Val Gly Leu Ser Tyr Gly Ser Ile Ala Thr Asp Thr
675 680 685

Leu Thr Ser Met Lys Met His Cys Gly Gly Trp Arg Ser Val Tyr Cys
690 695 700

Met Pro Lys Arg Asp Pro Phe Arg Gly Thr Ala Pro Ile Asn Leu Thr
705 710 715 720

Glu Arg Leu Asn Gln Val Leu Arg Trp Ala Val Gly Ser Leu Gln Ile
725 730 735

Leu Phe Ser Ser His Cys Pro Leu Val Tyr Gly Leu Asn Gly Gly Arg
740 745 750

Leu Lys Gly Leu Gln Arg Ile Ala Tyr Ile Asn Ser Thr Val Tyr Pro
755 760 765

Phe Thr Ser Ile Pro Leu Leu Ile Tyr Cys Thr Ile Pro Ala Ile Cys
770 775 780

Leu Leu Thr Asp Lys Phe Ile Thr Pro Ser Val Gly Thr Phe Ala Ser
785 790 795 800

Leu Ile Phe Ile Ala Leu Phe Ile Ser Ile Phe Ala Ser Ala Ile Leu
805 810 815

Glu Leu Arg Trp Ser Arg Val Ser Leu Glu Glu Trp Trp Arg Ser Gln
820 825 830

Gln Phe Trp Val Ile Gly Ser Val Ser Ala Asn Leu Phe Ala Val Leu
835 840 845

Gln Gly Ile Met Gly Ala Leu Pro Leu Ser Ser Arg Val Asn Lys Asn
850 855 860

Phe Ser Ile Val Ser Lys Ala Pro Asp Glu Val Glu Phe Arg Glu Leu
865 870 875 880

Tyr Ala Ile Arg Trp Thr Ala Leu Leu Ile Pro Pro Thr Thr Ile Ile
885 890 895

Ile Ile Asn Leu Ile Gly Ile Val Ala Gly Phe Thr Asp Ala Ile Asn
900 905 910

Ser Gly Glu His Ser Trp Gly Ala Leu Leu Gly Lys Leu Phe Phe Ser
915 920 925

Leu Trp Val Ile Val His Leu Tyr Pro Phe Leu Lys Gly Leu Met Gly
930 935 940

Arg Gln Asn Arg Thr Pro Thr Leu Ile Val Ile Trp Ser Val Leu Leu
945 950 955 960

Ala Ser Ile Phe Ser Leu Val Trp Val Arg Val Asp Pro Phe Val Leu
965 970 975

Lys Thr Lys Gly Pro Asp Val Lys Gln Cys Gly Ile Ser Cys
980 985 990

<210> SEQ ID NO 34
<211> LENGTH: 1084
<212> TYPE: PRT
<213> ORGANISM: Glycine max

<400> SEQUENCE: 34

Met Glu Ala Ser Ala Gly Met Val Ala Gly Ser His Lys Arg Asn Glu
1 5 10 15

```
Leu Val Arg Ile Arg His Asp Ser Ser Asp Ser Gly Ser Lys Pro Leu
            20                  25                  30

Lys Ser Leu Asn Gly Gln Ile Cys Gln Ile Cys Gly Asp Thr Val Gly
        35                  40                  45

Leu Thr Ala Thr Gly Asp Val Phe Val Ala Cys Asn Glu Cys Ala Phe
    50                  55                  60

Pro Val Cys Arg Pro Cys Tyr Glu Tyr Glu Arg Lys Asp Gly Asn Gln
65                  70                  75                  80

Ser Cys Pro Gln Cys Lys Thr Arg Tyr Lys Arg His Arg Gly Ser Pro
                85                  90                  95

Arg Val Glu Gly Asp Glu Asp Glu Asp Asp Ser Asp Asp Ile Glu Asn
            100                 105                 110

Glu Phe Asn Tyr Ala Gln Gly Lys Ala Lys Ala Arg Arg Gln Trp Glu
        115                 120                 125

Asp Asp Ala Asp Leu Ser Ser Ser Ser Arg Arg Glu Ser Gln Gln Pro
    130                 135                 140

Ile Pro Leu Leu Thr Asn Gly Gln Thr Met Ser Gly Glu Ile Pro Cys
145                 150                 155                 160

Ala Thr Pro Asp Thr Gln Ser Val Arg Thr Thr Ser Gly Pro Leu Gly
                165                 170                 175

Pro Ser Glu Lys Val His Ser Leu Pro Tyr Val Asp Pro Arg Gln Pro
            180                 185                 190

Val Pro Val Arg Ile Val Asp Pro Ser Lys Asp Leu Asn Ser Tyr Gly
        195                 200                 205

Leu Gly Asn Val Asp Trp Lys Glu Arg Val Glu Gly Trp Lys Leu Lys
    210                 215                 220

Gln Glu Lys Asn Met Val Gln Met Thr Gly Arg Tyr Thr Glu Gly Lys
225                 230                 235                 240

Gly Gly Asp Val Glu Gly Thr Gly Ser Asn Gly Glu Glu Leu Gln Met
                245                 250                 255

Val Asp Asp Ala Arg Gln Pro Met Ser Arg Val Val Pro Ile Pro Ser
            260                 265                 270

Ser Gln Leu Thr Pro Tyr Arg Val Val Ile Ile Leu Arg Leu Ile Ile
        275                 280                 285

Leu Gly Phe Phe Leu Gln Tyr Arg Val Thr His Pro Val Lys Asp Ala
    290                 295                 300

Tyr Pro Leu Trp Leu Thr Ser Val Ile Cys Glu Ile Trp Phe Ala Leu
305                 310                 315                 320

Ser Trp Leu Leu Asp Gln Phe Pro Lys Trp Ser Pro Ile Asn Arg Glu
                325                 330                 335

Thr Tyr Leu Glu Arg Leu Ala Leu Arg Tyr Asp Arg Glu Gly Glu Pro
            340                 345                 350

Ser Gln Leu Asp Pro Val Asp Val Phe Val Ser Thr Val Asp Pro Leu
        355                 360                 365

Lys Glu Pro Pro Leu Val Thr Ala Asn Thr Val Leu Ser Ile Leu Ser
    370                 375                 380

Val Asp Tyr Pro Val Asp Lys Val Ser Cys Tyr Val Ser Asp Asp Gly
385                 390                 395                 400

Ser Ala Met Leu Thr Phe Glu Ala Leu Ser Glu Thr Ala Glu Phe Ala
                405                 410                 415

Lys Lys Trp Val Pro Phe Cys Lys Lys His Asn Ile Glu Pro Arg Ala
            420                 425                 430
```

-continued

```
Pro Glu Phe Tyr Phe Ala Gln Lys Ile Asp Tyr Leu Lys Asp Lys Ile
        435                 440                 445

Gln Pro Ser Phe Val Lys Glu Arg Arg Ala Met Lys Arg Glu Tyr Glu
    450                 455                 460

Glu Phe Lys Val Arg Ile Asn Ala Leu Val Ala Lys Ala Gln Lys Met
465                 470                 475                 480

Pro Glu Glu Gly Trp Thr Met Gln Asp Gly Thr Ala Trp Pro Gly Asn
                485                 490                 495

Asn Pro Arg Asp His Pro Gly Met Ile Gln Val Phe Leu Gly His Ser
            500                 505                 510

Gly Gly Leu Asp Thr Asp Gly Asn Glu Leu Pro Arg Leu Val Tyr Val
        515                 520                 525

Ser Arg Glu Lys Arg Pro Gly Phe Gln His His Lys Lys Ala Gly Ala
    530                 535                 540

Met Asn Ala Leu Ile Arg Val Ser Ala Val Leu Thr Asn Gly Ala Tyr
545                 550                 555                 560

Leu Leu Asn Val Asp Cys Asp His Tyr Phe Asn Asn Ser Lys Ala Leu
                565                 570                 575

Lys Glu Ala Met Cys Phe Met Met Asp Pro Val Ile Gly Lys Lys Thr
            580                 585                 590

Cys Tyr Val Gln Phe Pro Gln Arg Phe Asp Gly Ile Asp Leu His Asp
        595                 600                 605

Arg Tyr Ala Asn Arg Asn Ile Val Phe Phe Asp Ile Asn Met Lys Gly
    610                 615                 620

Gln Asp Gly Val Gln Gly Pro Val Tyr Val Gly Thr Gly Cys Cys Phe
625                 630                 635                 640

Asn Arg Gln Ala Leu Tyr Gly Tyr Asp Pro Val Leu Thr Glu Glu Asp
                645                 650                 655

Leu Glu Pro Asn Ile Ile Val Lys Ser Cys Trp Gly Ser Arg Lys Lys
            660                 665                 670

Gly Lys Gly Gly Asn Lys Lys Tyr Ser Asp Lys Lys Lys Ala Met Gly
        675                 680                 685

Arg Thr Glu Ser Thr Val Pro Ile Phe Asn Met Glu Asp Ile Glu Glu
    690                 695                 700

Gly Val Glu Gly Tyr Asp Asp Glu Arg Thr Leu Leu Met Ser Gln Lys
705                 710                 715                 720

Ser Leu Glu Lys Arg Phe Gly Gln Ser Pro Val Phe Ile Ala Ala Thr
                725                 730                 735

Phe Met Glu Gln Gly Gly Ile Pro Pro Ser Thr Asn Pro Ala Thr Leu
            740                 745                 750

Leu Lys Glu Ala Ile His Val Ile Ser Cys Gly Tyr Glu Asp Lys Thr
        755                 760                 765

Glu Trp Gly Lys Glu Ile Gly Trp Ile Tyr Gly Ser Val Thr Glu Asp
    770                 775                 780

Ile Leu Thr Gly Phe Lys Met His Ala Arg Gly Trp Ile Ser Ile Tyr
785                 790                 795                 800

Cys Met Pro Pro Arg Pro Ala Phe Lys Gly Ser Ala Pro Ile Asn Leu
                805                 810                 815

Ser Asp Arg Leu Asn Gln Val Leu Arg Trp Ala Leu Gly Ser Ile Glu
            820                 825                 830

Ile Phe Leu Ser Arg His Cys Pro Leu Trp Tyr Gly Tyr Asn Gly Lys
        835                 840                 845

Leu Lys Pro Leu Met Arg Leu Ala Tyr Ile Asn Thr Ile Val Tyr Pro
```

850 855 860

Phe Thr Ser Ile Pro Leu Ile Ala Tyr Cys Thr Leu Pro Ala Phe Cys
865 870 875 880

Leu Leu Thr Asn Lys Phe Ile Ile Pro Glu Ile Ser Asn Phe Ala Ser
885 890 895

Met Trp Phe Ile Leu Leu Phe Val Ser Ile Phe Thr Thr Ser Ile Leu
900 905 910

Glu Leu Arg Trp Ser Gly Val Ser Ile Glu Asp Trp Trp Arg Asn Glu
915 920 925

Gln Phe Trp Val Ile Gly Gly Thr Ser Ala His Leu Phe Ala Val Phe
930 935 940

Gln Gly Leu Leu Lys Val Leu Ala Gly Ile Asp Thr Asn Phe Thr Val
945 950 955 960

Thr Ser Lys Ala Ser Asp Glu Asp Gly Asp Phe Ala Glu Leu Tyr Val
965 970 975

Phe Lys Trp Thr Ser Leu Leu Ile Pro Pro Thr Thr Val Leu Ile Val
980 985 990

Asn Leu Val Gly Ile Val Ala Gly Val Ser Tyr Ala Ile Asn Ser Gly
995 1000 1005

Tyr Gln Ser Trp Gly Pro Leu Phe Gly Lys Leu Phe Phe Ala Ile
1010 1015 1020

Trp Val Ile Ala His Leu Tyr Pro Phe Leu Lys Gly Leu Leu Gly
1025 1030 1035

Arg Gln Asn Arg Thr Pro Thr Ile Val Ile Val Trp Ser Val Leu
1040 1045 1050

Leu Ala Ser Ile Phe Ser Leu Leu Trp Val Arg Ile Asp Pro Phe
1055 1060 1065

Thr Ser Asp Ser Asn Lys Leu Thr Asn Gly Gln Cys Gly Ile Asn
1070 1075 1080

Cys

<210> SEQ ID NO 35
<211> LENGTH: 1084
<212> TYPE: PRT
<213> ORGANISM: Glycine max

<400> SEQUENCE: 35

Met Glu Ala Ser Ala Gly Met Val Ala Gly Ser His Lys Arg Asn Glu
1 5 10 15

Leu Val Arg Ile Arg His Asp Ser Ser Asp Ser Gly Ser Lys Pro Met
20 25 30

Lys Asn Leu Asn Gly Gln Ile Cys Gln Ile Cys Gly Asp Thr Val Gly
35 40 45

Leu Thr Ala Thr Gly Asp Val Phe Val Ala Cys Asn Glu Cys Ala Phe
50 55 60

Pro Val Cys Arg Pro Cys Tyr Glu Tyr Glu Arg Lys Asp Gly Asn Gln
65 70 75 80

Ser Cys Pro Gln Cys Lys Thr Arg Tyr Lys Arg His Arg Gly Ser Pro
85 90 95

Arg Val Glu Gly Asp Glu Asp Glu Asp Asp Ser Asp Asp Ile Glu Asn
100 105 110

Glu Phe Asn Tyr Ala Gln Gly Lys Ala Lys Ala Arg Arg Gln Trp Glu
115 120 125

Asp Asp Pro Asp Leu Ser Ser Ser Ser Arg Arg Glu Ser Gln Gln Pro

```
    130                 135                 140

Ile Pro Leu Leu Thr Asn Gly Gln Thr Met Ser Gly Glu Ile Pro Cys
145                 150                 155                 160

Ala Thr Pro Asp Thr Gln Ser Val Arg Thr Thr Ser Gly Pro Leu Gly
                165                 170                 175

Pro Ser Glu Lys Val His Ser Leu Pro Tyr Val Asp Pro Arg Gln Pro
            180                 185                 190

Val Pro Val Arg Ile Val Asp Pro Ser Lys Asp Leu Asn Ser Tyr Gly
        195                 200                 205

Leu Gly Asn Val Asp Trp Lys Glu Arg Val Glu Gly Trp Lys Leu Lys
    210                 215                 220

Gln Glu Lys Asn Met Val Gln Met Thr Gly Arg Tyr Ala Glu Gly Lys
225                 230                 235                 240

Gly Gly Asp Val Glu Gly Thr Gly Ser Asn Gly Glu Glu Leu Gln Met
                245                 250                 255

Val Asp Asp Ala Arg Gln Pro Met Ser Arg Val Val Pro Ile Pro Ser
            260                 265                 270

Ser Gln Leu Thr Pro Tyr Arg Val Val Ile Ile Leu Arg Leu Ile Ile
        275                 280                 285

Leu Gly Phe Phe Leu Gln Tyr Arg Val Thr His Pro Val Lys Asp Ala
    290                 295                 300

Tyr Pro Leu Trp Leu Thr Ser Val Ile Cys Glu Ile Trp Phe Ala Leu
305                 310                 315                 320

Ser Trp Leu Leu Asp Gln Phe Pro Lys Trp Ser Pro Ile Asn Arg Glu
                325                 330                 335

Thr Tyr Leu Glu Arg Leu Ala Leu Arg Tyr Asp Arg Glu Gly Glu Pro
            340                 345                 350

Ser Gln Leu Asp Pro Val Asp Val Phe Val Ser Thr Val Asp Pro Leu
        355                 360                 365

Lys Glu Pro Pro Leu Val Thr Ala Asn Thr Val Leu Ser Ile Leu Ser
    370                 375                 380

Val Asp Tyr Pro Val Asp Lys Val Ser Cys Tyr Val Ser Asp Asp Gly
385                 390                 395                 400

Ser Ala Met Leu Thr Phe Glu Ala Leu Ser Glu Thr Ala Glu Phe Ala
                405                 410                 415

Lys Lys Trp Val Pro Phe Cys Lys Lys His Asn Ile Glu Pro Arg Ala
            420                 425                 430

Pro Glu Phe Tyr Phe Ala Gln Lys Ile Asp Tyr Leu Lys Asp Lys Ile
        435                 440                 445

Gln Pro Ser Phe Val Lys Glu Arg Arg Ala Met Lys Arg Glu Tyr Glu
    450                 455                 460

Glu Phe Lys Val Arg Ile Asn Ala Leu Val Ala Lys Ala Gln Lys Met
465                 470                 475                 480

Pro Glu Glu Gly Trp Thr Met Gln Asp Gly Thr Pro Trp Pro Gly Asn
                485                 490                 495

Asn Pro Arg Asp His Pro Gly Met Ile Gln Val Phe Leu Gly His Ser
            500                 505                 510

Gly Gly Leu Asp Thr Asp Gly Asn Glu Leu Pro Arg Leu Val Tyr Val
        515                 520                 525

Ser Arg Glu Lys Arg Pro Gly Phe Gln His His Lys Lys Ala Gly Ala
    530                 535                 540

Met Asn Ala Leu Ile Arg Val Ser Ala Val Leu Thr Asn Gly Ala Tyr
545                 550                 555                 560
```

```
Leu Leu Asn Val Asp Cys Asp His Tyr Phe Asn Asn Ser Lys Ala Leu
                565                 570                 575

Lys Glu Ala Met Cys Phe Met Met Asp Pro Val Leu Gly Lys Lys Thr
            580                 585                 590

Cys Tyr Val Gln Phe Pro Gln Arg Phe Asp Gly Ile Asp Leu His Asp
        595                 600                 605

Arg Tyr Ala Asn Arg Asn Ile Val Phe Phe Asp Ile Asn Met Lys Gly
    610                 615                 620

Gln Asp Gly Val Gln Gly Pro Val Tyr Val Gly Thr Gly Cys Cys Phe
625                 630                 635                 640

Asn Arg Gln Ala Leu Tyr Gly Tyr Asp Pro Val Leu Thr Glu Glu Asp
                645                 650                 655

Leu Glu Pro Asn Ile Ile Val Lys Ser Cys Cys Gly Ser Arg Lys Lys
            660                 665                 670

Gly Lys Gly Gly Asn Lys Lys Tyr Ser Asp Lys Lys Lys Ala Met Gly
        675                 680                 685

Arg Thr Glu Ser Thr Val Pro Ile Phe Asn Met Glu Asp Ile Glu Glu
    690                 695                 700

Gly Val Glu Gly Tyr Asp Asp Glu Arg Thr Leu Leu Met Ser Gln Lys
705                 710                 715                 720

Ser Leu Glu Lys Arg Phe Gly Gln Ser Pro Val Phe Ile Ala Ala Thr
                725                 730                 735

Phe Met Glu Gln Gly Gly Ile Pro Pro Ser Thr Asn Pro Ala Thr Leu
            740                 745                 750

Leu Lys Glu Ala Ile His Val Ile Ser Cys Gly Tyr Glu Asp Lys Thr
        755                 760                 765

Glu Trp Gly Lys Glu Ile Gly Trp Ile Tyr Gly Ser Val Thr Glu Asp
    770                 775                 780

Ile Leu Thr Gly Phe Lys Met His Ala Arg Gly Trp Ile Ser Ile Tyr
785                 790                 795                 800

Cys Met Pro Pro Arg Pro Ala Phe Lys Gly Ser Ala Pro Ile Asn Leu
                805                 810                 815

Ser Asp Arg Leu Asn Gln Val Leu Arg Trp Ala Leu Gly Ser Ile Glu
            820                 825                 830

Ile Phe Leu Ser Arg His Cys Pro Leu Trp Tyr Gly Tyr Asn Gly Lys
        835                 840                 845

Leu Lys Pro Leu Met Arg Leu Ala Tyr Ile Asn Thr Ile Val Tyr Pro
    850                 855                 860

Phe Thr Ser Ile Pro Leu Ile Ala Tyr Cys Thr Leu Pro Ala Phe Cys
865                 870                 875                 880

Leu Leu Thr Asn Lys Phe Ile Ile Pro Glu Ile Ser Asn Phe Ala Ser
                885                 890                 895

Met Trp Phe Ile Leu Leu Phe Val Ser Ile Phe Thr Thr Ser Ile Leu
            900                 905                 910

Glu Leu Arg Trp Ser Gly Val Ser Ile Glu Asp Trp Trp Arg Asn Glu
        915                 920                 925

Gln Phe Trp Val Ile Gly Gly Thr Ser Ala His Leu Phe Ala Val Phe
    930                 935                 940

Gln Gly Leu Leu Lys Val Leu Ala Gly Ile Asp Thr Asn Phe Thr Val
945                 950                 955                 960

Thr Ser Lys Ala Ser Asp Glu Asp Gly Asp Phe Ala Glu Leu Tyr Val
                965                 970                 975
```

Phe Lys Trp Thr Ser Leu Leu Ile Pro Pro Thr Thr Val Leu Ile Val
980 985 990

Asn Leu Val Gly Ile Val Ala Gly Val Ser Tyr Ala Ile Asn Ser Gly
995 1000 1005

Tyr Gln Ser Trp Gly Pro Leu Phe Gly Lys Leu Phe Phe Ala Ile
1010 1015 1020

Trp Val Ile Ala His Leu Tyr Pro Phe Leu Lys Gly Leu Leu Gly
1025 1030 1035

Arg Gln Asn Arg Thr Pro Thr Ile Val Ile Val Trp Ser Val Leu
1040 1045 1050

Leu Ala Ser Ile Phe Ser Leu Leu Trp Val Arg Ile Asp Pro Phe
1055 1060 1065

Thr Ser Asp Ser Asn Lys Leu Thr Asn Gly Gln Cys Gly Ile Asn
1070 1075 1080

Cys

<210> SEQ ID NO 36
<211> LENGTH: 976
<212> TYPE: PRT
<213> ORGANISM: Glycine max

<400> SEQUENCE: 36

Met Met Glu Ser Gly Ala His Phe Cys Asn Ser Cys Gly Glu Gln Ile
1 5 10 15

Gly Leu Asp Ala Asn Gly Glu Leu Phe Val Ala Cys His Glu Cys Tyr
20 25 30

Phe Pro Ile Cys Lys Ala Cys Phe Glu Tyr Glu Ile Asn Glu Gly Arg
35 40 45

Lys Val Cys Leu Arg Cys Ala Thr Pro Tyr Ser Asp Arg Val Lys Asp
50 55 60

Asn Asp Gly Thr Lys Val Tyr Glu Asn Gln Ser Thr Thr Ala Ala Gln
65 70 75 80

Ile Asn Val Ser Gln Asp Val Gly Leu His Ala Arg His Val Ser Thr
85 90 95

Val Ser Thr Val Asp Ser Glu Leu Asn Asp Glu Ser Gly Asn Pro Ile
100 105 110

Trp Lys Asn Arg Val Glu Ser Trp Lys Glu Lys Asp Lys Lys Lys Lys
115 120 125

Lys Lys Lys Lys Ser Val Pro Lys Ala Glu Asn Glu Ala Pro Ile Pro
130 135 140

Pro Glu Gln Gln Met Glu Glu Ile Gln Ser Ser Glu Ala Ser Ala Ala
145 150 155 160

Glu Pro Leu Ser Met Val Ile Pro Ile Ser Lys Thr Arg Leu Ala Pro
165 170 175

Tyr Arg Thr Val Ile Ile Val Arg Leu Ile Ile Leu Gly Leu Phe Phe
180 185 190

His Tyr Arg Val Thr Asn Pro Val Asp Ser Ala Phe Gly Leu Trp Leu
195 200 205

Thr Ser Ile Ile Cys Glu Ile Trp Phe Ala Phe Ser Trp Val Leu Asp
210 215 220

Gln Phe Pro Lys Trp Ser Pro Val Asn Arg Glu Ala Phe Val Asp Arg
225 230 235 240

Leu Ser Ala Arg Tyr Glu Arg Pro Gly Glu Pro Ser Gln Leu Ala Ala
245 250 255

```
Val Asp Phe Phe Val Ser Thr Val Asp Pro Leu Lys Glu Pro Pro Leu
            260                 265                 270

Ile Thr Ala Asn Thr Val Leu Ser Ile Leu Ala Val Asp Tyr Pro Val
        275                 280                 285

Asp Lys Val Ser Cys Tyr Val Ser Asp Asp Gly Ala Ala Met Leu Thr
    290                 295                 300

Phe Glu Ser Leu Val Glu Thr Ala Asp Phe Ala Arg Met Trp Val Pro
305                 310                 315                 320

Phe Cys Lys Lys Phe Ser Ile Glu Pro Arg Ala Pro Glu Phe Tyr Phe
                325                 330                 335

Ser Gln Lys Ile Asp Tyr Leu Lys Asp Lys Val Gln Pro Ser Phe Val
            340                 345                 350

Lys Glu Arg Arg Ala Met Lys Arg Glu Tyr Glu Glu Phe Lys Val Arg
        355                 360                 365

Val Asn Ala Leu Val Ala Lys Ala Gln Lys Thr Pro Asp Glu Gly Trp
    370                 375                 380

Thr Met Gln Asp Gly Thr Ser Trp Pro Gly Asn Asn Ser Arg Asp His
385                 390                 395                 400

Pro Gly Met Ile Gln Val Phe Leu Gly His Ser Gly Ala His Asp Val
                405                 410                 415

Glu Gly Asn Glu Leu Pro Arg Leu Val Tyr Val Ser Arg Glu Lys Arg
            420                 425                 430

Pro Gly Tyr Gln His His Lys Lys Ala Gly Ala Glu Asn Ala Leu Val
        435                 440                 445

Arg Val Ser Ala Val Leu Thr Asn Ala Pro Phe Ile Leu Asn Leu Asp
    450                 455                 460

Cys Asp His Tyr Val Asn Asn Ser Lys Ala Val Arg Glu Ala Met Cys
465                 470                 475                 480

Phe Leu Met Asp Pro Val Val Gly Arg Asp Leu Cys Tyr Val Gln Phe
                485                 490                 495

Pro Gln Arg Phe Asp Gly Ile Asp Arg Ser Asp Arg Tyr Ala Asn Arg
            500                 505                 510

Asn Thr Val Phe Phe Asp Val Asn Met Lys Gly Leu Asp Gly Ile Gln
        515                 520                 525

Gly Pro Met Tyr Val Gly Thr Gly Cys Val Phe Asn Arg Gln Ala Leu
    530                 535                 540

Tyr Gly Tyr Ser Pro Pro Ser Met Pro Lys Leu Pro Lys Ser Ser Ser
545                 550                 555                 560

Cys Cys Cys Cys Pro Ser Lys Lys Gln Thr Lys Asp Val Ser Glu Leu
                565                 570                 575

Tyr Arg Asp Ala Lys Arg Glu Glu Leu Asp Ala Ala Ile Phe Asn Leu
            580                 585                 590

Arg Glu Ile Asp Asn Tyr Asp Glu Tyr Glu Arg Ser Met Leu Ile Ser
        595                 600                 605

Gln Met Ser Phe Glu Lys Thr Phe Gly Leu Ser Thr Val Phe Ile Glu
    610                 615                 620

Ser Thr Leu Met Glu Asn Gly Gly Leu Pro Glu Ser Ser Asp Pro Ser
625                 630                 635                 640

Met Leu Ile Lys Glu Ala Ile His Val Ile Ser Cys Gly Tyr Glu Glu
                645                 650                 655

Lys Thr Ala Trp Gly Lys Glu Ile Gly Trp Ile Tyr Gly Ser Val Thr
            660                 665                 670

Glu Asp Ile Leu Thr Gly Phe Lys Met Gln Cys Arg Gly Trp Arg Ser
```

```
        675                 680                 685

Val Tyr Cys Met Pro Leu Arg Pro Ala Phe Lys Gly Ser Ala Pro Ile
    690                 695                 700

Asn Leu Ser Asp Arg Leu His Gln Val Leu Arg Trp Ala Leu Gly Ser
705                 710                 715                 720

Val Glu Ile Phe Phe Ser Arg His Cys Pro Leu Trp Tyr Gly Phe Ala
                725                 730                 735

Gly Gly Arg Leu Lys Trp Leu Gln Arg Leu Ala Tyr Ile Asn Thr Ile
            740                 745                 750

Val Tyr Pro Phe Thr Ser Leu Pro Leu Val Ala Tyr Cys Thr Leu Pro
        755                 760                 765

Ala Ile Cys Leu Leu Thr Gly Lys Phe Ile Ile Pro Thr Leu Ser Asn
    770                 775                 780

Leu Ala Ser Ala Leu Phe Leu Gly Leu Phe Leu Ser Ile Ile Val Thr
785                 790                 795                 800

Ser Val Leu Glu Leu Arg Trp Ser Gly Val Thr Ile Glu Ala Leu Trp
                805                 810                 815

Arg Asn Glu Gln Phe Trp Val Ile Gly Gly Val Ser Ala His Leu Phe
            820                 825                 830

Ala Val Phe Gln Gly Phe Leu Lys Met Leu Ala Gly Val Asp Thr Asn
        835                 840                 845

Phe Thr Val Thr Ala Lys Ala Ala Asp Asp Thr Glu Phe Gly Glu Leu
    850                 855                 860

Tyr Ile Ile Lys Trp Thr Thr Leu Leu Ile Pro Pro Thr Thr Leu Ile
865                 870                 875                 880

Ile Ile Asn Ile Val Gly Val Val Ala Gly Phe Ser Asp Ala Leu Asn
                885                 890                 895

Gly Gly Tyr Glu Ser Trp Gly Pro Leu Phe Gly Lys Val Phe Phe Ala
            900                 905                 910

Phe Trp Val Ile Phe His Leu Tyr Pro Phe Leu Lys Gly Leu Met Gly
        915                 920                 925

Arg Gln Asn Arg Thr Pro Thr Ile Val Ile Leu Trp Ser Val Leu Leu
    930                 935                 940

Ala Ser Val Phe Ser Leu Val Trp Val Lys Ile Asn Pro Phe Ile Ser
945                 950                 955                 960

Arg Pro Asp Ser Ala Ser Ile Ser Gln Thr Cys Ile Ser Ile Asp Cys
                965                 970                 975


<210> SEQ ID NO 37
<211> LENGTH: 1039
<212> TYPE: PRT
<213> ORGANISM: Glycine max

<400> SEQUENCE: 37

Met Glu Ala Ser Ala Gly Leu Val Ala Gly Ser His Asn Arg Asn Glu
1               5                   10                  15

Leu Val Val Ile His Gly His Glu Glu Pro Lys Ala Leu Lys Asn Leu
            20                  25                  30

Asp Gly Gln Val Cys Glu Ile Cys Gly Asp Gly Val Gly Leu Thr Val
        35                  40                  45

Asp Gly Asp Leu Phe Val Ala Cys Asn Glu Cys Gly Phe Pro Val Cys
    50                  55                  60

Arg Pro Cys Tyr Glu Tyr Glu Arg Arg Glu Gly Ser Gln Leu Cys Pro
65                  70                  75                  80
```

```
Gln Cys Lys Thr Arg Tyr Lys Arg Leu Lys Gly Ser Pro Arg Val Glu
                85                  90                  95

Gly Asp Asp Asp Glu Glu Asp Val Asp Asp Ile Glu His Glu Phe Asn
            100                 105                 110

Ile Asp Glu Gln Thr Asn Lys His Gly Gln Val Ala Glu Ala Met Leu
        115                 120                 125

His Gly Lys Met Ser Tyr Gly Arg Gly Pro Glu Asp Asp Glu Asn Ser
    130                 135                 140

Gln Phe Pro Thr Pro Val Ile Ala Gly Gly Arg Ser Arg Pro Val Ser
145                 150                 155                 160

Gly Glu Phe Pro Leu Ser Ser Asn Val Tyr Gly Asp Gln Met Leu Ser
                165                 170                 175

Ser Ser Leu His Lys Arg Val His Pro Tyr Pro Val Ser Glu Pro Gly
            180                 185                 190

Ser Ala Arg Trp Asp Glu Lys Lys Glu Asp Gly Trp Lys Asp Arg Met
        195                 200                 205

Asp Asp Trp Lys Leu Gln Gln Gly Asn Leu Gly Pro Glu Pro Asp Glu
    210                 215                 220

Asp Pro Asp Ala Ala Met Leu Asp Glu Ala Arg Gln Pro Leu Ser Arg
225                 230                 235                 240

Lys Val Pro Ile Ala Ser Ser Lys Ile Asn Pro Tyr Arg Met Val Ile
                245                 250                 255

Val Ala Arg Leu Val Ile Leu Ala Phe Phe Leu Arg Tyr Arg Leu Met
            260                 265                 270

Asn Pro Val His Asp Ala Leu Gly Leu Trp Leu Thr Ser Ile Ile Cys
        275                 280                 285

Glu Ile Trp Phe Ala Phe Ser Trp Ile Leu Asp Gln Phe Pro Lys Trp
    290                 295                 300

Phe Pro Ile Asp Arg Glu Thr Tyr Leu Asp Arg Leu Ser Ile Arg Tyr
305                 310                 315                 320

Glu Arg Glu Gly Glu Pro Asn Met Leu Ala Pro Val Asp Val Phe Val
                325                 330                 335

Ser Thr Val Asp Pro Met Lys Glu Pro Pro Leu Val Thr Ala Asn Thr
            340                 345                 350

Val Leu Ser Ile Leu Ala Met Asp Tyr Pro Val Asp Lys Ile Ser Cys
        355                 360                 365

Tyr Ile Ser Asp Asp Gly Ala Ser Met Cys Thr Phe Glu Ser Leu Ser
    370                 375                 380

Glu Thr Ala Glu Phe Ala Arg Lys Trp Val Pro Phe Cys Lys Lys Phe
385                 390                 395                 400

Ser Ile Glu Pro Arg Ala Pro Glu Met Tyr Phe Ser Glu Lys Ile Asp
                405                 410                 415

Tyr Leu Lys Asp Lys Val Gln Pro Thr Phe Val Lys Glu Arg Arg Ala
            420                 425                 430

Met Lys Arg Glu Tyr Glu Glu Phe Lys Val Arg Ile Asn Ala Leu Val
        435                 440                 445

Ala Lys Ala Gln Lys Val Pro Gln Gly Gly Trp Ile Met Gln Asp Gly
    450                 455                 460

Thr Pro Trp Pro Gly Asn Asn Thr Lys Asp His Pro Gly Met Ile Gln
465                 470                 475                 480

Val Phe Leu Gly Ser Ser Gly Gly Leu Asp Thr Glu Gly Asn Gln Leu
                485                 490                 495

Pro Arg Leu Val Tyr Val Ser Arg Glu Lys Arg Pro Gly Phe Gln His
```

```
            500                 505                 510

His Lys Lys Ala Gly Ala Met Asn Ala Leu Val Arg Val Ser Ala Val
        515                 520                 525

Leu Thr Asn Ala Pro Phe Met Leu Asn Leu Asp Cys Asp His Tyr Val
    530                 535                 540

Asn Asn Ser Lys Ala Ala Arg Glu Ala Met Cys Phe Leu Met Asp Pro
545                 550                 555                 560

Gln Thr Gly Lys Lys Val Cys Tyr Val Gln Phe Pro Gln Arg Phe Asp
                565                 570                 575

Gly Ile Asp Thr His Asp Arg Tyr Ala Asn Arg Asn Thr Val Phe Phe
            580                 585                 590

Asp Ile Asn Met Lys Gly Leu Asp Gly Ile Gln Gly Pro Val Tyr Val
        595                 600                 605

Gly Thr Gly Cys Val Phe Arg Arg Gln Ala Leu Tyr Gly Tyr Asn Pro
    610                 615                 620

Pro Lys Gly Pro Lys Arg Pro Lys Met Val Ser Cys Asp Cys Cys Pro
625                 630                 635                 640

Cys Phe Gly Ser Arg Lys Lys Tyr Lys Glu Lys Ser Asn Ala Asn Gly
                645                 650                 655

Glu Ala Ala Arg Leu Lys Gly Met Asp Asp Asp Lys Glu Val Leu Met
            660                 665                 670

Ser Gln Met Asn Phe Asp Lys Lys Phe Gly Gln Ser Ser Ile Phe Val
        675                 680                 685

Thr Ser Thr Leu Met Glu Glu Gly Gly Val Pro Pro Ser Ser Ser Pro
    690                 695                 700

Ala Ala Leu Leu Lys Glu Ala Ile His Val Ile Ser Cys Gly Tyr Glu
705                 710                 715                 720

Asp Lys Thr Glu Trp Gly Leu Glu Leu Gly Trp Ile Tyr Gly Ser Ile
                725                 730                 735

Thr Glu Asp Ile Leu Thr Gly Phe Lys Met His Cys Arg Gly Trp Arg
            740                 745                 750

Ser Ile Tyr Cys Met Pro Lys Arg Ala Ala Phe Lys Gly Thr Ala Pro
        755                 760                 765

Ile Asn Leu Ser Asp Arg Leu Asn Gln Val Leu Arg Trp Ala Leu Gly
    770                 775                 780

Ser Ile Glu Ile Phe Phe Ser His His Cys Pro Leu Trp Tyr Gly Phe
785                 790                 795                 800

Lys Glu Lys Lys Leu Lys Trp Leu Glu Arg Phe Ala Tyr Ala Asn Thr
                805                 810                 815

Thr Val Tyr Pro Phe Thr Ser Ile Pro Leu Val Ala Tyr Cys Ile Leu
            820                 825                 830

Pro Ala Val Cys Leu Leu Thr Asp Lys Phe Ile Met Pro Pro Ile Ser
        835                 840                 845

Thr Phe Ala Gly Leu Tyr Phe Val Ala Leu Phe Ser Ser Ile Ile Ala
    850                 855                 860

Thr Gly Ile Leu Glu Leu Lys Trp Ser Gly Val Ser Ile Glu Glu Trp
865                 870                 875                 880

Trp Arg Asn Glu Gln Phe Trp Val Ile Gly Gly Val Ser Ala His Leu
                885                 890                 895

Phe Ala Val Ile Gln Gly Leu Leu Lys Val Leu Ala Gly Ile Asp Thr
            900                 905                 910

Asn Phe Thr Val Thr Ser Lys Ala Thr Asp Asp Glu Glu Phe Gly Glu
        915                 920                 925
```

```
Leu Tyr Thr Phe Lys Trp Thr Thr Leu Leu Ile Pro Pro Thr Thr Ile
    930                 935                 940

Leu Ile Ile Asn Ile Val Gly Val Val Ala Gly Ile Ser Asp Ala Ile
945                 950                 955                 960

Asn Asn Gly Tyr Gln Ser Trp Gly Pro Leu Phe Gly Lys Leu Phe Phe
                965                 970                 975

Ser Phe Trp Val Ile Val His Leu Tyr Pro Phe Leu Lys Gly Leu Met
            980                 985                 990

Gly Arg Gln Asn Arg Thr Pro Thr  Ile Val Val Ile Trp  Ser Val Leu
        995                 1000                1005

Leu Ala  Ser Ile Phe Ser Leu  Leu Trp Val Arg Ile  Asp Pro Phe
    1010                 1015                 1020

Val Leu  Lys Asn Lys Gly Pro  Asp Thr Lys Leu Cys  Gly Ile Asn
    1025                 1030                 1035

Cys


<210> SEQ ID NO 38
<211> LENGTH: 1097
<212> TYPE: PRT
<213> ORGANISM: Glycine max

<400> SEQUENCE: 38

Met His Thr Gly Gly Arg Leu Val Ala Gly Ser His Asn Arg Asn Glu
1               5                   10                  15

Phe Val Leu Ile Asn Ala Asp Glu Asn Gly Arg Ile Lys Ser Val Arg
            20                  25                  30

Glu Leu Ser Gly Gln Ile Cys Gln Ile Cys Gly Asp Glu Ile Glu Ile
        35                  40                  45

Thr Val Asp Gly Glu Pro Phe Val Ala Cys Asn Glu Cys Ala Phe Pro
    50                  55                  60

Val Cys Arg Pro Cys Tyr Glu Tyr Glu Arg Arg Glu Gly Asn Gln Ala
65                  70                  75                  80

Cys Pro Gln Cys Lys Thr Arg Tyr Lys Arg Ile Lys Gly Ser Pro Arg
                85                  90                  95

Val Glu Gly Asp Glu Glu Glu Asp Asp Thr Asp Asp Leu Asp Asn Glu
            100                 105                 110

Phe Asp Tyr Gly Asp Ile Asp Ala Leu Gly Pro Gln Pro Met Ser Glu
        115                 120                 125

Ser Leu Tyr Ser Gly Arg Pro Asn Thr Gly Arg Gly Ala Asn Asn Gly
    130                 135                 140

Ser Gly Leu Ala Thr Asn Leu Glu His Gly Ser Ser Ala Leu Asn Ser
145                 150                 155                 160

Asp Ile Pro Leu Leu Thr Tyr Gly Glu Glu Asp Pro Glu Ile Ser Ser
                165                 170                 175

Asp Arg His Ala Leu Ile Val Pro Pro Tyr Val Asn His Gly Ser Arg
            180                 185                 190

Val His Pro Met Pro Tyr Thr Asp Pro Ser Ile Pro Leu Gln Pro Arg
        195                 200                 205

Pro Met Val Pro Lys Lys Asp Ile Ala Val Tyr Gly Tyr Gly Ser Val
    210                 215                 220

Ala Trp Lys Asp Arg Met Glu Asp Trp Lys Lys Arg Gln Ser Asp Lys
225                 230                 235                 240

Leu Gln Val Val Lys His Glu Gly Ser Asn Asp Gly Asn Phe Gly Asp
                245                 250                 255
```

```
Asp Phe Glu Asp Pro Asp Leu Pro Met Met Asp Glu Gly Arg Gln Pro
            260                 265                 270

Leu Ser Arg Lys Leu Pro Ile Pro Ser Ser Lys Ile Asn Pro Tyr Arg
        275                 280                 285

Met Ile Ile Ile Leu Arg Leu Val Val Leu Gly Leu Phe Phe His Tyr
    290                 295                 300

Arg Ile Leu His Pro Val Asn Asp Ala Tyr Gly Leu Trp Leu Thr Ser
305                 310                 315                 320

Val Ile Cys Glu Ile Trp Phe Ala Val Ser Trp Ile Met Asp Gln Phe
                325                 330                 335

Pro Lys Trp Tyr Pro Ile Gln Arg Glu Thr Tyr Leu Asp Arg Leu Ser
            340                 345                 350

Leu Arg Tyr Glu Lys Glu Gly Lys Pro Ser Glu Leu Ser Ser Val Asp
        355                 360                 365

Val Phe Val Ser Thr Val Asp Pro Met Lys Glu Pro Pro Leu Ile Thr
    370                 375                 380

Ala Asn Thr Val Leu Ser Ile Leu Ala Val Asp Tyr Pro Val Asp Lys
385                 390                 395                 400

Val Ala Cys Tyr Val Ser Asp Asp Gly Ala Ala Met Leu Thr Phe Glu
                405                 410                 415

Ala Leu Ser Glu Thr Ser Glu Phe Ala Arg Arg Trp Val Pro Phe Cys
            420                 425                 430

Lys Lys Tyr Asn Ile Glu Pro Arg Ala Pro Glu Trp Tyr Phe Gly Gln
        435                 440                 445

Lys Met Asp Tyr Leu Lys Asn Lys Val His Pro Ala Phe Val Arg Glu
    450                 455                 460

Arg Arg Ala Met Lys Arg Asp Tyr Glu Glu Phe Lys Val Arg Ile Asn
465                 470                 475                 480

Ser Leu Val Ala Thr Ala Gln Lys Val Pro Glu Asp Gly Trp Thr Met
                485                 490                 495

Gln Asp Gly Thr Pro Trp Pro Gly Asn Asn Val Arg Asp His Pro Gly
            500                 505                 510

Met Ile Gln Val Phe Leu Gly Gln Asp Gly Val Arg Asp Val Glu Gly
        515                 520                 525

Asn Glu Leu Pro Arg Leu Val Tyr Val Ser Arg Glu Lys Arg Pro Gly
    530                 535                 540

Phe Asp His His Lys Lys Ala Gly Ala Met Asn Ala Leu Val Arg Ala
545                 550                 555                 560

Ser Ala Ile Ile Thr Asn Ala Pro Tyr Leu Leu Asn Val Asp Cys Asp
                565                 570                 575

His Tyr Ile Asn Asn Ser Lys Ala Leu Arg Glu Ala Met Cys Phe Met
            580                 585                 590

Met Asp Pro Gln Leu Gly Lys Lys Val Cys Tyr Val Gln Phe Pro Gln
        595                 600                 605

Arg Phe Asp Gly Ile Asp Arg His Asp Arg Tyr Ser Asn Arg Asn Val
    610                 615                 620

Val Phe Phe Asp Ile Asn Met Lys Gly Leu Asp Gly Ile Gln Gly Pro
625                 630                 635                 640

Ile Tyr Val Gly Thr Gly Cys Val Phe Arg Arg Tyr Ala Leu Tyr Gly
                645                 650                 655

Tyr Asp Ala Pro Ala Lys Lys Lys Pro Pro Ser Lys Thr Cys Asn Cys
            660                 665                 670
```

-continued

```
Trp Pro Lys Trp Cys Cys Leu Cys Cys Gly Ser Arg Lys Lys Lys Asn
        675                 680                 685

Ala Asn Ser Lys Lys Glu Lys Lys Arg Lys Val Lys His Ser Glu Ala
    690                 695                 700

Ser Lys Gln Ile His Ala Leu Glu Asn Ile Glu Ala Gly Asn Glu Gly
705                 710                 715                 720

Thr Asn Asn Glu Lys Thr Ser Asn Leu Thr Gln Thr Lys Leu Glu Lys
                725                 730                 735

Arg Phe Gly Gln Ser Pro Val Phe Val Ala Ser Thr Leu Leu Asp Asp
            740                 745                 750

Gly Gly Val Pro His Gly Val Ser Pro Ala Ser Leu Leu Lys Glu Ala
        755                 760                 765

Ile Gln Val Ile Ser Cys Gly Tyr Glu Asp Lys Thr Glu Trp Gly Lys
    770                 775                 780

Glu Val Gly Trp Ile Tyr Gly Ser Val Thr Glu Asp Ile Leu Thr Gly
785                 790                 795                 800

Phe Lys Met His Cys His Gly Trp Arg Ser Val Tyr Cys Ile Pro Lys
                805                 810                 815

Arg Pro Ala Phe Lys Gly Ser Ala Pro Ile Asn Leu Ser Asp Arg Leu
            820                 825                 830

His Gln Val Leu Arg Trp Ala Leu Gly Ser Val Glu Ile Phe Phe Ser
        835                 840                 845

Arg His Cys Pro Ile Trp Tyr Gly Tyr Gly Gly Gly Leu Lys Leu Leu
    850                 855                 860

Glu Arg Phe Ser Tyr Ile Asn Ser Val Val Tyr Pro Trp Thr Ser Leu
865                 870                 875                 880

Pro Leu Leu Val Tyr Cys Thr Leu Pro Ala Ile Cys Leu Leu Thr Gly
                885                 890                 895

Lys Phe Ile Val Pro Glu Ile Ser Asn Tyr Ala Ser Leu Val Phe Met
            900                 905                 910

Ala Leu Phe Ile Ser Ile Ala Ala Thr Gly Ile Leu Glu Met Gln Trp
        915                 920                 925

Gly Gly Val Ser Ile Asp Asp Trp Trp Arg Asn Glu Gln Phe Trp Val
    930                 935                 940

Ile Gly Gly Val Ser Ser His Leu Phe Ala Leu Phe Gln Gly Leu Leu
945                 950                 955                 960

Lys Val Leu Ala Gly Val Asn Thr Asn Phe Thr Val Thr Ser Lys Ala
                965                 970                 975

Ala Asp Asp Gly Glu Phe Ser Glu Leu Tyr Ile Phe Lys Trp Thr Ser
            980                 985                 990

Leu Leu Ile Pro Pro Met Thr Leu  Leu Ile Met Asn Ile  Val Gly Val
        995                 1000                1005

Val Val  Gly Ile Ser Asp Ala  Ile Asn Asn Gly Tyr  Asp Ser Trp
    1010                1015                1020

Gly Pro  Leu Phe Gly Arg Leu  Phe Phe Ala Leu Trp  Val Ile Leu
    1025                1030                1035

His Leu  Tyr Pro Phe Leu Lys  Gly Leu Leu Gly Lys  Gln Asp Arg
    1040                1045                1050

Met Pro  Thr Ile Ile Leu Val  Trp Ser Ile Leu Leu  Ala Ser Ile
    1055                1060                1065

Leu Thr  Leu Met Trp Val Arg  Ile Asn Pro Phe Val  Ser Arg Asp
    1070                1075                1080

Gly Pro  Val Leu Glu Ile Cys  Gly Leu Asn Cys Asp  Glu Ser
```

```
    1085                1090                1095

<210> SEQ ID NO 39
<211> LENGTH: 989
<212> TYPE: PRT
<213> ORGANISM: Glycine max

<400> SEQUENCE: 39

Met Val Gln Ser Ser Val Pro Leu Cys Asn Thr Cys Gly Glu Gln Val
1               5                   10                  15

Gly Leu Asn Asp Asn Gly Glu Val Phe Val Ala Cys His Glu Cys Asn
            20                  25                  30

Phe Pro Ile Cys Lys Asp Cys Phe Glu His Glu Ile Asn Glu Asp His
        35                  40                  45

Arg Val Cys Met Arg Cys Gly Thr Pro Tyr Glu Glu Arg Thr Lys Glu
    50                  55                  60

Glu Asp Asp Phe His Glu Ile Lys Val His Glu Asn Glu Asp Asp Asp
65                  70                  75                  80

Phe His Glu Ile Lys Val His Glu Asn Gln Ser Ala Thr Pro Ser Glu
                85                  90                  95

Ile Ser Asn Ser Gln Asp Val Gly Leu His Ala Arg His Val Ser Thr
            100                 105                 110

Val Ser Ala Val Asp Ser Glu Val Asn Glu Glu Ser Gly Lys Ser Ile
        115                 120                 125

Trp Lys Asn Arg Val Glu Ser Trp Lys Gly Lys Asp Lys Lys Asn Lys
    130                 135                 140

Lys Lys Lys Ser Ala Pro Lys Glu Glu Lys Glu Ala Ser Ile Pro Pro
145                 150                 155                 160

Glu Gln Gln Met Glu Glu Thr Arg Pro Ala Glu Ala Ala Ala Ala Pro
                165                 170                 175

Leu Ser Val Val Ile Pro Met Ser Lys Ser Lys Ile Ala Pro Tyr Arg
            180                 185                 190

Thr Val Ile Ile Met Arg Leu Ile Ile Leu Gly Leu Phe Phe His Tyr
        195                 200                 205

Arg Val Thr Asn Pro Val Glu Ser Ala Phe Pro Leu Trp Leu Thr Ser
    210                 215                 220

Ile Ile Cys Glu Ile Trp Phe Ala Phe Ser Trp Val Leu Asp Gln Phe
225                 230                 235                 240

Pro Lys Trp Ser Pro Ile Asn Arg Gln Thr Phe Ile Asp Asn Leu Ser
                245                 250                 255

Ala Arg Phe Glu Arg Glu Gly Glu Pro Asn Glu Leu Ala Ala Val Asp
            260                 265                 270

Phe Phe Val Ser Thr Val Asp Pro Leu Lys Glu Pro Pro Leu Ile Thr
        275                 280                 285

Ala Asn Thr Val Leu Ser Ile Leu Ala Val Asp Tyr Pro Val Asp Lys
    290                 295                 300

Val Ser Cys Tyr Val Ser Asp Asp Gly Ala Ala Met Leu Thr Phe Glu
305                 310                 315                 320

Ser Leu Val Glu Thr Ala Asp Phe Ala Arg Lys Trp Val Pro Phe Cys
                325                 330                 335

Lys Lys Phe Ser Ile Glu Pro Arg Ala Pro Glu Phe Tyr Phe Ser Gln
            340                 345                 350

Lys Ile Asp Tyr Leu Lys Asp Lys Val Gln Pro Ser Phe Val Lys Glu
        355                 360                 365
```

-continued

```
Arg Arg Ala Met Lys Arg Asp Tyr Glu Glu Tyr Lys Val Arg Val Asn
    370                 375                 380

Ala Met Val Ala Lys Ala Gln Lys Thr Pro Glu Glu Gly Trp Thr Met
385                 390                 395                 400

Gln Asp Gly Thr Pro Trp Pro Gly Asn Asn Ser Arg Asp His Pro Gly
                405                 410                 415

Met Ile Gln Val Phe Leu Gly His Thr Gly Ala Arg Asp Ile Glu Gly
            420                 425                 430

Asn Glu Leu Pro Arg Leu Val Tyr Val Ser Arg Glu Lys Arg Pro Gly
        435                 440                 445

Tyr Gln His His Lys Lys Ala Gly Ala Glu Asn Ala Leu Val Arg Val
    450                 455                 460

Ser Ala Val Leu Thr Asn Ala Pro Phe Ile Leu Asn Leu Asp Cys Asp
465                 470                 475                 480

His Tyr Val Asn Asn Ser Lys Ala Val Arg Glu Ala Met Cys Phe Leu
                485                 490                 495

Met Asp Pro Glu Val Gly Arg Asp Val Cys Tyr Val Gln Phe Pro Gln
            500                 505                 510

Arg Phe Asp Gly Ile Asp Arg Ser Asp Arg Tyr Ala Asn Arg Asn Thr
        515                 520                 525

Val Phe Phe Asp Val Asn Met Lys Gly Leu Asp Gly Ile Gln Gly Pro
    530                 535                 540

Val Tyr Val Gly Thr Gly Cys Val Phe Asn Arg Gln Ala Leu Tyr Gly
545                 550                 555                 560

Tyr Ser Pro Pro Ser Met Pro Ser Val Pro Arg Ser Ser Cys Cys Cys
                565                 570                 575

Phe Pro Ser Lys Lys Ser Thr Asn Asp Val Ser Asp Phe Gln Arg Asn
            580                 585                 590

Ala Lys Arg Glu Glu Leu Glu Ala Ala Ile Phe Asn Leu Lys Glu Leu
        595                 600                 605

Asp Asn Tyr Asp Glu His Glu Arg Ser Met Leu Ile Ser Gln Met Ser
    610                 615                 620

Phe Glu Lys Thr Phe Gly Leu Ser Thr Val Phe Ile Glu Ser Thr Leu
625                 630                 635                 640

Met Glu Asn Gly Gly Val Pro Glu Ser Ala Asp Pro Ser Met Leu Ile
                645                 650                 655

Lys Glu Ala Ile His Val Ile Ser Cys Gly Tyr Glu Glu Lys Thr Leu
            660                 665                 670

Trp Gly Lys Glu Ile Gly Trp Ile Tyr Gly Ser Val Thr Glu Asp Ile
        675                 680                 685

Leu Ser Gly Phe Lys Met Gln Cys Arg Gly Trp Lys Ser Ile Tyr Cys
    690                 695                 700

Met Pro Leu Arg Pro Ala Phe Lys Gly Ser Ala Pro Ile Asn Leu Ser
705                 710                 715                 720

Asp Arg Leu His Gln Val Leu Arg Trp Ala Leu Gly Ser Ile Glu Ile
                725                 730                 735

Phe Leu Ser Arg His Cys Pro Leu Trp Tyr Gly Phe Ser Gly Gly Arg
            740                 745                 750

Leu Lys Trp Leu Gln Arg Met Ala Tyr Ile Asn Thr Ile Val Tyr Pro
        755                 760                 765

Phe Thr Ser Leu Pro Leu Ile Ala Tyr Cys Ser Leu Pro Ala Ile Cys
    770                 775                 780

Leu Leu Thr Gly Lys Phe Ile Ile Pro Thr Leu Ser Asn Val Ala Ser
```

785 790 795 800

Val Leu Phe Leu Gly Leu Phe Leu Ser Ile Ile Ile Thr Ser Val Leu
805 810 815

Glu Leu Arg Trp Ser Gly Val Ser Ile Glu Asp Leu Trp Arg Asn Glu
820 825 830

Gln Phe Trp Val Ile Gly Gly Val Ser Ala His Leu Phe Ala Val Phe
835 840 845

Gln Gly Leu Leu Lys Met Leu Ala Gly Val Asp Thr Asn Phe Thr Val
850 855 860

Thr Ala Lys Ala Ala Glu Asp Ser Glu Phe Gly Glu Leu Tyr Leu Val
865 870 875 880

Lys Trp Thr Thr Leu Leu Ile Pro Pro Thr Thr Leu Ile Val Val Asn
885 890 895

Met Val Gly Val Val Ala Gly Phe Ser Asp Ala Leu Asn Gly Gly Tyr
900 905 910

Glu Ser Trp Gly Pro Leu Phe Gly Lys Val Phe Phe Ala Phe Trp Val
915 920 925

Ile Phe His Leu Tyr Pro Phe Leu Lys Gly Leu Met Gly Arg Gln Asn
930 935 940

Arg Thr Pro Thr Ile Val Ile Leu Trp Ser Val Leu Leu Ala Ser Val
945 950 955 960

Phe Ser Leu Ile Trp Val Lys Ile Asn Pro Phe Val Asn Thr Val Asp
965 970 975

Ser Glu Thr Ile Ala Glu Thr Cys Ile Ala Ile Asp Cys
980 985

<210> SEQ ID NO 40
<211> LENGTH: 1033
<212> TYPE: PRT
<213> ORGANISM: Glycine max

<400> SEQUENCE: 40

Met Glu Ala Ser Ala Gly Leu Val Ala Gly Ser His Asn Arg Asn Glu
1 5 10 15

Leu Val Val Ile His Gly His Glu Glu His Lys Pro Leu Lys Asn Leu
20 25 30

Asp Gly Gln Val Cys Glu Ile Cys Gly Asp Asp Val Gly Leu Thr Val
35 40 45

Asp Gly Asp Leu Phe Val Ala Cys Asn Glu Cys Gly Phe Pro Ala Cys
50 55 60

Arg Pro Cys Tyr Glu Tyr Glu Arg Arg Glu Gly Arg Gln Val Cys Pro
65 70 75 80

Gln Cys Lys Thr Arg Tyr Lys Arg Leu Lys Gly Ser Pro Arg Val Glu
85 90 95

Gly Asp Asp Glu Glu Glu Asp Val Asp Asp Ile Glu His Glu Phe Asn
100 105 110

Ile Glu Glu Gln Lys Lys His Asn His Ser Ala Glu Ala Met Leu His
115 120 125

Gly Lys Met Ser Tyr Gly Arg Gly Pro Glu Asp Asp Glu Asn Ala Gln
130 135 140

Phe Pro Ala Val Ile Ala Gly Gly Arg Ser Arg Pro Val Ser Gly Glu
145 150 155 160

Phe Pro Ile Ala Ser His Tyr Gly Asp Gln Met Leu Ala Ser Ser Leu
165 170 175

```
Gln Asn Arg Val His Pro Tyr Pro Ala Ser Asp Pro Arg Asn Gly Lys
            180                 185                 190

Trp Asp Glu Ala Lys Glu Asp Arg Met Asp Asp Trp Lys Leu Gln Gln
        195                 200                 205

Gly Asn Leu Gly Pro Glu Pro Asp Glu Asp Pro Asp Ala Ala Met Leu
    210                 215                 220

Asp Glu Ala Arg Gln Pro Leu Ser Arg Lys Val Pro Ile Ala Ser Ser
225                 230                 235                 240

Lys Val Asn Pro Tyr Arg Met Val Ile Val Ala Arg Leu Val Ile Leu
                245                 250                 255

Ala Phe Phe Leu Arg Tyr Arg Leu Met Asn Pro Val His Asp Ala Leu
            260                 265                 270

Gly Leu Trp Leu Thr Ser Ile Ile Cys Glu Ile Trp Phe Ala Phe Ser
        275                 280                 285

Trp Ile Leu Asp Gln Phe Pro Lys Trp Tyr Pro Ile Asp Arg Glu Thr
    290                 295                 300

Tyr Leu Asp Arg Leu Ser Ile Arg Tyr Glu Arg Glu Gly Glu Pro Asn
305                 310                 315                 320

Met Leu Ala Pro Val Asp Val Phe Val Ser Thr Val Asp Pro Met Lys
                325                 330                 335

Glu Pro Pro Leu Val Thr Ala Asn Thr Val Leu Ser Ile Leu Ala Met
            340                 345                 350

Asp Tyr Pro Val Ala Lys Ile Ser Cys Tyr Ile Ser Asp Asp Gly Ala
        355                 360                 365

Ser Met Cys Thr Phe Glu Ala Leu Ser Glu Thr Ala Glu Phe Ala Arg
    370                 375                 380

Lys Trp Val Pro Phe Cys Lys Lys Phe Ser Ile Glu Pro Arg Ala Pro
385                 390                 395                 400

Glu Met Tyr Phe Ser Glu Lys Ile Asp Tyr Leu Lys Asp Lys Val Gln
                405                 410                 415

Pro Thr Phe Val Lys Glu Arg Arg Ala Met Lys Arg Glu Tyr Glu Glu
            420                 425                 430

Phe Lys Val Arg Ile Asn Ala Leu Val Ala Lys Ala Gln Lys Val Pro
        435                 440                 445

Gln Gly Gly Trp Ile Met Gln Asp Gly Thr Pro Trp Pro Gly Asn Asn
    450                 455                 460

Thr Lys Asp His Pro Gly Met Ile Gln Val Phe Leu Gly His Ser Gly
465                 470                 475                 480

Gly His Asp Thr Glu Gly Asn Glu Leu Pro Arg Leu Val Tyr Val Ser
                485                 490                 495

Arg Glu Lys Arg Pro Gly Phe Gln His His Lys Lys Ala Gly Ala Met
            500                 505                 510

Asn Ala Leu Ile Arg Val Ser Ala Val Leu Thr Asn Ala Pro Phe Met
        515                 520                 525

Leu Asn Leu Asp Cys Asp His Tyr Val Asn Asn Ser Lys Ala Ala Arg
    530                 535                 540

Glu Ala Met Cys Phe Leu Met Asp Pro Gln Thr Gly Lys Lys Val Cys
545                 550                 555                 560

Tyr Val Gln Phe Pro Gln Arg Phe Asp Gly Ile Asp Arg His Asp Arg
                565                 570                 575

Tyr Ala Asn Arg Asn Thr Val Phe Phe Asp Ile Asn Met Lys Gly Leu
            580                 585                 590

Asp Gly Ile Gln Gly Pro Ala Tyr Val Gly Thr Gly Cys Val Phe Arg
```

-continued

```
        595                 600                 605

Arg Gln Ala Leu Tyr Gly Tyr Asn Pro Pro Lys Gly Pro Lys Arg Pro
    610                 615                 620

Lys Met Val Ser Cys Asp Cys Cys Pro Cys Phe Gly Lys Arg Lys Lys
625                 630                 635                 640

Val Lys Tyr Glu Gly Asn Asp Ala Asn Gly Glu Ala Ala Ser Leu Arg
                645                 650                 655

Gly Val Asp Asp Asp Lys Glu Val Leu Met Ser Gln Met Asn Phe Glu
            660                 665                 670

Lys Lys Phe Gly Gln Ser Ser Ile Phe Val Thr Ser Thr Leu Met Glu
        675                 680                 685

Glu Gly Gly Val Pro Pro Ser Ala Ser Ser Ala Ser Gln Leu Lys Glu
    690                 695                 700

Ala Ile His Val Ile Ser Cys Gly Tyr Glu Asp Lys Thr Glu Trp Gly
705                 710                 715                 720

Ile Glu Leu Gly Trp Ile Tyr Gly Ser Ile Thr Glu Asp Ile Leu Thr
                725                 730                 735

Gly Phe Lys Met His Cys Arg Gly Trp Arg Ser Ile Tyr Cys Met Pro
            740                 745                 750

Lys Arg Ala Ala Phe Lys Gly Thr Ala Pro Ile Asn Leu Ser Asp Arg
        755                 760                 765

Leu Asn Gln Val Leu Arg Trp Ala Leu Gly Ser Ile Glu Ile Phe Phe
    770                 775                 780

Ser Arg His Cys Pro Leu Trp Tyr Gly Tyr Lys Glu Gly Lys Leu Lys
785                 790                 795                 800

Trp Leu Glu Arg Phe Ala Tyr Ala Asn Thr Thr Val Tyr Pro Phe Thr
                805                 810                 815

Ser Ile Pro Leu Val Ala Tyr Cys Val Leu Pro Ala Val Cys Leu Leu
            820                 825                 830

Thr Asp Lys Phe Ile Met Pro Pro Ile Ser Thr Phe Ala Gly Leu Tyr
        835                 840                 845

Phe Val Ala Leu Phe Ser Ser Ile Ile Ala Thr Gly Leu Leu Glu Leu
    850                 855                 860

Lys Trp Ser Gly Val Ser Ile Glu Glu Trp Trp Arg Asn Glu Gln Phe
865                 870                 875                 880

Trp Val Ile Gly Gly Val Ser Ala His Leu Phe Ala Val Ile Gln Gly
                885                 890                 895

Leu Leu Lys Val Leu Ala Gly Ile Asp Thr Asn Phe Thr Val Thr Ser
            900                 905                 910

Lys Ala Ala Asp Asp Glu Glu Phe Gly Glu Leu Tyr Thr Phe Lys Trp
        915                 920                 925

Thr Thr Leu Leu Ile Pro Pro Thr Thr Ile Leu Ile Ile Asn Ile Val
    930                 935                 940

Gly Val Val Ala Gly Ile Ser Asp Ala Ile Asn Asn Gly Tyr Gln Ser
945                 950                 955                 960

Trp Gly Pro Leu Phe Gly Lys Leu Phe Phe Ser Phe Trp Val Ile Val
                965                 970                 975

His Leu Tyr Pro Phe Leu Lys Gly Leu Met Gly Arg Gln Asn Arg Thr
            980                 985                 990

Pro Thr Ile Val Val Ile Trp Ser  Val Leu Leu Ala Ser  Ile Phe Ser
        995                 1000                1005

Leu Leu  Trp Val Arg Ile Asp  Pro Phe Val Leu Lys  Thr Lys Gly
    1010                1015                1020
```

Pro Asp Thr Lys Leu Cys Gly Ile Asn Cys
1025 1030

<210> SEQ ID NO 41
<211> LENGTH: 1080
<212> TYPE: PRT
<213> ORGANISM: Glycine max

<400> SEQUENCE: 41

Met Glu Ser Glu Gly Glu Ala Gly Ala Lys Pro Val Thr Ala Leu Gly
1 5 10 15

Ala Gln Val Cys Gln Ile Cys Ser Asp Gly Val Gly Lys Thr Val Asp
20 25 30

Gly Glu Pro Phe Val Ala Cys Asp Val Cys Ala Phe Pro Val Cys Arg
35 40 45

Pro Cys Tyr Glu Tyr Glu Arg Lys Asp Gly Asn Gln Ser Cys Pro Gln
50 55 60

Cys Lys Thr Arg Tyr Lys Arg His Lys Gly Ser Pro Ala Ile Leu Gly
65 70 75 80

Asp Met Glu Glu Asp Gly Ala Pro Ala Ala Asp Gly Ala Ser Asp Phe
85 90 95

Asn Tyr Asp Ser Glu Asn Gln Asn Gln Asn Gln Asn Gln Lys Gln Lys
100 105 110

Ile Ser Glu Arg Met Leu Ser Trp Gln Leu Thr Tyr Ser Arg Gly Glu
115 120 125

Glu Val Gly Ala Pro Asn Tyr Asp Lys Asp Val Ser His Asn His Ile
130 135 140

Pro Leu Leu Thr Ser Gly Gln Glu Val Ser Gly Glu Leu Ser Ala Ala
145 150 155 160

Ser Pro Glu Arg Leu Ser Met Ala Ser Pro Ala Val Gly Gly Gly Lys
165 170 175

Arg Val His Asn Ile Pro Tyr Ser Ser Asp Ile Asn Gln Ser Pro Asn
180 185 190

Ile Arg Ala Gly Asp Pro Gly Leu Gly Asn Val Ala Trp Lys Glu Arg
195 200 205

Val Asp Gly Trp Lys Met Lys Gln Glu Lys Asn Val Val Pro Met Ser
210 215 220

Thr Gly Leu Ala Ala Ser Glu Arg Gly Ala Gly Asp Val Asp Ala Ser
225 230 235 240

Thr Asp Val Leu Val Asp Asp Ser Leu Leu Asn Asp Glu Ala Arg Gln
245 250 255

Pro Leu Ser Arg Lys Val Ser Ile Pro Ser Ser Arg Ile Asn Pro Tyr
260 265 270

Arg Met Val Ile Met Leu Arg Leu Val Ile Leu Cys Ile Phe Leu His
275 280 285

Tyr Arg Ile Thr Asn Pro Val Pro Asn Ala Tyr Pro Leu Trp Leu Val
290 295 300

Ser Val Ile Cys Glu Ile Trp Phe Ala Ile Ser Trp Ile Leu Asp Gln
305 310 315 320

Phe Pro Lys Trp Leu Pro Val Asn Arg Glu Thr Tyr Leu Asp Arg Leu
325 330 335

Ala Leu Arg Tyr Asp Gln Glu Gly Glu Pro Ser Gln Leu Ala Ala Val
340 345 350

Asp Ile Phe Val Ser Thr Val Asp Pro Leu Lys Glu Pro Pro Leu Val

```
        355                 360                 365

Thr Ala Asn Thr Val Leu Ser Ile Leu Ala Val Asp Tyr Pro Val Asp
    370                 375                 380

Lys Val Ser Cys Tyr Val Ser Asp Asp Gly Ala Ala Met Leu Thr Phe
385                 390                 395                 400

Glu Ala Leu Ala Glu Thr Ser Glu Phe Ala Arg Lys Trp Val Pro Phe
                405                 410                 415

Ser Lys Lys Tyr Ser Ile Glu Pro Arg Ala Pro Glu Trp Tyr Phe Ala
            420                 425                 430

Gln Lys Ile Asp Tyr Leu Lys Asp Lys Val His Pro Ser Phe Val Lys
        435                 440                 445

Asp Arg Arg Ala Met Lys Arg Glu Tyr Glu Glu Phe Lys Val Arg Val
    450                 455                 460

Asn Gly Leu Val Ala Lys Ala Gln Lys Val Pro Glu Glu Gly Trp Val
465                 470                 475                 480

Met Gln Asp Gly Thr Pro Trp Pro Gly Asn Asn Ile Arg Asp His Pro
                485                 490                 495

Gly Met Ile Gln Val Phe Leu Gly Gln Ser Gly Gly Leu Asp Thr Glu
            500                 505                 510

Gly Asn Glu Leu Pro Arg Leu Val Tyr Val Ser Arg Glu Lys Arg Pro
        515                 520                 525

Gly Phe Gln His His Lys Lys Ala Gly Ala Met Asn Ala Leu Val Arg
    530                 535                 540

Val Ser Ala Val Leu Thr Asn Gly Pro Phe Leu Leu Asn Leu Asp Cys
545                 550                 555                 560

Asp His Tyr Ile Asn Asn Ser Lys Ala Leu Arg Glu Ala Met Cys Phe
                565                 570                 575

Met Met Asp Pro Asn Leu Gly Lys His Val Cys Tyr Val Gln Phe Pro
            580                 585                 590

Gln Arg Phe Asp Gly Ile Asp Arg Asn Asp Arg Tyr Ala Asn Arg Asn
        595                 600                 605

Thr Val Phe Phe Asp Ile Asn Leu Arg Gly Leu Asp Gly Ile Gln Gly
    610                 615                 620

Pro Val Tyr Val Gly Thr Gly Cys Val Phe Asn Arg Thr Ala Leu Tyr
625                 630                 635                 640

Gly Tyr Glu Pro Pro Leu Lys Pro Lys His Lys Lys Pro Gly Leu Leu
                645                 650                 655

Ser Ser Leu Cys Gly Gly Asn Arg Lys Lys Ser Ser Lys Ser Ser Lys
            660                 665                 670

Lys Gly Thr Asp Lys Lys Lys Ser Asn Lys His Val Asp Pro Thr Val
        675                 680                 685

Pro Ile Phe Asn Leu Glu Asp Ile Glu Glu Gly Val Glu Gly Thr Gly
    690                 695                 700

Phe Asp Asp Glu Lys Ser Leu Leu Met Ser Gln Met Ser Leu Glu Lys
705                 710                 715                 720

Arg Phe Gly Gln Ser Ala Val Phe Val Ala Ser Thr Leu Met Glu Asn
                725                 730                 735

Gly Gly Val Pro Gln Ser Ala Thr Pro Glu Thr Leu Leu Lys Glu Ala
            740                 745                 750

Ile His Val Ile Ser Cys Gly Tyr Glu Asp Lys Thr Asp Trp Gly Ser
        755                 760                 765

Glu Ile Gly Trp Ile Tyr Gly Ser Val Thr Glu Asp Ile Leu Thr Gly
    770                 775                 780
```

-continued

Phe Lys Met His Ala Arg Gly Trp Arg Ser Ile Tyr Cys Met Pro Lys
785 790 795 800

Arg Pro Ala Phe Lys Gly Ser Ala Pro Ile Asn Leu Ser Asp Arg Leu
805 810 815

Asn Gln Val Leu Arg Trp Ala Leu Gly Ser Val Glu Ile Leu Phe Ser
820 825 830

Arg His Cys Pro Ile Trp Tyr Gly Tyr Gly Gly Arg Leu Lys Trp Leu
835 840 845

Glu Arg Phe Ala Tyr Val Asn Thr Thr Ile Tyr Pro Val Thr Ala Ile
850 855 860

Pro Leu Leu Ile Tyr Cys Ile Leu Pro Ala Val Cys Leu Leu Thr Asn
865 870 875 880

Lys Phe Ile Ile Pro Gln Ile Ser Asn Leu Ala Ser Ile Trp Phe Ile
885 890 895

Ser Leu Phe Leu Ser Ile Phe Ala Thr Gly Ile Leu Glu Met Arg Trp
900 905 910

Ser Gly Val Gly Ile Asp Glu Trp Trp Arg Asn Glu Gln Phe Trp Val
915 920 925

Ile Gly Gly Val Ser Ala His Leu Phe Ala Val Phe Gln Gly Leu Leu
930 935 940

Lys Val Leu Ala Gly Ile Asp Thr Asn Phe Thr Val Thr Ser Lys Ala
945 950 955 960

Ser Asp Glu Asp Gly Asp Phe Ala Glu Leu Tyr Met Phe Lys Trp Thr
965 970 975

Thr Leu Leu Ile Pro Pro Thr Thr Leu Leu Ile Ile Asn Met Ile Gly
980 985 990

Val Val Ala Gly Ile Ser Tyr Ala Ile Asn Ser Gly Tyr Gln Ser Trp
995 1000 1005

Gly Pro Leu Phe Gly Lys Leu Phe Phe Ala Phe Trp Val Ile Ile
1010 1015 1020

His Leu Tyr Pro Phe Leu Lys Gly Leu Met Gly Arg Gln Asn Arg
1025 1030 1035

Thr Pro Thr Ile Val Val Val Trp Ser Ile Leu Leu Ala Ser Ile
1040 1045 1050

Phe Ser Leu Leu Trp Val Arg Ile Asp Pro Phe Thr Thr Arg Val
1055 1060 1065

Thr Gly Pro Asp Val Glu Glu Cys Gly Ile Asn Cys
1070 1075 1080

<210> SEQ ID NO 42
<211> LENGTH: 958
<212> TYPE: PRT
<213> ORGANISM: Glycine max

<400> SEQUENCE: 42

Met Val Gln Ser Ser Val Pro Leu Cys Asn Thr Cys Gly Glu Gln Val
1 5 10 15

Gly Leu Asn Ala Asn Gly Glu Val Phe Val Ala Cys His Glu Cys Asn
20 25 30

Phe Pro Ile Cys Lys Asp Cys Phe Glu His Glu Ile Asn Glu Asp His
35 40 45

Arg Val Cys Met Arg Cys Gly Thr Pro His Glu Glu Arg Thr Lys Glu
50 55 60

Glu Glu Glu Asp Phe His Glu Ile Lys Val His Glu Asn Glu Asp Asp

-continued

```
65                  70                  75                  80

Asp Phe His Glu Ile Lys Val His Glu Asn Gln Ser Thr Thr Pro Phe
                85                  90                  95

Gln Ile Asn Asn Ser Gln Asp Val Gly Leu His Ala Arg His Val Ser
            100                 105                 110

Thr Val Ser Thr Val Asp Ser Val Glu Ser Trp Lys Glu Lys Asp Lys
        115                 120                 125

Lys Asn Lys Lys Lys Lys Ala Ala Pro Lys Glu Glu Lys Asp Ala Ser
    130                 135                 140

Ile Pro Pro Glu Gln Gln Met Glu Glu Thr Arg Pro Thr Glu Ala Ala
145                 150                 155                 160

Ala Ala Ala Pro Leu Ser Val Val Ile Pro Met Ser Lys Ser Lys Ile
                165                 170                 175

Ala Pro Tyr Arg Thr Val Ile Ile Met Arg Leu Ile Ile Leu Gly Leu
            180                 185                 190

Phe Phe His Tyr Arg Val Thr Asn Pro Val Glu Ser Ala Phe Pro Leu
        195                 200                 205

Trp Leu Thr Ser Ile Ile Cys Glu Ile Trp Phe Ala Phe Ser Trp Val
    210                 215                 220

Leu Asp Gln Phe Pro Lys Trp Ser Pro Ile Asn Arg Gln Thr Phe Ile
225                 230                 235                 240

Asp Asn Leu Ser Ala Arg Phe Glu Arg Glu Gly Glu Pro Asn Glu Leu
                245                 250                 255

Ala Ala Val Asp Phe Phe Val Ser Thr Val Asp Pro Leu Lys Glu Pro
            260                 265                 270

Pro Leu Ile Thr Ala Asn Thr Val Leu Ser Ile Leu Ala Val Asp Tyr
        275                 280                 285

Pro Val Asp Lys Val Ser Cys Tyr Val Ser Asp Asp Gly Ala Ala Met
    290                 295                 300

Leu Thr Phe Glu Ser Leu Val Glu Thr Ala Asp Phe Ala Arg Lys Trp
305                 310                 315                 320

Val Pro Phe Cys Lys Lys Phe Ser Ile Glu Pro Arg Ala Pro Glu Phe
                325                 330                 335

Tyr Phe Ser Gln Lys Ile Asp Tyr Leu Lys Asp Lys Val Gln Pro Ser
            340                 345                 350

Phe Val Lys Glu Pro Arg Ala Met Arg Asp Tyr Glu Glu Tyr Lys Val
        355                 360                 365

Arg Val Asn Ala Met Val Ala Lys Ala Gln Lys Thr Pro Glu Glu Gly
    370                 375                 380

Trp Thr Met Gln Asp Gly Thr Pro Trp Pro Gly Asn Asn Ser Arg Asp
385                 390                 395                 400

His Pro Gly Met Ile Gln Val Phe Leu Gly His Thr Gly Ala Arg Asp
                405                 410                 415

Ile Glu Gly Asn Glu Leu Pro Arg Leu Val Tyr Val Ser Arg Glu Lys
            420                 425                 430

Arg Pro Gly Tyr Gln His His Lys Lys Ala Gly Ala Glu Asn Ala Leu
        435                 440                 445

Val Arg Val Ser Ala Val Leu Thr Asn Ala Pro Phe Ile Leu Asn Leu
    450                 455                 460

Asp Cys Asp His Tyr Val Asn Asn Ser Lys Ala Val Arg Glu Ala Met
465                 470                 475                 480

Cys Phe Leu Met Asp Pro Glu Val Gly Arg Asp Val Cys Tyr Val Gln
                485                 490                 495
```

-continued

```
Phe Pro Gln Arg Phe Asp Gly Ile Asp Arg Ser Asp Arg Tyr Ala Asn
            500                 505                 510

Arg Asn Thr Val Phe Phe Asp Val Asn Met Lys Gly Leu Asp Gly Ile
        515                 520                 525

Gln Gly Pro Val Tyr Val Gly Thr Gly Cys Val Phe Asn Arg Gln Ala
    530                 535                 540

Leu Tyr Gly Tyr Ser Pro Pro Ser Met Pro Ser Leu Pro Arg Ser Ser
545                 550                 555                 560

Cys Cys Cys Phe Pro Ser Lys Lys Ser Thr Asn Asp Val Ser Asp Phe
                565                 570                 575

Gln Arg Asn Ala Lys Arg Glu Glu Leu Glu Ala Ala Ile Phe Asn Leu
            580                 585                 590

Lys Glu Leu Asp Asn Tyr Asp Glu His Glu Arg Ser Met Leu Ile Ser
        595                 600                 605

Gln Met Ser Phe Glu Lys Thr Phe Gly Leu Ser Thr Val Phe Ile Glu
    610                 615                 620

Ser Thr Leu Met Glu Asn Gly Gly Val Pro Glu Ala Ala Asp Pro Ser
625                 630                 635                 640

Met Leu Ile Lys Glu Ala Ile His Val Ile Ser Cys Gly Tyr Glu Glu
                645                 650                 655

Lys Thr Leu Trp Gly Lys Glu Ile Gly Trp Ile Tyr Gly Ser Val Thr
            660                 665                 670

Glu Asp Ile Leu Ser Gly Phe Lys Met Gln Cys Arg Gly Trp Lys Ser
        675                 680                 685

Ile Tyr Cys Met Pro Leu Arg Pro Ala Phe Lys Gly Ser Ala Pro Ile
    690                 695                 700

Asn Leu Ser Asp Arg Leu His Gln Val Leu Arg Trp Ala Leu Gly Ser
705                 710                 715                 720

Ile Glu Ile Phe Leu Ser Arg His Cys Pro Leu Trp Tyr Gly Phe Ser
                725                 730                 735

Gly Gly Arg Leu Lys Trp Leu Gln Arg Met Ala Tyr Ile Asn Thr Ile
            740                 745                 750

Val Tyr Pro Phe Thr Ser Leu Pro Leu Val Ala Tyr Cys Ser Leu Pro
        755                 760                 765

Ala Ile Cys Leu Leu Thr Gly Lys Phe Ile Ile Pro Thr Leu Ser Asn
    770                 775                 780

Val Ala Ser Val Leu Phe Leu Gly Leu Phe Leu Ser Ile Ile Ile Thr
785                 790                 795                 800

Ser Val Leu Glu Leu Arg Trp Ser Gly Val Ser Ile Glu Asp Leu Trp
                805                 810                 815

Arg Asn Glu Gln Phe Trp Val Ile Gly Gly Val Ser Ala His Leu Phe
            820                 825                 830

Ala Val Phe Gln Gly Leu Leu Lys Met Leu Ala Gly Val Asp Thr Asn
        835                 840                 845

Phe Thr Trp Thr Thr Leu Leu Ile Pro Pro Thr Thr Leu Ile Ile Val
    850                 855                 860

Asn Met Val Gly Val Val Ala Gly Phe Ser Asp Ala Leu Asn Gly Gly
865                 870                 875                 880

Tyr Glu Ser Trp Gly Pro Leu Phe Gly Lys Val Phe Phe Ala Phe Trp
                885                 890                 895

Val Ile Phe His Leu Tyr Pro Phe Leu Lys Gly Leu Met Gly Arg Gln
            900                 905                 910
```

```
Asn Arg Thr Pro Thr Ile Val Val Leu Trp Ser Val Leu Leu Ala Ser
        915                 920                 925

Val Phe Ser Leu Val Trp Val Lys Ile Asn Pro Phe Val Asn Thr Val
    930                 935                 940

Asp Ser Glu Thr Ile Ala Glu Thr Cys Ile Ala Ile Asp Cys
945                 950                 955


<210> SEQ ID NO 43
<211> LENGTH: 1097
<212> TYPE: PRT
<213> ORGANISM: Glycine max

<400> SEQUENCE: 43

Met His Thr Gly Gly Arg Leu Val Ala Gly Ser His Asn Arg Asn Glu
1               5                   10                  15

Phe Val Leu Ile Asn Ala Asp Asp Asn Gly Arg Ile Lys Ser Val Arg
            20                  25                  30

Glu Leu Ser Gly Gln Ile Cys Gln Ile Cys Gly Asp Glu Ile Glu Ile
        35                  40                  45

Thr Val Asp Gly Glu Pro Phe Val Ala Cys Asn Glu Cys Ala Phe Pro
    50                  55                  60

Val Cys Arg Pro Cys Tyr Glu Tyr Glu Arg Arg Glu Gly Ile Gln Ala
65                  70                  75                  80

Cys Pro Gln Cys Asn Thr Arg Tyr Lys Arg Ile Lys Gly Ser Pro Arg
                85                  90                  95

Val Glu Gly Asp Glu Glu Glu Asp Asp Thr Asp Asp Leu Asp Asn Glu
            100                 105                 110

Phe Asp Tyr Gly Asp Val Asp Ala Leu Gly Pro Gln Pro Met Ser Glu
        115                 120                 125

Ser Leu Tyr Ser Gly Arg Pro Asn Thr Gly Arg Gly Ala Asn Asn Gly
    130                 135                 140

Ser Gly Met Ala Thr Asn Leu Glu His Gly Ser Ala Pro Gln Asn Ser
145                 150                 155                 160

Asp Ile Pro Leu Leu Thr Tyr Gly Glu Glu Asp Pro Glu Ile Ser Ser
                165                 170                 175

Asn Ser His Ala Leu Ile Val Pro Ser His Met Asn His Gly Asn Arg
            180                 185                 190

Val His Pro Met Pro Tyr Asn Asp Pro Ser Ile Pro Leu Gln Pro Arg
        195                 200                 205

Pro Met Ala Pro Lys Lys Asp Ile Ala Val Tyr Gly Tyr Gly Ser Val
    210                 215                 220

Ala Trp Lys Asp Arg Met Glu Glu Trp Lys Lys Arg Gln Ser Asp Lys
225                 230                 235                 240

Leu Gln Val Val Lys His Glu Gly Ser Asn Asp Gly Asn Phe Gly Asp
                245                 250                 255

Asp Phe Glu Asp Ser Asp Leu Pro Met Met Asp Glu Gly Arg Gln Pro
            260                 265                 270

Leu Ser Arg Lys Leu Pro Ile Pro Ser Ser Lys Ile Asn Pro Tyr Arg
        275                 280                 285

Met Ile Ile Val Leu Arg Leu Val Val Leu Gly Leu Phe Phe His Tyr
    290                 295                 300

Arg Ile Leu His Pro Val Asn Asp Ala Tyr Gly Leu Trp Leu Thr Ser
305                 310                 315                 320

Val Ile Cys Glu Ile Trp Phe Ala Val Ser Trp Ile Met Asp Gln Phe
                325                 330                 335
```

-continued

```
Pro Lys Trp Tyr Pro Ile Gln Arg Glu Thr Tyr Leu Asp Arg Leu Ser
            340                 345                 350

Leu Arg Tyr Glu Lys Glu Gly Lys Pro Ser Glu Leu Ser Ser Val Asp
        355                 360                 365

Val Phe Val Ser Thr Val Asp Pro Met Lys Glu Pro Pro Leu Ile Thr
    370                 375                 380

Ala Asn Thr Val Leu Ser Ile Leu Ala Val Asp Tyr Pro Val Asp Lys
385                 390                 395                 400

Val Ala Cys Tyr Val Ser Asp Asp Gly Ala Ala Met Leu Thr Phe Glu
                405                 410                 415

Ala Leu Ser Glu Thr Ser Glu Phe Ala Arg Arg Trp Val Pro Phe Cys
            420                 425                 430

Lys Lys Tyr Asn Ile Glu Pro Arg Ala Pro Glu Trp Tyr Phe Gly Gln
        435                 440                 445

Lys Met Asp Tyr Leu Lys Asn Lys Val His Pro Ala Phe Val Arg Glu
    450                 455                 460

Arg Arg Ala Met Lys Arg Asp Tyr Glu Glu Phe Lys Val Arg Ile Asn
465                 470                 475                 480

Ser Leu Val Ala Thr Ala Gln Lys Val Pro Glu Asp Gly Trp Thr Met
                485                 490                 495

Gln Asp Gly Thr Pro Trp Pro Gly Asn Asn Val Arg Asp His Pro Gly
            500                 505                 510

Met Ile Gln Val Phe Leu Gly Gln Asp Gly Val Arg Asp Val Glu Gly
        515                 520                 525

Asn Glu Leu Pro Arg Leu Val Tyr Val Ser Arg Glu Lys Arg Pro Gly
    530                 535                 540

Phe Asp His His Lys Lys Ala Gly Ala Met Asn Ala Leu Val Arg Ala
545                 550                 555                 560

Ser Ala Ile Ile Thr Asn Ala Pro Tyr Leu Leu Asn Val Asp Cys Asp
                565                 570                 575

His Tyr Ile Asn Asn Ser Lys Ala Leu Arg Glu Ala Met Cys Phe Met
            580                 585                 590

Met Asp Pro Gln Leu Gly Lys Lys Val Cys Tyr Val Gln Phe Pro Gln
        595                 600                 605

Arg Phe Asp Gly Ile Asp Arg His Asp Arg Tyr Ser Asn Arg Asn Val
    610                 615                 620

Val Phe Phe Asp Ile Asn Met Lys Gly Leu Asp Gly Ile Gln Gly Pro
625                 630                 635                 640

Ile Tyr Val Gly Thr Gly Cys Val Phe Arg Arg Tyr Ala Leu Tyr Gly
                645                 650                 655

Tyr Asp Ala Pro Ala Lys Lys Lys Pro Pro Ser Lys Thr Cys Asn Cys
            660                 665                 670

Trp Pro Lys Trp Cys Cys Leu Cys Cys Gly Ser Arg Lys Lys Lys Asn
        675                 680                 685

Ala Asn Thr Lys Lys Glu Lys Lys Arg Lys Val Lys His Ser Glu Ala
    690                 695                 700

Ser Lys Gln Ile His Ala Leu Glu Asn Ile Glu Ala Gly Asn Glu Gly
705                 710                 715                 720

Thr Asn Asn Glu Lys Thr Ser Asn Leu Thr Gln Thr Lys Leu Glu Lys
                725                 730                 735

Arg Phe Gly Gln Ser Pro Val Phe Val Ala Ser Thr Leu Leu Asp Asn
            740                 745                 750
```

```
Gly Gly Val Pro Gln Gly Val Ser Pro Ala Ser Leu Leu Lys Glu Ala
        755                 760                 765

Ile Gln Val Ile Ser Cys Gly Tyr Glu Asp Lys Thr Glu Trp Gly Lys
    770                 775                 780

Glu Val Gly Trp Ile Tyr Gly Ser Val Thr Glu Asp Ile Leu Thr Gly
785                 790                 795                 800

Phe Lys Met His Cys His Gly Trp Arg Ser Val Tyr Cys Ile Pro Lys
                805                 810                 815

Arg Pro Ala Phe Lys Gly Ser Ala Pro Ile Asn Leu Ser Asp Arg Leu
            820                 825                 830

His Gln Val Leu Arg Trp Ala Leu Gly Ser Val Glu Ile Phe Phe Ser
        835                 840                 845

Arg His Cys Pro Ile Trp Tyr Gly Tyr Gly Gly Gly Leu Lys Trp Leu
    850                 855                 860

Glu Arg Phe Ser Tyr Ile Asn Ser Val Val Tyr Pro Trp Thr Ser Leu
865                 870                 875                 880

Pro Leu Leu Val Tyr Cys Thr Leu Pro Ala Ile Cys Leu Leu Thr Gly
                885                 890                 895

Lys Phe Ile Val Pro Glu Ile Ser Asn Tyr Ala Ser Ile Val Phe Met
            900                 905                 910

Ala Leu Phe Ile Ser Ile Ala Ala Thr Gly Ile Leu Glu Met Gln Trp
        915                 920                 925

Gly Gly Val Ser Ile Asp Asp Trp Trp Arg Asn Glu Gln Phe Trp Val
    930                 935                 940

Ile Gly Gly Val Ser Ser His Leu Phe Ala Leu Phe Gln Gly Leu Leu
945                 950                 955                 960

Lys Val Leu Ala Gly Val Asn Thr Asn Phe Thr Val Thr Ser Lys Ala
                965                 970                 975

Ala Asp Asp Gly Glu Phe Ser Glu Leu Tyr Ile Phe Lys Trp Thr Ser
            980                 985                 990

Leu Leu Ile Pro Pro Met Thr Leu  Leu Ile Met Asn Ile  Val Gly Val
        995                 1000                1005

Val Val  Gly Val Ser Asp Ala  Ile Asn Asn Gly Tyr  Asp Ser Trp
    1010                1015                1020

Gly Pro  Leu Phe Gly Arg Leu  Phe Phe Ala Leu Trp  Val Ile Leu
    1025                1030                1035

His Leu  Tyr Pro Phe Leu Lys  Gly Leu Leu Gly Lys  Gln Asp Arg
    1040                1045                1050

Met Pro  Thr Ile Ile Leu Val  Trp Ser Ile Leu Leu  Ala Ser Ile
    1055                1060                1065

Leu Thr  Leu Met Trp Val Arg  Ile Asn Pro Phe Val  Ser Arg Asp
    1070                1075                1080

Gly Pro  Val Leu Glu Ile Cys  Gly Leu Asn Cys Asp  Glu Ser
    1085                1090                1095
```

<210> SEQ ID NO 44
<211> LENGTH: 1073
<212> TYPE: PRT
<213> ORGANISM: Glycine max

<400> SEQUENCE: 44

```
Met Thr Glu Ser Glu Glu Ala Gly Ala Lys Pro Met Asn Thr Leu Gly
1               5                   10                  15

Gly Gln Val Cys Gln Ile Cys Gly Asp Asn Ile Gly Asn Asn Val Asn
            20                  25                  30
```

Gly Asp Pro Phe Ile Ala Cys Asp Val Cys Ala Phe Pro Val Cys Arg
35 40 45

Ala Cys Tyr Glu Tyr Glu Arg Lys Asp Gly Asn Gln Ser Cys Pro Gln
50 55 60

Cys Lys Thr Arg Tyr Lys Arg His Lys Gly Ser Pro Ala Ile Leu Gly
65 70 75 80

Asp Gln Glu Glu Asp Gly Gly Ala Asp Glu Gly Ala Ser Asp Leu Asn
85 90 95

Tyr Asn Ser Glu Asn Gln Asn Glu Lys Gln Lys Ile Glu Arg Met Leu
100 105 110

Gly Trp Gln Met Ala His Gly Arg Ala Glu Glu Ala Val Ala Pro Asn
115 120 125

Tyr Asp Lys Glu Val Ser His Asn His Ile Pro Leu Leu Ser Gly Gly
130 135 140

Gln Glu Val Ser Gly Glu Leu Ser Ala Ala Ser Pro Glu Arg Leu Ser
145 150 155 160

Met Ala Ser Pro Gly Gly Arg Gly Lys Arg Val His Asn Leu Gln Tyr
165 170 175

Ser Ser Asp Leu Asn Gln Ser Pro Asn Ile Arg Val Gly Asp Pro Gly
180 185 190

Leu Gly Asn Val Ala Trp Lys Glu Arg Val Asp Gly Trp Lys Met Lys
195 200 205

Gln Asp Lys Asn Val Ala Pro Met Ser Thr Gly Gln Ala Thr Ser Glu
210 215 220

Arg Gly Ala Gly Asp Ile Asp Ala Ser Thr Asp Val Leu Val Asp Asp
225 230 235 240

Ser Leu Leu Asn Asp Glu Ala Arg Gln Pro Leu Ser Arg Lys Val Ser
245 250 255

Ile Pro Ser Ser Arg Ile Asn Pro Tyr Arg Met Val Ile Ala Leu Arg
260 265 270

Leu Val Ile Leu Cys Ile Phe Leu His Tyr Arg Ile Thr Asn Pro Val
275 280 285

Pro Asn Ala Tyr Ala Leu Trp Leu Ile Ser Val Ile Cys Glu Ile Trp
290 295 300

Phe Ala Ile Ser Trp Ile Phe Asp Gln Phe Pro Lys Trp Leu Pro Val
305 310 315 320

Asn Arg Glu Thr Tyr Leu Asp Arg Leu Ala Leu Arg Tyr Asp Gln Glu
325 330 335

Gly Glu Pro Ser Gln Leu Ala Ala Val Asp Ile Phe Val Ser Thr Val
340 345 350

Asp Pro Leu Lys Glu Pro Pro Leu Val Thr Ala Asn Thr Val Leu Ser
355 360 365

Ile Leu Ser Val Asp Tyr Pro Val Asp Lys Val Ser Cys Tyr Val Ser
370 375 380

Asp Asp Gly Ala Ala Met Leu Thr Phe Glu Ala Leu Ala Glu Thr Ser
385 390 395 400

Glu Phe Ala Arg Lys Trp Val Pro Phe Ser Lys Lys Tyr Asn Ile Glu
405 410 415

Pro Arg Ala Pro Glu Trp Tyr Phe Ala Gln Lys Ile Asp Tyr Leu Lys
420 425 430

Asp Lys Val Gln Pro Ser Phe Val Lys Asp Arg Arg Ala Met Lys Arg
435 440 445

-continued

```
Glu Tyr Glu Glu Phe Lys Ile Arg Val Asn Gly Leu Val Ala Lys Ala
    450                 455                 460

Gln Lys Val Pro Glu Glu Gly Trp Val Met Gln Asp Gly Thr Pro Trp
465                 470                 475                 480

Pro Gly Asn Asn Thr Arg Asp His Pro Gly Met Ile Gln Val Phe Leu
                485                 490                 495

Gly Gln Ser Gly Gly Leu Asp Thr Glu Gly Asn Glu Leu Pro Arg Leu
            500                 505                 510

Val Tyr Val Ser Arg Glu Lys Arg Pro Gly Phe Gln His His Lys Lys
        515                 520                 525

Ala Gly Ala Met Asn Ala Leu Val Arg Val Ser Ala Val Leu Thr Asn
    530                 535                 540

Gly Pro Phe Leu Leu Asn Leu Asp Cys Asp His Tyr Ile Asn Asn Ser
545                 550                 555                 560

Lys Ala Leu Arg Glu Ala Met Cys Phe Met Met Asp Pro Asn Leu Gly
                565                 570                 575

Lys Asn Val Cys Tyr Val Gln Phe Pro Gln Arg Phe Asp Gly Ile Asp
            580                 585                 590

Arg Asn Asp Arg Tyr Ala Asn Arg Asn Thr Val Phe Phe Asp Ile Asn
        595                 600                 605

Leu Arg Gly Leu Asp Gly Ile Gln Gly Pro Val Tyr Val Gly Thr Gly
    610                 615                 620

Cys Val Phe Asn Arg Thr Ala Leu Tyr Gly Tyr Glu Pro Pro Ile Lys
625                 630                 635                 640

Pro Lys His Lys Lys Pro Gly Leu Leu Ser Ser Leu Cys Gly Gly Asn
                645                 650                 655

Arg Lys Lys Arg Ser Lys Ser Ser Lys Lys Gly Ser Asp Lys Lys Lys
            660                 665                 670

Ser Ser Lys Asn Val Asp Pro Thr Val Pro Ile Phe Ser Leu Glu Asp
        675                 680                 685

Ile Glu Glu Gly Val Glu Gly Ala Gly Phe Asp Asp Glu Lys Ser Leu
    690                 695                 700

Leu Met Ser Gln Met Ser Leu Glu Lys Arg Phe Gly Gln Ser Ala Val
705                 710                 715                 720

Phe Val Ala Ser Thr Leu Met Glu Asn Gly Gly Val Pro Gln Ser Ala
                725                 730                 735

Thr Pro Glu Thr Leu Leu Lys Glu Ala Ile His Val Ile Ser Cys Gly
            740                 745                 750

Tyr Glu Asp Lys Thr Glu Trp Gly Ser Glu Ile Gly Trp Ile Tyr Gly
        755                 760                 765

Ser Val Thr Glu Asp Ile Leu Thr Gly Phe Lys Met His Ala Arg Gly
    770                 775                 780

Trp Arg Ser Ile Tyr Cys Met Pro Lys Leu Pro Ala Phe Lys Gly Ser
785                 790                 795                 800

Ala Pro Ile Asn Leu Ser Asp Arg Leu Asn Gln Val Leu Arg Trp Ala
                805                 810                 815

Leu Gly Ser Val Glu Ile Leu Phe Ser Arg His Cys Pro Ile Trp Tyr
            820                 825                 830

Gly Tyr Ser Gly Arg Leu Lys Trp Leu Glu Arg Phe Ala Tyr Val Asn
        835                 840                 845

Thr Thr Ile Tyr Pro Val Thr Ser Ile Pro Leu Leu Met Tyr Cys Thr
    850                 855                 860

Leu Pro Ala Val Cys Leu Leu Thr Asn Lys Phe Ile Ile Pro Gln Ile
```

-continued 865 870 875 880

Ser Asn Ile Ala Ser Ile Trp Phe Ile Ser Leu Phe Leu Ser Ile Phe
885 890 895

Ala Thr Gly Ile Leu Glu Met Arg Trp Ser Gly Val Gly Ile Asp Glu
900 905 910

Trp Trp Arg Asn Glu Gln Phe Trp Val Ile Gly Gly Val Ser Ala His
915 920 925

Leu Phe Ala Val Phe Gln Gly Leu Leu Lys Val Leu Ala Gly Ile Asp
930 935 940

Thr Asn Phe Thr Val Thr Ser Lys Ala Ser Asp Glu Asp Gly Asp Phe
945 950 955 960

Ala Glu Leu Tyr Leu Phe Lys Trp Thr Thr Leu Leu Ile Pro Pro Thr
965 970 975

Thr Leu Leu Ile Ile Asn Leu Val Gly Val Val Ala Gly Ile Ser Tyr
980 985 990

Ala Ile Asn Ser Gly Tyr Gln Ser Trp Gly Pro Leu Phe Gly Lys Leu
995 1000 1005

Phe Phe Ala Phe Trp Val Ile Ile His Leu Tyr Pro Phe Leu Lys
1010 1015 1020

Gly Leu Met Gly Arg Gln Asn Arg Thr Pro Thr Ile Val Val Val
1025 1030 1035

Trp Ser Ile Leu Leu Ala Ser Ile Phe Ser Leu Leu Trp Val Arg
1040 1045 1050

Ile Asp Pro Phe Thr Thr Arg Val Thr Gly Pro Asp Val Glu Gln
1055 1060 1065

Cys Gly Ile Asn Cys
1070

<210> SEQ ID NO 45
<211> LENGTH: 1074
<212> TYPE: PRT
<213> ORGANISM: Glycine max

<400> SEQUENCE: 45

Met Met Glu Ser Glu Gly Glu Ala Gly Ala Lys Pro Met Lys Thr Leu
1 5 10 15

Gly Gly Lys Ile Cys Gln Ile Cys Gly Asp Asn Ile Gly Asn Asn Ala
20 25 30

Asn Gly Asp Pro Phe Ile Ala Cys Asp Val Cys Ala Phe Pro Val Cys
35 40 45

Arg Ala Cys Tyr Glu Tyr Glu Arg Lys Asp Gly Asn Gln Ser Cys Pro
50 55 60

Gln Cys Lys Thr Arg Tyr Lys Arg His Lys Gly Ser Pro Ala Ile Leu
65 70 75 80

Gly Asp Arg Glu Glu Asp Gly Gly Ala Asp Asp Gly Ala Ser Asp Phe
85 90 95

Asn Tyr Asn Ser Glu Asn Gln Asn Glu Lys Gln Lys Ile Glu His Met
100 105 110

Leu Gly Trp Gln Met Ala Tyr Gly Arg Ala Glu Glu Ala Ile Ala Pro
115 120 125

Asn Tyr Asp Lys Glu Val Ser His Asn His Ile Pro Leu Leu Ser Gly
130 135 140

Gly Gln Glu Val Ser Gly Glu Leu Ser Ala Ala Ser Pro Glu Arg Leu
145 150 155 160

```
Ser Met Ala Ser Pro Gly Gly Arg Gly Lys Arg Ala His Asn Leu Gln
                165                 170                 175

Tyr Ser Ser Asp Leu Asn His Ser Pro Asn Ile Arg Val Gly Asp Pro
            180                 185                 190

Gly Leu Gly Asn Val Ala Trp Lys Glu Arg Val Asp Gly Trp Lys Met
        195                 200                 205

Lys Gln Asp Lys Asn Val Ala Pro Met Ser Thr Gly Gln Ala Thr Ser
    210                 215                 220

Glu Arg Gly Ala Gly Asp Ile Asp Ala Ser Thr Asp Val Leu Val Asp
225                 230                 235                 240

Asp Ser Leu Leu Asn Asp Glu Ala Arg Gln Pro Leu Ser Arg Lys Val
                245                 250                 255

Ser Ile Pro Ser Ser Arg Ile Asn Pro Tyr Arg Met Val Ile Ala Leu
            260                 265                 270

Arg Leu Val Ile Leu Cys Ile Phe Leu His Tyr Arg Ile Thr Asn Pro
        275                 280                 285

Val Pro Asn Ala Tyr Ala Leu Trp Leu Ile Ser Val Ile Cys Glu Ile
    290                 295                 300

Trp Phe Ala Ile Ser Trp Ile Leu Asp Gln Phe Pro Lys Trp Leu Pro
305                 310                 315                 320

Val Asn Arg Glu Thr Tyr Leu Asp Arg Leu Ala Leu Arg Tyr Asp Arg
                325                 330                 335

Glu Gly Glu Pro Ser Gln Leu Ala Ala Val Asp Ile Phe Val Ser Thr
            340                 345                 350

Val Asp Pro Leu Lys Glu Pro Pro Leu Val Thr Ala Asn Thr Val Leu
        355                 360                 365

Ser Ile Leu Ser Val Asp Tyr Pro Val Asp Lys Val Ser Cys Tyr Val
    370                 375                 380

Ser Asp Asp Gly Ala Ala Met Leu Thr Phe Glu Ala Leu Ala Glu Thr
385                 390                 395                 400

Ser Glu Phe Ala Arg Lys Trp Val Pro Phe Ser Lys Lys Tyr Asn Ile
                405                 410                 415

Glu Pro Arg Ala Pro Glu Trp Tyr Phe Ala Gln Lys Ile Asp Tyr Leu
            420                 425                 430

Lys Asp Lys Val Gln Pro Ser Phe Val Lys Asp Arg Arg Ala Met Lys
        435                 440                 445

Arg Glu Tyr Glu Glu Phe Lys Ile Arg Ile Asn Gly Leu Val Ala Lys
    450                 455                 460

Ala Gln Lys Ile Pro Glu Glu Gly Trp Val Met Gln Asp Gly Thr Pro
465                 470                 475                 480

Trp Pro Gly Asn Asn Thr Arg Asp His Pro Gly Met Ile Gln Val Phe
                485                 490                 495

Leu Gly Gln Ser Gly Gly Leu Asp Thr Glu Gly Asn Glu Leu Pro Arg
            500                 505                 510

Leu Val Tyr Val Ser Arg Glu Lys Arg Pro Gly Phe Gln His His Lys
        515                 520                 525

Lys Ala Gly Ala Met Asn Ala Leu Val Arg Val Ser Ala Val Leu Thr
    530                 535                 540

Asn Gly Pro Phe Leu Leu Asn Leu Asp Cys Asp His Tyr Ile Asn Asn
545                 550                 555                 560

Ser Lys Ala Leu Arg Glu Ala Met Cys Phe Met Met Asp Pro Asn Leu
                565                 570                 575

Gly Lys Asn Val Cys Tyr Val Gln Phe Pro Gln Arg Phe Asp Gly Ile
```

580 585 590

Asp Arg Asn Asp Arg Tyr Ala Asn Arg Asn Thr Val Phe Phe Asp Ile
595 600 605

Asn Leu Arg Gly Leu Asp Gly Ile Gln Gly Pro Val Tyr Val Gly Thr
610 615 620

Gly Cys Val Phe Asn Arg Thr Ala Leu Tyr Gly Tyr Glu Pro Pro Ile
625 630 635 640

Lys Pro Lys His Lys Lys Pro Gly Phe Leu Ser Ser Leu Cys Gly Gly
645 650 655

Asn Arg Lys Lys Arg Ser Lys Ser Ser Lys Lys Gly Ser Asp Lys Lys
660 665 670

Lys Ser Ser Lys Asn Val Asp Pro Thr Val Pro Ile Phe Ser Leu Glu
675 680 685

Asp Ile Glu Glu Gly Val Glu Gly Ala Gly Phe Asp Asp Glu Lys Ser
690 695 700

Leu Leu Met Ser Gln Met Ser Leu Glu Lys Arg Phe Gly Gln Ser Ala
705 710 715 720

Val Phe Val Ala Ser Thr Leu Met Glu Asn Gly Gly Val Pro Gln Ser
725 730 735

Ala Thr Pro Glu Thr Leu Leu Lys Glu Ala Ile His Val Ile Ser Cys
740 745 750

Gly Tyr Glu Asp Lys Ser Glu Trp Gly Ser Glu Ile Gly Trp Ile Tyr
755 760 765

Gly Ser Val Thr Glu Asp Ile Leu Thr Gly Phe Lys Met His Ala Arg
770 775 780

Gly Trp Arg Ser Ile Tyr Cys Met Pro Lys Leu Pro Ala Phe Lys Gly
785 790 795 800

Ser Ala Pro Ile Asn Leu Ser Asp Arg Leu Asn Gln Val Leu Arg Trp
805 810 815

Ala Leu Gly Ser Val Glu Ile Leu Phe Ser Arg His Cys Pro Ile Trp
820 825 830

Tyr Gly Tyr Ser Gly Arg Leu Lys Trp Leu Glu Arg Phe Ala Tyr Val
835 840 845

Asn Thr Thr Ile Tyr Pro Val Thr Ser Ile Pro Leu Leu Met Tyr Cys
850 855 860

Thr Leu Pro Ala Val Cys Leu Leu Thr Asn Lys Phe Ile Ile Pro Gln
865 870 875 880

Ile Ser Asn Ile Ala Ser Ile Trp Phe Ile Ser Leu Phe Leu Ser Ile
885 890 895

Phe Ala Thr Gly Ile Leu Glu Met Arg Trp Ser Gly Val Gly Ile Asp
900 905 910

Glu Trp Trp Arg Asn Glu Gln Phe Trp Val Ile Gly Gly Val Ser Ala
915 920 925

His Leu Phe Ala Val Phe Gln Gly Leu Leu Lys Val Leu Ala Gly Ile
930 935 940

Asp Thr Asn Phe Thr Val Thr Ser Lys Ala Ser Asp Glu Asp Gly Asp
945 950 955 960

Phe Ala Glu Leu Tyr Met Phe Lys Trp Thr Thr Leu Leu Ile Pro Pro
965 970 975

Thr Thr Leu Leu Ile Ile Asn Leu Val Gly Val Val Ala Gly Ile Ser
980 985 990

Tyr Ala Ile Asn Ser Gly Tyr Gln Ser Trp Gly Pro Leu Phe Gly Lys
995 1000 1005

```
Leu Phe  Phe Ala Phe Trp Val  Ile Ile His Leu Tyr  Pro Phe Leu
    1010                 1015                 1020

Lys Gly  Leu Met Gly Arg Gln  Asn Arg Thr Pro Thr  Ile Val Val
    1025                 1030                 1035

Val Trp  Ser Ile Leu Leu Ala  Ser Ile Phe Ser Leu  Leu Trp Val
    1040                 1045                 1050

Arg Ile  Asp Pro Phe Thr Thr  Arg Val Thr Gly Pro  Asp Val Glu
    1055                 1060                 1065

Gln Cys  Gly Ile Asn Cys
    1070


<210> SEQ ID NO 46
<211> LENGTH: 1095
<212> TYPE: PRT
<213> ORGANISM: Glycine max

<400> SEQUENCE: 46

Met Asp Thr Lys Gly Arg Leu Val Ala Gly Ser His Asn Arg Asn Glu
1               5                   10                  15

Phe Val Leu Ile Asn Ala Asp Glu Thr Ala Arg Val Asn Ala Val Thr
            20                  25                  30

Glu Leu Ser Gly Gln Ile Cys Gln Ile Cys Gly Asp Glu Ile Glu Val
        35                  40                  45

Thr Val Asp Gly Glu Pro Phe Val Ala Cys Asn Glu Cys Ala Phe Pro
    50                  55                  60

Val Cys Arg Pro Cys Tyr Glu Tyr Glu Arg Arg Glu Gly Asn Lys Ile
65                  70                  75                  80

Cys Pro Gln Cys Lys Thr Ile Tyr Lys Arg Leu Lys Gly Ser Pro Arg
                85                  90                  95

Val Glu Gly Asp Glu Glu Glu Glu Asp Ile Asp Asp Leu Glu Asn Glu
            100                 105                 110

Phe Asp Ile Gly Ser Asn Ile Arg His Asp Pro His His Val Ala Glu
        115                 120                 125

Ala Leu Leu Ser Ala Arg Leu Asn Ala Ala Arg Gly Ser Gln Met Asn
    130                 135                 140

Ala Pro Gly Ile Thr Thr Pro Ser Glu Phe Asp Ala Ala Ser Val Ala
145                 150                 155                 160

Ala Asp Ile Pro Leu Leu Thr Tyr Asp His Glu Asp Val Gly Ile Ser
                165                 170                 175

Ala Asp Lys His Ala Leu Ile Ile Pro Pro Phe Met His His Gly Lys
            180                 185                 190

Arg Val His Pro Met Pro Pro Asp Ser Ser Val Pro Val Gln Pro Arg
        195                 200                 205

Pro Met Asp Pro Lys Lys Asp Leu Ala Val Tyr Gly Tyr Gly Ser Val
    210                 215                 220

Ala Trp Lys Glu Arg Met Glu Glu Trp Lys Lys Arg Gln Asn Glu Lys
225                 230                 235                 240

Ile Glu Val Val Lys His Glu Gly Gly Asn Asp Gly Gly Lys Asn Gly
                245                 250                 255

Asp Glu Leu Asp Asp Pro Asp Leu Pro Lys Met Asp Glu Gly Arg Gln
            260                 265                 270

Pro Leu Trp Arg Lys Leu Pro Ile Ser Pro Ser Lys Ile Asn Pro Tyr
        275                 280                 285

Arg Ile Ile Ile Val Leu Arg Ile Ala Val Leu Gly Leu Phe Phe His
```

```
    290                 295                 300

Tyr Arg Ile Leu His Pro Val Asn Asp Ala Tyr Ala Leu Trp Leu Thr
305                 310                 315                 320

Ser Val Ile Cys Glu Ile Trp Phe Ala Val Ser Trp Ile Leu Asp Gln
                325                 330                 335

Phe Pro Lys Trp Cys Pro Ile Glu Arg Glu Thr Tyr Leu Asp Arg Leu
            340                 345                 350

Ser Ser Arg Tyr Glu Lys Glu Gly Lys Pro Ser Glu Leu Ala Asp Ile
        355                 360                 365

Asp Val Phe Val Ser Thr Val Asp Pro Met Lys Glu Pro Pro Leu Ile
    370                 375                 380

Thr Ala Asn Thr Val Leu Ser Ile Leu Ala Val Asp Tyr Pro Val Glu
385                 390                 395                 400

Lys Val Ser Cys Tyr Val Ser Asp Asp Gly Ala Ala Met Leu Thr Phe
                405                 410                 415

Glu Ala Ile Ser Glu Thr Ser Glu Phe Ala Arg Lys Trp Val Pro Phe
            420                 425                 430

Cys Lys Lys Phe Asn Ile Glu Pro Arg Ala Pro Glu Trp Tyr Phe Ala
        435                 440                 445

Gln Lys Val Asp Tyr Leu Lys Asp Lys Val Asp Ala Thr Phe Ile Arg
    450                 455                 460

Glu Arg Arg Ala Ile Lys Arg Glu Tyr Glu Glu Phe Lys Val Arg Ile
465                 470                 475                 480

Asn Ala Leu Val Ala Met Ala Gln Lys Val Pro Glu Asp Gly Trp Thr
                485                 490                 495

Met Gln Asp Gly Thr Pro Trp Pro Gly Asn Ser Val Arg Asp His Pro
            500                 505                 510

Gly Met Ile Gln Val Phe Leu Gly Gln Asn Gly Ile His Asn Ile Glu
        515                 520                 525

Gly Asn Glu Leu Pro Arg Leu Val Tyr Val Ser Arg Glu Lys Arg Pro
    530                 535                 540

Gly Tyr Glu His His Lys Lys Ala Gly Ala Met Asn Ala Leu Val Arg
545                 550                 555                 560

Val Ser Ala Val Ile Ser Asn Ala Pro Tyr Leu Leu Asn Val Asp Cys
                565                 570                 575

Asp His Tyr Ile Asn Asn Ser Lys Ala Leu Arg Glu Ala Met Cys Phe
            580                 585                 590

Met Met Asp Pro Thr Ser Gly Lys Lys Ile Cys Tyr Val Gln Phe Pro
        595                 600                 605

Gln Arg Phe Asp Gly Ile Asp Arg His Asp Arg Tyr Ser Asn Arg Asn
    610                 615                 620

Val Val Phe Phe Asp Ile Asn Met Lys Gly Leu Asp Gly Ile Gln Gly
625                 630                 635                 640

Pro Ile Tyr Val Gly Thr Gly Cys Val Phe Arg Arg Gln Ala Leu Tyr
                645                 650                 655

Gly Tyr Asp Ala Pro Ala Thr Lys Lys Pro Pro Arg Lys Thr Cys Asn
            660                 665                 670

Cys Trp Pro Lys Trp Cys Cys Leu Cys Cys Gly Ser Arg Asn Lys Asn
        675                 680                 685

Arg Lys Val Lys Ser Gly Pro Arg Lys Lys Ile Lys Asn Lys Asp Ala
    690                 695                 700

Thr Lys Gln Ile His Ala Leu Glu Asn Ile Glu Glu Gly Ile Glu Gly
705                 710                 715                 720
```

```
Ile Asp Ser Glu Lys Ser Trp Leu Met Ser Gln Leu Lys Phe Glu Lys
                725                 730                 735

Lys Phe Gly Gln Ser Ala Val Phe Ile Ala Ser Thr Leu Met Glu Asp
            740                 745                 750

Gly Gly Ile Leu Lys Gly Ala Thr Ser Ala Ser Leu Leu Lys Glu Ala
        755                 760                 765

Ile His Val Ile Ser Cys Gly Tyr Glu Asp Lys Thr Glu Trp Gly Lys
    770                 775                 780

Glu Val Gly Trp Ile Tyr Gly Ser Val Thr Glu Asp Ile Leu Thr Gly
785                 790                 795                 800

Phe Lys Met His Cys His Gly Trp Arg Ser Val Tyr Cys Met Pro Lys
                805                 810                 815

Arg Pro Ala Phe Lys Gly Ser Ala Pro Ile Asn Leu Ser Asp Arg Leu
            820                 825                 830

His Gln Val Leu Arg Trp Ala Leu Gly Ser Val Glu Ile Leu Leu Ser
        835                 840                 845

Lys His Cys Pro Ile Trp Tyr Gly Tyr Gly Cys Gly Leu Lys Trp Leu
    850                 855                 860

Glu Arg Phe Ser Tyr Ile Asn Ser Val Ile Tyr Pro Leu Thr Ser Leu
865                 870                 875                 880

Pro Leu Ile Ala Tyr Cys Thr Leu Pro Ala Val Cys Leu Leu Thr Gly
                885                 890                 895

Lys Phe Ile Val Pro Glu Ile Ser Asn Tyr Ala Ser Ile Ile Phe Met
            900                 905                 910

Ala Leu Phe Ile Ser Ile Ala Val Thr Ser Ile Leu Glu Met Gln Trp
        915                 920                 925

Gly Gly Val Gly Ile His Asp Trp Trp Arg Asn Glu Gln Phe Trp Val
    930                 935                 940

Ile Gly Gly Ala Ser Ser His Leu Phe Ala Leu Phe Gln Gly Leu Leu
945                 950                 955                 960

Lys Val Leu Ala Gly Val Asn Thr Asn Phe Thr Val Thr Ser Lys Ala
                965                 970                 975

Ala Asp Gly Gly Asp Phe Ala Glu Leu Tyr Leu Phe Lys Trp Thr Ser
            980                 985                 990

Leu Leu Ile Pro Pro Leu Thr Leu  Leu Ile Ile Asn Ile  Ile Gly Val
        995                 1000                 1005

Ile Val  Gly Val Ser Asp Ala  Ile Asn Asn Gly Tyr  Asp Ser Trp
    1010                 1015                 1020

Gly Pro  Leu Phe Gly Lys Leu  Phe Phe Ala Leu Trp  Val Ile Val
    1025                 1030                 1035

His Leu  Tyr Pro Phe Leu Lys  Gly Val Met Gly Lys  Gln Glu Gly
    1040                 1045                 1050

Val Pro  Thr Ile Ile Leu Val  Trp Ala Ile Leu Leu  Ala Ser Ile
    1055                 1060                 1065

Phe Ser  Leu Leu Trp Val Arg  Ile Asn Pro Phe Leu  Ser Lys Gly
    1070                 1075                 1080

Gly Ile  Val Leu Glu Leu Cys  Gly Leu Asn Cys Asp
    1085                 1090                 1095
```

<210> SEQ ID NO 47
<211> LENGTH: 1078
<212> TYPE: PRT
<213> ORGANISM: Glycine max

<400> SEQUENCE: 47

```
Met Asp Thr Lys Gly Arg Leu Val Ala Gly Ser His Asn Arg Asn Glu
1               5                   10                  15

Phe Val Leu Ile Asn Ala Asp Glu Thr Ala Arg Val Ala Val Thr Glu
            20                  25                  30

Leu Ser Gly Gln Ile Cys Gln Ile Cys Gly Asp Glu Leu Glu Val Thr
        35                  40                  45

Val Asn Gly Glu Pro Phe Val Ala Cys Asn Glu Cys Ala Phe Pro Val
    50                  55                  60

Cys Arg Pro Cys Tyr Glu Tyr Glu Arg Arg Glu Gly Asn Gln Val Cys
65                  70                  75                  80

Pro Gln Cys Lys Thr Arg Tyr Lys Arg Ile Lys Gly Ser Pro Arg Val
                85                  90                  95

Glu Gly Asp Glu Glu Glu Asp Asp Thr Asp Asp Leu Glu Ser Glu Phe
            100                 105                 110

Asp Ile Gly Ser Val Phe Ser Ala Arg Leu Asn Tyr Gly Ser Gln Val
        115                 120                 125

Asn Gly Ser Val Ile His Ala Pro Ser Glu Phe Asp Ala Ala Ser Val
    130                 135                 140

Ala Ser Glu Ile Pro Leu Leu Thr Tyr Gly Gln Glu Asp Val Gly Ile
145                 150                 155                 160

Ser Ala Asp Lys His Ala Leu Ile Leu Pro Pro Phe Thr Ala Arg Gly
                165                 170                 175

Lys Arg Val Tyr Pro Met Pro Phe Pro Asp Ser Ser Val Pro Val Gln
            180                 185                 190

Pro Arg Pro Met Asp Pro Lys Lys Asp Ile Ala Val Tyr Gly Tyr Gly
        195                 200                 205

Ser Val Ala Trp Lys Glu Arg Met Glu Asp Trp Lys Lys Lys Gln Ser
    210                 215                 220

Glu Lys Leu Gln Val Val Arg His Glu Gly Asp Lys Asp Ser Asp Glu
225                 230                 235                 240

Leu Asp Asp Pro Asp Leu Pro Lys Met Asp Glu Gly Arg Gln Pro Leu
                245                 250                 255

Trp Arg Lys Leu Pro Ile Ser Ser Ser Arg Ile Asn Pro Tyr Arg Ile
            260                 265                 270

Ile Ile Val Leu Arg Ile Ala Ile Leu Cys Leu Phe Phe His Tyr Arg
        275                 280                 285

Ile Leu His Pro Val Asn Asp Ala Tyr Ala Leu Trp Leu Thr Ser Val
    290                 295                 300

Ile Cys Glu Ile Trp Phe Ala Val Ser Trp Ile Phe Asp Gln Phe Pro
305                 310                 315                 320

Lys Trp Ser Pro Ile Leu Arg Glu Thr Tyr Leu Asp Arg Leu Ser Leu
                325                 330                 335

Arg Tyr Glu Lys Glu Gly Lys Pro Ser Gln Leu Ser Asp Ile Asp Val
            340                 345                 350

Phe Val Ser Thr Val Asp Pro Met Lys Glu Pro Pro Leu Ile Thr Ala
        355                 360                 365

Asn Thr Val Leu Ser Ile Leu Ala Val Asp Tyr Pro Val Asp Lys Val
    370                 375                 380

Ala Cys Tyr Val Ser Asp Asp Gly Ala Ala Met Leu Thr Phe Glu Ala
385                 390                 395                 400

Leu Ser Glu Thr Ser Glu Phe Ala Arg Lys Trp Val Pro Phe Cys Lys
                405                 410                 415
```

```
Lys Phe Cys Ile Glu Pro Arg Ala Pro Glu Trp Tyr Phe Ala Gln Lys
            420                 425                 430

Val Asp Tyr Leu Lys Asp Lys Val Asp Ala Thr Phe Ile Arg Glu Arg
        435                 440                 445

Arg Ala Ile Lys Arg Glu Tyr Glu Glu Phe Lys Val Arg Ile Asn Ala
    450                 455                 460

Leu Val Ala Leu Ala Gln Lys Val Pro Glu Asp Gly Trp Thr Met Gln
465                 470                 475                 480

Asp Gly Thr Pro Trp Pro Gly Asn Asn Val Arg Asp His Pro Gly Met
                485                 490                 495

Ile Gln Val Phe Leu Gly Gln Asn Gly Val Arg Asp Ile Glu Gly Asn
            500                 505                 510

Glu Leu Pro Arg Leu Val Tyr Val Ser Arg Glu Lys Arg Pro Gly Tyr
        515                 520                 525

Asp His His Lys Lys Ala Gly Ala Met Asn Ala Leu Val Arg Val Ser
    530                 535                 540

Ala Ile Ile Thr Asn Ala Pro Tyr Val Leu Asn Val Asp Cys Asp His
545                 550                 555                 560

Tyr Ile Asn Asn Ser Lys Ala Leu Arg Glu Ala Met Cys Phe Met Met
                565                 570                 575

Asp Pro Thr Ser Gly Lys Lys Ile Cys Tyr Val Gln Phe Pro Gln Arg
            580                 585                 590

Phe Asp Gly Ile Asp Arg His Asp Arg Tyr Ser Asn Arg Asn Val Val
        595                 600                 605

Phe Phe Asp Ile Asn Met Lys Gly Leu Asp Gly Ile Gln Gly Pro Ile
    610                 615                 620

Tyr Val Gly Thr Gly Cys Val Phe Arg Arg Gln Ala Phe Tyr Gly Cys
625                 630                 635                 640

Asp Ala Pro Thr Ser Lys Lys Ala Pro Arg Lys Thr Cys Asn Cys Trp
                645                 650                 655

Pro Lys Trp Cys Cys Cys Leu Cys Cys Gly Ser Arg Lys Lys Lys Ile
            660                 665                 670

Lys Ala Lys Ser Ser Val Lys Lys Lys Ile Lys Asn Lys Asp Asp Leu
        675                 680                 685

Lys Gln Met His Ala Leu Glu Asn Ile Glu Glu Gly Ile Glu Gly Ile
    690                 695                 700

Asp Asn Glu Lys Ser Ser Leu Met Ser Gln Ser Lys Phe Glu Lys Lys
705                 710                 715                 720

Phe Gly Gln Ser Ser Val Phe Ile Ala Ser Thr Leu Leu Glu Asp Gly
                725                 730                 735

Gly Val Pro Lys Ala Ala Ser Ser Ala Thr Leu Leu Lys Glu Ala Ile
            740                 745                 750

His Val Ile Ser Cys Gly Tyr Glu Asp Lys Thr Glu Trp Gly Lys Glu
        755                 760                 765

Val Gly Trp Ile Tyr Gly Ser Val Thr Glu Asp Ile Leu Thr Gly Phe
    770                 775                 780

Lys Met His Cys His Gly Trp Arg Ser Val Tyr Cys Met Pro Lys Arg
785                 790                 795                 800

Pro Ala Phe Lys Gly Ser Ala Pro Ile Asn Leu Ser Asp Arg Leu His
                805                 810                 815

Gln Val Leu Arg Trp Ala Leu Gly Ser Val Glu Ile Phe Phe Ser Arg
            820                 825                 830
```

```
His Cys Pro Ile Trp Tyr Gly Tyr Gly Gly Gly Leu Lys Ser Leu Glu
        835                 840                 845

Arg Phe Ser Tyr Ile Asn Ser Val Val Tyr Pro Leu Thr Ser Ile Pro
    850                 855                 860

Leu Ile Ala Tyr Cys Ala Leu Pro Ala Val Cys Leu Leu Thr Gly Lys
865                 870                 875                 880

Phe Ile Val Pro Glu Ile Ser Asn Tyr Ala Ser Ile Ile Phe Met Ala
                885                 890                 895

Leu Phe Ile Ser Ile Ala Ala Thr Gly Ile Leu Glu Met Gln Trp Gly
            900                 905                 910

Gly Val Gly Ile His Asp Trp Trp Arg Asn Glu Gln Phe Trp Val Ile
        915                 920                 925

Gly Gly Ala Ser Ser His Leu Phe Ala Leu Phe Gln Gly Leu Leu Lys
    930                 935                 940

Val Leu Ala Gly Val Asn Thr Asn Phe Thr Val Thr Ser Lys Ala Ala
945                 950                 955                 960

Asp Asp Gly Glu Phe Ala Glu Leu Tyr Ile Phe Lys Trp Thr Ser Leu
                965                 970                 975

Leu Ile Pro Pro Leu Thr Leu Leu Ile Leu Asn Ile Ile Gly Val Ile
            980                 985                 990

Val Gly Val Ser Asp Ala Ile Asn  Asn Gly Tyr Asp Ser  Trp Gly Pro
        995                 1000                1005

Leu Phe  Gly Arg Leu Phe Phe  Ala Leu Trp Val Ile  Val His Leu
    1010                1015                1020

Tyr Pro  Phe Leu Lys Gly Val  Met Gly Lys Gln Glu  Gly Val Pro
    1025                1030                1035

Thr Ile  Ile Leu Val Trp Ala  Ile Leu Leu Ala Ser  Ile Leu Thr
    1040                1045                1050

Leu Leu  Trp Val Arg Ile Asn  Pro Phe Leu Ala Lys  Asn Asp Val
    1055                1060                1065

Val Leu  Glu Ile Cys Gly Leu  Asn Cys Asp
    1070                1075


<210> SEQ ID NO 48
<211> LENGTH: 989
<212> TYPE: PRT
<213> ORGANISM: Oryza sativa

<400> SEQUENCE: 48

Met Met Glu Ser Gly Val Pro Pro Cys Ala Ala Cys Gly Asp Asp Ala
1               5                   10                  15

His Ala Ala Cys Arg Ala Cys Ser Tyr Ala Leu Cys Lys Ala Cys Leu
            20                  25                  30

Asp Glu Asp Ala Ala Glu Gly Arg Thr Thr Cys Ala Arg Cys Gly Gly
        35                  40                  45

Glu Tyr Gly Ala Pro Asp Pro Ala His Gly Gln Gly Ala Val Val Glu
    50                  55                  60

Glu Glu Val Glu Glu Ser His Glu Pro Ala Ala Gly Gly Val Arg Glu
65                  70                  75                  80

Arg Val Thr Met Ala Ser Gln Leu Ser Asp His Gln Asp Glu Gly Val
                85                  90                  95

His Ala Arg Thr Met Ser Thr His Ala Arg Thr Ile Ser Ser Val Ser
            100                 105                 110

Gly Val Gly Ser Glu Leu Asn Asp Glu Ser Gly Lys Pro Ile Trp Lys
        115                 120                 125
```

-continued

```
Asn Arg Val Glu Ser Trp Lys Glu Lys Lys Lys Glu Lys Lys Ala Ser
    130                 135                 140

Ala Lys Lys Ala Ala Ala Lys Ala Gln Ala Pro Pro Val Glu Glu Gln
145                 150                 155                 160

Ile Met Asp Glu Lys Asp Leu Thr Asp Ala Tyr Glu Pro Leu Ser Arg
                165                 170                 175

Ile Ile Pro Ile Ser Lys Asn Lys Leu Thr Pro Tyr Arg Ala Val Ile
            180                 185                 190

Ile Met Arg Leu Val Val Leu Gly Leu Phe Phe His Tyr Arg Ile Thr
        195                 200                 205

Asn Pro Val Tyr Ser Ala Phe Gly Leu Trp Met Thr Ser Val Ile Cys
    210                 215                 220

Glu Ile Trp Phe Gly Phe Ser Trp Ile Leu Asp Gln Phe Pro Lys Trp
225                 230                 235                 240

Cys Pro Ile Asn Arg Glu Thr Tyr Val Asp Arg Leu Ile Ala Arg Tyr
                245                 250                 255

Gly Asp Gly Glu Asp Ser Gly Leu Ala Pro Val Asp Phe Phe Val Ser
            260                 265                 270

Thr Val Asp Pro Leu Lys Glu Pro Pro Leu Ile Thr Ala Asn Thr Val
        275                 280                 285

Leu Ser Ile Leu Ala Val Asp Tyr Pro Val Glu Lys Ile Ser Cys Tyr
    290                 295                 300

Val Ser Asp Asp Gly Ser Ala Met Leu Thr Phe Glu Ser Leu Ala Glu
305                 310                 315                 320

Thr Ala Glu Phe Ala Arg Arg Trp Val Pro Phe Cys Lys Lys Tyr Ser
                325                 330                 335

Ile Glu Pro Arg Ala Pro Glu Phe Tyr Phe Ser Gln Lys Ile Asp Tyr
            340                 345                 350

Leu Lys Asp Lys Ile His Pro Ser Phe Val Lys Glu Arg Arg Ala Met
        355                 360                 365

Lys Arg Asp Tyr Glu Glu Tyr Lys Val Arg Ile Asn Ala Leu Val Ala
    370                 375                 380

Lys Ala Gln Lys Thr Pro Glu Glu Gly Trp Ile Met Gln Asp Gly Thr
385                 390                 395                 400

Pro Trp Pro Gly Asn Asn Pro Arg Asp His Pro Gly Met Ile Gln Val
                405                 410                 415

Phe Leu Gly Glu Thr Gly Ala Arg Asp Phe Asp Gly Asn Glu Leu Pro
            420                 425                 430

Arg Leu Val Tyr Val Ser Arg Glu Lys Arg Pro Gly Tyr Gln His His
        435                 440                 445

Lys Lys Ala Gly Ala Met Asn Ala Leu Val Arg Val Ser Ala Val Leu
    450                 455                 460

Thr Asn Ala Pro Tyr Ile Leu Asn Leu Asp Cys Asp His Tyr Val Asn
465                 470                 475                 480

Asn Ser Lys Ala Val Arg Glu Ala Met Cys Phe Met Met Asp Pro Ser
                485                 490                 495

Val Gly Arg Asp Val Cys Tyr Val Gln Phe Pro Gln Arg Phe Asp Gly
            500                 505                 510

Ile Asp Arg Ser Asp Arg Tyr Ala Asn Arg Asn Val Val Phe Phe Asp
        515                 520                 525

Val Asn Met Lys Gly Leu Asp Gly Leu Gln Gly Pro Val Tyr Val Gly
    530                 535                 540
```

Thr Gly Cys Cys Phe Tyr Arg Gln Ala Leu Tyr Gly Tyr Gly Pro Pro
545 550 555 560

Ser Leu Pro Ala Leu Pro Lys Ser Ser Val Cys Ser Trp Cys Cys Cys
565 570 575

Cys Cys Pro Lys Lys Lys Ala Glu Lys Ser Glu Lys Glu Met His Arg
580 585 590

Asp Ser Arg Arg Glu Asp Leu Glu Ser Ala Ile Phe Asn Leu Arg Glu
595 600 605

Ile Asp Asn Tyr Asp Glu Tyr Glu Arg Ser Met Leu Ile Ser Gln Met
610 615 620

Ser Phe Glu Lys Ser Phe Gly Leu Ser Ser Val Phe Ile Glu Ser Thr
625 630 635 640

Leu Met Glu Asn Gly Gly Val Pro Glu Ser Ala Asn Pro Ser Thr Leu
645 650 655

Ile Lys Glu Ala Ile His Val Ile Ser Cys Gly Tyr Glu Glu Lys Thr
660 665 670

Glu Trp Gly Lys Glu Ile Gly Trp Ile Tyr Gly Ser Val Thr Glu Asp
675 680 685

Ile Leu Thr Gly Phe Lys Met His Cys Arg Gly Trp Arg Ser Ile Tyr
690 695 700

Cys Met Pro Ile Arg Pro Ala Phe Lys Gly Ser Ala Pro Ile Asn Leu
705 710 715 720

Ser Asp Arg Leu His Gln Val Leu Arg Trp Ala Leu Gly Ser Val Glu
725 730 735

Ile Phe Leu Ser Arg His Cys Pro Leu Trp Tyr Gly Tyr Gly Gly Gly
740 745 750

Arg Leu Lys Trp Leu Gln Arg Leu Ser Tyr Ile Asn Thr Ile Val Tyr
755 760 765

Pro Phe Thr Ser Leu Pro Leu Ile Ala Tyr Cys Cys Leu Pro Ala Ile
770 775 780

Cys Leu Leu Thr Gly Lys Phe Ile Ile Pro Thr Leu Ser Asn Ala Ala
785 790 795 800

Thr Ile Trp Phe Leu Gly Leu Phe Ile Ser Ile Ile Val Thr Ser Val
805 810 815

Leu Glu Leu Arg Trp Ser Gly Ile Gly Ile Glu Asp Trp Trp Arg Asn
820 825 830

Glu Gln Phe Trp Val Ile Gly Gly Val Ser Ala His Leu Phe Ala Val
835 840 845

Phe Gln Gly Ile Leu Lys Met Ile Ala Gly Leu Asp Thr Asn Phe Thr
850 855 860

Val Thr Ala Lys Ala Thr Asp Asp Thr Glu Phe Gly Glu Leu Tyr Val
865 870 875 880

Phe Lys Trp Thr Thr Val Leu Ile Pro Pro Thr Ser Ile Leu Val Leu
885 890 895

Asn Leu Val Gly Val Val Ala Gly Phe Ser Asp Ala Leu Asn Ser Gly
900 905 910

Tyr Glu Ser Trp Gly Pro Leu Phe Gly Lys Val Phe Phe Ala Met Trp
915 920 925

Val Ile Met His Leu Tyr Pro Phe Leu Lys Gly Leu Met Gly Arg Gln
930 935 940

Asn Arg Thr Pro Thr Ile Val Val Leu Trp Ser Val Leu Leu Ala Ser
945 950 955 960

Val Phe Ser Leu Leu Trp Val Lys Ile Asp Pro Phe Ile Gly Ser Ser 965 970 975

Glu Thr Thr Thr Thr Asn Ser Cys Ala Asn Phe Asp Cys
980 985

<210> SEQ ID NO 49
<211> LENGTH: 1073
<212> TYPE: PRT
<213> ORGANISM: Oryza sativa

<400> SEQUENCE: 49

Met Asp Gly Ala Lys Ser Gly Lys Gln Cys His Val Cys Gln Ile Cys
1 5 10 15

Gly Asp Gly Val Gly Thr Ala Ala Asp Gly Glu Leu Phe Thr Ala Cys
20 25 30

Asp Val Cys Gly Phe Pro Val Cys Arg Pro Cys Tyr Glu Tyr Glu Arg
35 40 45

Lys Asp Gly Ser Gln Ala Cys Pro Gln Cys Lys Thr Lys Tyr Lys Arg
50 55 60

His Lys Gly Ser Pro Pro Ile Leu Gly Asp Glu Ser Asp Asp Val Asp
65 70 75 80

Ala Asp Asp Ala Ser Asp Val Asn Tyr Pro Thr Ser Gly Asn Gln Asp
85 90 95

His Lys His Lys Ile Ala Glu Arg Met Leu Thr Trp Arg Met Asn Ser
100 105 110

Gly Arg Asn Asp Asp Ile Val His Ser Lys Tyr Asp Ser Gly Glu Ile
115 120 125

Gly His Pro Lys Tyr Asp Ser Gly Glu Ile Pro Arg Ile Tyr Ile Pro
130 135 140

Ser Leu Thr His Ser Gln Ile Ser Gly Glu Ile Pro Gly Ala Ser Pro
145 150 155 160

Asp His Met Met Ser Pro Val Gly Asn Ile Gly Arg Arg Gly His Pro
165 170 175

Phe Pro Tyr Val Asn His Ser Pro Asn Pro Ser Arg Glu Phe Ser Gly
180 185 190

Ser Leu Gly Asn Val Ala Trp Lys Glu Arg Val Asp Gly Trp Lys Met
195 200 205

Lys Asp Lys Gly Ala Ile Pro Met Ala Asn Gly Thr Ser Ile Ala Pro
210 215 220

Ser Glu Gly Arg Gly Val Gly Asp Ile Asp Ala Ser Thr Asp Tyr Asn
225 230 235 240

Met Glu Asp Ala Leu Leu Asn Asp Glu Thr Arg Gln Pro Leu Ser Arg
245 250 255

Lys Val Pro Ile Ser Ser Ser Arg Ile Asn Pro Tyr Arg Met Val Ile
260 265 270

Val Leu Arg Leu Ile Val Leu Cys Ile Phe Leu His Tyr Arg Ile Thr
275 280 285

Asn Pro Val Arg Asn Ala Tyr Pro Leu Trp Leu Leu Ser Val Ile Cys
290 295 300

Glu Ile Trp Phe Ala Leu Ser Trp Ile Leu Asp Gln Phe Pro Lys Trp
305 310 315 320

Ser Pro Ile Asn Arg Glu Thr Tyr Leu Asp Arg Leu Ala Leu Arg Tyr
325 330 335

Asp Arg Glu Gly Glu Pro Ser Gln Leu Ala Pro Val Asp Ile Phe Val
340 345 350

-continued

```
Ser Thr Val Asp Pro Met Lys Glu Pro Pro Leu Val Thr Ala Asn Thr
        355                 360                 365

Val Leu Ser Ile Leu Ala Val Asp Tyr Pro Val Asp Lys Val Ser Cys
    370                 375                 380

Tyr Val Ser Asp Asp Gly Ala Ala Met Leu Thr Phe Asp Ala Leu Ala
385                 390                 395                 400

Glu Thr Ser Glu Phe Ala Arg Lys Trp Val Pro Phe Cys Lys Lys Tyr
                405                 410                 415

Ser Ile Glu Pro Arg Ala Pro Glu Trp Tyr Phe Ala Gln Lys Ile Asp
            420                 425                 430

Tyr Leu Lys Asp Lys Val Gln Ala Ser Phe Val Lys Asp Arg Arg Ala
        435                 440                 445

Met Lys Arg Glu Tyr Glu Glu Phe Lys Val Arg Val Asn Ala Leu Val
    450                 455                 460

Ala Lys Ala Gln Lys Val Pro Glu Glu Gly Trp Ile Met Gln Asp Gly
465                 470                 475                 480

Thr Pro Trp Pro Gly Asn Asn Thr Arg Asp His Pro Gly Met Ile Gln
                485                 490                 495

Val Phe Leu Gly His Ser Gly Gly Leu Asp Thr Glu Gly Asn Glu Leu
            500                 505                 510

Pro Arg Leu Val Tyr Val Ser Arg Glu Lys Arg Pro Gly Phe Gln His
        515                 520                 525

His Lys Lys Ala Gly Ala Met Asn Ala Leu Val Arg Val Ser Ala Val
    530                 535                 540

Leu Thr Asn Gly Gln Tyr Leu Leu Asn Leu Asp Cys Asp His Tyr Ile
545                 550                 555                 560

Asn Asn Ser Lys Ala Leu Arg Glu Ala Met Cys Phe Leu Met Asp Pro
                565                 570                 575

Asn Leu Gly Arg Arg Val Cys Tyr Val Gln Phe Pro Gln Arg Phe Asp
            580                 585                 590

Gly Ile Asp Arg Asn Asp Arg Tyr Ala Asn Arg Asn Thr Val Phe Phe
        595                 600                 605

Asp Ile Asn Leu Arg Gly Leu Asp Gly Leu Gln Gly Pro Val Tyr Val
    610                 615                 620

Gly Thr Gly Cys Val Phe Asn Arg Thr Ala Leu Tyr Gly Tyr Glu Pro
625                 630                 635                 640

Pro Ile Lys Gln Lys Arg Pro Gly Tyr Phe Ser Ser Leu Cys Gly Gly
                645                 650                 655

Arg Lys Lys Thr Lys Lys Ser Lys Glu Lys Ser Thr Glu Lys Lys Lys
            660                 665                 670

Ser His Lys His Val Asp Ser Ser Val Pro Val Phe Asn Leu Glu Asp
        675                 680                 685

Ile Glu Glu Gly Ile Glu Gly Ser Gly Phe Asp Asp Glu Lys Ser Leu
    690                 695                 700

Leu Met Ser Gln Met Ser Leu Glu Lys Arg Phe Gly Gln Ser Ser Val
705                 710                 715                 720

Phe Val Ala Ser Thr Leu Met Glu Tyr Gly Gly Val Pro Gln Ser Ala
                725                 730                 735

Thr Pro Glu Ser Leu Leu Lys Glu Ala Ile His Val Ile Ser Cys Gly
            740                 745                 750

Tyr Glu Asp Lys Ser Asp Trp Gly Thr Glu Ile Gly Trp Ile Tyr Gly
        755                 760                 765

Ser Val Thr Glu Asp Ile Leu Thr Gly Phe Lys Met His Ala Arg Gly
```

770 775 780

Trp Arg Ser Ile Tyr Cys Met Pro Lys Arg Pro Ala Phe Lys Gly Ser
785 790 795 800

Ala Pro Ile Asn Leu Ser Asp Arg Leu Asn Gln Val Leu Arg Trp Ala
805 810 815

Leu Gly Ser Val Glu Ile Leu Phe Ser Arg His Cys Pro Ile Trp Tyr
820 825 830

Gly Tyr Gly Gly Arg Leu Lys Phe Leu Glu Arg Phe Ala Tyr Ile Asn
835 840 845

Thr Thr Ile Tyr Pro Leu Thr Ser Ile Pro Leu Leu Leu Tyr Cys Ile
850 855 860

Leu Pro Ala Ile Cys Leu Leu Thr Gly Lys Phe Ile Ile Pro Glu Ile
865 870 875 880

Ser Asn Phe Ala Ser Ile Trp Phe Ile Ser Leu Phe Leu Ser Ile Phe
885 890 895

Ala Thr Gly Ile Leu Glu Met Arg Trp Ser Gly Val Gly Ile Asp Glu
900 905 910

Trp Trp Arg Asn Glu Gln Phe Trp Val Ile Gly Gly Ile Ser Ala His
915 920 925

Leu Phe Ala Val Phe Gln Gly Leu Leu Lys Val Leu Ala Gly Ile Asp
930 935 940

Thr Ser Phe Thr Val Thr Ser Lys Ala Ser Asp Glu Glu Gly Asp Phe
945 950 955 960

Ala Glu Leu Tyr Met Phe Lys Trp Thr Thr Leu Leu Ile Pro Pro Thr
965 970 975

Thr Ile Leu Ile Ile Asn Leu Val Gly Val Val Ala Gly Ile Ser Tyr
980 985 990

Ala Ile Asn Ser Gly Tyr Gln Ser Trp Gly Pro Leu Phe Gly Lys Leu
995 1000 1005

Phe Phe Ala Phe Trp Val Ile Val His Leu Tyr Pro Phe Leu Lys
1010 1015 1020

Gly Leu Met Gly Arg Gln Asn Arg Thr Pro Thr Ile Val Val Val
1025 1030 1035

Trp Ala Ile Leu Leu Ala Ser Ile Phe Ser Leu Leu Trp Val Arg
1040 1045 1050

Ile Asp Pro Phe Thr Thr Arg Val Thr Gly Pro Asp Thr Gln Lys
1055 1060 1065

Cys Gly Ile Asn Cys
1070

<210> SEQ ID NO 50
<211> LENGTH: 1092
<212> TYPE: PRT
<213> ORGANISM: Oryza sativa

<400> SEQUENCE: 50

Met Glu Ala Ser Ala Gly Leu Val Ala Gly Ser His Asn Arg Asn Glu
1 5 10 15

Leu Val Val Ile Arg Arg Asp Gly Glu Pro Gly Pro Lys Pro Val Lys
20 25 30

His Thr Asn Gly Gln Val Cys Gln Ile Cys Gly Asp Asp Val Gly Leu
35 40 45

Thr Pro Asp Gly Glu Pro Phe Val Ala Cys Asn Glu Cys Ala Phe Pro
50 55 60

```
Val Cys Arg Asp Cys Tyr Glu Tyr Glu Arg Arg Glu Gly Thr Gln Asn
65                  70                  75                  80

Cys Pro Gln Cys Lys Thr Arg Phe Lys Arg Leu Lys Gly Cys Ala Arg
                85                  90                  95

Val Pro Gly Asp Glu Glu Glu Glu Asp Val Asp Asp Leu Glu Asn Glu
            100                 105                 110

Phe Asn Trp Arg Asp Lys Thr Asp Ser Gln Tyr Val Ala Glu Ser Met
        115                 120                 125

Leu His Gly His Met Ser Tyr Gly Arg Gly Gly Asp Leu Asp Gly Val
    130                 135                 140

Pro Gln His Phe Gln Pro Ile Pro Asn Val Pro Leu Leu Thr Asn Gly
145                 150                 155                 160

Glu Met Ala Asp Asp Ile Pro Pro Glu Gln His Ala Leu Val Pro Ser
                165                 170                 175

Phe Met Gly Gly Gly Gly Lys Arg Ile His Pro Leu Pro Tyr Ala Asp
            180                 185                 190

Pro Asn Leu Pro Val Gln Pro Arg Ser Met Asp Pro Ser Lys Asp Leu
        195                 200                 205

Ala Ala Tyr Gly Tyr Gly Ser Val Ala Trp Lys Glu Arg Met Glu Ser
    210                 215                 220

Trp Lys Gln Lys Gln Glu Arg Leu His Gln Met Arg Asn Asp Gly Gly
225                 230                 235                 240

Gly Lys Asp Trp Asp Gly Asp Gly Asp Asp Ala Asp Leu Pro Leu Met
                245                 250                 255

Asp Glu Ala Arg Gln Pro Leu Ser Arg Lys Ile Pro Ile Ser Ser Ser
            260                 265                 270

Leu Val Asn Pro Tyr Arg Met Ile Ile Ile Ile Arg Leu Val Val Leu
        275                 280                 285

Gly Phe Phe Phe His Tyr Arg Val Met His Pro Val Pro Asp Ala Phe
    290                 295                 300

Ala Leu Trp Leu Ile Ser Val Ile Cys Glu Ile Trp Phe Ala Met Ser
305                 310                 315                 320

Trp Ile Leu Asp Gln Phe Pro Lys Trp Phe Pro Ile Glu Arg Glu Thr
                325                 330                 335

Tyr Leu Asp Arg Leu Thr Leu Arg Phe Asp Lys Glu Gly Gln Gln Ser
            340                 345                 350

Gln Leu Ala Pro Val Asp Phe Phe Val Ser Thr Val Asp Pro Met Lys
        355                 360                 365

Glu Pro Pro Leu Val Thr Ala Asn Thr Val Leu Ser Ile Leu Ala Val
    370                 375                 380

Asp Tyr Pro Val Asp Lys Val Ser Cys Tyr Val Ser Asp Asp Gly Ala
385                 390                 395                 400

Ala Met Leu Thr Phe Glu Ala Leu Ser Glu Thr Ser Glu Phe Ala Lys
                405                 410                 415

Lys Trp Val Pro Phe Cys Lys Arg Tyr Ser Leu Glu Pro Arg Ala Pro
            420                 425                 430

Glu Trp Tyr Phe Gln Gln Lys Ile Asp Tyr Leu Lys Asp Lys Val Ala
        435                 440                 445

Pro Asn Phe Val Arg Glu Arg Arg Ala Met Lys Arg Glu Tyr Glu Glu
    450                 455                 460

Phe Lys Val Arg Ile Asn Ala Leu Val Ala Lys Ala Gln Lys Val Pro
465                 470                 475                 480

Glu Glu Gly Trp Thr Met Gln Asp Gly Thr Pro Trp Pro Gly Asn Asn
```

```
                485                 490                 495

Val Arg Asp His Pro Gly Met Ile Gln Val Phe Leu Gly Gln Ser Gly
            500                 505                 510

Gly His Asp Val Glu Gly Asn Glu Leu Pro Arg Leu Val Tyr Val Ser
        515                 520                 525

Arg Glu Lys Arg Pro Gly Tyr Asn His His Lys Lys Ala Gly Ala Met
    530                 535                 540

Asn Ala Leu Val Arg Val Ser Ala Val Leu Thr Asn Ala Pro Tyr Met
545                 550                 555                 560

Leu Asn Leu Asp Cys Asp His Tyr Ile Asn Asn Ser Lys Ala Ile Lys
                565                 570                 575

Glu Ala Met Cys Phe Met Met Asp Pro Leu Val Gly Lys Lys Val Cys
            580                 585                 590

Tyr Val Gln Phe Pro Gln Arg Phe Asp Gly Ile Asp Arg His Asp Arg
        595                 600                 605

Tyr Ala Asn Arg Asn Val Val Phe Phe Asp Ile Asn Met Lys Gly Leu
    610                 615                 620

Asp Gly Ile Gln Gly Pro Ile Tyr Val Gly Thr Gly Cys Val Phe Arg
625                 630                 635                 640

Arg Gln Ala Leu Tyr Gly Tyr Asp Ala Pro Lys Ser Lys Lys Pro Pro
                645                 650                 655

Ser Arg Thr Cys Asn Cys Trp Pro Lys Trp Cys Ile Cys Cys Cys Cys
            660                 665                 670

Phe Gly Asn Arg Thr Asn Lys Lys Lys Thr Ala Lys Pro Lys Thr Glu
        675                 680                 685

Lys Lys Lys Arg Leu Phe Phe Lys Arg Ala Glu Asn Gln Ser Pro Ala
    690                 695                 700

Tyr Ala Leu Gly Glu Ile Asp Glu Gly Ala Pro Gly Ala Glu Asn Glu
705                 710                 715                 720

Lys Ala Gly Ile Val Asn Gln Gln Lys Leu Glu Lys Lys Phe Gly Gln
                725                 730                 735

Ser Ser Val Phe Val Ala Ser Thr Leu Leu Glu Asn Gly Gly Thr Leu
            740                 745                 750

Lys Ser Ala Ser Pro Ala Ser Leu Leu Lys Glu Ala Ile His Val Ile
        755                 760                 765

Ser Cys Gly Tyr Glu Asp Lys Thr Asp Trp Gly Lys Glu Ile Gly Trp
    770                 775                 780

Ile Tyr Gly Ser Val Thr Glu Asp Ile Leu Thr Gly Phe Lys Met His
785                 790                 795                 800

Cys His Gly Trp Arg Ser Ile Tyr Cys Ile Pro Lys Arg Ala Ala Phe
                805                 810                 815

Lys Gly Ser Ala Pro Leu Asn Leu Ser Asp Arg Leu His Gln Val Leu
            820                 825                 830

Arg Trp Ala Leu Gly Ser Ile Glu Ile Phe Phe Ser Asn His Cys Pro
        835                 840                 845

Leu Trp Tyr Gly Tyr Gly Gly Gly Leu Lys Cys Leu Glu Arg Phe Ser
    850                 855                 860

Tyr Ile Asn Ser Ile Val Tyr Pro Trp Thr Ser Ile Pro Leu Leu Ala
865                 870                 875                 880

Tyr Cys Thr Leu Pro Ala Ile Cys Leu Leu Thr Gly Lys Phe Ile Thr
                885                 890                 895

Pro Glu Leu Thr Asn Ile Ala Ser Leu Trp Phe Met Ser Leu Phe Ile
            900                 905                 910
```

```
Cys Ile Phe Ala Thr Gly Ile Leu Glu Met Arg Trp Ser Gly Val Gly
        915                 920                 925

Ile Asp Asp Trp Trp Arg Asn Glu Gln Phe Trp Val Ile Gly Gly Val
    930                 935                 940

Ser Ser His Leu Phe Ala Val Phe Gln Gly Leu Leu Lys Val Ile Ala
945                 950                 955                 960

Gly Ile Asp Thr Ser Phe Thr Val Thr Ser Lys Gly Gly Asp Asp Glu
                965                 970                 975

Glu Phe Ser Glu Leu Tyr Thr Phe Lys Trp Thr Thr Leu Leu Ile Pro
            980                 985                 990

Pro Thr Thr Leu Leu Leu Leu Asn  Phe Ile Gly Val Val  Ala Gly Val
        995                 1000                 1005

Ser Asn  Ala Ile Asn Asn Gly  Tyr Glu Ser Trp Gly  Pro Leu Phe
    1010                 1015                 1020

Gly Lys  Leu Phe Phe Ala Phe  Trp Val Ile Val His  Leu Tyr Pro
    1025                 1030                 1035

Phe Leu  Lys Gly Leu Val Gly  Arg Gln Asn Arg Thr  Pro Thr Ile
    1040                 1045                 1050

Val Ile  Val Trp Ser Ile Leu  Leu Ala Ser Ile Phe  Ser Leu Leu
    1055                 1060                 1065

Trp Val  Arg Ile Asp Pro Phe  Leu Ala Lys Asn Asp  Gly Pro Leu
    1070                 1075                 1080

Leu Glu  Glu Cys Gly Leu Asp  Cys Asn
    1085                 1090
```

<210> SEQ ID NO 51
<211> LENGTH: 1076
<212> TYPE: PRT
<213> ORGANISM: Oryza sativa

<400> SEQUENCE: 51

```
Met Ala Ala Asn Ala Gly Met Val Ala Gly Ser Arg Asn Arg Asn Glu
1               5                   10                  15

Phe Val Met Ile Arg Pro Asp Gly Asp Ala Pro Pro Pro Ala Lys Pro
            20                  25                  30

Gly Lys Ser Val Asn Gly Gln Val Cys Gln Ile Cys Gly Asp Thr Val
        35                  40                  45

Gly Val Ser Ala Thr Gly Asp Val Phe Val Ala Cys Asn Glu Cys Ala
    50                  55                  60

Phe Pro Val Cys Arg Pro Cys Tyr Glu Tyr Glu Arg Lys Glu Gly Asn
65                  70                  75                  80

Gln Cys Cys Pro Gln Cys Lys Thr Arg Tyr Lys Arg His Lys Gly Ser
                85                  90                  95

Pro Arg Val Gln Gly Asp Glu Glu Glu Glu Asp Val Asp Asp Leu Asp
            100                 105                 110

Asn Glu Phe Asn Tyr Lys His Gly Asn Gly Lys Gly Pro Glu Trp Gln
        115                 120                 125

Ile Gln Arg Gln Gly Glu Asp Val Asp Leu Ser Ser Ser Ser Arg His
    130                 135                 140

Glu Gln His Arg Ile Pro Arg Leu Thr Ser Gly Gln Gln Ile Ser Gly
145                 150                 155                 160

Glu Ile Pro Asp Ala Ser Pro Asp Arg His Ser Ile Arg Ser Gly Thr
                165                 170                 175

Ser Ser Tyr Val Asp Pro Ser Val Pro Val Pro Val Arg Ile Val Asp
```

-continued

```
            180                 185                 190

Pro Ser Lys Asp Leu Asn Ser Tyr Gly Ile Asn Ser Val Asp Trp Gln
        195                 200                 205

Glu Arg Val Ala Ser Trp Arg Asn Lys Gln Asp Lys Asn Met Met Gln
    210                 215                 220

Val Ala Asn Lys Tyr Pro Glu Ala Arg Gly Gly Asp Met Glu Gly Thr
225                 230                 235                 240

Gly Ser Asn Gly Glu Asp Met Gln Met Val Asp Asp Ala Arg Leu Pro
                245                 250                 255

Leu Ser Arg Ile Val Pro Ile Pro Ser Asn Gln Leu Asn Leu Tyr Arg
            260                 265                 270

Ile Val Ile Ile Leu Arg Leu Ile Ile Leu Met Phe Phe Phe Gln Tyr
        275                 280                 285

Arg Val Thr His Pro Val Arg Asp Ala Tyr Gly Leu Trp Leu Val Ser
    290                 295                 300

Val Ile Cys Glu Ile Trp Phe Ala Leu Ser Trp Leu Leu Asp Gln Phe
305                 310                 315                 320

Pro Lys Trp Tyr Pro Ile Asn Arg Glu Thr Tyr Leu Asp Arg Leu Ala
                325                 330                 335

Leu Arg Tyr Asp Arg Glu Gly Glu Pro Ser Gln Leu Ala Pro Ile Asp
            340                 345                 350

Val Phe Val Ser Thr Val Asp Pro Leu Lys Glu Pro Pro Leu Ile Thr
        355                 360                 365

Ala Asn Thr Val Leu Ser Ile Leu Ala Val Asp Tyr Pro Val Asp Lys
    370                 375                 380

Val Ser Cys Tyr Val Ser Asp Asp Gly Ser Ala Met Leu Thr Phe Glu
385                 390                 395                 400

Ala Leu Ser Glu Thr Ala Glu Phe Ala Arg Lys Trp Val Pro Phe Cys
                405                 410                 415

Lys Lys His Asn Ile Glu Pro Arg Ala Pro Glu Phe Tyr Phe Ala Gln
            420                 425                 430

Lys Ile Asp Tyr Leu Lys Asp Lys Ile Gln Pro Ser Phe Val Lys Glu
        435                 440                 445

Arg Arg Ala Met Lys Arg Glu Tyr Glu Glu Phe Lys Val Arg Ile Asn
    450                 455                 460

Ala Leu Val Ala Lys Ala Gln Lys Val Pro Glu Glu Gly Trp Thr Met
465                 470                 475                 480

Ala Asp Gly Thr Ala Trp Pro Gly Asn Asn Pro Arg Asp His Pro Gly
                485                 490                 495

Met Ile Gln Val Phe Leu Gly His Ser Gly Gly Leu Asp Thr Asp Gly
            500                 505                 510

Asn Glu Leu Pro Arg Leu Val Tyr Val Ser Arg Glu Lys Arg Pro Gly
        515                 520                 525

Phe Gln His His Lys Lys Ala Gly Ala Met Asn Ala Leu Ile Arg Val
    530                 535                 540

Ser Ala Val Leu Thr Asn Gly Ala Tyr Leu Leu Asn Val Asp Cys Asp
545                 550                 555                 560

His Tyr Phe Asn Ser Ser Lys Ala Leu Arg Glu Ala Met Cys Phe Met
                565                 570                 575

Met Asp Pro Ala Leu Gly Arg Lys Thr Cys Tyr Val Gln Phe Pro Gln
            580                 585                 590

Arg Phe Asp Gly Ile Asp Leu His Asp Arg Tyr Ala Asn Arg Asn Ile
        595                 600                 605
```

```
Val Phe Phe Asp Ile Asn Met Lys Gly Leu Asp Gly Ile Gln Gly Pro
    610                 615                 620

Val Tyr Val Gly Thr Gly Cys Cys Phe Asn Arg Gln Ala Leu Tyr Gly
625                 630                 635                 640

Tyr Asp Pro Val Leu Thr Glu Ala Asp Leu Glu Pro Asn Ile Val Val
                645                 650                 655

Lys Ser Cys Cys Gly Gly Arg Lys Lys Lys Ser Lys Ser Tyr Met Asp
            660                 665                 670

Ser Lys Asn Arg Met Met Lys Arg Thr Glu Ser Ser Ala Pro Ile Phe
        675                 680                 685

Asn Met Glu Asp Ile Glu Glu Gly Ile Glu Gly Tyr Glu Asp Glu Arg
    690                 695                 700

Ser Val Leu Met Ser Gln Lys Arg Leu Glu Lys Arg Phe Gly Gln Ser
705                 710                 715                 720

Pro Ile Phe Ile Ala Ser Thr Phe Met Thr Gln Gly Gly Ile Pro Pro
                725                 730                 735

Ser Thr Asn Pro Ala Ser Leu Leu Lys Glu Ala Ile His Val Ile Ser
            740                 745                 750

Cys Gly Tyr Glu Asp Lys Thr Glu Trp Gly Lys Glu Ile Gly Trp Ile
        755                 760                 765

Tyr Gly Ser Val Thr Glu Asp Ile Leu Thr Gly Phe Lys Met His Ala
    770                 775                 780

Arg Gly Trp Ile Ser Ile Tyr Cys Met Pro Pro Arg Pro Cys Phe Lys
785                 790                 795                 800

Gly Ser Ala Pro Ile Asn Leu Ser Asp Arg Leu Asn Gln Val Leu Arg
                805                 810                 815

Trp Ala Leu Gly Ser Val Glu Ile Leu Leu Ser Arg His Cys Pro Ile
            820                 825                 830

Trp Tyr Gly Tyr Asn Gly Arg Leu Lys Leu Leu Glu Arg Leu Ala Tyr
        835                 840                 845

Ile Asn Thr Ile Val Tyr Pro Ile Thr Ser Ile Pro Leu Ile Ala Tyr
    850                 855                 860

Cys Val Leu Pro Ala Ile Cys Leu Leu Thr Asn Lys Phe Ile Ile Pro
865                 870                 875                 880

Glu Ile Ser Asn Tyr Ala Gly Met Phe Phe Ile Leu Leu Phe Ala Ser
                885                 890                 895

Ile Phe Ala Thr Gly Ile Leu Glu Leu Arg Trp Ser Gly Val Gly Ile
            900                 905                 910

Glu Asp Trp Trp Arg Asn Glu Gln Phe Trp Val Ile Gly Gly Thr Ser
        915                 920                 925

Ala His Leu Phe Ala Val Phe Gln Gly Leu Leu Lys Val Leu Ala Gly
    930                 935                 940

Ile Asp Thr Asn Phe Thr Val Thr Ser Lys Ala Ser Asp Glu Asp Gly
945                 950                 955                 960

Asp Phe Ala Glu Leu Tyr Val Phe Lys Trp Thr Ser Leu Leu Ile Pro
                965                 970                 975

Pro Thr Thr Val Leu Val Ile Asn Leu Val Gly Met Val Ala Gly Ile
            980                 985                 990

Ser Tyr Ala Ile Asn Ser Gly Tyr  Gln Ser Trp Gly Pro  Leu Phe Gly
        995                 1000                1005

Lys Leu  Phe Phe Ser Ile Trp  Val Ile Leu His Leu  Tyr Pro Phe
    1010                1015                1020
```

-continued

```
Leu Lys  Gly Leu Met Gly Arg  Gln Asn Arg Thr Pro  Thr Ile Val
    1025                 1030                 1035

Ile Val  Trp Ser Ile Leu Leu  Ala Ser Ile Phe Ser  Leu Leu Trp
    1040                 1045                 1050

Val Lys  Ile Asp Pro Phe Ile  Ser Pro Thr Gln Lys  Ala Val Ala
    1055                 1060                 1065

Leu Gly  Gln Cys Gly Val Asn  Cys
    1070                 1075


<210> SEQ ID NO 52
<211> LENGTH: 1170
<212> TYPE: PRT
<213> ORGANISM: Oryza sativa

<400> SEQUENCE: 52

Met Ala Ser Ser Gly Gly Gly Gly Leu Arg His Ser Asn Ser Ser Arg
1               5                   10                  15

Leu Ser Arg Met Ser Tyr Ser Gly Glu Asp Gly Arg Ala Gln Ala Pro
            20                  25                  30

Gly Gly Gly Gly Asp Arg Pro Met Val Thr Phe Ala Arg Arg Thr His
        35                  40                  45

Ser Gly Arg Tyr Val Ser Tyr Ser Arg Asp Asp Leu Asp Ser Glu Leu
    50                  55                  60

Gly Asn Ser Gly Asp Met Ser Pro Glu Ser Gly Gln Glu Phe Leu Asn
65                  70                  75                  80

Tyr His Val Thr Ile Pro Ala Thr Pro Asp Asn Gln Pro Met Asp Pro
                85                  90                  95

Ala Ile Ser Ala Arg Val Glu Glu Gln Tyr Val Ser Asn Ser Leu Phe
            100                 105                 110

Thr Gly Gly Phe Asn Ser Val Thr Arg Ala His Leu Met Asp Lys Val
        115                 120                 125

Ile Glu Ser Glu Ala Ser His Pro Gln Met Ala Gly Ala Lys Gly Ser
    130                 135                 140

Ser Cys Ala Ile Asn Gly Cys Asp Ala Lys Val Met Ser Asp Glu Arg
145                 150                 155                 160

Gly Asp Asp Ile Leu Pro Cys Glu Cys Asp Phe Lys Ile Cys Ala Asp
                165                 170                 175

Cys Phe Ala Asp Ala Val Lys Asn Gly Gly Ala Cys Pro Gly Cys Lys
            180                 185                 190

Asp Pro Tyr Lys Ala Thr Glu Leu Asp Asp Val Val Gly Ala Arg Pro
        195                 200                 205

Thr Leu Ser Leu Pro Pro Pro Pro Gly Gly Leu Pro Ala Ser Arg Met
    210                 215                 220

Glu Arg Arg Leu Ser Ile Met Arg Ser Gln Lys Ala Met Thr Arg Ser
225                 230                 235                 240

Gln Thr Gly Asp Trp Asp His Asn Arg Trp Leu Phe Glu Thr Lys Gly
                245                 250                 255

Thr Tyr Gly Tyr Gly Asn Ala Ile Trp Pro Lys Glu Asn Glu Val Asp
            260                 265                 270

Asn Gly Gly Gly Gly Gly Gly Gly Gly Gly Leu Gly Gly Gly Asp Gly
        275                 280                 285

Gln Pro Ala Glu Phe Thr Ser Lys Pro Trp Arg Pro Leu Thr Arg Lys
    290                 295                 300

Leu Lys Ile Pro Ala Gly Val Leu Ser Pro Tyr Arg Leu Leu Ile Leu
305                 310                 315                 320
```

-continued

```
Ile Arg Met Ala Val Leu Gly Leu Phe Leu Ala Trp Arg Ile Lys His
                325                 330                 335

Lys Asn Glu Asp Ala Met Trp Leu Trp Gly Met Ser Val Val Cys Glu
            340                 345                 350

Leu Trp Phe Gly Leu Ser Trp Leu Leu Asp Gln Leu Pro Lys Leu Cys
        355                 360                 365

Pro Val Asn Arg Ala Thr Asp Leu Ala Val Leu Lys Asp Lys Phe Glu
    370                 375                 380

Thr Pro Thr Pro Ser Asn Pro Asn Gly Arg Ser Asp Leu Pro Gly Leu
385                 390                 395                 400

Asp Ile Phe Val Ser Thr Ala Asp Pro Glu Lys Glu Pro Pro Leu Val
                405                 410                 415

Thr Ala Asn Thr Ile Leu Ser Ile Leu Ala Ala Asp Tyr Pro Val Glu
            420                 425                 430

Lys Leu Ser Cys Tyr Val Ser Asp Asp Gly Gly Ala Leu Leu Thr Phe
        435                 440                 445

Glu Ala Met Ala Glu Ala Ala Ser Phe Ala Asn Met Trp Val Pro Phe
    450                 455                 460

Cys Arg Lys His Asp Ile Glu Pro Arg Asn Pro Glu Ser Tyr Phe Asn
465                 470                 475                 480

Leu Lys Arg Asp Pro Tyr Lys Asn Lys Val Arg Ser Asp Phe Val Lys
                485                 490                 495

Asp Arg Arg Arg Val Lys Arg Glu Tyr Asp Glu Phe Lys Val Arg Ile
            500                 505                 510

Asn Ser Leu Pro Asp Ser Ile Arg Arg Arg Ser Asp Ala Tyr His Ala
        515                 520                 525

Arg Glu Glu Ile Lys Ala Met Lys Arg Gln Arg Glu Ala Ala Leu Asp
    530                 535                 540

Asp Val Val Glu Ala Val Lys Ile Pro Lys Ala Thr Trp Met Ala Asp
545                 550                 555                 560

Gly Thr His Trp Pro Gly Thr Trp Ile Gln Pro Ser Ala Glu His Ala
                565                 570                 575

Arg Gly Asp His Ala Gly Ile Ile Gln Val Met Leu Lys Pro Pro Ser
            580                 585                 590

Asp Asp Pro Leu Tyr Gly Thr Ser Gly Glu Glu Gly Arg Pro Leu Asp
        595                 600                 605

Phe Thr Glu Val Asp Ile Arg Leu Pro Met Leu Val Tyr Val Ser Arg
    610                 615                 620

Glu Lys Arg Pro Gly Tyr Asp His Asn Lys Lys Ala Gly Ala Met Asn
625                 630                 635                 640

Ala Leu Val Arg Ser Ser Ala Val Met Ser Asn Gly Pro Phe Ile Leu
                645                 650                 655

Asn Leu Asp Cys Asp His Tyr Val Tyr Asn Ser Gln Ala Phe Arg Glu
            660                 665                 670

Gly Met Cys Phe Met Met Asp Arg Gly Gly Asp Arg Ile Gly Tyr Val
        675                 680                 685

Gln Phe Pro Gln Arg Phe Glu Gly Ile Asp Pro Ser Asp Arg Tyr Ala
    690                 695                 700

Asn His Asn Thr Val Phe Phe Asp Val Asn Met Arg Ala Leu Asp Gly
705                 710                 715                 720

Ile Met Gly Pro Val Tyr Val Gly Thr Gly Cys Leu Phe Arg Arg Ile
                725                 730                 735
```

```
Ala Leu Tyr Gly Phe Asp Pro Pro Arg Ser Lys Glu His Ser Gly Cys
            740                 745                 750

Cys Ser Cys Cys Phe Pro Gln Arg Arg Lys Val Lys Thr Ser Thr Val
        755                 760                 765

Ala Ser Glu Glu Arg Gln Ala Leu Arg Met Ala Asp Phe Asp Asp Glu
    770                 775                 780

Glu Met Asn Met Ser Gln Phe Pro Lys Lys Phe Gly Asn Ser Asn Phe
785                 790                 795                 800

Leu Ile Asn Ser Ile Pro Ile Ala Glu Phe Gln Gly Arg Pro Leu Ala
                805                 810                 815

Asp His Pro Gly Val Lys Asn Gly Arg Pro Pro Gly Ala Leu Thr Val
            820                 825                 830

Pro Arg Asp Leu Leu Asp Ala Ser Thr Val Ala Glu Ala Ile Ser Val
        835                 840                 845

Ile Ser Cys Trp Tyr Glu Asp Lys Thr Glu Trp Gly Gln Arg Val Gly
    850                 855                 860

Trp Ile Tyr Gly Ser Val Thr Glu Asp Val Val Thr Gly Tyr Arg Met
865                 870                 875                 880

His Asn Arg Gly Trp Lys Ser Val Tyr Cys Val Thr Lys Arg Asp Ala
                885                 890                 895

Phe Arg Gly Thr Ala Pro Ile Asn Leu Thr Asp Arg Leu His Gln Val
            900                 905                 910

Leu Arg Trp Ala Thr Gly Ser Val Glu Ile Phe Phe Ser Arg Asn Asn
        915                 920                 925

Ala Leu Leu Ala Ser Arg Lys Met Lys Phe Leu Gln Arg Ile Ala Tyr
    930                 935                 940

Leu Asn Val Gly Ile Tyr Pro Phe Thr Ser Ile Phe Leu Ile Val Tyr
945                 950                 955                 960

Cys Phe Leu Pro Ala Leu Ser Leu Phe Ser Gly Gln Phe Ile Val Arg
                965                 970                 975

Thr Leu Asn Val Thr Phe Leu Thr Tyr Leu Leu Val Ile Thr Leu Thr
            980                 985                 990

Met Cys Met Leu Ala Val Leu Glu  Ile Lys Trp Ser Gly  Ile Ser Leu
        995                 1000                1005

Glu Glu  Trp Trp Arg Asn Glu  Gln Phe Trp Leu Ile  Gly Gly Thr
    1010                1015                1020

Ser Ala  His Leu Ala Ala Val  Leu Gln Gly Leu Leu  Lys Val Ile
    1025                1030                1035

Ala Gly  Ile Glu Ile Ser Phe  Thr Leu Thr Ser Lys  Ser Gly Gly
    1040                1045                1050

Asp Glu  Ala Asp Asp Glu Phe  Ala Asp Leu Tyr Ile  Val Lys Trp
    1055                1060                1065

Thr Ser  Leu Met Ile Pro Pro  Ile Val Ile Met Met  Val Asn Leu
    1070                1075                1080

Ile Ala  Ile Ala Val Gly Phe  Ser Arg Thr Ile Tyr  Ser Glu Ile
    1085                1090                1095

Pro Gln  Trp Ser Lys Leu Leu  Gly Gly Val Phe Phe  Ser Phe Trp
    1100                1105                1110

Val Leu  Ala His Leu Tyr Pro  Phe Ala Lys Gly Leu  Met Gly Arg
    1115                1120                1125

Arg Gly  Arg Thr Pro Thr Ile  Val Phe Val Trp Ser  Gly Leu Leu
    1130                1135                1140

Ala Ile  Thr Ile Ser Leu Leu  Trp Val Ala Ile Asn  Pro Pro Ser
```

```
    1145                1150                1155

Gln Asn  Ser Gln Ile Gly Gly  Ser Phe Thr Phe Pro
    1160                1165                1170


<210> SEQ ID NO 53
<211> LENGTH: 1012
<212> TYPE: PRT
<213> ORGANISM: Oryza sativa

<400> SEQUENCE: 53

Met Ser Val Asp Tyr Ala Asn Tyr Thr Val Leu Met Pro Pro Thr Pro
1               5                   10                  15

Asp Asn Gln Pro Ser Gly Gly Ala Pro Pro Ala Ala Pro Ser Ala Gly
            20                  25                  30

Gly Ala Arg Pro Gly Asp Leu Pro Leu Pro Pro Tyr Gly Ser Ser Ser
        35                  40                  45

Ser Ser Arg Leu Val Asn Arg Arg Gly Gly Gly Asp Asp Gly Ala Lys
    50                  55                  60

Met Asp Arg Arg Leu Ser Thr Ala Arg Val Pro Ala Pro Ser Ser Asn
65                  70                  75                  80

Lys Ser Leu Leu Val Arg Ser Gln Thr Gly Asp Phe Asp His Asn Arg
                85                  90                  95

Trp Leu Phe Glu Thr Lys Gly Thr Tyr Gly Ile Gly Asn Ala Tyr Trp
            100                 105                 110

Pro Gln Asp Asn Val Tyr Gly Asp Asp Gly Gly Gly Gly Ala Val Lys
        115                 120                 125

Met Glu Asp Leu Val Glu Lys Pro Trp Lys Pro Leu Ser Arg Lys Val
    130                 135                 140

Pro Ile Pro Pro Gly Ile Leu Ser Pro Tyr Arg Leu Leu Val Leu Val
145                 150                 155                 160

Arg Phe Val Ala Leu Phe Leu Phe Leu Val Trp Arg Val Thr Asn Pro
                165                 170                 175

Asn Met Asp Ala Leu Trp Leu Trp Gly Ile Ser Ile Val Cys Glu Phe
            180                 185                 190

Trp Phe Ala Phe Ser Trp Leu Leu Asp Gln Met Pro Lys Leu Asn Pro
        195                 200                 205

Ile Asn Arg Ala Ala Asp Leu Ala Ala Leu Lys Glu Lys Phe Glu Ser
    210                 215                 220

Pro Ser Pro Thr Asn Pro Thr Gly Arg Ser Asp Leu Pro Gly Leu Asp
225                 230                 235                 240

Val Phe Ile Ser Thr Ala Asp Pro Tyr Lys Glu Pro Thr Leu Val Thr
                245                 250                 255

Ala Asn Thr Leu Leu Ser Ile Leu Ala Thr Glu Tyr Pro Val Glu Lys
            260                 265                 270

Leu Phe Val Tyr Ile Ser Asp Asp Gly Gly Ala Leu Leu Thr Phe Glu
        275                 280                 285

Ser Met Ala Glu Ala Cys Ala Phe Ala Lys Val Trp Val Pro Phe Cys
    290                 295                 300

Arg Lys His Ser Ile Glu Pro Arg Asn Pro Asp Ser Tyr Phe Thr Gln
305                 310                 315                 320

Lys Gly Asp Pro Thr Lys Gly Lys Lys Arg Pro Asp Phe Val Lys Asp
                325                 330                 335

Arg Arg Trp Ile Lys Arg Glu Tyr Asp Glu Phe Lys Ile Arg Val Asn
            340                 345                 350
```

```
Ser Leu Pro Asp Leu Ile Arg Arg Arg Ala Asn Ala Leu Asn Ala Arg
        355                 360                 365

Glu Arg Lys Leu Ala Arg Asp Lys Gln Ala Ala Gly Asp Ala Asp Ala
    370                 375                 380

Leu Ala Ser Val Lys Ala Ala Thr Trp Met Ala Asp Gly Thr His Trp
385                 390                 395                 400

Pro Gly Thr Trp Leu Asp Pro Ser Pro Asp His Ala Lys Gly Asp His
                405                 410                 415

Ala Ser Ile Val Gln Val Met Ile Lys Asn Pro His His Asp Val Val
            420                 425                 430

Tyr Gly Glu Ala Gly Asp His Pro Tyr Leu Asp Met Thr Asp Val Asp
        435                 440                 445

Met Arg Ile Pro Met Phe Ala Tyr Leu Ser Arg Glu Lys Arg Ala Gly
    450                 455                 460

Tyr Asp His Asn Lys Lys Ala Gly Ala Met Asn Ala Met Val Arg Ala
465                 470                 475                 480

Ser Ala Ile Leu Ser Asn Gly Pro Phe Met Leu Asn Phe Asp Cys Asp
                485                 490                 495

His Tyr Ile Tyr Asn Cys Gln Ala Ile Arg Glu Ala Met Cys Tyr Met
            500                 505                 510

Leu Asp Arg Gly Gly Asp Arg Ile Cys Tyr Ile Gln Phe Pro Gln Arg
        515                 520                 525

Phe Glu Gly Ile Asp Pro Ser Asp Arg Tyr Ala Asn His Asn Thr Val
    530                 535                 540

Phe Phe Asp Gly Asn Met Arg Ala Leu Asp Gly Leu Gln Gly Pro Met
545                 550                 555                 560

Tyr Val Gly Thr Gly Cys Leu Phe Arg Arg Tyr Ala Ile Tyr Gly Phe
                565                 570                 575

Asn Pro Pro Arg Ala Ile Glu Tyr Arg Gly Thr Tyr Gly Gln Thr Lys
            580                 585                 590

Val Pro Ile Asp Pro Arg Gln Gly Ser Glu Ala Met Pro Gly Ala Gly
        595                 600                 605

Gly Gly Arg Ser Gly Gly Gly Ser Val Gly Gly Asp His Glu Leu Gln
    610                 615                 620

Ala Leu Ser Thr Ala His Pro Asp His Glu Ala Pro Gln Lys Phe Gly
625                 630                 635                 640

Lys Ser Lys Met Phe Ile Glu Ser Ile Ala Val Ala Glu Tyr Gln Gly
                645                 650                 655

Arg Pro Leu Gln Asp His Pro Ser Val Leu Asn Gly Arg Pro Pro Gly
            660                 665                 670

Ala Leu Leu Met Pro Arg Pro Pro Leu Asp Ala Ala Thr Val Ala Glu
        675                 680                 685

Ser Val Ser Val Ile Ser Cys Trp Tyr Glu Asp Asn Thr Glu Trp Gly
    690                 695                 700

Gln Arg Val Gly Trp Ile Tyr Gly Ser Val Thr Glu Asp Val Val Thr
705                 710                 715                 720

Gly Tyr Arg Met His Asn Arg Gly Trp Arg Ser Val Tyr Cys Ile Thr
                725                 730                 735

Arg Arg Asp Ala Phe Arg Gly Thr Ala Pro Ile Asn Leu Thr Asp Arg
            740                 745                 750

Leu His Gln Val Leu Arg Trp Ala Thr Gly Ser Val Glu Ile Phe Phe
        755                 760                 765

Ser Lys Asn Asn Ala Val Leu Ala Ser Arg Arg Leu Lys Phe Leu Gln
```

```
    770                 775                 780

Arg Met Ala Tyr Leu Asn Val Gly Ile Tyr Pro Phe Thr Ser Leu Phe
785                 790                 795                 800

Leu Ile Met Tyr Cys Leu Leu Pro Ala Leu Ser Leu Phe Ser Gly Gln
                805                 810                 815

Phe Ile Val Ala Thr Leu Asp Pro Thr Phe Leu Ser Tyr Leu Leu Leu
            820                 825                 830

Ile Thr Ile Thr Leu Met Leu Leu Cys Leu Leu Glu Val Lys Trp Ser
        835                 840                 845

Gly Ile Gly Leu Glu Glu Trp Trp Arg Asn Glu Gln Phe Trp Val Ile
    850                 855                 860

Gly Gly Thr Ser Ala His Leu Ala Ala Val Leu Gln Gly Leu Leu Lys
865                 870                 875                 880

Val Val Ala Gly Ile Glu Ile Ser Phe Thr Leu Thr Ala Lys Ala Ala
                885                 890                 895

Ala Glu Asp Asp Asp Asp Pro Phe Ala Glu Leu Tyr Leu Ile Lys Trp
            900                 905                 910

Thr Ser Leu Phe Ile Pro Pro Leu Ala Val Ile Gly Ile Asn Ile Ile
        915                 920                 925

Ala Leu Val Val Gly Val Ser Arg Thr Val Tyr Ala Glu Ile Pro Gln
    930                 935                 940

Tyr Ser Lys Leu Leu Gly Gly Gly Phe Phe Ser Phe Trp Val Leu Ala
945                 950                 955                 960

His Tyr Tyr Pro Phe Ala Lys Gly Leu Met Gly Arg Arg Gly Arg Thr
                965                 970                 975

Pro Thr Ile Val Tyr Val Trp Ala Gly Leu Ile Ser Ile Thr Val Ser
            980                 985                 990

Leu Leu Trp Ile Thr Ile Ser Pro  Pro Asp Asp Ser Val  Ala Gln Gly
        995                 1000                1005

Gly Ile  Asp Val
    1010


<210> SEQ ID NO 54
<211> LENGTH: 860
<212> TYPE: PRT
<213> ORGANISM: Oryza sativa

<400> SEQUENCE: 54

Met Asp Gly Glu Ser Pro Glu Ile Met Pro Val Glu Cys Pro Asp Pro
1               5                   10                  15

Glu Pro Ala Ser Ser Glu Ser Gly Asp Asp His Asp Ile Pro Glu Pro
            20                  25                  30

Leu Ser Ser Arg Leu Ser Val Pro Ser Gly Glu Leu Asn Leu Tyr Arg
        35                  40                  45

Ala Ala Val Ala Leu Arg Leu Val Leu Leu Ala Ala Phe Phe Arg Tyr
    50                  55                  60

Arg Val Thr Arg Pro Val Ala Asp Ala His Ala Leu Trp Val Thr Ser
65                  70                  75                  80

Val Ala Cys Glu Leu Trp Leu Ala Ala Ser Trp Leu Ile Ala Gln Leu
                85                  90                  95

Pro Lys Leu Ser Pro Ala Asn Arg Val Thr Tyr Leu Asp Arg Leu Ala
            100                 105                 110

Ser Arg Tyr Glu Lys Gly Gly Glu Ala Ser Arg Leu Ala Gly Val Asp
        115                 120                 125
```

```
Val Phe Val Ala Ala Ala Asp Ala Ala Arg Glu Pro Pro Leu Ala Thr
    130                 135                 140

Ala Asn Thr Val Leu Ser Val Leu Ala Ala Asp Tyr Pro Ala Gly Gly
145                 150                 155                 160

Val Ala Cys Tyr Val His Asp Asp Gly Ala Asp Met Leu Val Phe Glu
                165                 170                 175

Ser Leu Phe Glu Ala Ala Gly Phe Ala Arg Arg Trp Ile Pro Phe Cys
            180                 185                 190

Arg Arg His Gly Val Glu Pro Arg Ala Pro Glu Leu Tyr Phe Ala Arg
        195                 200                 205

Gly Val Asp Tyr Leu Arg Asp Arg Ala Ala Pro Ser Phe Val Lys Asp
    210                 215                 220

Arg Arg Ala Met Lys Arg Glu Tyr Glu Glu Phe Lys Val Arg Met Asn
225                 230                 235                 240

His Leu Ala Ala Arg Ala Arg Lys Val Pro Glu Glu Gly Trp Ile Met
                245                 250                 255

Ser Asp Gly Thr Pro Trp Pro Gly Asn Asn Ser Arg Asp His Pro Ala
            260                 265                 270

Met Ile Gln Val Leu Leu Gly His Pro Gly Asp Arg Asp Val Asp Gly
        275                 280                 285

Gly Glu Leu Pro Arg Leu Phe Tyr Val Ser Arg Glu Lys Arg Pro Gly
    290                 295                 300

Phe Arg His His Gly Lys Ala Gly Ala Met Asn Ala Leu Leu Arg Val
305                 310                 315                 320

Ser Ala Val Leu Thr Asn Gly Ala Tyr Val Leu Asn Leu Asp Cys Asp
                325                 330                 335

His Cys Val Asn Asn Ser Ser Ala Leu Arg Glu Ala Met Cys Phe Met
            340                 345                 350

Met Asp Pro Val Ala Gly Asn Arg Thr Cys Phe Val Gln Phe Ala Leu
        355                 360                 365

Arg Asp Ser Gly Gly Gly Asp Ser Val Phe Phe Asp Ile Glu Met Lys
    370                 375                 380

Cys Leu Asp Gly Ile Gln Gly Pro Val Tyr Val Gly Ser Gly Cys Cys
385                 390                 395                 400

Phe Ser Arg Lys Ala Leu Tyr Gly Phe Glu Pro Ala Ala Ala Ala Asp
                405                 410                 415

Asp Gly Asp Asp Met Asp Thr Ala Ala Asp Trp Arg Arg Met Cys Cys
            420                 425                 430

Phe Gly Arg Gly Lys Arg Met Asn Ala Met Arg Arg Ser Met Ser Ala
        435                 440                 445

Val Pro Leu Leu Asp Ser Glu Asp Asp Ser Asp Glu Gln Glu Glu Glu
    450                 455                 460

Glu Ala Ala Gly Arg Arg Arg Arg Leu Arg Ala Tyr Arg Ala Ala Leu
465                 470                 475                 480

Glu Arg His Phe Gly Gln Ser Pro Ala Phe Ile Ala Ser Ala Phe Glu
                485                 490                 495

Glu Gln Gly Arg Arg Arg Gly Gly Asp Gly Gly Ser Pro Asp Ala Thr
            500                 505                 510

Val Ala Pro Ala Arg Ser Leu Leu Lys Glu Ala Ile His Val Val Ser
        515                 520                 525

Cys Ala Phe Glu Glu Arg Thr Arg Trp Gly Lys Glu Ile Gly Trp Met
    530                 535                 540

Tyr Gly Gly Gly Val Ala Thr Gly Phe Arg Met His Ala Arg Gly Trp
```

545 550 555 560

Ser Ser Ala Tyr Cys Ser Pro Ala Arg Pro Ala Phe Arg Arg Tyr Ala
565 570 575

Arg Ala Ser Pro Ala Asp Val Leu Ala Gly Ala Ser Arg Arg Ala Val
580 585 590

Ala Ala Met Gly Ile Leu Leu Ser Arg Arg His Ser Pro Val Trp Ala
595 600 605

Gly Arg Arg Leu Gly Leu Leu Gln Arg Leu Gly Tyr Val Ala Arg Ala
610 615 620

Ser Tyr Pro Leu Ala Ser Leu Pro Leu Thr Val Tyr Cys Ala Leu Pro
625 630 635 640

Ala Val Cys Leu Leu Thr Gly Lys Ser Thr Phe Pro Ser Asp Val Ser
645 650 655

Tyr Tyr Asp Gly Val Leu Leu Ile Leu Leu Leu Phe Ser Val Ala Ala
660 665 670

Ser Val Ala Leu Glu Leu Arg Trp Ser Arg Val Pro Leu Arg Ala Trp
675 680 685

Trp Arg Asp Glu Lys Leu Trp Met Val Thr Ala Thr Ser Ala Ser Leu
690 695 700

Ala Ala Val Phe Gln Gly Ile Leu Ser Ala Cys Thr Gly Ile Asp Val
705 710 715 720

Ala Phe Ser Thr Glu Thr Ala Ala Ser Pro Pro Lys Arg Pro Ala Ala
725 730 735

Gly Asn Asp Asp Gly Glu Glu Glu Ala Ala Leu Ala Ser Glu Ile Thr
740 745 750

Met Arg Trp Thr Asn Leu Leu Val Ala Pro Thr Ser Val Val Val Ala
755 760 765

Asn Leu Ala Gly Val Val Ala Ala Val Ala Tyr Gly Val Asp His Gly
770 775 780

Tyr Tyr Gln Ser Trp Gly Ala Leu Gly Ala Lys Leu Ala Leu Ala Gly
785 790 795 800

Trp Val Val Ala His Leu Gln Gly Phe Leu Arg Gly Leu Leu Ala Pro
805 810 815

Arg Asp Arg Ala Pro Pro Thr Ile Ala Val Leu Trp Ser Val Val Phe
820 825 830

Val Ser Val Ala Ser Leu Leu Trp Val His Ala Ala Ser Phe Ser Ala
835 840 845

Pro Thr Ala Ala Pro Thr Thr Glu Gln Pro Ile Leu
850 855 860

<210> SEQ ID NO 55
<211> LENGTH: 1081
<212> TYPE: PRT
<213> ORGANISM: Oryza sativa

<400> SEQUENCE: 55

Met Asp Gly Asp Ala Asp Ala Val Lys Ser Gly Arg His Gly Ser Gly
1 5 10 15

Gln Ala Cys Gln Ile Cys Gly Asp Gly Val Gly Thr Thr Ala Glu Gly
20 25 30

Asp Val Phe Ala Ala Cys Asp Val Cys Gly Phe Pro Val Cys Arg Pro
35 40 45

Cys Tyr Glu Tyr Glu Arg Lys Asp Gly Thr Gln Ala Cys Pro Gln Cys
50 55 60

```
Lys Thr Lys Tyr Lys Arg His Lys Gly Ser Pro Ala Ile Arg Gly Glu
65                  70                  75                  80

Glu Gly Glu Asp Thr Asp Ala Asp Asp Val Ser Asp Tyr Asn Tyr Pro
                85                  90                  95

Ala Ser Gly Ser Ala Asp Gln Lys Gln Lys Ile Ala Asp Arg Met Arg
            100                 105                 110

Ser Trp Arg Met Asn Ala Gly Gly Gly Gly Asp Val Gly Arg Pro Lys
        115                 120                 125

Tyr Asp Ser Gly Glu Ile Gly Leu Thr Lys Tyr Asp Ser Gly Glu Ile
    130                 135                 140

Pro Arg Gly Tyr Ile Pro Ser Val Thr Asn Ser Gln Ile Ser Gly Glu
145                 150                 155                 160

Ile Pro Gly Ala Ser Pro Asp His His Met Met Ser Pro Thr Gly Asn
                165                 170                 175

Ile Gly Lys Arg Ala Pro Phe Pro Tyr Val Asn His Ser Pro Asn Pro
            180                 185                 190

Ser Arg Glu Phe Ser Gly Ser Ile Gly Asn Val Ala Trp Lys Glu Arg
        195                 200                 205

Val Asp Gly Trp Lys Leu Lys Gln Asp Lys Gly Ala Ile Pro Met Thr
    210                 215                 220

Asn Gly Thr Ser Ile Ala Pro Ser Glu Gly Arg Gly Val Gly Asp Ile
225                 230                 235                 240

Asp Ala Ser Thr Asp Tyr Asn Met Glu Asp Ala Leu Leu Asn Asp Glu
                245                 250                 255

Thr Arg Gln Pro Leu Ser Arg Lys Val Pro Leu Pro Ser Ser Arg Ile
            260                 265                 270

Asn Pro Tyr Arg Met Val Ile Val Leu Arg Leu Val Val Leu Ser Ile
        275                 280                 285

Phe Leu His Tyr Arg Ile Thr Asn Pro Val Arg Asn Ala Tyr Pro Leu
    290                 295                 300

Trp Leu Leu Ser Val Ile Cys Glu Ile Trp Phe Ala Leu Ser Trp Ile
305                 310                 315                 320

Leu Asp Gln Phe Pro Lys Trp Phe Pro Ile Asn Arg Glu Thr Tyr Leu
                325                 330                 335

Asp Arg Leu Ala Leu Arg Tyr Asp Arg Glu Gly Glu Pro Ser Gln Leu
            340                 345                 350

Ala Ala Val Asp Ile Phe Val Ser Thr Val Asp Pro Met Lys Glu Pro
        355                 360                 365

Pro Leu Val Thr Ala Asn Thr Val Leu Ser Ile Leu Ala Val Asp Tyr
    370                 375                 380

Pro Val Asp Lys Val Ser Cys Tyr Val Ser Asp Asp Gly Ala Ala Met
385                 390                 395                 400

Leu Thr Phe Asp Ala Leu Ala Glu Thr Ser Glu Phe Ala Arg Lys Trp
                405                 410                 415

Val Pro Phe Val Lys Lys Tyr Asn Ile Glu Pro Arg Ala Pro Glu Trp
            420                 425                 430

Tyr Phe Ser Gln Lys Ile Asp Tyr Leu Lys Asp Lys Val His Pro Ser
        435                 440                 445

Phe Val Lys Asp Arg Arg Ala Met Lys Arg Glu Tyr Glu Glu Phe Lys
    450                 455                 460

Val Arg Ile Asn Gly Leu Val Ala Lys Ala Gln Lys Val Pro Glu Glu
465                 470                 475                 480

Gly Trp Ile Met Gln Asp Gly Thr Pro Trp Pro Gly Asn Asn Thr Arg
```

-continued

```
                485                 490                 495

Asp His Pro Gly Met Ile Gln Val Phe Leu Gly His Ser Gly Gly Leu
            500                 505                 510

Asp Thr Glu Gly Asn Glu Leu Pro Arg Leu Val Tyr Val Ser Arg Glu
        515                 520                 525

Lys Arg Pro Gly Phe Gln His His Lys Lys Ala Gly Ala Met Asn Ala
    530                 535                 540

Leu Val Arg Val Ser Ala Val Leu Thr Asn Gly Gln Tyr Met Leu Asn
545                 550                 555                 560

Leu Asp Cys Asp His Tyr Ile Asn Asn Ser Lys Ala Leu Arg Glu Ala
                565                 570                 575

Met Cys Phe Leu Met Asp Pro Asn Leu Gly Arg Ser Val Cys Tyr Val
            580                 585                 590

Gln Phe Pro Gln Arg Phe Asp Gly Ile Asp Arg Asn Asp Arg Tyr Ala
        595                 600                 605

Asn Arg Asn Thr Val Phe Phe Asp Ile Asn Leu Arg Gly Leu Asp Gly
    610                 615                 620

Ile Gln Gly Pro Val Tyr Val Gly Thr Gly Cys Val Phe Asn Arg Thr
625                 630                 635                 640

Ala Leu Tyr Gly Tyr Glu Pro Pro Ile Lys Gln Lys Lys Lys Gly Ser
                645                 650                 655

Phe Leu Ser Ser Leu Cys Gly Gly Arg Lys Lys Ala Ser Lys Ser Lys
            660                 665                 670

Lys Lys Ser Ser Asp Lys Lys Lys Ser Asn Lys His Val Asp Ser Ala
        675                 680                 685

Val Pro Val Phe Asn Leu Glu Asp Ile Glu Glu Gly Val Glu Gly Ala
    690                 695                 700

Gly Phe Asp Asp Glu Lys Ser Leu Leu Met Ser Gln Met Ser Leu Glu
705                 710                 715                 720

Lys Arg Phe Gly Gln Ser Ala Ala Phe Val Ala Ser Thr Leu Met Glu
                725                 730                 735

Tyr Gly Gly Val Pro Gln Ser Ala Thr Pro Glu Ser Leu Leu Lys Glu
            740                 745                 750

Ala Ile His Val Ile Ser Cys Gly Tyr Glu Asp Lys Thr Glu Trp Gly
        755                 760                 765

Thr Glu Ile Gly Trp Ile Tyr Gly Ser Val Thr Glu Asp Ile Leu Thr
    770                 775                 780

Gly Phe Lys Met His Ala Arg Gly Trp Arg Ser Ile Tyr Cys Met Pro
785                 790                 795                 800

Lys Arg Pro Ala Phe Lys Gly Ser Ala Pro Ile Asn Leu Ser Asp Arg
                805                 810                 815

Leu Asn Gln Val Leu Arg Trp Ala Leu Gly Ser Val Glu Ile Leu Phe
            820                 825                 830

Ser Arg His Cys Pro Ile Trp Tyr Gly Tyr Gly Gly Arg Leu Lys Phe
        835                 840                 845

Leu Glu Arg Phe Ala Tyr Ile Asn Thr Thr Ile Tyr Pro Leu Thr Ser
    850                 855                 860

Ile Pro Leu Leu Ile Tyr Cys Val Leu Pro Ala Ile Cys Leu Leu Thr
865                 870                 875                 880

Gly Lys Phe Ile Ile Pro Glu Ile Ser Asn Phe Ala Ser Ile Trp Phe
                885                 890                 895

Ile Ser Leu Phe Ile Ser Ile Phe Ala Thr Gly Ile Leu Glu Met Arg
            900                 905                 910
```

Trp Ser Gly Val Gly Ile Asp Glu Trp Trp Arg Asn Glu Gln Phe Trp
915 920 925

Val Ile Gly Gly Ile Ser Ala His Leu Phe Ala Val Phe Gln Gly Leu
930 935 940

Leu Lys Val Leu Ala Gly Ile Asp Thr Asn Phe Thr Val Thr Ser Lys
945 950 955 960

Ala Ser Asp Glu Asp Gly Asp Phe Ala Glu Leu Tyr Met Phe Lys Trp
965 970 975

Thr Thr Leu Leu Ile Pro Pro Thr Thr Ile Leu Ile Ile Asn Leu Val
980 985 990

Gly Val Val Ala Gly Ile Ser Tyr Ala Ile Asn Ser Gly Tyr Gln Ser
995 1000 1005

Trp Gly Pro Leu Phe Gly Lys Leu Phe Phe Ala Phe Trp Val Ile
1010 1015 1020

Val His Leu Tyr Pro Phe Leu Lys Gly Leu Met Gly Arg Gln Asn
1025 1030 1035

Arg Thr Pro Thr Ile Val Val Val Trp Ala Ile Leu Leu Ala Ser
1040 1045 1050

Ile Phe Ser Leu Leu Trp Val Arg Ile Asp Pro Phe Thr Thr Arg
1055 1060 1065

Val Thr Gly Pro Asp Thr Gln Thr Cys Gly Ile Asn Cys
1070 1075 1080

<210> SEQ ID NO 56
<211> LENGTH: 1092
<212> TYPE: PRT
<213> ORGANISM: Oryza sativa

<400> SEQUENCE: 56

Met Glu Ala Ser Ala Gly Leu Val Ala Gly Ser His Asn Arg Asn Glu
1 5 10 15

Leu Val Val Ile Arg Arg Asp Gly Gly Gly Gly Gly Gly Val Gly Gly
20 25 30

Arg Arg Ala Ala Glu Ala Lys Ala Ala Cys Gln Ile Cys Gly Asp Asp
35 40 45

Val Gly Glu Gly Pro Asp Gly Glu Pro Phe Val Ala Cys Asn Glu Cys
50 55 60

Ala Phe Pro Val Cys Arg Asn Cys Tyr Asp Tyr Glu Arg Arg Glu Gly
65 70 75 80

Ser Gln Ala Cys Pro Gln Cys Lys Thr Arg Phe Lys Arg Leu Lys Gly
85 90 95

Cys Pro Arg Val Ala Gly Asp Glu Glu Glu Asp Gly Val Asp Asp Leu
100 105 110

Glu Gly Glu Phe Gly Leu Asp Gly Arg Glu Asp Asp Pro Gln Tyr Ile
115 120 125

Ala Glu Ser Met Leu Arg Ala Asn Met Ser Tyr Gly Arg Gly Gly Asp
130 135 140

Leu Gln Pro Phe Gln Pro Ile Pro Asn Val Pro Leu Leu Thr Asn Gly
145 150 155 160

Gln Met Val Asp Asp Ile Pro Pro Glu Gln His Ala Leu Val Pro Ser
165 170 175

Tyr Met Gly Gly Gly Gly Gly Gly Gly Lys Arg Ile His Pro Leu Pro
180 185 190

Phe Ala Asp Pro Ser Val Pro Val Gln Pro Arg Ser Met Asp Pro Ser

```
        195                 200                 205

Lys Asp Leu Ala Ala Tyr Gly Tyr Gly Ser Val Ala Trp Lys Glu Arg
    210                 215                 220

Met Glu Gly Trp Lys Gln Lys Gln Glu Arg Met Gln Gln Leu Arg Ser
225                 230                 235                 240

Glu Gly Gly Gly Asp Trp Asp Gly Asp Gly Asp Ala Asp Leu Pro Leu
                245                 250                 255

Met Asp Glu Ala Arg Gln Pro Leu Ser Arg Lys Val Pro Ile Ser Ser
            260                 265                 270

Ser Arg Ile Asn Pro Tyr Arg Met Ile Ile Ile Ile Arg Leu Val Val
        275                 280                 285

Leu Gly Phe Phe Phe His Tyr Arg Val Met His Pro Val Asn Asp Ala
    290                 295                 300

Phe Ala Leu Trp Leu Ile Ser Val Ile Cys Glu Ile Trp Phe Ala Met
305                 310                 315                 320

Ser Trp Ile Leu Asp Gln Phe Pro Lys Trp Leu Pro Ile Glu Arg Glu
                325                 330                 335

Thr Tyr Leu Asp Arg Leu Ser Leu Arg Phe Asp Lys Glu Gly Gln Pro
            340                 345                 350

Ser Gln Leu Ala Pro Val Asp Phe Phe Val Ser Thr Val Asp Pro Ser
        355                 360                 365

Lys Glu Pro Pro Leu Val Thr Ala Asn Thr Val Leu Ser Ile Leu Ser
    370                 375                 380

Val Asp Tyr Pro Val Glu Lys Val Ser Cys Tyr Val Ser Asp Asp Gly
385                 390                 395                 400

Ala Ala Met Leu Thr Phe Glu Ala Leu Ser Glu Thr Ser Glu Phe Ala
                405                 410                 415

Lys Lys Trp Val Pro Phe Cys Lys Lys Phe Asn Ile Glu Pro Arg Ala
            420                 425                 430

Pro Glu Trp Tyr Phe Gln Gln Lys Ile Asp Tyr Leu Lys Asp Lys Val
        435                 440                 445

Ala Ala Ser Phe Val Arg Glu Arg Arg Ala Met Lys Arg Asp Tyr Glu
    450                 455                 460

Glu Phe Lys Val Arg Ile Asn Ala Leu Val Ala Lys Ala Gln Lys Val
465                 470                 475                 480

Pro Glu Glu Gly Trp Thr Met Gln Asp Gly Ser Pro Trp Pro Gly Asn
                485                 490                 495

Asn Val Arg Asp His Pro Gly Met Ile Gln Val Phe Leu Gly Gln Ser
            500                 505                 510

Gly Gly Arg Asp Val Glu Gly Asn Glu Leu Pro Arg Leu Val Tyr Val
        515                 520                 525

Ser Arg Glu Lys Arg Pro Gly Tyr Asn His His Lys Lys Ala Gly Ala
    530                 535                 540

Met Asn Ala Leu Val Arg Val Ser Ala Val Leu Ser Asn Ala Pro Tyr
545                 550                 555                 560

Leu Leu Asn Leu Asp Cys Asp His Tyr Ile Asn Asn Ser Lys Ala Ile
                565                 570                 575

Arg Glu Ala Met Cys Phe Met Met Asp Pro Leu Val Gly Lys Lys Val
            580                 585                 590

Cys Tyr Val Gln Phe Pro Gln Arg Phe Asp Gly Ile Asp Arg His Asp
        595                 600                 605

Arg Tyr Ala Asn Arg Asn Val Val Phe Phe Asp Ile Asn Met Lys Gly
    610                 615                 620
```

```
Leu Asp Gly Ile Gln Gly Pro Ile Tyr Val Gly Thr Gly Cys Val Phe
625                 630                 635                 640

Arg Arg Gln Ala Leu Tyr Gly Tyr Asp Ala Pro Lys Thr Lys Lys Pro
                645                 650                 655

Pro Ser Arg Thr Cys Asn Cys Trp Pro Lys Trp Cys Cys Cys Cys Cys
            660                 665                 670

Cys Gly Asn Arg His Thr Lys Lys Lys Thr Thr Lys Pro Lys Pro Glu
        675                 680                 685

Lys Lys Lys Arg Leu Phe Phe Lys Lys Ala Glu Asn Gln Ser Pro Ala
    690                 695                 700

Tyr Ala Leu Gly Glu Ile Glu Glu Gly Ala Pro Gly Ala Glu Thr Asp
705                 710                 715                 720

Lys Ala Gly Ile Val Asn Gln Gln Lys Leu Glu Lys Lys Phe Gly Gln
                725                 730                 735

Ser Ser Val Phe Val Ala Ser Thr Leu Leu Glu Asn Gly Gly Thr Leu
            740                 745                 750

Lys Ser Ala Ser Pro Ala Ser Leu Leu Lys Glu Ala Ile His Val Ile
        755                 760                 765

Ser Cys Gly Tyr Glu Asp Lys Thr Asp Trp Gly Lys Glu Ile Gly Trp
    770                 775                 780

Ile Tyr Gly Ser Ile Thr Glu Asp Ile Leu Thr Gly Phe Lys Met His
785                 790                 795                 800

Cys His Gly Trp Arg Ser Ile Tyr Cys Ile Pro Lys Arg Pro Ala Phe
                805                 810                 815

Lys Gly Ser Ala Pro Leu Asn Leu Ser Asp Arg Leu His Gln Val Leu
            820                 825                 830

Arg Trp Ala Leu Gly Ser Val Glu Ile Phe Phe Ser Lys His Cys Pro
        835                 840                 845

Leu Trp Tyr Gly Tyr Gly Gly Gly Leu Lys Phe Leu Glu Arg Phe Ser
    850                 855                 860

Tyr Ile Asn Ser Ile Val Tyr Pro Trp Thr Ser Ile Pro Leu Leu Ala
865                 870                 875                 880

Tyr Cys Thr Leu Pro Ala Ile Cys Leu Leu Thr Gly Lys Phe Ile Thr
                885                 890                 895

Pro Glu Leu Thr Asn Val Ala Ser Leu Trp Phe Met Ser Leu Phe Ile
            900                 905                 910

Cys Ile Phe Val Thr Gly Ile Leu Glu Met Arg Trp Ser Gly Val Ala
        915                 920                 925

Ile Asp Asp Trp Trp Arg Asn Glu Gln Phe Trp Val Ile Gly Gly Val
    930                 935                 940

Ser Ser His Leu Phe Ala Val Phe Gln Gly Leu Leu Lys Val Leu Ala
945                 950                 955                 960

Gly Val Asp Thr Ser Phe Thr Val Thr Ser Lys Ala Gly Asp Asp Glu
                965                 970                 975

Glu Phe Ser Glu Leu Tyr Thr Phe Lys Trp Thr Thr Leu Leu Ile Pro
            980                 985                 990

Pro Thr Thr Leu Leu Leu Leu Asn  Phe Ile Gly Val Val  Ala Gly Val
        995                 1000                1005

Ser Asn  Ala Ile Asn Asn Gly  Tyr Glu Ser Trp Gly  Pro Leu Phe
    1010                1015                1020

Gly Lys  Leu Phe Phe Ala Phe  Trp Val Ile Val His  Leu Tyr Pro
    1025                1030                1035
```

Phe Leu Lys Gly Leu Val Gly Arg Gln Asn Arg Thr Pro Thr Ile
    1040                1045                1050

Val Ile Val Trp Ser Ile Leu Leu Ala Ser Ile Phe Ser Leu Leu
    1055                1060                1065

Trp Val Arg Ile Asp Pro Phe Leu Ala Lys Asn Asn Gly Pro Leu
    1070                1075                1080

Leu Glu Glu Cys Gly Leu Asp Cys Asn
    1085                1090

<210> SEQ ID NO 57
<211> LENGTH: 1093
<212> TYPE: PRT
<213> ORGANISM: Oryza sativa

<400> SEQUENCE: 57

Met Glu Ala Ser Ala Gly Leu Val Ala Gly Ser His Asn Arg Asn Glu
1               5                   10                  15

Leu Val Val Ile Arg Arg Asp Gly Asp Pro Gly Pro Lys Pro Leu Arg
            20                  25                  30

Gln Gln Asn Gly Gln Val Cys Gln Ile Cys Gly Asp Asp Val Gly Leu
        35                  40                  45

Asn Pro Asp Gly Glu Pro Phe Val Ala Cys Asn Glu Cys Ala Phe Pro
    50                  55                  60

Val Cys Arg Asp Cys Tyr Glu Tyr Glu Arg Arg Glu Gly Thr Gln Asn
65                  70                  75                  80

Cys Pro Gln Cys Lys Thr Arg Phe Lys Arg Leu Arg Gly Cys Ala Arg
                85                  90                  95

Val Pro Gly Asp Glu Glu Glu Asp Gly Val Asp Asp Leu Glu Asn Glu
            100                 105                 110

Phe Asn Trp Arg Asp Arg Asn Asp Ser Gln Tyr Val Ala Glu Ser Met
        115                 120                 125

Leu His Ala His Met Ser Tyr Gly Arg Gly Gly Val Asp Val Asn Gly
    130                 135                 140

Val Pro Gln Pro Phe Gln Pro Asn Pro Asn Val Pro Leu Leu Thr Asp
145                 150                 155                 160

Gly Gln Met Val Asp Asp Ile Pro Pro Glu Gln His Ala Leu Val Pro
                165                 170                 175

Ser Phe Met Gly Gly Gly Gly Lys Arg Ile His Pro Leu Pro Tyr Ala
            180                 185                 190

Asp Pro Asn Leu Pro Val Gln Pro Arg Ser Met Asp Pro Ser Lys Asp
        195                 200                 205

Leu Ala Ala Tyr Gly Tyr Gly Ser Val Ala Trp Lys Glu Arg Met Glu
    210                 215                 220

Ser Trp Lys Gln Lys Gln Glu Arg Leu His Gln Met Arg Asn Asp Gly
225                 230                 235                 240

Gly Gly Lys Asp Trp Asp Gly Asp Gly Asp Asp Gly Asp Leu Pro Leu
                245                 250                 255

Met Asp Glu Ala Arg Gln Pro Leu Ser Arg Lys Val Pro Ile Pro Ser
            260                 265                 270

Ser Gln Ile Asn Pro Tyr Arg Met Val Ile Ile Ile Arg Leu Val Val
        275                 280                 285

Leu Gly Phe Phe Phe His Tyr Arg Val Met His Pro Val Pro Asp Ala
    290                 295                 300

Phe Ala Leu Trp Leu Ile Ser Val Ile Cys Glu Ile Trp Phe Ala Met
305                 310                 315                 320

-continued

```
Ser Trp Ile Leu Asp Gln Phe Pro Lys Trp Phe Pro Ile Glu Arg Glu
                325                 330                 335

Thr Tyr Leu Asp Arg Leu Thr Leu Arg Phe Asp Lys Glu Gly Gln Thr
            340                 345                 350

Ser Gln Leu Ala Pro Ile Asp Phe Phe Val Ser Thr Val Asp Pro Leu
        355                 360                 365

Lys Glu Pro Pro Leu Val Thr Ala Asn Thr Val Leu Ser Ile Leu Ala
    370                 375                 380

Val Asp Tyr Pro Val Asp Lys Val Ser Cys Tyr Val Ser Asp Asp Gly
385                 390                 395                 400

Ala Ala Met Leu Thr Phe Glu Ala Leu Ser Glu Thr Ser Glu Phe Ala
                405                 410                 415

Lys Lys Trp Val Pro Phe Cys Lys Lys Tyr Ser Ile Glu Pro Arg Ala
            420                 425                 430

Pro Glu Trp Tyr Phe Gln Gln Lys Ile Asp Tyr Leu Lys Asp Lys Val
        435                 440                 445

Ala Pro Tyr Phe Val Arg Glu Arg Arg Ala Met Lys Arg Glu Tyr Glu
    450                 455                 460

Glu Phe Lys Val Arg Ile Asn Ala Leu Val Ala Lys Ala Gln Lys Val
465                 470                 475                 480

Pro Glu Glu Gly Trp Thr Met Gln Asp Gly Thr Pro Trp Pro Gly Asn
                485                 490                 495

Asn Val Arg Asp His Pro Gly Met Ile Gln Val Phe Leu Gly Gln Ser
            500                 505                 510

Gly Gly His Asp Ile Glu Gly Asn Glu Leu Pro Arg Leu Val Tyr Val
        515                 520                 525

Ser Arg Glu Lys Arg Pro Gly Tyr Asn His His Lys Lys Ala Gly Ala
    530                 535                 540

Met Asn Ala Leu Val Arg Val Ser Ala Val Leu Thr Asn Ala Pro Tyr
545                 550                 555                 560

Met Leu Asn Leu Asp Cys Asp His Tyr Ile Asn Asn Ser Lys Ala Ile
                565                 570                 575

Lys Glu Ala Met Cys Phe Met Met Asp Pro Leu Val Gly Lys Lys Val
            580                 585                 590

Cys Tyr Val Gln Phe Pro Gln Arg Phe Asp Gly Ile Asp Arg His Asp
        595                 600                 605

Arg Tyr Ala Asn Arg Asn Val Val Phe Phe Asp Ile Asn Met Lys Gly
    610                 615                 620

Leu Asp Gly Ile Gln Gly Pro Ile Tyr Val Gly Thr Gly Cys Val Phe
625                 630                 635                 640

Arg Arg Gln Ala Leu Tyr Gly Tyr Asp Ala Pro Lys Thr Lys Lys Pro
                645                 650                 655

Pro Ser Arg Thr Cys Asn Cys Trp Pro Lys Trp Cys Ile Cys Cys Cys
            660                 665                 670

Cys Phe Gly Asp Arg Lys Ser Lys Lys Lys Thr Thr Lys Pro Lys Thr
        675                 680                 685

Glu Lys Lys Lys Arg Ser Phe Phe Lys Arg Ala Glu Asn Gln Ser Pro
    690                 695                 700

Ala Tyr Ala Leu Gly Glu Ile Glu Glu Gly Ala Pro Gly Ala Glu Asn
705                 710                 715                 720

Glu Lys Ala Gly Ile Val Asn Gln Gln Lys Leu Glu Lys Lys Phe Gly
                725                 730                 735
```

```
Gln Ser Ser Val Phe Val Ala Ser Thr Leu Leu Glu Asn Gly Gly Thr
            740                 745                 750

Leu Lys Ser Ala Ser Pro Ala Ser Leu Leu Lys Glu Ala Ile His Val
        755                 760                 765

Ile Ser Cys Gly Tyr Glu Asp Lys Thr Asp Trp Gly Lys Glu Ile Gly
    770                 775                 780

Trp Ile Tyr Gly Ser Val Thr Glu Asp Ile Leu Thr Gly Phe Lys Met
785                 790                 795                 800

His Cys His Gly Trp Arg Ser Ile Tyr Cys Ile Pro Lys Leu Pro Ala
                805                 810                 815

Phe Lys Gly Ser Ala Pro Leu Asn Leu Ser Asp Arg Leu His Gln Val
            820                 825                 830

Leu Arg Trp Ala Leu Gly Ser Val Glu Ile Phe Phe Ser Asn His Cys
        835                 840                 845

Pro Leu Trp Tyr Gly Tyr Gly Gly Gly Leu Lys Cys Leu Glu Arg Phe
    850                 855                 860

Ser Tyr Ile Asn Ser Ile Val Tyr Pro Phe Thr Ser Ile Pro Leu Leu
865                 870                 875                 880

Ala Tyr Cys Thr Leu Pro Ala Ile Cys Leu Leu Thr Gly Lys Phe Ile
                885                 890                 895

Thr Pro Glu Leu Thr Asn Val Ala Ser Leu Trp Phe Met Ser Leu Phe
            900                 905                 910

Ile Cys Ile Phe Ala Thr Gly Ile Leu Glu Met Arg Trp Ser Gly Val
        915                 920                 925

Gly Ile Asp Asp Trp Trp Arg Asn Glu Gln Phe Trp Val Ile Gly Gly
    930                 935                 940

Val Ser Ser His Leu Phe Ala Leu Phe Gln Gly Leu Leu Lys Val Ile
945                 950                 955                 960

Ala Gly Ile Asp Thr Ser Phe Thr Val Thr Ser Lys Gly Gly Asp Asp
                965                 970                 975

Glu Glu Phe Ser Glu Leu Tyr Thr Phe Lys Trp Thr Thr Leu Leu Ile
            980                 985                 990

Pro Pro Thr Thr Leu Leu Leu Leu  Asn Phe Ile Gly Val  Val Ala Gly
        995                 1000                1005

Val Ser  Asn Ala Ile Asn Asn  Gly Tyr Glu Ser Trp  Gly Pro Leu
    1010                1015                1020

Phe Gly  Lys Leu Phe Phe Ala  Phe Trp Val Ile Val  His Leu Tyr
    1025                1030                1035

Pro Phe  Leu Lys Gly Leu Val  Gly Arg Gln Asn Arg  Thr Pro Thr
    1040                1045                1050

Ile Val  Ile Val Trp Ser Ile  Leu Leu Ala Ser Ile  Phe Ser Leu
    1055                1060                1065

Leu Trp  Val Arg Ile Asp Pro  Phe Leu Ala Lys Asn  Asp Gly Pro
    1070                1075                1080

Leu Leu  Glu Glu Cys Gly Leu  Asp Cys Asn
    1085                1090
```

<210> SEQ ID NO 58
<211> LENGTH: 837
<212> TYPE: PRT
<213> ORGANISM: Oryza sativa

<400> SEQUENCE: 58

```
Met Asp Glu Ala Arg Gln Pro Leu Ser Arg Lys Val Pro Ile Pro Ser
1               5                   10                  15
```

-continued

```
Ser Gln Ile Asn Pro Tyr Arg Met Val Ile Ile Ile Arg Leu Val Val
            20                  25                  30

Leu Gly Phe Phe Phe His Tyr Arg Val Met His Pro Val Pro Asp Ala
        35                  40                  45

Phe Ala Leu Trp Leu Ile Ser Val Ile Cys Glu Ile Trp Phe Ala Met
    50                  55                  60

Ser Trp Ile Leu Asp Gln Phe Pro Lys Trp Phe Pro Ile Glu Arg Glu
65                  70                  75                  80

Thr Tyr Leu Asp Arg Leu Thr Leu Arg Phe Asp Lys Glu Gly Gln Thr
                85                  90                  95

Ser Gln Leu Ala Pro Ile Asp Phe Phe Val Ser Thr Val Asp Pro Leu
            100                 105                 110

Lys Glu Pro Pro Leu Val Thr Ala Asn Thr Val Leu Ser Ile Leu Ala
        115                 120                 125

Val Asp Tyr Pro Val Asp Lys Val Ser Cys Tyr Val Ser Asp Asp Gly
    130                 135                 140

Ala Ala Met Leu Thr Phe Glu Ala Leu Ser Glu Thr Ser Glu Phe Ala
145                 150                 155                 160

Lys Lys Trp Val Pro Phe Cys Lys Lys Tyr Ser Ile Glu Pro Arg Ala
                165                 170                 175

Pro Glu Trp Tyr Phe Gln Gln Lys Ile Asp Tyr Leu Lys Asp Lys Val
            180                 185                 190

Ala Pro Tyr Phe Val Arg Glu Arg Arg Ala Met Lys Arg Glu Tyr Glu
        195                 200                 205

Glu Phe Lys Val Arg Ile Asn Ala Leu Val Ala Lys Ala Gln Lys Val
    210                 215                 220

Pro Glu Glu Gly Trp Thr Met Gln Asp Gly Thr Pro Trp Pro Gly Asn
225                 230                 235                 240

Asn Val Arg Asp His Pro Gly Met Ile Gln Val Phe Leu Gly Gln Ser
                245                 250                 255

Gly Gly His Asp Ile Glu Gly Asn Glu Leu Pro Arg Leu Val Tyr Val
            260                 265                 270

Ser Arg Glu Lys Arg Pro Gly Tyr Asn His His Lys Lys Ala Gly Ala
        275                 280                 285

Met Asn Ala Leu Val Arg Val Ser Ala Val Leu Thr Asn Ala Pro Tyr
    290                 295                 300

Met Leu Asn Leu Asp Cys Asp His Tyr Ile Asn Asn Ser Lys Ala Ile
305                 310                 315                 320

Lys Glu Ala Met Cys Phe Met Met Asp Pro Leu Val Gly Lys Lys Val
                325                 330                 335

Cys Tyr Val Gln Phe Pro Gln Arg Phe Asp Gly Ile Asp Arg His Asp
            340                 345                 350

Arg Tyr Ala Asn Arg Asn Val Val Phe Phe Asp Ile Asn Met Lys Gly
        355                 360                 365

Leu Asp Gly Ile Gln Gly Pro Ile Tyr Val Gly Thr Gly Cys Val Phe
    370                 375                 380

Arg Arg Gln Ala Leu Tyr Gly Tyr Asp Ala Pro Lys Thr Lys Lys Pro
385                 390                 395                 400

Pro Ser Arg Thr Cys Asn Cys Trp Pro Lys Trp Cys Ile Cys Cys Cys
                405                 410                 415

Cys Phe Gly Asp Arg Lys Ser Lys Lys Lys Thr Thr Lys Pro Lys Thr
            420                 425                 430
```

```
Glu Lys Lys Lys Arg Ser Phe Phe Lys Arg Ala Glu Asn Gln Ser Pro
        435                 440                 445

Ala Tyr Ala Leu Gly Glu Ile Glu Glu Gly Ala Pro Gly Ala Glu Asn
    450                 455                 460

Glu Lys Ala Gly Ile Val Asn Gln Gln Lys Leu Glu Lys Lys Phe Gly
465                 470                 475                 480

Gln Ser Ser Val Phe Val Ala Ser Thr Leu Leu Glu Asn Gly Gly Thr
                485                 490                 495

Leu Lys Ser Ala Ser Pro Ala Ser Leu Leu Lys Glu Ala Ile His Val
            500                 505                 510

Ile Ser Cys Gly Tyr Glu Asp Lys Thr Asp Trp Gly Lys Glu Ile Gly
        515                 520                 525

Trp Ile Tyr Gly Ser Val Thr Glu Asp Ile Leu Thr Gly Phe Lys Met
    530                 535                 540

His Cys His Gly Trp Arg Ser Ile Tyr Cys Ile Pro Lys Leu Pro Ala
545                 550                 555                 560

Phe Lys Gly Ser Ala Pro Leu Asn Leu Ser Asp Arg Leu His Gln Val
                565                 570                 575

Leu Arg Trp Ala Leu Gly Ser Val Glu Ile Phe Phe Ser Asn His Cys
            580                 585                 590

Pro Leu Trp Tyr Gly Tyr Gly Gly Gly Leu Lys Cys Leu Glu Arg Phe
        595                 600                 605

Ser Tyr Ile Asn Ser Ile Val Tyr Pro Phe Thr Ser Ile Pro Leu Leu
    610                 615                 620

Ala Tyr Cys Thr Leu Pro Ala Ile Cys Leu Leu Thr Gly Lys Phe Ile
625                 630                 635                 640

Thr Pro Glu Leu Thr Asn Val Ala Ser Leu Trp Phe Met Ser Leu Phe
                645                 650                 655

Ile Cys Ile Phe Ala Thr Gly Ile Leu Glu Met Arg Trp Ser Gly Val
            660                 665                 670

Gly Ile Asp Asp Trp Trp Arg Asn Glu Gln Phe Trp Val Ile Gly Gly
        675                 680                 685

Val Ser Ser His Leu Phe Ala Leu Phe Gln Gly Leu Leu Lys Val Ile
    690                 695                 700

Ala Gly Ile Asp Thr Ser Phe Thr Val Thr Ser Lys Gly Gly Asp Asp
705                 710                 715                 720

Glu Glu Phe Ser Glu Leu Tyr Thr Phe Lys Trp Thr Thr Leu Leu Ile
                725                 730                 735

Pro Pro Thr Thr Leu Leu Leu Leu Asn Phe Ile Gly Val Val Ala Gly
            740                 745                 750

Val Ser Asn Ala Ile Asn Asn Gly Tyr Glu Ser Trp Gly Pro Leu Phe
        755                 760                 765

Gly Lys Leu Phe Phe Ala Phe Trp Val Ile Val His Leu Tyr Pro Phe
    770                 775                 780

Leu Lys Gly Leu Val Gly Arg Gln Asn Arg Thr Pro Thr Ile Val Ile
785                 790                 795                 800

Val Trp Ser Ile Leu Leu Ala Ser Ile Phe Ser Leu Leu Trp Val Arg
                805                 810                 815

Ile Asp Pro Phe Leu Ala Lys Asn Asp Gly Pro Leu Leu Glu Glu Cys
            820                 825                 830

Gly Leu Asp Cys Asn
        835
```

<210> SEQ ID NO 59
<211> LENGTH: 966
<212> TYPE: PRT
<213> ORGANISM: Oryza sativa

<400> SEQUENCE: 59

```
Met Leu His Ala His Met Ser Tyr Gly Arg Gly Gly Val Asp Val Asn
1               5                   10                  15

Gly Val Pro Gln Pro Phe Gln Pro Asn Pro Asn Val Pro Leu Leu Thr
            20                  25                  30

Asp Gly Gln Met Val Asp Asp Ile Pro Pro Glu Gln His Ala Leu Val
        35                  40                  45

Pro Ser Phe Met Gly Gly Gly Gly Lys Arg Ile His Pro Leu Pro Tyr
    50                  55                  60

Ala Asp Pro Asn Leu Pro Val Gln Pro Arg Ser Met Asp Pro Ser Lys
65                  70                  75                  80

Asp Leu Ala Ala Tyr Gly Tyr Gly Ser Val Ala Trp Lys Glu Arg Met
                85                  90                  95

Glu Ser Trp Lys Gln Lys Gln Glu Arg Leu His Gln Met Arg Asn Asp
            100                 105                 110

Gly Gly Gly Lys Asp Trp Asp Gly Asp Gly Asp Asp Gly Asp Leu Pro
        115                 120                 125

Leu Met Asp Glu Ala Arg Gln Pro Leu Ser Arg Lys Val Pro Ile Pro
    130                 135                 140

Ser Ser Gln Ile Asn Pro Tyr Arg Met Val Ile Ile Ile Arg Leu Val
145                 150                 155                 160

Val Leu Gly Phe Phe Phe His Tyr Arg Val Met His Pro Val Pro Asp
                165                 170                 175

Ala Phe Ala Leu Trp Leu Ile Ser Val Ile Cys Glu Ile Trp Phe Ala
            180                 185                 190

Met Ser Trp Ile Leu Asp Gln Phe Pro Lys Trp Phe Pro Ile Glu Arg
        195                 200                 205

Glu Thr Tyr Leu Asp Arg Leu Thr Leu Arg Phe Asp Lys Glu Gly Gln
    210                 215                 220

Thr Ser Gln Leu Ala Pro Ile Asp Phe Phe Val Ser Thr Val Asp Pro
225                 230                 235                 240

Leu Lys Glu Pro Pro Leu Val Thr Ala Asn Thr Val Leu Ser Ile Leu
                245                 250                 255

Ala Val Asp Tyr Pro Val Asp Lys Val Ser Cys Tyr Val Ser Asp Asp
            260                 265                 270

Gly Ala Ala Met Leu Thr Phe Glu Ala Leu Ser Glu Thr Ser Glu Phe
        275                 280                 285

Ala Lys Lys Trp Val Pro Phe Cys Lys Lys Tyr Ser Ile Glu Pro Arg
    290                 295                 300

Ala Pro Glu Trp Tyr Phe Gln Gln Lys Ile Asp Tyr Leu Lys Asp Lys
305                 310                 315                 320

Val Ala Pro Tyr Phe Val Arg Glu Arg Arg Ala Met Lys Arg Glu Tyr
                325                 330                 335

Glu Glu Phe Lys Val Arg Ile Asn Ala Leu Val Ala Lys Ala Gln Lys
            340                 345                 350

Val Pro Glu Glu Gly Trp Thr Met Gln Asp Gly Thr Pro Trp Pro Gly
        355                 360                 365

Asn Asn Val Arg Asp His Pro Gly Met Ile Gln Val Phe Leu Gly Gln
    370                 375                 380
```

-continued

```
Ser Gly Gly His Asp Ile Glu Gly Asn Glu Leu Pro Arg Leu Val Tyr
385                 390                 395                 400

Val Ser Arg Glu Lys Arg Pro Gly Tyr Asn His His Lys Lys Ala Gly
                405                 410                 415

Ala Met Asn Ala Leu Val Arg Val Ser Ala Val Leu Thr Asn Ala Pro
            420                 425                 430

Tyr Met Leu Asn Leu Asp Cys Asp His Tyr Ile Asn Asn Ser Lys Ala
        435                 440                 445

Ile Lys Glu Ala Met Cys Phe Met Met Asp Pro Leu Val Gly Lys Lys
    450                 455                 460

Val Cys Tyr Val Gln Phe Pro Gln Arg Phe Asp Gly Ile Asp Arg His
465                 470                 475                 480

Asp Arg Tyr Ala Asn Arg Asn Val Val Phe Phe Asp Ile Asn Met Lys
                485                 490                 495

Gly Leu Asp Gly Ile Gln Gly Pro Ile Tyr Val Gly Thr Gly Cys Val
            500                 505                 510

Phe Arg Arg Gln Ala Leu Tyr Gly Tyr Asp Ala Pro Lys Thr Lys Lys
        515                 520                 525

Pro Pro Ser Arg Thr Cys Asn Cys Trp Pro Lys Trp Cys Ile Cys Cys
    530                 535                 540

Cys Cys Phe Gly Asp Arg Lys Ser Lys Lys Lys Thr Thr Lys Pro Lys
545                 550                 555                 560

Thr Glu Lys Lys Lys Arg Ser Phe Phe Lys Arg Ala Glu Asn Gln Ser
                565                 570                 575

Pro Ala Tyr Ala Leu Gly Glu Ile Glu Glu Gly Ala Pro Gly Ala Glu
            580                 585                 590

Asn Glu Lys Ala Gly Ile Val Asn Gln Gln Lys Leu Glu Lys Lys Phe
        595                 600                 605

Gly Gln Ser Ser Val Phe Val Ala Ser Thr Leu Leu Glu Asn Gly Gly
    610                 615                 620

Thr Leu Lys Ser Ala Ser Pro Ala Ser Leu Leu Lys Glu Ala Ile His
625                 630                 635                 640

Val Ile Ser Cys Gly Tyr Glu Asp Lys Thr Asp Trp Gly Lys Glu Ile
                645                 650                 655

Gly Trp Ile Tyr Gly Ser Val Thr Glu Asp Ile Leu Thr Gly Phe Lys
            660                 665                 670

Met His Cys His Gly Trp Arg Ser Ile Tyr Cys Ile Pro Lys Leu Pro
        675                 680                 685

Ala Phe Lys Gly Ser Ala Pro Leu Asn Leu Ser Asp Arg Leu His Gln
    690                 695                 700

Val Leu Arg Trp Ala Leu Gly Ser Val Glu Ile Phe Phe Ser Asn His
705                 710                 715                 720

Cys Pro Leu Trp Tyr Gly Tyr Gly Gly Gly Leu Lys Cys Leu Glu Arg
                725                 730                 735

Phe Ser Tyr Ile Asn Ser Ile Val Tyr Pro Phe Thr Ser Ile Pro Leu
            740                 745                 750

Leu Ala Tyr Cys Thr Leu Pro Ala Ile Cys Leu Leu Thr Gly Lys Phe
        755                 760                 765

Ile Thr Pro Glu Leu Thr Asn Val Ala Ser Leu Trp Phe Met Ser Leu
    770                 775                 780

Phe Ile Cys Ile Phe Ala Thr Gly Ile Leu Glu Met Arg Trp Ser Gly
785                 790                 795                 800

Val Gly Ile Asp Asp Trp Trp Arg Asn Glu Gln Phe Trp Val Ile Gly
```

```
                805                 810                 815

Gly Val Ser Ser His Leu Phe Ala Leu Phe Gln Gly Leu Leu Lys Val
            820                 825                 830

Ile Ala Gly Ile Asp Thr Ser Phe Thr Val Thr Ser Lys Gly Gly Asp
        835                 840                 845

Asp Glu Glu Phe Ser Glu Leu Tyr Thr Phe Lys Trp Thr Thr Leu Leu
    850                 855                 860

Ile Pro Pro Thr Thr Leu Leu Leu Leu Asn Phe Ile Gly Val Val Ala
865                 870                 875                 880

Gly Val Ser Asn Ala Ile Asn Asn Gly Tyr Glu Ser Trp Gly Pro Leu
                885                 890                 895

Phe Gly Lys Leu Phe Phe Ala Phe Trp Val Ile Val His Leu Tyr Pro
            900                 905                 910

Phe Leu Lys Gly Leu Val Gly Arg Gln Asn Arg Thr Pro Thr Ile Val
        915                 920                 925

Ile Val Trp Ser Ile Leu Leu Ala Ser Ile Phe Ser Leu Leu Trp Val
    930                 935                 940

Arg Ile Asp Pro Phe Leu Ala Lys Asn Asp Gly Pro Leu Leu Glu Glu
945                 950                 955                 960

Cys Gly Leu Asp Cys Asn
                965
```

<210> SEQ ID NO 60
<211> LENGTH: 1115
<212> TYPE: PRT
<213> ORGANISM: Oryza sativa

<400> SEQUENCE: 60

```
Met Ser Thr Gly Pro Gly Lys Lys Ala Ile Arg Asn Ala Gly Gly Val
1               5                   10                  15

Gly Gly Gly Ala Gly Pro Ser Ala Gly Gly Pro Arg Gly Pro Ala Gly
            20                  25                  30

Gln Ala Val Lys Phe Ala Arg Arg Thr Ser Ser Gly Arg Tyr Val Ser
        35                  40                  45

Leu Ser Arg Glu Asp Ile Asp Met Glu Gly Glu Leu Ala Ala Asp Tyr
    50                  55                  60

Thr Asn Tyr Thr Val Gln Ile Pro Pro Thr Pro Asp Asn Gln Pro Met
65                  70                  75                  80

Leu Asn Gly Ala Glu Pro Ala Ser Val Ala Met Lys Ala Glu Glu Gln
                85                  90                  95

Tyr Val Ser Asn Ser Leu Phe Thr Gly Gly Phe Asn Ser Ala Thr Arg
            100                 105                 110

Ala His Leu Met Asp Lys Val Ile Glu Ser Ser Val Ser His Pro Gln
        115                 120                 125

Met Ala Gly Ala Lys Gly Ser Arg Cys Ala Met Pro Ala Cys Asp Gly
    130                 135                 140

Ser Ala Met Arg Asn Glu Arg Gly Glu Asp Val Asp Pro Cys Glu Cys
145                 150                 155                 160

His Phe Lys Ile Cys Arg Asp Cys Tyr Leu Asp Ala Gln Lys Asp Gly
                165                 170                 175

Cys Ile Cys Pro Gly Cys Lys Glu His Tyr Lys Ile Gly Glu Tyr Ala
            180                 185                 190

Asp Asp Asp Pro His Asp Gly Lys Leu His Leu Pro Gly Pro Gly Gly
        195                 200                 205
```

```
Gly Gly Asn Lys Ser Leu Leu Ala Arg Asn Gln Asn Gly Glu Phe Asp
    210                 215                 220

His Asn Arg Trp Leu Phe Glu Ser Ser Gly Thr Tyr Gly Tyr Gly Asn
225                 230                 235                 240

Ala Phe Trp Pro Lys Gly Gly Met Tyr Asp Asp Asp Leu Asp Asp Asp
                245                 250                 255

Val Asp Lys Leu Gly Gly Asp Gly Gly Gly Gly Gly Gly Gly Gly Pro
            260                 265                 270

Leu Pro Glu Gln Lys Pro Phe Lys Pro Leu Thr Arg Lys Ile Pro Met
        275                 280                 285

Pro Thr Ser Val Ile Ser Pro Tyr Arg Ile Phe Ile Val Ile Arg Met
    290                 295                 300

Phe Val Leu Leu Phe Tyr Leu Thr Trp Arg Ile Arg Asn Pro Asn Met
305                 310                 315                 320

Glu Ala Leu Trp Leu Trp Gly Met Ser Ile Val Cys Glu Leu Trp Phe
                325                 330                 335

Ala Phe Ser Trp Leu Leu Asp Met Leu Pro Lys Val Asn Pro Val Asn
            340                 345                 350

Arg Ser Thr Asp Leu Ala Val Leu Lys Glu Lys Phe Glu Thr Pro Ser
        355                 360                 365

Pro Ser Asn Pro His Gly Arg Ser Asp Leu Pro Gly Leu Asp Val Phe
    370                 375                 380

Val Ser Thr Ala Asp Pro Glu Lys Glu Pro Val Leu Thr Thr Ala Thr
385                 390                 395                 400

Thr Ile Leu Ser Ile Leu Ala Val Asp Tyr Pro Val Glu Lys Leu Ala
                405                 410                 415

Cys Tyr Val Ser Asp Asp Gly Gly Ala Leu Leu Thr Phe Glu Ala Met
            420                 425                 430

Ala Glu Ala Ala Ser Phe Ala Asn Val Trp Val Pro Phe Cys Lys Lys
        435                 440                 445

His Asp Ile Glu Pro Arg Asn Pro Asp Ser Tyr Phe Ser Val Lys Gly
    450                 455                 460

Asp Pro Thr Lys Gly Lys Arg Arg Asn Asp Phe Val Lys Asp Arg Arg
465                 470                 475                 480

Arg Val Lys Arg Glu Phe Asp Glu Phe Lys Val Arg Ile Asn Gly Leu
                485                 490                 495

Pro Asp Ser Ile Arg Arg Arg Ser Asp Ala Phe Asn Ala Arg Glu Asp
            500                 505                 510

Met Lys Met Leu Lys His Leu Arg Glu Thr Gly Ala Asp Pro Ser Glu
        515                 520                 525

Gln Pro Lys Val Lys Lys Ala Thr Trp Met Ala Asp Gly Ser His Trp
    530                 535                 540

Pro Gly Thr Trp Ala Ala Ser Ala Pro Asp His Ala Lys Gly Asn His
545                 550                 555                 560

Ala Gly Ile Leu Gln Val Met Leu Lys Pro Pro Ser Pro Asp Pro Leu
                565                 570                 575

Tyr Gly Met His Asp Asp Asp Gln Met Ile Asp Phe Ser Asp Val Asp
            580                 585                 590

Ile Arg Leu Pro Met Leu Val Tyr Met Ser Arg Glu Lys Arg Pro Gly
        595                 600                 605

Tyr Asp His Asn Lys Lys Ala Gly Ala Met Asn Ala Leu Val Arg Cys
    610                 615                 620

Ser Ala Val Met Ser Asn Gly Pro Phe Met Leu Asn Phe Asp Cys Asp
```

-continued

```
625                 630                 635                 640

His Tyr Ile Asn Asn Ala Gln Ala Val Arg Glu Ala Met Cys Phe Phe
                645                 650                 655

Met Asp Arg Gly Gly Glu Arg Ile Ala Tyr Ile Gln Phe Pro Gln Arg
            660                 665                 670

Phe Glu Gly Ile Asp Pro Ser Asp Arg Tyr Ala Asn Asn Asn Thr Val
        675                 680                 685

Phe Phe Asp Gly Asn Met Arg Ala Leu Asp Gly Leu Gln Gly Pro Met
    690                 695                 700

Tyr Val Gly Thr Gly Cys Met Phe Arg Arg Phe Ala Val Tyr Gly Phe
705                 710                 715                 720

Asp Pro Pro Arg Thr Ala Glu Tyr Thr Gly Trp Leu Phe Thr Lys Lys
                725                 730                 735

Lys Val Thr Thr Phe Lys Asp Pro Glu Ser Asp Thr Gln Thr Leu Lys
            740                 745                 750

Ala Glu Asp Phe Asp Ala Glu Leu Thr Ser His Leu Val Pro Arg Arg
        755                 760                 765

Phe Gly Asn Ser Ser Pro Phe Met Ala Ser Ile Pro Val Ala Glu Phe
    770                 775                 780

Gln Ala Arg Pro Leu Ala Asp His Pro Ala Val Leu His Gly Arg Pro
785                 790                 795                 800

Ser Gly Ala Leu Thr Val Pro Arg Pro Pro Leu Asp Pro Pro Thr Val
                805                 810                 815

Ala Glu Ala Val Ser Val Ile Ser Cys Trp Tyr Glu Asp Lys Thr Glu
            820                 825                 830

Trp Gly Asp Arg Val Gly Trp Ile Tyr Gly Ser Val Thr Glu Asp Val
        835                 840                 845

Val Thr Gly Tyr Arg Met His Asn Arg Gly Trp Arg Ser Val Tyr Cys
    850                 855                 860

Ile Thr Lys Arg Asp Ala Phe Leu Gly Thr Ala Pro Ile Asn Leu Thr
865                 870                 875                 880

Asp Arg Leu His Gln Val Leu Arg Trp Ala Thr Gly Ser Val Glu Ile
                885                 890                 895

Phe Phe Ser Arg Asn Asn Ala Phe Leu Ala Ser Arg Lys Leu Met Leu
            900                 905                 910

Leu Gln Arg Ile Ser Tyr Leu Asn Val Gly Ile Tyr Pro Phe Thr Ser
        915                 920                 925

Ile Phe Leu Leu Val Tyr Cys Phe Ile Pro Ala Leu Ser Leu Phe Ser
    930                 935                 940

Gly Phe Phe Ile Val Gln Lys Leu Asp Ile Ala Phe Leu Cys Tyr Leu
945                 950                 955                 960

Leu Thr Met Thr Ile Thr Leu Val Ala Leu Gly Ile Leu Glu Gly Leu
                965                 970                 975

Leu Lys Val Met Ala Gly Ile Glu Ile Ser Phe Thr Leu Thr Ala Lys
            980                 985                 990

Ala Ala Ala Asp Asp Asn Glu Asp  Ile Tyr Ala Asp Leu  Tyr Ile Val
        995                 1000                1005

Lys Trp  Ser Ser Leu Leu Ile  Pro Pro Ile Thr Ile  Gly Met Val
    1010                1015                1020

Asn Ile  Ile Ala Ile Ala Phe  Ala Phe Ala Arg Thr  Ile Tyr Ser
    1025                1030                1035

Asp Asn  Pro Arg Trp Gly Lys  Phe Ile Gly Gly Gly  Phe Phe Ser
    1040                1045                1050
```

```
Phe Trp  Val Leu Ala His Leu  Asn Pro Phe Ala Lys  Gly Leu Met
    1055                 1060                 1065

Gly Arg  Arg Gly Lys Thr Pro  Thr Ile Val Phe Val  Trp Ser Gly
    1070                 1075                 1080

Leu Leu  Ser Ile Thr Val Ser  Leu Leu Trp Val Ala  Ile Ser Pro
    1085                 1090                 1095

Pro Glu  Ala Asn Ser Asn Gly  Gly Ala Arg Gly Gly  Gly Phe Gln
    1100                 1105                 1110

Phe Pro
    1115


<210> SEQ ID NO 61
<211> LENGTH: 1055
<212> TYPE: PRT
<213> ORGANISM: Oryza sativa

<400> SEQUENCE: 61

Met Glu Ala Ser Ala Gly Leu Val Ala Gly Ser His Asn Arg Asn Glu
1               5                   10                  15

Leu Val Leu Ile Arg Gly His Glu Glu Pro Lys Pro Leu Arg Ala Leu
            20                  25                  30

Ser Gly Gln Val Cys Glu Ile Cys Gly Asp Glu Val Gly Arg Thr Val
        35                  40                  45

Asp Gly Asp Leu Phe Val Ala Cys Asn Glu Cys Gly Phe Pro Val Cys
    50                  55                  60

Arg Pro Cys Tyr Glu Tyr Glu Arg Arg Glu Gly Thr Gln Asn Cys Pro
65                  70                  75                  80

Gln Cys Lys Thr Arg Tyr Lys Arg Leu Lys Gly Ser Pro Arg Val Pro
                85                  90                  95

Gly Asp Glu Asp Glu Glu Asp Ile Asp Asp Leu Glu His Glu Phe Asn
            100                 105                 110

Ile Asp Asp Glu Lys Gln Lys Gln Leu Gln Gln Asp Gln Asp Gly Met
        115                 120                 125

Gln Asn Ser His Ile Thr Glu Ala Met Leu His Gly Lys Met Ser Tyr
    130                 135                 140

Gly Arg Gly Pro Asp Asp Gly Asp Gly Asn Ser Thr Pro Leu Pro Pro
145                 150                 155                 160

Ile Ile Thr Gly Ala Arg Ser Val Pro Val Ser Gly Glu Phe Pro Ile
                165                 170                 175

Ser Asn Ser His Gly His Gly Glu Phe Ser Ser Ser Leu His Lys Arg
            180                 185                 190

Ile His Pro Tyr Pro Val Ser Glu Pro Gly Ser Ala Lys Trp Asp Glu
        195                 200                 205

Lys Lys Glu Val Ser Trp Lys Glu Arg Met Asp Asp Trp Lys Ser Lys
    210                 215                 220

Gln Gly Ile Val Ala Gly Gly Ala Pro Asp Pro Asp Asp Tyr Asp Ala
225                 230                 235                 240

Asp Val Pro Leu Asn Asp Glu Ala Arg Gln Pro Leu Ser Arg Lys Val
                245                 250                 255

Ser Ile Ala Ser Ser Lys Val Asn Pro Tyr Arg Met Val Ile Ile Leu
            260                 265                 270

Arg Leu Val Val Leu Gly Phe Phe Leu Arg Tyr Arg Ile Leu His Pro
        275                 280                 285

Val Pro Asp Ala Ile Pro Leu Trp Leu Thr Ser Ile Ile Cys Glu Ile
```

-continued

```
    290                 295                 300

Trp Phe Ala Val Ser Trp Ile Leu Asp Gln Phe Pro Lys Trp Tyr Pro
305                 310                 315                 320

Ile Asp Arg Glu Thr Tyr Leu Asp Arg Leu Ser Leu Arg Tyr Glu Arg
                325                 330                 335

Glu Gly Glu Pro Ser Leu Leu Ser Ala Val Asp Leu Phe Val Ser Thr
            340                 345                 350

Val Asp Pro Leu Lys Glu Pro Pro Leu Val Thr Ala Asn Thr Val Leu
        355                 360                 365

Ser Ile Leu Ala Val Asp Tyr Pro Val Asp Lys Val Ser Cys Tyr Val
    370                 375                 380

Ser Asp Asp Gly Ala Ser Met Leu Thr Phe Glu Ser Leu Ser Glu Thr
385                 390                 395                 400

Ala Glu Phe Ala Arg Lys Trp Val Pro Phe Cys Lys Lys Phe Ser Ile
                405                 410                 415

Glu Pro Arg Ala Pro Glu Phe Tyr Phe Ser Gln Lys Val Asp Tyr Leu
            420                 425                 430

Lys Asp Lys Val His Pro Asn Phe Val Gln Glu Arg Arg Ala Met Lys
        435                 440                 445

Arg Glu Tyr Glu Glu Phe Lys Val Arg Ile Asn Ala Leu Val Ala Lys
    450                 455                 460

Ala Gln Lys Val Pro Ala Glu Gly Trp Ile Met Lys Asp Gly Thr Pro
465                 470                 475                 480

Trp Pro Gly Asn Asn Thr Arg Asp His Pro Gly Met Ile Gln Val Phe
                485                 490                 495

Leu Gly His Ser Gly Gly His Asp Thr Glu Gly Asn Glu Leu Pro Arg
            500                 505                 510

Leu Val Tyr Val Ser Arg Glu Lys Arg Pro Gly Phe Gln His His Lys
        515                 520                 525

Lys Ala Gly Ala Met Asn Ala Leu Ile Arg Val Ser Ala Val Leu Thr
    530                 535                 540

Asn Ala Pro Phe Met Leu Asn Leu Asp Cys Asp His Tyr Ile Asn Asn
545                 550                 555                 560

Ser Lys Ala Ile Arg Glu Ala Met Cys Phe Leu Met Asp Pro Gln Val
                565                 570                 575

Gly Arg Lys Val Cys Tyr Val Gln Phe Pro Gln Arg Phe Asp Gly Ile
            580                 585                 590

Asp Val His Asp Arg Tyr Ala Asn Arg Asn Thr Val Phe Phe Asp Ile
        595                 600                 605

Asn Met Lys Gly Leu Asp Gly Ile Gln Gly Pro Val Tyr Val Gly Thr
    610                 615                 620

Gly Cys Val Phe Arg Arg Gln Ala Leu Tyr Gly Tyr Asn Pro Pro Lys
625                 630                 635                 640

Gly Pro Lys Arg Pro Lys Met Val Thr Cys Asp Cys Cys Pro Cys Phe
                645                 650                 655

Gly Arg Lys Lys Arg Lys His Gly Lys Asp Gly Leu Pro Glu Ala Val
            660                 665                 670

Ala Ala Asp Gly Gly Met Asp Ser Asp Lys Glu Met Leu Met Ser Gln
        675                 680                 685

Met Asn Phe Glu Lys Arg Phe Gly Gln Ser Ala Ala Phe Val Thr Ser
    690                 695                 700

Thr Leu Met Glu Glu Gly Gly Val Pro Pro Ser Ser Ser Pro Ala Ala
705                 710                 715                 720
```

Leu Leu Lys Glu Ala Ile His Val Ile Ser Cys Gly Tyr Glu Asp Lys
725 730 735

Thr Asp Trp Gly Leu Glu Leu Gly Trp Ile Tyr Gly Ser Ile Thr Glu
740 745 750

Asp Ile Leu Thr Gly Phe Lys Met His Cys Arg Gly Trp Arg Ser Val
755 760 765

Tyr Cys Met Pro Lys Arg Ala Ala Phe Lys Gly Ser Ala Pro Ile Asn
770 775 780

Leu Ser Asp Arg Leu Asn Gln Val Leu Arg Trp Ala Leu Gly Ser Val
785 790 795 800

Glu Ile Phe Phe Ser Arg His Ser Pro Leu Leu Tyr Gly Tyr Lys Asn
805 810 815

Gly Asn Leu Lys Trp Leu Glu Arg Phe Ser Tyr Ile Asn Thr Thr Ile
820 825 830

Tyr Pro Phe Thr Ser Leu Pro Leu Leu Ala Tyr Cys Thr Leu Pro Ala
835 840 845

Val Cys Leu Leu Thr Gly Lys Phe Ile Met Pro Pro Ile Ser Thr Phe
850 855 860

Ala Ser Leu Phe Phe Ile Ala Leu Phe Ile Ser Ile Phe Ala Thr Gly
865 870 875 880

Ile Leu Glu Met Arg Trp Ser Gly Val Ser Ile Glu Glu Trp Trp Arg
885 890 895

Asn Glu Gln Phe Trp Val Ile Gly Gly Val Ser Ala His Leu Phe Ala
900 905 910

Val Val Gln Gly Leu Leu Lys Val Leu Ala Gly Ile Asp Thr Asn Phe
915 920 925

Thr Val Thr Ser Lys Ala Thr Gly Asp Glu Asp Asp Glu Phe Ala Glu
930 935 940

Leu Tyr Ala Phe Lys Trp Thr Thr Leu Leu Ile Pro Pro Thr Thr Leu
945 950 955 960

Leu Ile Leu Asn Ile Ile Gly Val Val Ala Gly Val Ser Asp Ala Ile
965 970 975

Asn Asn Gly Ser Glu Ala Trp Gly Pro Leu Phe Gly Lys Leu Phe Phe
980 985 990

Ala Phe Trp Val Ile Val His Leu Tyr Pro Phe Leu Lys Gly Leu Met
995 1000 1005

Gly Arg Gln Asn Arg Thr Pro Thr Ile Val Val Ile Trp Ser Val
1010 1015 1020

Leu Leu Ala Ser Ile Phe Ser Leu Leu Trp Val Arg Ile Asp Pro
1025 1030 1035

Phe Thr Ile Lys Ala Arg Gly Pro Asp Val Arg Gln Cys Gly Ile
1040 1045 1050

Asn Cys
1055

<210> SEQ ID NO 62
<211> LENGTH: 1063
<212> TYPE: PRT
<213> ORGANISM: Oryza sativa

<400> SEQUENCE: 62

Met Asp Thr Ala Ser Val Thr Gly Gly Glu His Lys Gly Lys Glu Lys
1 5 10 15

Thr Cys Arg Val Cys Gly Glu Glu Val Ala Ala Arg Glu Asp Gly Lys

```
            20                  25                  30

Pro Phe Val Ala Cys Ala Glu Cys Gly Phe Pro Val Cys Lys Pro Cys
        35                  40                  45

Tyr Glu Tyr Glu Arg Ser Glu Gly Thr Gln Cys Cys Pro Gln Cys Asn
    50                  55                  60

Thr Arg Tyr Lys Arg His Lys Gly Cys Pro Arg Val Glu Gly Asp Glu
65                  70                  75                  80

Asp Asp Gly Gly Asp Met Asp Asp Phe Glu Glu Glu Phe Gln Ile Lys
                85                  90                  95

Ser Pro Thr Lys Gln Lys Pro Pro His Glu Pro Val Asn Phe Asp Val
            100                 105                 110

Tyr Ser Glu Asn Gly Glu Gln Pro Ala Gln Lys Trp Arg Pro Gly Gly
        115                 120                 125

Pro Ala Leu Ser Ser Phe Thr Gly Ser Val Ala Gly Lys Asp Leu Glu
    130                 135                 140

Gln Glu Arg Glu Met Glu Gly Gly Met Glu Trp Lys Asp Arg Ile Asp
145                 150                 155                 160

Lys Trp Lys Thr Lys Gln Glu Lys Arg Gly Lys Leu Asn Arg Asp Asp
                165                 170                 175

Ser Asp Asp Asp Asp Asp Lys Asn Asp Asp Glu Tyr Met Leu Leu Ala
            180                 185                 190

Glu Ala Arg Gln Pro Leu Trp Arg Lys Val Pro Ile Pro Ser Ser Lys
        195                 200                 205

Ile Asn Pro Tyr Arg Ile Val Ile Val Leu Arg Leu Val Val Leu Cys
    210                 215                 220

Phe Phe Leu Lys Phe Arg Ile Thr Thr Pro Ala Met Asp Ala Val Pro
225                 230                 235                 240

Leu Trp Leu Ala Ser Val Ile Cys Glu Leu Trp Phe Ala Leu Ser Trp
                245                 250                 255

Ile Leu Asp Gln Leu Pro Lys Trp Ser Pro Val Thr Arg Glu Thr Tyr
            260                 265                 270

Leu Asp Arg Leu Ala Leu Arg Tyr Glu Arg Asp Gly Glu Pro Cys Arg
        275                 280                 285

Leu Ala Pro Ile Asp Phe Phe Val Ser Thr Val Asp Pro Leu Lys Glu
    290                 295                 300

Pro Pro Ile Ile Thr Ala Asn Thr Val Leu Ser Ile Leu Ala Val Asp
305                 310                 315                 320

Tyr Pro Val Asp Arg Val Ser Cys Tyr Val Ser Asp Asp Gly Ala Ser
                325                 330                 335

Met Leu Leu Phe Asp Thr Leu Ser Glu Thr Ala Glu Phe Ala Arg Arg
            340                 345                 350

Trp Val Pro Phe Cys Lys Lys Phe Thr Ile Glu Pro Arg Ala Pro Glu
        355                 360                 365

Phe Tyr Phe Ser Gln Lys Ile Asp Tyr Leu Lys Asp Lys Val Gln Pro
    370                 375                 380

Thr Phe Val Lys Glu Arg Arg Ala Met Lys Arg Glu Tyr Glu Glu Phe
385                 390                 395                 400

Lys Val Arg Ile Asn Ala Leu Val Ala Lys Ala Gln Lys Lys Pro Glu
                405                 410                 415

Glu Gly Trp Val Met Gln Asp Gly Thr Pro Trp Pro Gly Asn Asn Thr
            420                 425                 430

Arg Asp His Pro Gly Met Ile Gln Val Tyr Leu Gly Ser Gln Gly Ala
        435                 440                 445
```

Leu Asp Val Glu Gly Ser Glu Leu Pro Arg Leu Val Tyr Val Ser Arg
    450                 455                 460

Glu Lys Arg Pro Gly Tyr Asn His His Lys Lys Ala Gly Ala Met Asn
465                 470                 475                 480

Ser Leu Val Arg Val Ser Ala Val Leu Thr Asn Ala Pro Phe Ile Leu
                485                 490                 495

Asn Leu Asp Cys Asp His Tyr Val Asn Asn Ser Lys Ala Val Arg Glu
            500                 505                 510

Ala Met Cys Phe Leu Met Asp Lys Gln Leu Gly Lys Lys Leu Cys Tyr
        515                 520                 525

Val Gln Phe Pro Gln Arg Phe Asp Gly Ile Asp Arg His Asp Arg Tyr
    530                 535                 540

Ala Asn Arg Asn Thr Val Phe Phe Asp Ile Asn Met Lys Gly Leu Asp
545                 550                 555                 560

Gly Ile Gln Gly Pro Val Tyr Val Gly Thr Gly Thr Val Phe Asn Arg
                565                 570                 575

Gln Ala Leu Tyr Gly Tyr Asp Pro Pro Arg Pro Glu Lys Arg Pro Lys
            580                 585                 590

Met Thr Cys Asp Cys Trp Pro Ser Trp Cys Cys Cys Cys Cys Cys Phe
        595                 600                 605

Gly Gly Gly Lys Arg Gly Lys Ser His Lys Asn Lys Lys Gly Gly Gly
    610                 615                 620

Gly Gly Glu Gly Gly Gly Leu Asp Glu Pro Arg Arg Gly Leu Leu Gly
625                 630                 635                 640

Phe Tyr Lys Lys Arg Ser Lys Lys Asp Lys Leu Gly Gly Gly Ala Ala
                645                 650                 655

Ser Leu Ala Gly Gly Lys Lys Gly Tyr Arg Lys His Gln Arg Gly Phe
            660                 665                 670

Glu Leu Glu Glu Ile Glu Glu Gly Leu Glu Gly Tyr Asp Glu Leu Glu
        675                 680                 685

Arg Ser Ser Leu Met Ser Gln Lys Ser Phe Glu Lys Arg Phe Gly Gln
    690                 695                 700

Ser Pro Val Phe Ile Ala Ser Thr Leu Val Glu Asp Gly Gly Leu Pro
705                 710                 715                 720

Gln Gly Ala Ala Ala Asp Pro Ala Ala Leu Ile Lys Glu Ala Ile His
                725                 730                 735

Val Ile Ser Cys Gly Tyr Glu Glu Lys Thr Glu Trp Gly Lys Glu Ile
            740                 745                 750

Gly Trp Ile Tyr Gly Ser Val Thr Glu Asp Ile Leu Thr Gly Phe Lys
        755                 760                 765

Met His Cys Arg Gly Trp Lys Ser Val Tyr Cys Thr Pro Ala Arg Ala
    770                 775                 780

Ala Phe Lys Gly Ser Ala Pro Ile Asn Leu Ser Asp Arg Leu His Gln
785                 790                 795                 800

Val Leu Arg Trp Ala Leu Gly Ser Val Glu Ile Phe Met Ser Arg His
                805                 810                 815

Cys Pro Leu Trp Tyr Ala Tyr Gly Gly Arg Leu Lys Trp Leu Glu Arg
            820                 825                 830

Phe Ala Tyr Thr Asn Thr Ile Val Tyr Pro Phe Thr Ser Ile Pro Leu
        835                 840                 845

Leu Ala Tyr Cys Thr Ile Pro Ala Val Cys Leu Leu Thr Gly Lys Phe
    850                 855                 860

```
Ile Ile Pro Thr Leu Asn Asn Leu Ala Ser Ile Trp Phe Ile Ala Leu
865                 870                 875                 880

Phe Leu Ser Ile Ile Ala Thr Gly Val Leu Glu Leu Arg Trp Ser Gly
                885                 890                 895

Val Ser Ile Glu Asp Trp Trp Arg Asn Glu Gln Phe Trp Val Ile Gly
            900                 905                 910

Gly Val Ser Ala His Leu Phe Ala Val Phe Gln Gly Leu Leu Lys Val
        915                 920                 925

Leu Gly Gly Val Asp Thr Asn Phe Thr Val Thr Ser Lys Ala Ala Ala
    930                 935                 940

Asp Glu Thr Asp Ala Phe Gly Glu Leu Tyr Leu Phe Lys Trp Thr Thr
945                 950                 955                 960

Leu Leu Val Pro Pro Thr Thr Leu Ile Ile Ile Asn Met Val Gly Ile
                965                 970                 975

Val Ala Gly Val Ser Asp Ala Val Asn Asn Gly Tyr Gly Ser Trp Gly
            980                 985                 990

Pro Leu Phe Gly Lys Leu Phe Phe  Ser Phe Trp Val Ile  Leu His Leu
        995                 1000                 1005

Tyr Pro  Phe Leu Lys Gly Leu  Met Gly Arg Gln Asn  Arg Thr Pro
    1010                 1015                 1020

Thr Ile  Val Val Leu Trp Ser  Ile Leu Leu Ala Ser  Ile Phe Ser
    1025                 1030                 1035

Leu Val  Trp Val Arg Ile Asp  Pro Phe Ile Pro Lys  Pro Lys Gly
    1040                 1045                 1050

Pro Val  Leu Lys Pro Cys Gly  Val Ser Cys
    1055                 1060


<210> SEQ ID NO 63
<211> LENGTH: 1127
<212> TYPE: PRT
<213> ORGANISM: Oryza sativa

<400> SEQUENCE: 63

Met Ala Ser Lys Gly Ile Leu Lys Asn Gly Gly Lys Pro Pro Thr Ala
1               5                   10                  15

Pro Ser Ser Ala Ala Pro Thr Val Val Phe Gly Arg Arg Thr Asp Ser
            20                  25                  30

Gly Arg Phe Ile Ser Tyr Ser Arg Asp Asp Leu Asp Ser Glu Ile Ser
        35                  40                  45

Ser Val Asp Phe Gln Asp Tyr His Val His Ile Pro Met Thr Pro Asp
    50                  55                  60

Asn Gln Pro Met Asp Pro Ala Ala Gly Asp Glu Gln Gln Tyr Val Ser
65                  70                  75                  80

Ser Ser Leu Phe Thr Gly Gly Phe Asn Ser Val Thr Arg Ala His Val
                85                  90                  95

Met Glu Lys Gln Ala Ser Ser Ala Arg Ala Thr Val Ser Ala Cys Met
            100                 105                 110

Val Gln Gly Cys Gly Ser Lys Ile Met Arg Asn Gly Arg Gly Ala Asp
        115                 120                 125

Ile Leu Pro Cys Glu Cys Asp Phe Lys Ile Cys Val Asp Cys Phe Thr
    130                 135                 140

Asp Ala Val Lys Gly Gly Gly Gly Val Cys Pro Gly Cys Lys Glu Pro
145                 150                 155                 160

Tyr Lys His Ala Glu Trp Glu Glu Val Val Ser Ala Ser Asn His Asp
                165                 170                 175
```

```
Ala Ile Asn Arg Ala Leu Ser Leu Pro His Gly His Gly His Gly Pro
            180                 185                 190

Lys Met Glu Arg Arg Leu Ser Leu Val Lys Gln Asn Gly Gly Ala Pro
        195                 200                 205

Gly Glu Phe Asp His Asn Arg Trp Leu Phe Glu Thr Lys Gly Thr Tyr
    210                 215                 220

Gly Tyr Gly Asn Ala Ile Trp Pro Glu Asp Asp Gly Val Ala Gly His
225                 230                 235                 240

Pro Lys Glu Leu Met Ser Lys Pro Trp Arg Pro Leu Thr Arg Lys Leu
                245                 250                 255

Arg Ile Gln Ala Ala Val Ile Ser Pro Tyr Arg Leu Leu Val Leu Ile
            260                 265                 270

Arg Leu Val Ala Leu Gly Leu Phe Leu Met Trp Arg Ile Lys His Gln
        275                 280                 285

Asn Glu Asp Ala Ile Trp Leu Trp Gly Met Ser Ile Val Cys Glu Leu
    290                 295                 300

Trp Phe Ala Leu Ser Trp Val Leu Asp Gln Leu Pro Lys Leu Cys Pro
305                 310                 315                 320

Ile Asn Arg Ala Thr Asp Leu Ser Val Leu Lys Asp Lys Phe Glu Thr
                325                 330                 335

Pro Thr Pro Ser Asn Pro Thr Gly Lys Ser Asp Leu Pro Gly Ile Asp
            340                 345                 350

Ile Phe Val Ser Thr Ala Asp Pro Glu Lys Glu Pro Val Leu Val Thr
        355                 360                 365

Ala Asn Thr Ile Leu Ser Ile Leu Ala Ala Asp Tyr Pro Val Asp Lys
    370                 375                 380

Leu Ala Cys Tyr Val Ser Asp Asp Gly Gly Ala Leu Leu Thr Phe Glu
385                 390                 395                 400

Ala Met Ala Glu Ala Ala Ser Phe Ala Asn Leu Trp Val Pro Phe Cys
                405                 410                 415

Arg Lys His Glu Ile Glu Pro Arg Asn Pro Asp Ser Tyr Phe Asn Leu
            420                 425                 430

Lys Arg Asp Pro Phe Lys Asn Lys Val Lys Gly Asp Phe Val Lys Asp
        435                 440                 445

Arg Arg Arg Val Lys Arg Glu Tyr Asp Glu Phe Lys Val Arg Val Asn
    450                 455                 460

Gly Leu Pro Asp Ala Ile Arg Arg Arg Ser Asp Ala Tyr His Ala Arg
465                 470                 475                 480

Glu Glu Ile Gln Ala Met Asn Leu Gln Arg Glu Lys Met Lys Ala Gly
                485                 490                 495

Gly Asp Glu Gln Gln Leu Glu Pro Ile Lys Ile Pro Lys Ala Thr Trp
            500                 505                 510

Met Ala Asp Gly Thr His Trp Pro Gly Thr Trp Leu Gln Ala Ser Pro
        515                 520                 525

Glu His Ala Arg Gly Asp His Ala Gly Ile Ile Gln Val Met Leu Lys
    530                 535                 540

Pro Pro Ser Pro Ser Pro Ser Ser Ser Gly Gly Asp Met Glu Lys Arg
545                 550                 555                 560

Val Asp Leu Ser Gly Val Asp Thr Arg Leu Pro Met Leu Val Tyr Val
                565                 570                 575

Ser Arg Glu Lys Arg Pro Gly Tyr Asp His Asn Lys Lys Ala Gly Ala
            580                 585                 590
```

```
Met Asn Ala Leu Val Arg Ala Ser Ala Ile Met Ser Asn Gly Pro Phe
        595                 600                 605

Ile Leu Asn Leu Asp Cys Asp His Tyr Val Tyr Asn Ser Lys Ala Phe
    610                 615                 620

Arg Glu Gly Met Cys Phe Met Met Asp Arg Gly Gly Asp Arg Leu Cys
625                 630                 635                 640

Tyr Val Gln Phe Pro Gln Arg Phe Glu Gly Ile Asp Pro Ser Asp Arg
                645                 650                 655

Tyr Ala Asn His Asn Thr Val Phe Phe Asp Val Asn Met Arg Ala Leu
            660                 665                 670

Asp Gly Leu Gln Gly Pro Val Tyr Val Gly Thr Gly Cys Leu Phe Arg
        675                 680                 685

Arg Ile Ala Leu Tyr Gly Phe Asp Pro Pro Arg Ser Lys Asp His Thr
    690                 695                 700

Thr Pro Trp Ser Cys Cys Leu Pro Arg Arg Arg Arg Thr Arg Ser Gln
705                 710                 715                 720

Pro Gln Pro Gln Glu Glu Glu Glu Glu Thr Met Ala Leu Arg Met Asp
                725                 730                 735

Met Asp Gly Ala Met Asn Met Ala Ser Phe Pro Lys Lys Phe Gly Asn
            740                 745                 750

Ser Ser Phe Leu Ile Asp Ser Ile Pro Val Ala Glu Phe Gln Gly Arg
        755                 760                 765

Pro Leu Ala Asp His Pro Ser Val Lys Asn Gly Arg Pro Pro Gly Ala
    770                 775                 780

Leu Thr Ile Pro Arg Glu Thr Leu Asp Ala Ser Ile Val Ala Glu Ala
785                 790                 795                 800

Ile Ser Val Val Ser Cys Trp Tyr Glu Glu Lys Thr Glu Trp Gly Thr
                805                 810                 815

Arg Val Gly Trp Ile Tyr Gly Ser Val Thr Glu Asp Val Val Thr Gly
            820                 825                 830

Tyr Arg Met His Asn Arg Gly Trp Lys Ser Val Tyr Cys Val Thr His
        835                 840                 845

Arg Asp Ala Phe Arg Gly Thr Ala Pro Ile Asn Leu Thr Asp Arg Leu
    850                 855                 860

His Gln Val Leu Arg Trp Ala Thr Gly Ser Val Glu Ile Phe Phe Ser
865                 870                 875                 880

Arg Asn Asn Ala Leu Phe Ala Ser Ser Lys Met Lys Val Leu Gln Arg
                885                 890                 895

Ile Ala Tyr Leu Asn Val Gly Ile Tyr Pro Phe Thr Ser Val Phe Leu
            900                 905                 910

Ile Val Tyr Cys Phe Leu Pro Ala Leu Ser Leu Phe Ser Gly Gln Phe
        915                 920                 925

Ile Val Gln Thr Leu Asn Val Thr Phe Leu Thr Tyr Leu Leu Ile Ile
    930                 935                 940

Thr Ile Thr Leu Cys Leu Leu Ala Met Leu Glu Ile Lys Trp Ser Gly
945                 950                 955                 960

Ile Ala Leu Glu Glu Trp Trp Arg Asn Glu Gln Phe Trp Leu Ile Gly
                965                 970                 975

Gly Thr Ser Ala His Leu Ala Ala Val Leu Gln Gly Leu Leu Lys Val
            980                 985                 990

Ile Ala Gly Ile Glu Ile Ser Phe  Thr Leu Thr Ser Lys  Gln Leu Gly
        995                 1000                1005

Asp Asp  Val Asp Asp Glu Phe  Ala Glu Leu Tyr Ala  Val Lys Trp
```

```
    1010                1015                1020

Thr Ser  Leu Met Ile Pro Pro  Leu Thr Ile Ile Met  Ile Asn Leu
    1025                1030                1035

Val Ala  Ile Ala Val Gly Phe  Ser Arg Thr Ile Tyr  Ser Thr Ile
    1040                1045                1050

Pro Gln  Trp Ser Lys Leu Leu  Gly Gly Val Phe Phe  Ser Phe Trp
    1055                1060                1065

Val Leu  Ala His Leu Tyr Pro  Phe Ala Lys Gly Leu  Met Gly Arg
    1070                1075                1080

Arg Gly  Arg Thr Pro Thr Ile  Val Tyr Val Trp Ser  Gly Leu Val
    1085                1090                1095

Ala Ile  Thr Ile Ser Leu Leu  Trp Ile Ala Ile Lys  Pro Pro Ser
    1100                1105                1110

Ala Gln  Ala Asn Ser Gln Leu  Gly Gly Ser Phe Ser  Phe Pro
    1115                1120                1125


<210> SEQ ID NO 64
<211> LENGTH: 1215
<212> TYPE: PRT
<213> ORGANISM: Oryza sative

<400> SEQUENCE: 64

Met Ser Arg Arg Leu Ser Leu Pro Ala Gly Ala Pro Val Thr Val Ala
1               5                   10                  15

Val Ser Pro Val Arg Ser Pro Gly Gly Asp Ala Val Val Arg Arg Gly
            20                  25                  30

Ser Gly Leu Thr Ser Pro Val Pro Arg His Ser Leu Gly Ser Ser Thr
        35                  40                  45

Ala Thr Leu Gln Val Ser Pro Val Arg Arg Ser Gly Gly Ser Arg Tyr
    50                  55                  60

Leu Gly Ala Ser Arg Asp Gly Gly Ala Asp Glu Ser Ala Glu Phe Val
65                  70                  75                  80

His Tyr Thr Val His Ile Pro Pro Thr Pro Asp Arg Ala Thr Ala Ser
                85                  90                  95

Val Ala Ser Glu Ala Glu Ala Ala Ala Glu Ala Glu Glu Val His Arg
            100                 105                 110

Pro Gln Arg Ser Tyr Ile Ser Gly Thr Ile Phe Thr Gly Gly Leu Asn
        115                 120                 125

Cys Ala Thr Arg Gly His Val Leu Asn Phe Ser Gly Glu Gly Gly Ala
    130                 135                 140

Thr Ala Ala Ser Arg Ala Ala Ala Ser Gly Asn Met Ser Cys Lys Met
145                 150                 155                 160

Arg Gly Cys Asp Met Pro Ala Phe Leu Asn Gly Gly Arg Pro Pro Cys
                165                 170                 175

Asp Cys Gly Phe Met Ile Cys Lys Glu Cys Tyr Ala Glu Cys Ala Ala
            180                 185                 190

Gly Asn Cys Pro Gly Cys Lys Glu Ala Phe Ser Ala Gly Ser Asp Thr
        195                 200                 205

Asp Glu Ser Asp Ser Val Thr Asp Asp Asp Asp Asp Glu Ala Val Ser
    210                 215                 220

Ser Ser Glu Glu Arg Asp Gln Leu Pro Leu Thr Ser Met Ala Arg Lys
225                 230                 235                 240

Phe Ser Val Val His Ser Met Lys Val Pro Gly Ala Ala Ala Asn Gly
                245                 250                 255
```

```
Asn Gly Lys Pro Ala Glu Phe Asp His Ala Arg Trp Leu Phe Glu Thr
            260                 265                 270

Lys Gly Thr Tyr Gly Tyr Gly Asn Ala Leu Trp Pro Lys Asp Gly His
        275                 280                 285

Ala His Ser Gly Ala Gly Phe Val Ala Ala Asp Glu Pro Pro Asn Phe
    290                 295                 300

Gly Ala Arg Cys Arg Arg Pro Leu Thr Arg Lys Thr Ser Val Ser Gln
305                 310                 315                 320

Ala Ile Leu Ser Pro Tyr Arg Leu Leu Ile Ala Ile Arg Leu Val Ala
                325                 330                 335

Leu Gly Phe Phe Leu Ala Trp Arg Ile Arg His Pro Asn Pro Glu Ala
            340                 345                 350

Val Trp Leu Trp Ala Met Ser Val Ala Cys Glu Val Trp Phe Ala Phe
        355                 360                 365

Ser Trp Leu Leu Asp Ser Leu Pro Lys Leu Cys Pro Val His Arg Ala
    370                 375                 380

Ala Asp Leu Ala Val Leu Ala Glu Arg Phe Glu Ser Pro Thr Ala Arg
385                 390                 395                 400

Asn Pro Lys Gly Arg Ser Asp Leu Pro Gly Ile Asp Val Phe Val Thr
                405                 410                 415

Ser Ala Asp Pro Glu Lys Glu Pro Pro Leu Val Thr Ala Asn Thr Ile
            420                 425                 430

Leu Ser Ile Leu Ala Ala Asp Tyr Pro Val Glu Lys Leu Ala Cys Tyr
        435                 440                 445

Leu Ser Asp Asp Gly Gly Ala Leu Leu Ser Phe Glu Ala Leu Ala Glu
    450                 455                 460

Thr Ala Ser Phe Ala Arg Thr Trp Val Pro Phe Cys Arg Lys His Gly
465                 470                 475                 480

Val Glu Pro Arg Cys Pro Glu Ala Tyr Phe Gly Gln Lys Arg Asp Phe
                485                 490                 495

Leu Lys Asn Lys Val Arg Val Asp Phe Val Arg Glu Arg Arg Lys Val
            500                 505                 510

Lys Arg Glu Tyr Asp Glu Phe Lys Val Arg Val Asn Ser Leu Pro Glu
        515                 520                 525

Ala Ile Arg Arg Arg Ser Asp Ala Tyr Asn Ala Gly Glu Glu Leu Arg
    530                 535                 540

Ala Arg Arg Arg Gln Gln Glu Glu Ala Ala Ala Ala Ala Ala Ala Gly
545                 550                 555                 560

Asn Gly Glu Leu Gly Ala Ala Ala Val Glu Thr Ala Ala Val Lys Ala
                565                 570                 575

Thr Trp Met Ser Asp Gly Ser His Trp Pro Gly Thr Trp Thr Cys Pro
            580                 585                 590

Ala Ala Asp His Ala Arg Gly Asp His Ala Gly Ile Ile Gln Ala Met
        595                 600                 605

Leu Ala Pro Pro Thr Ser Glu Pro Val Met Gly Gly Glu Ala Ala Glu
    610                 615                 620

Cys Gly Gly Leu Ile Asp Thr Thr Gly Val Asp Val Arg Leu Pro Met
625                 630                 635                 640

Leu Val Tyr Val Ser Arg Glu Lys Arg Pro Gly Tyr Asp His Asn Lys
                645                 650                 655

Lys Ala Gly Ala Met Asn Ala Leu Val Arg Thr Ser Ala Ile Met Ser
            660                 665                 670

Asn Gly Pro Phe Ile Leu Asn Leu Asp Cys Asp His Tyr Val His Asn
```

```
        675                 680                 685

Ser Ser Ala Leu Arg Glu Gly Met Cys Phe Met Leu Asp Arg Gly Gly
    690                 695                 700

Asp Arg Val Cys Phe Val Gln Phe Pro Gln Arg Phe Glu Gly Val Asp
705                 710                 715                 720

Pro Ser Asp Arg Tyr Ala Asn His Asn Leu Val Phe Phe Asp Val Ser
                725                 730                 735

Met Arg Ala Met Asp Gly Leu Gln Gly Pro Met Tyr Val Gly Thr Gly
            740                 745                 750

Cys Val Phe Arg Arg Thr Ala Leu Tyr Gly Phe Ser Pro Pro Arg Ala
        755                 760                 765

Thr Glu His His Gly Trp Leu Gly Arg Arg Lys Ile Lys Leu Phe Leu
    770                 775                 780

Thr Lys Lys Lys Ser Met Gly Lys Lys Thr Asp Arg Ala Glu Asp Asp
785                 790                 795                 800

Thr Glu Met Met Leu Pro Pro Ile Glu Asp Asp Asp Gly Gly Ala Asp
                805                 810                 815

Ile Glu Ala Ser Ala Met Leu Pro Lys Arg Phe Gly Gly Ser Ala Thr
            820                 825                 830

Phe Val Ala Ser Ile Pro Val Ala Glu Tyr Gln Gly Arg Leu Leu Gln
        835                 840                 845

Asp Thr Pro Gly Cys His His Gly Arg Pro Ala Gly Ala Leu Ala Val
    850                 855                 860

Pro Arg Glu Pro Leu Asp Ala Ala Thr Val Ala Glu Ala Ile Gly Val
865                 870                 875                 880

Ile Ser Cys Phe Tyr Glu Glu Lys Thr Glu Trp Gly Arg Arg Ile Gly
                885                 890                 895

Trp Ile Tyr Gly Ser Val Thr Glu Asp Val Val Thr Gly Tyr Arg Met
            900                 905                 910

His Asn Arg Gly Trp Arg Ser Val Tyr Cys Val Thr Pro Arg Arg Asp
        915                 920                 925

Ala Phe Arg Gly Thr Ala Pro Ile Asn Leu Thr Asp Arg Leu His Gln
    930                 935                 940

Val Leu Arg Trp Ala Thr Gly Ser Val Glu Ile Phe Phe Ser Arg Asn
945                 950                 955                 960

Asn Ala Leu Phe Ala Ser Pro Arg Met Lys Leu Leu Gln Arg Val Ala
                965                 970                 975

Tyr Phe Asn Ala Gly Met Tyr Pro Phe Thr Ser Val Phe Leu Leu Ala
            980                 985                 990

Tyr Cys Leu Leu Pro Ala Val Ser  Leu Phe Ser Gly Lys  Phe Ile Val
        995                 1000                1005

Gln Arg  Leu Ser Ala Thr Phe  Leu Ala Phe Leu Leu  Val Ile Thr
    1010                1015                1020

Leu Thr  Leu Cys Leu Leu Ala  Leu Leu Glu Ile Lys  Trp Ser Gly
    1025                1030                1035

Ile Thr  Leu His Glu Trp Trp  Arg Asn Glu Gln Phe  Trp Val Ile
    1040                1045                1050

Gly Gly  Thr Ser Ala His Pro  Ala Ala Val Leu Gln  Gly Leu Leu
    1055                1060                1065

Lys Val  Ile Ala Gly Val Asp  Ile Ser Phe Thr Leu  Thr Ser Lys
    1070                1075                1080

Pro Gly  Asn Gly Gly Gly Asp  Gly Gly Val Gly Gly  Glu Gly Asn
    1085                1090                1095
```

```
Asp Asp  Glu Ala Phe Ala Glu  Leu Tyr Glu Val Arg  Trp Ser Tyr
    1100                 1105                 1110

Leu Met  Val Pro Pro Val Thr  Ile Met Met Val Asn  Ala Val Ala
    1115                 1120                 1125

Ile Ala  Val Ala Ala Ala Arg  Thr Leu Tyr Ser Glu  Phe Pro Gln
    1130                 1135                 1140

Trp Ser  Lys Leu Leu Gly Gly  Ala Phe Phe Ser Phe  Trp Val Leu
    1145                 1150                 1155

Cys His  Leu Tyr Pro Phe Ala  Lys Gly Leu Leu Gly  Arg Arg Gly
    1160                 1165                 1170

Arg Val  Pro Thr Ile Val Phe  Val Trp Ser Gly Leu  Ile Ser Met
    1175                 1180                 1185

Ile Ile  Ser Leu Leu Trp Val  Tyr Ile Asn Pro Pro  Ala Gly Ala
    1190                 1195                 1200

Arg Glu  Arg Ile Gly Gly Gly  Gly Phe Ser Phe Pro
    1205                 1210                 1215
```

<210> SEQ ID NO 65
<211> LENGTH: 3255
<212> TYPE: DNA
<213> ORGANISM: Glycine max

<400> SEQUENCE: 65

```
atggaagcaa gtgcgggaat ggttgccggt tcgcataaac ggaacgagct cgttcggatt      60

cgccacgatt cttctgacag cgggtctaaa cccatgaaga atttgaatgg gcaaatctgt     120

caaatatgcg gtgatactgt tggattaact gctactggtg atgtgtttgt tgcttgcaac     180

gagtgtgctt tccctgtgtg tcgtccttgt tatgaatatg agcggaagga tgggaaccag     240

tcttgtccac agtgcaagac tagatacaag aggcacagag ggagtcctcg agttgagggt     300

gatgaagatg aagatgattc tgatgatatc gagaatgagt tcaattatgc ccaaggaaaa     360

gccaaggcca ggcggcagtg ggaagacgat cctgacctgt cgtcgtcttc tagacgtgaa     420

tctcaacagc caattcccct cctcaccaat ggccaaacga tgtctggtga gattccatgt     480

gccacacctg atactcaatc tgtgcgaact acttcaggtc ctctgggccc atctgaaaag     540

gttcactcac ttccctatgt tgatccaagg caaccagttc cagtaagaat tgtggaccca     600

tcaaaggact tgaattctta tggtctggga aatgttgact ggaaagaaag ggttgaaggt     660

tggaagctta agcaggagaa aaatatggtg caaatgactg gtagatacgc tgaagggaaa     720

ggtggagatg ttgaagggac tggttctaat ggagaagaac ttcaaatggt agatgatgct     780

cgacaaccta tgagtcgtgt tgtgccaatt ccttcatctc agctgacgcc ttatcgtgtt     840

gttatcatcc tccggctgat tattcttggc ttcttcttac aatatcgtgt aactcatcct     900

gtgaaagatg catacccact gtggttgaca tcagttattt gtgagatttg gtttgcctta     960

tcctggctct tggatcagtt tccaaaatgg tctcccatta atcgtgagac ttatcttgaa    1020

cggcttgctt taaggtatga tcgtgaagga gaaccatcac agttagatcc tgttgatgtg    1080

tttgttagta cagtggatcc cctcaaagag ccacctcttg ttactgcaaa caccgttttg    1140

tctatacttt ctgttgatta ccctgtcgac aaagtttcct gctatgtatc agatgatggt    1200

tcagctatgt tgacctttga agcactatct gaaacagctg agtttgcgaa gaagtgggtg    1260

ccctttttgca aaaagcacaa tattgaacca agagccccag agttttattt tgcccagaag    1320

attgattact taaaggacaa gattcagccc tcgtttgtaa aagagcgacg ggcaatgaag    1380
```

-continued

```
agagaatatg aagaattcaa agtacggatc aatgcccttg tagccaaagc tcagaagatg   1440
ccagaggaag gttggacaat gcaggatgga actccttggc ctggaaataa tcctagggat   1500
catccgggaa tgattcaggt gtttttaggt catagtgggg ggctggatac agatggaaat   1560
gagctgccta gacttgttta tgtttctcgt gagaagcgac caggcttcca acatcacaag   1620
aaggctggag ctatgaatgc tttgattcga gtttctgctg tcttgaccaa tggtgcatat   1680
cttctgaatg tggattgtga tcactatttc aataatagca aagccctcaa agaagccatg   1740
tgtttcatga tggatcctgt tcttggaaag aagacatgct atgttcaatt tcctcagaga   1800
tttgacggca ttgacttgca cgatcgatat gccaatcgca atattgtgtt ctttgatatc   1860
aacatgaaag gtcaggatgg tgttcagggc ccagtctatg tgggaactgg ttgttgtttc   1920
aataggcaag ctttgtatgg ttatgatcct gttttgactg aggaagattt ggaacctaac   1980
attattgtaa agagttgttg cggttctaga aagaagggaa agggtggcaa taagaagtac   2040
agtgacaaga agaaggcgat gggaagaact gaatccactg tacccatatt taatatggaa   2100
gacatagagg agggtgttga aggttatgat gatgaaagga cactacttat gtctcaaaag   2160
agcttggaga agcgttttgg tcagtctcca gtttttattg ctgccacttt catggagcag   2220
ggtggcattc caccttcaac gaaccctgca actcttctta aggaagcaat ccatgttatc   2280
agctgtggtt acgaagacaa gacagaatgg ggcaaagaga ttggatggat ctatggctct   2340
gtgacagaag atatcttgac tgggttcaag atgcatgctc gtggttggat ttccatctat   2400
tgcatgccac ctcgcccagc atttaagggt tctgctccta tcaatctttc tgatcgtctc   2460
aatcaggtgc ttcggtgggc cttgggttca attgagatct ttctaagcag gcattgtccc   2520
ttgtggtatg gctacaatgg gaagttgaag cctctgatga ggcttgctta tattaacacc   2580
attgtctacc cgtttacctc aatcccattg attgcttact gtacgcttcc tgcattttgt   2640
cttctcacaa ataaatttat tattcctgag ataagcaact ttgccagtat gtggttcatt   2700
cttctctttg tctccatttt taccacttca attcttgagc ttaggtggag tggggtcagt   2760
atagaagact ggtggagaaa tgaacagttc tgggttatcg gtgggacatc tgcgcatctc   2820
tttgctgtgt tccaggggct tctaaaagtg cttgctggga tcgatacaaa ttttactgtt   2880
acatcgaagg catcggacga ggatggggac tttgccgagc tttatgtgtt taaatggaca   2940
tcacttctca tccctcctac aacagtgctt attgtgaatt tggttgggat tgtggctggt   3000
gtatcctatg ccataaacag tggttaccag tcttggggtc cactatttgg caagctgttc   3060
tttgctatct gggtcattgc ccatctatac ccattcttga agggtctctt gggcaggcaa   3120
aatcgtaccc caaccattgt tattgtttgg tccgttcttc ttgcttcaat attctccttg   3180
ctgtgggtga ggattgatcc cttcacctct gactccaaca aattaaccaa tggtcaatgt   3240
ggcatcaact gttag                                                     3255
```

<210> SEQ ID NO 66
<211> LENGTH: 3225
<212> TYPE: DNA
<213> ORGANISM: Glycine max

<400> SEQUENCE: 66

```
atgatggagt cagaaggaga agctggggca aagccaatga aaacattggg tggcaaaatc     60
tgccagatct gtggtgataa tattgggaac aatgcgaatg gcgatccttt cattgcctgc    120
gatgtttgcg ctttccctgt ctgcagggcg tgctatgaat atgaaaggaa ggatggaaat    180
cagtcttgcc ctcagtgcaa gacccggtac aagaggcaca aaggaagtcc tgcaattctt    240
```

```
ggagaccgag aagaggatgg gggtgctgat gatggtgcca gtgacttcaa ttacaattca   300
gagaatcaga atgaaaagca gaagattgag catatgttgg gctggcaaat ggcatatggg   360
cgtgcagagg aggccattgc tccgaattat gataaggaag tttctcacaa tcacattcct   420
ctgctctccg gtggacaaga ggtttctgga gaattatctg ctgcctcacc tgagaggctg   480
tcaatggcat ccccaggtgg ccgagggaag cgtgcccata atcttcaata ttcgtctgac   540
cttaatcatt caccaaatat cagggttggg gatcctggat tgggcaatgt ggcatggaaa   600
gaaagagttg atggctggaa aatgaagcaa gataagaatg ttgctccaat gagcacgggc   660
caagctactt ctgaaagagg agctggagat attgatgcta gtactgatgt gcttgtggac   720
gattccttgt tgaatgatga ggctcggcaa cccctctcta ggaaggtttc tattccatca   780
tctaggatca atccataccg tatggtcatt gctctgcggt tggttatcct atgcattttt   840
ctgcattatc gaataacaaa tcctgtgccc aatgcatatg cattgtggtt gatatcagtt   900
atatgtgaga tttggtttgc catatcttgg atattggatc aattccccaa gtggctccct   960
gtgaaccgtg aaacatatct tgacagactt gcactaagat atgatcggga aggggaacca  1020
tcacagctag cagctgttga catttttgtc agtactgttg atccattaaa agaacccccg  1080
cttgtgactg ctaacactgt cctatctatt ctttctgttg actacccagt ggataaggtc  1140
tcctgttatg tctctgatga tggtgctgct atgttgacat ttgaagctct ggctgagaca  1200
tcagaatttg ctaggaaatg ggttcctttc agcaagaaat ataatatcga acctcgggca  1260
cctgagtggt attttgcaca gaagattgac tacttgaaag ataaggttca accatcattt  1320
gtcaaagatc gtagagcaat gaagagagaa tatgaagaat ttaaaattcg catcaatgga  1380
cttgttgcaa aggcacaaaa gattcctgaa gaaggatggg tgatgcaaga tggtacgcca  1440
tggcctggaa acaacactag agaccatcca ggaatgattc aggttttctt gggccaaagt  1500
ggaggacttg acactgaggg taatgaactt ccacgtttag tctatgtttc tcgtgaaaag  1560
cgtccagggt tccaacatca caagaaggct ggtgccatga atgcacttgt tcgagtgtca  1620
gcagtcctta ctaatggacc tttcttattg aatcttgatt gtgatcacta cataaacaac  1680
agtaaagcct tgagggaagc tatgtgcttt atgatggatc ccaaccttgg gaaaaatgtt  1740
tgctatgtcc agtttccaca gaggtttgat ggtattgata ggaatgatcg atatgccaat  1800
cgcaatactg ttttctttga tataaacttg agaggtttgg atggcattca aggtcctgtt  1860
tatgtgggta ctggatgtgt ctttaataga acagctttgt atggctacga acctcctatt  1920
aaacccaagc ataaaaagcc tgggtttctt tcttcactct gtggtggtaa ccgaaagaag  1980
agatcaaaat ctagcaagaa aggctcagac aagaaaaaat ctagcaagaa tgttgaccca  2040
actgtgccca tctttagtct tgaggatata gaagaggggg tggaaggtgc tggatttgat  2100
gatgagaaat cactacttat gtcacaaatg agcctcgaga aaaggtttgg tcagtctgct  2160
gtctttgttg cctctacact catggagaat ggtggcgttc ctcagtctgc aactccagaa  2220
actcttctta aggaagctat tcatgttatc agttgtggtt acgaggataa atcagaatgg  2280
ggaagtgaga taggatggat ctatggttct gtcacagaag atattcttac tggattcaag  2340
atgcatgccc gaggttggag gtctatttac tgcatgccca agctcccagc gtttaaaggt  2400
tctgctccta tcaatctttc agatcgtctg aaccaagtgc ttcgatgggc tttaggttcg  2460
gtggaaattc tttttagtcg acattgtccc atctggtatg gttatagtgg aaggctaaag  2520
tggctcgaga ggttcgcata tgtgaacacc acaatctatc cagtcacttc cattcccctt  2580
```

```
ctcatgtatt gtaccttacc tgctgtctgt ctcctgacta acaagttcat tattccacag   2640

attagtaaca ttgcaagtat atggtttatc tctctctttc tttccatctt tgccacgggt   2700

atccttgaga tgaggtggag tggtgttgga attgatgagt ggtggagaaa tgaacaattt   2760

tgggttatcg gtggtgtctc ggcccatctt tttgccgtgt tccaaggttt actcaaagtg   2820

cttgctggaa ttgacactaa cttcactgtt acctcaaaag catcagatga ggatggagac   2880

tttgcagaac tctacatgtt caaatggaca acccttctca tcccacccac gacgcttctc   2940

atcataaacc tggtgggggt tgttgcaggc atctcctatg ccatcaacag tggctaccaa   3000

tcatggggtc ccctctttgg taagcttttc tttgcatttt gggtgatcat ccatctctac   3060

cctttcctca aaggtctcat gggtcgccag aacagaacac caaccattgt ggtggtctgg   3120

tccattcttc ttgcatctat cttctctctg ttgtgggtcc gaattgaccc gtttacgaca   3180

agagtcactg gtcctgatgt tgagcagtgt ggaatcaact gctag                   3225
```

<210> SEQ ID NO 67
<211> LENGTH: 3240
<212> TYPE: DNA
<213> ORGANISM: Glycine max

<400> SEQUENCE: 67

```
atggaatcag aaggggaagc tggggcaaag ccagtgacag cattgggtgc ccaagtgtgc     60

cagatttgtg gtgatggtgt tgggaagact gtggatggtg aaccgttcgt tgcgtgcgat    120

gtttgcgctt tccctgtctg caggccttgc tatgagtatg agaggaagga tgggaatcaa    180

tcttgccccc agtgcaaaac ccggtacaag aggcacaagg gaagtcctgc aattcttgga    240

gacatggaag aggatggtgc tgctgctgct gatgccagtg acttcaatta tgattcagaa    300

aatcaaaatc aaaatcaaaa ccaaaagcag aagatttcag agcgcatgtt aagctggcaa    360

ttgacatacc cacgaggaga ggaggttggt gctccaaatt atgataagga tgtttctcac    420

aaccacattc ctctgctgac cagtggacaa gaggtatctg gagagttgtc tgcagcctca    480

cctgagaggc tctcaatggc atctcctgca gttggtggtg gaaagcgtgt ccataatatt    540

ccatattcat ctgacattaa tcaatctcca aatatcaggg ctggggatcc aggattgggc    600

aatgttgcat ggaaagaaag agttgatggc tggaagatga agcaagaaaa gaatgttgtt    660

ccaatgagca caggccaggc tgcttctgaa agaggagctg gagatattga tgctagtact    720

gatgtgcttg tagatgattc tttattgaat gatgaagctc gacagcctct ttccaggaag    780

gtttctattc catcttctag gataaatcca tatcgtatgg tcattatgct gcggctggtt    840

atcctttgca ttttcttgca ttatcggata acaaatcctg ttcccaatgc atatccattg    900

tggttggtat cagttatatg tgagatttgg tttgccatat cttggatatt ggatcaattt    960

cccaagtggc ttcctgtaaa ccgtgaaaca tatcttgaca ggcttgcact gaggtatgat   1020

cgggaaggag aaccgtcaca actagctgct gttgacattt ttgtcagtac tgttgatcca   1080

ttaaaggagc ctccacttgt gactgccaat accgtactat ctattcttgc agttgactat   1140

ccagtggata aggtctcctg ctatgtgtct gatgatggtg ctgctatgtt gacatttgaa   1200

gcacttgctg agacatcgga atttgcaagg aaatgggttc cttttagcaa gaagtatagc   1260

attgaacccc gtgcgcctga gtggtatttt tctcaaaaga ttgactactt gaaagataag   1320

gttcatccat catttgtcaa ggatcgtaga gcaatgaaga gagaatatga ggaatttaaa   1380

gttcgtatta atggacttgt ttcaaaggca cagaaagttc ctgaagaagg atgggttatg   1440

caagatggta ccccgtggcc tggaaataac accagagacc atccaggaat gatccaggtt   1500
```

```
ttcttgggcc aaagtggagg acttgacact gagggtaatg aacttccacg tttagtctat   1560

gtttctcgtg aaaagcgtcc agggttccaa catcacaaga aagctggtgc catgaatgcc   1620

cttgttcgag tatctgcagt ccttaccaat ggacctttct tattgaatct tgattgtgat   1680

cactacataa acaacagcaa ggccttgagg gaagctatgt gctttatgat ggatcccaat   1740

cttggtaaac atgtttgcta tgtccagttt ccgcagaggt ttgacggtat tgataggaat   1800

gatcgatatg ccaatcgtaa tacagttttc tttgatataa acttgagagg tttggatggc   1860

attcaaggtc ctgtttatgt gggtactgga tgtgtcttca acaggacagc tttatatggt   1920

tatgaacctc ctcttaaacc caagcataaa aagcctgggt tgttatcatc actctgtggt   1980

ggaactcgga agaagagttc aaaatctagt aagaaaggat cagacaagaa aaaatctagc   2040

aagcatgttg acccaactgt gcccattttc aatttagagg atatagaaga aggagtagaa   2100

ggtactggat ttgatgatga gaaatcacta cttatgtcac aaatgagtct tgagaaaagg   2160

tttggtcagt ccgctgtctt tgttgcctct acgcttatgg agaatggtgg tgttcctcaa   2220

tctgctactc cagaaactct tcttaaggag gctattcatg ttatcagctg tggttacgag   2280

gataaaactg attggggaag tgagatagga tggatttatg gttctgtcac agaagatatt   2340

cttaccggat ttaagatgca tgcccggggt tggcggtcta tatactgcat gcctaagcgc   2400

ccagcgttta aaggttctgc tcccatcaat ctttcggatc gtctaaacca agtgcttcga   2460

tgggctttag gttccgtgga aattcttttc agccgacact gtcccatctg gtatggttat   2520

ggtggaaggt taaagtggct tgaaaggttt gcttatgtga acaccaccat ctatccagtc   2580

actgccattc cccttctcat ttattgtatc ttgcctgctg tctgtctgct gactaataag   2640

ttcattattc cacagatcag caaccttgct agcatatggt tcatctccct ctttctgtcc   2700

atctttgcta ctggaatcct ggagatgagg tggagtggtg tcggaatcga cgagtggtgg   2760

aggaatgaac agttttgggt catcggtggt gtctcggcac atctctttgc tgtttttcaa   2820

ggcttgctca aagtgcttgc tggaattgac accaacttca ctgtcacctc caaggcctcg   2880

gatgaagacg gagactttgc cgaactatac atgttcaaat ggaccaccct tcttattcct   2940

ccaacaaccc ttctcataat aaacttggtg gggtggttg ctggcatctc ctatgccatc    3000

aacagtggct accaatcttg ggacccctc tttggtaagc ttttctttgc attttgggtg    3060

atcatccatc tatacccttt cctcaaaggt ctcatggggc gccaaaacag aacaccaacc   3120

attgtggtgg tgtggtccgt tctgcttgca tccattttct cactcttgtg ggttagaatt   3180

gatccattca ccacaagggt cactggtcct gatgttgagg agtgtggcat taactgctag   3240
```

<210> SEQ ID NO 68
<211> LENGTH: 3228
<212> TYPE: DNA
<213> ORGANISM: Zea mays

<400> SEQUENCE: 68

```
atggcggcca acaaggggat ggtggcgggc tcgcacaacc gcaacgagtt cgtcatgatc     60

cgccacgacg gcgatgcgcc gggctcggct aagcccacaa agagtgcgaa tgggcaggtc    120

tgccagattt gtggtgactc tgtgggtgtt tcagccactg gtgatgtctt tgttgcctgc    180

aatgagtgtg ccttccctgt ctgccgccca tgctatgagt atgagcgcaa ggaggggaac    240

caatgctgcc cccagtgcaa gactagatac aagagacaga aaggtagccc tcgagttcat    300

ggtgatgagg atgaggaaga tgttgatgac ctagacaatg aattcaacta caagcaaggc    360
```

-continued

```
aatgggaaag gcccagagtg gcaactgcaa ggagatgatg ctgatctgtc ttcatctgct    420
cgccatgagc cacatcatcg gattccacgc ctgacaagcg gtcaacagat atctggagag    480
attcctgatg cttcccctga ccgtcattct atccgcagtc caacatcgag ctatgttgat    540
ccaagcgtcc cagttcctgt gaggattgtg gacccctcga aggacttgaa ttcctatggg    600
cttaatagtg ttgactggaa ggaaagagtt gagagctgga gggttaaaca ggacaaaaat    660
atgatgcaag tgactaataa atatccagag gctagaggag gagacatgga ggggactggc    720
tcaaatggag aagatatgca aatggttgat gatgcacggc tacctttgag ccgtatcgtg    780
ccaatttcct caaaccagct caacctttac cgggtagtga tcattctccg tcttatcatc    840
ctgtgcttct tcttccagta tcgtgtcagt catccagtgc gtaatgctta tggattatgg    900
ctagtatctg ttatctgcga ggtctggttt gccttgtctt ggcttctaga tcagttccca    960
aaatggtatc caatcaaccg tgagacatat cttgacaggc ttgcattgag gtatgataga   1020
gagggagagc catcacagct ggctcccatt gatgtcttcg tcagtacagt ggatccattg   1080
aaggaacctc cactgatcac agccaacact gttttgtcca ttctttctgt ggattaccct   1140
gttgacaaag tgtcatgcta tgtttctgat gatggttcag ctatgctgac ttttgagtct   1200
ctctcagaaa ccgcagaatt tgctagaaag tgggttccct tttgtaagaa gcacaatatt   1260
gaaccaagag ctccagaatt ttactttgct caaaaaatag attacctgaa ggacaaaatt   1320
caaccttcat ttgttaagga aagacgcgca atgaagaggg agtatgaaga attcaaagta   1380
agaatcaatg cccttgttgc caaagcacag aaagtgcctg aagaggggtg gaccatggct   1440
gatggaactg catggcctgg gaataatcct agggaccatc ctggcatgat tcaggttttc   1500
ttggggcaca gtggtgggct cgacactgat ggaaatgagt taccacgtct tgtctatgtc   1560
tctcgtgaaa agagaccagg ctttcagcat cacaagaagg ctggtgcaat gaatgcgctg   1620
attcgtgtat ctgctgtgct gacaaatggt gcctatcttc tcaatgtgga ttgcgaccat   1680
tacttcaata gcagcaaagc tcttagagaa gcaatgtgct tcatgatgga tccggctcta   1740
ggaaggaaaa cttgttatgt acaatttcca cagagatttg atggcattga cttgcacgat   1800
cgatatgcta atcggaacat agttttcttt gatatcaaca tgaaaggtct ggatggcatt   1860
cagggtccag tttacgtggg aacaggatgc tgtttcaata gacaggcttt gtatggatac   1920
gatcctgttt tgactgaagc tgatctggag ccaaacattg ttattaagag ctgctgtggt   1980
agaaggaaga aaaagaacaa gagttatatg gatagtcaaa gccgtattat gaagagaaca   2040
gaatcttcag ctcccatctt caatatggaa gacatcgaag agggtattga aggttatgag   2100
gatgaaaggt cagtgcttat gtcccagagg aaattggaga aacgctttgg tcagtctcct   2160
attttcattg catccacctt tatgacacaa ggtggcatac caccttcaac aaacccagct   2220
tctctactaa aggaagctat ccatgtcatc agttgtggat atgaggacaa aactgaatgg   2280
ggaaaagaga ttggctggat ctatggttca gtaacggagg atattctgac tgggtttaaa   2340
atgcatgcaa ggggctggca atcaatctac tgcatgccac cacgaccttg tttcaagggt   2400
tctgcaccaa tcaatctttc cgatcgtctt aatcaggtgc tccgttgggc tcttgggtca   2460
gtggaaattc tgcttagtag acattgtcct atctggtatg gttacaatgg acgattgaag   2520
cttttggaga ggctggctta catcaacact attgtatatc caatcacatc cattccgctt   2580
attgcctatt gtgtgcttcc cgctatctgc ctccttacca ataaatttat cattcctgag   2640
attagcaatt atgctgggat gttcttcatt cttcttttcg cctccatttt tgccactggt   2700
atattggagc ttagatggag tggtgttggc attgaagatt ggtggagaaa tgagcagttt   2760
```

```
tgggttattg gtggcacctc tgcccatctc ttcgcagtgt tccagggtct gctgaaagtg   2820

ttggctggga ttgataccaa cttcacagtt acctcaaagg catctgatga ggatggcgac   2880

tttgctgagc tatatgtgtt caagtggacc agtttgctca ttcctccgac cactgttctt   2940

gtcattaacc tggtcggaat ggtggctgga atttcttatg ccattaacag tggctaccaa   3000

tcctggggtc cgctctttgg aaagctgttc ttctcgatct gggtgatcct ccatctctac   3060

cccttcctca agggtctcat gggaaggcag aaccgcacac caacaatcgt cattgtctgg   3120

tccatccttc ttgcatctat cttctccttg ctgtgggtga agatcgatcc tttcatctcc   3180

ccgacacaga aagctgctgc cttggggcaa tgtggcgtca actgctga                3228
```

<210> SEQ ID NO 69
<211> LENGTH: 3225
<212> TYPE: DNA
<213> ORGANISM: Zea mays

<400> SEQUENCE: 69

```
atggcggcca acaaggggat ggtggcaggc tctcacaacc gcaacgagtt cgtcatgatc     60

cgccacgacg gcgacgcgcc tgtcccggct aagcccacga agagtgcgaa tgggcaggtc    120

tgccagattt gtggcgacac tgttggcgtt tcagccactg gtgatgtctt tgttgcctgc    180

aatgagtgtg ccttccctgt ctgccgccct tgctatgagt acgagcgcaa ggaagggaac    240

caatgctgcc ctcagtgcaa gactagatac aagagacaga aaggtagccc tcgagttcat    300

ggtgatgatg aggaggaaga tgttgatgac ctggacaatg aattcaacta taagcaaggc    360

aatgggaagg gcccagagtg gcagcttcaa ggagatgacg ctgatctgtc ttcatctgct    420

cgccatgacc cacaccatcg gattccacgc cttacaagtg gacaacagat atctggagag    480

atccctgatg catcccctga ccgtcattct atccgcagtc caacatcgag ctatgttgat    540

ccaagcgttc cagttcctgt gaggattgtg gacccctcga aggacttgaa ttcctatggg    600

cttaatagtg ttgactggaa ggaaagagtt gagagctgga gggttaaaca ggacaaaaat    660

atgttgcaag tgactaataa atatccagag gctagaggag acatggaggg gactggctca    720

aatggagaag atatgcaaat ggttgatgat gcacgcctac ctttgagccg cattgtgcca    780

atttcctcaa accagctcaa cctttaccgg atagtaatca ttctccgtct tatcatcctg    840

tgcttcttct tccaatatcg tatcagtcat ccagtgcgta atgcttatgg attgtggcta    900

gtatctgtta tctgtgaggt ctggtttgcc ttgtcctggc ttctagatca gttcccaaaa    960

tggtatccaa tcaaccgtga gacatatctc gacaggcttg cattgaggta tgatagagag   1020

ggagagccat cacagctggc tcccattgat gtctttgtca gtacagtgga tccattgaag   1080

gaacctccac tgatcacagc caacactgtt ttgtccattc ttgctgtgga ttaccctgtt   1140

gacaaagtgt catgctatgt ttctgatgat ggctcagcta tgctgacttt tgagtctctc   1200

tctgaaactg ccgaatttgc tagaaagtgg gttccctttt gtaagaagca caatattgaa   1260

ccaagagctc cagaatttta ctttgctcaa aaaatagatt acctgaagga caaaattcaa   1320

ccttcatttg ttaaggaaag acgagcaatg aagagagagt atgaagaatt caaaataaga   1380

atcaatgccc ttgttgccaa agcacagaaa gtgcctgaag aggggtggac catggctgat   1440

ggaactgctt ggcctgggaa taaccctagg gaccatcctg gcatgattca ggtgttcttg   1500

gggcacagtg gtgggcttga cactgatgga aatgaattac cacgtcttgt ctatgtctct   1560

cgtgaaaaga gaccaggctt tcagcatcac aagaaggctg gtgcaatgaa tgcactgatt   1620
```

-continued

```
cgtgtatctg ctgtgctgac aaatggtgcc tatcttctca atgtggattg tgaccattac   1680

ttcaatagca gcaaagctct tagagaagca atgtgcttca tgatggatcc agctctagga   1740

aggaaaactt gttatgtaca atttccacaa agatttgatg gcattgactt gcacgatcga   1800

tatgctaata ggaacatagt cttctttgat atcaacatga aaggtctaga tggcattcag   1860

ggtccagtct atgtgggaac aggatgctgt ttcaataggc aggctttgta tggatatgat   1920

cctgttttga ctgaagctga tctggaacct aacattgttg ttaagagctg ctgtggtaga   1980

aggaagagaa agaacaagag ttatatggat agtcaaagcc gtattatgaa gagaacagaa   2040

tcttcagctc ccatctttaa catggaagac atcgaggagg gtattgaagg ttatgaggat   2100

gaaaggtcag tgcttatgtc ccagaggaaa ttggagaaac gctttggtca gtctccaatc   2160

ttcattgcat ccacctttat gactcaaggt ggcataccac cttcaacaaa cccagcttct   2220

ctactgaagg aagctatcca tgttatcagc tgtgggtacg aggacaaaac tgaatgggga   2280

aaagagattg gctggatcta tggttcagtt acagaggata ttctgactgg gtttaaaatg   2340

catgcaagag gctggcaatc aatctactgc atgccaccac gaccttgttt caagggttct   2400

gcaccaatca atctttctga tcgtcttaat caggtgctcc gttgggctct tgggtcagtg   2460

gaaattctgc ttagcagaca ttgtcctata tggtatggct acaatgggcg attgaagctt   2520

ttggagaggc tggcttacat taacaccatt gtttatccaa tcacatctgt tccgcttatc   2580

gcctattgtg tgcttcctgc tatctgtctt cttaccaata aatttatcat tcctgagatt   2640

agtaattatg ctggaatgtt cttcattctt ctttttgcct ccattttcgc aactggtata   2700

ttggagctca gatggagtgg tgttggcatt gaagattggt ggagaaatga gcagttttgg   2760

gttattggtg gcacctctgc ccatctcttc gcggtgttcc agggtctgct gaaagtgttg   2820

gctgggattg ataccaactt cacagttacc tcaaaggcat ctgatgagga tggcgacttt   2880

gctgagctat atgtgttcaa gtggaccagt ttgctcatcc ctccgaccac tgttcttgtc   2940

attaacctgg tcggaatggt ggcaggaatt tcgtatgcca ttaacagcgg ctaccaatcc   3000

tggggtccgc tctttggaaa gctgttcttc tcgatctggg tgatcctcca tctctacccc   3060

ttcctcaagg gtctcatggg caggcagaac cgcacgccaa caatcgtcat cgtttggtcc   3120

atcctccttg cgtctatctt ctccttgctg tgggtgaaga tcgatccttt catctccccg   3180

acacagaaag ctgccgcctt ggggcaatgt ggtgtgaact gctga                  3225


<210> SEQ ID NO 70
<211> LENGTH: 3240
<212> TYPE: DNA
<213> ORGANISM: Zea mays

<400> SEQUENCE: 70

atggagggcg acgcggacgg cgtgaagtcg gggaggcgcg ggggagggca ggtgtgccag     60

atctgcggcg atggcgtggg cactacggcg gagggagacg tcttcaccgc ctgcgacgtc    120

tgcgggttcc cggtgtgccg cccctgctac gagtacgagc gcaaggacgg cacacaagcg    180

tgcccccagt gcaaaaacaa gtacaagcgc cacaagggga gtccagcgat ccgaggggag    240

gaaggagacg atactgatgc cgatgatgct agcgacttca actaccctgc atctggcaat    300

gacgaccaga agcagaagat tgctgacagg atgcgcagct ggcgcatgaa tgctgggggc    360

agcggggatg ttggccgccc caagtatgac agtggtgaga tcgggcttac caagtacgac    420

agtggtgaga tccctcgggg atacatcccg tcagtcacta acagccagat ttcgggagaa    480

atccctggtg cttcccctga ccatcatatg atgtctccta ctgggaacat tggcaggcgc    540
```

```
gccccatttc cctatatgaa tcattcatca aatccgtcga gggaattctc tggtagcgtt    600
gggaatgttg cctggaaaga gagggttgat ggctggaaaa tgaagcagga caagggaaca    660
attcccatga cgaatggcac aagcattgct ccctctgagg gccggggtgt tggtgatatt    720
gatgcatcaa ctgattacaa catggaagat gccttattaa acgatgaaac tcgccagcct    780
ctatctagga aagttccact tccttcctcc aggataaatc catacaggat ggtcattgtg    840
ctacgattga ttgttctaag catcttcttg cactaccgga tcacaaatcc tgtgcgtaat    900
gcatacccac tgtggcttct atctgttata tgtgagatct ggtttgctct ttcctggata    960
ttggatcagt ttccaaagtg gtttccaatc aaccgcgaga cttaccttga tagactcgca   1020
ttaaggtatg accgggaagg tgagccatct cagttggctg ctgttgacat tttgtcagt   1080
actgtcgacc caatgaagga gcctcctctt gtcactgcca ataccgtgct atccattctc   1140
gctgtggact atcctgtgga taaggtctct tgctatgtat ctgatgatgg agctgctatg   1200
ctgacatttg atgcactagc tgagacttca gagtttgcta gaaaatgggt gccatttgtt   1260
aagaagtaca acattgaacc tagagctcct gaatggtact tctcccagaa aattgattac   1320
ttgaaggaca aagtgcaccc ttcatttgtt aaagaccgcc gggccatgaa gagagaatat   1380
gaagaattca aaattagggt aaatggcctt gttgctaagg cacaaaaagt ccctgaggaa   1440
ggatggatca tgcaagatgg cacaccatgg ccaggaaaca ataccaggga ccatcctgga   1500
atgattcagg ttttccttgg tcacagtggt ggtcttgata ctgagggtaa tgagctaccc   1560
cgtttggtct atgtttctcg tgaaaaacgt cctggattcc agcatcacaa gaaagctggt   1620
gccatgaatg ctcttgtccg cgtctcagct gtgcttacca atggacaata catgttgaat   1680
cttgattgtg atcactacat caacaacagt aaggctctca gggaagctat gtgcttcctt   1740
atggatccta acctaggaag gagtgtctgc tatgttcagt ttccccagag gttcgatggt   1800
attgatagga atgatcgata tgccaacagg aacaccgtgt ttttcgatat taacttgaga   1860
ggtcttgatg gcatccaagg accagtttat gtgggcactg gctgtgtttt caacagaaca   1920
gctctatatg gttatgagcc cccaattaag caaaagaagg gtggtttctt gtcatcacta   1980
tgtggtggca ggaagaaggg aagcaaatca aagaagggct cagacaagaa aaagtcacag   2040
aagcatgtgg acagttctgt gccagtattc aatcttgaag atatagagga gggagttgaa   2100
ggcgctggat ttgatgatga gaaatcactt cttatgtctc aaatgagctt ggagaagaga   2160
tttggccaat ctgcagcttt tgttgcgtcc actctgatgg aatatggtgg tgttcctcag   2220
tctgcgactc cagaatctct tctgaaagaa gctatccatg tcataagttg tggctacgag   2280
gacaagactg aatggggaac tgagattggg tggatctatg gttctgtgac ggaagatatt   2340
ctcactgggt tcaagatgca cgcacgaggc tggcggtcga tctactgcat gcctaagcgg   2400
ccggccttca agggatcggc tcccatcaat ctctcagacc gtctgaacca ggtgctccgg   2460
tgggctctcg gttcagtgga aatccttttc agccggcatt gccccctatg gtacggctac   2520
ggaggacgcc tgaagttctt ggagagattc gcctacatca acaccaccat ctacccgctc   2580
acgtccctcc cgctcctcat ttactgtatc ctgcctgcca tctgcctgct cacggggaag   2640
ttcatcatcc cagagatcag caacttcgct agtatctggt tcatctctct cttcatctcg   2700
atcttcgcca cgggtatcct ggagatgagg tggagcggcg tgggcatcga cgagtggtgg   2760
aggaacgagc agttctgggt catcggaggc atctccgccc acctcttcgc cgtcttccag   2820
ggcctcctca aggtgcttgc cggcatcgac accaacttca ccgtcacctc caaggcctcg   2880
```

gatgaagacg gcgacttcgc ggagctgtac atgttcaagt ggacgacact tctgatcccg 2940
cccaccacca tcctgatcat caacctggtc ggcgttgttg ccggcatctc ctacgccatc 3000
aacagcgggt accagtcgtg ggtccgctc ttcggcaagc tcttcttcgc cttctgggtg 3060
atcgttcacc tgtacccgtt cctcaagggt ctcatgggtc ggcagaaccg caccccgacc 3120
atcgtggttg tctgggcgat cctgctggcg tcgatcttct ccttgctgtg ggttcgcatc 3180
gatccgttca ccacccgcgt cactggcccg gatactcgaa cgtgtggcat caactgctag 3240

<210> SEQ ID NO 71
<211> LENGTH: 3234
<212> TYPE: DNA
<213> ORGANISM: Zea mays

<400> SEQUENCE: 71
atggagggcg acgcggacgg cgtgaagtcg gggaggcgcg gtggcggaca ggtgtgccag 60
atctgcggcg acggcgtggg caccacggcg gagggggacg tcttcgccgc ctgcgacgtc 120
tgcgggtttc cggtgtgccg cccctgctac gagtacgagc gcaaggacgg cacgcaggcg 180
tgcccccagt gcaagaccaa gtacaagcgc cacaagggga gcccggcgat ccgtggggag 240
gaaggagacg acactgatgc cgatagcgac ttcaactacc ctgcatctgg caatgaagac 300
cagaagcaga agattgccga cagaatgcgc agctggcgca tgaacgctgg gggcagcggg 360
gatgttggtc gccccaagta tgacagtggc gagatcgggc ttaccaagta tgacagtggc 420
gagatccctc ggggatacat cccatcagtc actaacagcc agatctcagg agaaatccct 480
ggtgcttccc ctgaccatca tatgatgtcc ccaactggga acattggcaa gcgtgctcca 540
tttccctatg tgaaccattc gccaaatccg tcaagggagt tctctggtag cattgggaat 600
gttgcctgga aagagagggt tgatggctgg aaaatgaagc aggacaaggg gacgattccc 660
atgacgaatg gcacaagcat tgctccctct gagggtcggg gtgttggtga tattgatgca 720
tcaactgatt acaacatgga agatgcctta ttgaacgacg aaactcgaca gcctctatct 780
aggaaagttc cacttccttc ctccaggata aatccataca ggatggtcat tgtgctgcga 840
ttgattgttc taagcatctt cttgcactac cgtatcacaa atcctgtgcg caatgcatac 900
ccattatggc ttctatctgt tatatgtgag atctggtttg ctctttcgtg gatattggat 960
cagttcccta agtggtttcc aatcaaccgg gagacgtacc ttgataggct ggcattaagg 1020
tatgaccggg aaggtgagcc atctcagttg gctgctgttg acattttcgt cagtacagtc 1080
gacccaatga aggagcctcc tcttgtcact gccaataccg tgctatccat tcttgctgtg 1140
gattaccctg tggataaggt ctcttgctat gtatctgatg atggagctgc gatgctgaca 1200
tttgatgcac tagctgagac ttcagagttt gctagaaaat gggtaccatt tgttaagaag 1260
tacaacattg aacctagagc tcctgaatgg tacttctccc agaaaattga ttacttgaag 1320
gacaaagtgc acccttcatt tgttaaagac cgccgggcca tgaagagaga atatgaagaa 1380
ttcaaagtta gggtaaatgg ccttgttgct aaggcacaga aagttcctga ggaaggatgg 1440
atcatgcaag atggcacacc atggccagga aacaatacca gggaccatcc tggaatgatt 1500
caggttttcc ttggtcacag tggtggcctt gatactgagg gcaatgagct accccgtttg 1560
gtctatgttt ctcgtgaaaa gcgtcctgga ttccagcatc acaagaaagc tggtgccatg 1620
aatgctcttg ttcgtgtctc agctgtgctt accaatggac aatacatgtt gaatcttgat 1680
tgtgatcact acattaacaa cagtaaggct ctcagggaag ctatgtgctt ccttatggac 1740
cctaacctag gaaggagtgt ctgctacgtc cagtttcccc agagattcga tggcattgac 1800
aggaatgatc gatatgccaa caggaacacc gtgtttttcg atattaactt gagaggtctt 1860
gatggcatcc aaggaccagt ttatgtcgga actggctgtg ttttcaaccg aacagctcta 1920
tatggttatg agcccccaat taagcagaag aagggtggtt tcttgtcatc actatgtggc 1980
ggtaggaaga aggcaagcaa atcaaagaag ggctcggaca agaagaagtc gcagaagcat 2040
gtggacagtt ctgtgccagt attcaacctt gaagatatag aggagggagt tgaaggcgct 2100
ggatttgacg acgagaaatc acttcttatg tctcaaatga gcctggagaa gagatttggc 2160
cagtccgcag cgtttgttgc ctccactctg atggagtatg gtggtgttcc tcagtccgca 2220
actccggagt ctcttctgaa agaagctatc catgttataa gctgtggcta tgaggacaag 2280
actgaatggg gaactgagat cgggtggatc tacggttctg tgacagaaga cattctcacc 2340
ggattcaaga tgcacgcgcg aggctggcgg tcgatctact gcatgcccaa gcggccagct 2400
ttcaaggggt ctgcccccat caatctttcg gaccgtctga accaggtgct ccggtgggct 2460
cttgggtccg tggagatcct cttcagccgg cactgccccc tgtggtacgg ctacggaggg 2520
cggctcaagt tcctggagag attcgcgtac atcaacacca ccatctaccc gctcacgtcc 2580
atcccgcttc tcatctactg catcctgccc gccatctgtc tgctcaccgg aaagttcatc 2640
attccagaga tcagcaactt cgccagcatc tggttcatct ccctcttcat ctcgatcttc 2700
gccacgggca tcctggagat gaggtggagc ggggtgggca tcgacgagtg gtggaggaac 2760
gagcagttct gggtgatcgg gggcatctcc gcgcacctct tcgccgtgtt ccagggcctg 2820
ctcaaggtgc tggccggcat cgacaccaac ttcaccgtca cctccaaggc ctcggacgag 2880
gacggcgact tcgcggagct gtacatgttc aagtggacga cgctcctgat cccgcccacc 2940
accatcctga tcatcaacct ggtcggcgtc gtcgccggca tctcctacgc catcaacagc 3000
ggataccagt cgtggggccc gctcttcggc aagctcttct tcgccttctg ggtcatcgtc 3060
cacctgtacc cgttcctcaa gggcctcatg ggcaggcaga accgcacccc gaccatcgtc 3120
gtcgtctggg ccatcctgct ggcgtccatc ttctccttgc tgtgggttcg catcgacccc 3180
ttcaccaccc gcgtcactgg cccggatacc cagacgtgtg gcatcaactg ctag 3234

<210> SEQ ID NO 72
<211> LENGTH: 3246
<212> TYPE: DNA
<213> ORGANISM: Arabidopsis thaliana

<400> SEQUENCE: 72
atggaagctt cagctggact tgttgctgga tcttacagaa gaaacgagct tgttaggatc 60
aggcacgagt ctgatggtgg aactaagcct ctcaagaaca tgaacggaca gatctgccaa 120
atctgcggag atgatgttgg actcgctgag actggtgatg ttttcgttgc ttgtaacgag 180
tgcgctttcc ctgtgtgtag accttgttac gagtacgaga gaaaggatgg aactcagtgt 240
tgccctcagt gcaagaccag attcagaagg catagaggat ctccaagggt tgagggtgat 300
gaagatgagg atgatgtgga tgatatcgag aacgagttca actacgctca gggtgctaac 360
aaggctagac atcagagaca cggtgaagag ttctcttcat cttctaggca cgagagtcag 420
cctatccctc ttctcactca tggacacact gtgtctggtg agatcagaac ccctgatacc 480
cagtctgtga gaactacttc tggacctctc ggaccttctg ataggaacgc tatctcttct 540
ccttacatcg atcctaggca gcctgtgcct gttagaatcg tggatccttc taaggatctc 600
aactcttacg gactcggaaa tgtggattgg aaagagagag ttgagggttg gaagctcaag 660

-continued

```
caagagaaga acatgctcca gatgaccgga aagtaccacg aaggtaaggg tggtgagatt    720
gagggaactg gatctaacgg tgaggaactc cagatggctg atgataccag actccctatg    780
tctagggttg tgccaatccc ttcatctagg ctcacccctt acagagtggt gatcatcctt    840
aggcttatca tcctctgctt tttcttgcag tacaggacca cccaccctgt gaagaatgct    900
taccctcttt ggctcacctc tgtgatctgc gagatttggt tcgctttctc ttggctcctc    960
gatcagttcc ctaagtggta tcctatcaac agggaaacct acctcgatag gctcgctatc   1020
aggtacgata gagatggtga gccttctcag ctcgttcctg ttgatgtgtt cgtgtctact   1080
gtggatcctc tcaaagagcc tcctctcgtt actgctaaca ccgtgctttc tatcctctca   1140
gtggattacc ctgtggataa ggtggcatgc tacgtgtcag atgatggatc tgctatgctc   1200
accttcgagt ctctcagtga gactgctgag ttcgctaaga agtgggttcc attctgcaag   1260
aagttcaata tcgagcctag ggctcctgag ttctacttcg cacagaagat cgattacctc   1320
aaggataaga tccaaccatc tttcgtgaaa gaaagaaggg ctatgaagag ggaatacgaa   1380
gagttcaagg tgaggatcaa cgctctcgtt gctaaggctc aaaagatccc tgaagagggt   1440
tggactatgc aggatggtac tccttggcct ggaaacaaca ctagagatca ccctggaatg   1500
atccaggtgt tcctcggaca ttctggtgga ctcgatactg atggtaacga gcttcctagg   1560
ctcatctacg tgagtagaga aaagaggcct ggattccagc accacaagaa agctggtgct   1620
atgaacgctc tcatcagggt ttcagctgtg cttaccaacg gtgcttacct cctcaatgtt   1680
gattgcgatc actacttcaa caactctaag gctatcaaag aggctatgtg cttcatgatg   1740
gatccagcta tcggaaagaa gtgctgctac gttcagttcc cacagaggtt cgatggaatc   1800
gatctccacg ataggtacgc taacagaaac atcgtgttct tcgatattaa catgaaggga   1860
ctcgatggta tccagggacc tgtttacgtt ggaactggtt gctgcttcaa caggcaggct   1920
ctttacggat acgatcctgt gctcactgag gaagatctcg agcctaacat catcgtgaag   1980
tcttgctgcg gatctaggaa gaagggaaag tcatctaaga agtacaacta cgagaagaga   2040
aggggaatca acaggtctga ttctaacgct ccactcttca acatggaaga tatcgatgag   2100
ggattcgagg gatacgatga tgagagatca atcctcatgt ctcagagatc tgtggaaaag   2160
aggttcggac agtctcctgt gttcattgct gcaaccttca tggaacaggg tggaatccct   2220
cctactacta accctgctac tctcctcaaa gaagctatcc acgttatctc ttgcggatac   2280
gaggataaga ccgagtgggg aaaagaaatc ggatggatct acggatctgt gaccgaggat   2340
atcttgaccg gattcaagat gcacgctagg ggatggatca gtatctactg caatcctcct   2400
aggcctgctt tcaagggatc tgctccaatc aacctctcag ataggctcaa ccaggttctc   2460
agatgggcac ttggatctat cgagatcctc cttagtaggc actgccctat ctggtacgga   2520
taccacggta gacttagact cctcgagagg atcgcttaca tcaacaccat cgtgtaccct   2580
atcacctcta tcccacttat cgcttactgc atccttcctg ctttctgcct catcaccgat   2640
agattcatca tccctgagat ctctaactac gcttctatct ggttcatcct cctttttcatc   2700
tcaatcgctg tgaccggaat cctcgagctt agatggtctg gtgtgtctat cgaggattgg   2760
tggaggaatg agcagttctg ggttatcgga ggaacttctg ctcatctctt cgctgttttc   2820
cagggactcc ttaaggttct cgctggaatt gataccaact tcactgtgac ctcaaaggct   2880
accgatgagg atggtgattt cgctgagctt tacatcttca agtggaccgc tctcctcatc   2940
cctccaacaa ctgttctcct cgttaacctc atcggaatcg tggctggtgt ttcttacgct   3000
gtgaactctg gttaccagtc ttggggacca ctcttcggaa agcttttctt cgctctttgg   3060
```

```
gtgatcgcac acctctaccc attccttaag ggacttctcg gaaggcagaa caggactcct   3120

actatcgtta tcgtgtggtc tgtgctcctc gcttcaatct tctcattgct ctgggtgaga   3180

atcaaccctt tcgtggatgc taaccctaac gctaacaact tcaacggaaa aggtggtgtg   3240

ttctga                                                              3246
```

<210> SEQ ID NO 73
<211> LENGTH: 3246
<212> TYPE: DNA
<213> ORGANISM: Arabidopsis thaliana

<400> SEQUENCE: 73

```
atggaagctt cagctggact tgttgctgga tcttacagaa gaaacgagct tgttaggatc     60

aggcacgagt ctgatggtgg aactaagcct ctcaagaaca tgaacggaca gatctgccaa    120

atctgcggag atgatgttgg actcgctgag actggtgatg ttttcgttgc ttgtaacgag    180

tgcgctttcc ctgtgtgtag accttgttac gagtacgaga gaaaggatgg aactcagtgt    240

tgccctcagt gcaagaccag attcagaagg catagaggat ctccaagggt tgagggtgat    300

gaagatgagg atgatgtgga tgatatcgag aacgagttca actacgctca gggtgctaac    360

aaggctagac atcagagaca cggtgaagag ttctcttcat cttctaggca cgagagtcag    420

cctatccctc ttctcactca tggacacact gtgtctggtg agatcagaac ccctgatacc    480

cagtctgtga gaactacttc tggacctctc ggaccttctg ataggaacgc tatctcttct    540

ccttacatcg atcctaggca gcctgtgcct gttagaatcg tggatccttc taaggatctc    600

aactcttacg gactcggaaa tgtggattgg aaagagagag ttgagggttg gaagctcaag    660

caagagaaga acatgctcca gatgaccgga aagtaccacg aaggtaaggg tggtgagatt    720

gagggaactg gatctaacgg tgaggaactc cagatggctg atgataccag actccctatg    780

tctagggttg tgccaatccc ttcatctagg ctcacccctt acagagtggt gatcatcctt    840

aggcttatca tcctctgctt tttcttgcag tacaggacca cccaccctgt gaagaatgct    900

taccctcttt ggctcacctc tgtgatctgc gagatttggt tcgctttctc ttggctcctc    960

gatcagttcc ctaagtggta tcctatcaac agggaaacct acctcgatag gctcgctatc   1020

aggtacgata gagatggtga gccttctcag ctcgttcctg ttgatgtgtt cgtgtctact   1080

gtggatcctc tcaaagagcc tcctctcgtt actgctaaca ccgtgctttc tatcctctca   1140

gtggattacc ctgtggataa ggtggcatgc tacgtgtcag atgatggatc tgctatgctc   1200

accttcgagt ctctcagtga gactgctgag ttcgctaaga agtgggttcc attctgcaag   1260

aagttcaata tcgagcctag ggctcctgag ttctacttcg cacagaagat cgattacctc   1320

aaggataaga tccaaccatc tttcgtgaaa gaaagaaggg ctatgaagag ggaatacgaa   1380

gagttcaagg tgaggatcaa cgctctcgtt gctaaggctc aaaagatccc tgaagagggt   1440

tggactatgc aggatggtac tccttggcct ggaaacaaca ctagagatca ccctggaatg   1500

atccaggtgt tcctcggaca ttctggtgga ctcgatactg atggtaacga gcttcctagg   1560

ctcatctacg tgagtagaga aaagaggcct ggattccagc accacaagaa agctggtgct   1620

atgaacgctc tcatcagggt ttcagctgtg cttaccaacg gtgcttacct cctcaatgtt   1680

gattgcgatc actacttcaa caactctaag gctatcaaag aggctatgtg cttcatgatg   1740

gatccagcta tcggaaagaa gtgctgctac gttcagttcc cacagaggtt cgatggaatc   1800

gatctccacg ataggtacgc taacagaaac atcgtgttct tcgatattaa catgaaggga   1860
```

```
ctcgatggta tccagggacc tgtttacgtt ggaactggtt gctgcttcaa caggcaggct   1920
ctttacggat acgatcctgt gctcactgag gaagatctcg agcctaacat catcgtgaag   1980
tcttgctgcg gatctaggaa gaagggaaag tcatctaaga agtacaacta cgagaagaga   2040
aggggaatca acaggtctga ttctaacgct ccactcttca acatggaaga tatcgatgag   2100
ggattcgagg gatacgatga tgagagatca atcctcatgt ctcagagatc tgtggaaaag   2160
aggttcggac agtctcctgt gttcattgct gcaaccttca tggaacaggg tggaatccct   2220
cctactacta accctgctac tctcctcaaa gaagctatcc acgttatctc ttgcggatac   2280
gaggataaga ccgagtgggg aaaagaaatc ggatggatct acggatctgt gaccgaggat   2340
atcttgaccg gattcaagat gcacgctagg ggatggatca gtatctactg caatcctcct   2400
aggcctgctt tcaagggatc tgctccaatc aacctctcag ataggctcaa ccaggttctc   2460
agatgggcac ttggatctat cgagatcctc cttagtaggc actgccctat ctggtacgga   2520
taccacggta gacttagact cctcgagagg atcgcttaca tcaacaccat cgtgtaccct   2580
atcacctcta tcccacttat cgcttactgc atccttcctg ctttctgcct catcaccgat   2640
agattcatca tccctgagat ctctaactac gcttctatct ggttcatcct ccttttcatc   2700
tcaatcgctg tgaccggaat cctcgagctt agatggtctg gtgtgtctat cgaggattgg   2760
tggaggaatg agcagttctg ggttatcgga ggaacttctg ctcatctctt cgctgttttc   2820
cagggactcc ttaaggttct cgctggaatt gataccaact tcactgtgac ctcaaaggct   2880
accgatgagg atggtgattt cgctgagctt tacatcttca agtggaccgc tctcctcatc   2940
cctccaacaa ctgttctcct cgttaacctc atcggaatcg tggctggtgt ttcttacgct   3000
gtgaactctg gttaccagtc ttggggacca ctcttcagaa agcttttctt cgctctttgg   3060
gtgatcgcac acctctaccc attccttaag ggacttctcg gaaggcagaa caggactcct   3120
actatcgtta tcgtgtggtc tgtgctcctc gcttcaatct tctcattgct ctgggtgaga   3180
atcaaccctt tcgtggatgc taaccctaac gctaacaact tcaacggaaa aggtggtgtg   3240
ttctga                                                              3246
```

```
<210> SEQ ID NO 74
<211> LENGTH: 3198
<212> TYPE: DNA
<213> ORGANISM: Arabidopsis thaliana

<400> SEQUENCE: 74

atggaatctg aaggtgaaac tgctggaaag cctatgaaga acatcgtgcc tcagacttgc     60
cagatctgct ctgataacgt gggaaagacc gtggatggtg atagattcgt ggcttgcgat    120
atctgctcat tccctgtgtg tagaccttgc tacgagtacg agaggaagga tggaaaccag    180
tcttgtcctc agtgcaagac cagatacaag aggctcaagg gatctcctgc tatccctggt    240
gataaggatg aggatggact tgctgatgag ggaaccgttg agttcaacta ccctcagaaa    300
gagaagatct ctgagaggat gctcggatgg catctcacta gaggtaaggg tgaagaaatg    360
ggagagcctc agtacgataa ggaagtgtct cataaccacc tccctaggct cacctctaga    420
caggatactt ctggtgagtt ctctgctgct tctcctgaga ggctctctgt gtcatctact    480
atcgctggtg gaaagaggct cccttactct tctgatgtga accagtctcc taacagaagg    540
atcgttgatc ctgttggact cggaaacgtg gcatggaaag aaagagtgga tggatggaag    600
atgaagcaag agaagaacac cggacctgtg tctactcaag ctgcttctga aaggggtggt    660
gtggatatcg atgcttctac cgatatcctc gcagatgagg cacttctcaa cgatgaggct    720
```

-continued

```
agacagccac tctctaggaa ggtgtcaatc ccatcttcta ggatcaaccc ttacagaatg    780
gtgatcatgc tcaggctcgt tatcctctgc ttgttcctcc actacaggat cactaaccct    840
gtgcctaacg ctttcgctct ctggctcgtt tctgttatct gcgagatctg gttcgcactc    900
tcttggatcc ttgatcagtt ccctaagtgg ttccctgtga acagagagac ttacctcgat    960
agactcgctc tcaggtacga tagagagggt gagccttctc aactcgctgc agttgatatc   1020
ttcgtgtcta ccgtggatcc tctcaaagag cctcctctcg ttactgctaa caccgtgctt   1080
tctatcctcg ctgtggatta ccctgtggat aaggtgtcat gctacgtgtc agatgatggt   1140
gctgctatgc tctcattcga gtctctcgct gagacttctg agttcgctag aaagtgggtg   1200
ccattctgca agaagtactc tatcgaacct agggctcctg agtggtactt cgctgctaag   1260
atcgattacc tcaaggataa ggttcagacc tctttcgtga aggatagaag ggctatgaag   1320
agagagtacg aagagttcaa gatcagaatc aacgctctcg tgtctaaggc tctcaagtgt   1380
cctgaagagg gatgggttat gcaggatgga actccttggc ctggaaacaa cactagagat   1440
caccctggaa tgatccaggt gttccttgga caaaacggtg gattggatgc tgagggaaac   1500
gagcttccta gactcgtgta cgtgtcaaga gaaaagaggc ctggattcca gcaccacaag   1560
aaagctggtg ctatgaacgc tcttgtgagg gtttcagctg tgctcactaa cggacctttc   1620
atcctcaacc tcgattgcga tcactacatc aacaactcta aggcactcag ggaagctatg   1680
tgcttcctca tggatcctaa cctcggaaag caggtttgct acgttcagtt cccacagagg   1740
ttcgatggaa tcgataagaa cgataggtac gctaatagga acaccgtgtt cttcgatatc   1800
aacctcagag gactcgatgg tatccaggga cctgtttacg ttggaactgg atgcgtgttc   1860
aacaggactg ctctttacgg atacgagcct cctatcaagg tgaagcacaa gaagccttca   1920
ctcctcagta agctctgcgg aggatctagg aagaagaact caaaggctaa gaaagagagt   1980
gataagaaga agtctggaag gcacaccgat tctaccgtgc ctgtgttcaa ccttgatgat   2040
attgaagagg gtgttgaggg tgctggattc gatgatgaga aagctctcct catgtctcag   2100
atgtctctcg agaagaggtt cggacagtct gctgtgttcg ttgcttcaac cctcatggaa   2160
aatggtggtg tgcctccttc tgctacccct gaaaaccttc ttaaagaggc tattcacgtt   2220
atctcttgcg gttacgagga taagtctgat tggggaatgg aaatcggatg gatctacgga   2280
tctgtgaccg aggatattct caccggattc aagatgcacg ctaggggttg gagatctatc   2340
tactgcatgc ctaagctccc tgctttcaag ggttctgctc caatcaacct ctctgatagg   2400
ctcaaccagg ttctcagatg ggctttggga tctgttgaga tcctcttcag taggcactgc   2460
cctatctggt acggatacaa cggtagactc aagttcctcg agaggttcgc ttacgtgaac   2520
actaccatct accctattac ctctatccct ctcttgatgt actgcaccct tcctgctgtt   2580
tgcctcttca ccaaccagtt catcatccct cagatctcta acattgcttc tatctggttc   2640
ctcagtctct tcctctcaat cttcgctacc ggaatccttg agatgaggtg gtctggtgtg   2700
ggaattgatg agtggtggag aaatgagcag ttctgggtta tcggtggtgt gtctgctcat   2760
ctcttcgctg ttttccaggg aatcctcaag gttctcgctg gaattgatac caacttcacc   2820
gtgacctcta aggcttctga tgaagatggt gatttcgctg agctttacct cttcaagtgg   2880
actaccctcc ttatccctcc tacaacactc ctcatcgtga acctcgttgg agttgtggct   2940
ggtgtgtcat acgctatcaa ctctggttac cagtcatggg gaccactctt cggaaagctt   3000
ttcttcgctt tctgggtgat cgtgcacctc tacccattcc ttaagggact catgggtaga   3060
```

cagaacagga ctcctactat cgttgtggtg tggtctgtgc tcctcgcttc aatcttctca 3120
ctcctctggg tgagaatcga tccattcact tctagagtga ccggtcctga tatcttggag 3180
tgcggaatca actgctga 3198

<210> SEQ ID NO 75
<211> LENGTH: 3198
<212> TYPE: DNA
<213> ORGANISM: Arabidopsis thaliana

<400> SEQUENCE: 75
atggaatctg aaggtgaaac tgctggaaag cctatgaaga acatcgtgcc tcagacttgc 60
cagatctgct ctgataacgt gggaaagacc gtggatggtg atagattcgt ggcttgcgat 120
atctgctcat tccctgtgtg tagaccttgc tacgagtacg agaggaagga tggaaaccag 180
tcttgtcctc agtgcaagac cagatacaag aggctcaagg gatctcctgc tatccctggt 240
gataaggatg aggatggact tgctgatgag ggaaccgttg agttcaacta ccctcagaaa 300
gagaagatct ctgagaggat gctcggatgg catctcacta gaggtaaggg tgaagaaatg 360
ggagagcctc agtacgataa ggaagtgtct cataaccacc tccctaggct cacctctaga 420
caggatactt ctggtgagtt ctctgctgct tctcctgaga ggctctctgt gtcatctact 480
atcgctggtg gaaagaggct cccttactct tctgatgtga accagtctcc taacagaagg 540
atcgttgatc ctgttggact cggaaacgtg gcatggaaag aaagagtgga tggatggaag 600
atgaagcaag agaagaacac cggacctgtg tctactcaag ctgcttctga aaggggtggt 660
gtggatatcg atgcttctac cgatatcctc gcagatgagg cacttctcaa cgatgaggct 720
agacagccac tctctaggaa ggtgtcaatc ccatcttcta ggatcaaccc ttacagaatg 780
gtgatcatgc tcaggctcgt tatcctctgc ttgttcctcc actacaggat cactaaccct 840
gtgcctaacg ctttcgctct ctggctcgtt tctgttatct gcgagatctg gttcgcactc 900
tcttggatcc ttgatcagtt ccctaagtgg ttccctgtga acagagagac ttacctcgat 960
agactcgctc tcaggtacga tagagagggt gagccttctc aactcgctgc agttgatatc 1020
ttcgtgtcta ccgtggatcc tctcaaagag cctcctctcg ttactgctaa caccgtgctt 1080
tctatcctcg ctgtggatta ccctgtggat aaggtgtcat gctacgtgtc agatgatggt 1140
gctgctatgc tctcattcga gtctctcgct gagacttctg agttcgctag aaagtgggtg 1200
ccattctgca agaagtactc tatcgaacct agggctcctg agtggtactt cgctgctaag 1260
atcgattacc tcaaggataa ggttcagacc tctttcgtga aggatagaag ggctatgaag 1320
agagagtacg aagagttcaa gatcagaatc aacgctctcg tgtctaaggc tctcaagtgt 1380
cctgaagagg gatgggttat gcaggatgga actccttggc ctggaaacaa cactagagat 1440
caccctggaa tgatccaggt gttccttgga caaaacggtg gattggatgc tgagggaaac 1500
gagcttccta gactcgtgta cgtgtcaaga gaaaagaggc ctggattcca gcaccacaag 1560
aaagctggtg ctatgaacgc tcttgtgagg gtttcagctg tgctcactaa cggacctttc 1620
atcctcaacc tcgattgcga tcactacatc aacaactcta aggcactcag ggaagctatg 1680
tgcttcctca tggatcctaa cctcggaaag caggtttgct acgttcagtt cccacagagg 1740
ttcgatggaa tcgataagaa cgataggtac gctaatagga acaccgtgtt cttcgatatc 1800
aacctcagag gactcgatgg tatccaggga cctgtttacg ttggaactgg atgcgtgttc 1860
aacaggactg ctctttacgg atacgagcct cctatcaagg tgaagcacaa gaagccttca 1920
ctcctcagta agctctgcgg aggatctagg aagaagaact caaaggctaa gaaagagagt 1980
gataagaaga agtctggaag gcacaccgat tctaccgtgc ctgtgttcaa ccttgatgat 2040
attgaagagg gtgttgaggg tgctggattc gatgatgaga aagctctcct catgtctcag 2100
atgtctctcg agaagaggtt cggacagtct gctgtgttcg ttgcttcaac cctcatggaa 2160
aatggtggtg tgcctccttc tgctacccct gaaaaccttc ttaaagaggc tattcacgtt 2220
atctcttgcg gttacgagga taagtctgat tggggaatgg aaatcggatg gatctacgga 2280
tctgtgaccg aggatattct caccggattc aagatgcacg ctaggggttg gagatctatc 2340
tactgcatgc ctaagctccc tgctttcaag ggttctgctc caatcaacct ctctgatagg 2400
ctcaaccagg ttctcagatg ggctttggga tctgttgaga tcctcttcag taggcactgc 2460
cctatctggt acggatacaa cggtagactc aagttcctcg agaggttcgc ttacgtgaac 2520
actaccatct accctattac ctctatccct ctcttgatgt actgcaccct tcctgctgtt 2580
tgcctcttca ccaaccagtt catcatccct cagatctcta acattgcttc tatctggttc 2640
ctcagtctct tcctctcaat cttcgctacc ggaatccttg agatgaggtg gtctggtgtg 2700
ggaattgatg agtggtggag aaatgagcag ttctgggtta tcggtggtgt gtctgctcat 2760
ctcttcgctg ttttccaggg aatcctcaag gttctcgctg gaattgatac caacttcacc 2820
gtgacctcta aggcttctga tgaagatggt gatttcgctg agctttacct cttcaagtgg 2880
actaccctcc ttatccctcc tacaacactc ctcatcgtga acctcgttgg agttgtggct 2940
ggtgtgtcat acgctatcaa ctctggttac cagtcatggg gaccactctt cggaaagctt 3000
ttcttcgctt tctgggtgat cgtgcacctc tacccattcc ttaagggact catgggtaga 3060
cagaacagga ctcctactat cgttgtggtg tggtctgtgc tcctcgcttc aatcttcttg 3120
ctcctctggg tgagaatcga tccattcact tctagagtga ccggtcctga tatcttggag 3180
tgcggaatca actgctga 3198

<210> SEQ ID NO 76
<211> LENGTH: 3198
<212> TYPE: DNA
<213> ORGANISM: Arabidopsis thaliana

<400> SEQUENCE: 76
atggaatctg aaggtgaaac tgctggaaag cctatgaaga acatcgtgcc tcagacttgc 60
cagatctgct ctgataacgt gggaaagacc gtggatggtg atagattcgt ggcttgcgat 120
atctgctcat tccctgtgtg tagaccttgc tacgagtacg agaggaagga tggaaaccag 180
tcttgtcctc agtgcaagac cagatacaag aggctcaagg gatctcctgc tatccctggt 240
gataaggatg aggatggact tgctgatgag ggaaccgttg agttcaacta ccctcagaaa 300
gagaagatct ctgagaggat gctcggatgg catctcacta gaggtaaggg tgaagaaatg 360
ggagagcctc agtacgataa ggaagtgtct cataaccacc tccctaggct cacctctaga 420
caggatactt ctggtgagtt ctctgctgct tctcctgaga ggctctctgt gtcatctact 480
atcgctggtg gaaagaggct ccccttactct tctgatgtga accagtctcc taacagaagg 540
atcgttgatc ctgttggact cggaaacgtg gcatggaaag aaagagtgga tggatggaag 600
atgaagcaag agaagaacac cggacctgtg tctactcaag ctgcttctga aaggggtggt 660
gtggatatcg atgcttctac cgatatcctc gcagatgagg cacttctcaa cgatgaggct 720
agacagccac tctctaggaa ggtgtcaatc ccatcttcta ggatcaaccc ttacagaatg 780
gtgatcatgc tcaggctcgt tatcctctgc ttgttcctcc actacaggat cactaaccct 840

-continued

```
gtgcctaacg ctttcgctct ctggctcgtt tctgttatct gcgagatctg gttcgcactc    900
tcttggatcc ttgatcagtt ccctaagtgg ttccctgtga acagagagac ttacctcgat    960
agactcgctc tcaggtacga tagagagggt gagccttctc aactcgctgc agttgatatc   1020
ttcgtgtcta ccgtggatcc tctcaaagag cctcctctcg ttactgctaa caccgtgctt   1080
tctatcctcg ctgtggatta ccctgtggat aaggtgtcat gctacgtgtc agatgatggt   1140
gctgctatgc tctcattcga gtctctcgct gagacttctg agttcgctag aaagtgggtg   1200
ccattctgca agaagtactc tatcgaacct agggctcctg agtggtactt cgctgctaag   1260
atcgattacc tcaaggataa ggttcagacc tctttcgtga aggatagaag ggctatgaag   1320
agagagtacg aagagttcaa gatcagaatc aacgctctcg tgtctaaggc tctcaagtgt   1380
cctgaagagg gatgggttat gcaggatgga actccttggc ctggaaacaa cactagagat   1440
caccctggaa tgatccaggt gttccttgga caaaacggtg gattggatgc tgagggaaac   1500
gagcttccta gactcgtgta cgtgtcaaga gaaaagaggc ctggattcca gcaccacaag   1560
aaagctggtg ctatgaacgc tcttgtgagg gtttcagctg tgctcactaa cggacctttc   1620
atcctcaacc tcgattgcga tcactacatc aacaactcta aggcactcag ggaagctatg   1680
tgcttcctca tggatcctaa cctcggaaag caggtttgct acgttcagtt cccacagagg   1740
ttcgatggaa tcgataagaa cgataggtac gctaatagga acaccgtgtt cttcgatatc   1800
aacctcagag gactcgatgg tatccaggga cctgtttacg ttggaactgg atgcgtgttc   1860
aacaggactg ctctttacgg atacgagcct cctatcaagg tgaagcacaa gaagccttca   1920
ctcctcagta agctctgcgg aggatctagg aagaagaact caaaggctaa gaaagagagt   1980
gataagaaga agtctggaag gcacaccgat tctaccgtgc ctgtgttcaa ccttgatgat   2040
attgaagagg gtgttgaggg tgctggattc gatgatgaga aagctctcct catgtctcag   2100
atgtctctcg agaagaggtt cggacagtct gctgtgttcg ttgcttcaac cctcatggaa   2160
aatggtggtg tgcctccttc tgctacccct gaaaaccttc ttaaagaggc tattcacgtt   2220
atctcttgcg gttacgagga taagtctgat tggggaatgg aaatcggatg gatctacgga   2280
tctgtgaccg aggatattct caccggattc aagatgcacg ctaggggttg gagatctatc   2340
tactgcatgc ctaagctccc tgctttcaag ggttctgctc caatcaacct ctctgatagg   2400
ctcaaccagg ttctcagatg ggctttggga tctgttgaga tcctcttcag taggcactgc   2460
cctatctggt acggatacaa cggtagactc aagttcctcg agaggttcgc ttacgtgaac   2520
actaccatct accctattac ctctatccct ctcttgatgt actgcaccct tcctgctgtt   2580
tgcctcttca ccaaccagtt catcatccct cagatctcta acattgcttc tatctggttc   2640
ctcagtctct tcctctcaat cttcgctacc ggaatccttg agatgaggtg gtctggtgtg   2700
ggaattgatg agtggtggag aaatgagcag ttctgggtta tcggtggtgt gtctgctcat   2760
ctcttcgctg ttttccaggg aatcctcaag gttctcgctg gaattgatac caacttcacc   2820
gtgacctcta aggcttctga tgaagatggt gatttcgctg agctttacct cttcaagtgg   2880
actaccctcc ttatccctcc tacaacactc ctcatcgtga acctcgttgg agttgtggct   2940
ggtgtgtcat acgctatcaa ctctggttac cagtcatggg gaccactctt cgataagctt   3000
ttcttcgctt tctgggtgat cgtgcacctc tacccattcc ttaagggact catgggtaga   3060
cagaacagga ctcctactat cgttgtggtg tggtctgtgc tcctcgcttc aatcttctca   3120
ctcctctggg tgagaatcga tccattcact tctagagtga ccggtcctga tatcttggag   3180
tgcggaatca actgctga                                                 3198
```

<210> SEQ ID NO 77
<211> LENGTH: 3198
<212> TYPE: DNA
<213> ORGANISM: Arabidopsis thaliana

<400> SEQUENCE: 77
atggaatctg aaggtgaaac tgctggaaag cctatgaaga acatcgtgcc tcagacttgc 60
cagatctgct ctgataacgt gggaaagacc gtggatggtg atagattcgt ggcttgcgat 120
atctgctcat tccctgtgtg tagaccttgc tacgagtacg agaggaagga tggaaaccag 180
tcttgtcctc agtgcaagac cagatacaag aggctcaagg gatctcctgc tatccctggt 240
gataaggatg aggatggact tgctgatgag ggaaccgttg agttcaacta ccctcagaaa 300
gagaagatct ctgagaggat gctcggatgg catctcacta gaggtaaggg tgaagaaatg 360
ggagagcctc agtacgataa ggaagtgtct cataaccacc tccctaggct cacctctaga 420
caggatactt ctggtgagtt ctctgctgct tctcctgaga ggctctctgt gtcatctact 480
atcgctggtg gaaagaggct cccttactct tctgatgtga accagtctcc taacagaagg 540
atcgttgatc ctgttggact cggaaacgtg gcatggaaag aaagagtgga tggatggaag 600
atgaagcaag agaagaacac cggacctgtg tctactcaag ctgcttctga aaggggtggt 660
gtggatatcg atgcttctac cgatatcctc gcagatgagg cacttctcaa cgatgaggct 720
agacagccac tctctaggaa ggtgtcaatc ccatcttcta ggatcaaccc ttacagaatg 780
gtgatcatgc tcaggctcgt tatcctctgc ttgttcctcc actacaggat cactaaccct 840
gtgcctaacg ctttcgctct ctggctcgtt tctgttatct gcgagatctg gttcgcactc 900
tcttggatcc ttgatcagtt ccctaagtgg ttccctgtga acagagagac ttacctcgat 960
agactcgctc tcaggtacga tagagagggt gagccttctc aactcgctgc agttgatatc 1020
ttcgtgtcta ccgtggatcc tctcaaagag cctcctctcg ttactgctaa caccgtgctt 1080
tctatcctcg ctgtggatta ccctgtggat aaggtgtcat gctacgtgtc agatgatggt 1140
gctgctatgc tctcattcga gtctctcgct gagacttctg agttcgctag aaagtgggtg 1200
ccattctgca agaagtactc tatcgaacct agggctcctg agtggtactt cgctgctaag 1260
atcgattacc tcaaggataa ggttcagacc tctttcgtga aggatagaag ggctatgaag 1320
agagagtacg aagagttcaa gatcagaatc aacgctctcg tgtctaaggc tctcaagtgt 1380
cctgaagagg gatgggttat gcaggatgga actccttggc ctggaaacaa cactagagat 1440
caccctggaa tgatccaggt gttccttgga caaaacggtg gattggatgc tgagggaaac 1500
gagcttccta gactcgtgta cgtgtcaaga gaaaagaggc ctggattcca gcaccacaag 1560
aaagctggtg ctatgaacgc tcttgtgagg gtttcagctg tgctcactaa cggacctttc 1620
atcctcaacc tcgattgcga tcactacatc aacaactcta aggcactcag ggaagctatg 1680
tgcttcctca tggatcctaa cctcggaaag caggtttgct acgttcagtt cccacagagg 1740
ttcgatggaa tcgataagaa cgataggtac gctaatagga acaccgtgtt cttcgatatc 1800
aacctcagag gactcgatgg tatccaggga cctgtttacg ttggaactgg atgcgtgttc 1860
aacaggactg ctctttacgg atacgagcct cctatcaagg tgaagcacaa gaagccttca 1920
ctcctcagta agctctgcgg aggatctagg aagaagaact caaaggctaa gaaagagagt 1980
gataagaaga agtctggaag gcacaccgat tctaccgtgc ctgtgttcaa ccttgatgat 2040
attgaagagg gtgttgaggg tgctggattc gatgatgaga aagctctcct catgtctcag 2100

-continued

```
atgtctctcg agaagaggtt cggacagtct gctgtgttcg ttgcttcaac cctcatggaa   2160

aatggtggtg tgcctccttc tgctacccct gaaaaccttc ttaaagaggc tattcacgtt   2220

atctcttgcg gttacgagga taagtctgat tggggaatgg aaatcggatg gatctacgga   2280

tctgtgaccg aggatattct caccggattc aagatgcacg ctaggggttg gagatctatc   2340

tactgcatgc ctaagctccc tgctttcaag ggttctgctc caatcaacct ctctgatagg   2400

ctcaaccagg ttctcagatg ggctttggga tctgttgaga tcctcttcag taggcactgc   2460

cctatctggt acggatacaa cggtagactc aagttcctcg agaggttcgc ttacgtgaac   2520

actaccatct accctattac ctctatccct ctcttgatgt actgcaccct tcctgctgtt   2580

tgcctcttca ccaaccagtt catcatccct cagatctcta acattgcttc tatctggttc   2640

ctcagtctct tcctctcaat cttcgctacc ggaatccttg agatgaggtg gtctggtgtg   2700

ggaattgatg agtggtggag aaatgagcag ttctgggtta tcggtggtgt gtctgctcat   2760

ctcttcgctg ttttccaggg aatcctcaag gttctcgctg gaattgatac caacttcacc   2820

gtgacctcta aggcttctga tgaagatggt gatttcgctg agctttacct cttcaagtgg   2880

actaccctcc ttatccctcc tacaacactc ctcatcgtga acctcgttgg agttgtggct   2940

ggtgtgtcat acgctatcaa ctctggttac cagtcatggg gaccactctt cggaaagctt   3000

ttcttcgctt tctgggtgat cgtgcacctc tacccattcc ttaagggact catgggtaga   3060

cagaacagga ctcctactat cgttgtggtg tggtctgtgc tcctcgcttt tatcttctca   3120

ctcctctggg tgagaatcga tccattcact tctagagtga ccggtcctga tatcttggag   3180

tgcggaatca actgctga                                                 3198
```

```
<210> SEQ ID NO 78
<211> LENGTH: 24
<212> TYPE: PRT
<213> ORGANISM: Artificial
<220> FEATURE:
<223> OTHER INFORMATION: Motif 1a
<220> FEATURE:
<221> NAME/KEY: VARIANT
<222> LOCATION: (1)..(1)
<223> OTHER INFORMATION: / replace = "Ile"
<220> FEATURE:
<221> NAME/KEY: VARIANT
<222> LOCATION: (2)..(2)
<223> OTHER INFORMATION: / replace = "Val"
<220> FEATURE:
<221> NAME/KEY: VARIANT
<222> LOCATION: (4)..(4)
<223> OTHER INFORMATION: / replace = "Ile" or "Phe"
<220> FEATURE:
<221> NAME/KEY: VARIANT
<222> LOCATION: (5)..(5)
<223> OTHER INFORMATION: / replace = "Thr"
<220> FEATURE:
<221> NAME/KEY: VARIANT
<222> LOCATION: (6)..(6)
<223> OTHER INFORMATION: / replace = "Asp", "Asn", or "Ala"
<220> FEATURE:
<221> NAME/KEY: VARIANT
<222> LOCATION: (8)..(8)
<223> OTHER INFORMATION: / replace = "Ile", or "Leu"
<220> FEATURE:
<221> NAME/KEY: VARIANT
<222> LOCATION: (9)..(9)
<223> OTHER INFORMATION: / replace = "Ser", or "Gly"
<220> FEATURE:
<221> NAME/KEY: VARIANT
<222> LOCATION: (10)..(10)
<223> OTHER INFORMATION: / replace = "Asn"
<220> FEATURE:
<221> NAME/KEY: VARIANT
```

<222> LOCATION: (12)..(12)
<223> OTHER INFORMATION: / replace = "Phe", or "Glu"
<220> FEATURE:
<221> NAME/KEY: VARIANT
<222> LOCATION: (13)..(13)
<223> OTHER INFORMATION: / replace = "Asp", "Gly", "Glu", or "His"
<220> FEATURE:
<221> NAME/KEY: VARIANT
<222> LOCATION: (14)..(14)
<223> OTHER INFORMATION: / replace = "Ala"
<220> FEATURE:
<221> NAME/KEY: VARIANT
<222> LOCATION: (17)..(17)
<223> OTHER INFORMATION: / replace = "Ala"
<220> FEATURE:
<221> NAME/KEY: VARIANT
<222> LOCATION: (19)..(19)
<223> OTHER INFORMATION: / replace = "Met", or "Leu"
<220> FEATURE:
<221> NAME/KEY: VARIANT
<222> LOCATION: (21)..(21)
<223> OTHER INFORMATION: / replace = "Arg"
<220> FEATURE:
<221> NAME/KEY: VARIANT
<222> LOCATION: (22)..(22)
<223> OTHER INFORMATION: / replace = "Val"
<220> FEATURE:
<221> NAME/KEY: VARIANT
<222> LOCATION: (23)..(23)
<223> OTHER INFORMATION: / replace = "Leu"

<400> SEQUENCE: 78

```
Val Ala Gly Val Ser Tyr Ala Val Asn Ser Gly Tyr Gln Ser Trp Gly
1               5                   10                  15

Pro Leu Phe Gly Lys Leu Phe Phe
            20
```

<210> SEQ ID NO 79
<211> LENGTH: 24
<212> TYPE: PRT
<213> ORGANISM: Artificial
<220> FEATURE:
<223> OTHER INFORMATION: Motif 1b
<220> FEATURE:
<221> NAME/KEY: VARIANT
<222> LOCATION: (1)..(1)
<223> OTHER INFORMATION: / replace = "Ile"
<220> FEATURE:
<221> NAME/KEY: VARIANT
<222> LOCATION: (4)..(4)
<223> OTHER INFORMATION: / replace = "Ile"
<220> FEATURE:
<221> NAME/KEY: VARIANT
<222> LOCATION: (6)..(6)
<223> OTHER INFORMATION: / replace = "Asp" or "Asn"
<220> FEATURE:
<221> NAME/KEY: VARIANT
<222> LOCATION: (8)..(8)
<223> OTHER INFORMATION: / replace = "Ile"
<220> FEATURE:
<221> NAME/KEY: VARIANT
<222> LOCATION: (9)..(9)
<223> OTHER INFORMATION: / replace = "Ser"
<220> FEATURE:
<221> NAME/KEY: VARIANT
<222> LOCATION: (10)..(10)
<223> OTHER INFORMATION: / replace = "Asn"
<220> FEATURE:
<221> NAME/KEY: VARIANT
<222> LOCATION: (12)..(12)
<223> OTHER INFORMATION: / replace = "Phe"
<220> FEATURE:
<221> NAME/KEY: VARIANT
<222> LOCATION: (13)..(13)
<223> OTHER INFORMATION: / replace = "Asp"
<220> FEATURE:

<221> NAME/KEY: VARIANT
<222> LOCATION: (19)..(19)
<223> OTHER INFORMATION: / replace = "Met" or "Leu"
<220> FEATURE:
<221> NAME/KEY: VARIANT
<222> LOCATION: (21)..(21)
<223> OTHER INFORMATION: / replace = "Arg"
<220> FEATURE:
<221> NAME/KEY: VARIANT
<222> LOCATION: (23)..(23)
<223> OTHER INFORMATION: / replace = "Leu"

<400> SEQUENCE: 79

```
Val Ala Gly Val Ser Tyr Ala Val Asn Ser Gly Tyr Gln Ser Trp Gly
1               5                   10                  15

Pro Leu Phe Gly Lys Leu Phe Phe
            20
```

<210> SEQ ID NO 80
<211> LENGTH: 24
<212> TYPE: PRT
<213> ORGANISM: Artificial
<220> FEATURE:
<223> OTHER INFORMATION: Motif 1c
<220> FEATURE:
<221> NAME/KEY: VARIANT
<222> LOCATION: (4)..(4)
<223> OTHER INFORMATION: / replace = "Ile"
<220> FEATURE:
<221> NAME/KEY: VARIANT
<222> LOCATION: (8)..(8)
<223> OTHER INFORMATION: / replace = "Ile"
<220> FEATURE:
<221> NAME/KEY: VARIANT
<222> LOCATION: (19)..(19)
<223> OTHER INFORMATION: / replace = "Met"
<220> FEATURE:
<221> NAME/KEY: VARIANT
<222> LOCATION: (23)..(23)
<223> OTHER INFORMATION: / replace = "Leu"

<400> SEQUENCE: 80

```
Val Ala Gly Val Ser Tyr Ala Val Asn Ser Gly Tyr Gln Ser Trp Gly
1               5                   10                  15

Pro Leu Phe Gly Lys Leu Phe Phe
            20
```

<210> SEQ ID NO 81
<211> LENGTH: 20
<212> TYPE: PRT
<213> ORGANISM: Artificial
<220> FEATURE:
<223> OTHER INFORMATION: Motif 2a
<220> FEATURE:
<221> NAME/KEY: VARIANT
<222> LOCATION: (1)..(1)
<223> OTHER INFORMATION: / replace = "Leu" or "Ile"
<220> FEATURE:
<221> NAME/KEY: VARIANT
<222> LOCATION: (3)..(3)
<223> OTHER INFORMATION: / replace = "Ala"
<220> FEATURE:
<221> NAME/KEY: VARIANT
<222> LOCATION: (4)..(4)
<223> OTHER INFORMATION: / replace = "Ala" or "Ile"
<220> FEATURE:
<221> NAME/KEY: VARIANT
<222> LOCATION: (7)..(7)
<223> OTHER INFORMATION: / replace = "Ser"
<220> FEATURE:
<221> NAME/KEY: VARIANT
<222> LOCATION: (9)..(9)
<223> OTHER INFORMATION: / replace = "Phe" or "Val"

```
<220> FEATURE:
<221> NAME/KEY: VARIANT
<222> LOCATION: (10)..(10)
<223> OTHER INFORMATION: / replace = “Leu”
<220> FEATURE:
<221> NAME/KEY: VARIANT
<222> LOCATION: (11)..(11)
<223> OTHER INFORMATION: / replace = “Thr”
<220> FEATURE:
<221> NAME/KEY: VARIANT
<222> LOCATION: (12)..(12)
<223> OTHER INFORMATION: / replace = “Val”
<220> FEATURE:
<221> NAME/KEY: VARIANT
<222> LOCATION: (13)..(13)
<223> OTHER INFORMATION: / replace = “Met”, “Val”, or “Ile”
<220> FEATURE:
<221> NAME/KEY: VARIANT
<222> LOCATION: (16)..(16)
<223> OTHER INFORMATION: / replace = “Lys”
<220> FEATURE:
<221> NAME/KEY: VARIANT
<222> LOCATION: (17)..(17)
<223> OTHER INFORMATION: / replace = “Val”
<220> FEATURE:
<221> NAME/KEY: VARIANT
<222> LOCATION: (18)..(18)
<223> OTHER INFORMATION: / replace = “Asp”

<400> SEQUENCE: 81

Val Trp Ser Val Leu Leu Ala Ser Ile Phe Ser Leu Leu Trp Val Arg
1               5                   10                  15

Ile Asn Pro Phe
            20


<210> SEQ ID NO 82
<211> LENGTH: 20
<212> TYPE: PRT
<213> ORGANISM: Artificial
<220> FEATURE:
<223> OTHER INFORMATION: Motif 2b
<220> FEATURE:
<221> NAME/KEY: VARIANT
<222> LOCATION: (3)..(3)
<223> OTHER INFORMATION: / replace = “Ala”
<220> FEATURE:
<221> NAME/KEY: VARIANT
<222> LOCATION: (4)..(4)
<223> OTHER INFORMATION: / replace = “Ala” or “Ile”
<220> FEATURE:
<221> NAME/KEY: VARIANT
<222> LOCATION: (7)..(7)
<223> OTHER INFORMATION: / replace = “Ser”
<220> FEATURE:
<221> NAME/KEY: VARIANT
<222> LOCATION: (9)..(9)
<223> OTHER INFORMATION: / replace = “Phe”
<220> FEATURE:
<221> NAME/KEY: VARIANT
<222> LOCATION: (10)..(10)
<223> OTHER INFORMATION: / replace = “Leu”
<220> FEATURE:
<221> NAME/KEY: VARIANT
<222> LOCATION: (11)..(11)
<223> OTHER INFORMATION: / replace = “Thr”
<220> FEATURE:
<221> NAME/KEY: VARIANT
<222> LOCATION: (13)..(13)
<223> OTHER INFORMATION: / replace = “Met”
<220> FEATURE:
<221> NAME/KEY: VARIANT
<222> LOCATION: (16)..(16)
<223> OTHER INFORMATION: / replace = “Lys”
<220> FEATURE:
<221> NAME/KEY: VARIANT
<222> LOCATION: (17)..(17)
```

-continued

```
<223> OTHER INFORMATION: / replace = "Val"
<220> FEATURE:
<221> NAME/KEY: VARIANT
<222> LOCATION: (18)..(18)
<223> OTHER INFORMATION: / replace = "Asp"

<400> SEQUENCE: 82

Val Trp Ser Val Leu Leu Ala Ser Ile Phe Ser Leu Leu Trp Val Arg
1               5                   10                  15

Ile Asn Pro Phe
            20


<210> SEQ ID NO 83
<211> LENGTH: 20
<212> TYPE: PRT
<213> ORGANISM: Artificial
<220> FEATURE:
<223> OTHER INFORMATION: Motif 2c
<220> FEATURE:
<221> NAME/KEY: VARIANT
<222> LOCATION: (3)..(3)
<223> OTHER INFORMATION: / replace = "Ala"
<220> FEATURE:
<221> NAME/KEY: VARIANT
<222> LOCATION: (4)..(4)
<223> OTHER INFORMATION: / replace = "Ala" or "Ile"
<220> FEATURE:
<221> NAME/KEY: VARIANT
<222> LOCATION: (13)..(13)
<223> OTHER INFORMATION: / replace = "Met"
<220> FEATURE:
<221> NAME/KEY: VARIANT
<222> LOCATION: (16)..(16)
<223> OTHER INFORMATION: / replace = "Lys"
<220> FEATURE:
<221> NAME/KEY: VARIANT
<222> LOCATION: (18)..(18)
<223> OTHER INFORMATION: / replace = "Asp"

<400> SEQUENCE: 83

Val Trp Ser Val Leu Leu Ala Ser Ile Phe Ser Leu Leu Trp Val Arg
1               5                   10                  15

Ile Asn Pro Phe
            20
```